US012435330B2

(12) United States Patent
Liu et al.

(10) Patent No.: US 12,435,330 B2
(45) Date of Patent: Oct. 7, 2025

(54) METHODS AND COMPOSITIONS FOR PRIME EDITING RNA

(71) Applicants: The Broad Institute, Inc., Cambridge, MA (US); President and Fellows of Harvard College, Cambridge, MA (US)

(72) Inventors: David R. Liu, Cambridge, MA (US); Andrew Vito Anzalone, Cambridge, MA (US); James William Nelson, Cambridge, MA (US); Peter J. Chen, Cambridge, MA (US)

(73) Assignees: The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 166 days.

(21) Appl. No.: 17/767,777

(22) PCT Filed: Oct. 9, 2020

(86) PCT No.: PCT/US2020/055156

§ 371 (c)(1),
(2) Date: Apr. 8, 2022

(87) PCT Pub. No.: WO2021/072328

PCT Pub. Date: Apr. 15, 2021

(65) Prior Publication Data

US 2024/0417715 A1 Dec. 19, 2024

Related U.S. Application Data

(60) Provisional application No. 62/913,480, filed on Oct. 10, 2019.

(51) Int. Cl.

| | |
|---|---|
| *C12N 15/10* | (2006.01) |
| *C12N 9/12* | (2006.01) |

(Continued)

(52) U.S. Cl.

CPC ........... *C12N 15/102* (2013.01); *C12N 9/127* (2013.01); *C12N 9/22* (2013.01); *C12N 15/111* (2013.01);

(Continued)

(58) Field of Classification Search

CPC .................................................... C12N 15/102

See application file for complete search history.

(56) References Cited

U.S. PATENT DOCUMENTS

| | | | |
|---|---|---|---|
| 4,182,449 | A | 1/1980 | Kozlow |
| 4,186,183 | A | 1/1980 | Steck et al. |

(Continued)

FOREIGN PATENT DOCUMENTS

| | | | |
|---|---|---|---|
| AU | 2012244264 | A1 | 11/2012 |
| AU | 2015252023 | A1 | 11/2015 |

(Continued)

OTHER PUBLICATIONS

[No Author Listed] NCBI Reference Sequence: WP_032188360.1. Apr. 6, 2015. 1 page.

(Continued)

*Primary Examiner* — Mark L Shibuya

(74) *Attorney, Agent, or Firm* — Wolf, Greenfield & Sacks, P.C.

(57) ABSTRACT

The present disclosure provides compositions and methods for the targeted modification of RNA molecules by RNA prime editing. The compositions and methods may be conducted invitro or in vivo within cells (e.g., human cells) for the therapeutic correction of disease-causing mutations and/or installation of motifs or mutations in RNA molecules of interest as a tool for scientific research. The disclosure provides compositions and methods for conducting RNA prime editing of a target RNA molecule (e.g., an RNA transcript) that enables the incorporation of one or more (Continued)

nucleotide changes and/or targeted mutagenesis of a target RNA molecule. The nucleotide change can include a single-nucleotide change, an insertion of one or more nucleotides, or a deletion of one or more nucleotides. More in particular, the disclosure provides a variety of configurations of the RNA prime editors each comprising a nucleic acid programmable RNA binding proteins (napRNAbp), such as Cas13, and an RNA-dependent RNA polymerase (RDRP), which are provided as fusion proteins or which can be separately provided in trans. The RNA prime editors are guided to a target RNA site by a guide RNA, which can be a rpegRNA that includes a template region for the synthesis of an RNA sequence to be installed on the RNA molecule attached to an available 3' terminus. In others embodiments, the RNA template can be provided in trans.

20 Claims, 2 Drawing Sheets

Specification includes a Sequence Listing.

(51) Int. Cl.
*C12N 9/22* (2006.01)
*C12N 15/11* (2006.01)
(52) U.S. Cl.
CPC ...... *C07K 2319/85* (2013.01); *C12N 2310/20* (2017.05); *C12Y 207/07048* (2013.01)

(56) References Cited

U.S. PATENT DOCUMENTS

| | | | |
|---|---|---|---|
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,663,290 | A | 5/1987 | Weis et al. |
| 4,737,323 | A | 4/1988 | Martin et al. |
| 4,774,085 | A | 9/1988 | Fidler |
| 4,797,368 | A | 1/1989 | Carter et al. |
| 4,837,028 | A | 6/1989 | Allen |
| 4,873,316 | A | 10/1989 | Meade et al. |
| 4,880,635 | A | 11/1989 | Janoff et al. |
| 4,889,818 | A | 12/1989 | Gelfand et al. |
| 4,897,355 | A | 1/1990 | Eppstein et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 4,946,787 | A | 8/1990 | Eppstein et al. |
| 4,965,185 | A | 10/1990 | Grischenko et al. |
| 5,017,492 | A | 5/1991 | Kotewicz et al. |
| 5,047,342 | A | 9/1991 | Chatterjee |
| 5,049,386 | A | 9/1991 | Eppstein et al. |
| 5,079,352 | A | 1/1992 | Gelfand et al. |
| 5,139,941 | A | 8/1992 | Muzyczka et al. |
| 5,173,414 | A | 12/1992 | Lebkowski et al. |
| 5,223,409 | A | 6/1993 | Ladner et al. |
| 5,244,797 | A | 9/1993 | Kotewicz et al. |
| 5,270,179 | A | 12/1993 | Chatterjee |
| 5,374,553 | A | 12/1994 | Gelfand et al. |
| 5,405,776 | A | 4/1995 | Kotewicz et al. |
| 5,436,149 | A | 7/1995 | Barnes |
| 5,449,639 | A | 9/1995 | Wei et al. |
| 5,496,714 | A | 3/1996 | Comb et al. |
| 5,512,462 | A | 4/1996 | Cheng |
| 5,580,737 | A | 12/1996 | Polisky et al. |
| 5,614,365 | A | 3/1997 | Tabor et al. |
| 5,652,094 | A | 7/1997 | Usman et al. |
| 5,658,727 | A | 8/1997 | Barbas et al. |
| 5,668,005 | A | 9/1997 | Kotewicz et al. |
| 5,677,152 | A | 10/1997 | Birch et al. |
| 5,767,099 | A | 6/1998 | Harris et al. |
| 5,780,053 | A | 7/1998 | Ashley et al. |
| 5,830,430 | A | 11/1998 | Unger et al. |
| 5,834,247 | A | 11/1998 | Comb et al. |
| 5,835,699 | A | 11/1998 | Kimura |
| 5,844,075 | A | 12/1998 | Kawakami et al. |
| 5,849,548 | A | 12/1998 | Haseloff et al. |
| 5,851,548 | A | 12/1998 | Dattagupta et al. |
| 5,855,910 | A | 1/1999 | Ashley et al. |
| 5,856,463 | A | 1/1999 | Blankenborg et al. |
| 5,962,313 | A | 10/1999 | Podsakoff et al. |
| 5,981,182 | A | 11/1999 | Jacobs, Jr. et al. |
| 6,015,794 | A | 1/2000 | Haseloff et al. |
| 6,057,153 | A | 5/2000 | George et al. |
| 6,063,608 | A | 5/2000 | Kotewicz et al. |
| 6,077,705 | A | 6/2000 | Duan et al. |
| 6,156,509 | A | 12/2000 | Schellenberger |
| 6,183,998 | B1 | 2/2001 | Ivanov et al. |
| 6,355,415 | B1 | 3/2002 | Wagner et al. |
| 6,429,298 | B1 | 8/2002 | Ellington et al. |
| 6,453,242 | B1 | 9/2002 | Eisenberg et al. |
| 6,479,264 | B1 | 11/2002 | Louwrier |
| 6,503,717 | B2 | 1/2003 | Case et al. |
| 6,534,261 | B1 | 3/2003 | Cox, III et al. |
| 6,558,671 | B1 | 5/2003 | Slingluff et al. |
| 6,589,768 | B1 | 7/2003 | Kotewicz et al. |
| 6,599,692 | B1 | 7/2003 | Case et al. |
| 6,607,882 | B1 | 8/2003 | Cox, III et al. |
| 6,610,522 | B1 | 8/2003 | Kotewicz et al. |
| 6,689,558 | B2 | 2/2004 | Case et al. |
| 6,716,973 | B2 | 4/2004 | Baskerville et al. |
| 6,824,978 | B1 | 11/2004 | Cox, III et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,045,337 | B2 | 5/2006 | Schultz et al. |
| 7,067,650 | B1 | 6/2006 | Tanaka |
| 7,070,928 | B2 | 7/2006 | Liu et al. |
| 7,078,208 | B2 | 7/2006 | Smith et al. |
| 7,083,970 | B2 | 8/2006 | Schultz et al. |
| 7,163,824 | B2 | 1/2007 | Cox, III et al. |
| 7,192,739 | B2 | 3/2007 | Liu et al. |
| 7,223,545 | B2 | 5/2007 | Liu et al. |
| 7,354,761 | B2 | 4/2008 | Schultz et al. |
| 7,368,275 | B2 | 5/2008 | Schultz et al. |
| 7,419,669 | B2 | 9/2008 | Kosmatopoulos et al. |
| 7,442,160 | B2 | 10/2008 | Liu et al. |
| 7,476,500 | B1 | 1/2009 | Liu et al. |
| 7,476,734 | B2 | 1/2009 | Liu |
| 7,479,573 | B2 | 1/2009 | Chu et al. |
| 7,488,718 | B2 | 2/2009 | Scheinberg et al. |
| 7,491,494 | B2 | 2/2009 | Liu et al. |
| 7,541,450 | B2 | 6/2009 | Liu et al. |
| 7,557,068 | B2 | 7/2009 | Liu et al. |
| 7,595,179 | B2 | 9/2009 | Chen et al. |
| 7,638,300 | B2 | 12/2009 | Schultz et al. |
| 7,670,807 | B2 | 3/2010 | Lampson et al. |
| 7,678,554 | B2 | 3/2010 | Liu et al. |
| 7,713,721 | B2 | 5/2010 | Schultz et al. |
| 7,771,935 | B2 | 8/2010 | Liu et al. |
| 7,794,931 | B2 | 9/2010 | Breaker et al. |
| 7,807,408 | B2 | 10/2010 | Liu et al. |
| 7,851,658 | B2 | 12/2010 | Liu et al. |
| 7,915,025 | B2 | 3/2011 | Schultz et al. |
| 7,919,277 | B2 | 4/2011 | Russell et al. |
| 7,993,672 | B2 | 8/2011 | Huang et al. |
| 7,998,904 | B2 | 8/2011 | Liu et al. |
| 7,999,071 | B2 | 8/2011 | Schlom et al. |
| 8,012,739 | B2 | 9/2011 | Schultz et al. |
| 8,017,323 | B2 | 9/2011 | Liu et al. |
| 8,017,755 | B2 | 9/2011 | Liu et al. |
| 8,030,074 | B2 | 10/2011 | Schultz et al. |
| 8,067,556 | B2 | 11/2011 | Hogrefe et al. |
| 8,114,648 | B2 | 2/2012 | Schultz et al. |
| 8,173,364 | B2 | 5/2012 | Schultz et al. |
| 8,173,392 | B2 | 5/2012 | Schultz et al. |
| 8,183,012 | B2 | 5/2012 | Schultz et al. |

(56) References Cited

U.S. PATENT DOCUMENTS

| | | | |
|---|---|---|---|
| 8,183,178 | B2 | 5/2012 | Liu et al. |
| 8,206,914 | B2 | 6/2012 | Liu et al. |
| 8,354,380 | B2 | 1/2013 | Liu et al. |
| 8,361,725 | B2 | 1/2013 | Russell et al. |
| 8,394,604 | B2 | 3/2013 | Liu et al. |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,492,082 | B2 | 7/2013 | De Franciscis et al. |
| 8,546,553 | B2 | 10/2013 | Terns et al. |
| 8,569,256 | B2 | 10/2013 | Heyes et al. |
| 8,586,363 | B2 | 11/2013 | Voytas et al. |
| 8,680,069 | B2 | 3/2014 | de Fougerolles et al. |
| 8,691,729 | B2 | 4/2014 | Liu et al. |
| 8,691,750 | B2 | 4/2014 | Constien et al. |
| 8,697,359 | B1 | 4/2014 | Zhang |
| 8,697,439 | B2 | 4/2014 | Mangeot et al. |
| 8,697,853 | B2 | 4/2014 | Voytas et al. |
| 8,709,466 | B2 | 4/2014 | Coady et al. |
| 8,728,526 | B2 | 5/2014 | Heller |
| 8,748,667 | B2 | 6/2014 | Budzik et al. |
| 8,758,810 | B2 | 6/2014 | Okada et al. |
| 8,759,103 | B2 | 6/2014 | Kim et al. |
| 8,759,104 | B2 | 6/2014 | Unciti-Broceta et al. |
| 8,771,728 | B2 | 7/2014 | Huang et al. |
| 8,790,664 | B2 | 7/2014 | Pitard et al. |
| 8,795,965 | B2 | 8/2014 | Zhang |
| 8,822,663 | B2 | 9/2014 | Schrum et al. |
| 8,835,148 | B2 | 9/2014 | Janulaitis et al. |
| 8,846,578 | B2 | 9/2014 | McCray et al. |
| 8,871,445 | B2 | 10/2014 | Cong et al. |
| 8,889,418 | B2 | 11/2014 | Zhang et al. |
| 8,900,814 | B2 | 12/2014 | Yasukawa et al. |
| 8,945,839 | B2 | 2/2015 | Zhang |
| 8,975,232 | B2 | 3/2015 | Liu et al. |
| 8,993,233 | B2 | 3/2015 | Zhang et al. |
| 8,999,641 | B2 | 4/2015 | Zhang et al. |
| 9,023,594 | B2 | 5/2015 | Liu et al. |
| 9,023,649 | B2 | 5/2015 | Mali et al. |
| 9,034,650 | B2 | 5/2015 | Padidam |
| 9,068,179 | B1 | 6/2015 | Liu et al. |
| 9,150,626 | B2 | 10/2015 | Liu et al. |
| 9,163,271 | B2 | 10/2015 | Schultz et al. |
| 9,163,284 | B2 | 10/2015 | Liu et al. |
| 9,181,535 | B2 | 11/2015 | Liu et al. |
| 9,200,045 | B2 | 12/2015 | Liu et al. |
| 9,221,886 | B2 | 12/2015 | Liu et al. |
| 9,228,207 | B2 | 1/2016 | Liu et al. |
| 9,234,213 | B2 | 1/2016 | Wu |
| 9,243,038 | B2 | 1/2016 | Liu et al. |
| 9,267,127 | B2 | 2/2016 | Liu et al. |
| 9,322,006 | B2 | 4/2016 | Liu et al. |
| 9,322,037 | B2 | 4/2016 | Liu et al. |
| 9,340,799 | B2 | 5/2016 | Liu et al. |
| 9,340,800 | B2 | 5/2016 | Liu et al. |
| 9,359,599 | B2 | 6/2016 | Liu et al. |
| 9,388,430 | B2 | 7/2016 | Liu et al. |
| 9,394,537 | B2 | 7/2016 | Liu et al. |
| 9,434,774 | B2 | 9/2016 | Liu et al. |
| 9,458,484 | B2 | 10/2016 | Ma et al. |
| 9,512,446 | B1 | 12/2016 | Joung et al. |
| 9,526,784 | B2 | 12/2016 | Liu et al. |
| 9,534,210 | B2 | 1/2017 | Park et al. |
| 9,580,698 | B1 | 2/2017 | Xu et al. |
| 9,610,322 | B2 | 4/2017 | Liu et al. |
| 9,637,739 | B2 | 5/2017 | Siksnys et al. |
| 9,663,770 | B2 | 5/2017 | Rogers et al. |
| 9,695,446 | B2 | 7/2017 | Mangeot et al. |
| 9,737,604 | B2 | 8/2017 | Jin et al. |
| 9,738,693 | B2 | 8/2017 | Telford et al. |
| 9,753,340 | B2 | 9/2017 | Saitou |
| 9,771,574 | B2 | 9/2017 | Liu et al. |
| 9,783,791 | B2 | 10/2017 | Hogrefe et al. |
| 9,816,093 | B1 | 11/2017 | Donohoue et al. |
| 9,840,538 | B2 | 12/2017 | Telford et al. |
| 9,840,690 | B2 | 12/2017 | Karli et al. |
| 9,840,699 | B2 | 12/2017 | Liu et al. |
| 9,840,702 | B2 | 12/2017 | Collingwood et al. |
| 9,850,521 | B2 | 12/2017 | Braman et al. |
| 9,873,907 | B2 | 1/2018 | Zeiner et al. |
| 9,879,270 | B2 | 1/2018 | Hittinger et al. |
| 9,914,939 | B2 | 3/2018 | Church et al. |
| 9,932,567 | B1 | 4/2018 | Xu et al. |
| 9,938,288 | B1 | 4/2018 | Kishi et al. |
| 9,944,933 | B2 | 4/2018 | Storici et al. |
| 9,982,279 | B1 | 5/2018 | Gill et al. |
| 9,999,671 | B2 | 6/2018 | Liu et al. |
| 10,011,868 | B2 | 7/2018 | Liu et al. |
| 10,053,725 | B2 | 8/2018 | Liu et al. |
| 10,059,940 | B2 | 8/2018 | Zhong |
| 10,077,453 | B2 | 9/2018 | Liu et al. |
| 10,113,163 | B2 | 10/2018 | Liu et al. |
| 10,150,955 | B2 | 12/2018 | Lambowitz et al. |
| 10,167,457 | B2 | 1/2019 | Liu et al. |
| 10,179,911 | B2 | 1/2019 | Liu et al. |
| 10,189,831 | B2 | 1/2019 | Arrington et al. |
| 10,202,593 | B2 | 2/2019 | Liu et al. |
| 10,202,658 | B2 | 2/2019 | Parkin et al. |
| 10,227,581 | B2 | 3/2019 | Liu et al. |
| 10,323,236 | B2 | 6/2019 | Liu et al. |
| 10,336,997 | B2 | 7/2019 | Liu et al. |
| 10,358,670 | B2 | 7/2019 | Janulaitis et al. |
| 10,392,674 | B2 | 8/2019 | Liu et al. |
| 10,407,474 | B2 | 9/2019 | Liu et al. |
| 10,407,697 | B2 | 9/2019 | Doudna et al. |
| 10,465,176 | B2 | 11/2019 | Liu et al. |
| 10,508,298 | B2 | 12/2019 | Liu et al. |
| 10,583,201 | B2 | 3/2020 | Chen et al. |
| 10,597,679 | B2 | 3/2020 | Liu et al. |
| 10,612,011 | B2 | 4/2020 | Liu et al. |
| 10,640,767 | B2 | 5/2020 | Maianti et al. |
| 10,682,410 | B2 | 6/2020 | Liu et al. |
| 10,704,062 | B2 | 7/2020 | Liu et al. |
| 10,745,677 | B2 | 8/2020 | Maianti et al. |
| 10,858,639 | B2 | 12/2020 | Liu et al. |
| 10,912,833 | B2 | 2/2021 | Liu et al. |
| 10,930,367 | B2 | 2/2021 | Zhang et al. |
| 10,947,530 | B2 | 3/2021 | Liu et al. |
| 10,954,548 | B2 | 3/2021 | Liu et al. |
| 10,968,253 | B2 | 4/2021 | Ohlmann et al. |
| 11,046,948 | B2 | 6/2021 | Liu et al. |
| 11,053,481 | B2 | 7/2021 | Liu et al. |
| 11,124,782 | B2 | 9/2021 | Liu et al. |
| 11,214,780 | B2 | 1/2022 | Liu et al. |
| 11,268,082 | B2 | 3/2022 | Liu et al. |
| 11,299,755 | B2 | 4/2022 | Liu et al. |
| 11,306,324 | B2 | 4/2022 | Liu et al. |
| 11,319,532 | B2 | 5/2022 | Liu et al. |
| 11,421,016 | B2 | 8/2022 | Nguyen et al. |
| 11,447,770 | B1 | 9/2022 | Liu et al. |
| 11,542,496 | B2 | 1/2023 | Liu et al. |
| 11,542,509 | B2 | 1/2023 | Maianti et al. |
| 11,560,566 | B2 | 1/2023 | Liu et al. |
| 11,578,343 | B2 | 2/2023 | Liu et al. |
| 11,643,652 | B2 | 5/2023 | Liu et al. |
| 11,661,590 | B2 | 5/2023 | Liu et al. |
| 11,702,651 | B2 | 7/2023 | Liu et al. |
| 11,732,274 | B2 | 8/2023 | Liu et al. |
| 11,795,443 | B2 | 10/2023 | Liu et al. |
| 11,795,452 | B2 | 10/2023 | Liu et al. |
| 11,820,969 | B2 | 11/2023 | Maianti et al. |
| 11,898,179 | B2 | 2/2024 | Maianti et al. |
| 11,912,985 | B2 | 2/2024 | Liu et al. |
| 11,920,181 | B2 | 3/2024 | Liu et al. |
| 11,932,884 | B2 | 3/2024 | Liu et al. |
| 11,999,947 | B2 | 6/2024 | Liu et al. |
| 12,006,520 | B2 | 6/2024 | Liu et al. |
| 12,031,126 | B2 | 7/2024 | Liu et al. |
| 12,043,852 | B2 | 7/2024 | Liu et al. |
| 2003/0082575 | A1 | 5/2003 | Schultz et al. |
| 2003/0087817 | A1 | 5/2003 | Cox et al. |
| 2003/0096337 | A1 | 5/2003 | Hillman et al. |
| 2003/0108885 | A1 | 6/2003 | Schultz et al. |
| 2003/0119764 | A1 | 6/2003 | Loeb et al. |

(56) References Cited

U.S. PATENT DOCUMENTS

2003/0167533 A1 9/2003 Yadav et al.
2003/0203480 A1 10/2003 Kovesdi et al.
2004/0003420 A1 1/2004 Kuhn et al.
2004/0115184 A1 6/2004 Smith et al.
2004/0156861 A1 8/2004 Figdor et al.
2004/0197892 A1 10/2004 Moore et al.
2004/0203109 A1 10/2004 Lal et al.
2005/0136429 A1 6/2005 Guarente et al.
2005/0222030 A1 10/2005 Allison
2005/0260626 A1 11/2005 Lorens et al.
2006/0088864 A1 4/2006 Smolke et al.
2006/0104984 A1 5/2006 Littlefield et al.
2006/0246568 A1 11/2006 Honjo et al.
2007/0015238 A1 1/2007 Snyder et al.
2007/0049533 A1 3/2007 Liu et al.
2007/0264692 A1 11/2007 Liu et al.
2007/0269817 A1 11/2007 Shapero
2008/0008697 A1 1/2008 Mintier et al.
2008/0051317 A1 2/2008 Church et al.
2008/0124725 A1 5/2008 Barrangou et al.
2008/0182254 A1 7/2008 Hall et al.
2008/0220502 A1 9/2008 Schellenberger et al.
2008/0241917 A1 10/2008 Akita et al.
2008/0268516 A1 10/2008 Perreault et al.
2009/0111119 A1 4/2009 Doyon et al.
2009/0130718 A1 5/2009 Short
2009/0215878 A1 8/2009 Tan et al.
2009/0234109 A1 9/2009 Han et al.
2010/0076057 A1 3/2010 Sontheimer et al.
2010/0093617 A1 4/2010 Barrangou et al.
2010/0104690 A1 4/2010 Barrangou et al.
2010/0273857 A1 10/2010 Thakker et al.
2010/0305197 A1 12/2010 Che
2010/0316643 A1 12/2010 Eckert et al.
2011/0016540 A1 1/2011 Weinstein et al.
2011/0059160 A1 3/2011 Essner et al.
2011/0059502 A1 3/2011 Chalasani
2011/0104787 A1 5/2011 Church et al.
2011/0177495 A1 7/2011 Liu et al.
2011/0189775 A1 8/2011 Ainley et al.
2011/0189776 A1 8/2011 Terns et al.
2011/0217739 A1 9/2011 Terns et al.
2011/0301073 A1 12/2011 Gregory et al.
2012/0129759 A1 5/2012 Liu et al.
2012/0141523 A1 6/2012 Castado et al.
2012/0244601 A1 9/2012 Bertozzi et al.
2012/0270273 A1 10/2012 Zhang et al.
2012/0322861 A1 12/2012 Byrne et al.
2013/0022980 A1 1/2013 Nelson et al.
2013/0059931 A1 3/2013 Petersen-Mahrt et al.
2013/0108657 A1 5/2013 Yee et al.
2013/0117869 A1 5/2013 Duchateau et al.
2013/0130248 A1 5/2013 Haurwitz et al.
2013/0158245 A1 6/2013 Russell et al.
2013/0165389 A1 6/2013 Schellenberger et al.
2013/0212725 A1 8/2013 Kuhn et al.
2013/0309720 A1 11/2013 Schultz et al.
2013/0344117 A1 12/2013 Mirosevich et al.
2013/0345064 A1 12/2013 Liu et al.
2014/0004280 A1 1/2014 Loomis
2014/0005269 A1 1/2014 Ngwuluka et al.
2014/0017214 A1 1/2014 Cost
2014/0018404 A1 1/2014 Chen et al.
2014/0044793 A1 2/2014 Goll et al.
2014/0065711 A1 3/2014 Liu et al.
2014/0068797 A1 3/2014 Doudna et al.
2014/0127752 A1 5/2014 Zhou et al.
2014/0128449 A1 5/2014 Liu et al.
2014/0141094 A1 5/2014 Smyth et al.
2014/0141487 A1 5/2014 Feldman et al.
2014/0179770 A1 6/2014 Zhang et al.
2014/0186843 A1 7/2014 Zhang et al.
2014/0186919 A1 7/2014 Zhang et al.
2014/0186958 A1 7/2014 Zhang et al.
2014/0201858 A1 7/2014 Ostertag et al.
2014/0234289 A1 8/2014 Liu et al.
2014/0248702 A1 9/2014 Zhang et al.
2014/0273037 A1 9/2014 Wu
2014/0273226 A1 9/2014 Wu
2014/0273230 A1 9/2014 Chen et al.
2014/0273234 A1 9/2014 Zhang et al.
2014/0283156 A1 9/2014 Zador et al.
2014/0295556 A1 10/2014 Joung et al.
2014/0295557 A1 10/2014 Joung et al.
2014/0342456 A1 11/2014 Mali et al.
2014/0342457 A1 11/2014 Mali et al.
2014/0342458 A1 11/2014 Mali et al.
2014/0349400 A1 11/2014 Jakimo et al.
2014/0356867 A1 12/2014 Peter et al.
2014/0356956 A1 12/2014 Church et al.
2014/0356958 A1 12/2014 Mali et al.
2014/0356959 A1 12/2014 Church et al.
2014/0357523 A1 12/2014 Zeiner et al.
2014/0377868 A1 12/2014 Joung et al.
2015/0010526 A1 1/2015 Liu et al.
2015/0031089 A1 1/2015 Lindstrom
2015/0031132 A1 1/2015 Church et al.
2015/0031133 A1 1/2015 Church et al.
2015/0044191 A1 2/2015 Liu et al.
2015/0044192 A1 2/2015 Liu et al.
2015/0044772 A1 2/2015 Zhao
2015/0050699 A1 2/2015 Siksnys et al.
2015/0056177 A1 2/2015 Liu et al.
2015/0056629 A1 2/2015 Guthrie-Honea
2015/0064138 A1 3/2015 Lu et al.
2015/0064789 A1 3/2015 Paschon et al.
2015/0071898 A1 3/2015 Liu et al.
2015/0071899 A1 3/2015 Liu et al.
2015/0071900 A1 3/2015 Liu et al.
2015/0071901 A1 3/2015 Liu et al.
2015/0071902 A1 3/2015 Liu et al.
2015/0071903 A1 3/2015 Liu et al.
2015/0071906 A1 3/2015 Liu et al.
2015/0079680 A1 3/2015 Bradley et al.
2015/0079681 A1 3/2015 Zhang
2015/0098954 A1 4/2015 Hyde et al.
2015/0118216 A1 4/2015 Liu et al.
2015/0128300 A1 5/2015 Warming et al.
2015/0132269 A1 5/2015 Orkin et al.
2015/0140664 A1 5/2015 Byrne et al.
2015/0159172 A1 6/2015 Miller et al.
2015/0165054 A1 6/2015 Liu et al.
2015/0166980 A1 6/2015 Liu et al.
2015/0166981 A1 6/2015 Liu et al.
2015/0166982 A1 6/2015 Liu et al.
2015/0166983 A1 6/2015 Liu et al.
2015/0166984 A1 6/2015 Liu et al.
2015/0166985 A1 6/2015 Liu et al.
2015/0191744 A1 7/2015 Wolfe et al.
2015/0197759 A1 7/2015 Xu et al.
2015/0211058 A1 7/2015 Carstens
2015/0218573 A1 8/2015 Loque et al.
2015/0225773 A1 8/2015 Farmer et al.
2015/0241440 A1 8/2015 Fasan et al.
2015/0252358 A1 9/2015 Maeder et al.
2015/0275202 A1 10/2015 Liu et al.
2015/0291965 A1 10/2015 Zhang et al.
2015/0307889 A1 10/2015 Petolino et al.
2015/0315252 A1 11/2015 Haugwitz et al.
2015/0344549 A1 12/2015 Muir et al.
2016/0017393 A1 1/2016 Jacobson et al.
2016/0017396 A1 1/2016 Cann et al.
2016/0032292 A1 2/2016 Storici et al.
2016/0032353 A1 2/2016 Braman et al.
2016/0040155 A1 2/2016 Maizels et al.
2016/0046952 A1 2/2016 Hittinger et al.
2016/0046961 A1 2/2016 Jinek et al.
2016/0046962 A1 2/2016 May et al.
2016/0053272 A1 2/2016 Wurtzel et al.
2016/0053304 A1 2/2016 Wurtzel et al.
2016/0074535 A1 3/2016 Ranganathan et al.
2016/0076093 A1 3/2016 Shendure et al.
2016/0090603 A1 3/2016 Carnes et al.
2016/0090622 A1 3/2016 Liu et al.

(56) References Cited

U.S. PATENT DOCUMENTS

| | | | |
|---|---|---|---|
| 2016/0115488 | A1 | 4/2016 | Zhang et al. |
| 2016/0138046 | A1 | 5/2016 | Wu |
| 2016/0153003 | A1 | 6/2016 | Joung et al. |
| 2016/0186214 | A1 | 6/2016 | Brouns et al. |
| 2016/0200779 | A1 | 7/2016 | Liu et al. |
| 2016/0201040 | A1 | 7/2016 | Liu et al. |
| 2016/0201089 | A1 | 7/2016 | Gersbach et al. |
| 2016/0206566 | A1 | 7/2016 | Lu et al. |
| 2016/0208243 | A1 | 7/2016 | Zhang et al. |
| 2016/0208288 | A1 | 7/2016 | Liu et al. |
| 2016/0215275 | A1 | 7/2016 | Zhong |
| 2016/0215276 | A1 | 7/2016 | Liu et al. |
| 2016/0215300 | A1 | 7/2016 | May et al. |
| 2016/0244784 | A1 | 8/2016 | Jacobson et al. |
| 2016/0244829 | A1 | 8/2016 | Bang et al. |
| 2016/0264934 | A1 | 9/2016 | Giallourakis et al. |
| 2016/0272593 | A1 | 9/2016 | Ritter et al. |
| 2016/0272965 | A1 | 9/2016 | Zhang et al. |
| 2016/0281072 | A1 | 9/2016 | Zhang |
| 2016/0298136 | A1 | 10/2016 | Chen et al. |
| 2016/0304846 | A1 | 10/2016 | Liu et al. |
| 2016/0304855 | A1 | 10/2016 | Stark et al. |
| 2016/0312304 | A1 | 10/2016 | Sorrentino et al. |
| 2016/0319262 | A1 | 11/2016 | Doudna et al. |
| 2016/0333389 | A1 | 11/2016 | Liu et al. |
| 2016/0340622 | A1 | 11/2016 | Abdou |
| 2016/0340661 | A1 | 11/2016 | Cong et al. |
| 2016/0340662 | A1 | 11/2016 | Zhang et al. |
| 2016/0345578 | A1 | 12/2016 | Barrangou et al. |
| 2016/0346360 | A1 | 12/2016 | Quake et al. |
| 2016/0346361 | A1 | 12/2016 | Quake et al. |
| 2016/0346362 | A1 | 12/2016 | Quake et al. |
| 2016/0348074 | A1 | 12/2016 | Quake et al. |
| 2016/0348096 | A1 | 12/2016 | Liu et al. |
| 2016/0350476 | A1 | 12/2016 | Quake et al. |
| 2016/0355796 | A1 | 12/2016 | Davidson et al. |
| 2016/0369262 | A1 | 12/2016 | Reik et al. |
| 2017/0009224 | A1 | 1/2017 | Liu et al. |
| 2017/0009242 | A1 | 1/2017 | McKinley et al. |
| 2017/0014449 | A1 | 1/2017 | Bangera et al. |
| 2017/0020922 | A1 | 1/2017 | Wagner et al. |
| 2017/0022251 | A1 | 1/2017 | Rammensee et al. |
| 2017/0037432 | A1 | 2/2017 | Donohoue et al. |
| 2017/0044520 | A1 | 2/2017 | Liu et al. |
| 2017/0044592 | A1 | 2/2017 | Peter et al. |
| 2017/0053729 | A1 | 2/2017 | Kotani et al. |
| 2017/0058271 | A1 | 3/2017 | Joung et al. |
| 2017/0058272 | A1 | 3/2017 | Carter et al. |
| 2017/0058298 | A1 | 3/2017 | Kennedy et al. |
| 2017/0073663 | A1 | 3/2017 | Wang et al. |
| 2017/0073670 | A1 | 3/2017 | Nishida et al. |
| 2017/0087224 | A1 | 3/2017 | Quake |
| 2017/0087225 | A1 | 3/2017 | Quake |
| 2017/0088587 | A1 | 3/2017 | Quake |
| 2017/0088828 | A1 | 3/2017 | Quake |
| 2017/0107536 | A1 | 4/2017 | Zhang et al. |
| 2017/0107560 | A1 | 4/2017 | Peter et al. |
| 2017/0114367 | A1 | 4/2017 | Hu et al. |
| 2017/0121693 | A1 | 5/2017 | Liu et al. |
| 2017/0145394 | A1 | 5/2017 | Yeo et al. |
| 2017/0145405 | A1 | 5/2017 | Tang et al. |
| 2017/0145438 | A1 | 5/2017 | Kantor |
| 2017/0152528 | A1 | 6/2017 | Zhang |
| 2017/0152787 | A1 | 6/2017 | Kubo et al. |
| 2017/0159033 | A1 | 6/2017 | Kamtekar et al. |
| 2017/0166928 | A1 | 6/2017 | Vyas et al. |
| 2017/0175104 | A1 | 6/2017 | Doudna et al. |
| 2017/0175142 | A1 | 6/2017 | Zhang et al. |
| 2017/0191047 | A1 | 7/2017 | Terns et al. |
| 2017/0191078 | A1 | 7/2017 | Zhang et al. |
| 2017/0198269 | A1 | 7/2017 | Zhang et al. |
| 2017/0198277 | A1 | 7/2017 | Kmiec et al. |
| 2017/0198302 | A1 | 7/2017 | Feng et al. |
| 2017/0211061 | A1 | 7/2017 | Weiss et al. |
| 2017/0224843 | A1 | 8/2017 | Deglon et al. |
| 2017/0226522 | A1 | 8/2017 | Hu et al. |
| 2017/0233703 | A1 | 8/2017 | Xie et al. |
| 2017/0233708 | A1 | 8/2017 | Liu et al. |
| 2017/0233756 | A1 | 8/2017 | Begemann et al. |
| 2017/0247671 | A1 | 8/2017 | Yung et al. |
| 2017/0247703 | A1 | 8/2017 | Sloan et al. |
| 2017/0268022 | A1 | 9/2017 | Liu et al. |
| 2017/0275648 | A1 | 9/2017 | Barrangou et al. |
| 2017/0275665 | A1 | 9/2017 | Silas et al. |
| 2017/0283797 | A1 | 10/2017 | Robb et al. |
| 2017/0283831 | A1 | 10/2017 | Zhang et al. |
| 2017/0306306 | A1 | 10/2017 | Potter et al. |
| 2017/0314016 | A1 | 11/2017 | Kim et al. |
| 2017/0362635 | A1 | 12/2017 | Chamberlain et al. |
| 2018/0023062 | A1 | 1/2018 | Lamb et al. |
| 2018/0064077 | A1 | 3/2018 | Dunham et al. |
| 2018/0066258 | A1 | 3/2018 | Powell |
| 2018/0068062 | A1 | 3/2018 | Zhang et al. |
| 2018/0073012 | A1 | 3/2018 | Liu et al. |
| 2018/0080051 | A1 | 3/2018 | Sheikh et al. |
| 2018/0087046 | A1 | 3/2018 | Badran et al. |
| 2018/0100147 | A1 | 4/2018 | Yates et al. |
| 2018/0105867 | A1 | 4/2018 | Xiao et al. |
| 2018/0119118 | A1 | 5/2018 | Lu et al. |
| 2018/0127759 | A1 | 5/2018 | Lu et al. |
| 2018/0127780 | A1 | 5/2018 | Liu et al. |
| 2018/0155708 | A1 | 6/2018 | Church et al. |
| 2018/0155720 | A1 | 6/2018 | Donohoue et al. |
| 2018/0163213 | A1 | 6/2018 | Aneja et al. |
| 2018/0170984 | A1 | 6/2018 | Harris et al. |
| 2018/0179503 | A1 | 6/2018 | Maianti et al. |
| 2018/0179547 | A1 | 6/2018 | Zhang et al. |
| 2018/0201921 | A1 | 7/2018 | Malcolm |
| 2018/0230464 | A1 | 8/2018 | Zhong |
| 2018/0230471 | A1 | 8/2018 | Storici et al. |
| 2018/0236081 | A1 | 8/2018 | Liu et al. |
| 2018/0237787 | A1 | 8/2018 | Maianti et al. |
| 2018/0245066 | A1 | 8/2018 | Yao et al. |
| 2018/0245075 | A1 | 8/2018 | Khalil et al. |
| 2018/0258418 | A1 | 9/2018 | Kim |
| 2018/0265864 | A1 | 9/2018 | Li et al. |
| 2018/0273939 | A1 | 9/2018 | Yu et al. |
| 2018/0273976 | A1 | 9/2018 | Ümit et al. |
| 2018/0282722 | A1 | 10/2018 | Jakimo et al. |
| 2018/0298391 | A1 | 10/2018 | Jakimo et al. |
| 2018/0305688 | A1 | 10/2018 | Zhong |
| 2018/0305704 | A1 | 10/2018 | Zhang |
| 2018/0312822 | A1 | 11/2018 | Lee et al. |
| 2018/0312825 | A1 | 11/2018 | Liu et al. |
| 2018/0312828 | A1 | 11/2018 | Liu et al. |
| 2018/0312835 | A1 | 11/2018 | Yao et al. |
| 2018/0327756 | A1 | 11/2018 | Zhang et al. |
| 2018/0346927 | A1 | 12/2018 | Doudna et al. |
| 2018/0371497 | A1 | 12/2018 | Gill et al. |
| 2019/0010481 | A1 | 1/2019 | Joung et al. |
| 2019/0055543 | A1 | 2/2019 | Tran et al. |
| 2019/0055549 | A1 | 2/2019 | Capurso et al. |
| 2019/0062734 | A1 | 2/2019 | Cotta-Ramusino et al. |
| 2019/0093099 | A1 | 3/2019 | Liu et al. |
| 2019/0185883 | A1 | 6/2019 | Liu et al. |
| 2019/0218547 | A1 | 7/2019 | Lee et al. |
| 2019/0225955 | A1 | 7/2019 | Liu et al. |
| 2019/0233847 | A1 | 8/2019 | Savage et al. |
| 2019/0241633 | A1 | 8/2019 | Fotin-Mleczek et al. |
| 2019/0256842 | A1 | 8/2019 | Liu et al. |
| 2019/0264202 | A1 | 8/2019 | Church et al. |
| 2019/0276816 | A1 | 9/2019 | Liu et al. |
| 2019/0309290 | A1 | 10/2019 | Neuteboom et al. |
| 2019/0322992 | A1 | 10/2019 | Liu et al. |
| 2019/0330619 | A1 | 10/2019 | Smith et al. |
| 2019/0352632 | A1 | 11/2019 | Liu et al. |
| 2019/0367891 | A1 | 12/2019 | Liu et al. |
| 2020/0010818 | A1 | 1/2020 | Liu et al. |
| 2020/0010835 | A1 | 1/2020 | Maianti et al. |
| 2020/0056206 | A1 | 2/2020 | Tremblay et al. |
| 2020/0063127 | A1 | 2/2020 | Lu et al. |
| 2020/0071722 | A1 | 3/2020 | Liu et al. |
| 2020/0109398 | A1 | 4/2020 | Rubens et al. |
| 2020/0157570 | A1 | 5/2020 | Loiler |

(56) References Cited

U.S. PATENT DOCUMENTS

2020/0172931 A1 6/2020 Liu et al.
2020/0181619 A1 6/2020 Tang et al.
2020/0190493 A1 6/2020 Liu et al.
2020/0216833 A1 7/2020 Liu et al.
2020/0255868 A1 8/2020 Liu et al.
2020/0277587 A1 9/2020 Liu et al.
2020/0318116 A1 10/2020 Freier
2020/0323984 A1 10/2020 Liu et al.
2020/0399619 A1 12/2020 Maianti et al.
2020/0399626 A1 12/2020 Liu et al.
2021/0054416 A1 2/2021 Liu et al.
2021/0115428 A1 4/2021 Maianti et al.
2021/0196809 A1 7/2021 Maianti et al.
2021/0198330 A1 7/2021 Liu et al.
2021/0214698 A1 7/2021 Liu et al.
2021/0230577 A1 7/2021 Liu et al.
2021/0254127 A1 8/2021 Liu et al.
2021/0284697 A1 9/2021 Ohlmann et al.
2021/0292753 A1 9/2021 Halperin
2021/0315994 A1 10/2021 Liu et al.
2021/0317440 A1 10/2021 Liu et al.
2021/0380955 A1 12/2021 Bryson et al.
2022/0033785 A1 2/2022 Liu et al.
2022/0098593 A1 3/2022 Gaudelli et al.
2022/0119785 A1 4/2022 Liu et al.
2022/0154224 A1 5/2022 Abudayyeh et al.
2022/0170013 A1 6/2022 Liu et al.
2022/0177877 A1 6/2022 Church et al.
2022/0186216 A1 6/2022 Dokshin et al.
2022/0204975 A1 6/2022 Liu et al.
2022/0213507 A1 7/2022 Liu et al.
2022/0220462 A1 7/2022 Liu et al.
2022/0238182 A1 7/2022 Shen et al.
2022/0249697 A1 8/2022 Liu et al.
2022/0282275 A1 9/2022 Liu et al.
2022/0290115 A1 9/2022 Liu et al.
2022/0307001 A1 9/2022 Liu et al.
2022/0307003 A1 9/2022 Liu et al.
2022/0315906 A1 10/2022 Liu et al.
2022/0356469 A1 11/2022 Liu et al.
2022/0380740 A1 12/2022 Liu et al.
2022/0389395 A1 12/2022 Liu et al.
2023/0002745 A1 1/2023 Liu et al.
2023/0021641 A1 1/2023 Liu et al.
2023/0056852 A1 2/2023 Liu et al.
2023/0058176 A1 2/2023 Liu et al.
2023/0078265 A1 3/2023 Liu et al.
2023/0086199 A1 3/2023 Liu et al.
2023/0090221 A1 3/2023 Liu et al.
2023/0108687 A1 4/2023 Liu et al.
2023/0123669 A1 4/2023 Liu et al.
2023/0127008 A1 4/2023 Liu et al.
2023/0159913 A1 5/2023 Liu et al.
2023/0193295 A1 6/2023 Maianti et al.
2023/0220374 A1 7/2023 Liu et al.
2023/0272425 A1 8/2023 Liu et al.
2023/0279443 A1 9/2023 Liu et al.
2023/0332144 A1 10/2023 Liu et al.
2023/0340465 A1 10/2023 Liu et al.
2023/0340466 A1 10/2023 Liu et al.
2023/0340467 A1 10/2023 Liu et al.
2023/0348883 A1 11/2023 Liu et al.
2023/0357766 A1 11/2023 Liu et al.
2023/0383289 A1 11/2023 Liu et al.
2024/0035017 A1 2/2024 Liu et al.
2024/0076652 A1 3/2024 Liu et al.
2024/0110166 A1 4/2024 Maianti et al.
2024/0124866 A1 4/2024 Liu et al.
2024/0173430 A1 5/2024 Liu et al.
2024/0229077 A1 7/2024 Liu et al.

FOREIGN PATENT DOCUMENTS

AU 2015101792 A4 1/2016
AU 2012354062 B2 9/2017
BR 112015013786 A2 7/2017
CA 2480696 A1 10/2003
CA 2894668 A1 6/2014
CA 2894681 A1 6/2014
CA 2894684 A1 6/2014
CA 2852593 A1 11/2015
CA 3193022 A1 3/2022
CN 1069962 A 3/1993
CN 101460619 A 6/2009
CN 101873862 A 10/2010
CN 102057039 A 5/2011
CN 102892777 A 1/2013
CN 103224947 A 7/2013
CN 103233028 A 8/2013
CN 103388006 A 11/2013
CN 103614415 A 3/2014
CN 103642836 A 3/2014
CN 103668472 A 3/2014
CN 103820441 A 5/2014
CN 103820454 A 5/2014
CN 103911376 A 7/2014
CN 103923911 A 7/2014
CN 103088008 A 8/2014
CN 103981211 A 8/2014
CN 103981212 A 8/2014
CN 104004778 A 8/2014
CN 104004782 A 8/2014
CN 104017821 A 9/2014
CN 104109687 A 10/2014
CN 104178461 A 12/2014
CN 104342457 A 2/2015
CN 104404036 A 3/2015
CN 104450774 A 3/2015
CN 104480144 A 4/2015
CN 104498493 A 4/2015
CN 104504304 A 4/2015
CN 104531704 A 4/2015
CN 104531705 A 4/2015
CN 104560864 A 4/2015
CN 104561095 A 4/2015
CN 104593418 A 5/2015
CN 104593422 A 5/2015
CN 104611370 A 5/2015
CN 104651392 A 5/2015
CN 104651398 A 5/2015
CN 104651399 A 5/2015
CN 104651401 A 5/2015
CN 104673816 A 6/2015
CN 104725626 A 6/2015
CN 104726449 A 6/2015
CN 104726494 A 6/2015
CN 104745626 A 7/2015
CN 104762321 A 7/2015
CN 104805078 A 7/2015
CN 104805099 A 7/2015
CN 104805118 A 7/2015
CN 104846010 A 8/2015
CN 104894068 A 9/2015
CN 104894075 A 9/2015
CN 104928321 A 9/2015
CN 105039339 A 11/2015
CN 105039399 A 11/2015
CN 105063061 A 11/2015
CN 105087620 A 11/2015
CN 105112422 A 12/2015
CN 105112445 A 12/2015
CN 105112519 A 12/2015
CN 105121648 A 12/2015
CN 105132427 A 12/2015
CN 105132451 A 12/2015
CN 105177038 A 12/2015
CN 105177126 A 12/2015
CN 105210981 A 1/2016
CN 105219799 A 1/2016
CN 105238806 A 1/2016
CN 105255937 A 1/2016
CN 105274144 A 1/2016
CN 105296518 A 2/2016
CN 105296537 A 2/2016

(56) References Cited

FOREIGN PATENT DOCUMENTS

| | | | |
|---|---|---|---|
| CN | 105316324 | A | 2/2016 |
| CN | 105316327 | A | 2/2016 |
| CN | 105316337 | A | 2/2016 |
| CN | 105331607 | A | 2/2016 |
| CN | 105331608 | A | 2/2016 |
| CN | 105331609 | A | 2/2016 |
| CN | 105331627 | A | 2/2016 |
| CN | 105400773 | A | 3/2016 |
| CN | 105400779 | A | 3/2016 |
| CN | 105400810 | A | 3/2016 |
| CN | 105441451 | A | 3/2016 |
| CN | 105462968 | A | 4/2016 |
| CN | 105463003 | A | 4/2016 |
| CN | 105463027 | A | 4/2016 |
| CN | 105492608 | A | 4/2016 |
| CN | 105492609 | A | 4/2016 |
| CN | 105505976 | A | 4/2016 |
| CN | 105505979 | A | 4/2016 |
| CN | 105518134 | A | 4/2016 |
| CN | 105518135 | A | 4/2016 |
| CN | 105518137 | A | 4/2016 |
| CN | 105518138 | A | 4/2016 |
| CN | 105518139 | A | 4/2016 |
| CN | 105518140 | A | 4/2016 |
| CN | 105543228 | A | 5/2016 |
| CN | 105543266 | A | 5/2016 |
| CN | 105543270 | A | 5/2016 |
| CN | 105567688 | A | 5/2016 |
| CN | 105567689 | A | 5/2016 |
| CN | 105567734 | A | 5/2016 |
| CN | 105567735 | A | 5/2016 |
| CN | 105567738 | A | 5/2016 |
| CN | 105593367 | A | 5/2016 |
| CN | 105594664 | A | 5/2016 |
| CN | 105602987 | A | 5/2016 |
| CN | 105624146 | A | 6/2016 |
| CN | 105624187 | A | 6/2016 |
| CN | 105646719 | A | 6/2016 |
| CN | 105647922 | A | 6/2016 |
| CN | 105647962 | A | 6/2016 |
| CN | 105647968 | A | 6/2016 |
| CN | 105647969 | A | 6/2016 |
| CN | 105671070 | A | 6/2016 |
| CN | 105671083 | A | 6/2016 |
| CN | 105695485 | A | 6/2016 |
| CN | 105779448 | A | 7/2016 |
| CN | 105779449 | A | 7/2016 |
| CN | 105802980 | A | 7/2016 |
| CN | 105821039 | A | 8/2016 |
| CN | 105821040 | A | 8/2016 |
| CN | 105821049 | A | 8/2016 |
| CN | 105821072 | A | 8/2016 |
| CN | 105821075 | A | 8/2016 |
| CN | 105821116 | A | 8/2016 |
| CN | 105838733 | A | 8/2016 |
| CN | 105861547 | A | 8/2016 |
| CN | 105861552 | A | 8/2016 |
| CN | 105861554 | A | 8/2016 |
| CN | 105886498 | A | 8/2016 |
| CN | 105886534 | A | 8/2016 |
| CN | 105886616 | A | 8/2016 |
| CN | 105907758 | A | 8/2016 |
| CN | 105907785 | A | 8/2016 |
| CN | 105925608 | A | 9/2016 |
| CN | 105934516 | A | 9/2016 |
| CN | 105950560 | A | 9/2016 |
| CN | 105950626 | A | 9/2016 |
| CN | 105950633 | A | 9/2016 |
| CN | 105950639 | A | 9/2016 |
| CN | 105985985 | A | 10/2016 |
| CN | 106011104 | A | 10/2016 |
| CN | 106011150 | A | 10/2016 |
| CN | 106011167 | A | 10/2016 |
| CN | 106011171 | A | 10/2016 |
| CN | 106032540 | A | 10/2016 |
| CN | 106047803 | A | 10/2016 |
| CN | 106047877 | A | 10/2016 |
| CN | 106047930 | A | 10/2016 |
| CN | 106086008 | A | 11/2016 |
| CN | 106086028 | A | 11/2016 |
| CN | 106086061 | A | 11/2016 |
| CN | 106086062 | A | 11/2016 |
| CN | 106103475 | A | 11/2016 |
| CN | 106109417 | A | 11/2016 |
| CN | 106119275 | A | 11/2016 |
| CN | 106119283 | A | 11/2016 |
| CN | 106148286 | A | 11/2016 |
| CN | 106148370 | A | 11/2016 |
| CN | 106148416 | A | 11/2016 |
| CN | 106167525 | A | 11/2016 |
| CN | 106167808 | A | 11/2016 |
| CN | 106167810 | A | 11/2016 |
| CN | 106167821 | A | 11/2016 |
| CN | 106172238 | A | 12/2016 |
| CN | 106190903 | A | 12/2016 |
| CN | 106191057 | A | 12/2016 |
| CN | 106191061 | A | 12/2016 |
| CN | 106191062 | A | 12/2016 |
| CN | 106191064 | A | 12/2016 |
| CN | 106191071 | A | 12/2016 |
| CN | 106191099 | A | 12/2016 |
| CN | 106191107 | A | 12/2016 |
| CN | 106191113 | A | 12/2016 |
| CN | 106191114 | A | 12/2016 |
| CN | 106191116 | A | 12/2016 |
| CN | 106191124 | A | 12/2016 |
| CN | 106222177 | A | 12/2016 |
| CN | 106222193 | A | 12/2016 |
| CN | 106222203 | A | 12/2016 |
| CN | 106232823 | A | 12/2016 |
| CN | 106244555 | A | 12/2016 |
| CN | 106244557 | A | 12/2016 |
| CN | 106244591 | A | 12/2016 |
| CN | 106244609 | A | 12/2016 |
| CN | 106282241 | A | 1/2017 |
| CN | 106318934 | A | 1/2017 |
| CN | 106318973 | A | 1/2017 |
| CN | 106350540 | A | 1/2017 |
| CN | 106367435 | A | 2/2017 |
| CN | 106399306 | A | 2/2017 |
| CN | 106399311 | A | 2/2017 |
| CN | 106399360 | A | 2/2017 |
| CN | 106399367 | A | 2/2017 |
| CN | 106399375 | A | 2/2017 |
| CN | 106399377 | A | 2/2017 |
| CN | 106434651 | A | 2/2017 |
| CN | 106434663 | A | 2/2017 |
| CN | 106434688 | A | 2/2017 |
| CN | 106434737 | A | 2/2017 |
| CN | 106434748 | A | 2/2017 |
| CN | 106434752 | A | 2/2017 |
| CN | 106434782 | A | 2/2017 |
| CN | 106446600 | A | 2/2017 |
| CN | 106479985 | A | 3/2017 |
| CN | 106480027 | A | 3/2017 |
| CN | 106480036 | A | 3/2017 |
| CN | 106480067 | A | 3/2017 |
| CN | 106480080 | A | 3/2017 |
| CN | 106480083 | A | 3/2017 |
| CN | 106480097 | A | 3/2017 |
| CN | 106544351 | A | 3/2017 |
| CN | 106544353 | A | 3/2017 |
| CN | 106544357 | A | 3/2017 |
| CN | 106554969 | A | 4/2017 |
| CN | 106566838 | A | 4/2017 |
| CN | 106701763 | A | 5/2017 |
| CN | 106701808 | A | 5/2017 |
| CN | 106701818 | A | 5/2017 |
| CN | 106701823 | A | 5/2017 |
| CN | 106701830 | A | 5/2017 |
| CN | 106754912 | A | 5/2017 |
| CN | 106755026 | A | 5/2017 |
| CN | 106755077 | A | 5/2017 |
| CN | 106755088 | A | 5/2017 |

(56) References Cited

FOREIGN PATENT DOCUMENTS

| | | | |
|---|---|---|---|
| CN | 106755091 | A | 5/2017 |
| CN | 106755097 | A | 5/2017 |
| CN | 106755424 | A | 5/2017 |
| CN | 106801056 | A | 6/2017 |
| CN | 106834323 | A | 6/2017 |
| CN | 106834341 | A | 6/2017 |
| CN | 106834347 | A | 6/2017 |
| CN | 106845151 | A | 6/2017 |
| CN | 106868008 | A | 6/2017 |
| CN | 106868031 | A | 6/2017 |
| CN | 106906240 | A | 6/2017 |
| CN | 106906242 | A | 6/2017 |
| CN | 106916820 | A | 7/2017 |
| CN | 106916852 | A | 7/2017 |
| CN | 106939303 | A | 7/2017 |
| CN | 106947750 | A | 7/2017 |
| CN | 106947780 | A | 7/2017 |
| CN | 106957830 | A | 7/2017 |
| CN | 106957831 | A | 7/2017 |
| CN | 106957844 | A | 7/2017 |
| CN | 106957855 | A | 7/2017 |
| CN | 106957858 | A | 7/2017 |
| CN | 106967697 | A | 7/2017 |
| CN | 106967726 | A | 7/2017 |
| CN | 106978428 | A | 7/2017 |
| CN | 106987570 | A | 7/2017 |
| CN | 106987757 | A | 7/2017 |
| CN | 107012164 | A | 8/2017 |
| CN | 107012174 | A | 8/2017 |
| CN | 107012213 | A | 8/2017 |
| CN | 107012250 | A | 8/2017 |
| CN | 107022562 | A | 8/2017 |
| CN | 107034188 | A | 8/2017 |
| CN | 107034218 | A | 8/2017 |
| CN | 107034229 | A | 8/2017 |
| CN | 107043775 | A | 8/2017 |
| CN | 107043779 | A | 8/2017 |
| CN | 107043787 | A | 8/2017 |
| CN | 107058320 | A | 8/2017 |
| CN | 107058328 | A | 8/2017 |
| CN | 107058358 | A | 8/2017 |
| CN | 107058372 | A | 8/2017 |
| CN | 107083392 | A | 8/2017 |
| CN | 107099533 | A | 8/2017 |
| CN | 107099850 | A | 8/2017 |
| CN | 107119053 | A | 9/2017 |
| CN | 107119071 | A | 9/2017 |
| CN | 107129999 | A | 9/2017 |
| CN | 107130000 | A | 9/2017 |
| CN | 107142272 | A | 9/2017 |
| CN | 107142282 | A | 9/2017 |
| CN | 107177591 | A | 9/2017 |
| CN | 107177595 | A | 9/2017 |
| CN | 107177625 | A | 9/2017 |
| CN | 107177631 | A | 9/2017 |
| CN | 107190006 | A | 9/2017 |
| CN | 107190008 | A | 9/2017 |
| CN | 107217042 | A | 9/2017 |
| CN | 107217075 | A | 9/2017 |
| CN | 107227307 | A | 10/2017 |
| CN | 107227352 | A | 10/2017 |
| CN | 107236737 | A | 10/2017 |
| CN | 107236739 | A | 10/2017 |
| CN | 107236741 | A | 10/2017 |
| CN | 107245502 | A | 10/2017 |
| CN | 107254485 | A | 10/2017 |
| CN | 107266541 | A | 10/2017 |
| CN | 107267515 | A | 10/2017 |
| CN | 107287245 | A | 10/2017 |
| CN | 107298701 | A | 10/2017 |
| CN | 107299114 | A | 10/2017 |
| CN | 107304435 | A | 10/2017 |
| CN | 107312785 | A | 11/2017 |
| CN | 107312793 | A | 11/2017 |
| CN | 107312795 | A | 11/2017 |
| CN | 107312798 | A | 11/2017 |
| CN | 107326042 | A | 11/2017 |
| CN | 107326046 | A | 11/2017 |
| CN | 107354156 | A | 11/2017 |
| CN | 107354173 | A | 11/2017 |
| CN | 107356793 | A | 11/2017 |
| CN | 107362372 | A | 11/2017 |
| CN | 107365786 | A | 11/2017 |
| CN | 107365804 | A | 11/2017 |
| CN | 107384894 | A | 11/2017 |
| CN | 107384922 | A | 11/2017 |
| CN | 107384926 | A | 11/2017 |
| CN | 107400677 | A | 11/2017 |
| CN | 107418974 | A | 12/2017 |
| CN | 107435051 | A | 12/2017 |
| CN | 107435069 | A | 12/2017 |
| CN | 107446922 | A | 12/2017 |
| CN | 107446923 | A | 12/2017 |
| CN | 107446924 | A | 12/2017 |
| CN | 107446932 | A | 12/2017 |
| CN | 107446951 | A | 12/2017 |
| CN | 107446954 | A | 12/2017 |
| CN | 107460196 | A | 12/2017 |
| CN | 107474129 | A | 12/2017 |
| CN | 107475300 | A | 12/2017 |
| CN | 107488649 | A | 12/2017 |
| CN | 107502608 | A | 12/2017 |
| CN | 107502618 | A | 12/2017 |
| CN | 107513531 | A | 12/2017 |
| CN | 107519492 | A | 12/2017 |
| CN | 107523567 | A | 12/2017 |
| CN | 107523583 | A | 12/2017 |
| CN | 107541525 | A | 1/2018 |
| CN | 107557373 | A | 1/2018 |
| CN | 107557378 | A | 1/2018 |
| CN | 107557381 | A | 1/2018 |
| CN | 107557390 | A | 1/2018 |
| CN | 107557393 | A | 1/2018 |
| CN | 107557394 | A | 1/2018 |
| CN | 107557455 | A | 1/2018 |
| CN | 107574179 | A | 1/2018 |
| CN | 107586777 | A | 1/2018 |
| CN | 107586779 | A | 1/2018 |
| CN | 107604003 | A | 1/2018 |
| CN | 107619829 | A | 1/2018 |
| CN | 107619837 | A | 1/2018 |
| CN | 107630006 | A | 1/2018 |
| CN | 107630041 | A | 1/2018 |
| CN | 107630042 | A | 1/2018 |
| CN | 107630043 | A | 1/2018 |
| CN | 107641631 | A | 1/2018 |
| CN | 107653256 | A | 2/2018 |
| CN | 107686848 | A | 2/2018 |
| CN | 206970581 | A | 2/2018 |
| CN | 107760652 | A | 3/2018 |
| CN | 107760663 | A | 3/2018 |
| CN | 107760684 | A | 3/2018 |
| CN | 107760715 | A | 3/2018 |
| CN | 107784200 | A | 3/2018 |
| CN | 107794272 | A | 3/2018 |
| CN | 107794276 | A | 3/2018 |
| CN | 107815463 | A | 3/2018 |
| CN | 107828738 | A | 3/2018 |
| CN | 107828794 | A | 3/2018 |
| CN | 107828826 | A | 3/2018 |
| CN | 107828874 | A | 3/2018 |
| CN | 107858346 | A | 3/2018 |
| CN | 107858373 | A | 3/2018 |
| CN | 107880132 | A | 4/2018 |
| CN | 107881184 | A | 4/2018 |
| CN | 107893074 | A | 4/2018 |
| CN | 107893075 | A | 4/2018 |
| CN | 107893076 | A | 4/2018 |
| CN | 107893080 | A | 4/2018 |
| CN | 107893086 | A | 4/2018 |
| CN | 107904261 | A | 4/2018 |
| CN | 107937427 | A | 4/2018 |
| CN | 107937432 | A | 4/2018 |
| CN | 107937501 | A | 4/2018 |

(56) References Cited

FOREIGN PATENT DOCUMENTS

| | | | |
|---|---|---|---|
| CN | 107974466 | A | 5/2018 |
| CN | 107988229 | A | 5/2018 |
| CN | 107988246 | A | 5/2018 |
| CN | 107988256 | A | 5/2018 |
| CN | 107988268 | A | 5/2018 |
| CN | 108018316 | A | 5/2018 |
| CN | 108034656 | A | 5/2018 |
| CN | 108048466 | A | 5/2018 |
| CN | 108102940 | A | 6/2018 |
| CN | 108103090 | A | 6/2018 |
| CN | 108103092 | A | 6/2018 |
| CN | 108103098 | A | 6/2018 |
| CN | 108103586 | A | 6/2018 |
| CN | 108148835 | A | 6/2018 |
| CN | 108148837 | A | 6/2018 |
| CN | 108148873 | A | 6/2018 |
| CN | 108192956 | A | 6/2018 |
| CN | 108243575 | A | 7/2018 |
| CN | 108251423 | A | 7/2018 |
| CN | 108251451 | A | 7/2018 |
| CN | 108251452 | A | 7/2018 |
| CN | 108342480 | A | 7/2018 |
| CN | 108359691 | A | 8/2018 |
| CN | 108359712 | A | 8/2018 |
| CN | 108384784 | A | 8/2018 |
| CN | 108396027 | A | 8/2018 |
| CN | 108410877 | A | 8/2018 |
| CN | 108410906 | A | 8/2018 |
| CN | 108410907 | A | 8/2018 |
| CN | 108410911 | A | 8/2018 |
| CN | 108424931 | A | 8/2018 |
| CN | 108441519 | A | 8/2018 |
| CN | 108441520 | A | 8/2018 |
| CN | 108472314 | A | 8/2018 |
| CN | 108486108 | A | 9/2018 |
| CN | 108486111 | A | 9/2018 |
| CN | 108486145 | A | 9/2018 |
| CN | 108486146 | A | 9/2018 |
| CN | 108486154 | A | 9/2018 |
| CN | 108486159 | A | 9/2018 |
| CN | 108486234 | A | 9/2018 |
| CN | 108504657 | A | 9/2018 |
| CN | 108504685 | A | 9/2018 |
| CN | 108504693 | A | 9/2018 |
| CN | 108513575 | A | 9/2018 |
| CN | 108546712 | A | 9/2018 |
| CN | 108546717 | A | 9/2018 |
| CN | 108546718 | A | 9/2018 |
| CN | 108559730 | A | 9/2018 |
| CN | 108559732 | A | 9/2018 |
| CN | 108559745 | A | 9/2018 |
| CN | 108559760 | A | 9/2018 |
| CN | 108570479 | A | 9/2018 |
| CN | 108588071 | A | 9/2018 |
| CN | 108588123 | A | 9/2018 |
| CN | 108588128 | A | 9/2018 |
| CN | 108588182 | A | 9/2018 |
| CN | 108610399 | A | 10/2018 |
| CN | 108611364 | A | 10/2018 |
| CN | 108624622 | A | 10/2018 |
| CN | 108642053 | A | 10/2018 |
| CN | 108642055 | A | 10/2018 |
| CN | 108642077 | A | 10/2018 |
| CN | 108642078 | A | 10/2018 |
| CN | 108642090 | A | 10/2018 |
| CN | 108690844 | A | 10/2018 |
| CN | 108699542 | A | 10/2018 |
| CN | 108707604 | A | 10/2018 |
| CN | 108707620 | A | 10/2018 |
| CN | 108707621 | A | 10/2018 |
| CN | 108707628 | A | 10/2018 |
| CN | 108707629 | A | 10/2018 |
| CN | 108715850 | A | 10/2018 |
| CN | 108728476 | A | 11/2018 |
| CN | 108728486 | A | 11/2018 |
| CN | 108753772 | A | 11/2018 |
| CN | 108753783 | A | 11/2018 |
| CN | 108753813 | A | 11/2018 |
| CN | 108753817 | A | 11/2018 |
| CN | 108753832 | A | 11/2018 |
| CN | 108753835 | A | 11/2018 |
| CN | 108753836 | A | 11/2018 |
| CN | 108795902 | A | 11/2018 |
| CN | 108822217 | A | 11/2018 |
| CN | 108823248 | A | 11/2018 |
| CN | 108823249 | A | 11/2018 |
| CN | 108823291 | A | 11/2018 |
| CN | 108841845 | A | 11/2018 |
| CN | 108853133 | A | 11/2018 |
| CN | 108866093 | A | 11/2018 |
| CN | 108893529 | A | 11/2018 |
| CN | 108913664 | A | 11/2018 |
| CN | 108913691 | A | 11/2018 |
| CN | 108913714 | A | 11/2018 |
| CN | 108913717 | A | 11/2018 |
| CN | 109517841 | A | 3/2019 |
| EP | 0264166 | A1 | 4/1988 |
| EP | 0321201 | B2 | 6/1989 |
| EP | 0519463 | A1 | 12/1992 |
| EP | 1085892 | A2 | 3/2001 |
| EP | 1092770 | A2 | 4/2001 |
| EP | 2604255 | A1 | 6/2013 |
| EP | 2840140 | A1 | 2/2015 |
| EP | 2877490 | A2 | 6/2015 |
| EP | 2966170 | A1 | 1/2016 |
| EP | 3009511 | A2 | 4/2016 |
| EP | 3031921 | A1 | 6/2016 |
| EP | 3045537 | A1 | 7/2016 |
| EP | 3115457 | A1 | 1/2017 |
| EP | 3144390 | A1 | 3/2017 |
| EP | 3199632 | A1 | 8/2017 |
| EP | 3216867 | A1 | 9/2017 |
| EP | 3252160 | A1 | 12/2017 |
| EP | 2498823 | B1 | 8/2018 |
| EP | 3365437 | A1 | 8/2018 |
| EP | 3450553 | B1 | 12/2019 |
| EP | 3177726 | B1 | 1/2021 |
| EP | 3856898 | A1 | 8/2021 |
| ES | 2740248 | T3 | 2/2020 |
| GB | 2528177 | A | 1/2016 |
| GB | 2531454 | A1 | 4/2016 |
| GB | 2542653 | A | 3/2017 |
| HK | 1208045 | A1 | 2/2016 |
| JP | 2007-501626 | A | 2/2007 |
| JP | 2008-515405 | A | 5/2008 |
| JP | 2010-033344 | A | 2/2010 |
| JP | 2010-535744 | A | 11/2010 |
| JP | 2010-539929 | A | 12/2010 |
| JP | 2011-081011 | A | 4/2011 |
| JP | 2011-523353 | A | 8/2011 |
| JP | 2012-525146 | A | 10/2012 |
| JP | 2012-210172 | A | 11/2012 |
| JP | 2012-531909 | A | 12/2012 |
| JP | 2015-523856 | A | 8/2015 |
| JP | 2015-532654 | A | 11/2015 |
| JP | 2016-525888 | A | 9/2016 |
| JP | 2016-534132 | A | 11/2016 |
| JP | 2017-500035 | A | 1/2017 |
| JP | 2018-521045 | A | 8/2018 |
| JP | 2019-506123 | A | 2/2019 |
| JP | 6629734 | B2 | 1/2020 |
| JP | 6633524 | B2 | 1/2020 |
| KR | 101584933 | B1 | 1/2016 |
| KR | 2016-0050069 | A | 5/2016 |
| KR | 20160133380 | A | 11/2016 |
| KR | 20170037025 | A | 4/2017 |
| KR | 20170037028 | A | 4/2017 |
| KR | 101748575 | B1 | 6/2017 |
| KR | 20170128137 | A | 11/2017 |
| KR | 2018-0022465 | A | 3/2018 |
| RU | 2016104674 | A | 8/2017 |
| RU | 2634395 | C1 | 10/2017 |
| RU | 2652899 | C1 | 5/2018 |
| RU | 2015128057 | A | 3/2019 |

(56) References Cited

FOREIGN PATENT DOCUMENTS

| | | | |
|---|---|---|---|
| RU | 2015128098 | A | 3/2019 |
| RU | 2687451 | C1 | 5/2019 |
| RU | 2019112514 | A | 6/2019 |
| RU | 2019127300 | A | 9/2019 |
| RU | 2701850 | C2 | 10/2019 |
| SG | 10201707569 | Y | 10/2017 |
| SG | 10201710486 | A | 1/2018 |
| SG | 10201710487 | A | 1/2018 |
| SG | 10201710488 | T | 1/2018 |
| TW | I608100 | B | 12/2017 |
| TW | 201809272 | A | 3/2018 |
| TW | 2018-29773 | A | 8/2018 |
| WO | WO 1990/002809 | | 3/1990 |
| WO | WO 1991/003162 | A1 | 3/1991 |
| WO | WO 1991/016024 | A1 | 10/1991 |
| WO | WO 1991/017271 | A1 | 11/1991 |
| WO | WO 1991/017424 | A1 | 11/1991 |
| WO | WO 1992/006188 | A2 | 4/1992 |
| WO | WO 1992/006200 | A1 | 4/1992 |
| WO | WO 1992/007065 | A1 | 4/1992 |
| WO | WO 1993/015187 | A1 | 8/1993 |
| WO | WO 1993/024641 | A2 | 12/1993 |
| WO | WO 1994/018316 | A2 | 8/1994 |
| WO | WO 1994/026877 | A1 | 11/1994 |
| WO | WO 1996/004403 | A1 | 2/1996 |
| WO | WO 1996/010640 | A1 | 4/1996 |
| WO | WO 1998/032845 | A1 | 7/1998 |
| WO | WO 2001/036452 | A2 | 5/2001 |
| WO | WO 2001/038547 | A2 | 5/2001 |
| WO | WO 2002/059296 | A2 | 8/2002 |
| WO | WO 2002/068676 | A2 | 9/2002 |
| WO | WO 2002/103028 | A2 | 12/2002 |
| WO | WO 2004/007684 | A2 | 1/2004 |
| WO | WO 2005/014791 | A2 | 2/2005 |
| WO | WO 2005/019415 | A2 | 3/2005 |
| WO | WO 2006/002547 | A1 | 1/2006 |
| WO | WO 2006/042112 | A2 | 4/2006 |
| WO | WO 2007/025097 | A2 | 3/2007 |
| WO | 2007/037444 | A1 | 4/2007 |
| WO | WO 2007/066923 | A1 | 6/2007 |
| WO | WO 2007/136815 | A2 | 11/2007 |
| WO | WO 2007/143574 | A1 | 12/2007 |
| WO | WO 2008/005529 | A2 | 1/2008 |
| WO | WO 2008/108989 | A2 | 9/2008 |
| WO | WO 2009/002418 | A2 | 12/2008 |
| WO | WO 2009/019317 | A1 | 2/2009 |
| WO | WO 2009/098290 | A1 | 8/2009 |
| WO | WO 2009/134808 | A2 | 11/2009 |
| WO | WO 2010/011961 | A2 | 1/2010 |
| WO | WO 2010/012902 | A1 | 2/2010 |
| WO | WO 2010/028347 | A2 | 3/2010 |
| WO | WO 2010/054108 | A2 | 5/2010 |
| WO | WO 2010/054154 | A2 | 5/2010 |
| WO | WO 2010/068289 | A2 | 6/2010 |
| WO | WO 2010/075424 | A2 | 7/2010 |
| WO | WO 2010/091122 | A1 | 8/2010 |
| WO | WO 2010/102257 | A2 | 9/2010 |
| WO | WO 2010/104749 | A2 | 9/2010 |
| WO | WO 2010/129019 | A2 | 11/2010 |
| WO | WO 2010/129023 | A2 | 11/2010 |
| WO | WO 2010/132092 | A2 | 11/2010 |
| WO | WO 2010/144150 | A2 | 12/2010 |
| WO | WO 2011/002503 | A1 | 1/2011 |
| WO | WO 2011/017293 | A2 | 2/2011 |
| WO | WO 2011/053868 | A1 | 5/2011 |
| WO | WO 2011/053982 | A2 | 5/2011 |
| WO | WO 2011/068810 | A1 | 6/2011 |
| WO | WO 2011/075627 | A1 | 6/2011 |
| WO | WO 2011/091311 | A2 | 7/2011 |
| WO | WO 2011/091396 | A1 | 7/2011 |
| WO | WO 2011/109031 | A1 | 9/2011 |
| WO | WO 2011/143124 | A2 | 11/2011 |
| WO | WO 2011/147590 | A2 | 12/2011 |
| WO | WO 2011/159369 | A1 | 12/2011 |
| WO | WO 2012/054726 | A1 | 4/2012 |
| WO | WO 2012/061815 | A2 | 5/2012 |
| WO | WO 2012/065043 | A2 | 5/2012 |
| WO | WO 2012/088381 | A2 | 6/2012 |
| WO | WO 2012/125445 | A2 | 9/2012 |
| WO | WO 2012/138927 | A2 | 10/2012 |
| WO | WO 2012/149470 | A1 | 11/2012 |
| WO | WO 2012/158985 | A2 | 11/2012 |
| WO | WO 2012/158986 | A2 | 11/2012 |
| WO | WO 2012/164565 | A1 | 12/2012 |
| WO | WO 2012/170930 | A1 | 12/2012 |
| WO | WO 2013/012674 | A1 | 1/2013 |
| WO | WO 2013/013105 | A1 | 1/2013 |
| WO | WO 2013/039857 | A1 | 3/2013 |
| WO | WO 2013/039861 | A2 | 3/2013 |
| WO | WO 2013/040093 | A2 | 3/2013 |
| WO | WO 2013/045632 | A1 | 4/2013 |
| WO | WO 2013/047844 | A1 | 4/2013 |
| WO | WO 2013/066438 | A2 | 5/2013 |
| WO | WO 2013/086441 | A2 | 6/2013 |
| WO | WO 2013/086444 | A2 | 6/2013 |
| WO | WO 2013/098244 | A1 | 7/2013 |
| WO | WO 2013/119602 | A1 | 8/2013 |
| WO | WO 2013/120022 | A2 | 8/2013 |
| WO | WO 2013/122617 | A1 | 8/2013 |
| WO | WO 2013/126794 | A1 | 8/2013 |
| WO | WO 2013/130683 | A2 | 9/2013 |
| WO | WO 2013/130824 | A1 | 9/2013 |
| WO | WO 2013/141680 | A1 | 9/2013 |
| WO | WO 2013/142578 | A1 | 9/2013 |
| WO | WO 2013/152359 | A1 | 10/2013 |
| WO | WO 2013/160230 | A1 | 10/2013 |
| WO | WO 2013/166315 | A1 | 11/2013 |
| WO | WO 2013/169398 | A2 | 11/2013 |
| WO | WO 2013/169802 | A1 | 11/2013 |
| WO | WO 2013/176772 | A1 | 11/2013 |
| WO | WO 2013/176915 | A1 | 11/2013 |
| WO | WO 2013/176916 | A1 | 11/2013 |
| WO | WO 2013/181440 | A1 | 12/2013 |
| WO | WO 2013/186754 | A2 | 12/2013 |
| WO | WO 2013/188037 | A2 | 12/2013 |
| WO | WO 2013/188522 | A2 | 12/2013 |
| WO | WO 2013/188638 | A2 | 12/2013 |
| WO | WO 2013/192278 | A1 | 12/2013 |
| WO | WO 2013/142378 | A9 | 1/2014 |
| WO | WO 2014/004336 | A2 | 1/2014 |
| WO | WO 2014/005042 | A2 | 1/2014 |
| WO | WO 2014/011237 | A1 | 1/2014 |
| WO | WO 2014/011901 | A2 | 1/2014 |
| WO | WO 2014/018423 | A2 | 1/2014 |
| WO | WO 2014/020608 | A1 | 2/2014 |
| WO | WO 2014/022120 | A1 | 2/2014 |
| WO | WO 2014/022702 | A2 | 2/2014 |
| WO | WO 2014/036219 | A2 | 3/2014 |
| WO | WO 2014/039513 | A2 | 3/2014 |
| WO | WO 2014/039523 | A1 | 3/2014 |
| WO | WO 2014/039585 | A2 | 3/2014 |
| WO | WO 2014/039684 | A1 | 3/2014 |
| WO | WO 2014/039692 | A2 | 3/2014 |
| WO | WO 2014/039702 | A2 | 3/2014 |
| WO | WO 2014/039872 | A1 | 3/2014 |
| WO | WO 2014/039970 | A1 | 3/2014 |
| WO | WO 2014/041327 | A1 | 3/2014 |
| WO | WO 2014/043143 | A1 | 3/2014 |
| WO | WO 2014/047103 | A2 | 3/2014 |
| WO | WO 2014/055782 | A1 | 4/2014 |
| WO | WO 2014/059173 | A2 | 4/2014 |
| WO | WO 2014/059255 | A1 | 4/2014 |
| WO | WO 2014/065596 | A1 | 5/2014 |
| WO | WO 2014/066505 | A1 | 5/2014 |
| WO | WO 2014/068346 | A2 | 5/2014 |
| WO | WO 2014/070887 | A1 | 5/2014 |
| WO | WO 2014/071006 | A1 | 5/2014 |
| WO | WO 2014/071219 | A1 | 5/2014 |
| WO | WO 2014/071235 | A1 | 5/2014 |
| WO | WO 2014/072941 | A1 | 5/2014 |
| WO | WO 2014/081729 | A1 | 5/2014 |
| WO | WO 2014/081730 | A1 | 5/2014 |
| WO | WO 2014/081855 | A1 | 5/2014 |
| WO | WO 2014/082644 | A1 | 6/2014 |

(56) References Cited

FOREIGN PATENT DOCUMENTS

| | | | |
|---|---|---|---|
| WO | WO 2014/085261 | A1 | 6/2014 |
| WO | WO 2014/085593 | A1 | 6/2014 |
| WO | WO 2014/085830 | A2 | 6/2014 |
| WO | WO 2014/089212 | A1 | 6/2014 |
| WO | WO 2014/089290 | A1 | 6/2014 |
| WO | WO 2014/089348 | A1 | 6/2014 |
| WO | WO 2014/089513 | A1 | 6/2014 |
| WO | WO 2014/089533 | A2 | 6/2014 |
| WO | WO 2014/089541 | A2 | 6/2014 |
| WO | WO 2014/093479 | A1 | 6/2014 |
| WO | WO 2014/093595 | A1 | 6/2014 |
| WO | WO 2014/093622 | A2 | 6/2014 |
| WO | WO 2014/093635 | A1 | 6/2014 |
| WO | WO 2014/093655 | A2 | 6/2014 |
| WO | WO 2014/093661 | A2 | 6/2014 |
| WO | WO 2014/093694 | A1 | 6/2014 |
| WO | WO 2014/093701 | A1 | 6/2014 |
| WO | WO 2014/093709 | A1 | 6/2014 |
| WO | WO 2014/093712 | A1 | 6/2014 |
| WO | WO 2014/093718 | A1 | 6/2014 |
| WO | WO 2014/093736 | A1 | 6/2014 |
| WO | WO 2014/093768 | A1 | 6/2014 |
| WO | WO 2014/093852 | A1 | 6/2014 |
| WO | WO 2014/096972 | A2 | 6/2014 |
| WO | WO 2014/099744 | A1 | 6/2014 |
| WO | WO 2014/099750 | A2 | 6/2014 |
| WO | WO 2014/104878 | A1 | 7/2014 |
| WO | WO 2014/110006 | A1 | 7/2014 |
| WO | WO 2014/110552 | A1 | 7/2014 |
| WO | WO 2014/113493 | A1 | 7/2014 |
| WO | WO 2014/123967 | A2 | 8/2014 |
| WO | WO 2014/124226 | A1 | 8/2014 |
| WO | WO 2014/125668 | A1 | 8/2014 |
| WO | WO 2014/127287 | A1 | 8/2014 |
| WO | WO 2014/128324 | A1 | 8/2014 |
| WO | WO 2014/128659 | A1 | 8/2014 |
| WO | WO 2014/130706 | A1 | 8/2014 |
| WO | WO 2014/130955 | A1 | 8/2014 |
| WO | WO 2014/131833 | A1 | 9/2014 |
| WO | WO 2014/138379 | A1 | 9/2014 |
| WO | WO 2014/143381 | A1 | 9/2014 |
| WO | WO 2014/144094 | A1 | 9/2014 |
| WO | WO 2014/144155 | A1 | 9/2014 |
| WO | WO 2014/144288 | A1 | 9/2014 |
| WO | WO 2014/144592 | A2 | 9/2014 |
| WO | WO 2014/144761 | A2 | 9/2014 |
| WO | WO 2014/144951 | A1 | 9/2014 |
| WO | WO 2014/145599 | A2 | 9/2014 |
| WO | WO 2014/145736 | A2 | 9/2014 |
| WO | WO 2014/150624 | A1 | 9/2014 |
| WO | WO 2014/152432 | A2 | 9/2014 |
| WO | WO 2014/152940 | A1 | 9/2014 |
| WO | WO 2014/153118 | A1 | 9/2014 |
| WO | WO 2014/153470 | A2 | 9/2014 |
| WO | WO 2014/158593 | A1 | 10/2014 |
| WO | WO 2014/161821 | A1 | 10/2014 |
| WO | WO 2014/164466 | A1 | 10/2014 |
| WO | WO 2014/165177 | A1 | 10/2014 |
| WO | WO 2014/165349 | A1 | 10/2014 |
| WO | WO 2014/165612 | A2 | 10/2014 |
| WO | WO 2014/165707 | A2 | 10/2014 |
| WO | WO 2014/165825 | A2 | 10/2014 |
| WO | WO 2014/172458 | A1 | 10/2014 |
| WO | WO 2014/172470 | A2 | 10/2014 |
| WO | WO 2014/172489 | A2 | 10/2014 |
| WO | WO 2014/173955 | A1 | 10/2014 |
| WO | WO 2014/182700 | A1 | 11/2014 |
| WO | WO 2014/183071 | A2 | 11/2014 |
| WO | WO 2014/184143 | A1 | 11/2014 |
| WO | WO 2014/184741 | A1 | 11/2014 |
| WO | WO 2014/184744 | A1 | 11/2014 |
| WO | WO 2014/186585 | A2 | 11/2014 |
| WO | WO 2014/186686 | A2 | 11/2014 |
| WO | WO 2014/190181 | A1 | 11/2014 |
| WO | WO 2014/191128 | A1 | 12/2014 |
| WO | WO 2014/191518 | A1 | 12/2014 |
| WO | WO 2014/191521 | A2 | 12/2014 |
| WO | WO 2014/191525 | A1 | 12/2014 |
| WO | WO 2014/191527 | A1 | 12/2014 |
| WO | WO 2014/193583 | A2 | 12/2014 |
| WO | WO 2014/194190 | A1 | 12/2014 |
| WO | WO 2014/197568 | A2 | 12/2014 |
| WO | WO 2014/197748 | A2 | 12/2014 |
| WO | WO 2014/199358 | A1 | 12/2014 |
| WO | WO 2014/200659 | A1 | 12/2014 |
| WO | WO 2014/201015 | A2 | 12/2014 |
| WO | WO 2014/204578 | A1 | 12/2014 |
| WO | WO 2014/204723 | A1 | 12/2014 |
| WO | WO 2014/204724 | A1 | 12/2014 |
| WO | WO 2014/204725 | A1 | 12/2014 |
| WO | WO 2014/204726 | A1 | 12/2014 |
| WO | WO 2014/204727 | A1 | 12/2014 |
| WO | WO 2014/204728 | A1 | 12/2014 |
| WO | WO 2014/204729 | A1 | 12/2014 |
| WO | WO 2014/205192 | A2 | 12/2014 |
| WO | WO 2014/207043 | A1 | 12/2014 |
| WO | WO 2015/002780 | A1 | 1/2015 |
| WO | WO 2015/004241 | A2 | 1/2015 |
| WO | WO 2015/006290 | A1 | 1/2015 |
| WO | WO 2015/006294 | A2 | 1/2015 |
| WO | WO 2015/006437 | A1 | 1/2015 |
| WO | WO 2015/006498 | A2 | 1/2015 |
| WO | WO 2015/006747 | A2 | 1/2015 |
| WO | WO 2015/007194 | A1 | 1/2015 |
| WO | WO 2015/010114 | A1 | 1/2015 |
| WO | WO 2015/011483 | A1 | 1/2015 |
| WO | WO 2015/013583 | A2 | 1/2015 |
| WO | WO 2015/017866 | A1 | 2/2015 |
| WO | WO 2015/018503 | A1 | 2/2015 |
| WO | WO 2015/021353 | A1 | 2/2015 |
| WO | WO 2015/021426 | A1 | 2/2015 |
| WO | WO 2015/021990 | A1 | 2/2015 |
| WO | WO 2015/024017 | A2 | 2/2015 |
| WO | WO 2015/024986 | A1 | 2/2015 |
| WO | WO 2015/026883 | A1 | 2/2015 |
| WO | WO 2015/026885 | A1 | 2/2015 |
| WO | WO 2015/026886 | A1 | 2/2015 |
| WO | WO 2015/026887 | A1 | 2/2015 |
| WO | WO 2015/027134 | A1 | 2/2015 |
| WO | WO 2015/028969 | A2 | 3/2015 |
| WO | WO 2015/030881 | A1 | 3/2015 |
| WO | WO 2015/031619 | A1 | 3/2015 |
| WO | WO 2015/031775 | A1 | 3/2015 |
| WO | WO 2015/032494 | A2 | 3/2015 |
| WO | WO 2015/033293 | A1 | 3/2015 |
| WO | WO 2015/034872 | A2 | 3/2015 |
| WO | WO 2015/034885 | A1 | 3/2015 |
| WO | WO 2015/035136 | A2 | 3/2015 |
| WO | WO 2015/035139 | A2 | 3/2015 |
| WO | WO 2015/035162 | A2 | 3/2015 |
| WO | WO 2015/040075 | A1 | 3/2015 |
| WO | WO 2015/040402 | A1 | 3/2015 |
| WO | WO 2015/042393 | A2 | 3/2015 |
| WO | WO 2015/042585 | A1 | 3/2015 |
| WO | WO 2015/048577 | A2 | 4/2015 |
| WO | WO 2015/048690 | A1 | 4/2015 |
| WO | WO 2015/048707 | A2 | 4/2015 |
| WO | WO 2015/048801 | A2 | 4/2015 |
| WO | WO 2015/049897 | A1 | 4/2015 |
| WO | WO 2015/051191 | A1 | 4/2015 |
| WO | WO 2015/052133 | A1 | 4/2015 |
| WO | WO 2015/052231 | A2 | 4/2015 |
| WO | WO 2015/052335 | A1 | 4/2015 |
| WO | WO 2015/053995 | A1 | 4/2015 |
| WO | WO 2015/054253 | A1 | 4/2015 |
| WO | WO 2015/054315 | A1 | 4/2015 |
| WO | WO 2015/057671 | A1 | 4/2015 |
| WO | WO 2015/057834 | A1 | 4/2015 |
| WO | WO 2015/057852 | A1 | 4/2015 |
| WO | WO 2015/057976 | A1 | 4/2015 |
| WO | WO 2015/057980 | A1 | 4/2015 |
| WO | WO 2015/059265 | A1 | 4/2015 |
| WO | WO 2015/065964 | A1 | 5/2015 |
| WO | WO 2015/066119 | A1 | 5/2015 |

(56) References Cited

FOREIGN PATENT DOCUMENTS

| | | | |
|---|---|---|---|
| WO | WO 2015/066634 | A2 | 5/2015 |
| WO | WO 2015/066636 | A2 | 5/2015 |
| WO | WO 2015/066637 | A1 | 5/2015 |
| WO | WO 2015/066638 | A2 | 5/2015 |
| WO | WO 2015/066643 | A1 | 5/2015 |
| WO | WO 2015/069682 | A2 | 5/2015 |
| WO | WO 2015/070083 | A1 | 5/2015 |
| WO | WO 2015/070193 | A1 | 5/2015 |
| WO | WO 2015/070212 | A1 | 5/2015 |
| WO | WO 2015/071474 | A2 | 5/2015 |
| WO | WO 2015/073683 | A2 | 5/2015 |
| WO | WO 2015/073867 | A1 | 5/2015 |
| WO | WO 2015/073990 | A1 | 5/2015 |
| WO | WO 2015/075056 | A1 | 5/2015 |
| WO | WO 2015/075154 | A2 | 5/2015 |
| WO | WO 2015/075175 | A1 | 5/2015 |
| WO | WO 2015/075195 | A1 | 5/2015 |
| WO | WO 2015/075557 | A2 | 5/2015 |
| WO | WO 2015/077058 | A2 | 5/2015 |
| WO | WO 2015/077290 | A2 | 5/2015 |
| WO | WO 2015/077318 | A1 | 5/2015 |
| WO | WO 2015/079056 | A1 | 6/2015 |
| WO | WO 2015/079057 | A2 | 6/2015 |
| WO | WO 2015/086795 | A1 | 6/2015 |
| WO | WO 2015/086798 | A2 | 6/2015 |
| WO | WO 2015/088643 | A1 | 6/2015 |
| WO | WO 2015/089046 | A1 | 6/2015 |
| WO | WO 2015/089077 | A2 | 6/2015 |
| WO | WO 2015/089277 | A1 | 6/2015 |
| WO | WO 2015/089351 | A1 | 6/2015 |
| WO | WO 2015/089354 | A1 | 6/2015 |
| WO | WO 2015/089364 | A1 | 6/2015 |
| WO | WO 2015/089406 | A1 | 6/2015 |
| WO | WO 2015/089419 | A2 | 6/2015 |
| WO | WO 2015/089427 | A1 | 6/2015 |
| WO | WO 2015/089462 | A1 | 6/2015 |
| WO | WO 2015/089465 | A1 | 6/2015 |
| WO | WO 2015/089473 | A1 | 6/2015 |
| WO | WO 2015/089486 | A1 | 6/2015 |
| WO | WO 2015/095804 | A1 | 6/2015 |
| WO | WO 2015/099850 | A1 | 7/2015 |
| WO | WO 2015/100929 | A1 | 7/2015 |
| WO | WO 2015/103057 | A1 | 7/2015 |
| WO | WO 2015/103153 | A1 | 7/2015 |
| WO | WO 2015/105928 | A1 | 7/2015 |
| WO | WO 2015/108993 | A1 | 7/2015 |
| WO | WO 2015/109752 | A1 | 7/2015 |
| WO | WO 2015/110474 | A1 | 7/2015 |
| WO | WO 2015/112790 | A2 | 7/2015 |
| WO | WO 2015/112896 | A2 | 7/2015 |
| WO | WO 2015/113063 | A1 | 7/2015 |
| WO | WO 2015/114365 | A1 | 8/2015 |
| WO | WO 2015/115903 | A1 | 8/2015 |
| WO | WO 2015/116686 | A1 | 8/2015 |
| WO | WO 2015/116969 | A2 | 8/2015 |
| WO | WO 2015/117021 | A1 | 8/2015 |
| WO | WO 2015/117041 | A1 | 8/2015 |
| WO | WO 2015/117081 | A2 | 8/2015 |
| WO | WO 2015/118156 | A1 | 8/2015 |
| WO | WO 2015/119941 | A2 | 8/2015 |
| WO | WO 2015/121454 | A1 | 8/2015 |
| WO | WO 2015/122967 | A1 | 8/2015 |
| WO | WO 2015/123339 | A1 | 8/2015 |
| WO | WO 2015/124715 | A1 | 8/2015 |
| WO | WO 2015/124718 | A1 | 8/2015 |
| WO | WO 2015/126927 | A2 | 8/2015 |
| WO | WO 2015/127428 | A1 | 8/2015 |
| WO | WO 2015/127439 | A1 | 8/2015 |
| WO | WO 2015/129686 | A1 | 9/2015 |
| WO | WO 2015/131101 | A1 | 9/2015 |
| WO | WO 2015/133554 | A1 | 9/2015 |
| WO | WO 2015/134121 | A2 | 9/2015 |
| WO | WO 2015/134812 | A1 | 9/2015 |
| WO | WO 2015/136001 | A1 | 9/2015 |
| WO | WO 2015/138510 | A1 | 9/2015 |
| WO | WO 2015/138739 | A2 | 9/2015 |
| WO | WO 2015/138855 | A1 | 9/2015 |
| WO | WO 2015/138870 | A2 | 9/2015 |
| WO | WO 2015/139008 | A1 | 9/2015 |
| WO | WO 2015/139139 | A1 | 9/2015 |
| WO | WO 2015/143046 | A2 | 9/2015 |
| WO | WO 2015/143177 | A1 | 9/2015 |
| WO | WO 2015/145417 | A1 | 10/2015 |
| WO | WO 2015/148431 | A1 | 10/2015 |
| WO | WO 2015/148670 | A1 | 10/2015 |
| WO | WO 2015/148680 | A1 | 10/2015 |
| WO | WO 2015/148760 | A1 | 10/2015 |
| WO | WO 2015/148761 | A1 | 10/2015 |
| WO | WO 2015/148860 | A1 | 10/2015 |
| WO | WO 2015/148863 | A2 | 10/2015 |
| WO | WO 2015/153760 | A2 | 10/2015 |
| WO | WO 2015/153780 | A1 | 10/2015 |
| WO | WO 2015/153789 | A1 | 10/2015 |
| WO | WO 2015/153791 | A1 | 10/2015 |
| WO | WO 2015/153889 | A2 | 10/2015 |
| WO | WO 2015/153940 | A1 | 10/2015 |
| WO | WO 2015/155341 | A1 | 10/2015 |
| WO | WO 2015/155686 | A2 | 10/2015 |
| WO | WO 2015/157070 | A2 | 10/2015 |
| WO | WO 2015/157534 | A1 | 10/2015 |
| WO | WO 2015/159068 | A1 | 10/2015 |
| WO | WO 2015/159086 | A1 | 10/2015 |
| WO | WO 2015/159087 | A1 | 10/2015 |
| WO | WO 2015/160683 | A1 | 10/2015 |
| WO | WO 2015/161276 | A2 | 10/2015 |
| WO | WO 2015/163733 | A1 | 10/2015 |
| WO | WO 2015/164740 | A1 | 10/2015 |
| WO | WO 2015/164748 | A1 | 10/2015 |
| WO | WO 2015/165274 | A1 | 11/2015 |
| WO | WO 2015/165275 | A1 | 11/2015 |
| WO | WO 2015/165276 | A1 | 11/2015 |
| WO | WO 2015/166272 | A2 | 11/2015 |
| WO | WO 2015/167766 | A1 | 11/2015 |
| WO | WO 2015/167956 | A1 | 11/2015 |
| WO | WO 2015/168125 | A1 | 11/2015 |
| WO | WO 2015/168158 | A1 | 11/2015 |
| WO | WO 2015/168404 | A1 | 11/2015 |
| WO | WO 2015/168547 | A2 | 11/2015 |
| WO | WO 2015/168800 | A1 | 11/2015 |
| WO | WO 2015/171603 | A1 | 11/2015 |
| WO | WO 2015/171894 | A1 | 11/2015 |
| WO | WO 2015/171932 | A1 | 11/2015 |
| WO | WO 2015/172128 | A1 | 11/2015 |
| WO | WO 2015/173436 | A1 | 11/2015 |
| WO | WO 2015/175642 | A2 | 11/2015 |
| WO | WO 2015/179540 | A1 | 11/2015 |
| WO | WO 2015/183025 | A1 | 12/2015 |
| WO | WO 2015/183026 | A1 | 12/2015 |
| WO | WO 2015/183885 | A1 | 12/2015 |
| WO | WO 2015/184259 | A1 | 12/2015 |
| WO | WO 2015/184262 | A1 | 12/2015 |
| WO | WO 2015/184268 | A1 | 12/2015 |
| WO | WO 2015/188056 | A1 | 12/2015 |
| WO | WO 2015/188065 | A1 | 12/2015 |
| WO | WO 2015/188094 | A1 | 12/2015 |
| WO | WO 2015/188109 | A1 | 12/2015 |
| WO | WO 2015/188132 | A1 | 12/2015 |
| WO | WO 2015/188135 | A1 | 12/2015 |
| WO | WO 2015/188191 | A1 | 12/2015 |
| WO | WO 2015/189693 | A1 | 12/2015 |
| WO | WO 2015/191693 | A2 | 12/2015 |
| WO | WO 2015/191899 | A1 | 12/2015 |
| WO | WO 2015/191911 | A2 | 12/2015 |
| WO | WO 2015/193858 | A1 | 12/2015 |
| WO | WO 2015/195547 | A1 | 12/2015 |
| WO | WO 2015/195621 | A1 | 12/2015 |
| WO | WO 2015/195798 | A1 | 12/2015 |
| WO | WO 2015/198020 | A1 | 12/2015 |
| WO | WO 2015/200334 | A1 | 12/2015 |
| WO | WO 2015/200378 | A1 | 12/2015 |
| WO | WO 2015/200555 | A2 | 12/2015 |
| WO | WO 2015/200805 | A2 | 12/2015 |
| WO | WO 2016/001978 | A1 | 1/2016 |
| WO | WO 2016/004010 | A1 | 1/2016 |

(56) References Cited

FOREIGN PATENT DOCUMENTS

WO WO 2016/004318 A1 1/2016
WO WO 2016/007347 A1 1/2016
WO WO 2016/007604 A1 1/2016
WO WO 2016/007948 A1 1/2016
WO WO 2016/011080 A2 1/2016
WO WO 2016/011210 A2 1/2016
WO WO 2016/011428 A1 1/2016
WO WO 2016/012544 A2 1/2016
WO WO 2016/012552 A1 1/2016
WO WO 2016/014409 A1 1/2016
WO WO 2016/014565 A2 1/2016
WO WO 2016/014794 A1 1/2016
WO WO 2016/014837 A1 1/2016
WO WO 2016/016119 A1 2/2016
WO WO 2016/016358 A1 2/2016
WO WO 2016/019144 A2 2/2016
WO WO 2016/020399 A1 2/2016
WO WO 2016/021972 A1 2/2016
WO WO 2016/021973 A1 2/2016
WO WO 2016/022363 A2 2/2016
WO WO 2016/022866 A1 2/2016
WO WO 2016/022931 A1 2/2016
WO WO 2016/025131 A1 2/2016
WO WO 2016/025469 A1 2/2016
WO WO 2016/025759 A1 2/2016
WO WO 2016/026444 A1 2/2016
WO WO 2016/028682 A1 2/2016
WO WO 2016/028843 A1 2/2016
WO WO 2016/028887 A1 2/2016
WO WO 2016/033088 A1 3/2016
WO WO 2016/033230 A1 3/2016
WO WO 2016/033246 A1 3/2016
WO WO 2016/033298 A1 3/2016
WO WO 2016/035044 A1 3/2016
WO WO 2016/035918 A1 3/2016
WO WO 2016/036754 A1 3/2016
WO WO 2016/037157 A2 3/2016
WO WO 2016/040030 A1 3/2016
WO WO 2016/040594 A1 3/2016
WO WO 2016/044182 A1 3/2016
WO WO 2016/044416 A1 3/2016
WO WO 2016/046635 A1 3/2016
WO WO 2016/049024 A2 3/2016
WO WO 2016/049163 A2 3/2016
WO WO 2016/049230 A1 3/2016
WO WO 2016/049251 A1 3/2016
WO WO 2016/049258 A2 3/2016
WO WO 2016/053397 A2 4/2016
WO WO 2016/054326 A1 4/2016
WO WO 2016/057061 A2 4/2016
WO WO 2016/057821 A2 4/2016
WO WO 2016/057835 A2 4/2016
WO WO 2016/057850 A1 4/2016
WO WO 2016/057951 A2 4/2016
WO WO 2016/057961 A1 4/2016
WO WO 2016/061073 A1 4/2016
WO WO 2016/061374 A1 4/2016
WO WO 2016/061481 A1 4/2016
WO WO 2016/061523 A1 4/2016
WO WO 2016/064894 A2 4/2016
WO WO 2016/065364 A1 4/2016
WO WO 2016/069282 A1 5/2016
WO WO 2016/069283 A1 5/2016
WO WO 2016/069591 A2 5/2016
WO WO 2016/069774 A1 5/2016
WO WO 2016/069910 A1 5/2016
WO WO 2016/069912 A1 5/2016
WO WO 2016/070037 A2 5/2016
WO WO 2016/070070 A1 5/2016
WO WO 2016/070129 A1 5/2016
WO WO 2016/072399 A1 5/2016
WO WO 2016/072936 A1 5/2016
WO WO 2016/073433 A1 5/2016
WO WO 2016/073559 A1 5/2016
WO WO 2016/073990 A2 5/2016
WO WO 2016/075662 A2 5/2016
WO WO 2016/076672 A1 5/2016
WO WO 2016/077273 A1 5/2016
WO WO 2016/077350 A1 5/2016
WO WO 2016/080097 A1 5/2016
WO WO 2016/080795 A1 5/2016
WO WO 2016/081923 A2 5/2016
WO WO 2016/081924 A1 5/2016
WO WO 2016/082135 A1 6/2016
WO WO 2016/083811 A1 6/2016
WO WO 2016/084084 A1 6/2016
WO WO 2016/084088 A1 6/2016
WO WO 2016/086177 A2 6/2016
WO WO 2016/089433 A1 6/2016
WO WO 2016/089866 A1 6/2016
WO WO 2016/089883 A1 6/2016
WO WO 2016/090385 A1 6/2016
WO WO 2016/094679 A1 6/2016
WO WO 2016/094845 A2 6/2016
WO WO 2016/094867 A1 6/2016
WO WO 2016/094872 A1 6/2016
WO WO 2016/094874 A1 6/2016
WO WO 2016/094880 A1 6/2016
WO WO 2016/094888 A1 6/2016
WO WO 2016/097212 A1 6/2016
WO WO 2016/097231 A2 6/2016
WO WO 2016/097751 A1 6/2016
WO WO 2016/099887 A1 6/2016
WO WO 2016/100272 A1 6/2016
WO WO 2016/100389 A1 6/2016
WO WO 2016/100568 A1 6/2016
WO WO 2016/100571 A1 6/2016
WO WO 2016/100951 A2 6/2016
WO WO 2016/100955 A2 6/2016
WO WO 2016/100974 A1 6/2016
WO WO 2016/103233 A2 6/2016
WO WO 2016/104716 A1 6/2016
WO WO 2016/106236 A1 6/2016
WO WO 2016/106239 A1 6/2016
WO WO 2016/106244 A1 6/2016
WO WO 2016/106338 A2 6/2016
WO WO 2016/108926 A1 7/2016
WO WO 2016/109255 A1 7/2016
WO WO 2016/109840 A2 7/2016
WO WO 2016/110214 A1 7/2016
WO WO 2016/110453 A1 7/2016
WO WO 2016/110511 A1 7/2016
WO WO 2016/110512 A1 7/2016
WO WO 2016/111546 A2 7/2016
WO WO 2016/112242 A1 7/2016
WO WO 2016/112351 A1 7/2016
WO WO 2016/112963 A1 7/2016
WO WO 2016/113357 A1 7/2016
WO WO 2016/114972 A1 7/2016
WO WO 2016/115179 A1 7/2016
WO WO 2016/115326 A1 7/2016
WO WO 2016/115355 A1 7/2016
WO WO 2016/116032 A1 7/2016
WO WO 2016/120480 A1 8/2016
WO WO 2016/123071 A1 8/2016
WO WO 2016/123230 A1 8/2016
WO WO 2016/123243 A1 8/2016
WO WO 2016/123578 A1 8/2016
WO WO 2016/126747 A1 8/2016
WO WO 2016/130600 A2 8/2016
WO WO 2016/130697 A1 8/2016
WO WO 2016/131009 A1 8/2016
WO WO 2016/132122 A1 8/2016
WO WO 2016/133165 A1 8/2016
WO WO 2016/135507 A1 9/2016
WO WO 2016/135557 A2 9/2016
WO WO 2016/135558 A2 9/2016
WO WO 2016/135559 A2 9/2016
WO WO 2016/137774 A1 9/2016
WO WO 2016/137949 A1 9/2016
WO WO 2016/141224 A1 9/2016
WO WO 2016/141893 A1 9/2016
WO WO 2016/142719 A1 9/2016
WO WO 2016/145150 A2 9/2016

(56) References Cited

FOREIGN PATENT DOCUMENTS

| | | | |
|---|---|---|---|
| WO | WO 2016/148994 | A1 | 9/2016 |
| WO | WO 2016/149484 | A2 | 9/2016 |
| WO | WO 2016/149547 | A1 | 9/2016 |
| WO | WO 2016/150336 | A1 | 9/2016 |
| WO | WO 2016/150855 | A1 | 9/2016 |
| WO | WO 2016/154016 | A2 | 9/2016 |
| WO | WO 2016/154579 | A2 | 9/2016 |
| WO | WO 2016/154596 | A1 | 9/2016 |
| WO | WO 2016/155482 | A1 | 10/2016 |
| WO | WO 2016/161004 | A1 | 10/2016 |
| WO | WO 2016/161207 | A1 | 10/2016 |
| WO | WO 2016/161260 | A1 | 10/2016 |
| WO | WO 2016/161380 | A1 | 10/2016 |
| WO | WO 2016/161446 | A1 | 10/2016 |
| WO | WO 2016/164356 | A1 | 10/2016 |
| WO | WO 2016/164797 | A1 | 10/2016 |
| WO | WO 2016/166340 | A1 | 10/2016 |
| WO | WO 2016/167300 | A1 | 10/2016 |
| WO | WO 2016/168631 | A1 | 10/2016 |
| WO | WO 2016/170484 | A1 | 10/2016 |
| WO | WO 2016/172359 | A2 | 10/2016 |
| WO | WO 2016/172727 | A1 | 10/2016 |
| WO | WO 2016/174056 | A1 | 11/2016 |
| WO | WO 2016/174151 | A1 | 11/2016 |
| WO | WO 2016/174250 | A1 | 11/2016 |
| WO | WO 2016/176191 | A1 | 11/2016 |
| WO | WO 2016/176404 | A1 | 11/2016 |
| WO | WO 2016/176690 | A2 | 11/2016 |
| WO | WO 2016/177682 | A1 | 11/2016 |
| WO | WO 2016/178207 | A1 | 11/2016 |
| WO | WO 2016/179038 | A1 | 11/2016 |
| WO | WO 2016/179112 | A1 | 11/2016 |
| WO | WO 2016/181357 | A1 | 11/2016 |
| WO | WO 2016/182893 | A1 | 11/2016 |
| WO | WO 2016/182917 | A1 | 11/2016 |
| WO | WO 2016/182959 | A1 | 11/2016 |
| WO | WO 2016/183236 | A1 | 11/2016 |
| WO | WO 2016/183298 | A2 | 11/2016 |
| WO | WO 2016/183345 | A1 | 11/2016 |
| WO | WO 2016/183402 | A2 | 11/2016 |
| WO | WO 2016/183438 | A1 | 11/2016 |
| WO | WO 2016/183448 | A1 | 11/2016 |
| WO | WO 2016/184955 | A2 | 11/2016 |
| WO | WO 2016/184989 | A1 | 11/2016 |
| WO | WO 2016/185411 | A1 | 11/2016 |
| WO | WO 2016/186745 | A1 | 11/2016 |
| WO | WO 2016/186772 | A2 | 11/2016 |
| WO | WO 2016/186946 | A1 | 11/2016 |
| WO | WO 2016/186953 | A1 | 11/2016 |
| WO | WO 2016/187717 | A1 | 12/2016 |
| WO | WO 2016/187904 | A1 | 12/2016 |
| WO | WO 2016/191684 | A1 | 12/2016 |
| WO | WO 2016/191869 | A1 | 12/2016 |
| WO | WO 2016/196273 | A1 | 12/2016 |
| WO | WO 2016/196282 | A1 | 12/2016 |
| WO | WO 2016/196308 | A1 | 12/2016 |
| WO | WO 2016/196361 | A1 | 12/2016 |
| WO | WO 2016/196499 | A1 | 12/2016 |
| WO | WO 2016/196539 | A2 | 12/2016 |
| WO | WO 2016/196655 | A1 | 12/2016 |
| WO | WO 2016/196805 | A1 | 12/2016 |
| WO | WO 2016/196887 | A1 | 12/2016 |
| WO | WO 2016/197132 | A1 | 12/2016 |
| WO | WO 2016/197133 | A1 | 12/2016 |
| WO | WO 2016/197354 | A1 | 12/2016 |
| WO | WO 2016/197355 | A1 | 12/2016 |
| WO | WO 2016/197356 | A1 | 12/2016 |
| WO | WO 2016/197357 | A1 | 12/2016 |
| WO | WO 2016/197358 | A1 | 12/2016 |
| WO | WO 2016/197359 | A1 | 12/2016 |
| WO | WO 2016/197360 | A1 | 12/2016 |
| WO | WO 2016/197361 | A1 | 12/2016 |
| WO | WO 2016/197362 | A1 | 12/2016 |
| WO | WO 2016/198361 | A1 | 12/2016 |
| WO | WO 2016/198500 | A1 | 12/2016 |
| WO | WO 2016/200263 | A1 | 12/2016 |
| WO | WO 2016/201047 | A1 | 12/2016 |
| WO | WO 2016/201138 | A1 | 12/2016 |
| WO | WO 2016/201152 | A1 | 12/2016 |
| WO | WO 2016/201153 | A1 | 12/2016 |
| WO | WO 2016/201155 | A1 | 12/2016 |
| WO | WO 2016/205276 | A1 | 12/2016 |
| WO | WO 2016/205613 | A1 | 12/2016 |
| WO | WO 2016/205623 | A1 | 12/2016 |
| WO | WO 2016/205680 | A1 | 12/2016 |
| WO | WO 2016/205688 | A2 | 12/2016 |
| WO | WO 2016/205703 | A1 | 12/2016 |
| WO | WO 2016/205711 | A1 | 12/2016 |
| WO | WO 2016/205728 | A1 | 12/2016 |
| WO | WO 2016/205745 | A2 | 12/2016 |
| WO | WO 2016/205749 | A1 | 12/2016 |
| WO | WO 2016/205759 | A1 | 12/2016 |
| WO | WO 2016/205764 | A1 | 12/2016 |
| WO | WO 2017/001572 | A1 | 1/2017 |
| WO | WO 2017/001988 | A1 | 1/2017 |
| WO | WO 2017/004261 | A1 | 1/2017 |
| WO | WO 2017/004279 | A2 | 1/2017 |
| WO | WO 2017/004616 | A1 | 1/2017 |
| WO | WO 2017/005807 | A1 | 1/2017 |
| WO | WO 2017/009399 | A1 | 1/2017 |
| WO | WO 2017/010556 | A1 | 1/2017 |
| WO | WO 2017/011519 | A1 | 1/2017 |
| WO | WO 2017/011721 | A1 | 1/2017 |
| WO | WO 2017/011804 | A1 | 1/2017 |
| WO | WO 2017/015015 | A1 | 1/2017 |
| WO | WO 2017/015101 | A1 | 1/2017 |
| WO | WO 2017/015545 | A1 | 1/2017 |
| WO | WO 2017/015567 | A1 | 1/2017 |
| WO | WO 2017/015637 | A1 | 1/2017 |
| WO | WO 2017/017016 | A1 | 2/2017 |
| WO | WO 2017/019867 | A1 | 2/2017 |
| WO | WO 2017/019895 | A1 | 2/2017 |
| WO | WO 2017/023803 | A1 | 2/2017 |
| WO | WO 2017/023974 | A1 | 2/2017 |
| WO | WO 2017/024047 | A1 | 2/2017 |
| WO | WO 2017/024319 | A1 | 2/2017 |
| WO | WO 2017/024343 | A1 | 2/2017 |
| WO | WO 2017/024602 | A1 | 2/2017 |
| WO | WO 2017/025323 | A1 | 2/2017 |
| WO | WO 2017/027423 | A1 | 2/2017 |
| WO | WO 2017/028768 | A1 | 2/2017 |
| WO | WO 2017/029664 | A1 | 2/2017 |
| WO | WO 2017/031360 | A1 | 2/2017 |
| WO | WO 2017/031483 | A1 | 2/2017 |
| WO | WO 2017/035416 | A2 | 3/2017 |
| WO | WO 2017/040348 | A1 | 3/2017 |
| WO | WO 2017/040511 | A1 | 3/2017 |
| WO | WO 2017/040709 | A1 | 3/2017 |
| WO | WO 2017/040786 | A1 | 3/2017 |
| WO | WO 2017/040793 | A1 | 3/2017 |
| WO | WO 2017/040813 | A2 | 3/2017 |
| WO | WO 2017/043573 | A1 | 3/2017 |
| WO | WO 2017/043656 | A1 | 3/2017 |
| WO | WO 2017/044419 | A1 | 3/2017 |
| WO | WO 2017/044776 | A1 | 3/2017 |
| WO | WO 2017/044857 | A2 | 3/2017 |
| WO | WO 2017/048390 | A1 | 3/2017 |
| WO | WO 2017/049129 | A2 | 3/2017 |
| WO | WO 2017/050963 | A1 | 3/2017 |
| WO | WO 2017/053312 | A1 | 3/2017 |
| WO | WO 2017/053431 | A2 | 3/2017 |
| WO | WO 2017/053713 | A1 | 3/2017 |
| WO | WO 2017/053729 | A1 | 3/2017 |
| WO | WO 2017/053753 | A1 | 3/2017 |
| WO | WO 2017/053762 | A1 | 3/2017 |
| WO | WO 2017/053879 | A1 | 3/2017 |
| WO | WO 2017/054721 | A1 | 4/2017 |
| WO | WO 2017/058658 | A2 | 4/2017 |
| WO | WO 2017/059241 | A1 | 4/2017 |
| WO | WO 2017/062605 | A1 | 4/2017 |
| WO | WO 2017/062723 | A1 | 4/2017 |
| WO | WO 2017/062754 | A1 | 4/2017 |
| WO | WO 2017/062855 | A1 | 4/2017 |
| WO | WO 2017/062886 | A1 | 4/2017 |

(56) References Cited

FOREIGN PATENT DOCUMENTS

WO WO 2017/062983 A1 4/2017
WO WO 2017/064439 A1 4/2017
WO WO 2017/064546 A1 4/2017
WO WO 2017/064566 A2 4/2017
WO WO 2017/066175 A1 4/2017
WO WO 2017/066497 A2 4/2017
WO WO 2017/066588 A2 4/2017
WO WO 2017/066707 A1 4/2017
WO WO 2017/066781 A1 4/2017
WO WO 2017/068077 A1 4/2017
WO WO 2017/068377 A1 4/2017
WO WO 2017/069829 A2 4/2017
WO WO 2017/070029 A1 4/2017
WO WO 2017/070032 A1 4/2017
WO WO 2017/070169 A1 4/2017
WO WO 2017/070284 A1 4/2017
WO WO 2017/070598 A1 4/2017
WO WO 2017/070605 A1 4/2017
WO WO 2017/070632 A2 4/2017
WO WO 2017/070633 A2 4/2017
WO WO 2017/072590 A1 5/2017
WO WO 2017/074526 A1 5/2017
WO WO 2017/074962 A1 5/2017
WO WO 2017/075261 A1 5/2017
WO WO 2017/075335 A1 5/2017
WO WO 2017/075475 A1 5/2017
WO WO 2017/077135 A1 5/2017
WO WO 2017/077329 A2 5/2017
WO WO 2017/078751 A1 5/2017
WO WO 2017/079400 A1 5/2017
WO WO 2017/079428 A1 5/2017
WO WO 2017/079673 A1 5/2017
WO WO 2017/079724 A1 5/2017
WO WO 2017/081097 A1 5/2017
WO WO 2017/081288 A1 5/2017
WO WO 2017/083368 A1 5/2017
WO WO 2017/083722 A1 5/2017
WO WO 2017/083766 A1 5/2017
WO WO 2017/087395 A1 5/2017
WO WO 2017/090724 A1 6/2017
WO WO 2017/091510 A1 6/2017
WO WO 2017/091630 A1 6/2017
WO WO 2017/092201 A1 6/2017
WO WO 2017/093370 A1 6/2017
WO WO 2017/093969 A1 6/2017
WO WO 2017/095111 A1 6/2017
WO WO 2017/096041 A1 6/2017
WO WO 2017/096237 A1 6/2017
WO WO 2017/100158 A1 6/2017
WO WO 2017/100431 A2 6/2017
WO WO 2017/104404 A1 6/2017
WO WO 2017/105251 A1 6/2017
WO WO 2017/105350 A1 6/2017
WO WO 2017/105991 A1 6/2017
WO WO 2017/106414 A1 6/2017
WO WO 2017/106528 A2 6/2017
WO WO 2017/106537 A2 6/2017
WO WO 2017/106569 A1 6/2017
WO WO 2017/106616 A1 6/2017
WO WO 2017/106657 A1 6/2017
WO WO 2017/106767 A1 6/2017
WO WO 2017/109134 A1 6/2017
WO WO 2017/109757 A1 6/2017
WO WO 2017/112620 A1 6/2017
WO WO 2017/115268 A1 7/2017
WO WO 2017/117395 A1 7/2017
WO WO 2017/118598 A1 7/2017
WO WO 2017/118720 A1 7/2017
WO WO 2017/123609 A1 7/2017
WO WO 2017/123910 A1 7/2017
WO WO 2017/124086 A1 7/2017
WO WO 2017/124100 A1 7/2017
WO WO 2017/124652 A1 7/2017
WO WO 2017/126987 A1 7/2017
WO WO 2017/127807 A1 7/2017
WO WO 2017/131237 A1 8/2017
WO WO 2017/132112 A1 8/2017
WO WO 2017/132580 A2 8/2017
WO WO 2017/136520 A1 8/2017
WO WO 2017/136629 A1 8/2017
WO WO 2017/136794 A1 8/2017
WO WO 2017/139264 A1 8/2017
WO WO 2017/139505 A2 8/2017
WO WO 2017/141173 A2 8/2017
WO WO 2017/142835 A1 8/2017
WO WO 2017/142923 A1 8/2017
WO WO 2017/142999 A2 8/2017
WO WO 2017/143042 A2 8/2017
WO WO 2017/147056 A1 8/2017
WO WO 2017/147278 A1 8/2017
WO WO 2017/147432 A1 8/2017
WO WO 2017/147446 A1 8/2017
WO WO 2017/147555 A1 8/2017
WO WO 2017/151444 A1 9/2017
WO WO 2017/151719 A1 9/2017
WO WO 2017/152015 A1 9/2017
WO WO 2017/155717 A1 9/2017
WO WO 2017/157422 A1 9/2017
WO WO 2017/158153 A1 9/2017
WO WO 2017/160689 A1 9/2017
WO WO 2017/160752 A1 9/2017
WO WO 2017/160890 A1 9/2017
WO WO 2017/161068 A1 9/2017
WO WO 2017/165741 A1 9/2017
WO WO 2017/165826 A1 9/2017
WO WO 2017/165862 A1 9/2017
WO WO 2017/167712 A1 10/2017
WO WO 2017/172644 A2 10/2017
WO WO 2017/172645 A2 10/2017
WO WO 2017/172860 A1 10/2017
WO WO 2017/173004 A1 10/2017
WO WO 2017/173054 A1 10/2017
WO WO 2017/173092 A1 10/2017
WO WO 2017/174329 A1 10/2017
WO WO 2017/176529 A1 10/2017
WO WO 2017/176806 A1 10/2017
WO WO 2017/178590 A1 10/2017
WO WO 2017/180694 A1 10/2017
WO WO 2017/180711 A1 10/2017
WO WO 2017/180915 A2 10/2017
WO WO 2017/180926 A1 10/2017
WO WO 2017/181107 A2 10/2017
WO WO 2017/181735 A2 10/2017
WO WO 2017/182468 A1 10/2017
WO WO 2017/184334 A1 10/2017
WO WO 2017/184768 A1 10/2017
WO WO 2017/184786 A1 10/2017
WO WO 2017/186550 A1 11/2017
WO WO 2017/189308 A1 11/2017
WO WO 2017/189336 A1 11/2017
WO WO 2017/190041 A1 11/2017
WO WO 2017/190257 A1 11/2017
WO WO 2017/190664 A1 11/2017
WO WO 2017/191210 A1 11/2017
WO WO 2017/191274 A2 11/2017
WO WO 2017/192172 A1 11/2017
WO WO 2017/192512 A2 11/2017
WO WO 2017/192544 A1 11/2017
WO WO 2017/192573 A1 11/2017
WO WO 2017/193029 A2 11/2017
WO WO 2017/193053 A1 11/2017
WO WO 2017/196768 A1 11/2017
WO WO 2017/197038 A1 11/2017
WO WO 2017/197238 A1 11/2017
WO WO 2017/197301 A1 11/2017
WO WO 2017/201476 A1 11/2017
WO WO 2017/205290 A1 11/2017
WO WO 2017/205423 A1 11/2017
WO WO 2017/207589 A1 12/2017
WO WO 2017/208247 A1 12/2017
WO WO 2017/209809 A1 12/2017
WO WO 2017/213896 A1 12/2017
WO WO 2017/213898 A2 12/2017
WO WO 2017/214460 A1 12/2017

(56) References Cited

FOREIGN PATENT DOCUMENTS

| | | | |
|---|---|---|---|
| WO | WO 2017/216392 | A1 | 12/2017 |
| WO | WO 2017/216771 | A2 | 12/2017 |
| WO | WO 2017/218185 | A1 | 12/2017 |
| WO | WO 2017/219027 | A1 | 12/2017 |
| WO | WO 2017/219033 | A1 | 12/2017 |
| WO | WO 2017/220751 | A1 | 12/2017 |
| WO | WO 2017/222370 | A1 | 12/2017 |
| WO | WO 2017/222773 | A1 | 12/2017 |
| WO | WO 2017/222834 | A1 | 12/2017 |
| WO | WO 2017/223107 | A1 | 12/2017 |
| WO | WO 2017/223330 | A1 | 12/2017 |
| WO | WO 2018/000657 | A1 | 1/2018 |
| WO | WO 2018/002719 | A1 | 1/2018 |
| WO | WO 2018/005117 | A1 | 1/2018 |
| WO | WO 2018/005289 | A2 | 1/2018 |
| WO | WO 2018/005691 | A1 | 1/2018 |
| WO | WO 2018/005782 | A1 | 1/2018 |
| WO | WO 2018/005873 | A1 | 1/2018 |
| WO | WO 2018/06693 | A1 | 1/2018 |
| WO | WO 2018/009520 | A1 | 1/2018 |
| WO | WO 2018/009562 | A1 | 1/2018 |
| WO | WO 2018/009822 | A1 | 1/2018 |
| WO | WO 2018/013821 | A1 | 1/2018 |
| WO | WO 2018/013932 | A1 | 1/2018 |
| WO | WO 2018/013990 | A1 | 1/2018 |
| WO | WO 2018/014384 | A1 | 1/2018 |
| WO | WO 2018/015444 | A1 | 1/2018 |
| WO | WO 2018/015936 | A2 | 1/2018 |
| WO | WO 2018/017754 | A1 | 1/2018 |
| WO | WO 2018/018979 | A1 | 2/2018 |
| WO | WO 2018/020248 | A1 | 2/2018 |
| WO | WO 2018/021878 | A1 | 2/2018 |
| WO | WO 2018/022480 | A1 | 2/2018 |
| WO | WO 2018/022634 | A1 | 2/2018 |
| WO | WO 2018/025206 | A1 | 2/2018 |
| WO | WO 2018/026723 | A1 | 2/2018 |
| WO | WO 2018/026976 | A1 | 2/2018 |
| WO | WO 2018/027078 | A1 | 2/2018 |
| WO | WO 2018/030608 | A1 | 2/2018 |
| WO | WO 2018/031683 | A1 | 2/2018 |
| WO | WO 2018/035250 | A1 | 2/2018 |
| WO | WO 2018/035300 | A1 | 2/2018 |
| WO | WO 2018/035423 | A1 | 2/2018 |
| WO | WO 2018/035503 | A1 | 2/2018 |
| WO | WO 2018/039145 | A1 | 3/2018 |
| WO | WO 2018/039438 | A1 | 3/2018 |
| WO | WO 2018/039440 | A1 | 3/2018 |
| WO | WO 2018/039448 | A1 | 3/2018 |
| WO | WO 2018/045630 | A1 | 3/2018 |
| WO | WO 2018/048827 | A1 | 3/2018 |
| WO | WO 2018/049073 | A1 | 3/2018 |
| WO | WO 2018/049168 | A1 | 3/2018 |
| WO | WO 2018/051347 | A1 | 3/2018 |
| WO | WO 2018/058064 | A1 | 3/2018 |
| WO | WO 2018/062866 | A2 | 4/2018 |
| WO | WO 2018/064352 | A1 | 4/2018 |
| WO | WO 2018/064371 | A1 | 4/2018 |
| WO | WO 2018/064516 | A1 | 4/2018 |
| WO | WO 2018/067546 | A1 | 4/2018 |
| WO | WO 2018/067846 | A1 | 4/2018 |
| WO | WO 2018/068053 | A2 | 4/2018 |
| WO | WO 2018/069474 | A1 | 4/2018 |
| WO | WO 2018/071623 | A2 | 4/2018 |
| WO | WO 2018/071663 | A1 | 4/2018 |
| WO | WO 2018/071868 | A1 | 4/2018 |
| WO | WO 2018/071892 | A1 | 4/2018 |
| WO | WO 2018/074979 | A1 | 4/2018 |
| WO | WO 2018/079134 | A1 | 5/2018 |
| WO | WO 2018/080573 | A1 | 5/2018 |
| WO | WO 2018/081504 | A1 | 5/2018 |
| WO | WO 2018/081535 | A2 | 5/2018 |
| WO | WO 2018/081728 | A1 | 5/2018 |
| WO | WO 2018/083128 | A2 | 5/2018 |
| WO | WO 2018/083606 | A1 | 5/2018 |
| WO | WO 2018/085288 | A1 | 5/2018 |
| WO | WO 2018/085414 | A1 | 5/2018 |
| WO | WO 2018/086623 | A1 | 5/2018 |
| WO | WO 2018/089664 | A1 | 5/2018 |
| WO | WO 2018/093990 | A1 | 5/2018 |
| WO | WO 2018/098383 | A1 | 5/2018 |
| WO | WO 2018/098480 | A1 | 5/2018 |
| WO | WO 2018/098587 | A1 | 6/2018 |
| WO | WO 2018/099256 | A1 | 6/2018 |
| WO | WO 2018/103686 | A1 | 6/2018 |
| WO | WO 2018/106268 | A1 | 6/2018 |
| WO | WO 2018/107028 | A1 | 6/2018 |
| WO | WO 2018/107103 | A1 | 6/2018 |
| WO | WO 2018/107129 | A1 | 6/2018 |
| WO | WO 2018/108272 | A1 | 6/2018 |
| WO | WO 2018/109101 | A1 | 6/2018 |
| WO | WO 2018/111946 | A1 | 6/2018 |
| WO | WO 2018/111947 | A1 | 6/2018 |
| WO | WO 2018/112336 | A1 | 6/2018 |
| WO | WO 2018/112446 | A2 | 6/2018 |
| WO | WO 2018/119354 | A1 | 6/2018 |
| WO | WO 2018/119359 | A1 | 6/2018 |
| WO | WO 2018/120283 | A1 | 7/2018 |
| WO | WO 2018/130830 | A1 | 7/2018 |
| WO | WO 2018/135838 | A2 | 7/2018 |
| WO | WO 2018/136396 | A2 | 7/2018 |
| WO | WO 2018/138385 | A1 | 8/2018 |
| WO | WO 2018/142364 | A1 | 8/2018 |
| WO | WO 2018/148246 | A1 | 8/2018 |
| WO | WO 2018/148256 | A1 | 8/2018 |
| WO | WO 2018/148647 | A2 | 8/2018 |
| WO | WO 2018/149418 | A1 | 8/2018 |
| WO | WO 2018/149888 | A1 | 8/2018 |
| WO | WO 2018/149915 | A1 | 8/2018 |
| WO | WO 2018/152197 | A1 | 8/2018 |
| WO | WO 2018/152418 | A1 | 8/2018 |
| WO | WO 2018/154380 | A1 | 8/2018 |
| WO | WO 2018/154387 | A1 | 8/2018 |
| WO | WO 2018/154412 | A1 | 8/2018 |
| WO | WO 2018/154413 | A1 | 8/2018 |
| WO | WO 2018/154418 | A1 | 8/2018 |
| WO | WO 2018/154439 | A1 | 8/2018 |
| WO | WO 2018/154459 | A1 | 8/2018 |
| WO | WO 2018/154462 | A2 | 8/2018 |
| WO | WO 2018/156372 | A1 | 8/2018 |
| WO | WO 2018/156824 | A1 | 8/2018 |
| WO | WO 2018/161009 | A1 | 9/2018 |
| WO | WO 2018/161032 | A1 | 9/2018 |
| WO | WO 2018/165504 | A1 | 9/2018 |
| WO | WO 2018/165629 | A1 | 9/2018 |
| WO | WO 2018/170015 | A1 | 9/2018 |
| WO | WO 2018/170340 | A1 | 9/2018 |
| WO | WO 2018/175502 | A2 | 9/2018 |
| WO | WO 2018/176009 | A1 | 9/2018 |
| WO | WO 2018/177351 | A1 | 10/2018 |
| WO | WO 2018/179578 | A1 | 10/2018 |
| WO | WO 2018/183403 | A1 | 10/2018 |
| WO | WO 2018/189184 | A1 | 10/2018 |
| WO | WO 2018/191388 | A1 | 10/2018 |
| WO | WO 2018/195402 | A1 | 10/2018 |
| WO | WO 2018/195545 | A2 | 10/2018 |
| WO | WO 2018/195555 | A1 | 10/2018 |
| WO | WO 2018/197020 | A1 | 11/2018 |
| WO | WO 2018/197495 | A1 | 11/2018 |
| WO | WO 2018/202800 | A1 | 11/2018 |
| WO | WO 2018/204493 | A1 | 11/2018 |
| WO | WO 2018/208755 | A1 | 11/2018 |
| WO | WO 2018/208998 | A1 | 11/2018 |
| WO | WO 2018/209158 | A2 | 11/2018 |
| WO | WO 2018/209320 | A1 | 11/2018 |
| WO | WO 2018/213351 | A1 | 11/2018 |
| WO | WO 2018/213708 | A1 | 11/2018 |
| WO | WO 2018/213726 | A1 | 11/2018 |
| WO | WO 2018/213771 | A1 | 11/2018 |
| WO | WO 2018/213791 | A1 | 11/2018 |
| WO | WO 2018/217852 | A1 | 11/2018 |
| WO | WO 2018/217981 | A1 | 11/2018 |
| WO | WO 2018/218166 | A1 | 11/2018 |
| WO | WO 2018/218188 | A2 | 11/2018 |
| WO | WO 2018/218206 | A1 | 11/2018 |

(56) References Cited

FOREIGN PATENT DOCUMENTS

| | | | |
|---|---|---|---|
| WO | WO 2018/226855 | A1 | 12/2018 |
| WO | WO 2019/005884 | A1 | 1/2019 |
| WO | WO 2019/005886 | A1 | 1/2019 |
| WO | WO 2019/010384 | A1 | 1/2019 |
| WO | WO 2019/023680 | A1 | 1/2019 |
| WO | WO 2019/042284 | A1 | 3/2019 |
| WO | WO 2019/051097 | A1 | 3/2019 |
| WO | WO 2019/075357 | A1 | 4/2019 |
| WO | WO 2019/079347 | A1 | 4/2019 |
| WO | WO 2019/084062 | A1 | 5/2019 |
| WO | WO 2019/090169 | A1 | 5/2019 |
| WO | WO 2019/090367 | A1 | 5/2019 |
| WO | WO 2019/092042 | A1 | 5/2019 |
| WO | WO 2019/118935 | A1 | 6/2019 |
| WO | WO 2019/118949 | A1 | 6/2019 |
| WO | WO 2019/123430 | A1 | 6/2019 |
| WO | WO 2019/126709 | A1 | 6/2019 |
| WO | WO 2019/139645 | A2 | 7/2019 |
| WO | WO 2019/139951 | A1 | 7/2019 |
| WO | WO 2019/147014 | A1 | 8/2019 |
| WO | WO 2019/161251 | A1 | 8/2019 |
| WO | WO 2019/168953 | A1 | 9/2019 |
| WO | WO 2019/183641 | A1 | 9/2019 |
| WO | WO 2019/204369 | A1 | 10/2019 |
| WO | WO 2019/217942 | A1 | 11/2019 |
| WO | WO 2019/226593 | A1 | 11/2019 |
| WO | WO 2019/226953 | A1 | 11/2019 |
| WO | WO 2019/236566 | A1 | 12/2019 |
| WO | WO 2019/241649 | A1 | 12/2019 |
| WO | WO 2020/014261 | A1 | 1/2020 |
| WO | WO 2020/028555 | A2 | 2/2020 |
| WO | WO 2020/028823 | A1 | 2/2020 |
| WO | WO 2020/041751 | A1 | 2/2020 |
| WO | WO 2020/047124 | A1 | 3/2020 |
| WO | WO 2020/051360 | A1 | 3/2020 |
| WO | WO 2020/081568 | A1 | 4/2020 |
| WO | WO 2020/086908 | A1 | 4/2020 |
| WO | WO 2020/092453 | A1 | 5/2020 |
| WO | WO 2020/102659 | A1 | 5/2020 |
| WO | WO 2020/102709 | A1 | 5/2020 |
| WO | WO 2020/154500 | A1 | 7/2020 |
| WO | WO 2020/157008 | A1 | 8/2020 |
| WO | WO 2020/160071 | A1 | 8/2020 |
| WO | WO 2020/160517 | A1 | 8/2020 |
| WO | WO 2020/180975 | A1 | 9/2020 |
| WO | WO 2020/181178 | A1 | 9/2020 |
| WO | WO 2020/181180 | A1 | 9/2020 |
| WO | WO 2020/181193 | A1 | 9/2020 |
| WO | WO 2020/181195 | A1 | 9/2020 |
| WO | WO 2020/181202 | A1 | 9/2020 |
| WO | WO 2020/191153 | A1 | 9/2020 |
| WO | WO 2020/191171 | A1 | 9/2020 |
| WO | WO 2020/191233 | A1 | 9/2020 |
| WO | WO 2020/191234 | A1 | 9/2020 |
| WO | WO 2020/191239 | A1 | 9/2020 |
| WO | WO 2020/191241 | A1 | 9/2020 |
| WO | WO 2020/191242 | A1 | 9/2020 |
| WO | WO 2020/191243 | A1 | 9/2020 |
| WO | WO 2020/191245 | A1 | 9/2020 |
| WO | WO 2020/191246 | A1 | 9/2020 |
| WO | WO 2020/191248 | A1 | 9/2020 |
| WO | WO 2020/191249 | A1 | 9/2020 |
| WO | WO 2020/210751 | A1 | 10/2020 |
| WO | WO 2020/214842 | A1 | 10/2020 |
| WO | WO 2020/236982 | A1 | 11/2020 |
| WO | WO 2020/247587 | A1 | 12/2020 |
| WO | WO 2021/022043 | A2 | 2/2021 |
| WO | WO 2021/025750 | A1 | 2/2021 |
| WO | WO 2021/030344 | A1 | 2/2021 |
| WO | WO 2021/030666 | A1 | 2/2021 |
| WO | WO 2021/042047 | A1 | 3/2021 |
| WO | WO 2021/042062 | A2 | 3/2021 |
| WO | WO 2021/072328 | A1 | 4/2021 |
| WO | WO 2021/080922 | A1 | 4/2021 |
| WO | WO 2021/081264 | A1 | 4/2021 |
| WO | WO 2021/087182 | A1 | 5/2021 |
| WO | WO 2021/087401 | A1 | 5/2021 |
| WO | WO 2021/108717 | A2 | 6/2021 |
| WO | WO 2021/138469 | A1 | 7/2021 |
| WO | WO 2021/155065 | A1 | 8/2021 |
| WO | WO 2021/158921 | A2 | 8/2021 |
| WO | WO 2021/158995 | A1 | 8/2021 |
| WO | WO 2021/158999 | A1 | 8/2021 |
| WO | WO 2021/178709 | A1 | 9/2021 |
| WO | WO 2021/178717 | A2 | 9/2021 |
| WO | WO 2021/178720 | A2 | 9/2021 |
| WO | WO 2021/178898 | A1 | 9/2021 |
| WO | WO 2021/220020 | A1 | 11/2021 |
| WO | WO 2021/222318 | A1 | 11/2021 |
| WO | WO 2021/226558 | A1 | 11/2021 |
| WO | WO 2022/051250 | A1 | 3/2022 |
| WO | WO 2022/067130 | A2 | 3/2022 |
| WO | WO 2022/075813 | A1 | 4/2022 |
| WO | WO 2022/075816 | A1 | 4/2022 |
| WO | WO 2022/092317 | A1 | 5/2022 |
| WO | WO 2022/150790 | A2 | 7/2022 |
| WO | WO 2022/203905 | A1 | 9/2022 |
| WO | WO 2022/204543 | A1 | 9/2022 |

OTHER PUBLICATIONS

[No Author Listed], "Enediyne" from Wikipedia. Retrieved from https://en.wikipedia.org/w/index.php?title=Enediyne&oldid=1114086576. Page last edited Oct. 4, 2022. Printed on Oct. 7, 2022. 8 pages.

[No Author Listed], "Lambda DNA" from Catalog & Technical Reference. New England Biolabs Inc. 2002/2003. pp. 133 and 270-273.

[No Author Listed], Adenine deaminase polypeptide SEQ: 49. EBI Acc. No. BJG44493. Jun. 10, 2021. 1 page.

[No Author Listed], Cas14a1 protein-N terminal adenine deaminase. EBI Acc. No. BKX98589, Seq. ID 265. May 26, 2022. 3 pages.

[No Author Listed], dCas9-5xPlat2AflD-P2A-scFvGCN4sfGFPTET1CD [Cloning vector pPlatTET-gRNA2]. GenBank No. BAV54124. Apr. 18, 2017. 5 pages.

[No Author Listed], Gag-Pol polyprotein. UniProtKB/Swiss-Prot No. P03355.5. Sep. 18, 2019. 18 pages.

[No Author Listed], *Homo sapiens* signal transducer and activator of transcription 3 (STAT3), transcript variant 1, mRNA. NCBI Ref Seq No. NM_139276.2. Retrieved from https://www.ncbi.nlm.nih.gov/nuccore/nm_139276.2. Feb. 26, 2020. 8 pages.

[No Author Listed], *Homo sapiens* survival of motor neuron 2, centromeric (SMN2), RefSeqGene (LRG_677) on chromosome 5. NCBI Ref Seq No. NG_008728.1. Aug. 21, 2022. Accessible at https://www.ncbi.nlm.nih.gov/nuccore/NG_008728.1/. 14 pages.

[No Author Listed], Multispecies: tRNA adenosine(34) deaminase TadA [Enterobacteriaceae]. NCBI Ref Seq No. WP_001297409.1. Feb. 28, 2022. Retrieved from https://www.ncbi.nlm.nih.gov/protein/WP_001297409.1/. 2 pages.

[No Author Listed], MutL homolog 1. UniProtKB Acc. No. F1MPG0. May 3, 2011. Accessible at https://rest.uniprot.org/unisave/F1MPG0?format=txt&versions=1. 1 page.

[No Author Listed], *Streptococcus pyogenes* Cas9 protein. EBI Acc. No. BIR16744. Jan. 21, 2021. 1 page.

[No Author Listed], *Streptococcus pyogenes* Cas9 protein. EBI Acc. No. BIR16747. Jan. 21, 2021. 1 page.

[No Author Listed], tRNA-specific adenosine deaminase [*Escherichia coli*]. GenBank Acc. No. CTS26096.1. Accessible at https://www.ncbi.nlm.nih.gov/protein/CTS26096.1. Aug. 22, 2015. 1 page.

[No Author Listed], tumor-specific antigen. Retrieved from http://www.cancer.gov/publications/dictionaries/cancer-terms/def/tumor-specific-antigen. Retrieved on Oct. 7, 2022. 1 page.

Acharya et al., hMSH2 forms specific mispair-binding complexes with hMSH3 and hMSH6. Proc Natl Acad Sci U S A. Nov. 26, 1996;93(24):13629-34. doi: 10.1073/pnas.93.24.13629.

Ai et al., C-terminal Loop Mutations Determine Folding and Secretion Properties of PCSK9. iMedPub J: Biochem Mol Biol J. Nov. 5, 2016;2(3):17. doi: 10.21767/2471-8084.100026. 12 pages.

(56) References Cited

OTHER PUBLICATIONS

Alizadeh et al., HR9: An Important Cell Penetrating Peptide for Delivery of HCV NS3 DNA into HEK-293T Cells. Avicenna J Med Biotechnol. Jan.-Mar. 2020;12(1):44-51.

Alves et al., Immunogenicity of the carcinoembryonic antigen derived peptide 694 in HLA-A2 healthy donors and colorectal carcinoma patients. Cancer Immunol Immunother. Nov. 2007;56(11):1795-805. doi: 10.1007/s00262-007-0323-2. Epub Apr. 20, 2007.

Anzalone et al., Search-and-replace genome editing without double-strand breaks or donor DNA. Nature. Dec. 2019;576(7785):149-157 and Suppl Info. doi: 10.1038/s41586-019-1711-4. Epub Oct. 21, 2019. 72 pages.

Asemissen et al., Identification of a highly immunogenic HLA-A*01-binding T cell epitope of WT1. Clin Cancer Res. Dec. 15, 2006;12(24):7476-82. doi: 10.1158/1078-0432.CCR-06-1337.

Attia et al., Autoimmunity correlates with tumor regression in patients with metastatic melanoma treated with anti-cytotoxic T-lymphocyte antigen-4. J Clin Oncol. Sep. 1, 2005;23(25):6043-53. doi: 10.1200/JCO.2005.06.205. Epub Aug. 8, 2005.

Aurisicchio et al., A novel minigene scaffold for therapeutic cancer vaccines. Oncoimmunology. Jan. 1, 2014;3(1):e27529. doi: 10.4161/onci.27529. Epub Jan. 16, 2014.

Avidan et al., Expression and characterization of a recombinant novel reverse transcriptase of a porcine endogenous retrovirus. Virology. Mar. 15, 2003;307(2):341-57. doi: 10.1016/s0042-6822(02)00131-9.

Baba et al., Construction of *Escherichia coli* K-12 in-frame, single-gene knockout mutants: the Keio collection. Mol Syst Biol. 2006;2:2006.0008. doi: 10.1038/msb4100050. Epub Feb. 21, 2006.

Bae et al., Heteroclitic CD33 peptide with enhanced anti-acute myeloid leukemic immunogenicity. Clin Cancer Res. Oct. 15, 2004;10(20):7043-52. doi: 10.1158/1078-0432.CCR-04-0322.

Bae et al., Identification of novel CD33 antigen-specific peptides for the generation of cytotoxic T lymphocytes against acute myeloid leukemia. Cell Immunol. Jan. 2004;227(1):38-50. doi: 10.1016/j.cellimm.2004.01.002.

Bakker et al., Analogues of CTL epitopes with improved MHC class-I binding capacity elicit anti-melanoma CTL recognizing the wild-type epitope. Int J Cancer. Jan. 27, 1997;70(3):302-9. doi: 10.1002/(sici)1097-0215(19970127)70:3<302::aid-ijc10>3.0.co;2-h.

Banerjee et al., Viral glycoproteins: biological role and application in diagnosis. Virusdisease. Mar. 2016;27(1):1-11. doi: 10.1007/s13337-015-0293-5. Epub Jan. 18, 2016.

Banskota et al., Engineered virus-like particles for efficient in vivo delivery of therapeutic proteins. Cell. Jan. 20, 2022;185(2):250-265.e16. doi: 10.1016/j.cell.2021.12.021. Epub Jan. 11, 2022.

Barrera-Paez et al., Mitochondrial genome engineering coming-of-age. Trends Genet. Aug. 2022;38(8):869-880. doi: 10.1016/j.tig.2022.04.011. Epub May 19, 2022. Erratum in: Trends Genet. Aug. 26, 2022.

Barve et al., Induction of immune responses and clinical efficacy in a phase II trial of IDM-2101, a 10-epitope cytotoxic T-lymphocyte vaccine, in metastatic non-small-cell lung cancer. J Clin Oncol. Sep. 20, 2008;26(27):4418-25. doi: 10.1200/JCO.2008.16.6462.

Basila et al., Minimal 2'-O-methyl phosphorothioate linkage modification pattern of synthetic guide RNAs for increased stability and efficient CRISPR-Cas9 gene editing avoiding cellular toxicity. PLoS One. Nov. 27, 2017;12(11):e0188593. doi: 10.1371/journal.pone.0188593.

Bass, B.L., RNA editing by adenosine deaminases that act on RNA. Annu Rev Biochem. 2002;71:817-46. doi: 10.1146/annurev.biochem.71.110601.135501. Epub Nov. 9, 2001.

Baños-Sanz et al., Crystal structure and functional insights into uracil-DNA glycosylase inhibition by phage Φ29 DNA mimic protein p56. Nucleic Acids Res. Jul. 2013;41(13):6761-73. doi: 10.1093/nar/gkt395. Epub May 13, 2013.

Benlalam et al., Identification of five new HLA-B*3501-restricted epitopes derived from common melanoma-associated antigens, spontaneously recognized by tumor-infiltrating lymphocytes. J Immunol. Dec. 1, 2003;171(11):6283-9. doi: 10.4049/jimmunol.171.11.6283.

Bernatchez et al., Altered decamer and nonamer from an HLA-A0201-restricted epitope of Survivin differentially stimulate T-cell responses in different individuals. Vaccine. Apr. 5, 2011;29(16):3021-30. doi: 10.1016/j.vaccine.2011.01.115. Epub Feb. 12, 2011.

Bertsimas et al., Simulated annealing. Statistical Science. Feb. 1993;8(1):10-15. doi: 10.1214/ss/1177011077.

Bibikova et al., Targeted chromosomal cleavage and mutagenesis in *Drosophila* using zinc-finger nucleases. Genetics. Jul. 2002;161(3):1169-75. doi: 10.1093/genetics/161.3.1169.

Bioley et al., Melan-A/MART-1-specific CD4 T cells in melanoma patients: identification of new epitopes and ex vivo visualization of specific T cells by MHC class II tetramers. J Immunol. Nov. 15, 2006;177(10):6769-79. doi: 10.4049/jimmunol.177.10.6769.

Blanchet et al., A new generation of Melan-A/MART-1 peptides that fulfill both increased immunogenicity and high resistance to biodegradation: implication for molecular anti-melanoma immunotherapy. J Immunol. Nov. 15, 2001;167(10):5852-61. doi: 10.4049/jimmunol.167.10.5852.

Blauw et al., SMN1 gene duplications are associated with sporadic ALS. Neurology. Mar. 13, 2012;78(11):776-80. doi: 10.1212/WNL.0b013e318249f697. Epub Feb. 8, 2012.

Borbulevych et al., Increased immunogenicity of an anchor-modified tumor-associated antigen is due to the enhanced stability of the peptide/MHC complex: implications for vaccine design. J Immunol. Apr. 15, 2005;174(8):4812-20. doi: 10.4049/jimmunol.174.8.4812.

Bosch et al., Precise genome engineering in *Drosophila* using prime editing. Proc Natl Acad Sci U S A. Jan. 5, 2021;118(1):e2021996118. doi: 10.1073/pnas.2021996118.

Bothmer et al., Characterization of the interplay between DNA repair and CRISPR/Cas9-induced DNA lesions at an endogenous locus. Nat Commun. Jan. 9, 2017;8:13905. doi: 10.1038/ncomms13905.

Brichard et al., A tyrosinase nonapeptide presented by HLA-B44 is recognized on a human melanoma by autologous cytolytic T lymphocytes. Eur J Immunol. Jan. 1996;26(1):224-30. doi: 10.1002/eji.1830260135.

Brutlag et al., Improved sensitivity of biological sequence database searches. Comput Appl Biosci. Jul. 1990;6(3):237-45. doi: 10.1093/bioinformatics/6.3.237.

Cacabelos et al., Chapter 1—The Epigenetic Machinery in the Life Cycle and Pharmacoepigenetics. Pharmacoepigenetics. vol. 10 in Translational Epigenetics. 2019:1-100. doi: https://doi.org/10.1016/B978-0-12-813939-4.00001-2. 7 pages.

Campbell et al., Gesicle-Mediated Delivery of CRISPR/Cas9 Ribonucleoprotein Complex for Inactivating the HIV Provirus. Mol Ther. Jan. 2, 2019;27(1):151-163. doi: 10.1016/j.ymthe.2018.10.002. Epub Oct. 11, 2018.

Campi et al., CD4(+) T cells from healthy subjects and colon cancer patients recognize a carcinoembryonic antigen-specific immunodominant epitope. Cancer Res. Dec. 1, 2003;63(23):8481-6.

Canny et al., Inhibition of 53BP1 Favors Homology-Dependent DNA Repair and Increases CRISPR-Cas9 Genome-Editing Efficiency. Nat Biotechnol. Jan. 2018;36(1):95-102. doi: 10.1038/nbt.4021. Epub Nov. 27, 2017.

Cao et al., Rapamycin reverses cellular phenotypes and enhances mutant protein clearance in Hutchinson-Gilford progeria syndrome cells. Sci Transl Med. Jun. 29, 2011;3(89):89ra58. doi: 10.1126/scitranslmed.3002346.

Carlier et al., Genome Sequence of Burkholderia cenocepacia H111, a Cystic Fibrosis Airway Isolate. Genome Announc. Apr. 10, 2014;2(2):e00298-14. doi: 10.1128/genomeA.00298-14.

Cartegni et al., Determinants of exon 7 splicing in the spinal muscular atrophy genes, SMN1 and SMN2. Am J Hum Genet. Jan. 2006;78(1):63-77. doi: 10.1086/498853. Epub Nov. 16, 2005.

Casnici et al., Immunologic evaluation of peptides derived from BCR/ABL-out-of-frame fusion protein in HLA A2.1 transgenic mice. J Immunother. May 2012;35(4):321-8. doi: 10.1097/CJI.0b013e3182562d37.

(56) References Cited

OTHER PUBLICATIONS

Casnici et al., Out of frame peptides from BCR/ABL alternative splicing are immunogenic in HLA A2.1 transgenic mice. Cancer Lett. Apr. 8, 2009;276(1):61-7. doi: 10.1016/j.canlet.2008.10.032. Epub Dec. 4, 2008.
Castelli et al., Mass spectrometric identification of a naturally processed melanoma peptide recognized by CD8+ cytotoxic T lymphocytes. J Exp Med. Jan. 1, 1995;181(1):363-8. doi: 10.1084/jem.181.1.363.
Castelli et al., Novel HLA-Cw8-restricted T cell epitopes derived from tyrosinase-related protein-2 and gp100 melanoma antigens. J Immunol. Feb. 1, 1999;162(3):1739-48.
Castle et al., Exploiting the mutanome for tumor vaccination. Cancer Res. Mar. 1, 2012;72(5):1081-91. doi: 10.1158/0008-5472.CAN-11-3722. Epub Jan. 11, 2012.
Cervera et al., Generation of HIV-1 Gag VLPs by transient transfection of HEK 293 suspension cell cultures using an optimized animal-derived component free medium. J Biotechnol. Jul. 20, 2013;166(4):152-65. doi: 10.1016/j.jbiotec.2013.05.001. Epub May 17, 2013.
Chang et al., Degradation of survival motor neuron (SMN) protein is mediated via the ubiquitin/proteasome pathway. Neurochem Int. Dec. 2004;45(7):1107-12. doi: 10.1016/j.neuint.2004.04.005.
Chao et al., Measurement of large serine integrase enzymatic characteristics in HEK293 cells reveals variability and influence on downstream reporter expression. FEBS J. Nov. 2021;288(22):6410-6427. doi: 10.1111/febs.16037. Epub Jun. 23, 2021.
Chatterjee et al., A Cas9 with PAM recognition for adenine dinucleotides. Nat Commun. May 18, 2020;11(1):2474. doi: 10.1038/s41467-020-16117-8.
Chatterjee et al., Robust Genome Editing of Single-Base PAM Targets; with Engineered ScCas9 Variants. bioRxiv. doi: 10.1101/620351. Posted Apr. 26, 2019.
Chen et al., Dynamic imaging of genomic loci in living human cells by an optimized CRISPR/Cas system. Cell. Dec. 19, 2013;155(7):1479-91. doi: 10.1016/j.cell.2013.12.001. Erratum in: Cell. Jan. 16, 2014;156(1-2):373.
Chen et al., Identification of NY-ESO-1 peptide analogues capable of improved stimulation of tumor-reactive CTL. J Immunol. Jul. 15, 2000;165(2):948-55. doi: 10.4049/jimmunol.165.2.948.
Chen et al., Programmable C:G to G:C genome editing with CRISPR-Cas9-directed base excision repair proteins. Nat Commun. Mar. 2, 2021;12(1):1384. doi: 10.1038/s41467-021-21559-9.
Cheng et al., [Cloning,expression and activity identification of human innate immune protein apolipoprotein B mRNA editing enzyme catalytic subunit 3A(APOBEC3A)]. Xi Bao Yu Fen Zi Mian Yi Xue Za Zhi. Chinese Journal of Cellular and Molecular Immunology, Feb. 2017;33(2):179-84. Chinese.
Cheriyan et al., Faster protein splicing with the Nostoc punctiforme DnaE intein using non-native extein residues. J Biol Chem. Mar. 1, 2013;288(9):6202-11. doi: 10.1074/jbc.M112.433094. Epub Jan. 10, 2013.
Cho et al., A degron created by SMN2 exon 7 skipping is a principal contributor to spinal muscular atrophy severity. Genes Dev. Mar. 1, 2010;24(5):438-42. doi: 10.1101/gad.1884910.
Cho et al., Optimized peptide vaccines eliciting extensive CD8 T-cell responses with therapeutic antitumor effects. Cancer Res. Dec. 1, 2009;69(23):9012-9. doi: 10.1158/0008-5472.CAN-Sep. 2019. Epub Nov. 10, 2009.
Choi et al., Lentivirus pre-packed with Cas9 protein for safer gene editing. Gene Ther. Jul. 2016;23(7):627-33. doi: 10.1038/gt.2016.27. Epub Apr. 7, 2016.
Choi et al., Optimization of AAV expression cassettes to improve packaging capacity and transgene expression in neurons. Mol Brain. Mar. 11, 2014;7:17. doi: 10.1186/1756-6606-7-17.
Christensen et al., Melan-A/MART1 analog peptide triggers anti-myeloma T-cells through crossreactivity with HM1.24. J Immunother. Jul.-Aug. 2009 32(6):613-21. doi: 10.1097/CJI.0b013e3181a95198.
Corcia et al., The importance of the SMN genes in the genetics of sporadic ALS. Amyotroph Lateral Scler. Oct.-Dec. 2009;10(5-6):436-40. doi: 10.3109/17482960902759162.
Correale et al., In vitro generation of human cytotoxic T lymphocytes specific for peptides derived from prostate-specific antigen. J Natl Cancer Inst. Feb. 19, 1997;89(4):293-300. doi: 10.1093/jnci/89.4.293.
Corti et al., Genetic correction of human induced pluripotent stem cells from patients with spinal muscular atrophy. Sci Transl Med. Dec. 19, 2012;4(165):165ra162. doi: 10.1126/scitranslmed.3004108.
Cox et al., Identification of a peptide recognized by five melanoma-specific human cytotoxic T cell lines. Science. Apr. 29, 1994;264(5159):716-9. doi: 10.1126/science.7513441.
Cronin et al., Altering the tropism of lentiviral vectors through pseudotyping. Curr Gene Ther. Aug. 2005;5(4):387-98. doi: 10.2174/1566523054546224. Erratum in: Curr Gene Ther. Oct. 2005;5(5):531. Author Manuscript, 19 pages.
Crosti et al., Identification of novel subdominant epitopes on the carcinoembryonic antigen recognized by CD4+ T cells of lung cancer patients. J Immunol. Apr. 15, 2006;176(8):5093-9. doi: 10.4049/jimmunol.176.8.5093.
Cucchiarini et al., Enhanced expression of the central survival of motor neuron (SMN) protein during the pathogenesis of osteoarthritis. J Cell Mol Med. Jan. 2014;18(1):115-24. doi: 10.1111/jcmm.12170. Epub Nov. 17, 2013.
Cui et al., KPT330 improves Cas9 precision genome- and base-editing by selectively regulating mRNA nuclear export. Commun Biol. Mar. 17, 2022;5(1):237. doi: 10.1038/s42003-022-03188-0.
D'Ydewalle et al., The Antisense Transcript SMN-AS1 Regulates SMN Expression and Is a Novel Therapeutic Target for Spinal Muscular Atrophy. Neuron. Jan. 4, 2017;93(1):66-79 and Supplemental Information. doi: 10.1016/j.neuron.2016.11.033. Epub Dec. 22, 2016.
Dalet et al., An antigenic peptide produced by reverse splicing and double asparagine deamidation. Proc Natl Acad Sci U S A. Jul. 19, 2011;108(29):E323-31. doi: 10.1073/pnas.1101892108. Epub Jun. 13, 2011.
Damdindorj et al., A comparative analysis of constitutive promoters located in adeno-associated viral vectors. PLoS One. Aug. 29, 2014;9(8):e106472. doi: 10.1371/journal.pone.0106472.
David et al., Viral Vectors: The Road to Reducing Genotoxicity. Toxicol Sci. Feb. 2017;155(2):315-325. doi: 10.1093/toxsci/kfw220. Epub Nov. 1, 2016.
Davis et al., Assaying Repair at DNA Nicks. Methods Enzymol. 2018;601:71-89. doi: 10.1016/bs.mie.2017.12.001. Epub Feb. 1, 2018.
Davis et al., Efficient in vivo base editing via single adeno-associated viruses with size-optimized genomes encoding compact adenine base editors. Nat Biomed Eng. Nov. 2022;6(11):1272-1283. doi: 10.1038/s41551-022-00911-4. Epub Jul. 28, 2022. Erratum in: Nat Biomed Eng. Aug. 5, 2022.
Davis et al., Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014.
Davis et al., Two Distinct Pathways Support Gene Correction by Single-Stranded Donors at DNA Nicks. Cell Rep. Nov. 8, 2016;17(7):1872-1881. doi: 10.1016/j.celrep.2016.10.049.
De Sandre-Giovannoli et al., Lamin a truncation in Hutchinson-Gilford progeria. Science. Jun. 27, 2003;300(5628):2055. doi: 10.1126/science.1084125. Epub Apr. 17, 2003.
Depontieu et al., Identification of tumor-associated, MHC class II-restricted phosphopeptides as targets for immunotherapy. Proc Natl Acad Sci U S A. Jul. 21, 2009;106(29):12073-8. doi: 10.1073/pnas.0903852106. Epub Jul. 6, 2009.
Di Stasi et al., Review of the Results of WT1 Peptide Vaccination Strategies for Myelodysplastic Syndromes and Acute Myeloid Leukemia from Nine Different Studies. Front Immunol. Feb. 4, 2015;6:36. doi: 10.3389/fimmu.2015.00036.
Dickinson et al., A system for the continuous directed evolution of proteases rapidly reveals drug-resistance mutations. Nat Commun. Oct. 30, 2014;5:5352. doi: 10.1038/ncomms6352.

(56) References Cited

OTHER PUBLICATIONS

Ding et al., Gene therapy for cardiovascular disease. Journal of Shanghai University (Natural Science Edition) . 2016;3:270-9 . DOI: 10.3969/j.issn.1007-2861.2016.03.013.
Doman et al., Designing and executing prime editing experiments in mammalian cells. Nat Protoc. Nov. 2022;17(11):2431-2468. doi: 10.1038/s41596-022-00724-4. Epub Aug. 8, 2022.
Drenth et al., Mutations in sodium-channel gene SCN9A cause a spectrum of human genetic pain disorders. J Clin Invest. Dec. 2007;117(12):3603-9. doi: 10.1172/JCI33297.
Drost et al., Inactivation of DNA mismatch repair by variants of uncertain significance in the PMS2 gene. Hum Mutat. Nov. 2013;34(11):1477-80. doi: 10.1002/humu.22426. Epub Sep. 11, 2013.
Duan et al., Immune rejection of mouse tumors expressing mutated self. Cancer Res. Apr. 15, 2009;69(8):3545-53. doi: 10.1158/0008-5472.CAN-08-2779. Epub Apr. 7, 2009. Author Manuscript. 18 pages.
Dugar et al., CRISPR RNA-Dependent Binding and Cleavage of Endogenous RNAs by the Campylobacter jejuni Cas9. Mol Cell. Mar. 1, 2018;69(5):893-905.e7. doi: 10.1016/j.molcel.2018.01.032.
Duportet et al., A platform for rapid prototyping of synthetic gene networks in mammalian cells. Nucleic Acids Res. Dec. 1, 2014;42(21):13440-51. doi: 10.1093/nar/gku1082. Epub Nov. 5, 2014.
Edraki et al., A Compact, High-Accuracy Cas9 with a Dinucleotide PAM for in Vivo Genome Editing. Mol Cell. Feb. 21, 2019;73(4):714-726.e4 and Supplemental Info. doi: 10.1016/j.molcel.2018.12.003. Epub Dec. 20, 2018.
Eisenberg et al., A-to-I RNA editing—immune protector and transcriptome diversifier. Nat Rev Genet. Aug. 2018;19(8):473-490. doi: 10.1038/s41576-018-0006-1.
Ekman et al., CRISPR-Cas9-Mediated Genome Editing Increases Lifespan and Improves Motor Deficits in a Huntington's Disease Mouse Model. Mol Ther Nucleic Acids. Sep. 6, 2019;17:829-839. doi: 10.1016/j.omtn.2019.07.009. Epub Jul. 26, 2019.
Ekstrand et al., Frequent alterations of the PI3K/AKT/mTOR pathways in hereditary nonpolyposis colorectal cancer. Fam Cancer. Jun. 2010;9(2):125-9. doi: 10.1007/s10689-009-9293-1.
Entin-Meer et al., The role of phenylalanine-119 of the reverse transcriptase of mouse mammary tumour virus in DNA synthesis, ribose selection and drug resistance. Biochem J. Oct. 15, 2002;367(Pt 2):381-91. doi: 10.1042/BJ20020712.
Eriksen et al., Occlusion of the Ribosome Binding Site Connects the Translational Initiation Frequency, mRNA Stability and Premature Transcription Termination. Front Microbiol. Mar. 14, 2017;8:362. doi: 10.3389/fmicb.2017.00362.
Fang et al., Human strand-specific mismatch repair occurs by a bidirectional mechanism similar to that of the bacterial reaction. J Biol Chem. Jun. 5, 1993;268(16):11838-44.
Fang et al., The Menu of Features that Define Primary MicroRNAs and Enable De Novo Design of MicroRNA Genes. Mol Cell. Oct. 1, 2015;60(1):131-45. doi: 10.1016/j.molcel.2015.08.015. Epub Sep. 24, 2015.
Feng et al., Efficient genome editing in plants using a CRISPR/Cas system. Cell Res. Oct. 2013;23(10):1229-32. doi: 10.1038/cr.2013.114. Epub Aug. 20, 2013.
Fields et al., Gene targeting techniques for Huntington's disease. Ageing Res Rev. Sep. 2021;70:101385. doi: 10.1016/j.arr.2021.101385. Epub Jun. 5, 2021.
Fikes et al., Design of multi-epitope, analogue-based cancer vaccines. Expert Opin Biol Ther. Sep. 2003;3(6):985-93. doi: 10.1517/14712598.3.6.985.
Fishel et al., The human mutator gene homolog MSH2 and its association with hereditary nonpolyposis colon cancer. Cell. Dec. 3, 1993;75(5):1027-38. doi: 10.1016/0092-8674(93)90546-3. Erratum in: Cell. Apr. 8, 1994;77(1):1 p following 166.
Fontana et al., Rabies virus-like particles expressed in HEK293 cells. Vaccine. May 19, 2014;32(24):2799-804. doi: 10.1016/j.vaccine.2014.02.031. Epub Mar. 12, 2014.
Fonteneau et al., The Tumor Antigen NY-ESO-1 Mediates Direct Recognition of Melanoma Cells by CD4+ T Cells after Intercellular Antigen Transfer. J Immunol. Jan. 1, 2016;196(1):64-71. doi: 10.4049/jimmunol.1402664. Epub Nov. 25, 2015.
Fourcade et al., PD-1 and Tim-3 regulate the expansion of tumor antigen-specific CD8? T cells induced by melanoma vaccines. Cancer Res. Feb. 15, 2014;74(4):1045-55. doi: 10.1158/0008-5472.CAN-13-2908. Epub Dec. 16, 2013.
Fridman et al., An efficient T-cell epitope discovery strategy using in silico prediction and the iTopia assay platform. Oncoimmunology. Nov. 1, 2012;1(8):1258-1270. doi: 10.4161/onci.21355.
Friedman, J. H., Greedy function approximation: A gradient boosting machine. Ann. Statist. Oct. 2001;29(5):1189-232. doi: 10.1214/aos/1013203451.
Fu et al., Targeted genome editing in human cells using CRISPR/Cas nucleases and truncated guide RNAs. Methods Enzymol. 2014;546:21-45. doi: 10.1016/B978-0-12-801185-0.00002-7.
Fujiki et al., Identification and characterization of a WT1 (Wilms Tumor Gene) protein-derived HLA-DRB1*0405-restricted 16-mer helper peptide that promotes the induction and activation of WT1-specific cytotoxic T lymphocytes. J Immunother. Apr. 2007;30(3):282-93. doi: 10.1097/01.cji.0000211337.91513.94.
Gao et al., A truncated reverse transcriptase enhances prime editing by split AAV vectors. Mol Ther. Sep. 7, 2022;30(9):2942-2951 and Supplemental Info. doi: 10.1016/j.ymthe.2022.07.001. Epub Jul. 8, 2022. 23 pages.
Gaudelli et al., Directed evolution of adenine base editors with increased activity and therapeutic application. Nat Biotechnol. Jul. 2020;38(7):892-900. doi: 10.1038/s41587-020-0491-6. Epub Apr. 13, 2020.
Gee et al., Extracellular nanovesicles for packaging of CRISPR-Cas9 protein and sgRNA to induce therapeutic exon skipping. Nat Commun. Mar. 13, 2020;11(1):1334. doi: 10.1038/s41467-020-14957-y.
Geisberg et al., Global analysis of mRNA isoform half-lives reveals stabilizing and destabilizing elements in yeast. Cell. Feb. 13, 2014;156(4):812-24. doi: 10.1016/j.cell.2013.12.026.
GenBank Access No. BAP64357. Aug. 1, 2013 1 page.
Genbank Submission; NIH/NCBI, Accession No. NC_000001.11. Gregory et al., Jun. 6, 2016. 3 pages.
Genbank Submission; NIH/NCBI, Accession No. NG_008692.2. McClintock et al., Aug. 27, 2018. 33 pages.
Genbank Submission; NIH/NCBI, Accession No. NM_206933.2. Khalaileh et al., Sep. 16, 2018. 12 pages.
Genbank Submission; NIH/NCBI, Accession No. NP_001075493.1. Schiaffella et al., Jun. 24, 2018. 2 pages.
Genbank Submission; NIH/NCBI, Accession No. NP_001157741.1. Zeng et al., Sep. 17, 2018. 3 pages.
Genbank Submission; NIH/NCBI, Accession No. NP_001157742.1. Zeng et al., Oct. 21, 2018. 3 pages.
Genbank Submission; NIH/NCBI, Accession No. NP_033040.2. Liu et al., Jun. 23, 2018. 2 pages.
Genbank Submission; NIH/NCBI, Accession No. NP_060228.2. Bi et al., Dec. 21, 2005. 1 page.
Genbank Submission; NIH/NCBI, Accession No. NP_062826.2. Bokar et al., Sep. 18, 2004. 2 pages.
Genbank Submission; NIH/NCBI, Accession No. NP_066012.1. Ota et al., Apr. 3, 2005. 2 pages.
Genbank Submission; NIH/NCBI, Accession No. NP_996816.2. Fu et al., Sep. 22, 2019. 9 pages.
Genbank Submission; NIH/NCBI, Accession No. WP_042518169.1. No Author, Feb. 10, 2015. 1 page.
Genbank Submission; NIH/NCBI, Accession No. XP_003314669.1. No Author Listed, Mar. 20, 2018. 2 pages.
Genbank Submission; NIH/NCBI, Accession No. XP_026671085.1. No Author Listed, Oct. 17, 2018. 1 page.
Geng et al., In vitro studies of DNA mismatch repair proteins. Anal Biochem. Jun. 15, 2011;413(2):179-84. doi: 10.1016/j.ab.2011.02.017. Epub Feb. 15, 2011.
Genschel et al., Human exonuclease I is required for 5' and 3' mismatch repair. J Biol Chem. Apr. 12, 2002;277(15):13302-11. doi: 10.1074/jbc.M111854200. Epub Jan. 24, 2002.

(56) References Cited

OTHER PUBLICATIONS

Genschel et al., Isolation of MutSbeta from human cells and comparison of the mismatch repair specificities of MutSbeta and MutSalpha. J Biol Chem. Jul. 31, 1998;273(31):19895-901. doi: 10.1074/jbc.273.31.19895. Erratum in: J Biol Chem Oct. 9, 1998;273(41):27034.

Geynisman et al., A randomized pilot phase I study of modified carcinoembryonic antigen (CEA) peptide (CAP1-6D)/montanide/GM-CSF-vaccine in patients with pancreatic adenocarcinoma. J Immunother Cancer. Jun. 27, 2013;1:8. doi: 10.1186/2051-1426-1-8.

Ghosh et al., Synapsis in phage Bxb1 integration: selection mechanism for the correct pair of recombination sites. J Mol Biol. Jun. 3, 2005;349(2):331-48. doi: 10.1016/j.jmb.2005.03.043. Epub Apr. 7, 2005.

Girard-Gagnepain et al., Baboon envelope pseudotyped LVs outperform VSV-G-LVs for gene transfer into early-cytokine-stimulated and resting HSCs. Blood. Aug. 21, 2014;124(8):1221-31. doi: 10.1182/blood-2014-02-558163. Epub Jun. 20, 2014.

Godefroy et al., Identification of two Melan-A CD4+ T cell epitopes presented by frequently expressed MHC class II alleles. Clin Immunol. Oct. 2006;121(1):54-62. doi: 10.1016/j.clim.2006.05.007. Epub Jun. 30, 2006.

Graff-Dubois et al., Generation of CTL recognizing an HLA-A*0201-restricted epitope shared by MAGE-A1, -A2, -A3, -A4, -A6, -A10, and -A12 tumor antigens: implication in a broad-spectrum tumor immunotherapy. J Immunol. Jul. 1, 2002;169(1):575-80. doi: 10.4049/jimmunol.169.1.575.

Grati et al., Localization of PDZD7 to the stereocilia ankle-link associates this scaffolding protein with the Usher syndrome protein network. J Neurosci. Oct. 10, 2012;32(41):14288-93. doi: 10.1523/JNEUROSCI.3071-12.2012.

Green et al., Characterization of the mechanical unfolding of RNA pseudoknots. J Mol Biol. Jan. 11, 2008;375(2):511-28. doi: 10.1016/j.jmb.2007.05.058. Epub May 26, 2007.

Gross et al., High vaccination efficiency of low-affinity epitopes in antitumor immunotherapy. J Clin Invest. Feb. 2004;113(3):425-33. doi: 10.1172/JCI19418.

Gueneau et al., Structure of the MutLα C-terminal domain reveals how Mlh1 contributes to Pms1 endonuclease site. Nat Struct Mol Biol. Apr. 2013;20(4):461-8. doi: 10.1038/nsmb.2511. Epub Feb. 24, 2013.

Guerrette et al., The interaction of the human MutL homologues in hereditary nonpolyposis colon cancer. J Biol Chem. Mar. 5, 1999;274(10):6336-41. doi: 10.1074/jbc.274.10.6336.

Guevara-Patiño et al., Optimization of a self antigen for presentation of multiple epitopes in cancer immunity. J Clin Invest. May 2006;116(5):1382-90. doi: 10.1172/JCI25591. Epub Apr. 13, 2006.

Guibinga et al., Cell surface heparan sulfate is a receptor for attachment of envelope protein-free retrovirus-like particles and VSV-G pseudotyped MLV-derived retrovirus vectors to target cells. Mol Ther. May 2002;5(5 Pt 1):538-46. doi: 10.1006/mthe.2002.0578.

Gulley et al., Combining a Recombinant Cancer Vaccine with Standard Definitive Radiotherapy in Patients with Localized Prostate Cancer. Clin Cancer Res. May 2, 2005;11(9):3353-62. doi: 10.1158/1078-0432.CCR-04-2062.

Guo et al., Direct recognition and lysis of leukemia cells by WT1-specific CD4+ T lymphocytes in an HLA class II-restricted manner. Blood. Aug. 15, 2005;106(4):1415-8. doi: 10.1182/blood-2005-01-0413. Epub Apr. 21, 2005.

Guo et al., Precision modeling of mitochondrial diseases in zebrafish via DdCBE-mediated mtDNA base editing. Cell Discov. Sep. 3, 2021;7(1):78. doi: 10.1038/s41421-021-00307-9.

Gupta et al., Mechanism of mismatch recognition revealed by human MutSβ bound to unpaired DNA loops. Nat Struct Mol Biol. Dec. 18, 2011;19(1):72-8. doi: 10.1038/nsmb.2175.

Gutkin et al., RNA delivery with a human virus-like particle. Nat Biotechnol. Dec. 2021;39(12):1514-1515. doi: 10.1038/s41587-021-01124-x.

Gutschner et al., Post-translational Regulation of Cas9 during G1 Enhances Homology-Directed Repair. Cell Rep. Feb. 16, 2016;14(6):1555-1566. doi: 10.1016/j.celrep.2016.01.019. Epub Feb. 4, 2016.

Haeussler et al., Genome Editing with CRISPR-Cas9: Can It Get Any Better? J Genet Genomics. May 20, 2016;43(5):239-50. doi: 10.1016/j.jgg.2016.04.008. Epub Apr. 24, 2016. Author Manuscript. 22 pages.

Hagen et al., A high rate of polymerization during synthesis of mouse mammary tumor virus DNA alleviates hypermutation by APOBEC3 proteins. PLoS Pathog. Feb. 15, 2019;15(2):e1007533. doi: 10.1371/journal.ppat.1007533.

Hamilton et al., Targeted delivery of CRISPR-Cas9 and transgenes enables complex immune cell engineering. Cell Rep. Jun. 1, 2021;35(9):109207 and Suppl Info. doi: 10.1016/j.celrep.2021.109207.

Hamilton et al., Targeted delivery of CRISPR-Cas9 and transgenes enables complex immune cell engineering. Cell Rep. Jun. 1, 2021;35(9):109207. doi: 10.1016/j.celrep.2021.109207.

Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.

Hart et al., High-Resolution CRISPR Screens Reveal Fitness Genes and Genotype-Specific Cancer Liabilities. Cell. Dec. 3, 2015;163(6):1515-26. doi: 10.1016/j.cell.2015.11.015. Epub Nov. 25, 2015.

Hawley-Nelson et al., Transfection of Cultured Eukaryotic Cells Using Cationic Lipid Reagents. Curr Prot Mol Biol. Jan. 2008;9.4.1-9.4.17. doi: 10.102/0471142727.mb0904s81. 17 pages.

Hendel et al., Chemically modified guide RNAs enhance CRISPR-Cas genome editing in human primary cells. Nat Biotechnol. Sep. 2015;33(9):985-989. doi: 10.1038/nbt.3290. Epub Jun. 29, 2015. Author Manuscript. 14 pages.

Herbst-Kralovetz et al., Norwalk virus-like particles as vaccines. Expert Rev Vaccines. Mar. 2010;9(3):299-307. doi: 10.1586/erv.09.163. Author Manuscript, 16 pages.

Heyer et al., Regulation of homologous recombination in eukaryotes. Annu Rev Genet. 2010;44:113-39. doi: 10.1146/annurev-genet-051710-150955. Author Manuscript. 33 pages.

Hirohashi et al., An HLA-A24-restricted cytotoxic T lymphocyte epitope of a tumor-associated protein, survivin. Clin Cancer Res. Jun. 2002;8(6):1731-9.

Hizi et al., Retroviral reverse transcriptases (other than those of HIV-1 and murine leukemia virus): a comparison of their molecular and biochemical properties. Virus Res. Jun. 2008;134(1-2):203-20. doi: 10.1016/j.virusres.2007.12.008. Epub Mar. 3, 2008.

Hong et al., Novel recombinant hepatitis B virus vectors efficiently deliver protein and RNA encoding genes into primary hepatocytes. J Virol. Jun. 2013;87(12):6615-24. doi: 10.1128/JVI.03328-12. Epub Apr. 3, 2013.

Houck-Loomis et al., An equilibrium-dependent retroviral mRNA switch regulates translational recoding. Nature. Nov. 27, 2011;480(7378):561-4. doi: 10.1038/nature 10657.

Houghton et al., Immunological validation of the EpitOptimizer program for streamlined design of heteroclitic epitopes. Vaccine. Jul. 20, 2007;25(29):5330-42. doi: 10.1016/j.vaccine.2007.05.008. Epub Jun. 4, 2007.

Houseley et al., The many pathways of RNA degradation. Cell. Feb. 20, 2009;136(4):763-76. doi: 10.1016/j.cell.2009.01.019.

Hu et al., Discovery and engineering of small SlugCas9 with broad targeting range and high specificity and activity. Nucleic Acids Res. Apr. 19, 2021;49(7):4008-4019. doi: 10.1093/nar/gkab148.

Huang et al., Gain-of-function mutations in sodium channel Na(v)1.9 in painful neuropathy. Brain. Jun. 2014;137(Pt 6):1627-42. doi: 10.1093/brain/awu079. Epub Apr. 27, 2014.

Humbel et al., Maximizing lentiviral vector gene transfer in the CNS. Gene Ther. Feb. 2021;28(1-2):75-88. doi: 10.1038/s41434-020-0172-6. Epub Jul. 6, 2020. Erratum in: Gene Ther. May 2022;29(5):312.

Hussman et al., Mapping the genetic landscape of DNA double-strand break repair. Cell. Oct. 28, 2021;184(22):5653-5669.e25. doi: 10.1016/j.cell.2021.10.002. Epub Oct. 20, 2021.

(56) References Cited

OTHER PUBLICATIONS

Hwang et al., Heritable and precise zebrafish genome editing using a CRISPR-Cas system. PLoS One. Jul. 9, 2013;8(7):e68708. doi: 10.1371/journal.pone.0068708.

Hänsel-Hertsch et al., DNA G-quadruplexes in the human genome: detection, functions and therapeutic potential. Nat Rev Mol Cell Biol. May 2017;18(5):279-284. doi: 10.1038/nrm.2017.3. Epub Feb. 22, 2017.

Iaccarino et al., hMSH2 and hMSH6 play distinct roles in mismatch binding and contribute differently to the ATPase activity of hMutSalpha. EMBO J. May 1, 1998;17(9):2677-86. doi: 10.1093/emboj/17.9.2677.

Ibrahim et al., RNA recognition by 3'-to-5' exonucleases: the substrate perspective. Biochim Biophys Acta. Apr. 2008;1779(4):256-65. doi: 10.1016/j.bbagrm.2007.11.004. Epub Dec. 3, 2007.

Indikova et al., Highly efficient 'hit-and-run' genome editing with unconcentrated lentivectors carrying Vpr.Prot.Cas9 protein produced from RRE-containing transcripts. Nucleic Acids Res. Aug. 20, 2020;48(14):8178-8187. doi: 10.1093/nar/gkaa561.

Ishizuka et al., Loss of ADAR1 in tumours overcomes resistance to immune checkpoint blockade. Nature. Jan. 2019;565(7737):43-48. doi: 10.1038/s41586-018-0768-9. Epub Dec. 17, 2018.

Iyama et al., DNA repair mechanisms in dividing and non-dividing cells. DNA Repair (Amst). Aug. 2013;12(8):620-36. doi: 10.1016/j.dnarep.2013.04.015. Epub May 16, 2013.

Iyer et al., DNA mismatch repair: functions and mechanisms. Chem Rev. Feb. 2006;106(2):302-23. doi: 10.1021/cr0404794.

Jakimo et al., A Cas9 with Complete PAM Recognition for Adenine Dinucleotides. bioRxiv preprint. Sep. 27, 2018. doi.org/10.1101/429654. 29 pages.

Jalaguier et al., Efficient production of HIV-1 virus-like particles from a mammalian expression vector requires the N-terminal capsid domain. PLoS One. 2011;6(11):e28314. doi: 10.1371/journal.pone.0028314. Epub Nov. 30, 2011.

Jaramillo et al., Identification of HLA-A3-restricted CD8+ T cell epitopes derived from mammaglobin-A, a tumor-associated antigen of human breast cancer. Int J Cancer. Dec. 10, 2002;102(5):499-506. doi: 10.1002/ijc.10736.

Jeong et al., Current Status and Challenges of DNA Base Editing Tools. Mol Ther. Sep. 2, 2020;28(9):1938-1952. doi: 10.1016/j.ymthe.2020.07.021. Epub Jul. 23, 2020.

Jiao et al., Random-PE: an efficient integration of random sequences into mammalian genome by prime editing. Mol Biomed. Nov. 18, 2021;2(1):36. doi: 10.1186/s43556-021-00057-w.

Jost et al., Titrating gene expression using libraries of systematically attenuated CRISPR guide RNAs. Nat Biotechnol. Mar. 2020;38(3):355-364. doi: 10.1038/s41587-019-0387-5. Epub Jan. 13, 2020.

Kaczmarczyk et al., Protein delivery using engineered virus-like particles. Proc Natl Acad Sci U S A. Oct. 11, 2011;108(41):16998-7003. doi: 10.1073/pnas.1101874108. Epub Sep. 26, 2011.

Kadyrov et al., Endonucleolytic function of MutLalpha in human mismatch repair. Cell. Jul. 28, 2006;126(2):297-308. doi: 10.1016/j.cell.2006.05.039.

Kan et al., Mechanisms of precise genome editing using oligonucleotide donors. Genome Res. Jul. 2017;27(7):1099-1111. doi: 10.1101/gr.214775.116. Epub Mar. 29, 2017.

Kang et al., Chimeric rabies virus-like particles containing membrane-anchored GM-CSF enhances the immune response against rabies virus. Viruses. Mar. 11, 2015;7(3):1134-52. doi: 10.3390/v7031134.

Kang et al., Chloroplast and mitochondrial DNA editing in plants. Nat Plants. Jul. 2021;7(7):899-905. doi: 10.1038/s41477-021-00943-9. Epub Jul. 1, 2021.

Kang et al., Identification of a tyrosinase epitope recognized by HLA-A24-restricted, tumor-infiltrating lymphocytes. J Immunol. Aug. 1, 1995;155(3):1343-8.

Karbach et al., Long-term complete remission following radiosurgery and immunotherapy in a melanoma patient with brain metastasis: immunologic correlates. Cancer Immunol Res. May 2014;2(5):404-9. doi: 10.1158/2326-6066.CIR-13-0200. Epub Feb. 5, 2014.

Karimian et al., CRISPR/Cas9 novel therapeutic road for the treatment of neurodegenerative diseases. Life Sci. Oct. 15, 2020;259:118165. doi: 10.1016/j.lfs.2020.118165. Epub Jul. 29, 2020.

Kato et al., A lentiviral strategy for highly efficient retrograde gene transfer by pseudotyping with fusion envelope glycoprotein. Hum Gene Ther. Feb. 2011;22(2):197-206. doi: 10.1089/hum.2009.179. Epub Jan. 27, 2011.

Kato et al., Selective neural pathway targeting reveals key roles of thalamostriatal projection in the control of visual discrimination. J Neurosci. Nov. 23, 2011;31(47):17169-79. doi: 10.1523/JNEUROSCI.4005-11.2011.

Kawakami et al., Identification of a human melanoma antigen recognized by tumor-infiltrating lymphocytes associated with in vivo tumor rejection. Proc Natl Acad Sci U S A. Jul. 5, 1994;91(14):6458-62. doi: 10.1073/pnas.91.14.6458.

Kawakami et al., Identification of new melanoma epitopes on melanosomal proteins recognized by tumor infiltrating T lymphocytes restricted by HLA-A1, -A2, and -A3 alleles. J Immunol. Dec. 15, 1998;161(12):6985-92.

Kawakami et al., Identification of the immunodominant peptides of the MART-1 human melanoma antigen recognized by the majority of HLA-A2-restricted tumor infiltrating lymphocytes. J Exp Med. Jul. 1, 1994;180(1):347-52. doi: 10.1084/jem.180.1.347.

Kawakami et al., Recognition of multiple epitopes in the human melanoma antigen gp100 by tumor-infiltrating T lymphocytes associated with in vivo tumor regression. J Immunol. Apr. 15, 1995;154(8):3961-8.

Kawashima et al., Identification of gp100-derived, melanoma-specific cytotoxic T-lymphocyte epitopes restricted by HLA-A3 supertype molecules by primary in vitro immunization with peptide-pulsed dendritic cells. Int J Cancer. Nov. 9, 1998;78(4):518-24. doi: 10.1002/(sici)1097-0215(19981109)78:4<518::aid-ijc20>3.0.co;2-0.

Kawashima et al., Identification of HLA-A3-restricted cytotoxic T lymphocyte epitopes from carcinoembryonic antigen and HER-2/neu by primary in vitro immunization with peptide-pulsed dendritic cells. Cancer Res. Jan. 15, 1999;59(2):431-5.

Kawashima et al., The multi-epitope approach for immunotherapy for cancer: identification of several CTL epitopes from various tumor-associated antigens expressed on solid epithelial tumors. Hum Immunol. Jan. 1998;59(1):1-14. doi: 10.1016/s0198-8859(97)00255-3.

Kemmler et al., Elevated tumor-associated antigen expression suppresses variant peptide vaccine responses. J Immunol. Nov. 1, 2011;187(9):4431-9. doi: 10.4049/jimmunol.1101555. Epub Sep. 21, 2011.

Kim et al., AAV-deliverable hypercompact adenine base editors based on transposase B guided by engineered RNA. Research Square. Apr. 12, 2022. DOI: 10.21203/r9.3.rs-1326630/v1. Retrieved from https://www.researchsquare.com/articlelrs-1326630/v1 on Aug. 1, 2023. 20 pages.

Kim et al., Adenine base editors catalyze cytosine conversions in human cells. Nat Biotechnol. Oct. 2019;37(10):1145-1148. doi: 10.1038/s41587-019-0254-4. Epub Sep. 23, 2019.

Kim et al., RAD51 mutants cause replication defects and chromosomal instability. Mol Cell Biol. Sep. 2012;32(18):3663-80. doi: 10.1128/MCB.00406-12. Epub Jul. 9, 2012.

Kirshenboim et al., Expression and characterization of a novel reverse transcriptase of the LTR retrotransposon Tf1. Virology. Sep. 30, 2007;366(2):263-76. doi: 10.1016/j.virol.2007.04.002. Epub May 23, 2007.

Kittlesen et al., Human melanoma patients recognize an HLA-A1-restricted CTL epitope from tyrosinase containing two cysteine residues: implications for tumor vaccine development. J Immunol. Mar. 1, 1998;160(5):2099-106. Erratum in: J Immunol Mar. 1, 1999;162(5):3106. Shabanowitz JA [corrected to Shabanowitz J].

Kizer et al., Application of functional genomics to pathway optimization for increased isoprenoid production. Appl Environ Microbiol. May 2008;74(10):3229-41. doi: 10.1128/AEM.02750-07. Epub Mar. 14, 2008.

Knipping et al., Disruption of HIV-1 co-receptors CCR5 and CXCR4 in primary human T cells and hematopoietic stem and

(56) References Cited

OTHER PUBLICATIONS progenitor cells using base editing. Mol Ther. Jan. 5, 2022;30(1):130-144. doi: 10.1016/j.ymthe.2021.10.026. Epub Nov. 2, 2021.
Knott et al., CRISPR-Cas guides the future of genetic engineering. Science. Aug. 31, 2018;361(6405):866-869. doi: 10.1126/science.aat5011.
Kobayashi et al., CD4+ T cells from peripheral blood of a melanoma patient recognize peptides derived from nonmutated tyrosinase. Cancer Res. Jan. 15, 1998;58(2):296-301.
Kobayashi et al., Identification of an antigenic epitope for helper T lymphocytes from carcinoembryonic antigen. Clin Cancer Res. Oct. 2002;8(10):3219-25.
Kobayashi et al., Identification of helper T-cell epitopes that encompass or lie proximal to cytotoxic T-cell epitopes in the gp100 melanoma tumor antigen. Cancer Res. Oct. 15, 2001;61(20):7577-84.
Konishi et al., Amino acid substitutions away from the RNase H catalytic site increase the thermal stability of Moloney murine leukemia virus reverse transcriptase through RNase H inactivation. Biochem Biophys Res Commun. Nov. 14, 2014;454(2):269-74. doi: 10.1016/j.bbrc.2014.10.044. Epub Oct. 17, 2014.
Ku et al., Nucleic Acid Aptamers: An Emerging Tool for Biotechnology and Biomedical Sensing. Sensors (Basel). Jul. 6, 2015;15(7):16281-313. doi: 10.3390/s150716281.
Kuan et al., A systematic evaluation of nucleotide properties for CRISPR sgRNA design. BMC Bioinformatics. Jun. 6, 2017;18(1):297. doi: 10.1186/s12859-017-1697-6.
Kuang et al., Advances in base editing with an emphasis on an AAV-based strategy. Methods. Oct. 2021;194:56-64. doi: 10.1016/j.ymeth.2021.03.015. Epub Mar. 25, 2021.
Kueh et al., The new editor-targeted genome engineering in the absence of homology-directed repair. Cell Death Discov. Jun. 13, 2016;2:16042. doi: 10.1038/cddiscovery.2016.42.
Kunkel et al., DNA mismatch repair. Annu Rev Biochem. 2005;74:681-710. doi: 10.1146/annurev.biochem.74.082803.133243.
Kurt et al., CRISPR C-to-G base editors for inducing targeted DNA transversions in human cells. Nat Biotechnol. Jan. 2021;39(1):41-46. doi: 10.1038/s41587-020-0609-x. Epub Jul. 20, 2020.
Kushnir et al., Virus-like particles as a highly efficient vaccine platform: diversity of targets and production systems and advances in clinical development. Vaccine. Dec. 17, 2012;31(1):58-83. doi: 10.1016/j.vaccine.2012.10.083. Epub Nov. 6, 2012.
Kweon et al., A CRISPR-based base-editing screen for the functional assessment of BRCA1 variants. Oncogene. Jan. 2020;39(1):30-35. doi: 10.1038/s41388-019-0968-2. Epub Aug. 29, 2019.
Kwok et al., G-Quadruplexes: Prediction, Characterization, and Biological Application. Trends Biotechnol. Oct. 2017;35(10):997-1013. doi: 10.1016/j.tibtech.2017.06.012. Epub Jul. 26, 2017.
Kwon et al., Precision targeting tumor cells using cancer-specific InDel mutations with CRISPR-Cas9. Proc Natl Acad Sci U S A. Mar. 1, 2022;119(9):e2103532119. doi: 10.1073/pnas.2103532119.
Lahue et al., DNA mismatch correction in a defined system. Science. Jul. 14, 1989;245(4914):160-4. doi: 10.1126/science.2665076.
Lally et al., Unmasking cryptic epitopes after loss of immunodominant tumor antigen expression through epitope spreading. Int J Cancer. Sep. 2001;93(6):841-7. doi: 10.1002/ijc.1420.
Langer et al., Chemical and Physical Structure of Polymers as Carriers for Controlled Release of Bioactive Agents: A Review. J Macromol Sci, Part C, 1983;23(1):61-126. doi: 10.1080/07366578308079439.
Lapointe et al., Retrovirally transduced human dendritic cells can generate T cells recognizing multiple MHC class I and class II epitopes from the melanoma antigen glycoprotein 100. J Immunol. Oct. 15, 2001;167(8):4758-64. doi: 10.4049/jimmunol.167.8.4758.
Larrieu et al., A HLA-Cw*0701 restricted Melan-A/MART1 epitope presented by melanoma tumor cells to CD8+ tumor infiltrating lymphocytes. Cancer Immunol Immunother. May 2008;57(5):745-52. doi: 10.1007/s00262-007-0436-7. Epub Dec. 21, 2007.
Latham et al., Formation of wild-type and chimeric influenza virus-like particles following simultaneous expression of only four structural proteins. J Virol. Jul. 2001;75(13):6154-65. doi: 10.1128/JVI.75.13.6154-6165.2001.
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. doi: 10.1093/hmg/ddi078. Epub Feb. 9, 2005.
Leach et al., Mutations of a mutS homolog in hereditary nonpolyposis colorectal cancer. Cell. Dec. 17, 1993;75(6):1215-25. doi: 10.1016/0092-8674(93)90330-s.
Lee et al., Mitochondrial DNA editing in mice with DddA-TALE fusion deaminases. Nat Commun. Feb. 19, 2021;12(1):1190. doi: 10.1038/s41467-021-21464-1.
Lee et al., Single C-to-T substitution using engineered APOBEC3G-nCas9 base editors with minimum genome- and transcriptome-wide off-target effects. Sci Adv. Jul. 15, 2020;6(29):eaba1773. doi: 10.1126/sciadv.aba1773.
Lee et al., Single C-to-T substitution using engineered APOBEC3G-nCas9 base editors with minimum genome- and transcriptome-wide off-target effects. Sci Adv. Jul. 15, 2020;6(29):eaba1773. doi: 10.1126/sciadv.aba1773. 13 pages.
Lefebvre et al., Identification and characterization of a spinal muscular atrophy-determining gene. Cell. Jan. 13, 1995;80(1):155-65. doi: 10.1016/0092-8674(95)90460-3.
Lennerz et al., The response of autologous T cells to a human melanoma is dominated by mutated neoantigens. Proc Natl Acad Sci U S A. Nov. 1, 2005;102(44):16013-8. doi: 10.1073/pnas.0500090102. Epub Oct. 24, 2005.
Lesinski et al., The potential for targeting the STAT3 pathway as a novel therapy for melanoma. Future Oncol. Jul. 2013;9(7):925-7. doi: 10.2217/fon.13.83. Author Manuscript. 4 pages.
Li et al., Expression and self-assembly of empty virus-like particles of hepatitis E virus. J Virol. Oct. 1997;71(10):7207-13. doi: 10.1128/JVI.71.10.7207-7213.1997.
Li et al., The Importance of Glycans of Viral and Host Proteins in Enveloped Virus Infection. Front Immunol. Apr. 29, 2021;12:638573. doi: 10.3389/fimmu.2021.638573.
Lim et al., Nuclear and mitochondrial DNA editing in human cells with zinc finger deaminases. Nat Commun. Jan. 18, 2022;13(1):366. doi: 10.1038/s41467-022-27962-0.
Lin et al., [Construction and evaluation of DnaB split intein high expression vector and a six amino acids cyclic peptide library]. Sheng Wu Gong Cheng Xue Bao. Nov. 2008;24(11):1924-30. Chinese.
Lin et al., Base editing-mediated splicing correction therapy for spinal muscular atrophy. Cell Res. Jun. 2020;30(6):548-550. doi: 10.1038/s41422-020-0304-y. Epub Mar. 24, 2020.
Lin et al., HLA-DPB1*05: 01-restricted WT1332-specific TCR-transduced CD4+ T lymphocytes display a helper activity for WT1-specific CTL induction and a cytotoxicity against leukemia cells. J Immunother. Apr. 2013;36(3):159-70. doi: 10.1097/CJI.0b013e3182873581.
Lindahl, T., Instability and decay of the primary structure of DNA. Nature. Apr. 22, 1993;362(6422):709-15. doi: 10.1038/362709a0.
Liu et al., Human BRCA2 protein promotes RAD51 filament formation on RPA-covered single-stranded DNA. Nat Struct Mol Biol. Oct. 2010;17(10):1260-2. doi: 10.1038/nsmb.1904. Epub Aug. 22, 2010.
Liu et al., Improving Editing Efficiency for the Sequences with NGH PAM Using xCas9-Derived Base Editors. Mol Ther Nucleic Acids. Sep. 6, 2019;17:626-635. doi: 10.1016/j.omtn.2019.06.024. Epub Jul. 12, 2019.
Liu et al., Intrinsic Nucleotide Preference of Diversifying Base Editors Guides Antibody Ex Vivo Affinity Maturation. Cell Rep. Oct. 23, 2018;25(4):884-892.e3. doi: 10.1016/j.celrep.2018.09.090.
Liu et al., Usherin is required for maintenance of retinal photoreceptors and normal development of cochlear hair cells. Proc Natl Acad Sci U S A. Mar. 13, 2007;104(11):4413-8. doi: 10.1073/pnas.0610950104. Epub Mar. 5, 2007.

(56) References Cited

OTHER PUBLICATIONS

Longsworth, Expanding the Enzymatic Activity of the Programmable Endonuclease Cas9 in Zebrafish. Thesis. Rice University. Houston, TX. May 17, 2019. 41 pages.
Lorson et al., A single nucleotide in the SMN gene regulates splicing and is responsible for spinal muscular atrophy. Proc Natl Acad Sci U S A. May 25, 1999;96(11):6307-11. doi: 10.1073/pnas.96.11.6307.
Lu, periodic chart of amino acid.pdf. Accessed on the internet at https://figshare.com/articles/figure/periodic_chart_of_amino_acid_pdf/3445001/1. Posted Jun. 21, 2016 www.bachem.com. 1 page.
Ludwig et al., Virus-like particles-universal molecular toolboxes. Curr Opin Biotechnol. Dec. 2007;18(6):537-45. doi: 10.1016/j.copbio.2007.10.013.
Lueck et al., Engineered transfer RNAs for suppression of premature termination codons. Nat Commun. Feb. 18, 2019;10(1):822. doi: 10.1038/s41467-019-08329-4.
Lujan et al., Heterogeneous polymerase fidelity and mismatch repair bias genome variation and composition. Genome Res. Nov. 2014;24(11):1751-64. doi: 10.1101/gr.178335.114. Epub Sep. 12, 2014.
Lupetti et al., Translation of a retained intron in tyrosinase-related protein (TRP) 2 mRNA generates a new cytotoxic T lymphocyte (CTL)-defined and shared human melanoma antigen not expressed in normal cells of the melanocytic lineage. J Exp Med. Sep. 21, 1998;188(6):1005-16. doi: 10.1084/jem.188.6.1005.
Lutz et al., Postsymptomatic restoration of SMN rescues the disease phenotype in a mouse model of severe spinal muscular atrophy. J Clin Invest. Aug. 2011;121(8):3029-41. doi: 10.1172/JCI57291. Epub Jul. 25, 2011.
Lyu et al., Adenine Base Editor Ribonucleoproteins Delivered by Lentivirus-Like Particles Show High On-Target Base Editing and Undetectable RNA Off-Target Activities. Crispr J. Feb. 2021;4(1):69-81. doi: 10.1089/crispr.2020.0095.
Lyu et al., Delivering Cas9/sgRNA ribonucleoprotein (RNP) by lentiviral capsid-based bionanoparticles for efficient 'hit-and-run' genome editing. Nucleic Acids Res. Sep. 26, 2019;47(17):e99. doi: 10.1093/nar/gkz605.
Lyu et al., Virus-Like Particle Mediated CRISPR/Cas9 Delivery for Efficient and Safe Genome Editing. Life (Basel). Dec. 21, 2020;10(12):366. doi: 10.3390/life10120366.
Ma et al., Human RAD52 interactions with replication protein A and the RAD51 presynaptic complex. J Biol Chem. Jul. 14, 2017;292(28):11702-11713. doi: 10.1074/jbc.M117.794545. Epub May 27, 2017.
MacFadden et al., Mechanism and structural diversity of exoribonuclease-resistant RNA structures in flaviviral RNAs. Nat Commun. Jan. 9, 2018;9(1):119. doi: 10.1038/s41467-017-02604-y.
Maerker et al., A novel Usher protein network at the periciliary reloading point between molecular transport machineries in vertebrate photoreceptor cells. Hum Mol Genet. Jan. 1, 2008;17(1):71-86. doi: 10.1093/hmg/ddm285. Epub Sep. 28, 2007.
Maetzig et al., Retroviral protein transfer: falling apart to make an impact. Curr Gene Ther. Oct. 2012;12(5):389-409. doi: 10.2174/156652312802762581.
Mahoney et al., The Next Immune-Checkpoint Inhibitors: PD-1/PD-L1 Blockade in Melanoma. Clin Ther. Apr. 1, 2015;37(4):764-82. doi: 10.1016/j.clinthera.2015.02.018. Epub Mar. 29, 2015.
Mali et al., CAS9 transcriptional activators for target specificity screening and paired nickases for cooperative genome engineering. Nat Biotechnol. Sep. 2013;31(9):833-8, Supplemental Info. doi: 10.1038/nbt.2675. Epub Aug. 1, 2013.
Mandic et al., The alternative open reading frame of LAGE-1 gives rise to multiple promiscuous HLA-DR-restricted epitopes recognized by T-helper 1-type tumor-reactive CD4+ T cells. Cancer Res. Oct. 1, 2003;63(19):6506-15.
Mangeot et al., A universal transgene silencing method based on RNA interference. Nucleic Acids Res. Jul. 12, 2004;32(12):e102. doi: 10.1093/nar/gnh105.
Mangeot et al., Development of minimal lentivirus vectors derived from simian immunodeficiency virus (SIVmac251) and their use for gene transfer into human dendritic cells. J Virol. Sep. 2000;74(18):8307-15. doi: 10.1128/jvi.74.18.8307-8315.2000.
Mangeot et al., Genome editing in primary cells and in vivo using viral-derived Nanoblades loaded with Cas9-sgRNA ribonucleoproteins. Nat Commun. Jan. 3, 2019;10(1):45. doi: 10.1038/s41467-018-07845-z.
Mangeot et al., Protein transfer into human cells by VSV-G-induced nanovesicles. Mol Ther. Sep. 2011;19(9):1656-66. doi: 10.1038/mt.2011.138. Epub Jul. 12, 2011.
Marcovitz et al., Frustration in protein-DNA binding influences conformational switching and target search kinetics. Proc Natl Acad Sci U S A. Nov. 1, 2011;108(44):17957-62. doi: 10.1073/pnas.1109594108. Epub Oct. 14, 2011.
Mariani et al., Species-specific exclusion of APOBEC3G from HIV-1 virions by Vif. Cell. Jul. 11, 2003;114(1):21-31. doi: 10.1016/s0092-8674(03)00515-4.
Marsden et al., The Tumor-Associated Variant RAD51 G151D Induces a Hyper-Recombination Phenotype. PLoS Genet. Aug. 11, 2016;12(8):e1006208. doi: 10.1371/journal.pgen.1006208.
Mason et al., Non-enzymatic roles of human RAD51 at stalled replication forks. bioRxiv. Jul. 31, 2019; doi.org/10.1101/359380. 36 pages. bioRxiv preprint first posted online Jul. 31, 2019.
Mendell et al., Single-Dose Gene-Replacement Therapy for Spinal Muscular Atrophy. N Engl J Med. Nov. 2, 2017;377(18):1713-1722. doi: 10.1056/NEJMoa1706198.
Meng et al., Identification of an HLA-DPB1*0501 restricted Melan-A/MART-1 epitope recognized by CD4+ T lymphocytes: prevalence for immunotherapy in Asian populations. J Immunother. Sep. 2011;34(7):525-34. doi: 10.1097/CJI.0b013e318226bd45. Author Manuscript. 16 pages.
Michaux et al., A spliced antigenic peptide comprising a single spliced amino acid is produced in the proteasome by reverse splicing of a longer peptide fragment followed by trimming. J Immunol. Feb. 15, 2014;192(4):1962-71. doi: 10.4049/jimmunol.1302032. Epub Jan. 22, 2014.
Micozzi et al., Human cytidine deaminase: a biochemical characterization of its naturally occurring variants. Int J Biol Macromol. Feb. 2014;63:64-74. doi: 10.1016/j.ijbiomac.2013.10.029. Epub Oct. 29, 2013. Erratum in: Int J Biol Macromol. Feb. 2014;63:262.
Millevoi et al., G-quadruplexes in RNA biology. Wiley Interdiscip Rev RNA. Jul.-Aug. 2012;3(4):495-507. doi: 10.1002/wrna.1113. Epub Apr. 4, 2012.
Milone et al., Clinical use of lentiviral vectors. Leukemia. Jul. 2018;32(7):1529-1541. doi: 10.1038/s41375-018-0106-0. Epub Mar. 22, 2018.
Min et al., Deep learning in bioinformatics. Brief Bioinform. Sep. 1, 2017;18(5):851-869. doi: 10.1093/bib/bbw068.
Misra et al., An enzymatically active chimeric HIV-1 reverse transcriptase (RT) with the RNase-H domain of murine leukemia virus RT exists as a monomer. J Biol Chem. Apr. 17, 1998;273(16):9785-9. doi: 10.1074/jbc.273.16.9785.
Momose et al., Diving into marine genomics with CRISPR/Cas9 systems. Mar Genomics. Dec. 2016;30:55-65. doi: 10.1016/j.margen.2016.10.003. Epub Oct. 12, 2016.
Monani et al., A single nucleotide difference that alters splicing patterns distinguishes the SMA gene SMN1 from the copy gene SMN2. Hum Mol Genet. Jul. 1999;8(7):1177-83. doi: 10.1093/hmg/8.7.1177.
Morel et al., A tyrosinase peptide presented by HLA-B35 is recognized on a human melanoma by autologous cytotoxic T lymphocytes. Int J Cancer. Dec. 10, 1999;83(6):755-9. doi: 10.1002/(sici)1097-0215(19991210)83:6<755::aid-ijc10>3.0.co;2-s.
Mselli-Lakhal et al., Gene transfer system derived from the caprine arthritis-encephalitis lentivirus. J Virol Methods. Sep. 2006;136(1-2):177-84. doi: 10.1016/j.jviromet.2006.05.006. Epub Jun. 21, 2006.
Murawski et al., Newcastle disease virus-like particles containing respiratory syncytial virus G protein induced protection in BALB/c mice, with no evidence of immunopathology. J Virol. Jan. 2010;84(2):1110-23. doi: 10.1128/JVI.01709-09. Epub Nov. 4, 2009.
Murray et al., Selective vulnerability of motor neurons and dissociation of pre- and post-synaptic pathology at the neuromuscular

(56) References Cited

OTHER PUBLICATIONS junction in mouse models of spinal muscular atrophy. Hum Mol Genet. Apr. 1, 2008;17(7):949-62. doi: 10.1093/hmg/ddm367. Epub Dec. 8, 2007.
Murugan et al., The Revolution Continues: Newly Discovered Systems Expand the CRISPR-Cas Toolkit. Mol Cell. Oct. 5, 2017;68(1):15-25. doi: 10.1016/j.molcel.2017.09.007.
Naskalska et al., Virus Like Particles as Immunogens and Universal Nanocarriers. Pol J Microbiol. 2015;64(1):3-13.
Negre et al., Characterization of novel safe lentiviral vectors derived from simian immunodeficiency virus (SIVmac251) that efficiently transduce mature human dendritic cells. Gene Ther. Oct. 2000;7(19):1613-23. doi: 10.1038/sj.gt.3301292.
Nelson et al., Engineered pegRNAs improve prime editing efficiency. Nat Biotechnol. Mar. 2022;40(3):402-410. doi: 10.1038/s41587-021-01039-7. Epub Oct. 4, 2021. Erratum in: Nat Biotechnol. Mar. 2022;40(3):432. doi: 10.1038/s41587-021-01175-0 and Supplemental Information. 15 pages.
Nelson et al., In vivo genome editing improves muscle function in a mouse model of Duchenne muscular dystrophy. Science. Jan. 22, 2016;351(6271):403-7. doi: 10.1126/science.aad5143. Epub Dec. 31, 2015.
Nelson et al., The unstable repeats—three evolving faces of neurological disease. Neuron. Mar. 6, 2013;77(5):825-43. doi: 10.1016/j.neuron.2013.02.022.
Newby et al., In vivo somatic cell base editing and prime editing. Mol Ther. Nov. 3, 2021;29(11):3107-3124. doi: 10.1016/j.ymthe.2021.09.002. Epub Sep. 10, 2021.
Nguyen Tran et al., Engineering domain-inlaid SaCas9 adenine base editors with reduced RNA off-targets and increased on-target DNA editing. Nat Commun. Sep. 25, 2020;11(1):4871. doi: 10.1038/s41467-020-18715-y.
Niemeyer, C.M., Semisynthetic DNA-protein conjugates for biosensing and nanofabrication. Angew Chem Int Ed Engl. Feb. 8, 2010;49(7):1200-16. doi: 10.1002/anie.200904930.
Noppen et al., Naturally processed and concealed HLA-A2.1-restricted epitopes from tumor-associated antigen tyrosinase-related protein-2. Int J Cancer. Jul. 15, 2000;87(2):241-6.
Nowak et al., Ty3 reverse transcriptase complexed with an RNA-DNA hybrid shows structural and functional asymmetry. Nat Struct Mol Biol. Apr. 2014;21(4):389-96. doi: 10.1038/nsmb.2785. Epub Mar. 9, 2014. Author Manuscript, 22 pages.
Nukaya et al., Identification of HLA-A24 epitope peptides of carcinoembryonic antigen which induce tumor-reactive cytotoxic T lymphocyte. Int J Cancer. Jan. 5, 1999;80(1):92-7. doi:10.1002/(sici)1097-0215(19990105)80:1<92::aid-ijc18>3.0.co;2-m.
Ogasawara et al., Recombinant viral-like particles of parvovirus B19 as antigen carriers of anthrax protective antigen. In Vivo. May-Jun. 2006;20(3):319-24.
Ohminami et al., HLA class I-restricted lysis of leukemia cells by a CD8(+) cytotoxic T-lymphocyte clone specific for WT1 peptide. Blood. Jan. 1, 2000;95(1):286-93.
Oka et al., WT1 peptide vaccine for the treatment of cancer. Curr Opin Immunol. Apr. 2008;20(2):211-20. doi: 10.1016/j.coi.2008.04.009. Epub May 24, 2008.
Olsen, J.C., Gene transfer vectors derived from equine infectious anemia virus. Gene Ther. Nov. 1998;5(11):1481-7. doi: 10.1038/sj.gt.3300768.
Olson et al., HLA-A2-restricted T-cell epitopes specific for prostatic acid phosphatase. Cancer Immunol Immunother. Jun. 2010;59(6):943-53. doi: 10.1007/s00262-010-0820-6. Epub Feb. 6, 2010.
Osen et al., Screening of human tumor antigens for CD4 T cell epitopes by combination of HLA-transgenic mice, recombinant adenovirus and antigen peptide libraries. PLoS One. Nov. 30, 2010;5(11):e14137. doi: 10.1371/journal.pone.0014137.
Ottesen, ISS-N1 makes the First FDA-approved Drug for Spinal Muscular Atrophy. Transl Neurosci. Jan. 26, 2017;8:1-6. doi: 10.1515/tnsci-2017-0001.
Ousterout et al., Multiplex CRISPR/Cas9-based genome editing for correction of dystrophin mutations that cause Duchenne muscular dystrophy. Nat Commun. Feb. 18, 2015;6:6244. doi: 10.1038/ncomms7244.
Pandey et al., Effect of loops and G-quartets on the stability of RNA G-quadruplexes. J Phys Chem B. Jun. 13, 2013;117(23):6896-905. doi: 10.1021/jp401739m. Epub May 29, 2013. Supplementary Information, 21 pages.
Parente et al., Advances in spinal muscular atrophy therapeutics. Ther Adv Neurol Disord. Feb. 5, 2018;11:1756285618754501. doi: 10.1177/1756285618754501. 13 pages.
Parkhurst et al., Identification of a shared HLA-A*0201-restricted T-cell epitope from the melanoma antigen tyrosinase-related protein 2 (TRP2). Cancer Res. Nov. 1, 1998;58(21):4895-901.
Parkhurst et al., Induction of CD4+ Th1 lymphocytes that recognize known and novel class II MHC restricted epitopes from the melanoma antigen gp100 by stimulation with recombinant protein. J Immunother. Mar.-Apr. 2004;27(2):79-91. doi: 10.1097/00002371-200403000-00001. Author Manuscript. 22 pages.
Parsons et al., Hypermutability and mismatch repair deficiency in RER+ tumor cells. Cell. Dec. 17, 1993;75(6):1227-36. doi: 10.1016/0092-8674(93)90331-j.
Paschen et al., Detection of spontaneous CD4+ T-cell responses in melanoma patients against a tyrosinase-related protein-2-derived epitope identified in HLA-DRB1*0301 transgenic mice. Clin Cancer Res. Jul. 15, 2005;11(14):5241-7. doi: 10.1158/1078-0432.CCR-05-0170.
Passini et al., Antisense oligonucleotides delivered to the mouse CNS ameliorate symptoms of severe spinal muscular atrophy. Sci Transl Med. Mar. 2, 2011;3(72):72ra18. doi: 10.1126/scitranslmed.3001777.
Pellegrini et al., Insights into DNA recombination from the structure of a RAD51-BRCA2 complex. Nature. Nov. 21, 2002;420(6913):287-93. doi: 10.1038/nature01230. Epub Nov. 10, 2002.
Pendse et al., Exon 13-skipped USH2A protein retains functional integrity in mice, suggesting an exo-skipping therapeutic approach to treat USH2A-associated disease. bioRxiv preprint. Feb. 4, 2020. Retrieved from www.biorxiv.org. doi: 10.1101/2020.02.04.934240. 34 pages.
Pendse et al., In Vivo Assessment of Potential Therapeutic Approaches for USH2A-Associated Diseases. Adv Exp Med Biol. 2019;1185:91-96. doi: 10.1007/978-3-030-27378-1_15.
Perez-Palma et al., Simple ClinVar: an interactive web server to explore and retrieve gene and disease variants aggregated in Clin Var database. Nucleic Acids Res. Jul. 2, 2019;47(W1):W99-W105. doi: 10.1093/nar/gkz411.
Petit et al., Powerful mutators lurking in the genome. Philos Trans R Soc Lond B Biol Sci. Mar. 12, 2009;364(1517):705-15. doi: 10.1098/rstb.2008.0272.
Petri et al., CRISPR prime editing with ribonucleoprotein complexes in zebrafish and primary human cells. Nat Biotechnol. Feb. 2022;40(2):189-193. doi: 10.1038/s41587-021-00901-y. Epub Apr. 29, 2021. Erratum in: Nat Biotechnol. May 13, 2021.
Pijlman et al., A highly structured, nuclease-resistant, noncoding RNA produced by flaviviruses is required for pathogenicity. Cell Host Microbe. Dec. 11, 2008;4(6):579-91. doi: 10.1016/j.chom.2008.10.007.
Pinilla et al., Combinatorial peptide libraries as an alternative approach to the identification of ligands for tumor-reactive cytolytic T lymphocytes. Cancer Res. Jul. 1, 2001;61(13):5153-60.
Pinilla-Ibarz et al., Improved human T-cell responses against synthetic HLA-0201 analog peptides derived from the WT1 oncoprotein. Leukemia. Nov. 2006;20(11):2025-33. doi: 10.1038/sj.leu.2404380. Epub Aug. 31, 2006.
Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.
Plotz et al., N-terminus of hMLH1 confers interaction of hMutLalpha and hMutLbeta with hMutSalpha. Nucleic Acids Res. Jun. 15, 2003;31(12):3217-26. doi: 10.1093/nar/gkg420.
Podracky et al., Laboratory evolution of a sortase enzyme that modifies amyloid-β protein. Nat Chem Biol. Mar. 2021;17(3):317-325. doi: 10.1038/s41589-020-00706-1. Epub Jan. 11, 2021.

(56) References Cited

OTHER PUBLICATIONS

Porensky et al., A single administration of morpholino antisense oligomer rescues spinal muscular atrophy in mouse. Hum Mol Genet. Apr. 1, 2012;21(7):1625-38. doi: 10.1093/hmg/ddr600. Epub Dec. 20, 2011.
Prasad et al., Visualizing the assembly of human Rad51 filaments on double-stranded DNA. J Mol Biol. Oct. 27, 2006;363(3):713-28. doi: 10.1016/j.jmb.2006.08.046. Epub Aug. 22, 2006.
Prather et al., De novo biosynthetic pathways: rational design of microbial chemical factories. Curr Opin Biotechnol. Oct. 2008; 19(5):468-74. doi: 10.1016/j.copbio.2008.07.009. Epub Sep. 5, 2008.
Quan et al., Influenza M1 VLPs containing neuraminidase induce heterosubtypic cross-protection. Virology. Sep. 1, 2012;430(2):127-35. doi: 10.1016/j.virol.2012.05.006. Epub Jun. 2, 2012.
Raaijmakers et al., CRISPR/Cas Applications in Myotonic Dystrophy: Expanding Opportunities. Int J Mol Sci. Jul. 27, 2019;20(15):3689. doi: 10.3390/ijms20153689.
Rajagopal et al., High-throughput mapping of regulatory DNA. Nat Biotechnol. Feb. 2016;34(2):167-74. doi: 10.1038/nbt.3468. Epub Jan. 25, 2016.
Ramos et al., Age-dependent SMN expression in disease-relevant tissue and implications for SMA treatment. J Clin Invest. Nov. 1, 2019;129(11):4817-4831. doi: 10.1172/JCI124120.
Rasmussen et al., Characterization of virus-like particles produced by a recombinant baculovirus containing the gag gene of the bovine immunodeficiency-like virus. Virology. Oct. 1990;178(2):435-51. doi: 10.1016/0042-6822(90)90341-n.
Reiners et al., Scaffold protein harmonin (USH1C) provides molecular links between Usher syndrome type 1 and type 2. Hum Mol Genet. Dec. 15, 2005;14(24):3933-43. doi: 10.1093/hmg/ddi417. Epub Nov. 21, 2005.
Renner et al., Intact Viral Particle Counts Measured by Flow Virometry Provide Insight into the Infectivity and Genome Packaging Efficiency of Moloney Murine Leukemia Virus. J Virol. Jan. 6, 2020;94(2):e01600-19. doi: 10.1128/JVI.01600-19.
Richardson et al., CRISPR-Cas9 genome editing in human cells occurs via the Fanconi anemia pathway. Nat Genet. Aug. 2018;50(8):1132-1139. doi: 10.1038/s41588-018-0174-0. Epub Jul. 27, 2018.
Richardson et al., Frequent chromosomal translocations induced by DNA double-strand breaks. Nature. Jun. 8, 2000;405(6787):697-700. doi: 10.1038/35015097.
Riddle et al., Frameshift suppression: a nucleotide addition in the anticodon of a glycine transfer RNA. Nat New Biol. Apr. 25, 1973;242(121):230-4. doi: 10.1038/newbio242230a0.
Riddle et al., Frameshift suppressors. II. Genetic mapping and dominance studies. J Mol Biol. May 28, 1972;66(3):483-93. doi: 10.1016/0022-2836(72)90428-7.
Riddle et al., Suppressors of frameshift mutations in *Salmonella typhimurium*. J Mol Biol. Nov. 28, 1970;54(1):131-44. doi: 10.1016/0022-2836(70)90451-1.
Riley et al., Identification of a new shared HLA-A2.1 restricted epitope from the melanoma antigen tyrosinase. J Immunother. May-Jun. 2001;24(3):212-20.
Rimoldi et al., Efficient simultaneous presentation of NY-ESO-1/LAGE-1 primary and nonprimary open reading frame-derived CTL epitopes in melanoma. J Immunol. Dec. 15, 2000;165(12):7253-61. doi: 10.4049/jimmunol.165.12.7253.
Robbins et al., Multiple HLA class II-restricted melanocyte differentiation antigens are recognized by tumor-infiltrating lymphocytes from a patient with melanoma. J Immunol. Nov. 15, 2002;169(10):6036-47. doi: 10.4049/jimmunol.169.10.6036.
Robbins et al., The intronic region of an incompletely spliced gp100 gene transcript encodes an epitope recognized by melanoma-reactive tumor-infiltrating lymphocytes. J Immunol. Jul. 1, 1997;159(1):303-8.
Robert et al., Virus-Like Particles Derived from HIV-1 for Delivery of Nuclear Proteins: Improvement of Production and Activity by Protein Engineering. Mol Biotechnol. Jan. 2017;59(1):9-23. doi: 10.1007/s12033-016-9987-1.
Rodriguez-Muela et al., Single-Cell Analysis of SMN Reveals Its Broader Role in Neuromuscular Disease. Cell Rep. Feb. 7, 2017;18(6):1484-1498 and Supplemental Information. doi: 10.1016/j.celrep.2017.01.035.
Rosenberg et al., Immunologic and therapeutic evaluation of a synthetic peptide vaccine for the treatment of patients with metastatic melanoma. Nat Med. Mar. 1998;4(3):321-7. doi: 10.1038/nm0398-321.
Rubio-Godoy et al., Toward synthetic combinatorial peptide libraries in positional scanning format (PS-SCL)-based identification of CD8+ Tumor-reactive T-Cell Ligands: a comparative analysis of PS-SCL recognition by a single tumor-reactive CD8+ cytolytic T-lymphocyte clone. Cancer Res. Apr. 1, 2002;62(7):2058-63.
Ruiz et al., Identification and characterization of a T-helper peptide from carcinoembryonic antigen. Clin Cancer Res. Apr. 15, 2004;10(8):2860-7. doi: 10.1158/1078-0432.ccr-03-0476.
Rusk, Cas9 and the importance of asymmetry. Nat Methods. Apr. 2016;13(4):286-7. doi: 10.1038/nmeth.3826.
Räschle et al., Mutations within the hMLH1 and hPMS2 subunits of the human MutLalpha mismatch repair factor affect its ATPase activity, but not its ability to interact with hMutSalpha. J Biol Chem. Jun. 14, 2002;277(24):21810-20. doi: 10.1074/jbc.M108787200. Epub Apr. 10, 2002.
Saayman et al., The therapeutic application of CRISPR/Cas9 technologies for HIV. Expert Opin Biol Ther. Jun. 2015;15(6):819-30. doi: 10.1517/14712598.2015.1036736. Epub Apr. 12, 2015.
Sadowski et al., The sequence-structure relationship and protein function prediction. Curr Opin Struct Biol. Jun. 2009;19(3):357-62. doi: 10.1016/j.sbi.2009.03.008. Epub May 4, 2009.
Saenger et al., Improved tumor immunity using anti-tyrosinase related protein-1 monoclonal antibody combined with DNA vaccines in murine melanoma. Cancer Res. Dec. 1, 2008;68(23):9884-91. doi: 10.1158/0008-5472.CAN-08-2233. Author Manuscript. 19 pages.
Saenz et al., Feline immunodeficiency virus-based lentiviral vectors. Cold Spring Harb Protoc. Jan. 1, 2012;2012(1):71-6. doi: 10.1101/pdb.ip067579.
Saenz et al., Production, harvest, and concentration of feline immunodeficiency virus-based lentiviral vector from cells grown in CF10 or CF2 devices. Cold Spring Harb Protoc. Jan. 1, 2012;2012(1):118-23. doi: 10.1101/pdb.prot067546.
San Filippo et al., Mechanism of eukaryotic homologous recombination. Annu Rev Biochem. 2008;77:229-57. doi: 10.1146/annurev.biochem.77.061306.125255.
Sanjurjo-Soriano et al., Genome Editing in Patient iPSCs Corrects the Most Prevalent USH2A Mutations and Reveals Intriguing Mutant mRNA Expression Profiles. Mol Ther Methods Clin Dev. Nov. 27, 2019;17:156-173. doi: 10.1016/j.omtm.2019.11.016.
Schlacher et al., Double-strand break repair-independent role for BRCA2 in blocking stalled replication fork degradation by MRE11. Cell. May 13, 2011;145(4):529-42. doi: 10.1016/j.cell.2011.03.041. Erratum in: Cell. Jun. 10, 2011;145(6):993.
Schneider et al., Overlapping peptides of melanocyte differentiation antigen Melan-A/MART-1 recognized by autologous cytolytic T lymphocytes in association with HLA-B45.1 and HLA-A2.1. Int J Cancer. Jan. 30, 1998;75(3):451-8. doi: 10.1002/(sici)1097-0215(19980130)75:3<451::aid-ijc20>3.0.co;2-a.
Schrank et al., Inactivation of the survival motor neuron gene, a candidate gene for human spinal muscular atrophy, leads to massive cell death in early mouse embryos. Proc Natl Acad Sci USA. Sep. 2, 1997;94(18):9920-5. doi: 10.1073/pnas.94.18.9920.
Score Results for US 2014-0186919 A1 to Zhang et al. Aug. 28, 2014. 3 pages.
Seffernick et al., Melamine deaminase and atrazine chlorohydrolase: 98 percent identical but functionally different. J Bacteriol. Apr. 2001;183(8):2405-10. doi: 10.1128/JB.183.8.2405-2410.2001.
Sensi et al., Identification of a novel gp100/pMel17 peptide presented by HLA-A*6801 and recognized on human melanoma by cytolytic T cell clones. Tissue Antigens. Apr. 2002;59(4):273-9. doi: 10.1034/j.1399-0039.2002.590404.x.
Shalaby et al., Tissue-Specific Delivery of CRISPR Therapeutics: Strategies and Mechanisms of Non-Viral Vectors. Int J Mol Sci. Oct. 5, 2020;21(19):7353. doi: 10.3390/ijms21197353.

(56) References Cited

OTHER PUBLICATIONS

Shang et al., The spontaneous CD8+ T-cell response to HLA-A2-restricted NY-ESO-1b peptide in hepatocellular carcinoma patients. Clin Cancer Res. Oct. 15, 2004;10(20):6946-55. doi: 10.1158/1078-0432.CCR-04-0502.
Sharma et al., Noninfectious virus-like particles produced by Moloney murine leukemia virus-based retrovirus packaging cells deficient in viral envelope become infectious in the presence of lipofection reagents. Proc Natl Acad Sci U S A. Sep. 30, 1997;94(20):10803-8. doi: 10.1073/pnas.94.20.10803.
Shcherbakova et al., Mutator phenotypes conferred by MLH1 overexpression and by heterozygosity for mlh1 mutations. Mol Cell Biol. Apr. 1999;19(4):3177-83. doi: 10.1128/MCB.19.4.3177.
Shen et al., Efficient genome modification by CRISPR-Cas9 nickase with minimal off-target effects. Nat Methods. Apr. 2014;11(4):399-402. doi: 10.1038/nmeth.2857. Epub Mar. 2, 2014.
Shen et al., Identification of a MHC class-II restricted epitope in carcinoembryonic antigen. Cancer Immunol Immunother. May 2004;53(5):391-403. doi: 10.1007/s00262-003-0455-y. Epub Nov. 18, 2003.
Simon et al., Retrons and their applications in genome engineering. Nucleic Acids Res. Dec. 2, 2019;47(21):11007-11019. doi: 10.1093/nar/gkz865.
Singh et al., Protein Engineering Approaches in the Post-Genomic Era. Curr Protein Pept Sci. 2018;19(1):5-15. doi: 10.2174/1389203718666161117114243.
Singh et al., Splicing of a critical exon of human Survival Motor Neuron is regulated by a unique silencer element located in the last intron. Mol Cell Biol. Feb. 2006;26(4):1333-46. doi: 10.1128/MCB.26.4.1333-1346.2006.
Skipper et al., An HLA-A2-restricted tyrosinase antigen on melanoma cells results from posttranslational modification and suggests a novel pathway for processing of membrane proteins. J Exp Med. Feb. 1, 1996;183(2):527-34. doi: 10.1084/jem.183.2.527.
Skipper et al., Shared epitopes for HLA-A3-restricted melanoma-reactive human CTL include a naturally processed epitope from Pmel-17/gp100. J Immunol. Dec. 1, 1996;157(11):5027-33.
Slansky et al., Enhanced antigen-specific antitumor immunity with altered peptide ligands that stabilize the MHC-peptide-TCR complex. Immunity. Oct. 2000;13(4):529-38. doi: 10.1016/s1074-7613(00)00052-2.
Slingluff et al., Clinical and immunologic results of a randomized phase II trial of vaccination using four melanoma peptides either administered in granulocyte-macrophage colony-stimulating factor in adjuvant or pulsed on dendritic cells. J Clin Oncol. Nov. 1, 2003;21(21):4016-26. doi: 10.1200/JCO.2003.10.005.
Slingluff et al., Immunologic and clinical outcomes of vaccination with a multiepitope melanoma peptide vaccine plus low-dose interleukin-2 administered either concurrently or on a delayed schedule. J Clin Oncol. Nov. 15, 2004;22(22):4474-85. doi: 10.1200/JCO.2004.10.212.
Song et al., RS-1 enhances CRISPR/Cas9- and TALEN-mediated knock-in efficiency. Nat Commun. Jan. 28, 2016;7:10548. doi: 10.1038/ncomms10548.
Sorusch et al., Characterization of the ternary Usher syndrome SANS/ush2a/whirlin protein complex. Hum Mol Genet. Mar. 15, 2017;26(6):1157-1172. doi: 10.1093/hmg/ddx027.
Stark et al., ATP hydrolysis by mammalian RAD51 has a key role during homology-directed DNA repair. J Biol Chem. Jun. 7, 2002;277(23):20185-94. doi: 10.1074/jbc.M112132200. Epub Mar. 28, 2002.
Steckelberg et al., A folded viral noncoding RNA blocks host cell exoribonucleases through a conformationally dynamic RNA structure. Proc Natl Acad Sci U S A. Jun. 19, 2018;115(25):6404-6409. doi: 10.1073/pnas.1802429115. Epub Jun. 4, 2018.
Strand et al., Destabilization of tracts of simple repetitive DNA in yeast by mutations affecting DNA mismatch repair. Nature. Sep. 16, 1993;365(6443):274-6. doi: 10.1038/365274a0. Erratum in: Nature Apr. 7, 1994;368(6471);569.
Studebaker et al., Depletion of uracil-DNA glycosylase activity is associated with decreased cell proliferation. Biochem Biophys Res Commun. Aug. 26, 2005;334(2):509-15. doi: 10.1016/j.bbrc.2005.06.118.
Su et al., Mispair specificity of methyl-directed DNA mismatch correction in vitro. J Biol Chem. May 15, 1988;263(14):6829-35. Erratum in: J Biol Chem Aug. 5, 1988;263(22):11015.
Sugawara et al., Heteroduplex rejection during single-strand annealing requires Sgs1 helicase and mismatch repair proteins Msh2 and Msh6 but not Pms1. Proc Natl Acad Sci U S A. Jun. 22, 2004;101(25):9315-20. doi: 10.1073/pnas.0305749101. Epub Jun. 15, 2004.
Suh et al., Publisher Correction: Restoration of visual function in adult mice with an inherited retinal disease via adenine base editing. Nat Biomed Eng. Nov. 2020;4(11):1119. doi: 10.1038/s41551-020-00652-2. Erratum for: Nat Biomed Eng. Oct. 19, 2020.
Sumner et al., Two breakthrough gene-targeted treatments for spinal muscular atrophy: challenges remain. J Clin Invest. Aug. 1, 2018;128(8):3219-3227. doi: 10.1172/JCI121658. Epub Jul. 9, 2018.
Supek et al., Differential DNA mismatch repair underlies mutation rate variation across the human genome. Nature. May 7, 2015;521(7550):81-4. doi: 10.1038/nature14173. Epub Feb. 23, 2015.
Svitashev et al., Targeted Mutagenesis, Precise Gene Editing, and Site-Specific Gene Insertion in Maize Using Cas9 and Guide RNA. Plant Physiol. Oct. 2015; 169(2):931-45. doi: 10.1104/p. 15.00793. Epub Aug. 12, 2015.
Talbot et al., Spinal muscular atrophy. Semin Neurol. Jun. 2001;21(2):189-97. doi: 10.1055/s-2001-15264.
Tan et al., Engineering of high-precision base editors for site-specific single nucleotide replacement. Nat Commun. Jan. 25, 2019;10(1):439. doi: 10.1038/s41467-018-08034-8. Erratum in: Nat Commun. May 1, 2019;10(1):2019.
Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.
Tang et al., The *Arabidopsis* TRM61/TRM6 complex is a bona fide tRNA N1-methyladenosine methyltransferase. J Exp Bot. May 30, 2020;71(10):3024-3036. doi: 10.1093/jxb/eraa100.
Tangri et al., Structural features of peptide analogs of human histocompatibility leukocyte antigen class I epitopes that are more potent and immunogenic than wild-type peptide. J Exp Med. Sep. 17, 2001;194(6):833-46. doi: 10.1084/jem.194.6.833.
Thandapani et al., Valine tRNA levels and availability regulate complex I assembly in leukaemia. Nature. Jan. 2022;601(7893):428-433. doi: 10.1038/s41586-021-04244-1. Epub Dec. 22, 2021.
Thomas et al., Heteroduplex repair in extracts of human HeLa cells. J Biol Chem. Feb. 25, 1991;266(6):3744-51.
Tomer et al., Contribution of human mlh1 and pms2 ATPase activities to DNA mismatch repair. J Biol Chem. Jun. 14, 2002;277(24):21801-9. doi: 10.1074/jbc.M111342200. Epub Mar. 15, 2002.
Tomé-Amat et al., Secreted production of assembled Norovirus virus-like particles from Pichia pastoris. Microb Cell Fact. Sep. 10, 2014;13:134. doi: 10.1186/s12934-014-0134-z.
Topalian et al., Melanoma-specific CD4+ T cells recognize nonmutated HLA-DR-restricted tyrosinase epitopes. J Exp Med. May 1, 1996;183(5):1965-71. doi: 10.1084/jem.183.5.1965.
Toro et al., Comprehensive phylogenetic analysis of bacterial reverse transcriptases. PLoS One. Nov. 25, 2014;9(11):e114083. doi: 10.1371/journal.pone.0114083.
Touloukian et al., Expression of a "self-"antigen by human tumor cells enhances tumor antigen-specific CD4(+) T-cell function. Cancer Res. Sep. 15, 2002;62(18):5144-7. Author Manuscript. 11 pages.
Touloukian et al., Identification of a MHC class II-restricted human gp100 epitope using DR4-IE transgenic mice. J Immunol. Apr. 1, 2000;164(7):3535-42. doi: 10.4049/jimmunol.164.7.3535.
Touloukian et al., Normal tissue depresses while tumor tissue enhances human T cell responses in vivo to a novel self/tumor melanoma antigen, OA1. J Immunol. Feb. 1, 2003;170(3):1579-85. doi: 10.4049/jimmunol.170.3.1579.

(56) References Cited

OTHER PUBLICATIONS

Tran et al., Hypermutability of homonucleotide runs in mismatch repair and DNA polymerase proofreading yeast mutants. Mol Cell Biol. May 1997;17(5):2859-65. doi: 10.1128/MCB.17.5.2859.

Trojan et al., Generation of cytotoxic T lymphocytes against native and altered peptides of human leukocyte antigen-A*0201 restricted epitopes from the human epithelial cell adhesion molecule. Cancer Res. Jun. 15, 2001;61(12):4761-5.

Tsai et al., Identification of subdominant CTL epitopes of the GP100 melanoma-associated tumor antigen by primary in vitro immunization with peptide-pulsed dendritic cells. J Immunol. Feb. 15, 1997;158(4):1796-802.

Tsang et al., A human cytotoxic T-lymphocyte epitope and its agonist epitope from the nonvariable number of tandem repeat sequence of MUC-1. Clin Cancer Res. Mar. 15, 2004;10(6):2139-49. doi: 10.1158/1078-0432.ccr-1011-03.

Tsang et al., Generation of human cytotoxic T cells specific for human carcinoembryonic antigen epitopes from patients immunized with recombinant vaccinia-CEA vaccine. J Natl Cancer Inst. Jul. 5, 1995;87(13):982-90. doi: 10.1093/jnci/87.13.982.

Tsuboi et al., Enhanced induction of human WT1-specific cytotoxic T lymphocytes with a 9-mer WT1 peptide modified at HLA-A*2402-binding residues. Cancer Immunol Immunother. Dec. 2002;51(11-12):614-20. doi: 10.1007/s00262-002-0328-9. Epub Oct. 18, 2002.

Tuorto et al., Genome recoding by tRNA modifications. Open Biol. Dec. 2016;6(12):160287. doi: 10.1098/rsob.160287.

Tycko et al., Methods for Optimizing CRISPR-Cas9 Genome Editing Specificity. Mol Cell. Aug. 4, 2016;63(3):355-70. doi: 10.1016/j.molcel.2016.07.004.

Umar et al., DNA loop repair by human cell extracts. Science. Nov. 4, 1994;266(5186):814-6. doi: 10.1126/science.7973637.

Vakulskas et al., A high-fidelity Cas9 mutant delivered as a ribonucleoprotein complex enables efficient gene editing in human hematopoietic stem and progenitor cells. Nat Med. Aug. 2018;24(8):1216-1224. doi: 10.1038/s41591-018-0137-0. Epub Aug. 6, 2018.

Valmori et al., Analysis of the cytolytic T lymphocyte response of melanoma patients to the naturally HLA-A*0201-associated tyrosinase peptide 368-376. Cancer Res. Aug. 15, 1999;59(16):4050-5.

Valmori et al., Enhanced generation of specific tumor-reactive CTL in vitro by selected Melan-A/MART-1 immunodominant peptide analogues. J Immunol. Feb. 15, 1998;160(4):1750-8.

Valmori et al., Naturally occurring human lymphocyte antigen-A2 restricted CD8+ T-cell response to the cancer testis antigen NY-ESO-1 in melanoma patients. Cancer Res. Aug. 15, 2000;60(16):4499-506.

Van Den Oord et al., Pixel Recurrent Neural Networks. Proceedings of the 33rd International Conference on Machine Learning. Journal of Machine Learning Research. Aug. 19, 2016. vol. 48. 11 pages.

Vidal et al., Yeast forward and reverse 'n'-hybrid systems. Nucleic Acids Res. Feb. 15, 1999;27(4):919-29. doi: 10.1093/nar/27.4.919.

Vigneron et al., A peptide derived from melanocytic protein gp100 and presented by HLA-B35 is recognized by autologous cytolytic T lymphocytes on melanoma cells. Tissue Antigens. Feb. 2005;65(2):156-62. doi: 10.1111/j.1399-0039.2005.00365.x.

Vigneron et al., An antigenic peptide produced by peptide splicing in the proteasome. Science. Apr. 23, 2004;304(5670):587-90. doi: 10.1126/science.1095522.

Visseren et al., Affinity, specificity and T-cell-receptor diversity of melanoma-specific CTL generated in vitro against a single tyrosinase epitope. Int J Cancer. Sep. 17, 1997;72(6):1122-8. doi: 10.1002/(sici)1097-0215(19970917)72:6<1122 :: aid-ijc30>3.0.co;2-3.

Voelkel et al., Protein transduction from retroviral Gag precursors. Proc Natl Acad Sci U S A. Apr. 27, 2010;107(17):7805-10. doi: 10.1073/pnas.0914517107. Epub Apr. 12, 2010.

Volpe et al., Alternative BCR/ABL splice variants in Philadelphia chromosome-positive leukemias result in novel tumor-specific fusion proteins that may represent potential targets for immunotherapy approaches. Cancer Res. Jun. 1, 2007;67(11):5300-7. doi: 10.1158/0008-5472.CAN-06-3737.

Voutev et al., Bxb1 phage recombinase assists genome engineering in *Drosophila melanogaster*. Biotechniques. Jan. 1, 2017;62(1):37-38. doi: 10.2144/000114494.

Walpita et al., Mammalian Cell-Derived Respiratory Syncytial Virus-Like Particles Protect the Lower as well as the Upper Respiratory Tract. PLoS One. Jul. 14, 2015;10(7):e0130755. doi: 10.1371/journal.pone.0130755.

Walton et al., Spontaneous CD8 T cell responses against the melanocyte differentiation antigen RAB38/NY-MEL-1 in melanoma patients. J Immunol. Dec. 1, 2006;177(11):8212-8. doi: 10.4049/jimmunol.177.11.8212.

Walton et al., Unconstrained genome targeting with near-PAMless engineered CRISPR-Cas9 variants. Science. Apr. 17, 2020;368(6488):290-296. doi: 10.1126/science.aba8853. Epub Mar. 26, 2020.

Wang et al., CRISPR-Based Therapeutic Genome Editing: Strategies and in Vivo Delivery by AAV Vectors. Cell. Apr. 2, 2020;181(1):136-150. doi: 10.1016/j.cell.2020.03.023.

Wang et al., CRISPR/Cas9 in Genome Editing and Beyond. Annu Rev Biochem. Jun. 2, 2016;85:227-64. doi: 10.1146/annurev-biochem-060815-014607. Epub Apr. 25, 2016.

Wang et al., Recognition of an antigenic peptide derived from tyrosinase-related protein-2 by CTL in the context of HLA-A31 and -A33. J Immunol. Jan. 15, 1998;160(2):890-7.

Wang et al., Recognition of breast cancer cells by CD8+ cytotoxic T-cell clones specific for NY-BR-1. Cancer Res. Jul. 1, 2006;66(13):6826-33. doi: 10.1158/0008-5472.CAN-05-3529.

Wang et al., Utilization of an alternative open reading frame of a normal gene in generating a novel human cancer antigen. J Exp Med. Mar. 1, 1996;183(3):1131-40. doi: 10.1084/jem.183.3.1131.

Wang et al., Virus-like particles for the prevention of human papillomavirus-associated malignancies. Expert Rev Vaccines. Feb. 2013; 12(2):129-41. doi: 10.1586/erv.12.151. Author Manuscript, 22 pages.

Warren et al., Structure of the human MutSalpha DNA lesion recognition complex. Mol Cell. May 25, 2007;26(4):579-92. doi: 10.1016/j.molcel.2007.04.018.

Wei et al., Systemic nanoparticle delivery of CRISPR-Cas9 ribonucleoproteins for effective tissue specific genome editing. Nat Commun. Jun. 26, 2020;11(1):3232. doi: 10.1038/s41467-020-17029-3.

Wirth et al., Mildly affected patients with spinal muscular atrophy are partially protected by an increased SMN2 copy number Hum Genet. May 2006;119(4):422-8. doi: 10.1007/s00439-006-0156-7. Epub Mar. 1, 2006.

Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

Woo et al., Gene activation of SMN by selective disruption of lncRNA-mediated recruitment of PRC2 for the treatment of spinal muscular atrophy. Proc Natl Acad Sci U S A. Feb. 21, 2017;114(8):E1509-E1518. doi:10.1073/pnas.1616521114. Epub Feb. 13, 2017.

Wu et al., A novel SCN9A mutation responsible for primary erythromelalgia and is resistant to the treatment of sodium channel blockers. PLoS One. 2013;8(1):e55212. doi: 10.1371/journal.pone.0055212. Epub Jan. 31, 2013. 15 pages.

Wu et al., MLV based viral-like-particles for delivery of toxic proteins and nuclear transcription factors. Biomaterials. Sep. 2014;35(29):8416-26. doi: 10.1016/j.biomaterials.2014.06.006. Epub Jul. 3, 2014.

Wu et al., Widespread Influence of 3'-End Structures on Mammalian mRNA Processing and Stability. Cell. May 18, 2017;169(5):905-917.e11. doi: 10.1016/j.cell.2017.04.036.

Wölfel et al., Two tyrosinase nonapeptides recognized on HLA-A2 melanomas by autologous cytolytic T lymphocytes. Eur J Immunol. Mar. 1994;24(3):759-64. doi: 10.1002/eji.1830240340.

Xi et al., C-terminal Loop Mutations Determine Folding and Secretion Properties of PCSK9. Biochem Mol Biol J. 2016;2(3):17. doi: 10.21767/2471-8084.100026. 12 pages.

(56) References Cited

OTHER PUBLICATIONS

Yamane et al., Deep-sequencing identification of the genomic targets of the cytidine deaminase AID and its cofactor RPA in B lymphocytes. Nat Immunol. Jan. 2011;12(1):62-9. doi: 10.1038/ni.1964. Epub Nov. 28, 2010.
Yang et al., BRCA2 function in DNA binding and recombination from a BRCA2-DSS1-ssDNA structure. Science. Sep. 13, 2002;297(5588):1837-48. doi: 10.1126/science.297.5588.1837.
Yang et al., HIV-1 virus-like particles produced by stably transfected *Drosophila* S2 cells: a desirable vaccine component. J Virol. Jul. 2012;86(14):7662-76. doi: 10.1128/JVI.07164-11. Epub May 2, 2012.
Yang et al., The BRCA2 homologue Brh2 nucleates RAD51 filament formation at a dsDNA-ssDNA junction. Nature. Feb. 10, 2005;433(7026):653-7. doi: 10.1038/nature03234.
Yao et al., Engineered extracellular vesicles as versatile ribonucleoprotein delivery vehicles for efficient and safe CRISPR genome editing. J Extracell Vesicles. Mar. 2021;10(5):e12076. doi: 10.1002/jev2.12076. Epub Mar. 16, 2021.
Yee et al., A general method for the generation of high-titer, pantropic retroviral vectors: highly efficient infection of primary hepatocytes. Proc Natl Acad Sci U S A. Sep. 27, 1994;91(20):9564-8. doi: 10.1073/pnas.91.20.9564.
Yi et al., Engineering of TEV protease variants by yeast ER sequestration screening (YESS) of combinatorial libraries. Proc Natl Acad Sci U S A. Apr. 30, 2013;110(18):7229-34. doi: 10.1073/pnas.1215994110. Epub Apr. 15, 2013.
Yin et al., Optimizing genome editing strategy by primer-extension-mediated sequencing. Cell Discov. Mar. 26, 2019;5:18. doi: 10.1038/s41421-019-0088-8.
Yu et al., Cytosine base editors with minimized unguided DNA and RNA off-target events and high on-target activity. Nat Commun. Apr. 28, 2020;11(1):2052. doi: 10.1038/s41467-020-15887-5.
Yu et al., Dynamic control of Rad51 recombinase by self-association and interaction with BRCA2. Mol Cell. Oct. 2003;12(4):1029-41. doi: 10.1016/s1097-2765(03)00394-0.
Yu et al., Poor immunogenicity of a self/tumor antigen derives from peptide-MHC-I instability and is independent of tolerance. J Clin Invest. Aug. 2004; 114(4):551-9. doi: 10.1172/JCI21695.
Zarour et al., Melan-A/MART-1(51-73) represents an immunogenic HLA-DR4-restricted epitope recognized by melanoma-reactive CD4(+) T cells. Proc Natl Acad Sci U S A. Jan. 4, 2000;97(1):400-5. doi: 10.1073/pnas.97.1.400.
Zeltins, A., Construction and characterization of virus-like particles: a review. Mol Biotechnol. Jan. 2013;53(1):92-107. doi: 10.1007/s12033-012-9598-4.
Zhang et al., Adenine Base Editing in Vivo with a Single Adeno-Associated Virus Vector. BioRxiv. Dec. 13, 2021. DOI: 10.1101/2021.12.13.472434. Retrieved from https://www.biorxiv.org/content/10.1101/2021.12.13.472434v1.full on Aug. 1, 2023. 47 pages.
Zhang et al., Efficient precise knockin with a double cut HDR donor after CRISPR/Cas9-mediated double-stranded DNA cleavage. Genome Biol. Feb. 20, 2017;18(1):35. doi: 10.1186/s13059-017-1164-8.
Zhang et al., Large genomic fragment deletions and insertions in mouse using CRISPR/Cas9. PLoS One. Mar. 24, 2015;10(3):e0120396. doi: 10.1371/journal.pone.0120396. 14 pages.
Zhang et al., Propagated Perturbations from a Peripheral Mutation Show Interactions Supporting WW Domain Thermostability. Structure. Nov. 6, 2018;26(11):1474-1485.e5. doi: 10.1016/j.str.2018.07.014. Epub Sep. 6, 2018.
Zhang et al., Reconstitution of 5'-directed human mismatch repair in a purified system. Cell. Sep. 9, 2005;122(5):693-705. doi: 10.1016/j.cell.2005.06.027.
Zhao et al., Glycosylase base editors enable C-to-A and C-to-G base changes. Nat Biotechnol. Jan. 2021;39(1):35-40. doi: 10.1038/s41587-020-0592-2. Epub Jul. 20, 2020. Erratum in: Nat Biotechnol. Jan. 2021;39(1):115. doi: 10.1038/s41587-020-0648-3.
Zhi et al., Dual-AAV delivering split prime editor system for in vivo genome editing. Mol Ther. Jan. 5, 2022;30(1):283-294 and Supplemental Info. doi: 10.1016/j.ymthe.2021.07.011. Epub Jul. 21, 2021. 35 pages.
Zhu et al., Novel Thrombotic Function of a Human SNP in STXBP5 Revealed by CRISPR/Cas9 Gene Editing in Mice. Arterioscler Thromb Vasc Biol. Feb. 2017;37(2):264-270. doi: 10.1161/ATVBAHA.116.308614. Epub Dec. 29, 2016.
U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 61/838,178, filed Jun. 21, 2013, Joung et al.
U.S. Appl. No. 61/874,682, filed Sep. 6, 2013, Liu et al.
U.S. Appl. No. 61/874,746, filed Sep. 6, 2013, Liu et al.
U.S. Appl. No. 62/288,661, filed Jan. 29, 2016, Muir et al.
U.S. Appl. No. 62/357,332, filed Jun. 30, 2016, Liu et al.
International Search Report and Written Opinion for Application No. PCT/US2020/055156, mailed Feb. 9, 2021.
International Preliminary Report on Patentability for Application No. PCT/US2020/055156, mailed Apr. 21, 2022.
[No Author Listed] "FokI" from New England Biolabs Inc. Last accessed online via https://www.neb.com/products/r0109-foki#Product%20Information on Mar. 19, 2021. 1 page.
[No Author Listed] "Nucleic Acids Sizes and Molecular Weights." Printed Mar. 19, 2021. 2 pages.
[No Author Listed] "Zinc Finger Nuclease" from Wikipedia. Retrieved from https://en.wikipedia.org/w/index.php?title=Zinc_finger_nuclease&oldid=1007053318. Page last edited Feb. 16, 2021. Printed on Mar. 19, 2021.
[No Author Listed] Beast2: Bayesian evolutionary analysis by sampling trees. http://www.beast2.org/ Last accessed Apr. 28, 2021,.
[No Author Listed] HyPhy—Hypothesis testing using Phylogenies. Last modified Apr. 21, 2017. Accessed online via http://hyphy.org/w/index.php/Main_Page on Apr. 28, 2021.
[No Author Listed] NCBI Accession No. XP_015843220.1. C ->U editing enzyme APOBEC-1 [Peromyscus maniculatus bairdii], XP002793540. Mar. 21, 2016.
[No Author Listed] NCBI Accession No. XP_021505673.1. C ->U editing enzyme APOBEC-1 [Meriones unguiculatus], XP002793541. Jun. 27, 2017.
[No Author Listed] NCBI Reference Sequence: WP_00087959824.1. Oct. 9, 2019. 2 pages.
[No Author Listed] NCBI Reference Sequence: WP_001516895.1. Mar. 13, 2021. 2 pages.
[No Author Listed] Nucleic Acid Data from New England Biolabs. Printed Sep. 28, 2021. 1 page.
[No Author Listed] Score result for SEQ 355 to W02017032580. Muir et al. 2016.
[No Author Listed] Theoretical Biochemistry Group. Institute for Theoretical Chemistry. The ViennaRNA Package. Universitat Wien. https://www.tbi.univie.ac.at/RNA/. Last accessed Apr. 28, 2021.
[No Author Listed] Transcription activator-like effector nuclease. Wikipedia. Last edited Sep. 27, 2021. Accessed via https://en.wikipedia.org/w/index.php?title=Transcription_activator-like_effector_nuclease&oldid=1046813325 on Sep. 28, 2021. 9 pages.
[No Author Listed], "Human genome." Encyclopedia Britannica. Encyclopedia Brittanica, Inc. Published Feb. 15, 2019. Last accessed online via https://www.britannica.com/science/human-genome on Mar. 19, 2021. 2 pages.
[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.

(56) References Cited

OTHER PUBLICATIONS

[No Author Listed], Mus musculus (Mouse). UniProtKB Accession No. P51908 (ABEC1_MOUSE). Oct. 1, 1996. 10 pages.
[No Author Listed], Thermo Fisher Scientific—How Cationic Lipid Mediated Transfection Works, retrieved from the internet Aug. 27, 2015. 2 pages.
Abremski et al., Bacteriophage P1 site-specific recombination. Purification and properties of the Cre recombinase protein. J Biol Chem. Feb. 10, 1984;259(3):1509-14.
Abudayyeh et al., C2c2 is a single-component programmable RNA-guided RNA-targeting CRISPR effector. Science Aug. 2016;353(6299):aaf5573. DOI: 10.1126/science.aaf5573.
Abudayyeh et al., A cytosine deaminase for programmable single-base RNA editing. Science. Jul. 26, 2019;365(6451):382-386. doi: 10.1126/science.aax7063. Epub Jul. 11, 2019.
Abudayyeh et al., RNA targeting with CRISPR-Cas13. Nature. Oct. 12, 2017;550(7675):280-284. doi: 10.1038/nature24049. Epub Oct. 4, 2017.
Ada et al., Carbohydrate-protein conjugate vaccines. Clin Microbiol Infect. Feb. 2003;9(2):79-85. doi: 10.1046/j.1469-0691.2003.00530.x.
Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.
Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Adli, The CRISPR tool kit for genome editing and beyond. Nat Commun. May 15, 2018;9(1):1911. doi: 10.1038/s41467-018-04252-2.
Aguilo et al., Coordination of m(6)A mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.
Ahmad et al., Antibody-mediated specific binding and cytotoxicity of liposome-entrapped doxorubicin to lung cancer cells in vitro. Cancer Res. Sep. 1, 1992;52(17):4817-20.
Aida et al., Prime editing primarily incudes undesired outcomes in mice. bioRxiv preprint and Supplemental Information. Aug. 6, 2020. Retrieved from www.biorxiv.org. doi: 10.1101/2020.08.06.239723. 40 pages.
Aihara et al., A conformational switch controls the DNA cleavage activity of lambda integrase. Mol Cell. Jul. 2003;12(1):187-98.
Aik et al., Structure of human RNA ?-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.
Aird et al., Increasing Cas9-mediated homology-directed repair efficiency through covalent tethering of DNA repair template. Commun Biol. May 31, 2018;1:54. doi: 10.1038/s42003-018-0054-2.
Akcakaya et al., In vivo CRISPR editing with no detectable genome-wide off-target mutations. Nature. Sep. 2018;561(7723):416-419. doi: 10.1038/s41586-018-0500-9. Epub Sep. 12, 2018. PMID: 30209390; PMCID: PMC6194229.
Akins et al., Mitochondrial plasmids of Neurospora: integration into mitochondrial DNA and evidence for reverse transcription in mitochondria. Cell. Nov. 21, 1986;47(4):505-16. doi: 10.1016/0092-8674(86)90615-x.
Akinsheye et al., Fetal hemoglobin in sickle cell anemia. Blood. Jul. 7, 2011;118(1):19-27. doi: 10.1182/blood-2011-03-325258. Epub Apr. 13, 2011.
Akopian et al., Chimeric recombinases with designed DNA sequence recognition. Proc Natl Acad Sci U S A. Jul. 22, 2003;100(15):8688-91. Epub Jul. 1, 2003.
Alarcón et al., HNRNPA2B1 Is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.
Alarcón et al., N6-methyladenosine marks primary microRNAs for processing. Nature. Mar. 26, 2015;519(7544):482-5. doi: 10.1038/nature14281. Epub Mar. 18, 2015.
Alexander, HFE-associated hereditary hemochromatosis. Genet Med. May 2009;11(5):307-13. doi: 10.1097/GIM.0b013e31819d30f2.
Alexandrov et al., Signatures of mutational processes in human cancer. Nature. Aug. 22, 2013;500(7463):415-21. doi: 10.1038/nature12477. Epub Aug. 14, 2013.
Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.
Altschul et al., Basic local alignment search tool. J Mol Biol. Oct. 5, 1990;215(3):403-10. doi: 10.1016/S0022-2836(05)80360-2.
Amato et al., Interpreting elevated fetal hemoglobin in pathology and health at the basic laboratory level: new and known Y-gene mutations associated with hereditary persistence of fetal hemoglobin. Int J Lab Hematol. Feb. 2014;36(1):13-9. doi: 10.1111/ijlh.12094. Epub Apr. 29, 2013.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Amrann et al., Tightly regulated tac promoter vectors useful for the expression of unfused and fused proteins in *Escherichia coli*. Gene. Sep. 30, 1988;69(2):301-15.
Anders et al., Chapter One: In Vitro Enzymology of Cas9. in Methods in Enzymology, eds Doudna et al. 2014: 546:1-20.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Anderson, Human gene therapy. Science. May 8, 1992;256(5058):808-13. doi: 10.1126/science. 1589762.
André et al., Axotomy-induced expression of calcium-activated chloride current in subpopulations of mouse dorsal root ganglion neurons. J Neurophysiol. Dec. 2003;90(6):3764-73. doi: 10.1152/jn.00449.2003. Epub Aug. 27, 2003.
Anzalone et al., Genome editing with CRISPR-Cas nucleases, base editors, transposases and prime editors. Nat Biotechnol. Jul. 2020;38(7):824-844. doi: 10.1038/s41587-020-0561-9. Epub Jun. 22, 2020
Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.
Anzalone et al., Search-and-replace genome editing without double-strand breaks or donor DNA. Nature. Dec. 2019;576(7785):149-157. doi: 10.1038/s41586-019-1711-4. Epub Oct. 21, 2019.
Aplan, Causes of oncogenic chromosomal translocation. Trends Genet. Jan. 2006;22(1):46-55. doi: 10.1016/j.tig.2005.10.002. Epub Oct. 28, 2005.
Arakawa et al., A method to convert mRNA into a gRNA library for CRISPR/Cas9 editing of any organism. Sci Adv. Aug. 24, 2016;2(8):e1600699. doi: 10.1126/sciadv.1600699.
Araki et al., Comparative analysis of right element mutant lox sites on recombination efficiency in embryonic stem cells. BMC Biotechnol. Mar. 31, 2010;10:29. doi: 10.1186/1472-6750-10-29.
Araki et al., Site-specific recombinase, R, encoded by yeast plasmid pSR1. J Mol Biol. May 5, 1992;225(1):25-37. doi: 10.1016/0022-2836(92)91023-i.
Araki et al., Targeted integration of DNA using mutant lox sites in embryonic stem cells. Nucleic Acids Res. Feb. 15, 1997;25(4):868-72. doi: 10.1093/nar/25.4.868.
Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.

(56) References Cited

OTHER PUBLICATIONS

Arazoe et al., Targeted Nucleotide Editing Technologies for Microbial Metabolic Engineering. Biotechnol J. Sep. 2018;13(9):e1700596. doi: 10.1002/biot.201700596. Epub Jun. 19, 2018.

Arbab et al., Cloning-free CRISPR. Stem Cell Reports. Nov. 10, 2015;5(5):908-917. doi: 10.1016/j.stemcr.2015.09.022. Epub Oct. 29, 2015.

Arbab et al., Determinants of Base Editing Outcomes from Target Library Analysis and Machine Learning. Cell. Jul. 23, 2020;182(2):463-480.e30. doi: 10.1016/j.cell.2020.05.037. Epub Jun. 12, 2020.

Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.

Arnold et al., Mutants of Tn3 resolvase which do not require accessory binding sites for recombination activity. EMBO J. Mar. 1, 1999;18(5):1407-14.

Asante et al., A naturally occurring variant of the human prion protein completely prevents prion disease. Nature. Jun. 25, 2015;522(7557):478-81. doi: 10.1038/nature14510. Epub Jun. 10, 2015.

Asokan et al., The AAV vector toolkit: poised at the clinical crossroads. Mol Ther. Apr. 2012;20(4):699-708. doi: 10.1038/mt.2011.287. Epub Jan. 24, 2012.

Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.

Auer et al., Highly efficient CRISPR/Cas9-mediated knock-in in zebrafish by homology-independent DNA repair. Genome Res. Jan. 2014;24(1):142-53. doi: 10.1101/gr.161638.113. Epub Oct. 31, 2013.

Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.

Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24.14731.

Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.

Babacic et al., CRISPR-cas gene-editing as plausible treatment of neuromuscular and nucleotide-repeat-expansion diseases: A systematic review. PLoS One. Feb. 22, 2019;14(2):e0212198. doi: 10.1371/journal.pone.0212198.

Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013. .

Badran et al., Continuous evolution of Bacillus thuringiensis toxins overcomes insect resistance. Nature. May 5, 2016;533(7601):58-63. doi: 10.1038/nature17938. Epub Apr. 27, 2016.

Badran et al., Development of potent in vivo mutagenesis plasmids with broad mutational spectra. Nat Commun. Oct. 7, 2015;6:8425. doi: 10.1038/ncomms9425.

Badran et al., In vivo continuous directed evolution. Curr Opin Chem Biol. Feb. 2015;24:1-10. doi: 10.1016/j.cbpa.2014.09.040. Epub Nov. 7, 2014.

Bae et al., Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014.

Bae et al., Microhomology-based choice of Cas9 nuclease target sites. Nat Methods. Jul. 2014;11(7):705-6. doi: 10.1038/nmeth.3015.

Bagal et al., Recent progress in sodium channel modulators for pain. Bioorg Med Chem Lett. Aug. 15, 2014;24(16):3690-9. doi: 10.1016/j.bmcl.2014.06.038. Epub Jun. 21, 2014.

Bagyinszky et al., Characterization of mutations in PRNP (prion) gene and their possible roles in neurodegenerative diseases. Neuropsychiatr Dis Treat. Aug. 14, 2018;14:2067-2085. doi: 10.2147/NDT.S165445.

Balakrishnan et al., Flap endonuclease 1. Annu Rev Biochem. 2013;82:119-38. doi: 10.1146/annurev-biochem-072511-122603. Epub Feb. 28, 2013.

Baldari et al., A novel leader peptide which allows efficient secretion of a fragment of human interleukin 1 beta in *Saccharomyces cerevisiae*. EMBO J. Jan. 1987;6(1):229-34.

Banerjee et al., Cadmium inhibits mismatch repair by blocking the ATPase activity of the MSH2-MSH6 complex [published correction appears in Nucleic Acids Res. 2005;33(5):1738]. Nucleic Acids Res. 2005;33(4):1410-1419. Published Mar. 3, 2005. doi: 10.1093/nar/gki291.

Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.

Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.

Banno et al., Deaminase-mediated multiplex genome editing in *Escherichia coli*. Nat Microbiol. Apr. 2018;3(4):423-429. doi: 10.1038/s41564-017-0102-6. Epub Feb. 5, 2018.

Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.

Barmania et al., C-C chemokine receptor type five (CCR5): An emerging target for the control of HIV infection. Appl Transl Genom. May 26, 2013;2:3-16. doi: 10.1016/j.atg.2013.05.004.

Barnes et al., Repair and genetic consequences of endogenous DNA base damage in mammalian cells. Annu Rev Genet. 2004;38:445-76.

Barnes et al., The fidelity of Taq polymerase catalyzing PCR is improved by an—terminal deletion. Gene. Mar. 1, 1992;112(1):29-35. doi: 10.1016/0378-1119(92)90299-5.

Barrangou et al., CRISPR provides acquired resistance against viruses in prokaryotes. Science. Mar. 23, 2007;315(5819):1709-12.

Barrangou, RNA-mediated programmable DNA cleavage. Nat Biotechnol. Sep. 2012;30(9):836-8. doi: 10.1038/nbt.2357.

Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.

Bartosovic et al., N6-methyladenosine demethylase FTO targets pre-mRNAs and regulates alternative splicing and 3'-end processing. Nucleic Acids Res. Nov. 2, 2017;45(19):11356-11370. doi: 10.1093/nar/gkx778.

Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.

Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.

Batey et al., Structure of a natural guanine-responsive riboswitch complexed with the metabolite hypoxanthine. Nature. Nov. 18, 2004;432(7015):411-5.

Beale et al., Comparison of the differential context-dependence of DNA deamination by APOBEC enzymes: correlation with mutation spectra in vivo. J Mol Biol. Mar. 26, 2004;337(3):585-96.

Beaudry et al., Directed evolution of an RNA enzyme. Science. Jul. 31, 1992;257(5070):635-41. doi: 10.1126/science.1496376.

Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.

Bedell et al., In vivo genome editing using a high-efficiency TALEN system. Nature. Nov. 1, 2012;491(7422):114-8. Doi: 10.1038/nature11537. Epub Sep. 23, 2012.

(56) References Cited

OTHER PUBLICATIONS

Begley, Scientists unveil the 'most clever CRISPR gadget' so far. STAT, Apr. 20, 2016. https://www.statnews.com/2016/04/20/clever-crispr-advance-unveiled/.
Behr, Gene transfer with synthetic cationic amphiphiles: prospects for gene therapy. Bioconjug Chem. Sep.-Oct. 1994;5(5):382-9. doi: 10.1021/bc00029a002.
Bell et al., Ribozyme-catalyzed excision of targeted sequences from within RNAs. Biochemistry. Dec. 24, 2002;41(51):15327-33. doi: 10.1021/bi0267386.
Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.
Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.
Benarroch, HCN channels: function and clinical implications. Neurology. Jan. 15, 2013;80(3):304-10. doi: 10.1212/WNL.0b013e31827dec42.
Bennett et al., Painful and painless channelopathies. Lancet Neurol. Jun. 2014;13(6):587-99. doi: 10.1016/S1474-4422(14)70024-9. Epub May 6, 2014.
Bentin, T., A ribozyme transcribed by a ribozyme. Artif DNA PNA XNA. Apr. 2011;2(2):40-42. doi: 10.4161/adna.2.2.16852.
Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.
Berges et al., Transduction of brain by herpes simplex virus vectors. Mol Ther. Jan. 2007;15(1):20-9. doi: 10.1038/sj.mt.6300018.
Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375.1999.
Bernhart et al., Local RNA base pairing probabilities in large sequences. Bioinformatics. Mar. 1, 2006;22(5):614-5. doi: 10.1093/bioinformatics/btk014. Epub Dec. 20, 2005.
Bernstein et al., Role for a bidentate ribonuclease in the initiation step of RNA interference. Nature. Jan. 18, 2001;409(6818):363-6. doi: 10.1038/35053110.
Bershtein et al., Advances in laboratory evolution of enzymes. Curr Opin; Chem Biol. Apr. 2008; 12(2):151-8. doi: 10.1016/j.cbpa.2008.01.027. Epub Mar. 7, 2008. Review.
Bertolotti et al., Toward genosafe endonuclease-boosted gene targeting using breakthrough CRISP/Cas9 for next generation stem cell gene therapy culminating in efficient ex VIVO in VIVO gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2005-May 16, 2015.
Bertrand et al., Localization of ASH1 mRNA particles in living yeast. Mol Cell. Oct. 1998;2(4):437-45. doi: 10.1016/s1097-2765(00)80143-4.
Bessen et al., High-resolution specificity profiling and off-target prediction for site-specific DNA recombinases. Nat Commun. Apr. 26, 2019;10(1):1937. doi: 10.1038/s41467-019-09987-0.
Beumer et al., Efficient gene targeting in *Drosophila* with zinc-finger nucleases. Genetics. Apr. 2006;172(4):2391-403. Epub Feb. 1, 2006.
Bhagwat, DNA-cytosine deaminases: from antibody maturation to antiviral defense. DNA Repair (Amst). Jan. 5, 2004;3(1):85-9.
Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.
Bibb et al., Integration and excision by the large serine recombinase phiRv1 integrase. Mol Microbiol. Mar. 2005;55(6):1896-910. doi: 10.1111/j.1365-2958.2005.04517.x.
Biehs et al., DNA Double-Strand Break Resection Occurs during Non-homologous End Joining in G1 but Is Distinct from Resection during Homologous Recombination. Mol Cell. Feb. 16, 2017;65(4):671-684.e5. doi: 10.1016/j.molcel.2016.12.016. Epub Jan. 26, 2017.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Biswas et al., A structural basis for allosteric control of DNA recombination by lambda integrase. Nature. Jun. 23, 2005;435(7045):1059-66. doi: 10.1038/nature03657.
Bitinaite et al., FokI dimerization is required for DNA cleavage. Proc Natl Acad Sci U S A. Sep. 1, 1998;95(18):10570-5.
Blaese et al., Vectors in cancer therapy: how will they deliver? Cancer Gene Ther. Dec. 1995;2(4):291-7.
Blain et al., Nuclease activities of Moloney murine leukemia virus reverse transcriptase. Mutants with altered substrate specificities. J Biol Chem. Nov. 5, 1993;268(31):23585-92.
Blaisonneau et al., A circular plasmid from the yeast Torulaspora delbrueckii. Plasmid. 1997;38(3):202-9. doi: 10.1006/plas.1997.1315.
Blau et al., A proliferation switch for genetically modified cells. PNAS Apr. 1, 1997 94 (7) 3076-3081; https://doi.org/10.1073/pnas.94.7.3076.
Bloom et al., Evolving strategies for enzyme engineering. Curr Opin Struct Biol. Aug. 2005;15(4):447-52.
Boch, TALEs of genome targeting. Nat Biotechnol. Feb. 2011;29(2):135-6. Doi: 10.1038/nbt.1767.
Bodi et al., Yeast m6A Methylated mRNAs are Enriched on Translating Ribosomes during Meiosis, and under Rapamycin Treatment. PLoS One. Jul. 17, 2015;10(7):e0132090. doi: 10.1371/journal.pone.0132090.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Boersma et al., Selection strategies for improved biocatalysts. Febs J. May 2007;274(9):2181-95.
Bogdanove et al., Engineering altered protein-DNA recognition specificity. Nucleic Acids Res. Jun. 1, 2018;46(10):4845-4871. doi: 10.1093/nar/gky289.
Bogdanove et al., TAL effectors: customizable proteins for DNA targeting. Science. Sep. 30, 2011;333(6051):1843-6. doi: 10.1126/science.1204094.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Bolotin et al., Clustered regularly interspaced short palindrome repeats (CRISPRs) have spacers of extrachromosomal origin. Microbiology. Aug. 2005;151(Pt 8):2551-61.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.
Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.
Borman, Improved route to single-base genome editing. Chemical & Engineering News, Apr. 25, 2016;94(17)p. 5. http://cen.acs.org/articles/94/il7/Improved-route-single-base-genome.html.
Bourinet et al., Silencing of the Cav3.2 T-type calcium channel gene in sensory neurons demonstrates its major role in nociception. EMBO J. Jan. 26, 2005;24(2):315-24. doi: 10.1038/sj.emboj.7600515. Epub Dec. 16, 2004.

(56) References Cited

OTHER PUBLICATIONS

Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.
Box et al., A multi-domain protein system based on the HC fragment of tetanus toxin for targeting DNA to neuronal cells. J Drug Target. Jul. 2003;11(6):333-43. doi: 10.1080/10611863100001634667.
Branden and Tooze, Introduction to Protein Structure. 1999; 2nd edition. Garland Science Publisher: 3-12.
Braun et al., Immunogenic duplex nucleic acids are nuclease resistant. J Immunol. Sep. 15, 1988;141(6):2084-9.
Brierley et al., Viral RNA pseudoknots: versatile motifs in gene expression and replication. Nat Rev Microbiol. Aug. 2007;5(8):598-610. doi: 10.1038/nrmicro1704.
Briner et al., Guide RNA functional modules direct Cas9 activity and orthogonality. Mol Cell. Oct. 23, 2014;56(2):333-339. doi: 10.1016/j.molcel.2014.09.019.
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brown et al., A mammalian protein targeted by G1-arresting rapamycin-receptor complex. Nature. Jun. 30, 1994;369(6483):756-8. doi: 10.1038/369756a0.
Brown et al., Characterization of the genetic elements required for site-specific integration of plasmid pSE211 in Saccharopolyspora erythraea. J Bacteriol. Apr. 1990;172(4):1877-88. doi: 10.1128/jb.172.4.1877-1888.1990.
Brown et al., Serine recombinases as tools for genome engineering. Methods. Apr. 2011;53(4):372-9. doi: 10.1016/j.ymeth.2010.12.031. Epub Dec. 30, 2010.
Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.
Brusse et al., Spinocerebellar ataxia associated with a mutation in the fibroblast growth factor 14 gene (SCA27): A new phenotype. Mov Disord. Mar. 2006;21(3):396-401.
Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gk1765. Epub Oct. 27, 2006.
Buchholz et al., Alteration of Cre recombinase site specificity by substrate-linked protein evolution. Nat Biotechnol. Nov. 2001;19(11):1047-52.
Buchschacher et al., Human immunodeficiency virus vectors for inducible expression of foreign genes. J Virol. May 1992;66(5):2731-9. doi: 10.1128/JVI.66.5.2731-2739.1992.
Buchwald et al., Long-term, continuous intravenous heparin administration by an implantable infusion pump in ambulatory patients with recurrent venous thrombosis. Surgery. Oct. 1980;88(4):507-16.
Buckley et al., Targeting the von Hippel-Lindau E3 ubiquitin ligase using small molecules to disrupt the VHL/HIF-1? interaction. J Am Chem Soc. Mar. 14, 2012;134(10):4465-8. doi: 10.1021/ja209924v. Epub Feb. 27, 2012.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.
Budker et al., Protein/amphipathic polyamine complexes enable highly efficient transfection with minimal toxicity. Biotechniques. Jul. 1997;23(1):139, 142-7. doi: 10.2144/97231rr02.
Budworth et al., A brief history of triplet repeat diseases. Methods Mol Biol. 2013; 1010:3-17. doi: 10.1007/978-1-62703-411-1_1.
Bulow et al., Multienzyme systems obtained by gene fusion. Trends Biotechnol. Jul. 1991;9(7):226-31.
Burke et al., Activating mutations of Tn3 resolvase marking interfaces important in recombination catalysis and its regulation. Mol Microbiol. Feb. 2004;51(4):937-48.
Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.
Burstein et al., New CRISPR-Cas systems from uncultivated microbes. Nature Feb. 2017;542(7640):237-240.
Burton et al., Gene delivery using herpes simplex virus vectors. DNA Cell Biol. Dec. 2002;21(12):915-36. doi: 10.1089/104454902762053864.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Buskirk et al., In vivo evolution of an RNA-based transcriptional activator. Chem Biol. Jun. 2003; 10(6):533-40. doi: 10.1016/s1074-5521(03)00109-1.
Butt et al., Efficient CRISPR/Cas9-Mediated Genome Editing Using a Chimeric Single-Guide RNA Molecule. Front Plant Sci. Aug. 24, 2017;8:1441(1-8). doi: 10.3389/fpls.2017.01441.
Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.
Böck et al., Selenocysteine: the 21st amino acid. Mol Microbiol. Mar. 1991;5(3):515-20.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cadwell et al., Randomization of genes by PCR mutagenesis. PCR Methods Appl. Aug. 1992;2(1):28-33. doi: 10.1101/gr.2.1.28.
Cai et al., Reconstruction of ancestral protein sequences and its applications. BMC Evol Biol. Sep. 17, 2004;4:33. doi: 10.1186/1471-2148-4-33.
Calame et al., Transcriptional controlling elements in the immunoglobulin and T cell receptor loci. Adv Immunol. 1988;43:235-75. doi: 10.1016/s0065-2776(08)60367-3.
Caldecott et al., Single-strand break repair and genetic disease. Nat Rev Genet. Aug. 2008;9(8):619-31. doi: 10.1038/nrg2380.
Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.
Cameron, Recent advances in transgenic technology. Mol Biotechnol. Jun. 1997;7(3):253-65.
Camper et al., Postnatal repression of the alpha-fetoprotein gene is enhancer independent. Genes Dev. Apr. 1989;3(4):537-46. doi: 10.1101/gad.3.4.537.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.
Canver et al., Customizing the genome as therapy for the ?-hemoglobinopathies. Blood. May 26, 2016;127(21):2536-45. doi: 10.1182/blood-2016-01-678128. Epub Apr. 6, 2016.
Cargill et al., Characterization of single-nucleotide polymorphisms in coding regions of human genes. Nat Genet. Jul. 1999;22(3):231-8.
Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Caron et al., Intracellular delivery of a Tat-eGFP fusion protein into muscle cells. Mol Ther. Mar. 2001;3(3):310-8.
Carr et al., Genome engineering. Nat Biotechnol. Dec. 2009;27(12):1151-62. doi: 10.1038/nbt.1590.
Carroll et al., Gene targeting in *Drosophila* and Caenorhabditis elegans with zinc-finger nucleases. Methods Mol Biol. 2008;435:63-77. doi: 10.1007/978-1-59745-232-8_5.

(56) References Cited

OTHER PUBLICATIONS

Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Carroll, Genome engineering with zinc-finger nucleases. Genetics. Aug. 2011;188(4):773-82. doi: 10.1534/genetics.111.131433. Review.
Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.
Caspi et al., Distribution of split DnaE inteins in cyanobacteria. Mol Microbiol. Dec. 2003;50(5):1569-77. doi: 10.1046/j.1365-2958.2003.03825.x.
Cattaneo et al., SEL1L affects human pancreatic cancer cell cycle and invasiveness through modulation of PTEN and genes related to cell-matrix interactions. Neoplasia. 2005;7(11):1030-1038.
Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Chadalavada et al., Wild-type is the optimal sequence of the HDV ribozyme under cotranscriptional conditions. RNA. Dec. 2007; 13(12):2189-201. doi: 10.1261/rna.778107. Epub Oct. 23, 2007.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.
Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.
Chan et al., Molecular recording of mammalian embryogenesis. Nature. Jun. 2019;570(7759):77-82. doi: 10.1038/s41586-019-1184-5. Epub May 13, 2019.
Chan et al., Novel selection methods for DNA-encoded chemical libraries. Curr Opin Chem Biol. 2015;26:55-61. doi:10.1016/j.cbpa.2015.02.010.
Chan et al., The choice of nucleotide inserted opposite abasic sites formed within chromosomal DNA reveals the polymerase activities participating in translesion DNA synthesis. DNA Repair (Amst). Nov. 2013;12(11):878-89. doi: 10.1016/j.dnarep.2013.07.008. Epub Aug. 26, 2013.
Chapman et al., Playing the end game: DNA double-strand break repair pathway choice. Mol Cell. Aug. 24, 2012;47(4):497-510. doi: 10.1016/j.molcel.2012.07.029.
Chari et al., Unraveling CRISPR-Cas9 genome engineering parameters via a library-on-library approach. Nat Methods. Sep. 2015;12(9):823-6. doi: 10.1038/nmeth.3473. Epub Jul. 13, 2015.
Charpentier et al., Biotechnology: Rewriting a genome. Nature. Mar. 7, 2013;495(7439):50-1. doi: 10.1038/495050a.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chavez et al., Highly efficient Cas9-mediated transcriptional programming. Nat Methods. Apr. 2015;12(4):326-8. doi: 10.1038/nmeth.3312. Epub Mar. 2, 2015.
Chavez et al., Precise Cas9 targeting enables genomic mutation prevention. bioRxiv. Jun. 14, 2016; http://dx/doi.oreg/10.1101/058974. 6 pages. bioRxiv preprint first posted online Jun. 14, 2016.
Chavez et al., Therapeutic applications of the ΦC31 integrase system. Curr Gene Ther. Oct. 2011;11(5):375-81. Review.
Chawla et al., An atlas of RNA base pairs involving modified nucleobases with optimal geometries and accurate energies. Nucleic Acids Res. Aug. 18, 2015;43(14):6714-29. doi: 10.1093/nar/gkv606. Epub Jun. 27, 2015.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.
Chen et al., Enhanced proofreading governs CRISPR-Cas9 targeting accuracy. Nature. Oct. 19, 2017;550(7676):407-410. doi: 10.1038/nature24268. Epub Sep. 20, 2017.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Chen et al., Alterations in PMS2, MSH2 and MLH1 expression in human prostate cancer. Int J Oncol. May 2003;22(5):1033-43.
Chen et al., Enhanced prime editing systems by manipulating cellular determinants of editing outcomes. Cell. Oct. 28, 2021;184(22):5635-5652.e29. doi: 10.1016/j.cell.2021.09.018. Epub Oct. 14, 2021.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Chen et al., Genome-wide CRISPR screen in a mouse model of tumor growth and metastasis. Cell. Mar. 12, 2015;160(6):1246-60. doi: 10.1016/j.cell.2015.02.038. Epub Mar. 5, 2015.
Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.
Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Chen et al., Targeting genomic rearrangements in tumor cells through Cas9-mediated insertion of a suicide gene. Nat Biotechnol. Jun. 2017;35(6):543-550. doi: 10.1038/nbt.3843. Epub May 1, 2017.
Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.
Chesnoy et al., Structure and function of lipid-DNA complexes for gene delivery. Annu Rev Biophys Biomol Struct. 2000;29:27-47.
Chester et al., The apolipoprotein B mRNA editing complex performs a multifunctional cycle and suppresses nonsense-mediated decay. EMBO J. Aug. 1, 2003;22(15):3971-82. doi: 10.1093/emboj/cdg369.
Chew et al., A multifunctional AAV-CRISPR-Cas9 and its host response. Nat Methods. Oct. 2016; 13(10):868-74. doi: 10.1038/nmeth.3993. Epub Sep. 5, 2016.
Chew et al., A multifunctional AAV-CRISPR-Cas9 and its host response. Nat Methods. Oct. 2016; 13(10):868-74. doi: 10.1038/nmeth.3993. Epub Sep. 5, 2016. Supplementary Information.
Chichili et al., Linkers in the structural biology of protein-protein interactions. Protein Science. 2013;22:153-67.
Chin, Expanding and reprogramming the genetic code of cells and animals. Annu Rev Biochem. 2014;83:379-408. doi: 10.1146/annurev-biochem-060713-035737. Epub Feb. 10, 2014.

(56) References Cited

OTHER PUBLICATIONS

Chipev et al., A leucine—proline mutation in the H1 subdomain of keratin 1 causes epidermolytic hyperkeratosis. Cell. Sep. 4, 1992;70(5):821-8.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Cho et al., Site-specific recombination of bacteriophage P22 does not require integration host factor. J Bacteriol. Jul. 1999;181(14):4245-9. doi: 10.1128/JB.181.14.4245-4249.1999.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Cho et al., The calcium-activated chloride channel anoctamin 1 acts as a heat sensor in nociceptive neurons. Nat Neurosci. May 27, 2012;15(7):1015-21. doi: 10.1038/nn.3111.
Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.
Choi et al., (6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 11, 2016.
Choi et al., Protein trans-splicing and characterization of a split family B-type DNA polymerase from the hyperthermophilic archaeal parasite Nanoarchaeum equitans. J Mol Biol. Mar. 10, 2006;356(5):1093-106. doi: 10.1016/j.jmb.2005.12.036. Epub Dec. 27, 2005.
Choi et at al., Translesion synthesis across abasic lesions by human B-family and Y-family DNA polymerases ?, ?, ?, ?, ?, and REV1. J Mol Biol. Nov. 19, 2010;404(1):34-44. doi: 10.1016/j.jmb.2010.09.015. Epub Oct. 1, 2010.
Chong et al., Modulation of protein splicing of the *Saccharomyces cerevisiae* vacuolar membrane ATPase intein. J Biol Chem. Apr. 24, 1998;273(17):10567-77. doi: 10.1074/jbc.273.17.10567.
Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.
Chong et al., Protein splicing involving the *Saccharomyces cerevisiae* VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.
Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.
Chong et al., Single-col. purification of free recombinant proteins using a self-cleavable affinity tag derived from a protein splicing element. Gene. Jun. 17, 1997;192(2):271-81. doi: 10.1016/s0378-1119(97)00105-4.
Choudhury et al., CRISPR-dCas9 mediated TET1 targeting for selective DNA demethylation at BRCA1 promoter. Oncotarget. Jul. 19, 2016;7(29):46545-46556. doi: 10.18632/oncotarget. 10234.
Choudhury et al., CRISPR/Cas9 recombineering-mediated deep mutational scanning of essential genes in *Escherichia coli*. Mol Syst Biol. Mar. 2020;16(3):e9265. doi: 10.15252/msb.20199265.
Choudhury et al., Engineering RNA endonucleases with customized sequence specificities. Nat Commun. 2012;3:1147. doi: 10.1038/ncomms2154.
Choulika et al., Induction of homologous recombination in mammalian chromosomes by using the I-SceI system of *Saccharomyces cerevisiae*. Mol Cell Biol. Apr. 1995; 15(4):1968-73. doi: 10.1128/MCB.15.4.1968.
Christian et al, Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Christiansen et al., Characterization of the lactococcal temperate phage TP901-1 and its site-specific integration. J Bacteriol. Feb. 1994;176(4):1069-76. doi: 10.1128/jb.176.4.1069-1076.1994.
Chu et al., Increasing the efficiency of homology-directed repair for CRISPR-Cas9-induced precise gene editing in mammalian cells. Nat Biotech. Feb. 13, 2015;33:543-8. doi: 10.1038/nbt.3198. Epub Mar. 24, 2015.
Chuai et al., DeepCRISPR: optimized CRISPR guide RNA design by deep learning. Genome Biol. Jun. 26, 2018;19(1):80. doi: 10.1186/s13059-018-1459-4.
Chuai et al., In Silico Meets in Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.
Chuang et al., Novel Heterotypic Rox Sites for Combinatorial Dre Recombination Strategies. G3 (Bethesda). Dec. 29, 2015;6(3):559-71. doi: 10.1534/g3.115.025841.
Chujo et al., Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.
Clement et al., CRISPResso2 provides accurate and rapid genome editing sequence analysis. Nat Biotechnol. Mar. 2019;37(3):224-226. doi: 10.1038/s41587-019-0032-3.
Cobb et al., Directed evolution as a powerful synthetic biology tool. Methods. Mar. 15, 2013;60(1):81-90. doi: 10.1016/j.ymeth.2012.03.009. Epub Mar. 23, 2012.
Coffey et al., The Economic Impact of BSE on the U.S. Beef Industry: Product Value Losses, Regulatory Costs, and Consumer Reactions. Kansas State University Agricultural Experiment Station and Cooperative Extension Service. MF-2678. May 2005. 68 pages. Accessed via https://bookstore.ksre.ksu.edu/pubs/MF2678.pdf.
Cokol et al., Finding nuclear localization signals. EMBO Rep. Nov. 2000;1(5):411-5. doi: 10.1093/embo-reports/kvd092.
Cole et al., Reconstructing evolutionary adaptive paths for protein engineering. Methods Mol Biol. 2013;978:115-25. doi: 10.1007/978-1-62703-293-3_8.
Cole-Strauss et al., Correction of the mutation responsible for sickle cell anemia by an RNA-DNA oligonucleotide. Science. Sep. 6, 1996;273(5280):1386-9.
Collinge, Prion diseases of humans and animals: their causes and molecular basis. Annu Rev Neurosci. 2001;24:519-50. doi: 10.1146/annurev.neuro.24.1.519.
Cong et al., Multiplex genome engineering using CRISPR/Cas systems. Science. Feb. 15, 2013;339(6121):819-23. doi: 10.1126/science.1231143. Epub Jan. 3, 2013.
Conrad et al., A Kaposi's sarcoma virus RNA element that increases the nuclear abundance of intronless transcripts. EMBO J. May 18, 2005;24(10):1831-41. doi: 10.1038/sj.emboj.7600662. Epub Apr. 28, 2005.
Conticello, The AID/APOBEC family of nucleic acid mutators. Genome Biol. 2008;9(6):229. doi: 10.1186/GB-2008-9-6-229. Epub Jun. 17, 2008.
Cornu et al., Refining strategies to translate genome editing to the clinic. Nat Med. Apr. 3, 2017;23(4):415-423. doi: 10.1038/nm.4313.
Costa et al., Frequent use of the same tertiary motif by self-folding RNAs. EMBO J. Mar. 15, 1995;14(6):1276-85.
Cotton et al., Insertion of a Synthetic Peptide into a Recombinant Protein Framework: A Protein Biosensor. J. Am. Chem. Soc. Jan. 22, 1999; 121(5):1100-1. https://doi.org/10.1021/ja983804b.
Covino et al., The CCL2/CCR2 Axis in the Pathogenesis of HIV-1 Infection: A New Cellular Target for Therapy? Current Drug Targets Dec. 2016;17(1):76-110. DOI: 10.2174/138945011701151217110917.

(56) References Cited

OTHER PUBLICATIONS

Cox et al., An SCN9A channelopathy causes congenital inability to experience pain. Nature. Dec. 14, 2006;444(7121):894-8. doi: 10.1038/nature05413.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Cox et al., Congenital insensitivity to pain: novel SCN9A missense and in-frame deletion mutations. Hum Mutat. Sep. 2010;31(9):E1670-86. doi: 10.1002/humu.21325.
Cox et al., RNA editing with CRISPR-Cas13. Science. Nov. 24, 2017;358(6366):1019-1027. doi: 10.1126/science.aaq0180. Epub Oct. 25, 2017.
Cox et al., Therapeutic genome editing: prospects and challenges. Nat Med. Feb. 2015;21(2):121-31. doi: 10.1038/nm.3793.
Cox, Proteins pinpoint double strand breaks. Elife. Oct. 29, 2013;2:e01561. doi: 10.7554/eLife.01561.
Crabtree et al., Three-part inventions: intracellular signaling and induced proximity. Trends Biochem Sci. Nov. 1996;21(11):418-22. doi: 10.1016/s0968-0004(96)20027-1.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Crick, On protein synthesis. Symp Soc Exp Biol. 1958;12:138-63.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into Mammalian cells in vitro and in vivo using a supercharged protein. ACS Chem Biol. Aug. 20, 2010;5(8):747-52. doi:10.1021/cb1001153.
Crystal, Transfer of genes to humans: early lessons and obstacles to success. Science. Oct. 20, 1995;270(5235):404-10. doi: 10.1126/science.270.5235.404.
Cui et al., Consequences of Cas9 cleavage in the chromosome of *Escherichia coli*. Nucleic Acids Res. May 19, 2016;44(9):4243-51. doi: 10.1093/nar/gkw223. Epub Apr. 8, 2016.
Cui et al., m6A RNA Methylation Regulates the Self-Renewal and Tumorigenesis of Glioblastoma Stem Cells. Cell Rep. Mar. 14, 2017;18(11):2622-2634. doi: 10.1016/j.celrep.2017.02.059.
Cui et al., Review of CRISPR/Cas9 sgRNA Design Tools. Interdiscip Sci. Jun. 2018;10(2):455-465. doi: 10.1007/s12539-018-0298-z. Epub Apr. 11, 2018.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Cunningham et al., Ensembl 2015. Nucleic Acids Res. Jan. 2015;43(Database issue):D662-9. doi: 10.1093/nar/gku1010. Epub Oct. 28, 2014.
Cupples et al., A set of lacZ mutations in *Escherichia coli* that allow rapid detection of each of the six base substitutions. Proc Natl Acad Sci U S A. Jul. 1989;86(14):5345-9.
D'adda di Fagagna et al., The Gam protein of bacteriophage Mu is an orthologue of eukaryotic Ku. EMBO Rep. Jan. 2003;4(1):47-52.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
Dahlgren et al., A novel mutation in ribosomal protein S4 that affects the function of a mutated RF1. Biochimie. Aug. 2000;82(8):683-91.
Dahlman et al., Orthogonal gene knockout and activation with a catalytically active Cas9 nuclease. Nat Biotechnol. Nov. 2015;33(11):1159-61. doi: 10.1038/nbt.3390.
Dandage et al., beditor: A Computational Workflow for Designing Libraries of Guide RNAs for CRISPR-Mediated Base Editing. Genetics. Jun. 2019;212(2):377-385. doi: 10.1534/genetics.119.302089. Epub Apr. 1, 2019.
Dang et al., Optimizing sgRNA structure to improve CRISPR-Cas9 knockout efficiency. Genome Biol. Dec. 15, 2015;16:280. doi: 10.1186/s13059-015-0846-3.
Das et al., The crystal structure of the monomeric reverse transcriptase from Moloney murine leukemia virus. Structure. May 2004;12(5):819-29. doi: 10.1016/j.str.2004.02.032.
Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.
Dassa et al., Trans protein splicing of cyanobacterial split inteins in endogenous and exogenous combinations. Biochemistry. Jan. 9, 2007;46(1):322-30. doi: 10.1021/bi0611762.
Database EBI Accession No. ADE34233 Jan. 29, 2004.
Database EBI Accession No. BFF09785. May 31, 2018. 2 pages.
Database EBI Accession No. BGE38086. Jul. 25, 2019. 2 pages.
Database UniProt Accession No. G813E0. Jan. 14, 2012.
Datsenko et al., One-step inactivation of chromosomal genes in *Escherichia coli* K-12 using PCR products. Proc Natl Acad Sci U S A. Jun. 6, 2000;97(12):6640-5.
Davidson et al., Viral vectors for gene delivery to the nervous system. Nat Rev Neurosci. May 2003;4(5):353-64. doi: 10.1038/nrn1104.
Davis et al., DNA double strand break repair via non-homologous end-joining. Transl Cancer Res. Jun. 2013;2(3):130-143.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
De Felipe et al., Co-translational, intraribosomal cleavage of polypeptides by the foot-and-mouth disease virus 2A peptide. J Biol Chem. Mar. 28, 2003;278(13):11441-8. doi: 10.1074/jbc.M211644200. Epub Jan. 8, 2003.
De La Peña et al., The Hammerhead Ribozyme: A Long History for a Short RNA. Molecules. Jan. 4, 2017;22(1):78. doi: 10.3390/molecules22010078.
De Souza, Primer: genome editing with engineered nucleases. Nat Methods. Jan. 2012;9(1):27.
De Wit et al., The Human CD4+ T Cell Response against Mumps Virus Targets a Broadly Recognized Nucleoprotein Epitope. J Virol. Mar. 5, 2019;93(6):e01883-18. doi: 10.1128/JVI.01883-18.
Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, Alive Study. Science. Sep. 27, 1996;273(5283):1856-62. doi: 10.1126/science.273.5283.1856.
DeKosky et al., Large-scale sequence and structural comparisons of human naive and antigen-experienced antibody repertoires. Proc Natl Acad Sci U S A. May 10, 2016;113(19):E2636-45. doi: 10.1073/pnas.1525510113. Epub Apr. 25, 2016.
Delebecque et al., Organization of intracellular reactions with rationally designed RNA assemblies. Science. Jul. 22, 2011;333(6041):470-4. doi: 10.1126/science.1206938. Epub Jun. 23, 2011.
Deltcheva et al., CRISPR RNA maturation by trans-encoded small RNA and host factor RNase III. Nature. Mar. 31, 2011;471(7340):602-7. doi: 10.1038/nature09886.
Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.
Denizio et al., Harnessing natural DNA modifying activities for editing of the genome and epigenome. Curr Opin Chem Biol. Aug. 2018;45:10-17. doi: 10.1016/j.cbpa.2018.01.016. Epub Feb. 13, 2018.
Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.

(56) References Cited

OTHER PUBLICATIONS

Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dever et al., CRISPR/Cas9 ?-globin gene targeting in human haematopoietic stem cells. Nature. Nov. 17, 2016;539(7629):384-389. doi: 10.1038/nature20134. Epub Nov. 7, 2016.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Devigili et al., Paroxysmal itch caused by gain-of-function Nav1.7 mutation. Pain. Sep. 2014;155(9):1702-1707. doi: 10.1016/j.pain.2014.05.006. Epub May 10, 2014.
Dianov et al., Mammalian base excision repair: the forgotten archangel. Nucleic Acids Res. Apr. 1, 2013;41(6):3483-90. doi: 10.1093/nar/gkt076. Epub Feb. 13, 2013.
Dicarlo et al., Genome engineering in *Saccharomyces cerevisiae* using CRISPR-Cas systems. Nucleic Acids Research Apr. 2013;41(7):4336-43.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.
Dickey et al., Single-stranded DNA-binding proteins: multiple domains for multiple functions. Structure. Jul. 2, 2013;21(7):1074-84. doi: 10.1016/j.str.2013.05.013.
Dickinson et al., Experimental interrogation of the path dependence and stochasticity of protein evolution using phage-assisted continuous evolution. Proc Natl Acad Sci USA. May 2013;110(22):9007-12.
Dillon, Regulating gene expression in gene therapy. Trends Biotechnol. May 1993;11(5):167-73. doi: 10.1016/0167-7799(93)90109-M.
Ding et al., A Talen genome-editing system for generating human stem cell-based disease models. Cell Stem Cell. Feb. 7, 2013;12(2):238-51. Doi: 10.1016/j.stem.2012.11.011. Epub Dec. 13, 2012.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Dingwall et al., Nuclear targeting sequences—a consensus? Trends Biochem Sci. Dec. 1991; 16(12):478-81. doi: 10.1016/0968-0004(91)90184-w.
Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Doench et al., Optimized sgRNA design to maximize activity and minimize off-target effects of CRISPR-Cas9. Nat Biotechnol. Feb. 2016;34(2):184-191. doi: 10.1038/nbt.3437.
Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.
Dolan et al., Trans-splicing with the group I intron ribozyme from Azoarcus. RNA. Feb. 2014;20(2):202-13. doi: 10.1261/rna.041012.113. Epub Dec. 16, 2013.
Doman et al., Evaluation and minimization of Cas9-independent off-target DNA editing by cytosine base editors. Nat Biotechnol. May 2020;38(5):620-628. doi: 10.1038/s41587-020-0414-6. Epub Feb. 10, 2020.
Dominissini et al., Topology of the human and mouse m6A RNA methylomes revealed by m6A-seq. Nature. Apr. 29, 2012;485(7397):201-6. doi: 10.1038/nature11112.
Dorgan et al., An enzyme-coupled continuous spectrophotometric assay for S-adenosylmethionine-dependent methyltransferases. Anal Biochem. Mar. 15, 2006;350(2):249-55. doi: 10.1016/j.ab.2006.01.004. Epub Feb. 7, 2006.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.
Doudna et al., Genome editing. The new frontier of genome engineering with CRISPR-Cas9. Science. Nov. 28, 2014;346(6213):1258096. doi: 10.1126/science.1258096.
Doudna, The promise and challenge of therapeutic genome editing. Nature. Feb. 2020;578(7794):229-236. doi: 10.1038/s41586-020-1978-5. Epub Feb. 12, 2020.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Drake, A constant rate of spontaneous mutation in DNA-based microbes. Proc Natl Acad Sci USA. Aug. 15, 1991;88(16):7160-4.
Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.
Dubois et al., Retroviral RNA Dimerization: From Structure to Functions. Front Microbiol. Mar. 22, 2018;9:527. doi: 10.3389/fmicb.2018.00527.
Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.
Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
Dunbar et al., Gene therapy comes of age. Science. Jan. 12, 2018;359(6372):eaan4672. doi: 10.1126/science.aan4672.
Dupuy et al., Le syndrome de De La Chapelle [De La Chapelle syndrome]. Presse Med. Mar. 3, 2001;30(8):369-72. French.
Durai et al., A bacterial one-hybrid selection system for interrogating zinc finger-DNA interactions. Comb Chem High Throughput Screen. May 2006;9(4):301-11.
Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Edlund et al., Cell-specific expression of the rat insulin gene: evidence for role of two distinct 5' flanking elements. Science. Nov. 22, 1985;230(4728):912-6. doi: 10.1126/science.3904002.
Edwards et al., An *Escherichia coli* tyrosine transfer RNA is a leucine-specific transfer RNA in the yeast *Saccharomyces cerevisiae*. Proc Natl Acad Sci U S A. Feb. 15, 1991;88(4):1153-6.
Edwards et al., Crystal structures of the thi-box riboswitch bound to thiamine pyrophosphate analogs reveal adaptive RNA-small molecule recognition. Structure. Sep. 2006;14(9):1459-68.
Eick et al., Robustness of Reconstructed Ancestral Protein Functions to Statistical Uncertainty. Mol Biol Evol. Feb. 1, 2017;34(2):247-261. doi: 10.1093/molbev/msw223.
Eiler et al., Structural Basis for the Fast Self-Cleavage Reaction Catalyzed by the Twister Ribozyme. Proc Natl Acad Sci U S A. Sep. 9, 2014;111(36):13028-33. doi: 10.1073/pnas.1414571111. Epub Aug. 25, 2014.

(56) References Cited

OTHER PUBLICATIONS

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Emery et al., HCN2 ion channels play a central role in inflammatory and neuropathic pain. Science. Sep. 9, 2011;333(6048):1462-6. doi: 10.1126/science.1206243.
Endo et al., Toward establishing an efficient and versatile gene targeting system in higher plants. Biocatalysis and Agricultural Biotechnology 2014;3,(1):2-6.
Engel et al., The emerging role of mRNA methylation in normal and pathological behavior. Genes Brain Behav. Mar. 2018;17(3):e12428. doi: 10.1111/gbb.12428. Epub Nov. 17, 2017.
Engelward et al., Base excision repair deficient mice lacking the Aag alkyladenine DNA glycosylase. Proc Natl Acad Sci U S A. Nov. 25, 1997;94(24):13087-92.
England, Unnatural amino acid mutagenesis: a precise tool for probing protein structure and function. Biochemistry. Sep. 21, 2004;43(37):11623-9.
Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.
Epstein, HSV-1-based amplicon vectors: design and applications. Gene Ther. Oct. 2005;12 Suppl 1:S154-8. doi: 10.1038/sj.gt.3302617.
Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.
Estacion et al., A sodium channel gene SCN9A polymorphism that increases nociceptor excitability. Ann Neurol. Dec. 2009;66(6):862-6. doi: 10.1002/ana.21895.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Evans et al., Protein trans-splicing and cyclization by a naturally split intein from the dnaE gene of Synechocystis species PCC6803. J Biol Chem. Mar. 31, 2000;275(13):9091-4. doi: 10.1074/jbc.275.13.9091.
Evans et al., Semisynthesis of cytotoxic proteins using a modified protein splicing element. Protein Sci. Nov. 1998;7(11):2256-64. doi: 10.1002/pro.5560071103.
Evans et al., The cyclization and polymerization of bacterially expressed proteins using modified self-splicing inteins. J Biol Chem. Jun. 25, 1999;274(26):18359-63. doi: 10.1074/jbc.274.26.18359.
Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.
Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.
Fagerlund et al., The Cpf1 CRISPR-Cas protein expands genome-editing tools. Genome Biology Nov. 17, 2015;16:251. https://doi.org/10.1186/s13059-015-0824-9.
Falnes et al., DNA repair by bacterial AlkB proteins. Res Microbiol. Oct. 2003;154(8):531-8. doi: 10.1016/S0923-2508(03)00150-5.
Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.
Fang et al., Synthetic Studies Towards Halichondrins: Synthesis of the Left Halves of Norhalichondrins and Homohalichondrins. Tetrahedron Letters 1992;33(12):1557-1560.
Farboud et al., Dramatic enhancement of genome editing by CRISPR/Cas9 through improved guide RNA design. Genetics. Apr. 2015;199(4):959-71. doi: 10.1534/genetics.115.175166. Epub Feb. 18, 2015.
Farhood et al., Codelivery to mammalian cells of a transcriptional factor with cis-acting element using cationic liposomes. Anal Biochem. Feb. 10, 1995;225(1):89-93.
Fawcett et al., Transposable elements controlling I-R hybrid dysgenesis in D. melanogaster are similar to mammalian LINEs. Cell. Dec. 26, 1986;47(6):1007-15. doi: 10.1016/0092-8674(86)90815-9.
Feldstein et al., Two sequences participating in the autolytic processing of satellite tobacco ringspot virus complementary RNA. Gene. Oct. 15, 1989;82(1):53-61. doi: 10.1016/0378-1119(89)90029-2.
Felletti et al., Twister Ribozymes as Highly Versatile Expression Platforms for Artificial Riboswitches. Nat Commun. Sep. 27, 2016;7:12834. doi: 10.1038/ncomms12834.
Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.
Feng et al., Human L1 retrotransposon encodes a conserved endonuclease required for retrotransposition. Cell. Nov. 29, 1996;87(5):905-16. doi: 10.1016/s0092-8674(00)81997-2.
Ferreira Da Silva et al., Prime editing efficiency and fidelity are enhanced in the absence of mismatch repair. Nat Commun. Feb. 9, 2022;13(1):760. doi: 10.1038/s41467-022-28442-1.
Ferretti et al., Complete genome sequence of an M1 strain of *Streptococcus pyogenes*. Proc Natl Acad Sci U S A. Apr. 10, 2001;98(8):4658-63.
Ferry et al., Rational design of inducible CRISPR guide RNAs for de novo assembly of transcriptional programs. Nat Commun. Mar. 3, 2017;8:14633. doi: 10.1038/ncomms14633.
Feuk, Inversion variants in the human genome: role in disease and genome architecture. Genome Med. Feb. 12, 2010;2(2):11. doi: 10.1186/gm132.
Filippov et al., A novel type of RNase III family proteins in eukaryotes. Gene. Mar. 7, 2000;245(1):213-21. doi: 10.1016/s0378-1119(99)00571-5.
Filippova et al., Guide RNA modification as a way to improve CRISPR/Cas9-based genome-editing systems. Biochimie. Dec. 2019;167:49-60. doi: 10.1016/j.biochi.2019.09.003. Epub Sep. 4, 2019.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fire et al., Potent and specific genetic interference by double-stranded RNA in Caenorhabditis elegans. Nature. Feb. 19, 1998;391(6669):806-11. doi: 10.1038/35888.
Fischbach et al., Directed evolution can rapidly improve the activity of chimeric assembly-line enzymes. Proc Natl Acad Sci U S A. Jul. 17, 2007;104(29):11951-6. doi: 10.1073/pnas.0705348104. Epub Jul. 9, 2007.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fitzjohn, Diversitree: comparative phylogenetic analyses of diversification in R. Methods in Evology and Evolution. Dec. 2012;3(6):1084-92 .doi: 10.1111/j.2041-210X.2012.00234.x.
Flajolet et al., Woodchuck hepatitis virus enhancer I and enhancer II are both involved in—myc2 activation in woodchuck liver tumors. J Virol. Jul. 1998;72(7):6175-80. doi: 10.1128/JVI.72.7.6175-6180.1998.
Flaman et al., A rapid PCR fidelity assay. Nucleic Acids Res. Aug. 11, 1994;22(15):3259-60. doi: 10.1093/nar/22.15.3259.
Flynn et al., CRISPR-mediated genotypic and phenotypic correction of a chronic granulomatous disease mutation in human iPS

(56) References Cited

OTHER PUBLICATIONS cells. Exp Hematol. Oct. 2015;43(10):838-848.e3. doi: 10.1016/j.exphem.2015.06.002. Epub Jun. 19, 2015. Including supplementary figures and data.
Fogg et al., New applications for phage integrases. J Mol Biol. Jul. 29, 2014;426(15):2703-16. doi: 10.1016/j.jmb.2014.05.014. Epub May 22, 2014.
Fogg et al., Genome Integration and Excision by a New Streptomyces Bacteriophage, ?Joe. Appl Environ Microbiol. Feb. 15, 2017;83(5):e02767-16. doi: 10.1128/AEM.02767-16.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Including Supplementary Information.
Forster et al., Self-cleavage of virusoid RNA is performed by the proposed 55-nucleotide active site. Cell. Jul. 3, 1987;50(1):9-16. doi: 10.1016/0092-8674(87)90657-x.
Fortini et al., Different DNA polymerases are involved in the short- and long-patch base excision repair in mammalian cells. Biochemistry. Mar. 17, 1998;37(11):3575-80. doi: 10.1021/bi972999h.
Fouts et al., Sequencing Bacillus anthracis typing phages gamma and cherry reveals a common ancestry. J Bacteriol. May 2006;188(9):3402-8. doi: 10.1128/JB.188.9.3402-3408.2006.
Freitas et al., Mechanisms and signals for the nuclear import of proteins. Curr Genomics. Dec. 2009;10(8):550-7. doi: 10.2174/138920209789503941.
Freshney, Culture of Animal Cells. A Manual of Basic Technique. Alan R. Liss, Inc. New York. 1983;4.
Fu et al., Improving CRISPR-Cas nuclease specificity using truncated guide RNAs. Nat Biotechnol. Mar. 2014;32(3):279-84. doi: 10.1038/nbt.2808. Epub Jan. 2, 20146.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fu et al., Promises and Pitfalls of Intracellular Delivery of Proteins. Bioconjugate Chemistry. Aug. 2014;25:1602-8.
Fuchs et al., Polyarginine as a multifunctional fusion tag. Protein Sci. Jun. 2005;14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Furukawa et al., In vitro selection of allosteric ribozymes that sense the bacterial second messenger c-di-GMP. Methods Mol Biol. 2014;1111:209-20. doi: 10.1007/978-1-62703-755-6_15.
Fusi et al., In Silico Predictive Modeling of CRISPR/Cas9 guide efficiency. Jun. 26, 2015; bioRxiv. http://dx.doi.org/10.1101/021568.
Gaj et al., 3rd. Genome engineering with custom recombinases. Methods Enzymol. 2014;546:79-91. doi: 10.1016/B978-0-12-801185-0.00004-0.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., Structure-guided reprogramming of serine recombinase DNA sequence specificity. Proc Natl Acad Sci US A. Jan. 11, 2011;108(2):498-503. doi: 10.1073/pnas.1014214108. Epub Dec. 27, 2010.
Gaj et al., Zfn, Talen, and CRISPR/Cas-based methods for genome engineering. Trends Biotechnol. Jul. 2013;31(7):397-405. doi: 10.1016/j.tibtech.2013.04.004. Epub May 9, 2013.
Gajula, Designing an Elusive CoG?GoC CRISPR Base Editor. Trends Biochem Sci. Feb. 2019;44(2):91-94. doi: 10.1016/j.tibs.2018.10.004. Epub Nov. 13, 2018.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gangopadhyay et al., Precision Control of CRISPR-Cas9 Using Small Molecules and Light. Biochemistry. Jan. 29, 2019;58(4):234-244. doi: 10.1021/acs.biochem.8b01202. Epub Jan. 22, 2019.
Gao et al., Cationic liposome-mediated gene transfer. Gene Ther. Dec. 1995;2(10):710-22.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gao et al., Prime editing in mice reveals the essentiality of a single base in driving tissue-specific gene expression. Genome Biol. Mar. 16, 2021;22(1):83. doi: 10.1186/s13059-021-02304-3.
Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.
Gao et al., Treatment of autosomal dominant hearing loss by in vivo delivery of genome editing agents. Nature. Jan. 11, 2018;553(7687):217-221. doi: 10.1038/nature25164. Epub Dec. 20, 2017.
Gapinske et al., CRISPR-SKIP: programmable gene splicing with single base editors. Genome Biol. Aug. 15, 2018;19(1):107. doi: 10.1186/s13059-018-1482-5.
Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.
Gardlik et al., Vectors and delivery systems in gene therapy. Med Sci Monit. Apr. 2005;11(4):RA110-21. Epub Mar. 24, 2005.
Garibyan et al., Use of the rpoB gene to determine the specificity of base substitution mutations on the *Escherichia coli* chromosome. DNA Repair (Amst). May 13, 2003;2(5):593-608.
Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gaudelli et al., Programmable base editing of AoT to GoC in genomic DNA without DNA cleavage. Nature. Nov. 23, 2017;551(7681):464-471. doi: 10.1038/nature24644. Epub Oct. 25, 2017. Erratum in: Nature. May 2, 2018.
Gearing, Addgene blog. CRISPR 101: Cas9 nickase design and homology directed repair. 2018. pp. 1-12. https://blog.addgene.org/crispr-101-cas9-nickase-design-and-homlogy-directed-repair. Last retrieved online Jun. 25, 2021.
Gehrke et al., An APOBEC3A-Cas9 base editor with minimized bystander and off-target activities. Nat Biotechnol. Nov. 2018;36(10):977-982. doi: 10.1038/nbt.4199. Epub Jul. 30, 2018.
GenBank Accession No. J01600.1. Brooks et al., *E.coli* dam gene coding for DNA adenine methylase. Apr. 26, 1993.
GenBank Accession No. U07651.1. Lu, *Escherichia coli* K12 negative regulator of replication initiation (seqA) gene, complete cds. Jul. 19, 1994.
Genbank Submission; NIH/NCBI Accession No. 4UN5_B. Anders et al., Jul. 23, 2014. 5 pages.

(56) References Cited

OTHER PUBLICATIONS

Genbank Submission; NIH/NCBI Accession No. NM_001319224.2. Umar et al., Apr. 21, 2021. 7 pages.
Genbank Submission; NIH/NCBI Accession No. NM_006027.4. Umar et al., Apr. 10, 2021. 7 pages.
Genbank Submission; NIH/NCBI, Accession No. AAA66622.1. Martinelli et al., May 18, 1995. 2 pages.
Genbank Submission; NIH/NCBI, Accession No. AGT42196. Farzadfar et al., Nov. 2, 2013. 2 pages.
Genbank Submission; NIH/NCBI, Accession No. AIT42264.1. Hyun et al., Oct. 15, 2014. 2 pages.
Genbank Submission; NIH/NCBI, Accession No. AKA60242.1. Tong et al., Apr. 5, 2015. 1 page.
Genbank Submission; NIH/NCBI, Accession No. AKQ21048.1. Gilles et al., Jul. 19, 2015. 1 page.
Genbank Submission; NIH/NCBI, Accession No. AKS40380.1. Nodvig et al., Aug. 2, 2015. 1 page.
Genbank Submission; NIH/NCBI, Accession No. APG80656.1. Burstein et al., Dec. 10, 2016. 1 pages.
Genbank Submission; NIH/NCBI, Accession No. AYD60528.1. Ram et al., Oct. 2, 2018. 1 page.
Genbank Submission; NIH/NCBI, Accession No. BDB43378. Zhang et al., Aug. 11, 2016. 2 pages.
Genbank Submission; NIH/NCBI, Accession No. J04623. Kita et al., Apr. 26, 1993. 2 pages.
Genbank Submission; NIH/NCBI, Accession No. KR710351.1. Sahni et al., Jun. 1, 2015. 2 pages.
Genbank Submission; NIH/NCBI, Accession No. NC 002737.2. Nasser et al., Feb. 7, 2021. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NM_000311.5. Alves et al., Mar. 7, 2021. 5 pages.
Genbank Submission; NIH/NCBI, Accession No. NM_001319224. Umar et al., Apr. 21, 2021. 7 pages.
Genbank Submission; NIH/NCBI, Accession No. NM_002945.3. Weiser et al., Sep. 3, 2017. 5 pages.
Genbank Submission; NIH/NCBI, Accession No. NM_002946.5. Kavli et al., Jun. 26, 2021. 5 pages.
Genbank Submission; NIH/NCBI, Accession No. NM_002947.4. Xiao et al., May 1, 2019. 4 pages.
Genbank Submission; NIH/NCBI, Accession No. NM_003686. Umar et al., Apr. 9, 2021. 7 pages.
Genbank Submission; NIH/NCBI, Accession No. NM_003686.4. Umar et al., Apr. 9, 2021. 7 pages.
Genbank Submission; NIH/NCBI, Accession No. NM_006027. Umar et al., Apr. 10, 2021. 7 pages.
Genbank Submission; NIH/NCBI, Accession No. NM_174936. Guo et al., Oct. 28, 2015. 6 pages.
Genbank Submission; NIH/NCBI, Accession No. NP_000302.1. Alves et al., Mar. 7, 2021. 4 pages.
Genbank Submission; NIH/NCBI, Accession No. NP_001243439.1. Lee et al., Jul. 26, 2021. 4 pages.
Genbank Submission; NIH/NCBI, Accession No. NP_076161.2. Wade et al., Jun. 20, 2021. 4 pages.
Genbank Submission; NIH/NCBI, Accession No. NP_358988.1. Hoskins et al., Jan. 11, 2017. 2 pages.
Genbank Submission; NIH/NCBI, Accession No. NP_391970.1. Borriss et al., Feb. 12, 2021. 3 pages.
Genbank Submission; NIH/NCBI, Accession No. NP_472073.1. Glaser et al., Jun. 27, 2013. 2 pages.
Genbank Submission; NIH/NCBI, Accession No. NP_628093.1. Hsiao et al., Aug. 3, 2016. 2 pages.
Genbank Submission; NIH/NCBI, Accession No. NP_955579.1. Chen et al., Aug. 13, 2018. 5 pages.
Genbank Submission; NIH/NCBI, Accession No. P42212. Prasher et al., Mar. 19, 2014. 7 pages.
Genbank Submission; NIH/NCBI, Accession No. QBJ66766. Duan et al. Aug. 12, 2020. 2 pages.
Genbank Submission; NIH/NCBI, Accession No. RFF81513.1. Zhou et al., Aug. 21, 2018. 2 pages.
Genbank Submission; NIH/NCBI, Accession No. SNX31424.1. Weckx, S., Feb. 16, 2018. 2 pages.
Genbank Submission; NIH/NCBI, Accession No. TGH57013. Xu et al., Apr. 9, 2019. 2 pages.
Genbank Submission; NIH/NCBI, Accession No. WP_002989955.1. No Author Listed, May 6, 2013. 1 page.
Genbank Submission; NIH/NCBI, Accession No. WP_010922251.1. No Author Listed, May 15, 2013. 1 page.
Genbank Submission; NIH/NCBI, Accession No. WP_011054416.1. No Author Listed, May 15, 2013. 1 page.
Genbank Submission; NIH/NCBI, Accession No. WP_011284745.1. No Author Listed, May 16, 2013. 1 page.
Genbank Submission; NIH/NCBI, Accession No. WP_011285506.1. No Author Listed, May 16, 2013. 1 page.
Genbank Submission; NIH/NCBI, Accession No. WP_011527619.1. No Author Listed, May 16, 2013. 1 page.
Genbank Submission; NIH/NCBI, Accession No. WP_012560673.1. No Author Listed, May 17, 2013. 1 page.
Genbank Submission; NIH/NCBI, Accession No. WP_014407541.1. No Author Listed, May 18, 2013. 1 page.
Genbank Submission; NIH/NCBI, Accession No. WP_016631044.1. Haft et al., Sep. 22, 2020. 1 page.
Genbank Submission; NIH/NCBI, Accession No. WP_020905136.1. No Author Listed, Jul. 25, 2013. 1 page.
Genbank Submission; NIH/NCBI, Accession No. WP_023080005.1. No Author Listed, Oct. 27, 2013. 1 page.
Genbank Submission; NIH/NCBI, Accession No. WP_023610282.1. No Author Listed, Nov. 27, 2013. 1 page.
Genbank Submission; NIH/NCBI, Accession No. WP_030125963.1. No Author Listed, Jul. 9, 2014. 1 page.
Genbank Submission; NIH/NCBI, Accession No. WP_030126706.1. No Author Listed, Jul. 9, 2014. 1 page.
Genbank Submission; NIH/NCBI, Accession No. WP_031386437.1. No Author Listed., Sep. 23, 2019. 1 page.
Genbank Submission; NIH/NCBI, Accession No. WP_031488318.1. No Author Listed., Aug. 5, 2014. 1 page.
Genbank Submission; NIH/NCBI, Accession No. WP_031589969.1. Haft et al., Oct. 9, 2019. 2 pages.
Genbank Submission; NIH/NCBI, Accession No. WP_032460140.1. No Author Listed, Oct. 4, 2014. 1 page.
Genbank Submission; NIH/NCBI, Accession No. WP_032461047.1. No Author Listed, Oct. 4, 2014. 1 page.
Genbank Submission; NIH/NCBI, Accession No. WP_032462016.1. Haft et al., Oct. 4, 2014. 1 page.
Genbank Submission; NIH/NCBI, Accession No. WP_032462936.1. No Author Listed, Oct. 4, 2014. 1 page.
Genbank Submission; NIH/NCBI, Accession No. WP_032464890.1. No Author Listed, Oct. 4, 2014. 1 page.

(56) References Cited

OTHER PUBLICATIONS

Genbank Submission; NIH/NCBI, Accession No. WP_038431314.1. No Author Listed, Dec. 26, 2014. 1 page.
Genbank Submission; NIH/NCBI, Accession No. WP_038432938.1. No Author Listed, Dec. 26, 2014. 1 page.
Genbank Submission; NIH/NCBI, Accession No. WP_038434062.1. No Author Listed, Dec. 26, 2014. 1 page.
Genbank Submission; NIH/NCBI, Accession No. WP_044924278.1. Haft et al., Oct. 9, 2019. 2 pages.
Genbank Submission; NIH/NCBI, Accession No. WP_047338501.1. Haft et al., Oct. 9, 2019. 2 pages.
Genbank Submission; NIH/NCBI, Accession No. WP_048327215.1. No Author Listed, Jun. 26, 2015. 1 page.
Genbank Submission; NIH/NCBI, Accession No. WP_049519324.1. No Author Listed, Jul. 20, 2015. 1 page.
Genbank Submission; NIH/NCBI, Accession No. WP_060798984.1. Haft et al., Oct. 9, 2019. 2 pages.
Genbank Submission; NIH/NCBI, Accession No. WP_062913273.1. Haft et al., Oct. 9, 2019, 2 pages.
Genbank Submission; NIH/NCBI, Accession No. WP_072754838. No Author Listed., Sep. 23, 2019. 1 page.
Genbank Submission; NIH/NCBI, Accession No. WP_095142515.1. No Author Listed., Sep. 23, 2019. 1 page.
Genbank Submission; NIH/NCBI, Accession No. WP_118538418.1. No Author Listed., Oct. 13, 2019. 1 page.
Genbank Submission; NIH/NCBI, Accession No. WP_119223642.1. No Author Listed., Oct. 13, 2019. 1 page.
Genbank Submission; NIH/NCBI, Accession No. WP_119227726.1. No Author Listed., Oct. 13, 2019. 1 page.
Genbank Submission; NIH/NCBI, Accession No. WP_119623382.1. No Author Listed., Oct. 13, 2019. 1 page.
Genbank Submission; NIH/NCBI, Accession No. WP_132221894.1. No Author Listed., Sep. 23, 2019. 1 page.
Genbank Submission; NIH/NCBI, Accession No. WP_133478044.1. Haft et al., Oct. 9, 2019. 2 pages.
Genbank Submission; NIH/NCBI, Accession No. YP_002004532.1. Villegas et al., Oct. 11, 2021. 2 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_006589943.1. Lynch et al., Oct. 15, 2021. 2 pages.
Genbank Submission; NIH/NCBI, Accession No. YP_009137104.1. Davison, Aug. 13, 2018. 2 pages.
Genbank Submission; NIH/NCBI, Accession No. YP_009283008.1. Bernardini et al., Sep. 23, 2016. 2 pages.
Genbank Submission; NIH/NCBI, Accession No. YP_820832.1. Makarova et al., Aug. 27, 2013. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.
Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.
Gerard et al., The role of template-primer in protection of reverse transcriptase from thermal inactivation. Nucleic Acids Res. Jul. 15, 2002;30(14):3118-29. doi: 10.1093/nar/gkf417.
Gerber et al., An adenosine deaminase that generates inosine at the wobble position of tRNAs. Science. Nov. 5, 1999;286(5442):1146-9. doi: 10.1126/science.286.5442.1146.
Gerber et al., RNA editing by base deamination: more enzymes, more targets, new mysteries. Trends Biochem Sci. Jun. 2001;26(6):376-84.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.
Gete et al., Mechanisms of angiogenic incompetence in Hutchinson-Gilford progeria via downregulation of endothelial NOS. Aging Cell. Jul. 2021;20(7):e13388. doi: 10.1111/acel.13388. Epub Jun. 4, 2021.
Ghahfarokhi et al., Blastocyst Formation Rate and Transgene Expression are Associated with Gene Insertion into Safe and Non-Safe Harbors in the Cattle Genome. Sci Rep. Nov. 13, 2017;7(1):15432. doi: 10.1038/s41598-017-15648-3.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Glasgow et al.,DNA-binding properties of the Hin recombinase. J Biol Chem. Jun. 15, 1989;264(17):10072-82.
Glassner et al., Generation of a strong mutator phenotype in yeast by imbalanced base excision repair. Proc Natl Acad Sci U S A. Aug. 18, 1998;95(17):9997-10002.
Goldberg et al., Epigenetics: a landscape takes shape. Cell. Feb. 23, 2007;128(4):635-8. doi: 10.1016/j.cell.2007.02.006.
Goldberg et al., Loss-of-function mutations in the Nav1.7 gene underlie congenital indifference to pain in multiple human populations. Clin Genet. Apr. 2007;71(4):311-9. doi: 10.1111/j.1399-0004.2007.00790.x.
Gong et al., Active DNA demethylation by oxidation and repair. Cell Res. Dec. 2011;21(12):1649-51. doi: 10.1038/cr.2011.140. Epub Aug. 23, 2011.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.
Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Gou et al., Designing single guide RNA for CIRSPR-Cas9 base editor by deep learning. Peer reviewed Thesis/Dissertation. UCLA Electronic Theses and Dissertations. Jan. 1, 2019. Retrieved from the Internet via https://escholarship.org/uc/item/7vf9z54t. Last accessed on Apr. 29, 2021.
Grainge et al., The integrase family of recombinase: organization and function of the active site. Mol Microbiol. Aug. 1999;33(3):449-56.
Gregory et al., Integration site for Streptomyces phage phiBT1 and development of site-specific integrating vectors. J Bacteriol. Sep. 2003;185(17):5320-3. doi: 10.1128/jb.185.17.5320-5323.2003.
Griffiths, Endogenous retroviruses in the human genome sequence. Genome Biol. 2001;2(6):REVIEWS1017. doi: 10.1186/GB-2001-2-6-reviews1017. Epub Jun. 5, 2001.
Grindley et al., Mechanisms of site-specific recombination. Annu Rev Biochem. 2006;75:567-605. doi: 10.1146/annurev.biochem.73.011303.073908.

(56) References Cited

OTHER PUBLICATIONS

Grishok et al., Genes and Mechanisms Related to RNA Interference Regulate Expression of the Small Temporal RNAs that Control C. elegans Developmental Timing. Jul. 13, 2001:106(1):P23-4.
Groher et al., Synthetic riboswitches—A tool comes of age. Biochim Biophys Acta. Oct. 2014;1839(10):964-973. doi: 10.1016/j.bbagrm.2014.05.005. Epub May 17, 2014.
Groth et al., Construction of transgenic *Drosophila* by using the site-specific integrase from phage phiC31. Genetics. Apr. 2004; 166(4):1775-82. doi: 10.1534/genetics.166.4.1775.
Groth et al., Phage integrases: biology and applications. J Mol Biol. Jan. 19, 2004;335(3):667-78.
Gruber et al., Strategies for measuring evolutionary conservation of RNA secondary structures. BMC Bioinformatics. Feb. 26, 2008;9:122. doi: 10.1186/1471-2105-9-122.
Gruber et al., The Vienna RNA websuite. Nucleic Acids Res. Jul. 1, 2008;36(Web Server issue): W70-4. doi: 10.1093/nar/gkn188. Epub Apr. 19, 2008.
Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.
Grünewald et al., Transcriptome-wide off-target RNA editing induced by CRISPR-guided DNA base editors. Nature. May 2019;569(7756):433-437. doi: 10.1038/s41586-019-1161-z. Epub Apr. 17, 2019.
Guedon et al., Current gene therapy using viral vectors for chronic pain. Mol Pain. May 13, 2015;11:27. doi: 10.1186/s12990-015-0018-1.
Guilinger et al., Broad specificity profiling of TALENs results in engineered nucleases with improved DNA-cleavage specificity. Nat Methods. Apr. 2014; 11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Gumulya et al., Exploring the past and the future of protein evolution with ancestral sequence reconstruction: the 'retro' approach to protein engineering. Biochem J. Jan. 1, 2017;474(1):1-19. doi: 10.1042/BCJ20160507.
Guo et al., Designing single guide RNA for CIRSPR-Cas9 base editor by deep learning. Peer reviewed Thesis/Dissertation. UCLA Electronic Theses and Dissertations. Jan. 1, 2019. Retrieved from the Internet via https://escholarship.org/uc/item/7vf9z54t. Last accessed on Apr. 29, 2021.
Guo et al., Evolution of Tetrahymena ribozyme mutants with increased structural stability. Nat Struct Biol. Nov. 2002;9(11):855-61. doi: 10.1038/nsb850.
Guo et al., Facile functionalization of FK506 for biological studies by the thiol-ene 'click' reaction. RSC Advances. 2014;22:11400-3.
Guo et al., Protein tolerance to random amino acid change. Proc Natl Acad Sci U S A. Jun. 22, 2004;101(25):9205-10. Epub Jun. 14, 2004.
Guo et al., Structure of Cre recombinase complexed with DNA in a site-specific recombination synapse. Nature. Sep. 4, 1997;389(6646):40-6.
Gupta et al., Cross-talk between cognate and noncognate RpoE sigma factors and Zn(2+)-binding anti-sigma factors regulates photooxidative stress response in Azospirillum brasilense. Antioxid Redox Signal. Jan. 1, 2014;20(1):42-59. doi: 10.1089/ars.2013.5314. Epub Jul. 19, 2013.
Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.
Guzman et al., Tight regulation, modulation, and high-level expression by vectors containing the arabinose PBAD promoter. J Bacteriol. 1995;177(14):4121-4130.
Haapaniemi et al., CRISPR-Cas9 genome editing induces a p53-mediated DNA damage response. Nat Med. Jul. 2018;24(7):927-930. doi: 10.1038/s41591-018-0049-z. Epub Jun. 11, 2018.
Haddada et al., Gene therapy using adenovirus vectors. Curr Top Microbiol Immunol. 1995;199 ( Pt 3):297-306. doi: 10.1007/978-3-642-79586-2_14.
Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.
Halbert et al., Repeat transduction in the mouse lung by using adeno-associated virus vectors with different serotypes. J Virol. Feb. 2000;74(3):1524-32. doi: 10.1128/jvi.74.3.1524-1532.2000.
Hale et al., RNA-guided RNA cleavage by a CRISPR RNA-Cas protein complex. Cell. Nov. 25, 2009;139(5):945-56. doi: 10.1016/j.cell.2009.07.040.
Halmai et al., Targeted CRIPSR/dCas9-mediated reactivation of epigenetically silenced genes suggests limited escape from the inactive X chromosome. 2nd Intl Conf on Epigenetics and Bioengineering. Oct. 4, 2018; Retrieved from the Internet: https://aiche.confex.com/aiche/epibio18/webprogram/paper544785.html. Retrieved Jun. 29, 2020.
Halperin et al., CRISPR-guided DNA polymerases enable diversification of all nucleotides in a tunable window. Nature. Aug. 2018;560(7717):248-252. doi: 10.1038/s41586-018-0384-8. Epub Aug. 1, 2018.
Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.
Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Handa et al., Template-assisted synthesis of adenine-mutagenized cDNA by a retroelement protein complex. Nucleic Acids Res. Oct. 12, 2018;46(18):9711-9725. doi: 10.1093/nar/gky620.
Hanna et al., Massively parallel assessment of human variants with base editor screens. Cell. Feb. 18, 2021;184(4):1064-1080.e20. doi: 10.1016/j.cell.2021.01.012.
Hanson et al., Codon optimality, bias and usage in translation and mRNA decay. Nat Rev Mol Cell Biol. Jan. 2018;19(1):20-30. doi: 10.1038/nrm.2017.91. Epub Oct. 11, 2017.
Hardt et al.,Missense variants in hMLH1 identified in patients from the German HNPCC consortium and functional studies. Fam Cancer. Jun. 2011;10(2):273-84. doi: 10.1007/s10689-011-9431-4.
Harms et al., Evolutionary biochemistry: revealing the historical and physical causes of protein properties. Nat Rev Genet. Aug. 2013;14(8):559-71. doi: 10.1038/nrg3540.
Harmsen et al., DNA mismatch repair and oligonucleotide end-protection promote base-pair substitution distal from a CRISPR/Cas9-induced DNA break. Nucleic Acids Res. Apr. 6, 2018;46(6):2945-2955. doi: 10.1093/nar/gky076.
Harrington et al., A thermostable Cas9 with increased lifetime in human plasma. Nat Commun. Nov. 10, 2017;8(1):1424. doi: 10.1038/s41467-017-01408-4. Posted May 16, 2017 as bioRxiv preprint. Doi.org/10.1101/138867.
Harris et al., RNA Editing Enzyme APOBEC1 and Some of Its Homologs Can Act as DNA Mutators. Mol Cell. Nov. 2002; 10(5):1247-53.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hartung et al., Cre mutants with altered DNA binding properties. J Biol Chem. Sep. 4, 1998;273(36):22884-91.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.

(56) References Cited

OTHER PUBLICATIONS

Hasegawa et al., Spontaneous mutagenesis associated with nucleotide excision repair in *Escherichia coli*. Genes Cells. May 2008;13(5):459-69. doi: 10.1111/j.1365-2443.2008.01185.x.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Hector et al., CDKL5 variants: Improving our understanding of a rare neurologic disorder. Neurol Genet. Dec. 15, 2017;3(6):e200. doi: 10.1212/NXG.0000000000000200.
Heidenreich et al., Non-homologous end joining as an important mutagenic process in cell cycle-arrested cells. EMBO J. May 1, 2003;22(9):2274-83. doi: 10.1093/emboj/cdg203.
Held et al., In vivo correction of murine hereditary tyrosinemia type I by phiC31 integrase-mediated gene delivery. Mol Ther. Mar. 2005;11(3):399-408. doi: 10.1016/j.ymthe.2004.11.001.
Heller et al., Replisome assembly and the direct restart of stalled replication forks. Nat Rev Mol Cell Biol. Dec. 2006;7(12):932-43. Epub Nov. 8, 2006.
Hendricks et al., The S. cerevisiae Mag1 3-methyladenine DNA glycosylase modulates susceptibility to homologous recombination. DNA Repair (Amst). 2002;1(8):645-659.
Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.
Herschhorn et al., Retroviral reverse transcriptases. Cell Mol Life Sci. Aug. 2010;67(16):2717-47. doi: 10.1007/s00018-010-0346-2. Epub Apr. 1, 2010.
Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Hickford et al., Antitumour polyether macrolides: four new halichondrins from the New Zealand deep-water marine sponge Lissodendoryx sp. Bioorg Med Chem. Mar. 15, 2009;17(6):2199-203. doi: 10.1016/j.bmc.2008.10.093. Epub Nov. 19, 2008.
Hida et al., Directed evolution for drug and nucleic acid; delivery. Adv Drug Deliv Rev. Dec. 22, 2007;59(15):1562-78. Epub Aug. 28, 2007.; Review.
Higgs et al., Genetic complexity in sickle cell disease. Proc Natl Acad Sci U S A. Aug. 19, 2008;105(33):11595-6. doi: 10.1073/pnas.0806633105. Epub Aug. 11, 2008.
Hilbers et al., New developments in structure determination of pseudoknots. Biopolymers. 1998;48(2-3):137-53. doi: 10.1002/(SICI)1097-0282(1998)48:2<137::AID-BIP4>3.0.CO;2-H.
Hill et al., Functional analysis of conserved histidines in ADP-glucose pyrophosphorylase from *Escherichia coli*.Biochem Biophys Res Commun. Mar. 17, 1998;244(2):573-7.
Hille et al., The Biology of CRISPR-Cas: Backward and Forward. Cell. Mar. 8, 2018;172(6):1239-1259. doi: 10.1016/j.cell.2017.11.032.
Hilton et al., Enabling functional genomics with genome engineering. Genome Res. Oct. 2015;25(10):1442-55. doi: 10.1101/gr.190124.115.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.
Hirano et al., Structural Basis for the Altered PAM Specificities of Engineered CRISPR-Cas9. Mol Cell. Mar. 17, 2016;61(6):886-94. doi: 10.1016/j.molcel.2016.02.018.
Hoang et al., UFBoot2: Improving the Ultrafast Bootstrap Approximation. Mol Biol Evol. Feb. 1, 2018;35(2):518-522. doi: 10.1093/molbev/msx281.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Hoernes et al., Translating the epitranscriptome. Wiley Interdiscip Rev RNA. Jan. 2017;8(1):e1375. doi: 10.1002/wrna.1375. Epub Jun. 27, 2016.
Hoess et al., DNA specificity of the Cre recombinase resides in the 25 kDa carboxyl domain of the protein. J Mol Biol. Dec. 20, 1990;216(4):873-82. doi: 10.1016/S0022-2836(99)80007-2.
Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.
Hollis et al., Phage integrases for the construction and manipulation of transgenic mammals. Reprod Biol Endocrinol. Nov. 7, 2003;1:79. doi: 10.1186/1477-7827-1-79.
Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.
Holt et al., Human hematopoietic stem/progenitor cells modified by zinc-finger nucleases targeted to CCR5 control HIV-1 in vivo. Nat Biotechnol. Aug. 2010;28(8):839-47. doi: 10.1038/nbt.1663. Epub Jul. 2, 2010.
Hondares et al., Peroxisome Proliferator-activated Receptor ? (PPAR?) Induces PPAR? Coactivator 1? (PGC-1?) Gene Expression and Contributes to Thermogenic Activation of Brown Fat. J Biol. Chem Oct. 2011; 286(50):43112-22. doi: 10.1074/jbc.M111.252775.
Hoogenboom et al., Natural and designer binding sites made by phage display technology. Immunol Today. Aug. 2000;21(8):371-8.
Horvath et al., CRISPR/Cas, the immune system of bacteria and archaea. Science. Jan. 8, 2010;327(5962):167-70. doi: 10.1126/science.1179555.
Horvath et al., Diversity, Activity, and Evolution of CRISPR Loci in *Streptococcus* Thermophilus. J Bacteriol. Feb. 2008;190(4):1401-12. doi: 10.1128/JB.01415-07. Epub Dec. 7, 2007.
Hotta et al., [Neurotropic viruses—classification, structure and characteristics]. Nihon Rinsho. Apr. 1997;55(4):777-82. Japanese.
Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.
Houdebine, The methods to generate transgenic animals and to control transgene expression. J Biotechnol. Sep. 25, 2002;98(2-3):145-60.
Housden et al., Identification of potential drug targets for tuberous sclerosis complex by synthetic screens combining CRISPR-based knockouts with RNAi. Sci Signal. Sep. 8, 2015;8(393):rs9. doi: 10.1126/scisignal.aab3729.
Howard et al., Intracerebral drug delivery in rats with lesion-induced memory deficits. J Neurosurg. Jul. 1989;71(1):105-12.
Hower et al., Shape-based peak identification for ChIP-Seq. BMC Bioinformatics. Jan. 12, 2011;12:15. doi: 10.1186/1471-2105-12-15.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.
Hsu et al., PrimeDesign software for rapid and simplified design of prime editing guide RNAs. Nat Commun. Feb. 15, 2021;12(1):1034. doi: 10.1038/s41467-021-21337-7.
Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.
Hu et al., Evolved Cas9 variants with broad PAM compatibility and high DNA specificity. Nature. Apr. 5, 2018;556(7699):57-63 and Extended/Supplementary Data. doi: 10.1038/nature26155. Epub Feb. 28, 2018. 21 pages.
Hu et al., Evolved Cas9 variants with broad PAM compatibility and high DNA specificity. Nature. Apr. 5, 2018;556(7699):57-63. doi: 10.1038/nature26155. Epub Feb. 28, 2018.

(56) References Cited

OTHER PUBLICATIONS

Hua et al., Expanding the base editing scope in rice by using Cas9 variants. Plant Biotechnol J. Feb. 2019;17(2):499-504. doi: 10.1111/pbi.12993. Epub Oct. 5, 2018.
Hua et al., Precise A•T to G•C Base Editing in the Rice Genome. Mol Plant. Apr. 2, 2018;11(4):627-630. doi: 10.1016/j.molp.2018.02.007. Epub Feb. 21, 2018.
Huang et al., Circularly permuted and PAM-modified Cas9 variants broaden the targeting scope of base editors. Nat Biotechnol. Jun. 2019;37(6):626-631. doi: 10.1038/s41587-019-0134-y. Epub May 20, 2019. Including Supplementary Information.
Huang et al., Heritable gene targeting in zebrafish using customized TALENs. Nat Biotechnol. Aug. 5, 2011;29(8):699-700. doi: 10.1038/nbt.1939.
Huang et al., Precision genome editing using cytosine and adenine base editors in mammalian cells. Nat Protoc. Feb. 2021;16(2):1089-1128. doi: 10.1038/s41596-020-00450-9. Epub Jan. 18, 2021.
Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.
Humbert et al., Targeted gene therapies: tools, applications, optimization. Crit Rev Biochem Mol Biol. May-Jun. 2012;47(3):264-81. doi: 10.3109/10409238.2012.658112.
Hung et al., Protein localization in disease and therapy. J Cell Sci. Oct. 15, 2011;124(Pt 20):3381-92. doi: 10.1242/jcs.089110.
Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.
Husimi, Selection and evolution of bacteriophages in cellstat. Adv Biophys. ; 1989;25:1-43. Review.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Hwang et al., Efficient in Vivo Genome Editing Using RNA-Guided Nucleases. Nat Biotechnol. Mar. 2013; 31(3): 227-229. doi: 10.1038/nbt.2501. Epub Jan. 29, 2013.
Hwang et al., Web-based design and analysis tools for CRISPR base editing. BMC Bioinformatics. Dec. 27, 2018;19(1):542. doi: 10.1186/s12859-018-2585-4.
Ibba et al., Relaxing the substrate specificity of an aminoacyl-tRNA synthetase allows in vitro and in vivo synthesis of proteins containing unnatural amino acids. FEBS Lett. May 15, 1995;364(3):272-5.
Ibba et al., Substrate specificity is determined by amino acid binding pocket size in *Escherichia coli* phenylalanyl-tRNA synthetase. Biochemistry. Jun. 14, 1994;33(23):7107-12.
Ihry et al., p53 inhibits CRISPR-Cas9 engineering in human pluripotent stem cells. Nat Med. Jul. 2018;24(7):939-946. doi: 10.1038/s41591-018-0050-6. Epub Jun. 11, 2018.
Iida et al., A site-specific, conservative recombination system carried by bacteriophage P1. Mapping the recombinase gene cin and the cross-over sites cix for the inversion of the C segment. EMBO J. 1982;1(11):1445-53.
Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.
Ikediobi et al., Mutation analysis of 24 known cancer genes in the NCI-60 cell line set. Mol Cancer Ther. Nov. 2006;5(11):2606-12. Epub Nov. 6, 2006.
Imanishi et al., Detection of N6-methyladenosine based on the methyl-sensitivity of MazF RNA endonuclease. Chem Commun (Camb). Nov. 30, 2017;53(96):12930-12933. doi: 10.1039/c7cc07699a.
Imburgio et al., Studies of promoter recognition and start site selection by T7 RNA polymerase using a comprehensive collection of promoter variants. Biochemistry. Aug. 29, 2000;39(34):10419-30.
Ingram, A specific chemical difference between the globins of normal human and sickle-cell anaemia haemoglobin. Nature. Oct. 13, 1956;178(4537):792-4. doi: 10.1038/178792a0.
Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.
Irrthum et al., Congenital hereditary lymphedema caused by a mutation that inactivates VEGFR3 tyrosine kinase. Am J Hum Genet. Aug. 2000;67(2):295-301. Epub Jun. 9, 2000.
Isaacs et al., Engineered riboregulators enable post-transcriptional control of gene expression. Nat Biotechnol. Jul. 2004;22(7):841-7. doi: 10.1038/nbt986. Epub Jun. 20, 2004.
Ishino et al., Nucleotide sequence of the iap gene, responsible for alkaline phosphatase isozyme conversion in *Escherichia coli*, and identification of the gene product. J Bacteriol. Dec. 1987;169(12):5429-33.
Iwai et al., Circular beta-lactamase: stability enhancement by cyclizing the backbone. FEBS Lett. Oct. 8, 1999;459(2):166-72. doi: 10.1016/s0014-5793(99)01220-x.
Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.
Jaffrey et al., Emerging links between m6A and misregulated mRNA methylation in cancer. Genome Med. Jan. 12, 2017;9(1):2. doi: 10.1186/s13073-016-0395-8.
Jamieson et al., Drug discovery with engineered zinc-finger proteins. Nat Rev Drug Discov. May 2003;2(5):361-8.
Jansen et al., Backbone and nucleobase contacts to glucosamine-6-phosphate in the glmS ribozyme. Nat Struct Mol Biol. Jun. 2006;13(6):517-23. Epub May 14, 2006.
Jansen et al., Identification of genes that are associated with DNA repeats in prokaryotes. Mol Microbiol. Mar. 2002;43(6):1565-75.
Jardine et al., HIV-1 Vaccines. Priming a broadly neutralizing antibody response to HIV-1 using a germline-targeting immunogen. Science. Jul. 10, 2015;349(6244):156-61. doi: 10.1126/science.aac5894. Epub Jun. 18, 2015.
Jasin et al., Repair of strand breaks by homologous recombination. Cold Spring Harb Perspect Biol. Nov. 1, 2013;5(11):a012740. doi: 10.1101/cshperspect.a012740.
Jeggo, DNA breakage and repair. Adv Genet. 1998;38:185-218. doi: 10.1016/s0065-2660(08)60144-3.
Jemielity et al., Novel "anti-reverse" cap analogs with superior translational properties. RNA. Sep. 2003;9(9):1108-22. doi: 10.1261/rna.5430403.
Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.
Jeong et al., Measurement of deoxyinosine adduct: Can it be a reliable tool to assess oxidative or nitrosative DNA damage? Toxicol Lett. Oct. 17, 2012;214(2):226-33. doi: 10.1016/j.toxlet.2012.08.013. Epub Aug. 23, 2012.
Jia et al., The MLH1 ATPase domain is needed for suppressing aberrant formation of interstitial telomeric sequences. DNA Repair (Amst). May 2018;65:20-25. doi: 10.1016/j.dnarep.2018.03.002. Epub Mar. 7, 2018.
Jiang et al., Chemical modifications of adenine base editor mRNA and guide RNA expand its application scope. Nat Commun. Apr. 24, 2020;11(1):1979. doi: 10.1038/s41467-020-15892-8.
Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.
Jiang et al., Prime editing efficiently generates W542L and S621I double mutations in two ALS genes of maize. bioRxiv preprint. Jul. 6, 2020. Retrieved from www.biorxiv.org. doi: 10.1101/2020.07.06.188896. 15 pages.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jiang et al., Structural Biology. A Cas9-guide RNA Complex Preorganized for Target DNA Recognition. Science. Jun. 26, 2015;348(6242):1477-81. doi: 10.1126/science.aab1452.

(56) References Cited

OTHER PUBLICATIONS

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.
Jin et al., Cytosine, but not adenine, base editors induce genome-wide off-target mutations in rice. Science. Apr. 19, 2019;364(6437):292-295. doi: 10.1126/science.aaw7166. Epub Feb. 28, 2019.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jiricny, The multifaceted mismatch-repair system. Nat Rev Mol Cell Biol. May 2006;7(5):335-46. doi: 10.1038/nrm1907.
Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.
Johansson et al., RNA Recognition by the MS2 Phage Coat Protein. Seminars in Virology. 1997;8(3):176-85. https://doi.org/10.1006/smvy.1997.0120.
Johansson et al., Selenocysteine in proteins-properties and biotechnological use. Biochim Biophys Acta. Oct. 30, 2005;1726(1):1-13. Epub Jun. 1, 2005.
Johns et al., The promise and peril of continuous in vitro evolution. J Mol Evol. Aug. 2005;61(2):253-63. Epub Jun. 27, 2005.
Johnson et al., Trans insertion-splicing: ribozyme-catalyzed insertion of targeted sequences into RNAs. Biochemistry. Aug. 9, 2005;44(31):10702-10. doi: 10.1021/bi0504815.
Joho et al., Identification of a region of the bacteriophage T3 and T7 RNA polymerases that determines promoter specificity. J Mol Biol. Sep. 5, 1990;215(1):31-9.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al., TALENs: a widely applicable technology for targeted genome editing. Nat Rev Mol Cell Biol. Jan. 2013; 14(1):49-55. doi: 10.1038/nrm3486. Epub Nov. 21, 2012.
Joyce et al., Amplification, mutation and selection of catalytic RNA. Gene. Oct. 15, 1989;82(1):83-7. doi: 10.1016/0378-1119(89)90033-4.
Jusiak et al., Comparison of Integrases Identifies Bxb1-GA Mutant as the Most Efficient Site-Specific Integrase System in Mammalian Cells. ACS Synth Biol. Jan. 18, 2019;8(1):16-24. doi: 10.1021/acssynbio.8b00089. Epub Jan. 9, 2019.
Jyothy et al., Translocation Down syndrome. Indian J Med Sci. Mar. 2002;56(3):122-6.
Kacian et al., Purification of the DNA polymerase of avian myeloblastosis virus. Biochim Biophys Acta. Sep. 24, 1971;246(3):365-83. doi: 10.1016/0005-2787(71)90773-8.
Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.
Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.
Kahmann et al., G inversion in bacteriophage Mu DNA is stimulated by a site within the invertase gene and a host factor. Cell. Jul. 1985;41(3):771-80. doi: 10.1016/s0092-8674(85)80058-1.
Kaiser et al., Gene therapy. Putting the fingers on gene repair. Science. Dec. 23, 2005;310(5756):1894-6.
Kakiyama et al., A peptide release system using a photo-cleavable linker in a cell array format for cell-toxicity analysis. Polymer J. Feb. 27, 2013;45:535-9.
Kalyaanamoorthy et al., ModelFinder: fast model selection for accurate phylogenetic estimates. Nat Methods. Jun. 2017; 14(6):587-589. doi: 10.1038/nmeth.4285. Epub May 8, 2017.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.
Kang et al., Precision genome engineering through adenine base editing in plants. Nat Plants. Jul. 2018;4(7):427-431. doi: 10.1038/s41477-018-0178-x. Epub Jun. 4, 2018. Erratum in: Nat Plants. Sep. 2018;4(9):730.
Kao et al., Cleavage specificity of *Saccharomyces cerevisiae* flap endonuclease 1 suggests a double-flap structure as the cellular substrate. J Biol Chem. Apr. 26, 2002;277(17):14379-89. doi: 10.1074/jbc.M110662200. Epub Feb. 1, 2002.
Kappel et al., Regulating gene expression in transgenic animals. Curr Opin Biotechnol. Oct. 1992;3(5):548-53.
Karimova et al., Discovery of Nigri/nox and Panto/pox site-specific recombinase systems facilitates advanced genome engineering. Sci Rep. Jul. 22, 2016;6:30130. doi: 10.1038/srep30130.
Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Katafuchi et al., DNA polymerases involved in the incorporation of oxidized nucleotides into DNA: their efficiency and template base preference. Mutat Res. Nov. 28, 2010;703(1):24-31. doi: 10.1016/j.mrgentox.2010.06.004. Epub Jun. 11, 2010.
Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.
Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.
Kaufman et al., Translational efficiency of polycistronic mRNAs and their utilization to express heterologous genes in mammalian cells. EMBO J. Jan. 1987;6(1):187-93.
Kavli et al., Excision of cytosine and thymine from DNA by mutants of human uracil-DNA glycosylase. EMBO J. Jul. 1, 1996;15(13):3442-7.
Kawarasaki et al., Enhanced crossover Scratchy: construction and high-throughput screening of a combinatorial library containing multiple non-homologous crossovers. Nucleic Acids Res. Nov. 1, 2003;31(21):e126.
Kay et al., Viral vectors for gene therapy: the art of turning infectious agents into vehicles of therapeutics. Nat Med. Jan. 2001;7(1):33-40.
Kaya et al., A bacterial Argonaute with noncanonical guide RNA specificity. Proc. Natl. Acad. Sci. USA Apr. 2016;113(15):4057-62.
Keijzers et al., Human exonuclease 1 (EXO1) activity characterization and its function on flap structures. Biosci Rep. Apr. 25, 2015;35(3):e00206. doi: 10.1042/BSR20150058.
Kellendonk et al., Regulation of Cre recombinase activity by the synthetic steroid RU 486. Nucleic Acids Res. Apr. 15, 1996;24(8):1404-11.
Kelman, PCNA: structure, functions and interactions. Oncogene. Feb. 13, 1997;14(6):629-40. doi: 10.1038/sj.onc. 1200886.
Keravala et al., A diversity of serine phage integrases mediate site-specific recombination in mammalian cells. Mol Genet Genomics. Aug. 2006;276(2):135-46. doi: 10.1007/s00438-006-0129-5. Epub May 13, 2006.
Kessel et al., Murine developmental control genes. Science. Jul. 27, 1990;249(4967):374-9. doi: 10.1126/science.1974085.

(56) References Cited

OTHER PUBLICATIONS

Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.

Ketha et al., Application of bioinformatics-coupled experimental analysis reveals a new transport-competent nuclear localization signal in the nucleoprotein of Influenza A virus strain. BMC Cell Biol. Apr. 28, 2008; 9:22. https://doi.org/10.1186/1471-2121-9-22.

Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.

Kilbride et al., Determinants of product topology in a hybrid Cre-Tn3 resolvase site-specific recombination system. J Mol Biol. Jan. 13, 2006;355(2):185-95. Epub Nov. 9, 2005.

Kilcher et al., Brochothrix thermosphacta bacteriophages feature heterogeneous and highly mosaic genomes and utilize unique prophage insertion sites. J Bacteriol. Oct. 2010;192(20):5441-53. doi: 10.1128/JB.00709-10. Epub Aug. 13, 2010.

Kim et al., DJ-1, a novel regulator of the tumor suppressor PTEN. Cancer Cell. 2005;7(3):263-273.

Kim et al., Genome-wide target specificity of CRISPR RNA-guided adenine base editors. Nat Biotechnol. Apr. 2019;37(4):430-435. doi: 10.1038/s41587-019-0050-1. Epub Mar. 4, 2019.

Kim et al., A library of TAL effector nucleases spanning the human genome. Nat Biotechnol. Mar. 2013;31(3):251-8. Doi: 10.1038/nbt.2517. Epub Feb. 17, 2013.

Kim et al., An anionic human protein mediates cationic liposome delivery of genome editing proteins into mammalian cells. Nat Commun. Jul. 2, 2019;10(1):2905. doi: 10.1038/s41467-019-10828-3.

Kim et al., Evaluating and Enhancing Target Specificity of Gene-Editing Nucleases and Deaminases. Annu Rev Biochem. Jun. 20, 2019;88:191-220. doi: 10.1146/annurev-biochem-013118-111730. Epub Mar. 18, 2019.

Kim et al., Genome-wide target specificities of CRISPR RNA-guided programmable deaminases. Nat Biotechnol. May 2017;35(5):475-480. doi: 10.1038/nbt.3852. Epub Apr. 10, 2017.

Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.

Kim et al., High-throughput analysis of the activities of xCas9, SpCas9-NG and SpCas9 at matched and mismatched target sequences in human cells. Nat Biomed Eng. Jan. 2020;4(1):111-124. doi: 10.1038/s41551-019-0505-1. Epub Jan. 14, 2020.

Kim et al., Highly efficient RNA-guided base editing in mouse embryos. Nat Biotechnol. May 2017;35(5):435-437. doi: 10.1038/nbt.3816. Epub Feb. 27, 2017.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Kim et al., In vivo genome editing with a small Cas9 orthologue derived from Campylobacter jejuni. Nat Commun. Feb. 21, 2017;8:14500. doi: 10.1038/ncomms14500. PMID: 28220790; PMCID: PMC5473640.

Kim et al., In vivo high-throughput profiling of CRISPR-Cpf1 activity. Nat Methods. Feb. 2017;14(2):153-159. doi: 10.1038/nmeth.4104. Epub Dec. 19, 2016.

Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.

Kim et al., Mycobacteriophage Bxb1 integrates into the Mycobacterium smegmatis groEL1 gene. Mol Microbiol. Oct. 2003;50(2):463-73. doi: 10.1046/j.1365-2958.2003.03723.x.

Kim et al., Predicting the efficiency of prime editing guide RNAs in human cells. Nat Biotechnol. Feb. 2021;39(2):198-206. doi: 10.1038/s41587-020-0677-y. Epub Sep. 21, 2020.

Kim et al., Rescue of high-specificity Cas9 variants using sgRNAs with matched 5' nucleotides. Genome Biol. Nov. 15, 2017;18(1):218. doi: 10.1186/s13059-017-1355-3.

Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.

Kim et al., TALENs and ZFNs are associated with different mutationsignatures. Nat Methods. Mar. 2013;10(3):185. doi: 10.1038/nmeth.2364. Epub Feb. 10, 2013.

Kim et al., Targeted genome editing in human cells with zinc finger nucleases constructed via modular assembly. Genome Res. Jul. 2009;19(7):1279-88. doi: 10.1101/gr.089417.108. Epub May 21, 2009.

Kim et al., The role of apolipoprotein E in Alzheimer's disease. Neuron. Aug. 13, 2009;63(3):287-303. doi: 10.1016/j.neuron.2009.06.026.

Kim et al., Transcriptional repression by zinc finger peptides. Exploring the potential for applications in gene therapy. J Biol Chem. Nov. 21, 1997;272(47):29795-800.

King et al., No gain, no pain: NaV1.7 as an analgesic target. ACS Chem Neurosci. Sep. 17, 2014;5(9):749-51. doi: 10.1021/cn500171p. Epub Aug. 11, 2014.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.

Klapacz et al., Frameshift mutagenesis and microsatellite instability induced by human alkyladenine DNA glycosylase. Mol Cell. Mar. 26, 2010;37(6):843-53. doi: 10.1016/j.molcel.2010.01.038.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.

Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.

Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.

Kleinstiver et al., Engineered CRISPR-Cas9 nucleases with altered PAM specificities. Nature. Jul. 23, 2015;523(7561):481-5 and Supplementary Materials. doi: 10.1038/nature14592. Epub Jun. 22, 2015. 27 pages.

Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. EMBO J. Apr. 1988;7(4):1229-37.

(56) References Cited

OTHER PUBLICATIONS

Klompe et al., Transposon-encoded CRISPR-Cas systems direct RNA-guided DNA integration. Nature. Jul. 2019;571(7764):219-225. doi: 10.1038/s41586-019-1323-z. Epub Jun. 12, 2019.
Kluesner et al., CRISPR-Cas9 cytidine and adenosine base editing of splice-sites mediates highly-efficient disruption of proteins in primary and immortalized cells. Nat Commun. Apr. 23, 2021;12(1):2437. doi: 10.1038/s41467-021-22009-2.
Knott et al., Guide-bound structures of an RNA-targeting A-cleaving CRISPR-Cas13a enzyme. Nat Struct Mol Biol. Oct. 2017;24(10):825-833. doi: 10.1038/nsmb.3466. Epub Sep. 11, 2017.
Koblan et al., In vivo base editing rescues Hutchinson-Gilford progeria syndrome in mice. Nature. Jan. 2021;589(7843):608-614. doi: 10.1038/s41586-020-03086-7. Epub Jan. 6, 2021.
Koblan et al., Efficient CoG-to-GoC base editors developed using CRISPRi screens, target-library analysis, and machine learning. Nature Biotechnol. Jun. 28, 2021. https://doi.org/10.1038/s41587-021-00938-z.
Koblan et al., Improving cytidine and adenine base editors by expression optimization and ancestral reconstruction. Nat Biotechnol. Oct. 2018;36(9):843-846. doi: 10.1038/nbt.4172. Epub May 29, 2018.
Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 14, 2017.
Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.
Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.
Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.
Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.
Kolot et al., Site-specific recombination in mammalian cells expressing the Int recombinase of bacteriophage HK022. Mol Biol Rep. Aug. 1999;26(3):207-13. doi: 10.1023/a:1007096701720.
Komor et al., CRISPR-Based Technologies for the Manipulation of Eukaryotic Genomes. Cell. Jan. 12, 2017;168(1-2):20-36. doi: 10.1016/j.cell.2016.10.044.
Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.
Komor et al., Programmable editing of a target base in genomic DNA without double-stranded DNA cleavage. Nature. Apr. 20, 2016;533(7603):420-4. doi: 10.1038/nature17946.
Komor, Editing the Genome Without Double-Stranded DNA Breaks. ACS Chem Biol. Feb. 16, 2018;13(2):383-388. doi: 10.1021/acschembio.7b00710. Epub Oct. 9, 2017.
Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.
Koonin et al., Diversity, classification and evolution of CRISPR-Cas systems. Curr Opin Microbiol. 2017;37:67?78. doi:10.1016/j.mib.2017.05.008.
Kosicki et al., Repair of double-strand breaks induced by CRISPR-Cas9 leads to large deletions and complex rearrangements. Nat Biotechnol. Sep. 2018;36(8):765-771. doi: 10.1038/nbt.4192. Epub Jul. 16, 2018.
Kotewicz et al., Cloning and overexpression of Moloney murine leukemia virus reverse transcriptase in *Escherichia coli*. Gene. 1985;35(3):249-58. doi: 10.1016/0378-1119(85)90003-4.
Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.
Kotin, Prospects for the use of adeno-associated virus as a vector for human gene therapy. Hum Gene Ther. Jul. 1994;5(7):793-801. doi: 10.1089/hum.1994.5.7-793.
Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.
Kowal et al., Exploiting unassigned codons in Micrococcus luteus for tRNA-based amino acid mutagenesis. Nucleic Acids Res. Nov. 15, 1997;25(22):4685-9.
Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.
Kozak, An analysis of 5'-noncoding sequences from 699 vertebrate messenger RNAs. Nucleic Acids Res. Oct. 26, 1987;15(20):8125-48. doi: 10.1093/nar/15.20.8125.
Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.
Kremer et al., Adenovirus and adeno-associated virus mediated gene transfer. Br Med Bull. Jan. 1995;51(1):31-44. doi: 10.1093/oxfordjournals.bmb.a072951.
Krokan et al, Uracil in DNA—occurrence, consequences and repair. Oncogene. Dec. 16, 2002;21(58):8935-48. doi: 10.1038/sj.onc.1205996.
Krokan et al., Base excision repair. Cold Spring Harb Perspect Biol. Apr. 1, 2013;5(4):a012583. doi: 10.1101/cshperspect.a012583.
Krzywkowski et al., Limited reverse transcriptase activity of phi29 DNA polymerase. Nucleic Acids Res. Apr. 20, 2018;46(7):3625-3632. doi: 10.1093/nar/gky190.
Kumar et al., Gene therapy for chronic neuropathic pain: how does it work and where do we stand today? Pain Med. May 2011;12(5):808-22. doi: 10.1111/j.1526-4637.2011.01120.x.
Kumar et al., Structural and functional consequences of the mutation of a conserved arginine residue in alphaA and alphaB crystallins. J Biol Chem. Aug. 20, 1999;274(34):24137-41.
Kundu et al., Leucine to proline substitution by SNP at position 197 in Caspase-9 gene expression leads to neuroblastoma: a bioinformatics analysis. 3 Biotech. 2013; 3:225-34.
Kunkel et al., Eukaryotic Mismatch Repair in Relation to DNA Replication. Annu Rev Genet. 2015;49:291-313. doi: 10.1146/annurev-genet-112414-054722.
Kunz et al., DNA Repair in mammalian cells: Mismatched repair: variations on a theme. Cell Mol Life Sci. Mar. 2009;66(6):1021-38. doi: 10.1007/s00018-009-8739-9.
Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.
Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.
Kuscu et al., CRISPR-Cas9-AID base editor is a powerful gain-of-function screening tool. Nat Methods. Nov. 29, 2016;13(12):983-984. doi: 10.1038/nmeth.4076.
Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.
Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.
Kwart et al., Precise and efficient scarless genome editing in stem cells using correct. Nat Protoc. Feb. 2017; 12(2):329-354. doi: 10.1038/nprot.2016.171. Epub Jan. 19, 2017.

(56) References Cited

OTHER PUBLICATIONS

Kweon et al., Fusion guide RNAs for orthogonal gene manipulation with Cas9 and Cpf1. Nat Commun. Nov. 23, 2017;8(1):1723. doi: 10.1038/s41467-017-01650-w. Erratum in: Nat Commun. Jan. 16, 2018;9(1):303.
Kwon et al., Chemical basis of glycine riboswitch cooperativity. RNA. Jan. 2008; 14(1):25-34. Epub Nov. 27, 2007.
Köhrer et al., A possible approach to site-specific insertion of two different unnatural amino acids into proteins in mammalian cells via nonsense suppression. Chem Biol. Nov. 2003;10(11):1095-102.
Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.
Kügler et al., Human synapsin 1 gene promoter confers highly neuron-specific long-term transgene expression from an adenoviral vector in the adult rat brain depending on the transduced area. Gene Ther. Feb. 2003;10(4):337-47. doi: 10.1038/sj.gt.3301905.
Lada et al., Mutator effects and mutation signatures of editing deaminases produced in bacteria and yeast. Biochemistry (Mosc). Jan. 2011;76(1):131-46.
Lakich et al., Inversions disrupting the factor VIII gene are a common cause of severe haemophilia A. Nat Genet. Nov. 1993;5(3):236-41. doi: 10.1038/ng1193-236.
Lancaster et al., Limited trafficking of a neurotropic virus through inefficient retrograde axonal transport and the type I interferon response. PLoS Pathog. Mar. 5, 2010;6(3):e1000791. doi: 10.1371/journal.ppat.1000791.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Landrum et al., ClinVar: public archive of relationships among sequence variation and human phenotype. Nucleic Acids Res. Jan. 2014;42(Database issue):D980-5. doi: 10.1093/nar/gkt1113. Epub Nov. 14, 2013.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.
Langer et al., New methods of drug delivery. Science. Sep. 28, 1990;249(4976):1527-33.
Lapinaite et al., DNA capture by a CRISPR-Cas9-guided adenine base editor. Science. Jul. 31, 2020;369(6503):566-571. doi: 10.1126/science.abb1390.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lau et al., Molecular basis for discriminating between normal and damaged bases by the human alkyladenine glycosylase, AAG. Proc Natl Acad Sci U S A. Dec. 5, 2000;97(25):13573-8.
Lauer et al., Construction, characterization, and use of two Listeria monocytogenes site-specific phage integration vectors. J Bacteriol. Aug. 2002;184(15):4177-86. doi: 10.1128/jb.184.15.4177-4186.2002.
Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.
Lawrence et al., Supercharging proteins can impart unusual resilience. J Am Chem Soc. Aug. 22, 2007;129(33):10110-2. Epub Aug. 1, 2007.
Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.
Lazar et al., Transforming growth factor alpha: mutation of aspartic acid 47 and leucine 48 results in different biological activities. Mol Cell Biol. Mar. 1988;8(3):1247-52.
Lazarevic et al., Nucleotide sequence of the Bacillus subtilis temperate bacteriophage SPbetac2. Microbiology (Reading). May 1999;145 ( Pt 5):1055-1067. doi: 10.1099/13500872-145-5-1055.
Le Grice et al., Purification and characterization of recombinant equine infectious anemia virus reverse transcriptase. J Virol. Dec. 1991;65(12):7004-7. doi: 10.1128/JVI.65.12.7004-7007.1991.
Leaver-Fay et al., ROSETTA3: an object-oriented software suite for the simulation and design of macromolecules. Methods Enzymol. 2011;487:545-74. doi: 10.1016/B978-0-12-381270-4.00019-6.
Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.
Ledford, Gene-editing hack yields pinpoint precision. Nature, Apr. 20, 2016. http://www.nature.com/news/gene-editing-hack-yields-pinpoint-precision-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Lee et al., A monoclonal antibody that targets a NaV1.7 channel voltage sensor for pain and itch relief. Cell. Jun. 5, 2014;157(6):1393-1404. doi: 10.1016/j.cell.2014.03.064. Epub May 22, 2014. Retraction in: Cell. Jun. 25, 2020;181(7):1695.
Lee et al., An allosteric self-splicing ribozyme triggered by a bacterial second messenger. Science. Aug. 13, 2010;329(5993):845-8. doi: 10.1126/science.1190713.
Lee et al., Failure to detect DNA-guided genome editing using Natronobacterium gregoryi Argonaute. Nat Biotechnol. Nov. 28, 2016;35(1):17-18. doi: 10.1038/nbt.3753.
Lee et al., Group I Intron-Based Therapeutics Through Trans-Splicing Reaction. Prog Mol Biol Transl Sci. 2018;159:79-100. doi: 10.1016/bs.pmbts.2018.07.001. Epub Aug. 9, 2018.
Lee et al., PIK3CA gene is frequently mutated in breast carcinomas and hepatocellular carcinomas. Oncogene. Feb. 17, 2005;24(8):1477-80.
Lee et al., Recognition of liposomes by cells: in vitro binding and endocytosis mediated by specific lipid headgroups and surface charge density. Biochim Biophys Acta. Jan. 31, 1992;1103(2):185-97.
Lee et al., Ribozyme Mediated gRNA Generation for in Vitro and in Vivo CRISPR/Cas9 Mutagenesis. PLoS One. Nov. 10, 2016;11(11):e0166020. doi: 10.1371/journal.pone.0166020. eCollection 2016.
Lee et al., Simultaneous targeting of linked loci in mouse embryos using base editing. Sci Rep. Feb. 7, 2019;9(1):1662. doi: 10.1038/s41598-018-33533-5.
Lee et al., Site-specific integration of mycobacteriophage L5: integration-proficient vectors for Mycobacterium smegmatis, Mycobacterium tuberculosis, and bacille Calmette-Guérin. Proc Natl Acad Sci U S A. Apr. 15, 1991;88(8):3111-5. doi: 10.1073/pnas.88.8.3111.
Lee et al., Synthetically modified guide RNA and donor DNA are a versatile platform for CRISPR-Cas9 engineering. Elife. May 2, 2017;6:e25312. doi: 10.7554/eLife.25312.
Lee et al., Targeted chromosomal deletions in human cells using zinc finger nucleases. Genome Res. Jan. 2010 20: 81-89; Published in Advance Dec. 1, 2009, doi: 10.1101/gr.099747.109.
Lee et al., Targeting fidelity of adenine and cytosine base editors in mouse embryos. Nat Commun. Nov. 15, 2018;9(1):4804. doi: 10.1038/s41467-018-07322-7.
Lee et al., Transcriptional regulation and its misregulation in disease. Cell. Mar. 14, 2013;152(6):1237-51. doi: 10.1016/j.cell.2013.02.014.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Lei et al., Site-specificity of serine integrase demonstrated by the attB sequence preference of ?BT1 integrase. FEBS Lett. Apr. 2018;592(8):1389-1399. doi: 10.1002/1873-3468.13023. Epub Mar. 25, 2018.

(56) References Cited

OTHER PUBLICATIONS

Leipold et al., A de novo gain-of-function mutation in SCN11A causes loss of pain perception. Nat Genet. Nov. 2013;45(11):1399-404. doi: 10.1038/ng.2767. Epub Sep. 15, 2013.
Lemos et al., CRISPR/Cas9 cleavages in budding yeast reveal templated insertions and strand-specific insertion/deletion profiles. Proc Natl Acad Sci U S A. Feb. 27, 2018;115(9):E2040-E2047. doi: 10.1073/pnas.1716855115. Epub Feb. 13, 2018.
Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.
Levy et al., Cytosine and adenine base editing of the brain, liver, retina, heart and skeletal muscle of mice via adeno-associated viruses. Nat Biomed Eng. 2020;4(1):97-110. doi:10.1038/s41551-019-0501-5.
Levy et al., Inhibition of calcification of bioprosthetic heart valves by local controlled-release diphosphonate. Science. Apr. 12, 1985;228(4696):190-2.
Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.
Lew et al., Protein splicing in vitro with a semisynthetic two-component minimal intein. J Biol Chem. Jun. 26, 1998;273(26):15887-90. doi: 10.1074/jbc.273.26.15887.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lewis et al., Building the Class 2 CRISPR-Cas Arsenal. Mol Cell 2017;65(3);377-379.
Lewis et al., Codon 129 polymorphism of the human prion protein influences the kinetics of amyloid formation. J Gen Virol. Aug. 2006;87(Pt 8):2443-9.
Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.
Lewis et al., RNA modifications and structures cooperate to guide RNA-protein interactions. Nat Rev Mol Cell Biol. Mar. 2017;18(3):202-210. doi: 10.1038/nrm.2016.163. Epub Feb. 1, 2017.
Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Current approaches for engineering proteins with diverse biological properties. Adv Exp Med Biol. 2007;620:18-33.
Li et al., Disruption of splicing-regulatory elements using CRISPR/Cas9 to rescue spinal muscular atrophy in human iPSCs and mice. National Science Review. Jan. 1, 2020:92-101. DOI: 10.1093/nsr/nwz131. Retrieved from the Internet via https://academic.oup.com/nsr/article-pdf/7/1/92/33321439/nwz131.pdf. Last accessed Apr. 28, 2021.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.
Li et al., Loss of post-translational modification sites in disease. Pac Symp Biocomput. 2010:337-47. doi: 10.1142/9789814295291_0036.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.
Li et al., Precise Modifications of Both Exogenous and Endogenous Genes in Rice by Prime Editing. Mol Plant. May 4, 2020;13(5):671-674. doi: 10.1016/j.molp.2020.03.011. Epub Mar. 25, 2020.
Li et al., Programmable Single and Multiplex Base-Editing in Bombyx mori Using RNA-Guided Cytidine Deaminases. G3 (Bethesda). May 4, 2018;8(5):1701-1709. doi: 10.1534/g3.118.200134.
Li et al., Protein trans-splicing as a means for viral vector-mediated in vivo gene therapy. Hum Gene Ther. Sep. 2008;19(9):958-64. doi: 10.1089/hum.2008.009.
Li et al., RSEM: accurate transcript quantification from RNA-Seq data with or without a reference genome. BMC Bioinformatics. Aug. 4, 2011;12:323. doi: 10.1186/1471-2105-12-323.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Li, Mechanisms and functions of DNA mismatch repair. Cell Res. Jan. 2008;18(1):85-98. doi: 10.1038/cr.2007.115.
Liang et al., Correction of ?-thalassemia mutant by base editor in human embryos. Protein Cell. Nov. 2017;8(11):811-822. doi: 10.1007/s13238-017-0475-6. Epub Sep. 23, 2017.
Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Liao et al., One-step assembly of large CRISPR arrays enables multi-functional targeting and reveals constraints on array design. bioRxiv. May 2, 2018. doi: 10.1101/312421. 45 pages.
Lieber et al., Mechanism and regulation of human non-homologous DNA end-joining. Nat Rev Mol Cell Biol. Sep. 2003;4(9):712-20.
Liefke et al., The oxidative demethylase ALKBH3 marks hyperactive gene promoters in human cancer cells. Genome Med. Jun. 30, 2015;7(1):66. doi: 10.1186/s13073-015-0180-0.
Lienert et al., Two- and three-input TALE-based and logic computation in embryonic stem cells. Nucleic Acids Res. Nov. 2013;41(21):9967-75. doi: 10.1093/nar/gkt758. Epub Aug. 27, 2013.
Lilley, D.M. The Varkud Satellite Ribozyme. RNA. Feb. 2004;10(2):151-8.doi: 10.1261/rna.5217104.
Lim et al., Crystal structure of the moloney murine leukemia virus RNase H domain. J Virol. Sep. 2006;80(17):8379-89. doi: 10.1128/JVI.00750-06.
Lim et al., Viral vectors for neurotrophic factor delivery: a gene therapy approach for neurodegenerative diseases of the CNS. Pharmacol Res. Jan. 2010;61(1):14-26. doi: 10.1016/j.phrs.2009.10.002. Epub Oct. 17, 2009.
Lin et al., Enhanced homology-directed human genome engineering by controlled timing of CRISPR/Cas9 delivery. Elife. Dec. 15, 2014;3:e04766. doi: 10.7554/eLife.04766.
Lin et al., High-efficiency prime editing with optimized, paired pegRNAs in plants. Nat Biotechnol. Aug. 2021;39(8):923-927. doi: 10.1038/s41587-021-00868-w. Epub Mar. 25, 2021.
Lin et al., Prime genome editing in rice and wheat. Nat Biotechnol. May 2020;38(5):582-585 and Supplemental Info. doi: 10.1038/s41587-020-0455-x. Epub Mar. 16, 2020. 8 pages.
Lin et al., Prime genome editing in rice and wheat. Nat Biotechnol. May 2020;38(5):582-585. doi: 10.1038/s41587-020-0455-x. Epub Mar. 16, 2020.
Lin et al., The human REV1 gene codes for a DNA template-dependent dCMP transferase. Nucleic Acids Res. Nov. 15, 1999;27(22):4468-75. doi: 10.1093/nar/27.22.4468.

(56) References Cited

OTHER PUBLICATIONS

Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.
Liu et al., C2c1-sgRNA Complex Structure Reveals RNA-Guided DNA Cleavage Mechanism. Molecular Cell Jan. 2017;65(2):310-22.
Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.
Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.
Liu et al., Adding new chemistries to the genetic code. Annu Rev Biochem. 2010;79:413-44. doi: 10.1146/annurev.biochem.052308.105824.
Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.
Liu et al., Balancing AID and DNA repair during somatic hypermutation. Trends Immunol. Apr. 2009;30(4):173-81. doi: 10.1016/j.it.2009.01.007.
Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.
Liu et al., CasX enzymes comprise a distinct family of RNA-guided genome editors. Nature. Feb. 2019;566(7743):218-223. doi: 10.1038/s41586-019-0908-x. Epub Feb. 4, 2019. Author manuscript entitled CRISPR-CasX is an RNA-dominated enzyme active for human genome editing.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Computational approaches for effective CRISPR guide RNA design and evaluation. Comput Struct Biotechnol J. Nov. 29, 2019;18:35-44. doi: 10.1016/j.csbj.2019.11.006.
Liu et al., Design of polydactyl zinc-finger proteins for unique addressing within complex genomes. Proc Natl Acad Sci U S A. May 27, 1997;94(11):5525-30.
Liu et al., Direct Promoter Repression by BCL11A Controls the Fetal to Adult Hemoglobin Switch. Cell. Apr. 5, 2018;173(2):430-442.e17. doi: 10.1016/j.cell.2018.03.016. Epub Mar. 29, 2018.
Liu et al., Distance determination by GIY-YIG intron endonucleases: discrimination between repression and cleavage functions. Nucleic Acids Res. Mar. 31, 2006;34(6): 1755-64. Print 2006.
Liu et al., Editing DNA Methylation in the Mammalian Genome. Cell. Sep. 22, 2016;167(1):233-247.e17. doi: 10.1016/j.cell.2016.08.056.
Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.
Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.
Liu et al., Fast Colorimetric Sensing of Adenosine and Cocaine Based on a General Sensor Design Involving Aptamers and Nanoparticles. Angew Chem. 2006;118(1):96-100.
Liu et al., Flap endonuclease 1: a central component of DNA metabolism. Annu Rev Biochem. 2004;73:589-615. doi:10.1146/annurev.biochem.73.012803.092453.
Liu et al., Functional Nucleic Acid Sensors. Chem Rev. May 2009; 109(5):1948-98. doi: 10.1021/cr030183i.
Liu et al., Genetic incorporation of unnatural amino acids into proteins in mammalian cells. Nat Methods. Mar. 2007;4(3):239-44. Epub Feb. 25, 2007.
Liu et al., Highly efficient RNA-guided base editing in rabbit. Nat Commun. Jul. 13, 2018;9(1):2717. doi: 10.1038/s41467-018-05232-2.
Liu et al., (6)-methyladenosine-dependent RNA structural switches regulate RNA-protein interactions. Nature. Feb. 26, 2015;518(7540):560-4. doi: 10.1038/nature14234.
Liu et al., Probing N6-methyladenosine RNA modification status at single nucleotide resolution in mRNA and long noncoding RNA. RNA. Dec. 2013;19(12):1848-56. doi: 10.1261/rna.041178.113. Epub Oct. 18, 2013.
Liu et al., Reverse transcriptase of foamy virus. Purification of the enzymes and immunological identification. Arch Virol. 1977;55(3):187-200. doi: 10.1007/BF01319905.
Liu et al., Reverse transcriptase-mediated tropism switching in Bordetella bacteriophage. Science. Mar. 15, 2002;295(5562):2091-4. doi: 10.1126/science.1067467.
Liu et al., *Saccharomyces cerevisiae* flap endonuclease 1 uses flap equilibration to maintain triplet repeat stability. Mol Cell Biol. May 2004;24(9):4049-64. doi: 10.1128/MCB.24.9.4049-4064.2004.
Liu et al., The Molecular Architecture for RNA-Guided RNA Cleavage by Cas13a. Cell. Aug. 10, 2017;170(4):714-726.e10. doi: 10.1016/j.cell.2017.06.050. Epub Jul. 27, 2017.
Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.
Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.
Lorenz et al., ViennaRNA Package 2.0. Algorithms Mol Biol. Nov. 24, 2011;6:26. doi: 10.1186/1748-7188-6-26.
Losey et al., Crystal structure of *Staphylococcus sureus* tRNA adenosine deaminase tadA in complex with RNA. Nature Struct. Mol. Biol. Feb. 2006;13(2):153-9.
Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.
Luan et al., Reverse transcription of R2Bm RNA is primed by a nick at the chromosomal target site: a mechanism for non-LTR retrotransposition. Cell. Feb. 26, 1993;72(4):595-605. doi: 10.1016/0092-8674(93)90078-5.
Luckow et al., High level expression of nonfused foreign genes with Autographa californica nuclear polyhedrosis virus expression vectors. Virology. May 1989;170(1):31-9. doi: 10.1016/0042-6822(89)90348-6.
Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.
Lundberg et al., Delivery of short interfering RNA using endosomolytic cell-penetrating peptides. Faseb J. Sep. 2007;21(11):2664-71. Epub Apr. 26, 2007.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Lynch, Evolution of the mutation rate. Trends Genet. Aug. 2010;26(8):345-52. doi: 10.1016/j.tig.2010.05.003. Epub Jun. 30, 2010.
Lyons et al., Efficient Recognition of an Unpaired Lesion by a DNA Repair Glycosylase. J. Am. Chem. Soc., 2009;131(49):17742-3. DOI: 10.1021/ja908378y.

(56) References Cited

OTHER PUBLICATIONS

Luke et al., Partial purification and characterization of the reverse transcriptase of the simian immunodeficiency virus TYO-7 isolated from an African green monkey. Biochemistry. Feb. 20, 1990;29(7):1764-9. doi: 10.1021/bi00459a015.
Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.
Ma et al., In vitro protein engineering using synthetic tRNA(Ala) with different anticodons. Biochemistry. Aug. 10, 1993;32(31):7939-45.
Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.
Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.
Ma et al., Targeted AID-mediated mutagenesis (TAM) enables efficient genomic diversification in mammalian cells. Nature Methods. Oct. 2016;13:1029-35. doi:10.1038/nmeth.4027 .
Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.
MacBeth et al., Inositol hexakisphosphate is bound in the ADAR2 core and required for RNA editing. Science. Sep. 2, 2005;309(5740):1534-9. doi: 10.1126/science.1113150.
Macrae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.
Madura et al., Structural basis for ineffective T-cell responses to MHC anchor residue-improved "heteroclitic" peptides. Eur J Immunol. Feb. 2015;45(2):584-91. doi: 10.1002/eji.201445114. Epub Dec. 28, 2014.
Maeder et al., CRISPR RNA-guided activation of endogenous human genes. Nat Methods. Oct. 2013;10(10):977-9. doi: 10.1038/nmeth.2598. Epub Jul. 25, 2013.
Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al., Robust, synergistic regulation of human gene expression using TALE activators. Nat Methods. Mar. 2013;10(3):243-5. doi: 10.1038/nmeth.2366. Epub Feb. 10, 2013.
Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.
Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.
Maizels et al., Initiation of homologous recombination at DNA nicks. Nucleic Acids Res. Aug. 21, 2018;46(14):6962-6973. doi: 10.1093/nar/gky588.
Maji et al., A High-Throughput Platform to Identify Small-Molecule Inhibitors of CRISPR-Cas9. Cell. May 2, 2019;177(4):1067-1079.e19. doi: 10.1016/j.cell.2019.04.009.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Makarova et al., Classification and Nomenclature of CRISPR-Cas Systems: Where from Here? Crispr J. Oct. 2018; 1(5):325-336. doi: 10.1089/crispr.2018.0033.
Makarova et al., Evolution and classification of the CRISPR-Cas systems. Nat Rev Microbiol. Jun. 2011;9(6):467-77. doi: 10.1038/nrmicro2577. Epub May 9, 2011.
Makarova et al., Prokaryotic homologs of Argonaute proteins are predicted to function as key components of a novel system of defense against mobile genetic elements. Biology Direct 2009;4:29. doi: 10.1186/1745-6150-4-29.
Makeyev et al., Evolutionary potential of an RNA virus. J Virol. Feb. 2004;78(4):2114-20.
Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).
Mali et al., Cas9 as a versatile tool for engineeringbiology. Nat Methods. Oct. 2013; 10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Mali et al., RNA-guided human genome engineering via Cas9. Science. Feb. 15, 2013;339(6121):823-6. doi: 10.1126/science.1232033. Epub Jan. 3, 2013.
Malito et al., Structural basis for lack of toxicity of the diphtheria toxin mutant CRM197. Proc Natl Acad Sci U S A. Apr. 3, 2012;109(14):5229-34. doi: 10.1073/pnas.1201964109. Epub Mar. 19, 2012.
Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.
Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.
Mani et al., Design, engineering, and characterization of zinc finger nucleases. Biochem Biophys Res Commun. Sep. 23, 2005;335(2):447-57.
Marceau, Functions of single-strand DNA-binding proteins in DNA replication, recombination, and repair. Methods Mol Biol. 2012;922:1-21. doi: 10.1007/978-1-62703-032-8_1.
Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.
Marioni et al., DNA methylation age of blood predicts all-cause mortality in later life. Genome Biol. Jan. 30, 2015;16:25. doi: 10.1186/s13059-015-0584-6.
Marquart et al., Predicting base editing outcomes with an attention-based deep learning algorithm trained on high-throughput target library screeen. bioRxiv. Jul. 5, 2020. DOI:10.1101/2020.07.05.186544. Retrieved from the Internet via https://www.biorxiv.org/content/10.1101/2020.07.05.186544v1.full.pdf lased accessed on Apr. 28, 2021.
Marraffini et al., CRISPR interference limits horizontal gene transfer in staphylococci by targeting DNA. Science. Dec. 19, 2008;322(5909):1843-5. doi: 10.1126/science.1165771.
Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.
Martsolf et al., Complete trisomy 17p a relatively new syndrome. Ann Genet. 1988;31(3):172-4.
Martz, L., Nav-i-gating antibodies for pain. Science-Business eXchange. Jun. 12, 2014;7(662):1-2. doi: 10.1038/scibx.2014.662.
Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.
Marzec et al., Prime Editing: A New Way for Genome Editing. Trends Cell Biol. Apr. 2020;30(4):257-259. doi: 10.1016/j.tcb.2020.01.004. Epub Jan. 27, 2020.
Mascola et al., HIV-1 neutralizing antibodies: understanding nature's pathways. Immunol Rev. Jul. 2013;254(1):225-44. doi: 10.1111/imr.12075.
Mathys et al., Characterization of a self-splicing mini-intein and its conversion into autocatalytic—and C-terminal cleavage elements:

(56) References Cited

OTHER PUBLICATIONS facile production of protein building blocks for protein ligation. Gene. Apr. 29 1999;231(1-2):1-13. doi: 10.1016/s0378-1119(99)00103-1.
Matsuura et al., A gene essential for the site-specific excision of actinophage r4 prophage genome from the chromosome of a lysogen. J Gen Appl Microbiol. 1995;41(1):53-61.
Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.
May et al., Emergent lineages of mumps virus suggest the need for a polyvalent vaccine. Int J Infect Dis. Jan. 2018;66:1-4. doi: 10.1016/j.ijid.2017.09.024. Epub Oct. 4, 2017.
McCarroll et al., Copy-number variation and association studies of human disease. Nat Genet. Jul. 2007;39(7 Suppl):S37-42. doi: 10.1038/ng2080.
McDonald et al., Characterization of mutations at the mouse phenylalanine hydroxylase locus. Genomics. Feb. 1, 1997;39(3):402-5. doi: 10.1006/geno.1996.4508.
McInerney et al., Error Rate Comparison during Polymerase Chain Reaction by DNA Polymerase. Mol Biol Int. 2014;2014:287430. doi: 10.1155/2014/287430. Epub Aug. 17, 2014.
McKenna et al., Recording development with single cell dynamic lineage tracing. Development. Jun. 27, 2019;146(12):dev169730. doi: 10.1242/dev.169730.
McKenna et al., Whole-organism lineage tracing by combinatorial and cumulative genome editing. Science. Jul. 29, 2016;353(6298):aaf7907. doi: 10.1126/science.aaf7907. Epub May 26, 2016.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.
Mead et al., A novel protective prion protein variant that colocalizes with kuru exposure. Engl J Med. Nov. 19, 2009;361(21):2056-65. doi: 10.1056/NEJMoa0809716.
Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.
Meinke et al., Cre Recombinase and Other Tyrosine Recombinases. Chem Rev. Oct. 26, 2016;116(20):12785-12820. doi: 10.1021/acs.chemrev.6b00077. Epub May 10, 2016.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.
Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.
Mertens et al., Site-specific recombination in bacteriophage Mu: characterization of binding sites for the DNA invertase Gin. EMBO J. Apr. 1988;7(4):1219-27.
Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.
Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.
Meyer et al., Confirmation of a second natural preQ1 aptamer class in *Streptococcaceae* bacteria. RNA. Apr. 2008;14(4):685-95. doi: 10.1261/rna.937308. Epub Feb. 27, 2008.
Meyer et al., Library generation by gene shuffling. Curr Protoc Mol Biol. Jan. 6, 2014;105:Unit 15.12.. doi: 10.1002/0471142727.mb1512s105.
Meyer et al., Ribosome biogenesis factor Tsr3 is the aminocarboxypropyl transferase responsible for 18S rRNA hypermodification in yeast and humans. Nucleic Acids Res. May 19, 2016;44(9):4304-16. doi: 10.1093/nar/gkw244. Epub Apr. 15, 2016.
Meyer et al., The dynamic epitranscriptome: N6-methyladenosine and gene expression control. Nat Rev Mol Cell Biol. May 2014;15(5):313-26. doi: 10.1038/nrm3785. Epub Apr. 9, 2014.
Michel et al., Mitochondrial class II introns encode proteins related to the reverse transcriptases of retroviruses. Nature. Aug. 15-21, 1985;316(6029):641-3. doi: 10.1038/316641a0.
Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.
Mihai et al., PTEN inhibition improves wound healing in lung epithelia through changes in cellular mechanics that enhance migration. Am J Physiol Lung Cell Mol Physiol. 2012;302(3):L287-L299.
Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.
Miller et al., A TALE nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Miller et al., Construction and properties of retrovirus packaging cells based on gibbon ape leukemia virus. J Virol. May 1991;65(5):2220-4. doi: 10.1128/JVI.65.5.2220-2224.1991.
Miller et al., Continuous evolution of SpCas9 variants compatible with non-G PAMs. Nat Biotechnol. Apr. 2020;38(4):471-481. doi: 10.1038/s41587-020-0412-8. Epub Feb. 10, 2020.
Miller et al., Phage-assisted continuous and non-continuous evolution. Nat Protoc. Dec. 2020; 15(12):4101-4127. doi: 10.1038/s41596-020-00410-3. Epub Nov. 16, 2020.
Miller, Human gene therapy comes of age. Nature. Jun. 11, 1992;357(6378):455-60. doi: 10.1038/357455a0.
Mills et al., Protein splicing in trans by purified- and C-terminal fragments of the Mycobacterium tuberculosis RecA intein. Proc Natl Acad Sci U S A. Mar. 31, 1998;95(7):3543-8. doi: 10.1073/pnas.95.7.3543.
Minoche et al., Evaluation of genomic high-throughput sequencing data generated on Illumina HiSeq and genome analyzer systems. Genome Biol. Nov. 8, 2011;12(11):R112. doi: 10.1186/GB-2011-12-11-r112.
Minoretti et al., A W148R mutation in the human FOXD4 gene segregating with dilated cardiomyopathy, obsessive-compulsive disorder, and suicidality. Int J Mol Med. Mar. 2007;19(3):369-72.
Mir et al., Two Active Site Divalent Ions in the Crystal Structure of the Hammerhead Ribozyme Bound to a Transition State Analogue. Biochemistry . . . Feb. 2, 2016;55(4):633-6. doi: 10.1021/acs.biochem.5b01139. Epub Jan. 19, 2016.
Mir et al., Type II-C CRISPR-Cas9 Biology, Mechanism, and Application. ACS Chem Biol. Feb. 16, 2018;13(2):357-365. doi: 10.1021/acschembio.7b00855. Epub Dec. 20, 2017.
Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.
Mitani et al., Delivering therapeutic genes—matching approach and application. Trends Biotechnol. May 1993;11(5):162-6. doi: 10.1016/0167-7799(93)90108-L.
Mitton-Fry et al., Poly(A) tail recognition by a viral RNA element through assembly of a triple helix. Science. Nov. 26, 2010;330(6008):1244-7. doi: 10.1126/science.1195858.
Miyaoka et al., Systematic quantification of HDR and NHEJ reveals effects of locus, nuclease, and cell type on genome-editing. Sci Rep. Mar. 31, 2016;6:23549. doi: 10.1038/srep23549.
Moede et al., Identification of a nuclear localization signal, RRMKWKK, in the homeodomain transcription factor PDX-1. FEBS Lett. Nov. 19, 1999;461(3):229-34. doi: 10.1016/s0014-5793(99)01446-5.

(56) References Cited

OTHER PUBLICATIONS

Mohr et al., A Reverse Transcriptase-Cas1 Fusion Protein Contains a Cas6 Domain Required for Both CRISPR RNA Biogenesis and RNA Spacer Acquisition. Mol Cell. Nov. 15, 2018;72(4):700-714. e8. doi: 10.1016/j.molcel.2018.09.013. Epub Oct. 18, 2018. Including Supplemental Information.
Mohr et al., Thermostable group II intron reverse transcriptase fusion proteins and their use in cDNA synthesis and next-generation RNA sequencing. RNA. Jul. 2013;19(7):958-70. doi: 10.1261/rna.039743.113. Epub May 22, 2013.
Mojica et al., Intervening sequences of regularly spaced prokaryotic repeats derive from foreign genetic elements. J Mol Evol. Feb. 2005;60(2):174-82.
Mok et al., A bacterial cytidine deaminase toxin enables CRISPR-free mitochondrial base editing. Nature. Jul. 2020;583(7817):631-637. doi: 10.1038/s41586-020-2477-4. Epub Jul. 8, 2020.
Mol et al., Crystal structure and mutational analysis of human uracil-DNA glycosylase: structural basis for specificity and catalysis. Cell. Mar. 24, 1995;80(6):869-78. doi: 10.1016/0092-8674(95)90290-2.
Mol et al., Crystal structure of human uracil-DNA glycosylase in complex with a protein inhibitor: protein mimicry of DNA. Cell. Sep. 8, 1995;82(5):701-8.
Molla et al., CRISPR/Cas-Mediated Base Editing: Technical Considerations and Practical Applications. Trends Biotechnol. Oct. 2019;37(10):1121-1142. doi: 10.1016/j.tibtech.2019.03.008. Epub Apr. 14, 2019.
Monahan et al., Site-specific incorporation of unnatural amino acids into receptors expressed in Mammalian cells. Chem Biol. Jun. 2003;10(6):573-80.
Monot et al., The specificity and flexibility of l1 reverse transcription priming at imperfect T-tracts. PLoS Genet. May 2013;9(5):e1003499. doi: 10.1371/journal.pgen.1003499. Epub May 9, 2013.
Montange et al., Structure of the S-adenosylmethionine riboswitch regulatory mRNA element. Nature. Jun. 29, 2006;441(7097):1172-5.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Mootz et al., Conditional protein splicing: a new tool to control protein structure and function in vitro and in vivo. J Am Chem Soc. Sep. 3, 2003;125(35):10561-9.
Mootz et al., Protein splicing triggered by a small molecule. J Am Chem Soc. Aug. 7, 2002;124(31):9044-5 and Supporting Information. doi: 10.1021/ja0267690. 4 pages.
Mootz et al., Protein splicing triggered by a small molecule. J Am Chem Soc. Aug. 7, 2002;124(31):9044-5.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.
Moreno-Mateos et al., CRISPRscan: designing highly efficient sgRNAs for CRISPR-Cas9 targeting in vivo. Nat Methods. Oct. 2015;12(10):982-8. doi: 10.1038/nmeth.3543. Epub Aug. 31, 2015.
Morita et al., The site-specific recombination system of actinophage TG1. Fems Microbiol Lett. Aug. 2009;297(2):234-40. doi: 10.1111/j.1574-6968.2009.01683.x.
Morris et al., A peptide carrier for the delivery of biologically active proteins into mammalian cells. Nat Biotechnol. Dec. 2001;19(12):1173-6.
Moscou et al., A simple cipher governs DNA recognition by TAL effectors. Science. Dec. 11, 2009;326(5959):1501. doi: 10.1126/science.1178817.
Mougiakos et al., Characterizing a thermostable Cas9 for bacterial genome editing and silencing. Nat Commun. Nov. 21, 2017;8(1):1647. doi: 10.1038/s41467-017-01591-4.
Muir et al., Expressed protein ligation: a general method for protein engineering. Proc Natl Acad Sci U S A. Jun. 9, 1998;95(12):6705-10. doi: 10.1073/pnas.95.12.6705.
Muller et al., Nucleotide exchange and excision technology (NExT) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.
Muller, U.F., Design and Experimental Evolution of trans-Splicing Group I Intron Ribozymes. Molecules. Jan. 2, 2017;22(1):75. doi: 10.3390/molecules22010075.
Mullins et al., Transgenesis in nonmurine species. Hypertension. Oct. 1993;22(4):630-3.
Mumtsidu et al., Structural features of the single-stranded DNA-binding protein of Epstein-Barr virus. J Struct Biol. Feb. 2008;161(2):172-87. doi: 10.1016/j.jsb.2007.10.014. Epub Nov. 1, 2007.
Murphy, Phage recombinases and their applications. Adv Virus Res. 2012;83:367-414. doi: 10.1016/B978-0-12-394438-2.00008-6. Review.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Muzyczka et al., Adeno-associated virus (AAV) vectors: will they work? J Clin Invest. Oct. 1994;94(4):1351. doi: 10.1172/JCI117468.
Myerowitz et al., The major defect in Ashkenazi Jews with Tay-Sachs disease is an insertion in the gene for the alpha-chain of beta-hexosaminidase. J Biol Chem. Dec. 15, 1988;263(35):18587-9.
Myers et al., Insulin signal transduction and the IRS proteins. Annu Rev Pharmacol Toxicol. 1996;36:615-58. doi: 10.1146/annurev.pa.36.040196.003151.
Nabel et al., Direct gene transfer for immunotherapy and immunization. Trends Biotechnol. May 1993;11(5):211-5. doi: 10.1016/0167-7799(93)90117-R.
Nahar et al., A G-quadruplex motif at the 3' end of sgRNAs improves CRISPR-Cas9 based genome editing efficiency. Chem Commun (Camb). Mar. 7, 2018;54(19):2377-2380. doi: 10.1039/c7cc08893k. Epub Feb. 16, 2018.
Nahvi et al., Coenzyme B12 riboswitches are widespread genetic control elements in prokaryotes. Nucleic Acids Res. Jan. 2, 2004;32(1):143-50.
Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.
Nakamura et al., Codon usage tabulated from international DNA sequence databases: status for the year 2000. Nucleic Acids Res. Jan. 1, 2000;28(1):292. doi: 10.1093/nar/28.1.292.
Naorem et al., DGR mutagenic transposition occurs via hypermutagenic reverse transcription primed by nicked template RNA. Proc Natl Acad Sci U S A. Nov. 21, 2017;114(47):E10187-E10195. doi: 10.1073/pnas.1715952114. Epub Nov. 6, 2017.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Neel et al., Riboswitches: Classification, function and in silico approach, International Journal of Pharma Sciences and Research. 2010;1(9):409-420.
Nelson et al., Engineered pegRNAs improve prime editing efficiency. Nat Biotechnol. Oct. 4, 2021. doi: 10.1038/s41587-021-01039-7. Epub ahead of print. Erratum in: Nat Biotechnol. Dec. 8, 2021. 14 pages.
Nelson et al., Filamentous phage DNA cloning vectors: a noninfective mutant with a nonpolar deletion in gene III. Virology. 1981; 108(2): 338-50.

(56) References Cited

OTHER PUBLICATIONS

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
Newby et al., Base editing of haematopoietic stem cells rescues sickle cell disease in mice. Nature. Jun. 2, 2021. doi: 10.1038/s41586-021-03609-w. Epub ahead of print.
Nguyen et al., Evolutionary drivers of thermoadaptation in enzyme catalysis. Science. Jan. 20, 2017;355(6322):289-294. doi: 10.1126/science.aah3717. Epub Dec. 22, 2016.
Nguyen et al., IQ-TREE: a fast and effective stochastic algorithm for estimating maximum-likelihood phylogenies. Mol Biol Evol. Jan. 2015;32(1):268-74. doi: 10.1093/molbev/msu300. Epub Nov. 3, 2014.
Ni et al., A PCSK9-binding antibody that structurally mimics the EGF(A) domain of LDL-receptor reduces LDL cholesterol in vivo. J Lipid Res. 2011;52:76-86.
Ni et al., Nucleic acid aptamers: clinical applications and promising new horizons. Curr Med Chem. 2011;18(27):4206-14. Review.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Nishikura, Functions and regulation of RNA editing by ADAR deaminases. Annu Rev Biochem. 2010;79:321-349. doi:10.1146/annurev-biochem-060208-105251.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nishimasu et al., Crystal Structure of *Staphylococcus aureus* Cas9. Cell. Aug. 27, 2015;162(5):1113-26. doi: 10.1016/j.cell.2015.08.007.
Nishimasu et al., Engineered CRISPR-Cas9 nuclease with expanded targeting space. Science. Sep. 21, 2018;361(6408):1259-1262. doi: 10.1126/science.aas9129. Epub Aug. 30, 2018.
Noack et al., Epitranscriptomics: A New Regulatory Mechanism of Brain Development and Function. Front Neurosci. Feb. 20, 2018;12:85. doi: 10.3389/fnins.2018.00085. 9 pages.
Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Noris et al., A phenylalanine-55 to serine amino-acid substitution in the human glycoprotein IX leucine-rich repeat is associated with Bernard-Soulier syndrome. Br J Haematol. May 1997;97(2):312-20.
Nottingham et al., RNA-seq of human reference RNA samples using a thermostable group II intron reverse transcriptase. RNA. Apr. 2016;22(4):597-613. doi: 10.1261/rna.055558.115. Epub Jan. 29, 2016.
Nowak et al., Characterization of single-stranded DNA-binding proteins from the psychrophilic bacteria Desulfotalea psychrophila, Flavobacterium psychrophilum, Psychrobacter arcticus, Psychrobacter cryohalolentis, Psychromonas ingrahamii, Psychroflexus torquis, and Photobacterium profundum. BMC Microbiol. Apr. 14, 2014;14:91. doi: 10.1186/1471-2180-14-91.
Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.
Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.
Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.
Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
O'Maille et al., Structure-based combinatorial protein engineering (SCOPE). J Mol Biol. Aug. 23, 2002;321(4):677-91.
Oakes et al., CRISPR-Cas9 Circular Permutants as Programmable Scaffolds for Genome Modification. Cell. Jan. 10, 2019;176(1-2):254-267.e16. doi: 10.1016/j.cell.2018.11.052.
Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.
Oakes et al., Protein engineering of Cas9 for enhanced function. Methods Enzymol. 2014;546:491-511.
Odsbu et al., Specific-terminal interactions of the *Escherichia coli* SeqA protein are required to form multimers that restrain negative supercoils and form foci. Genes Cells. Nov. 2005;10(11): 1039-49.
Oeemig et al., Solution structure of DnaE intein from Nostoc punctiforme: structural basis for the design of a new split intein suitable for site-specific chemical modification. FEBS Lett. May 6, 2009;583(9):1451-6.
Offord, Advances in Genome Editing. The Scientist, Apr. 20, 2016. http://www.the-scientist.com/?articles.view/articleNo/45903/title/Advances-in-Genome-Editing/.
Oh et al., Positional cloning of a gene for Hermansky-Pudlak syndrome, a disorder of cytoplasmic organelles. Nat Genet. Nov. 1996;14(3):300-6. doi: 10.1038/ng1196-300.
Ohe et al., Purification and properties of xanthine dehydrogenase from Streptomyces cyanogenus. J Biochem. Jul. 1979;86(1):45-53.
Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.
Olorunniji et al., Purification and in Vitro Characterization of Zinc Finger Recombinases. Methods Mol Biol. 2017; 1642:229-245. doi: 10.1007/978-1-4939-7169-5_15.
Olorunniji et al., Site-specific recombinases: molecular machines for the Genetic Revolution. Biochem J. Mar. 15, 2016;473(6):673-84. doi: 10.1042/BJ20151112.
Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.
Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Orthwein et al., A mechanism for the suppression of homologous recombination in G1 cells. Nature. Dec. 17, 2015;528(7582):422-6. doi: 10.1038/nature16142. Epub Dec. 9, 2015.
Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.
Osborn et al., Base Editor Correction of col. 7A1 in Recessive Dystrophic Epidermolysis Bullosa Patient-Derived Fibroblasts and iPSCs. J Invest Dermatol. Feb. 2020;140(2):338-347.e5. doi: 10.1016/j.jid.2019.07.701. Epub Aug. 19, 2019.
Osborn et al., TALEN-based gene correction for epidermolysis bullosa. Mol Ther. Jun. 2013;21(6):1151-9. doi: 10.1038/mt.2013.56. Epub Apr. 2, 2013.
Ostermeier et al., A combinatorial approach to hybrid enzymes independent of DNA homology. Nat Biotechnol. Dec. 1999;17(12):1205-9.
Ostertag et al., Biology of mammalian L1 retrotransposons. Annu Rev Genet. 2001;35:501-38. doi: 10.1146/annurev.genet.35.102401.091032.
Otomo et al., Improved segmental isotope labeling of proteins and application to a larger protein. J Biomol NMR. Jun. 1999;14(2):105-14. doi: 10.1023/a:1008308128050.

(56) References Cited

OTHER PUBLICATIONS

Otomo et al., NMR observation of selected segments in a larger protein: central-segment isotope labeling through intein-mediated ligation. Biochemistry. Dec. 7, 1999;38(49):16040-4. doi: 10.1021/bi991902j.
Otto et al., The probability of fixation in populations of changing size. Genetics. Jun. 1997;146(2):723-33.
Packer et al., Methods for the directed evolution of proteins. Nat Rev Genet. Jul. 2015;16(7):379-94. doi: 10.1038/nrg3927. Epub Jun. 9, 2015.
Packer et al., Phage-assisted continuous evolution of proteases with altered substrate specificity. Nat Commun. Oct. 16, 2017;8(1):956. doi: 10.1038/s41467-017-01055-9.
Paige et al., RNA mimics of green fluorescent protein. Science. Jul. 29, 2011;333(6042):642-6. doi:10.1126/science.1207339.
Paiva et al., Targeted protein degradation: elements of PROTAC design. Curr Opin Chem Biol. Jun. 2019;50:111-119. doi: 10.1016/j.cbpa.2019.02.022. Epub Apr. 17, 2019.
Pan et al., Biological and biomedical applications of engineered nucleases. Mol Biotechnol. Sep. 2013;55(1):54-62. doi: 10.1007/s12033-012-9613-9.
Paquet et al., Efficient introduction of specific homozygous and heterozygous mutations using CRISPR/Cas9. Nature. May 5, 2016;533(7601):125-9. doi: 10.1038/nature17664. Epub Apr. 27, 2016.
Park et al., Digenome-seq web tool for profiling CRISPR specificity. Nat Methods. May 30, 2017;14(6):548-549. doi: 10.1038/nmeth.4262.
Park et al., Highly efficient editing of the ?-globin gene in patient-derived hematopoietic stem and progenitor cells to treat sickle cell disease. Nucleic Acids Res. Sep. 5, 2019;47(15):7955-7972. doi: 10.1093/nar/gkz475.
Park et al., Sendai virus, an RNA virus with no risk of genomic integration, delivers CRISPR/Cas9 for efficient gene editing. Mol Ther Methods Clin Dev. Aug. 24, 2016;3:16057. doi: 10.1038/mtm.2016.57.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.
Pattanayak et al., Determining the specificities of TALENs, Cas9, and other genome-editing enzymes. Methods Enzymol. 2014;546:47-78. doi: 10.1016/B978-0-12-801185-0.00003-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pawson et al., Protein phosphorylation in signaling—50 years and counting. Trends Biochem Sci. Jun. 2005;30(6):286-90. doi: 10.1016/j.tibs.2005.04.013.
Pearl, Structure and function in the uracil-DNA glycosylase superfamily. Mutat Res. Aug. 30, 2000;460(3-4):165-81.
Peck et al., Directed evolution of a small-molecule-triggered intein with improved splicing properties in mammalian cells. Chem Biol. May 27, 2011;18(5):619-30. doi: 10.1016/j.chembiol.2011.02.014.
Pellenz et al., New human chromosomal safe harbor sites for genome engineering with CRISPR/Cas9, TAL effector and homing endonucleases. Aug. 20, 2018. bioRxiv doi: https://doi.org/10.1101/396390.
Pelletier, CRISPR-Cas systems for the study of the immune function. Nov. 15, 2016. https://doi.org/10.1002/9780470015902.a0026896.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perach et al., Catalytic features of the recombinant reverse transcriptase of bovine leukemia virus expressed in bacteria. Virology. Jun. 20, 1999;259(1):176-89. doi: 10.1006/viro. 1999.9761.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012; 16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Perler et al., Protein splicing and autoproteolysis mechanisms. Curr Opin Chem Biol. Oct. 1997;1(3):292-9. doi: 10.1016/s1367-5931(97)80065-8.
Perler et al., Protein splicing elements: inteins and exteins—a definition of terms and recommended nomenclature. Nucleic Acids Res. Apr. 11, 1994;22(7):1125-7. doi: 10.1093/nar/22.7.1125.
Perler, InBase, the New England Biolabs Intein Database. Nucleic Acids Res. Jan. 1, 1999;27(1):346-7. doi: 10.1093/nar/27.1.346.
Perler, Protein splicing of inteins and hedgehog autoproteolysis: structure, function, and evolution. Cell. Jan. 9, 1998;92(1):1-4. doi: 10.1016/s0092-8674(00)80892-2.
Perreault et al., Mixed deoxyribo- and ribo-oligonucleotides with catalytic activity. Nature. Apr. 5, 1990;344(6266):565-7. doi: 10.1038/344565a0.
Petek et al., Frequent endonuclease cleavage at off-target locations in vivo. Mol Ther. May 2010;18(5):983-6. Doi: 10.1038/mt.2010.35. Epub Mar. 9, 2010.
Petersen-Mahrt et al., AID mutates *E. coli* suggesting a DNA deamination mechanism for antibody diversification. Nature. Jul. 4, 2002;418(6893):99-103.
Petolino et al., Editing Plant Genomes: a new era of crop improvement. Plant Biotechnol J. Feb. 2016;14(2):435-6. doi: 10.1111/pbi.12542.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pfeiffer et al., Mechanisms of DNA double-strand break repair and their potential to induce chromosomal aberrations. Mutagenesis. Jul. 2000;15(4):289-302. doi: 10.1093/mutage/15.4.289.
Pieken et al., Kinetic characterization of ribonuclease-resistant 2'-modified hammerhead ribozymes. Science. Jul. 19, 1991;253(5017):314-7. doi: 10.1126/science.1857967.
Phillips, The challenge of gene therapy and DNA delivery. J Pharm Pharmacol. Sep. 2001;53(9):1169-74.
Pickart et al., Ubiquitin: structures, functions, mechanisms. Biochim Biophys Acta. Nov. 29, 2004;1695(1-3):55-72. doi: 10.1016/j.bbamcr.2004.09.019.
Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.
Pirakitikulr et al., PCRless library mutagenesis via oligonucleotide recombination in yeast. Protein Sci. Dec. 2010;19(12):2336-46. doi: 10.1002/pro.513.
Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutL? endonuclease in mismatch repair. Proc Natl

(56) References Cited

OTHER PUBLICATIONS

Acad Sci U S A. Sep. 14, 2010;107(37):16066-71. doi: 10.1073/pnas.1010662107. Epub Aug. 16, 2010.
Poller et al., A leucine-to-proline substitution causes a defective alpha 1-antichymotrypsin allele associated with familial obstructive lung disease. Genomics. Sep. 1993;17(3):740-3.
Popp et al., Sortagging: a versatile method for protein labeling. Nat Chem Biol. Nov. 2007;3(11):707-8. doi: 10.1038/nchembio.2007.31. Epub Sep. 23, 2007.
Porteus, Design and testing of zinc finger nucleases for use in mammalian cells. Methods Mol Biol. 2008;435:47-61. doi: 10.1007/978-1-59745-232-8_4.
Posnick et al., Imbalanced base excision repair increases spontaneous mutation and alkylation sensitivity in *Escherichia coli*. J Bacteriol. Nov. 1999;181(21):6763-71.
Pospísilová et al., Hydrolytic cleavage of N6-substituted adenine derivatives by eukaryotic adenine and adenosine deaminases. Biosci Rep. 2008;28(6):335-347. doi:10.1042/BSR20080081.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prasad et al., Rev1 is a base excision repair enzyme with 5'-deoxyribose phosphate lyase activity. Nucleic Acids Res. Dec. 15, 2016;44(22):10824-10833. doi: 10.1093/nar/gkw869. Epub Sep. 28, 2016.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.
Proudfoot et al., Zinc finger recombinases with adaptable DNA sequence specificity. PLoS One. Apr. 29, 2011;6(4):e19537. doi: 10.1371/journal.pone.0019537.
Pruschy et al., Mechanistic studies of a signaling pathway activated by the organic dimerizer FK1012. Chem Biol. Nov. 1994;1(3):163-72. doi: 10.1016/1074-5521(94)90006-x.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Pu et al., Evolution of a split RNA polymerase as a versatile biosensor platform. Nat Chem Biol. Apr. 2017; 13(4):432-438. doi: 10.1038/nchembio.2299. Epub Feb. 13, 2017.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.
Qu et al., Global mapping of binding sites for phic31 integrase in transgenic maden-darby bovine kidney cells using ChIP-seq. Hereditas. Jan. 14, 2019;156:3. doi: 10.1186/s41065-018-0079-z.
Queen et al., Immunoglobulin gene transcription is activated by downstream sequence elements. Cell. Jul. 1983;33(3):741-8. doi: 10.1016/0092-8674(83)90016-8.
Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.
Raghavan et al., Abstract 27: Therapeutic Targeting of Human Lipid Genes with in vivo CRISPR-Cas9 Genome Editing. Oral Abstract Presentations: Lipoprotein Metabolism and Therapeutic Targets. Arterioscler THromb Vasc Biol. 2015;35(Suppl. 1):Abstract 27. 5 pages.
Raillard et al., Targeting sites within HIV-1 cDNA with a DNA-cleaving ribozyme. Biochemistry. Sep. 10, 1996;35(36):11693-701. doi: 10.1021/bi960845g.
Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.
Rakonjac et al., Roles of PIII in filamentous phage assembly. J Mol Biol. 1998; 282(1)25-41.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Ramamurthy et al., Identification of immunogenic B-cell epitope peptides of rubella virus El glycoprotein towards development of highly specific immunoassays and/or vaccine. Conference Abstract. 2019.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ramirez et al., Unexpected failure rates for modular assembly of engineered zinc fingers. Nat Methods. May 2008;5(5):374-5. Doi: 10.1038/nmeth0508-374.
Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.
Ran et al., Genome engineering using the CRISPR-Cas9 system. Nat Protoc. Nov. 2013;8(11):2281-308. doi: 10.1038/nprot.2013.143. Epub Oct. 24, 2013.
Ran et al., In vivo genome editing using *Staphylococcus aureus* Cas9. Nature. Apr. 9, 2015;520(7546):186-91. doi: 10.1038/nature14299. Epub Apr. 1, 2015.
Ranzau et al., Genome, Epigenome, and Transcriptome Editing via Chemical Modification of Nucleobases in Living Cells. Biochemistry. Feb. 5, 2019;58(5):330-335. doi: 10.1021/acs.biochem.8b00958. Epub Dec. 12, 2018.
Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.
Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 Rna polymerase mutants with altered promoter specificities. Proc Natl Acad Sci U S A. Apr. 15, 1993;90(8):3147-51.
Rath et al., Fidelity of end joining in mammalian episomes and the impact of Metnase on joint processing. BMC Mol Biol. Mar. 22, 2014;15:6. doi: 10.1186/1471-2199-15-6.
Rauch et al., Programmable RNA Binding Proteins for Imaging and Therapeutics. Biochemistry. Jan. 30, 2018;57(4):363-364. doi: 10.1021/acs.biochem.7b01101. Epub Nov. 17, 2017.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).
Ray et al., A compendium of RNA-binding motifs for decoding gene regulation. Nature. Jul. 11, 2013;499(7457):172-7. doi: 10.1038/nature12311.
Ray et al., Homologous recombination: ends as the means. Trends Plant Sci. Oct. 2002;7(10):435-40.
Rebar et al., Phage display methods for selecting zinc finger proteins with novel DNA-binding specificities. Methods Enzymol. 1996;267:129-49.

(56) References Cited

OTHER PUBLICATIONS

Rebuzzini et al., New mammalian cellular systems to study mutations introduced at the break site by non-homologous end-joining. DNA Repair (Amst). May 2, 2005;4(5):546-55.
Rees et al., Analysis and minimization of cellular RNA editing by DNA adenine base editors. Sci Adv. May 8, 2019;5(5):eaax5717. doi: 10.1126/sciadv.aax5717.
Rees et al., Base editing: precision chemistry on the genome and transcriptome of living cells. Nat Rev Genet. Dec. 2018;19(12):770-788. doi: 10.1038/s41576-018-0059-1.
Rees et al., Development of hRad51-Cas9 nickase fusions that mediate HDR without double- stranded breaks. Nat Commun. May 17, 2019;10(1):2212. doi: 10.1038/s41467-019-09983-4.
Rees et al., Improving the DNA specificity and applicability of base editing through protein engineering and protein delivery. Nat Commun. Jun. 6, 2017;8:15790. doi: 10.1038/ncomms15790.
Relph et al., Recent developments and current status of gene therapy using viral vectors in the United Kingdom. BMJ. 2004;329(7470):839-842. doi:10.1136/bmj.329.7470.839.
Remy et al., Gene transfer with a series of lipophilic DNA-binding molecules. Bioconjug Chem. Nov.-Dec. 1994;5(6):647-54. doi: 10.1021/bc00030a021.
Ren et al., In-line Alignment and Mg$^{2}$? Coordination at the Cleavage Site of the env22 Twister Ribozyme. Nat Commun. Nov. 20, 2014;5:5534. doi: 10.1038/ncomms6534.
Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.
Reynaud et al., What role for AID: mutator, or assembler of the immunoglobulin mutasome? Nat Immunol. Jul. 2003;4(7):631-8.
Reyon et al., FLASH assembly of TALENs for high-throughput genome editing. Nat Biotechnol. May 2012;30(5):460-5. doi: 10.1038/nbt.2170.
Ribeiro et al., Protein Engineering Strategies to Expand CRISPR-Cas9 Applications. Int J Genomics. Aug. 2, 2018;2018:1652567. doi: 10.1155/2018/1652567.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.
Richter et al., Phage-assisted evolution of an adenine base editor with improved Cas domain compatibility and activity. Nat Biotechnol. Jul. 2020;38(7):883-891. doi: 10.1038/s41587-020-0453-z. Epub Mar. 16, 2020.
Riechmann et al., The C-terminal domain of TolA is the coreceptor for filamentous phage infection of *E. coli*. Cell. 1997; 90(2):351-60. PMID:9244308.
Ringrose et al., The Kw recombinase, an integrase from Kluyveromyces waltii. Eur J Biochem. Sep. 15, 1997;248(3):903-12. doi: 10.1111/j.1432-1033.1997.00903.x.
Risso et al., Hyperstability and substrate promiscuity in laboratory resurrections of Precambrian ?-lactamases. J Am Chem Soc. Feb. 27, 2013;135(8):2899-902. doi: 10.1021/ja311630a. Epub Feb. 14, 2013.
Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.
Robertson et al., DNA repair in mammalian cells: Base excision repair: the long and short of it. Cell Mol Life Sci. Mar. 2009;66(6):981-93. doi: 10.1007/s00018-009-8736-z.
Robertson et al., Selection in vitro of an RNA enzyme that specifically cleaves single-stranded DNA. Nature. Mar. 29, 1990;344(6265):467-8. doi: 10.1038/344467a0.
Robinson et al., The protein tyrosine kinase family of the human genome. Oncogene. Nov. 20, 2000;19(49):5548-57. doi: 10.1038/sj.onc.1203957.
Rogozin et al., Evolution and diversification of lamprey antigen receptors: evidence for involvement of an AID-APOBEC family cytosine deaminase. Nat Immunol. Jun. 2007;8(6):647-56. doi: 10.1038/ni1463. Epub Apr. 29, 2007.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rongrong et al., Effect of deletion mutation on the recombination activity of Cre recombinase. Acta Biochim Pol. 2005;52(2):541-4. Epub May 15, 2005.
Roth et al., A widespread self-cleaving ribozyme class is revealed by bioinformatics. Nat Chem Biol. Jan. 2014;10(1):56-60. doi: 10.1038/nchembio.1386. Epub Nov. 17, 2013.
Roth et al., Purification and characterization of murine retroviral reverse transcriptase expressed in *Escherichia coli*. J Biol Chem. Aug. 5, 1985;260(16):9326-35.
Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.
Rouet et al., Introduction of double-strand breaks into the genome of mouse cells by expression of a rare-cutting endonuclease. Mol Cell Biol. Dec. 1994;14(12):8096-106. doi: 10.1128/mcb.14.12.8096.
Rouet et al., Receptor-Mediated Delivery of CRISPR-Cas9 Endonuclease for Cell-Type-Specific Gene Editing. J Am Chem Soc. May 30, 2018;140(21):6596-6603. doi: 10.1021/jacs.8b01551. Epub May 18, 2018.
Roundtree et al., YTHDC1 mediates nuclear export of N6-methyladenosine methylated mRNAs. Elife. Oct. 6, 2017;6:e31311. doi: 10.7554/eLife.31311.
Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.
Rowland et al., Sin recombinase from *Staphylococcus aureus*: synaptic complex architecture and transposon targeting. Mol Microbiol. May 2002;44(3):607-19. doi: 10.1046/j.1365-2958.2002.02897.x.
Rowley, Chromosome translocations: dangerous liaisons revisited. Nat Rev Cancer. Dec. 2001;1(3):245-50. doi: 10.1038/35106108.
Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.
Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.
Rudolph et al., Synthetic riboswitches for the conditional control of gene expression in Streptomyces coelicolor. Microbiology. Jul. 2013; 159(Pt 7):1416-22. doi: 10.1099/mic.0.067322-0. Epub May 15, 2013.
Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.
Ryu et al., Adenine base editing in mouse embryos and an adult mouse model of Duchenne muscular dystrophy. Nat Biotechnol. Jul. 2018;36(6):536-539. doi: 10.1038/nbt.4148. Epub Apr. 27, 2018.
Rüfer et al., Non-contact positions impose site selectivity on Cre recombinase. Nucleic Acids Res. Jul. 1, 2002;30(13):2764-71. doi: 10.1093/nar/gkf399.
Sadelain et al., Safe harbours for the integration of new DNA in the human genome. Nat Rev Cancer. Dec. 1, 2011;12(1):51-8. doi: 10.1038/nrc3179.
Sadowski, The Flp recombinase of the 2-microns plasmid of *Saccharomyces cerevisiae*. Prog Nucleic Acid Res Mol Biol. 1995;51:53-91.
Safari et al., CRISPR Cpf1 proteins: structure, function and implications for genome editing. Cell Biosci. May 9, 2019;9:36. doi: 10.1186/s13578-019-0298-7.
Sage et al., Proliferation of functional hair cells in vivo in the absence of the retinoblastoma protein. Science. Feb. 18, 2005;307(5712):1114-8. Epub Jan. 13, 2005.

(56) References Cited

OTHER PUBLICATIONS

Saha et al., The NIH Somatic Cell Genome Editing program. Nature. Apr. 2021;592(7853):195-204. doi: 10.1038/s41586-021-03191-1. Epub Apr. 7, 2021.
Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.
Sale et al., Y-family DNA polymerases and their role in tolerance of cellular DNA damage. Nat Rev Mol Cell Biol. Feb. 23, 2012;13(3):141-52. doi: 10.1038/nrm3289.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Samal et al., Cationic polymers and their therapeutic potential. Chem Soc Rev. Nov. 7, 2012;41(21):7147-94. doi: 10.1039/c2cs35094g. Epub Aug. 10, 2012.
Samanta et al., A reverse transcriptase ribozyme. Elife. Sep. 26, 2017;6:e31153. doi: 10.7554/eLife.31153.
Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang et al., A unique uracil-DNA binding protein of the uracil DNA glycosylase superfamily. Nucleic Acids Res. Sep. 30, 2015;43(17):8452-63. doi: 10.1093/nar/gkv854. Epub Aug. 24, 2015.
Sang, Prospects for transgenesis in the chick. Mech Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Santoro et al., Directed evolution of the site specificity of Cre recombinase. Proc Natl Acad Sci U S A. Apr. 2, 2002;99(7):4185-90. Epub Mar. 19, 2002.
Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.
Sapranauskas et al., The *Streptococcus* thermophilus CRISPR/Cas system provides immunity in *Escherichia coli*. Nucleic Acids Res. Nov. 2011;39(21):9275-82. doi: 10.1093/nar/gkr606. Epub Aug. 3, 2011.
Sapunar et al., Dorsal root ganglion—a potential new therapeutic target for neuropathic pain. J Pain Res. 2012;5:31-8. doi: 10.2147/JPR.S26603. Epub Feb. 16, 2012.
Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.
Sarkar et al., HIV-1 proviral DNA excision using an evolved recombinase. Science. Jun. 29, 2007;316(5833):1912-5. doi: 10.1126/science.1141453.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
Sasidharan et al., The selection of acceptable protein mutations. PNAS; Jun. 12, 2007;104(24):10080-5. www.pnas.org/cgi/doi/10.1073.pnas.0703737104.
Satomura et al., Precise genome-wide base editing by the CRISPR Nickase system in yeast. Sci Rep. May 18, 2017;7(1):2095. doi: 10.1038/s41598-017-02013-7.
Saudek et al., A preliminary trial of the programmable implantable medication system for insulin delivery. Engl J Med. Aug. 31, 1989;321(9):574-9.
Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.
Savic et al., Covalent linkage of the DNA repair template to the CRISPR-Cas9 nuclease enhances homology-directed repair. Elife. May 29, 2018;7:e33761. doi: 10.7554/eLife.33761.
Saville et al., A site-specific self-cleavage reaction performed by a novel RNA in Neurospora mitochondria. Cell. May 18, 1990;61(4):685-96. doi: 10.1016/0092-8674(90)90480-3.
Savva et al., The structural basis of specific base-excision repair by uracil-DNA glycosylase. Nature. Feb. 9, 1995;373(6514):487-93. doi: 10.1038/373487a0.
Schaaper et al., Base selection, proofreading, and mismatch repair during DNA replication in *Escherichia coli*. J Biol Chem. Nov. 15, 1993;268(32):23762-5.
Schaaper et al., Spectra of spontaneous mutations in *Escherichia coli* strains defective in mismatch correction: the nature of in vivo DNA replication errors. Proc Natl Acad Sci U S A. Sep. 1987;84(17):6220-4.
Schaefer et al., Understanding RNA modifications: the promises and technological bottlenecks of the 'epitranscriptome'. Open Biol. May 2017;7(5):170077. doi: 10.1098/rsob.170077.
Schechner et al., Multiplexable, locus-specific targeting of long RNAs with CRISPR-Display. Nat Methods. Jul. 2015;12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.
Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.
Schenk et al., MPDU1 mutations underlie a novel human congenital disorder of glycosylation, designated type If. J Clin Invest. Dec. 2001;108(11):1687-95. doi: 10.1172/JCI13419.
Schmitz et al., Behavioral abnormalities in prion protein knockout mice and the potential relevance of PrP(C) for the cytoskeleton. Prion. 2014;8(6):381-6. doi: 10.4161/19336896.2014.983746.
Schriefer et al., Low pressure DNA shearing: a method for random DNA sequence analysis. Nucleic Acids Res. Dec. 25, 1990;18(24):7455-6.
Schultz et al., Expression and secretion in yeast of a 400-kDa envelope glycoprotein derived from Epstein-Barr virus. Gene. 1987;54(1):113-23. doi: 10.1016/0378-1119(87)90353-2.
Schultz et al., Oligo-2'-fluoro-2'-deoxynucleotide N3'—>P5' phosphoramidates: synthesis and properties. Nucleic Acids Res. Aug. 1, 1996;24(15):2966-73.
Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.
Schwartz et al., Post-translational enzyme activation in an animal via optimized conditional protein splicing. Nat Chem Biol. Jan. 2007;3(1):50-4. Epub Nov. 26, 2006.
Schwarze et al., In vivo protein transduction: delivery of a biologically active protein into the mouse. Science. Sep. 3, 1999;285(5433):1569-72.
Scholler et al., Interactions, localization, and phosphorylation of the m6A generating METTL3-METTL14-WTAP complex. RNA. Apr. 2018;24(4):499-512. doi: 10.1261/rna.064063.117. Epub Jan. 18, 2018.
Sclimenti et al., Directed evolution of a recombinase for improved genomic integration at a native human sequence. Nucleic Acids Res. Dec. 15, 2001;29(24):5044-51.

(56) References Cited

OTHER PUBLICATIONS

Score Results for Luetticken et al., Complete genome sequence of a *Streptococcus dysgalactiae* subsp. RT equisimilis strain possessing Lancefield's group A antigen. RL Submitted to the EMBL/GenBank/DDBJ databases. May 2012. 3 pages.
Score Results for Okumura et al., Evolutionary paths of *Streptococcal* and *Staphylococcal* superantigens. RL BMC Genomics. 2012;13:404-404. 3 pages.
Score Results for Shimomura et al., Complete Genome Sequencing and Analysis of a Lancefield Group G Rt *Streptococcus* Dysagalactiae Subsp. Equisimilis Strain Causing *Streptococcal* RT Toxic Shock Syndrome (STSS). RL BMC Genomics. 2011;12:17-17. 3 pages.
Scott et al., Production of cyclic peptides and proteins in vivo. Proc Natl Acad Sci U S A. Nov. 23, 1999;96(24):13638-43. doi: 10.1073/pnas.96.24.13638.
Sebastían-martín et al., Transcriptional inaccuracy threshold attenuates differences in RNA-dependent DNA synthesis fidelity between retroviral reverse transcriptases. Sci Rep. Jan. 12, 2018;8(1):627. doi: 10.1038/s41598-017-18974-8.
Seed, An LFA-3 cDNA encodes a phospholipid-linked membrane protein homologous to its receptor CD2. Nature. Oct. 29-Nov 4, 1987;329(6142):840-2. doi: 10.1038/329840a0.
Sefton et al., Implantable pumps. Crit Rev Biomed Eng. 1987;14(3):201-40.
Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.
Sells et al., Delivery of protein into cells using polycationic liposomes. Biotechniques. Jul. 1995;19(1):72-6, 78.
Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Semple et al., Rational design of cationic lipids for siRNA delivery. Nat Biotechnol. Feb. 2010;28(2):172-6. doi: 10.1038/nbt.1602. Epub Jan. 17, 2010.
Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.
Serganov et al., Structural basis for discriminative regulation of gene expression by adenine- and guanine-sensing mRNAs. Chem Biol. Dec. 2004;11(12):1729-41.
Serganov et al., Structural basis for gene regulation by a thiamine pyrophosphate-sensing riboswitch. Nature. Jun. 29, 2006;441(7097):1167-71. Epub May 21, 2006.
Seripa et al., The missing ApoE allele. Ann Hum Genet. Jul. 2007;71(Pt 4):496-500. Epub Jan. 22, 2007.
Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.
Setten et al., The current state and future directions of RNAi-based therapeutics. Nat Rev Drug Discov. Jun. 2019; 18(6):421-446. doi: 10.1038/s41573-019-0017-4.
Severinov et al., Expressed protein ligation, a novel method for studying protein-protein interactions in transcription. J Biol Chem. Jun. 26, 1998;273(26):16205-9. doi: 10.1074/jbc.273.26.16205.
Sha et al., Monobodies and other synthetic binding proteins for expanding protein science. Protein Sci. May 2017;26(5):910-924. doi: 10.1002/pro.3148. Epub Mar. 24, 2017.
Shah et al., Inteins: nature's gift to protein chemists. Chem Sci. 2014;5(1):446-461.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.
Shah et al., Protospacer recognition motifs: mixed identities and functional diversity. RNA Biol. May 2013;10(5):891-9. doi: 10.4161/rna.23764. Epub Feb. 12, 2013.
Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.
Shaikh et al., Chimeras of the Flp and Cre recombinases: tests of the mode of cleavage by Flp and Cre. J Mol Biol. Sep. 8, 2000;302(1):27-48.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Shalem et al., High-throughput functional genomics using CRISPR-Cas9. Nat Rev Genet. May 2015;16(5):299-311. doi: 10.1038/nrg3899. Epub Apr. 9, 2015.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharma et al., Efficient introduction of aryl bromide functionality into proteins in vivo. FEBS Lett. Feb. 4, 2000;467(1):37-40.
Sharma et al., Identification of novel methyltransferases, Bmt5 and Bmt6, responsible for the m3U methylations of 25S rRNA in *Saccharomyces cerevisiae*. Nucleic Acids Res. Mar. 2014;42(5):3246-60. doi: 10.1093/nar/gkt1281. Epub Dec. 11, 2013.
Sharon et al., Functional Genetic Variants Revealed by Massively Parallel Precise Genome Editing. Cell. Oct. 4, 2018;175(2):544-557.e16. doi: 10.1016/j.cell.2018.08.057. Epub Sep. 20, 2018.
Shaw et al., Implications of human genome architecture for rearrangement-based disorders: the genomic basis of disease. Hum Mol Genet. Apr. 1, 2004;13 Spec No. 1:R57-64. doi: 10.1093/hmg/ddh073. Epub Feb. 5, 2004.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shechner et al., Multiplexable, locus-specific targeting of long RNAs with CRISPR-Display. Nat Methods. Jul. 2015;12(7):664-70. doi: 10.1038/nmeth.3433. Epub Jun. 1, 2015.
Shee et al., Engineered proteins detect spontaneous DNA breakage in human and bacterial cells. Elife. Oct. 29, 2013;2:e01222. doi: 10.7554/eLife.01222.
Shen et al., Herpes simplex virus 1 (HSV-1) for cancer treatment. Cancer Gene Ther. Nov. 2006;13(11):975-92. doi: 10.1038/sj.cgt.7700946. Epub Apr. 7, 2006.
Shen et al., Predictable and precise template-free CRISPR editing of pathogenic variants. Nature. Nov. 2018;563(7733):646-651. doi: 10.1038/s41586-018-0686-x. Epub Nov. 7, 2018.
Shen, Data processing, Modeling and Analysis scripts for CRISPR-inDelphi. GitHub—maxwshen/indelphi-dataprocessinganalysis at 6b68e3cec73c9358fef6e5f178a935f3c2a4118f. Apr. 10, 2018. Retrieved online via https://github.com/maxwshen/indelphi-sataprocessinganalysis/tree/6b68e3cec73c9358fef6e5f178a935f3c2a4118f Last retrieved on Jul. 26, 2021. 2 pages.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.
Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.
Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimojima et al., Spinocerebellar ataxias type 27 derived from a disruption of the fibroblast growth factor 14 gene with mimicking

(56) References Cited

OTHER PUBLICATIONS phenotype of paroxysmal non-kinesigenic dyskinesia. Brain Dev. Mar. 2012;34(3):230-3. doi: 10.1016/j.braindev.2011.04.014. Epub May 19, 2011.
Shin et al., CRISPR/Cas9 targeting events cause complex deletions and insertions at 17 sites in the mouse genome. Nat Commun. May 31, 2017;8:15464. doi: 10.1038/ncomms15464.
Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.
Shingledecker et al., Molecular dissection of the Mycobacterium tuberculosis RecA intein: design of a minimal intein and of a trans-splicing system involving two intein fragments. Gene. Jan. 30, 1998;207(2):187-95. doi: 10.1016/s0378-1119(97)00624-0.
Shmakov et al., Discovery and Functional Characterization of Diverse Class 2 CRISPR Cas Systems. Molecular Cell Nov. 2015;60(3):385-97.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.
Shultz et al., A genome-wide analysis of FRT-like sequences in the human genome. PLoS One. Mar. 23, 2011;6(3):e18077. doi: 10.1371/journal.pone.0018077.
Siebert et al., An improved PCR method for walking in uncloned genomic DNA. Nucleic Acids Res. Mar. 25, 1995;23(6):1087-8.
Silas et al., Direct CRISPR spacer acquisition from RNA by a natural reverse transcriptase-Cas1 fusion protein. Science. Feb. 26, 2016;351(6276):aad4234. doi: 10.1126/science.aad4234.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Simonelli et al., Base excision repair intermediates are mutagenic in mammalian cells. Nucleic Acids Res. Aug. 2, 2005;33(14):4404-11. Print 2005.
Singh et al., Cross-talk between diverse serine integrases. J Mol Biol. Jan. 23, 2014;426(2):318-31. doi: 10.1016/j.jmb.2013.10.013. Epub Oct. 22, 2013.
Singh et al., Real-time observation of DNA recognition and rejection by the RNA-guided endonuclease Cas9. Nat Commun. Sep. 14, 2016;7:12778. doi: 10.1038/ncomms12778.
Singh et al., Real-time observation of DNA target interrogation and product release by the RNA-guided endonuclease CRISPR Cpf1 (Cas12a). Proc Natl Acad Sci U S A. May 22, 2018;115(21):5444-5449. doi: 10.1073/pnas.1718686115. Epub May 7, 2018.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Siu et al., Riboregulated toehold-gated gRNA for programmable CRISPR-Cas9 function. Nat Chem Biol. Mar. 2019;15(3):217-220. doi: 10.1038/s41589-018-0186-1. Epub Dec. 10, 2018.
Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005;14(2):523-32. Epub Jan. 4, 2005.
Slaymaker et al., Rationally engineered Cas9 nucleases with improved specificity. Science. Jan. 1, 2016;351(6268):84-8. doi: 10.1126/science.aad5227. Epub Dec. 1, 2015.
Sledz et al., Structural insights into the molecular mechanism of the m(6)A writer complex. Elife. Sep. 14, 2016;5:e18434. doi: 10.7554/eLife.18434.
Slupphaug et al., A nucleotide-flipping mechanism from the structure of human uracil-DNA glycosylase bound to DNA. Nature. Nov. 7, 1996;384(6604):87-92. doi: 10.1038/384087a0.
Smargon et al., Cas13b Is a Type VI-B CRISPR-Associated RNA-Guided RNase Differentially Regulated by Accessory Proteins Csx27 and Csx28. Mol Cell. Feb. 16, 2017;65(4):618-630.e7. doi: 10.1016/j.molcel.2016.12.023. Epub Jan. 5, 2017.
Smith et al., Diversity in the serine recombinases. Mol Microbiol. Apr. 2002;44(2):299-307. Review.
Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.
Smith et al., Herpesvirus transport to the nervous system and back again. Annu Rev Microbiol. 2012;66:153-76. doi: 10.1146/annurev-micro-092611-150051. Epub Jun. 15, 2012.
Smith et al., Production of human beta interferon in insect cells infected with a baculovirus expression vector. Mol Cell Biol. Dec. 1983;3(12):2156-65. doi: 10.1128/mcb.3.12.2156.
Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.
Smith, Filamentous fusion phage: novel expression vectors that display cloned antigens on the virion surface. Science. Jun. 14, 1985;228(4705):1315-7.
Smith, Phage-encoded Serine Integrases and Other Large Serine Recombinases. Microbiol Spectr. Aug. 2015;3(4). doi: 10.1128/microbiolspec.MDNA3-0059-2014.
Somanathan et al., AAV vectors expressing LDLR gain-of-function variants demonstrate increased efficacy in mouse models of familial hypercholesterolemia. Circ Res. Aug. 29, 2014;115(6):591-9. doi: 10.1161/CIRCRESAHA.115.304008. Epub Jul. 14, 2014.
Sommerfelt et al., Receptor interference groups of 20 retroviruses plating on human cells. Virology. May 1990;176(1):58-69. doi: 10.1016/0042-6822(90)90230-o.
Song et al., Adenine base editing in an adult mouse model of tyrosinaemia. Nat Biomed Eng. Jan. 2020;4(1):125-130. doi: 10.1038/s41551-019-0357-8. Epub Feb. 25, 2019.
Song et al., Delivery of CRISPR/Cas systems for cancer gene therapy and immunotherapy. Adv Drug Deliv Rev. Jan. 2021;168:158-180. doi: 10.1016/j.addr.2020.04.010. Epub May 1, 2020.
Southworth et al., Control of protein splicing by intein fragment reassembly. EMBO J. Feb. 16, 1998;17(4):918-26. doi: 10.1093/emboj/17.4.918.
Southworth et al., Purification of proteins fused to either the amino or carboxy terminus of the Mycobacterium xenopi gyrase A intein. Biotechniques. Jul. 1999;27(1):110-4, 116, 118-20. doi: 10.2144/99271st04.
Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.
Spencer et al., Controlling signal transduction with synthetic ligands. Science. Nov. 12, 1993;262(5136):1019-24. doi: 10.1126/science.7694365.
Spencer et al., Functional analysis of Fas signaling in vivo using synthetic inducers of dimerization. Curr Biol. Jul. 1, 1996;6(7):839-47. doi: 10.1016/s0960-9822(02)00607-3.
Srivastava et al., An inhibitor of nonhomologous end-joining abrogates double-strand break repair and impedes cancer progression. Cell. Dec. 21, 2012;151(7):1474-87. doi: 10.1016/j.cell.2012.11.054.
Stadtman, Selenocysteine. Annu Rev Biochem. 1996;65:83-100.
Stamos et al., Structure of a Thermostable Group II Intron Reverse Transcriptase with Template-Primer and Its Functional and Evolutionary Implications. Mol Cell. Dec. 7, 2017;68(5):926-939.e4. doi: 10.1016/j.molcel.2017.10.024. Epub Nov. 16, 2017.
Steele et al., The prion protein knockout mouse: a phenotype under challenge. Prion. Apr.-Jun. 2007;1(2):83-93. doi: 10.4161/pri.1.2.4346. Epub Apr. 25, 2007.
Steiner et al., The neurotropic herpes viruses: herpes simplex and varicella-zoster. Lancet Neurol. Nov. 2007;6(11):1015-28. doi: 10.1016/S1474-4422(07)70267-3.
Stella et al., Structure of the Cpf1 endonuclease R-loop complex after target DNA cleavage. Nature. Jun. 22, 2017;546(7659):559-563. doi: 10.1038/nature22398. Epub May 31, 2017.

(56) References Cited

OTHER PUBLICATIONS

Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.
Stenson et al., The Human Gene Mutation Database: towards a comprehensive repository of inherited mutation data for medical research, genetic diagnosis and next-generation sequencing studies. Hum Genet. Jun. 2017;136(6):665-677. doi: 10.1007/s00439-017-1779-6. Epub Mar. 27, 2017.
Stephens et al., The landscape of cancer genes and mutational processes in breast cancer. Nature Jun. 2012;486:400-404. doi: 10.1038/nature11017.
Sternberg et al., Conformational control of DNA target cleavage by CRISPR-Cas9. Nature. Nov. 5, 2015;527(7576):110-3. doi: 10.1038/nature15544. Epub Oct. 28, 2015.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.
Sterne-Weiler et al., Exon identity crisis: disease-causing mutations that disrupt the splicing code. Genome Biol. Jan. 23, 2014;15(1):201. doi: 10.1186/gb4150.
Stevens et al., A promiscuous split intein with expanded protein engineering applications. Proc Natl Acad Sci U S A. Aug. 8, 2017;114(32):8538-8543. doi: 10.1073/pnas. 1701083114. Epub Jul. 24, 2017.
Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.
Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.
Strecker et al., Engineering of CRISPR-Cas12b for human genome editing. Nat Commun. Jan. 22, 2019;10(1):212. doi: 10.1038/s41467-018-08224-4.
Strecker et al., RNA-guided DNA insertion with CRISPR-associated transposases. Science. Jul. 5, 2019;365(6448):48-53. doi: 10.1126/science.aax9181. Epub Jun. 6, 2019.
Strutt et al., RNA-dependent RNA targeting by CRISPR-Cas9. Elife. Jan. 5, 2018;7:e32724. doi: 10.7554/eLife.32724.
Su et al., Human DNA polymerase ? has reverse transcriptase activity in cellular environments. J Biol Chem. Apr. 12, 2019;294(15):6073-6081. doi: 10.1074/jbc.RA119.007925. Epub Mar. 6, 2019.
Sudarsan et al., An mRNA structure in bacteria that controls gene expression by binding lysine. Genes Dev. Nov. 1, 2003;17(21):2688-97.
Sudarsan et al., Riboswitches in eubacteria sense the second messenger cyclic di-GMP. Science. Jul. 18, 2008;321(5887):411-3. doi: 10.1126/science.1159519.
Suess et al., A theophylline responsive riboswitch based on helix slipping controls gene expression in vivo. Nucleic Acids Res. Mar. 5, 2004;32(4):1610-4.
Suh et al., Restoration of visual function in adult mice with an inherited retinal disease via adenine base editing. Nat Biomed Eng. Feb. 2021;5(2):169-178. doi: 10.1038/s41551-020-00632-6. Epub Oct. 19, 2020.
Sullenger et al., Ribozyme-mediated repair of defective mRNA by targeted, trans-splicing. Nature. Oct. 13, 1994;371(6498):619-22. doi: 10.1038/371619a0.
Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Sun et al., The CRISPR/Cas9 system for gene editing and its potential application in pain research. Transl Periop & Pain Med. Aug. 3, 2016;1(3):22-33.
Surun et al., High Efficiency Gene Correction in Hematopoietic Cells by Donor-Template-Free CRISPR/Cas9 Genome Editing. Mol Ther Nucleic Acids. Mar. 2, 2018;10:1-8. doi: 10.1016/j.omtn.2017.11.001. Epub Nov. 10, 2017.
Suzuki et al., Crystal structures reveal an elusive functional domain of pyrrolysyl-tRNA synthetase. Nat Chem Biol. Dec. 2017;13(12):1261-1266. doi: 10.1038/nchembio.2497. Epub Oct. 16, 2017.
Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.
Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.
Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.
Swarts et al., DNA-guided DNA interference by a prokaryotic Argonaute. Nature. Mar. 13, 2014;507(7491):258-61. doi: 10.1038/nature12971. Epub Feb. 16, 2014.
Swarts et al., The evolutionary journey of Argonaute proteins. Nat Struct Mol Biol. Sep. 2014;21(9):743-53. doi: 10.1038/nsmb.2879.
Szczepek et al., Structure-based redesign of the dimerization interface reduces the toxicity of zinc-finger nucleases. Nat Biotechnol. Jul. 2007;25(7):786-93. Epub Jul. 1, 2007.
Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.
Tagalakis et al., Lack of RNA-DNA oligonucleotide (chimeraplast) mutagenic activity in mouse embryos. Mol Reprod Dev. Jun. 2005;71(2):140-4.
Tahara et al., Potent and Selective Inhibitors of 8-Oxoguanine DNA Glycosylase. J Am Chem Soc. Feb. 14, 2018;140(6):2105-2114. doi: 10.1021/jacs.7b09316. Epub Feb. 5, 2018.
Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.
Takimoto et al., Stereochemical basis for engineered pyrrolysyl-tRNA synthetase and the efficient in vivo incorporation of structurally divergent non-native amino acids. ACS Chem Biol. Jul. 15, 2011;6(7):733-43. doi: 10.1021/cb200057a. Epub May 5, 2011.
Tambunan et al., Vaccine Design for H5N1 Based on B- and T-cell Epitope Predictions. Bioinform Biol Insights. Apr. 28, 2016;10:27-35. doi: 10.4137/BBI.S38378.
Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.
Tanese et al., Expression of enzymatically active reverse transcriptase in *Escherichia coli*. Proc Natl Acad Sci U S A. Aug. 1985;82(15):4944-8. doi: 10.1073/pnas.82.15.4944.
Tang et al., Aptazyme-embedded guide RNAs enable ligand-responsive genome editing and transcriptional activation. Nat Commun. Jun. 28, 2017;8:15939. doi: 10.1038/ncomms15939.
Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.
Tang et al., Rewritable multi-event analog recording in bacterial and mammalian cells. Science. Apr. 13, 2018;360(6385):eaap8992. doi: 10.1126/science.aap8992. Epub Feb. 15, 2018.
Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.
Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.
Tebas et al., Gene editing of CCR5 in autologous CD4 T cells of persons infected with HIV. Engl J Med. Mar. 6, 2014;370(10):901-10. doi: 10.1056/NEJMoa1300662.
Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.

(56) References Cited

OTHER PUBLICATIONS

Telenti et al., The Mycobacterium xenopi GyrA protein splicing element: characterization of a minimal intein. J Bacteriol. Oct. 1997;179(20):6378-82. doi: 10.1128/jb.179.20.6378-6382.1997.
Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.
Teng et al., Mutational analysis of apolipoprotein B mRNA editing enzyme (APOBEC1). structure-function relationships of RNA editing and dimerization. J Lipid Res. Apr. 1999;40(4):623-35.
Tessarollo et al., Targeted mutation in the neurotrophin-3 gene results in loss of muscle sensory neurons. Proc Natl Acad Sci U S A. Dec. 6, 1994;91(25):11844-8.
Tesson et al., Knockout rats generated by embryo microinjection of TALENs. Nat Biotechnol. Aug. 5, 2011;29(8):695-6. doi: 10.1038/nbt.1940.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Thompson et al., Engineering and identifying supercharged proteins for macromolecule delivery into mammalian cells. Methods Enzymol. 2012;503:293-319. doi: 10.1016/B978-0-12396962-0.00012-4.
Thompson et al., The Future of Multiplexed Eukaryotic Genome Engineering. ACS Chem Biol. Feb. 16, 2018;13(2):313-325. doi: 10.1021/acschembio.7b00842. Epub Dec. 28, 2017.
Thomson et al., Mutational analysis of loxP sites for efficient Cre-mediated insertion into genomic DNA. Genesis. Jul. 2003;36(3):162-7. doi: 10.1002/gene.10211.
Thorpe et al., Functional correction of episomal mutations with short DNA fragments and RNA-DNA oligonucleotides. J Gene Med. Mar.-Apr. 2002;4(2):195-204.
Thuronyi et al., Continuous evolution of base editors with expanded target compatibility and improved activity. Nat Biotechnol. Sep. 2019;37(9):1070-1079. doi: 10.1038/s41587-019-0193-0. Epub Jul. 22, 2019.
Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.
Thyagarajan et al., Mammalian genomes contain active recombinase recognition sites. Gene. Feb. 22, 2000;244(1-2):47-54.
Thyagarajan et al., Site-specific genomic integration in mammalian cells mediated by phage phiC31 integrase. Mol Cell Biol. Jun. 2001;21(12):3926-34.
Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.
Tirumalai et al., Recognition of core-type DNA sites by lambda integrase. J Mol Biol. Jun. 12, 1998;279(3):513-27.
Tom et al., Mechanism whereby proliferating cell nuclear antigen stimulates flap endonuclease 1. J Biol Chem. Apr. 7, 2000;275(14):10498-505. doi: 10.1074/jbc.275.14.10498.
Tone et al., Single-stranded DNA binding protein Gp5 of Bacillus subtilis phage ?29 is required for viral DNA replication in growth-temperature dependent fashion. Biosci Biotechnol Biochem. 2012;76(12):2351-3. doi: 10.1271/bbb.120587. Epub Dec. 7, 2012.
Toor et al., Crystal structure of a self-spliced group II intron. Science. Apr. 4, 2008;320(5872):77-82. doi: 10.1126/science.1153803.
Toro et al., On the Origin and Evolutionary Relationships of the Reverse Transcriptases Associated With Type III CRISPR-Cas Systems. Front Microbiol. Jun. 15, 2018;9:1317. doi: 10.3389/fmicb.2018.01317.
Toro et al., The Reverse Transcriptases Associated with CRISPR-Cas Systems. Sci Rep. Aug. 2, 2017;7(1):7089. doi: 10.1038/s41598-017-07828-y.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.
Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.
Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.
Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Traxler et al., A genome-editing strategy to treat ?-hemoglobinopathies that recapitulates a mutation associated with a benign genetic condition. Nat Med. Sep. 2016;22(9):987-90. doi: 10.1038/nm.4170. Epub Aug. 15, 2016.
Trojan et al., Functional analysis of hMLH1 variants and HNPCC-related mutations using a human expression system. Gastroenterology. Jan. 2002;122(1):211-9. doi: 10.1053/gast.2002.30296.
Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.
Tsai et al., CIRCLE-seq: a highly sensitive in vitro screen for genome-wide CRISPR-Cas9 nuclease off-targets. Nat Methods. Jun. 2017;14(6):607-614. doi: 10.1038/nmeth.4278. Epub May 1, 2017.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Tsang et al., Specialization of the DNA-cleaving activity of a group I ribozyme through in vitro evolution. J Mol Biol. Sep. 13, 1996;262(1):31-42. doi: 10.1006/jmbi.1996.0496.
Tsutakawa et al., Human flap endonuclease structures, DNA double-base flipping, and a unified understanding of the FEN1 superfamily. Cell. Apr. 15, 2011;145(2):198-211. doi: 10.1016/j.cell.2011.03.004.
Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.
Tycko et al., Pairwise library screen systematically interrogates *Staphylococcus aureus* Cas9 specificity in human cells. bioRxiv. doi: https://doi.org/10.1101/269399 Posted Feb. 22, 2018.
Uniprot Consortium, UniProt: the universal protein knowledgebase. Nucleic Acids Res. Mar. 16, 2018;46(5):2699. doi: 10.1093/nar/gky092.

(56) References Cited

OTHER PUBLICATIONS

Uniprot Submission; UniProt, Accession No. P01011. Last modified Jun. 11, 2014, version 2. 15 pages.
Uniprot Submission; UniProt, Accession No. P01011. Last modified Sep. 18, 2013, version 2. 15 pages.
Uniprot Submission; UniProt, Accession No. P04264. Last modified Jun. 11, 2014, version 6. 15 pages.
Uniprot Submission; UniProt, Accession No. P04275. Last modified Jul. 9, 2014, version 107. 29 pages.
UniProtein A0A1V6. Dec. 11, 2019.
Uniprotkb Submission; Accession No. F0NH53. May 3, 2011. 4 pages.
Uniprotkb Submission; Accession No. F0NN87. May 3, 2011. 4 pages.
Uniprotkb Submission; Accession No. G3ECR1.2. No Author Listed., Aug. 12, 2020, 8 pages.
Uniprotkb Submission; Accession No. P04264. No Author Listed., Apr. 7, 2021. 12 pages.
Uniprotkb Submission; Accession No. P0DOC6. No Author Listed., Oct. 5, 2016. 5 pages.
Uniprotkb Submission; Accession No. T0D7A2. Oct. 16, 2013. 10 pages.
Uniprotkb Submission; Accession No. U2UMQ6. No Author Listed., Apr. 7, 2021, 11 pages.
Urasaki et al., Functional dissection of the Tol2 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.
Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Usman et al., Exploiting the chemical synthesis of RNA. Trends Biochem Sci. Sep. 1992;17(9):334-9. doi: 10.1016/0968-0004(92)90306-t.
Vagner et al., Efficiency of homologous DNA recombination varies along the Bacillus subtilis chromosome. J Bacteriol. Sep. 1988;170(9):3978-82.
Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem.5b00359. Epub Sep. 11, 2015.
Van Brunt et al., Molecular Farming: Transgenic Animals as Bioreactors. Biotechnology (Y). 1988;6(10):1149-1154. doi: 10.1038/nbt1088-1149.
Van Duyne et al., Teaching Cre to follow directions. Proc Natl Acad Sci U S A. Jan. 6, 2009;106(1):4-5. doi: 10.1073/pnas.0811624106. Epub Dec. 31, 2008.
Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.
Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.
Van Wijk et al., Identification of 51 novel exons of the Usher syndrome type 2A (USH2A) gene that encode multiple conserved functional domains and that are mutated in patients with Usher syndrome type II. Am J Hum Genet. Apr. 2004;74(4):738-44. doi: 10.1086/383096. Epub Mar. 10, 2004.
Vanamee et al., FokI requires two specific DNA sites for cleavage. J Mol Biol. May 25, 2001;309(1):69-78.
Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas.0600012103. Epub Feb. 21, 2006.
Varshney et al., The regulation and functions of DNA and RNA G-quadruplexes. Nat Rev Mol Cell Biol. Aug. 2020;21(8):459-474. doi: 10.1038/s41580-020-0236-x. Epub Apr. 20, 2020.
Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.
Venken et al., Genome-wide manipulations of *Drosophila* melanogaster with transposons, Flp recombinase, and ΦC31 integrase. Methods Mol Biol. 2012;859:203-28. doi: 10.1007/978-1-61779-603-6_12.
Verma, The reverse transcriptase. Biochim Biophys Acta. Mar. 21, 1977;473(1):1-38. doi: 10.1016/0304-419x(77)90005-1.
Vigne et al., Third-generation adenovectors for gene therapy. Restor Neurol Neurosci. Jan. 1, 1995;8(1):35-6. doi: 10.3233/RNN-1995-81208.
Vik et al., Endonuclease V cleaves at inosines in RNA. Nat Commun. 2013;4:2271. doi: 10.1038/ncomms3271.
Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas.2135498100. Epub Oct. 17, 2003.
Villiger et al., Treatment of a metabolic liver disease by in vivo genome base editing in adult mice. Nat Med. Oct. 2018;24(10):1519-1525. doi: 10.1038/s41591-018-0209-1. Epub Oct. 8, 2018.
Vitreschak et al., Regulation of the vitamin B12 metabolism and transport in bacteria by a conserved RNA structural element. RNA. Sep. 2003;9(9):1084-97.
Voigt et al., Rational evolutionary design: the theory of in vitro protein evolution. Adv Protein Chem. 2000;55:79-160.
Vriend et al., Nick-initiated homologous recombination: Protecting the genome, one strand at a time. DNA Repair (Amst). Feb. 2017;50:1-13. doi: 10.1016/j.dnarep.2016.12.005. Epub Dec. 29, 2016.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wah et al., Structure of FokI has implications for DNA cleavage. Proc Natl Acad Sci U S A. Sep. 1, 1998;95(18):10564-9.
Wals et al., Unnatural amino acid incorporation in *E. coli*: current and future applications in the design of therapeutic proteins. Front Chem. Apr. 1, 2014;2:15. doi: 10.3389/fchem.2014.00015. eCollection 2014.
Wan et al., Material solutions for delivery of CRISPR/Cas-based genome editing tools: Current status and future outlook. Materials Today. Jun. 2019;26:40-66. doi: 10.1016/j.mattod.2018.12.003.
Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.
Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.
Wang et al., Continuous directed evolutions of proteins with improved soluble expression. Nature Chemical Biology. Nat Publishing Group. Aug. 20, 2018; 14(10):972-980.
Wang et al., CRISPR-Cas9 Targeting of PCSK9 in Human Hepatocytes in Vivo-Brief Report. Arterioscler Thromb Vasc Biol. May 2016;36(5):783-6. doi: 10.1161/ATVBAHA.116.307227. Epub Mar. 3, 2016.
Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Enhanced base editing by co-expression of free uracil DNA glycosylase inhibitor. Cell Res. Oct. 2017;27(1):1289-92. doi: 10.1038/cr.2017.111. Epub Aug. 29, 2017.

(56) References Cited

OTHER PUBLICATIONS

Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Expanding the genetic code. Annu Rev Biophys Biomol Struct. 2006;35:225-49. Review.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., Highly efficient CRISPR/HDR-mediated knock-in for mouse embryonic stem cells and zygotes. Biotechniques. 2015:59,201-2;204;206-8.
Wang et al., (6)-methyladenosine Modulates Messenger RNA Translation Efficiency. Cell. Jun. 4, 2015;161(6):1388-99. doi: 10.1016/j.cell.2015.05.014.
Wang et al., N6-methyladenosine-dependent regulation of messenger RNA stability. Nature. Jan. 2, 2014;505(7481): 117-20. doi: 10.1038/nature12730. Epub Nov. 27, 2013.
Wang et al., Nucleation, propagation and cleavage of target RNAs in Ago silencing complexes. Nature. Oct. 8, 2009;461(7265):754-61. doi: 10.1038/nature08434.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Optimized paired-sgRNA/Cas9 cloning and expression cassette triggers high-efficiency multiplex genome editing in kiwifruit. Plant Biotechnol J. Aug. 2018;16(8):1424-1433. doi: 10.1111/pbi.12884. Epub Feb. 6, 2018.
Wang et al., Programming cells by multiplex genome engineering and accelerated evolution. Nature. Aug. 13, 2009;460(7257):894-8. Epub Jul. 26, 2009.
Wang et al., Reading RNA methylation codes through methyl-specific binding proteins. RNA Biol. 2014;11(6):669-72. doi: 10.4161/rna.28829. Epub Apr. 24, 2014.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.
Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.
Wang et al., Structural basis of (6)-adenosine methylation by the METTL3-METTL14 complex. Nature. Jun. 23, 2016;534(7608):575-8. doi: 10.1038/nature18298. Epub May 25, 2016.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.
Warren et al., A chimeric Cre recombinase with regulated directionality. Proc Natl Acad Sci USA. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Watowich, The erythropoietin receptor: molecular structure and hematopoietic signaling pathways. J Investig Med. Oct. 2011;59(7):1067-72. doi: 10.2310/JIM.0b013e31820fb28c.
Waxman et al., Regulating excitability of peripheral afferents: emerging ion channel targets. Nat Neurosci. Feb. 2014;17(2):153-63. doi: 10.1038/nn.3602. Epub Jan. 28, 2014.
Weber et al., Assembly of designer TAL effectors by Golden Gate cloning. PLoS One. 2011;6(5):e19722. doi: 10.1371/journal.pone.0019722. Epub May 19, 2011.
Weill et al., DNA polymerases in adaptive immunity. Nat Rev Immunol. Apr. 2008;8(4):302-12. doi: 10.1038/nri2281. Epub Mar. 14, 2008.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human ClC-1 chloride channels in myotonia congenita. J Physiol. Aug. 1, 2012;590(Pt 15):3449-64. doi: 0.1113/jphysiol.2012.232785. Epub May 28, 2012.
Weinert et al., Unbiased detection of CRISPR off-targets in vivo using DISCOVER-Seq. Science. Apr. 19, 2019;364(6437):286-289. doi: 10.1126/science.aav9023. Epub Apr. 18, 2019.
Weiss et al., Loss-of-function mutations in sodium channel Nav1.7 cause anosmia. Nature. Apr. 14, 2011;472(7342):186-90. doi: 10.1038/nature09975. Epub Mar. 23, 2011.
Wen et al., Inclusion of a universal tetanus toxoid CD4(+) T cell epitope P2 significantly enhanced the immunogenicity of recombinant rotavirus ?VP8* subunit parenteral vaccines. Vaccine. Jul. 31, 2014;32(35):4420-4427. doi: 10.1016/j.vaccine.2014.06.060. Epub Jun. 21, 2014.
West et al., Gene expression in adeno-associated virus vectors: the effects of chimeric mRNA structure, helper virus, and adenovirus VA1 RNA. Virology. Sep. 1987;160(1):38-47. doi: 10.1016/0042-6822(87)90041-9.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wheeler et al., The thermostability and specificity of ancient proteins. Curr Opin Struct Biol. Jun. 2016;38:37-43. doi: 10.1016/j.sbi.2016.05.015. Epub Jun. 9, 2016.
Wiedenheft et al., RNA-guided genetic silencing systems in bacteria and archaea. Nature. Feb. 15, 2012;482(7385):331-8. doi: 10.1038/nature10886. Review.
Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.
Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.
Wijnker et al., Managing meiotic recombination in plant breeding. Trends Plant Sci. Dec. 2008;13(12):640-6. doi: 10.1016/j.tplants.2008.09.004. Epub Oct. 22, 2008.
Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.
Wills et al., Pseudoknot-dependent read-through of retroviral gag termination codons: importance of sequences in the spacer and loop 2. EMBO J. Sep. 1, 1994;13(17):4137-44. doi: 10.1002/j.1460-2075.1994.tb06731.x.
Wilson et al., Assessing annotation transfer for genomics: quantifying the relations between protein sequence, structure and function through traditional and probabilistic scores. J Mol Biol 2000;297:233-49.
Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.
Wilson et al., In Vitro Selection of Functional Nucleic Acids. Annu Rev Biochem. 1999;68:611-47. doi: 10.1146/annurev.biochem.68.1.611.
Wilson et al., Kinase dynamics. Using ancient protein kinases to unravel a modern cancer drug's mechanism. Science. Feb. 20, 2015;347(6224):882-6. doi: 10.1126/science.aaa1823.

(56) References Cited

OTHER PUBLICATIONS

Wilson et al., Programmable m6A modification of cellular RNAs with a Cas13-directed methyltransferase. Nat Biotechnol. Dec. 2020;38(12):1431-1440. doi: 10.1038/s41587-020-0572-6. Epub Jun. 29, 2020.
Winkler et al., An mRNA structure that controls gene expression by binding FMN. Proc Natl Acad Sci U S A. Dec. 10, 2002;99(25):15908-13. Epub Nov. 27, 2002.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Winoto et al., A novel, inducible and T cell-specific enhancer located at the 3' end of the T cell receptor alpha locus. EMBO J. Mar. 1989;8(3):729-33.
Winter et al., Drug Development. Phthalimide conjugation as a strategy for in vivo target protein degradation. Science. Jun. 19, 2015;348(6241):1376-81. doi :;10.1126/science.aab1433. Epub May 21, 2015.
Winter et al., Targeted exon skipping with AAV-mediated split adenine base editors. Cell Discov. Aug. 20, 2019;5:41. doi: 10.1038/s41421-019-0109-7.
Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1.61.
Wolf et al., tadA, an essential tRNA-specific adenosine deaminase from *Escherichia coli*. EMBO J. Jul. 15, 2002;21(14):3841-51.
Wolfe et al., Analysis of zinc fingers optimized via phage display: evaluating the utility of a recognition code. J Mol Biol. Feb. 5, 1999;285(5):1917-34.
Wong et al., A statistical analysis of random mutagenesis methods used for directed protein evolution. J Mol Biol. Jan. 27, 2006;355(4):858-71. Epub Nov. 17, 2005.
Wong et al., The Diversity Challenge in Directed Protein Evolution. Comb Chem High Throughput Screen. May 2006;9(4):271-88.
Wood et al., A genetic system yields self-cleaving inteins for bioseparations. Nat Biotechnol. Sep. 1999;17(9):889-92. doi: 10.1038/12879.
Wood et al., Targeted genome editing across species using ZFNs and TALENs. Science. Jul. 15, 2011;333(6040):307. doi: 10.1126/science.1207773. Epub Jun. 23, 2011.
Woods et al., The phenotype of congenital insensitivity to pain due to the NaV1.9 variant p.L811P. Eur J Hum Genet. May 2015;23(5):561-3. doi: 10.1038/ejhg.2014.166. Epub Aug. 13, 2014.
Wright et al., Continuous in vitro evolution of catalytic function. Science. Apr. 25, 1997;276(5312):614-7.
Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.
Wu et al., Correction of a genetic disease in mouse via use of CRISPR-Cas9. Cell Stem Cell. Dec. 5, 2013;13(6):659-62. doi: 10.1016/j.stem.2013.10.016.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.
Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.
Wu et al., Protein trans-splicing by a split intein encoded in a split DnaE gene of Synechocystis sp. PCC6803. Proc Natl Acad Sci U S A. Aug. 4, 1998;95(16):9226-31. doi: 10.1073/pnas.95.16.9226.
Wu et al., Readers, writers and erasers of N6-methylated adenosine modification. Curr Opin Struct Biol. Dec. 2017;47:67-76. doi: 10.1016/j.sbi.2017.05.011. Epub Jun. 16, 2017.
Xiang et al., RNA m6A methylation regulates the ultraviolet-induced DNA damage response. Nature. Mar. 23, 2017;543(7646):573-576. doi: 10.1038/nature21671. Epub Mar. 15, 2017.
Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.
Xiao et al., Nuclear m(6)A Reader YTHDC1 Regulates mRNA Splicing. Mol Cell. Feb. 18, 2016;61(4):507-519. doi: 10.1016/j.molcel.2016.01.012. Epub Feb. 11, 2016.
Xie et al., Adjusting the attB site in donor plasmid improves the efficiency of ?C31 integrase system. DNA Cell Biol. Jul. 2012;31(7):1335-40. doi: 10.1089/dna.2011.1590. Epub Apr. 10, 2012.
Xiong et al., Origin and evolution of retroelements based upon their reverse transcriptase sequences. EMBO J. Oct. 1990;9(10):3353-62.
Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.
Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.
Xu et al., Multiplex nucleotide editing by high-fidelity Cas9 variants with improved efficiency in rice. BMC Plant Biol. 2019;19(1):511. Published Nov. 21, 2019. doi: 10.1186/s12870-019-2131-1. Includes supplementary data and materials.
Xu et al., Protein splicing: an analysis of the branched intermediate and its resolution by succinimide formation. EMBO J. Dec. 1, 1994;13(23):5517-22.
Xu et al., PTMD: A Database of Human Disease-associated Post-translational Modifications. Genomics Proteomics Bioinformatics. Aug. 2018;16(4):244-251. doi: 10.1016/j.gpb.2018.06.004. Epub Sep. 21, 2018.
Xu et al., Sequence determinants of improved CRISPR sgRNA design. Genome Res. Aug. 2015;25(8):1147-57. doi: 10.1101/gr.191452.115. Epub Jun. 10, 2015.
Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.
Xu et al., The mechanism of protein splicing and its modulation by mutation. EMBO J. Oct. 1, 1996;15(19):5146-53.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamada et al., Crystal Structure of the Minimal Cas9 from Campylobacter jejuni Reveals the Molecular Diversity in the CRISPR-Cas9 Systems. Mol Cell. Mar. 16, 2017;65(6):P1109-1121. /doi.org/10.1016/j.molcel.2017.02.007.
Yamamoto et al., The ons and offs of inducible transgenic technology: a review. Neurobiol Dis. Dec. 2001;8(6):923-32.
Yamamoto et al., Virological and immunological bases for HIV-1 vaccine design. Uirusu 2007;57(2):133-139. https://doi.org/10.2222/jsv.57.133.
Yamano et al., Crystal Structure of Cpf1 in Complex with Guide RNA and Target DNA. Cell. May 5, 2016;165(4):949-62 and Supplemental Info. doi: 10.1016/j.cell.2016.04.003. Epub Apr. 21, 2016.
Yamano et al., Crystal Structure of Cpfl in Complex with Guide RNA and Target DNA. Cell. May 5, 2016;165(4):949-62. doi: 10.1016/j.cell.2016.04.003. Epub Apr. 21, 2016.
Yamazaki et al., Segmental Isotope Labeling for Protein NMR Using Peptide Splicing. J. Am. Chem. Soc. May 22, 1998; 120(22):5591-2. https://doi.org/10.1021/ja9807760.
Yan et al., Cas13d Is a Compact RNA-Targeting Type VI CRISPR Effector Positively Modulated by a WYL-Domain-Containing Accessory Protein. Mol Cell. Apr. 19, 2018;70(2):327-339.e5. doi: 10.1016/j.molcel.2018.02.028. Epub Mar. 15, 2018.

(56) References Cited

OTHER PUBLICATIONS

Yan et al., Functionally diverse type V CRISPR-Cas systems. Science. Jan. 4, 2019;363(6422):88-91. doi: 10.1126/science. aav7271. Epub Dec. 6, 2018.
Yan et al., Highly Efficient A•T to G•C Base Editing by Cas9n-Guided tRNA Adenosine Deaminase in Rice. Mol Plant. Apr. 2, 2018;11(4):631-634. doi: 10.1016/j.molp.2018.02.008. Epub Feb. 22, 2018.
Yang et al., A Tale of Two Moieties: Rapidly Evolving CRISPR/Cas-Based Genome Editing. Trends Biochem Sci. Oct. 2020;45(10):874-888. doi: 10.1016/j.tibs.2020.06.003. Epub Jun. 30, 2020.
Yang et al., APOBEC: From mutator to editor. J Genet Genomics. Sep. 20, 2017;44(9):423-437. doi: 10.1016/j.jgg.2017.04.009. Epub Aug. 7, 2017.
Yang et al., Construction of an integration-proficient vector based on the site-specific recombination mechanism of enterococcal temperate phage phiFC1. J Bacteriol. Apr. 2002; 184(7):1859-64. doi: 10.1128/jb.184.7.1859-1864.2002.
Yang et al., Engineering and optimising deaminase fusions for genome editing. Nat Commun. Nov. 2, 2016;7:13330. doi: 10.1038/ncomms13330.
Yang et al., Genome editing with targeted deaminases. BioRxiv. Preprint. First posted online Jul. 28, 2016.
Yang et al., Genome-wide inactivation of porcine endogenous retroviruses (PERVs). Science. Nov. 27, 2015;350(6264):1101-4. doi: 10.1126/science.aad1191. Epub Oct. 11, 2015.
Yang et al., Increasing targeting scope of adenosine base editors in mouse and rat embryos through fusion of TadA deaminase with Cas9 variants. Protein Cell. Sep. 2018;9(9):814-819. doi: 10.1007/s13238-018-0568-x.
Yang et al., Mutations in SCN9A, encoding a sodium channel alpha subunit, in patients with primary erythermalgia. J Med Genet. Mar. 2004;41(3):171-4. doi: 10.1136/jmg.2003.012153.
Yang et al., New CRISPR-Cas systems discovered. Cell Res. Mar. 2017;27(3):313-314. doi: 10.1038/cr.2017.21. Epub Feb. 21, 2017.
Yang et al., One Prime for All Editing. Cell. Dec. 12, 2019;179(7):1448-1450. doi: 10.1016/j.cell.2019.11.030.
Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.
Yang et al., PAM-dependent Target DNA Recognition and Cleavage by C2C1 CRISPR-Cas endonuclease. Cell Dec. 2016;167(7):1814-28.
Yang et al., Permanent genetic memory with >1-byte capacity. Nat Methods. Dec. 2014;11(12):1261-6. doi: 10.1038/nmeth.3147. Epub Oct. 26, 2014.
Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.
Yang et al., Small-molecule control of insulin and PDGF receptor signaling and the role of membrane attachment. Curr Biol. Jan. 1, 1998;8(1):11-8. doi: 10.1016/s0960-9822(98)70015-6.
Yang, Development of Human Genome Editing Tools for the Study of Genetic Variations and Gene Therapies. Doctoral Dissertation. Harvard University. 2013. Accessible via nrs.harvard.edu/urn-3:HUL.InstRepos:11181072. 277 pages.
Yang, Nucleases: diversity of structure, function and mechanism. Q Rev Biophys. Feb. 2011;44(1):1-93. doi: 10.1017/S0033583510000181. Epub Sep. 21, 2010.
Yang, Paml 4: phylogenetic analysis by maximum likelihood. Mol Biol Evol. Aug. 2007;24(8):1586-91. doi: 10.1093/molbev/msm088. Epub May 4, 2007.
Yang, Phylogenetic Analysis by Maximum Likelihood (PAML). //abacus.gene.ucl.ac.uk/software/paml.html Last accessed Apr. 28, 2021.
Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.
Yasui, Alternative excision repair pathways. Cold Spring Harb Perspect Biol. Jun. 1, 2013;5(6):a012617. doi: 10.1101/cshperspect.a012617.
Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.
Yazaki et al., Hereditary systemic amyloidosis associated with a new apolipoprotein AII stop codon mutation Stop78Arg. Kidney Int. Jul. 2003;64(1):11-6.
Yeh et al., In vivo base editing of post-mitotic sensory cells. Nat Commun. Jun. 5, 2018;9(1):2184. doi: 10.1038/s41467-018-04580-3.
Yeh et al., In vivo base editing restores sensory transduction and transiently improves auditory function in a mouse model of recessive deafness. Sci Transl Med. Jun. 3, 2020;12(546):eaay9101. doi: 10.1126/scitranslmed.aay9101.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Yokoe et al., Spatial dynamics of GFP-tagged proteins investigated by local fluorescence enhancement. Nat Biotechnol. Oct. 1996; 14(10):1252-6. doi: 10.1038/nbt1096-1252.
Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.
Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.
Yu et al., Liposome-mediated in vivo ELA gene transfer suppressed dissemination of ovarian cancer cells that overexpress HER-2/neu. Oncogene. Oct. 5, 1995;11(7):1383-8.
Yu et al., Progress towards gene therapy for HIV infection. Gene Ther. Jan. 1994;1(1):13-26.
Yu et al., Small molecules enhance CRISPR genome editing in pluripotent stem cells. Cell Stem Cell. Feb. 5, 2015;16(2):142-7. doi: 10.1016/j.stem.2015.01.003.
Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.
Yuan et al., Laboratory-directed protein evolution. Microbiol Mol Biol Rev. 2005; 69(3):373-92. PMID: 16148303.
Yuan et al., Tetrameric structure of a serine integrase catalytic domain. Structure. Aug. 6, 2008;16(8):1275-86. doi: 10.1016/j.str.2008.04.018.
Yuen et al., Control of transcription factor activity and osteoblast differentiation in mammalian cells using an evolved small-molecule-dependent intein. J Am Chem Soc. Jul. 12, 2006;128(27):8939-46.
Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.
Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 18, 2014.
Zelphati et al., Intracellular delivery of proteins with a new lipid-mediated delivery system. J Biol Chem. Sep. 14, 2001;276(37):35103-10. Epub Jul. 10, 2001.
Zeng et al., Correction of the Marfan Syndrome Pathogenic FBN1 Mutation by Base Editing in Human Cells and Heterozygous Embryos. Mol Ther. Nov. 7, 2018;26(11):2631-2637. doi: 10.1016/j.ymthe.2018.08.007. Epub Aug. 14, 2018.
Zetsche et al., A split-Cas9 architecture for inducible genome editing and transcription modulation. Nat Biotechnol. Feb. 2015;33(2):139-42. doi: 10.1038/nbt.3149.

(56) References Cited

OTHER PUBLICATIONS

Zetsche et al., Cpf1 is a single RNA-guided endonuclease of a class 2 CRISPR-Cas system. Cell. Oct. 22, 2015;163(3):759-71 and Supplemental Info. doi: 10.1016/j.cell.2015.09.038. Epub Sep. 25, 2015.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.
Zhang et al., Π-Clamp-mediated cysteine conjugation. Nat Chem. Feb. 2016;8(2):120-8. doi: 10.1038/nchem.2413. Epub Dec. 21, 2015.
Zhang et al., A new strategy for the site-specific modification of proteins in vivo. Biochemistry. Jun. 10, 2003;42(22):6735-46.
Zhang et al., Circular intronic long noncoding RNAs. Mol Cell. Sep. 26, 2013;51(6):792-806. doi: 10.1016/j.molcel.2013.08.017. Epub Sep. 12, 2013.
Zhang et al., Comparison of non-canonical PAMs for CRISPR/Cas9-mediated DNA cleavage in human cells. Sci Rep. Jun. 2014;4:5405.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., Copy number variation in human health, disease, and evolution. Annu Rev Genomics Hum Genet. 2009;10:451-81. doi: 10.1146/annurev.genom.9.081307.164217.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zhang et al., Global analysis of small RNA and mRNA targets of Hfq. Mol Microbiol. Nov. 2003;50(4):1111-24. doi: 10.1046/j.1365-2958.2003.03734.x.
Zhang et al., Myoediting: Toward Prevention of Muscular Dystrophy by Therapeutic Genome Editing. Physiol Rev. Jul. 1, 2018;98(3):1205-1240. doi: 10.1152/physrev.00046.2017.
Zhang et al., Programmable base editing of zebrafish genome using a modified CRISPR-Cas9 system. Nat Commun. Jul. 25, 2017;8(1):118. doi: 10.1038/s41467-017-00175-6.
Zhang et al., Reversible RNA Modification N1-methyladenosine (m1A) in mRNA and tRNA. Genomics Proteomics Bioinformatics. Jun. 2018;16(3):155-161. doi: 10.1016/j.gpb.2018.03.003. Epub Jun. 14, 2018.
Zhang et al., Ribozymes and Riboswitches: Modulation of RNA Function by Small Molecules. Biochemistry. Nov. 2, 2010;49(43):9123-31. doi: 10.1021/bi1012645.
Zhang et al., Stabilized plasmid-lipid particles for regional gene therapy: formulation and transfection properties. Gene Ther. Aug. 1999;6(8):1438-47.
Zhao et al., An ultraprocessive, accurate reverse transcriptase encoded by a metazoan group II intron. RNA. Feb. 2018;24(2):183-195. doi: 10.1261/rna.063479.117. Epub Nov. 6, 2017.
Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.
Zhao et al., Post-transcriptional gene regulation by mRNA modifications. Nat Rev Mol Cell Biol. Jan. 2017;18(1):31-42. doi: 10.1038/nrm.2016.132. Epub Nov. 3, 2016.
Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.
Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
Zheng et al., Highly efficient base editing in bacteria using a Cas9-cytidine deaminase fusion. Commun Biol. Apr. 19, 2018;1:32. doi: 10.1038/s42003-018-0035-5.
Zheng et al., Structural basis for the complete resistance of the human prion protein mutant G127V to prion disease. Sci Rep. Sep. 4, 2018;8(1):13211. doi: 10.1038/s41598-018-31394-6.
Zhong et al., Rational Design of Aptazyme Riboswitches for Efficient Control of Gene Expression in Mammalian Cells. Elife. Nov. 2, 2016;5:e18858. doi: 10.7554/eLife.18858.
Zhou et al., Cas12a variants designed for lower genome-wide off-target effect through stringent PAM recognition. Mol Ther. Jan. 5, 2022;30(1):244-255. doi: 10.1016/j.ymthe.2021.10.010. Epub Oct. 20, 2021.
Zhou et al., Dynamic m(6)A mRNA methylation directs translational control of heat shock response. Nature. Oct. 22, 2015;526(7574):591-4. doi: 10.1038/nature15377. Epub Oct. 12, 2015.
Zhou et al., GISSD: Group I Intron Sequence and Structure Database. Nucleic Acids Res. Jan. 2008;36(Database issue):D31-7. doi: 10.1093/nar/gkm766. Epub Oct. 16, 2007.
Zhou et al., Off-target RNA mutation induced by DNA base editing and its elimination by mutagenesis. Nature. Jul. 2019;571(7764):275-278. doi: 10.1038/s41586-019-1314-0. Epub Jun. 10, 2019.
Zhou et al., Protective V127 prion variant prevents prion disease by interrupting the formation of dimer and fibril from molecular dynamics simulations. Sci Rep. Feb. 24, 2016;6:21804. doi: 10.1038/srep21804.
Zhou et al., Seamless Genetic Conversion of SMN2 to SMN1 via CRISPR/Cpf1 and Single-Stranded Oligodeoxynucleotides in Spinal Muscular Atrophy Patient-Specific Induced Pluripotent Stem Cells. Hum Gene Ther. Nov. 2018;29(11):1252-1263. doi: 10.1089/hum.2017.255. Epub May 9, 2018.
Zielenski, Genotype and phenotype in cystic fibrosis. Respiration. 2000;67(2):117-33. doi: 10.1159/000029497.
Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.
Zimmerly et al., Group II intron mobility occurs by target DNA-primed reverse transcription. Cell. Aug. 25, 1995;82(4):545-54. doi: 10.1016/0092-8674(95)90027-6.
Zimmermann et al., Molecular interactions and metal binding in the theophylline-binding core of an RNA aptamer. RNA. May 2000;6(5):659-67.
Zolotukhin et al., Production and purification of serotype 1, 2, and 5 recombinant adeno-associated viral vectors. Methods. Oct. 2002;28(2):158-67. doi: 10.1016/s1046-2023(02)00220-7.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zorko et al., Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.
Zuker et al., Optimal computer folding of large RNA sequences using thermodynamics and auxiliary information. Nucleic Acids Res. Jan. 10, 1981;9(1):133-48. doi: 10.1093/nar/9.1.133.
Zuo et al., Cytosine base editor generates substantial off-target single-nucleotide variants in mouse embryos. Science. Apr. 19, 2019;364(6437):289-292. doi: 10.1126/science.aav9973. Epub Feb. 28, 2019.
Zuris et al., Cationic lipid-mediated delivery of proteins enables efficient protein-based genome editing in vitro and in vivo. Nat Biotechnol. 2015;33:73-80.

SEQUENCE LISTING

```
<160> NUMBER OF SEQ ID NOS: 61

<210> SEQ ID NO 1
<211> LENGTH: 1285
<212> TYPE: PRT
<213> ORGANISM: Unknown
<220> FEATURE:
<223> OTHER INFORMATION: Herbinix Hemicellulosilytica

<400> SEQUENCE: 1

Met Lys Leu Thr Arg Arg Arg Ile Ser Gly Asn Ser Val Asp Gln Lys
1               5                   10                  15

Ile Thr Ala Ala Phe Tyr Arg Asp Met Ser Gln Gly Leu Leu Tyr Tyr
            20                  25                  30

Asp Ser Glu Asp Asn Asp Cys Thr Asp Lys Val Ile Glu Ser Met Asp
        35                  40                  45

Phe Glu Arg Ser Trp Arg Gly Arg Ile Leu Lys Asn Gly Glu Asp Asp
    50                  55                  60

Lys Asn Pro Phe Tyr Met Phe Val Lys Gly Leu Val Gly Ser Asn Asp
65                  70                  75                  80

Lys Ile Val Cys Glu Pro Ile Asp Val Asp Ser Asp Pro Asp Asn Leu
                85                  90                  95

Asp Ile Leu Ile Asn Lys Asn Leu Thr Gly Phe Gly Arg Asn Leu Lys
            100                 105                 110

Ala Pro Asp Ser Asn Asp Thr Leu Glu Asn Leu Ile Arg Lys Ile Gln
        115                 120                 125

Ala Gly Ile Pro Glu Glu Glu Val Leu Pro Glu Leu Lys Lys Ile Lys
    130                 135                 140

Glu Met Ile Gln Lys Asp Ile Val Asn Arg Lys Glu Gln Leu Leu Lys
145                 150                 155                 160

Ser Ile Lys Asn Asn Arg Ile Pro Phe Ser Leu Glu Gly Ser Lys Leu
                165                 170                 175
```

```
Val Pro Ser Thr Lys Lys Met Lys Trp Leu Phe Lys Leu Ile Asp Val
            180                 185                 190

Pro Asn Lys Thr Phe Asn Glu Lys Met Leu Glu Lys Tyr Trp Glu Ile
        195                 200                 205

Tyr Asp Tyr Asp Lys Leu Lys Ala Asn Ile Thr Asn Arg Leu Asp Lys
    210                 215                 220

Thr Asp Lys Lys Ala Arg Ser Ile Ser Arg Ala Val Ser Glu Glu Leu
225                 230                 235                 240

Arg Glu Tyr His Lys Asn Leu Arg Thr Asn Tyr Asn Arg Phe Val Ser
                245                 250                 255

Gly Asp Arg Pro Ala Ala Gly Leu Asp Asn Gly Gly Ser Ala Lys Tyr
            260                 265                 270

Asn Pro Asp Lys Glu Glu Phe Leu Leu Phe Leu Lys Glu Val Glu Gln
        275                 280                 285

Tyr Phe Lys Lys Tyr Phe Pro Val Lys Ser Lys His Ser Asn Lys Ser
    290                 295                 300

Lys Asp Lys Ser Leu Val Asp Lys Tyr Lys Asn Tyr Cys Ser Tyr Lys
305                 310                 315                 320

Val Val Lys Lys Glu Val Asn Arg Ser Ile Ile Asn Gln Leu Val Ala
                325                 330                 335

Gly Leu Ile Gln Gln Gly Lys Leu Leu Tyr Tyr Phe Tyr Tyr Asn Asp
            340                 345                 350

Thr Trp Gln Glu Asp Phe Leu Asn Ser Tyr Gly Leu Ser Tyr Ile Gln
        355                 360                 365

Val Glu Glu Ala Phe Lys Lys Ser Val Met Thr Ser Leu Ser Trp Gly
    370                 375                 380

Ile Asn Arg Leu Thr Ser Phe Phe Ile Asp Asp Ser Asn Thr Val Lys
385                 390                 395                 400

Phe Asp Asp Ile Thr Thr Lys Lys Ala Lys Glu Ala Ile Glu Ser Asn
                405                 410                 415

Tyr Phe Asn Lys Leu Arg Thr Cys Ser Arg Met Gln Asp His Phe Lys
            420                 425                 430

Glu Lys Leu Ala Phe Phe Tyr Pro Val Tyr Val Lys Asp Lys Lys Asp
        435                 440                 445

Arg Pro Asp Asp Asp Ile Glu Asn Leu Ile Val Leu Val Lys Asn Ala
    450                 455                 460

Ile Glu Ser Val Ser Tyr Leu Arg Asn Arg Thr Phe His Phe Lys Glu
465                 470                 475                 480

Ser Ser Leu Leu Glu Leu Leu Lys Glu Leu Asp Asp Lys Asn Ser Gly
                485                 490                 495

Gln Asn Lys Ile Asp Tyr Ser Val Ala Ala Glu Phe Ile Lys Arg Asp
            500                 505                 510

Ile Glu Asn Leu Tyr Asp Val Phe Arg Glu Gln Ile Arg Ser Leu Gly
        515                 520                 525

Ile Ala Glu Tyr Tyr Lys Ala Asp Met Ile Ser Asp Cys Phe Lys Thr
    530                 535                 540

Cys Gly Leu Glu Phe Ala Leu Tyr Ser Pro Lys Asn Ser Leu Met Pro
545                 550                 555                 560

Ala Phe Lys Asn Val Tyr Lys Arg Gly Ala Asn Leu Asn Lys Ala Tyr
                565                 570                 575

Ile Arg Asp Lys Gly Pro Lys Glu Thr Gly Asp Gln Gly Gln Asn Ser
            580                 585                 590
```

```
Tyr Lys Ala Leu Glu Glu Tyr Arg Glu Leu Thr Trp Tyr Ile Glu Val
        595                 600                 605

Lys Asn Asn Asp Gln Ser Tyr Asn Ala Tyr Lys Asn Leu Leu Gln Leu
    610                 615                 620

Ile Tyr Tyr His Ala Phe Leu Pro Glu Val Arg Glu Asn Glu Ala Leu
625                 630                 635                 640

Ile Thr Asp Phe Ile Asn Arg Thr Lys Glu Trp Asn Arg Lys Glu Thr
                645                 650                 655

Glu Glu Arg Leu Asn Thr Lys Asn Asn Lys Lys His Lys Asn Phe Asp
            660                 665                 670

Glu Asn Asp Asp Ile Thr Val Asn Thr Tyr Arg Tyr Glu Ser Ile Pro
        675                 680                 685

Asp Tyr Gln Gly Glu Ser Leu Asp Asp Tyr Leu Lys Val Leu Gln Arg
    690                 695                 700

Lys Gln Met Ala Arg Ala Lys Glu Val Asn Glu Lys Glu Glu Gly Asn
705                 710                 715                 720

Asn Asn Tyr Ile Gln Phe Ile Arg Asp Val Val Val Trp Ala Phe Gly
                725                 730                 735

Ala Tyr Leu Glu Asn Lys Leu Lys Asn Tyr Lys Asn Glu Leu Gln Pro
            740                 745                 750

Pro Leu Ser Lys Glu Asn Ile Gly Leu Asn Asp Thr Leu Lys Glu Leu
        755                 760                 765

Phe Pro Glu Glu Lys Val Lys Ser Pro Phe Asn Ile Lys Cys Arg Phe
    770                 775                 780

Ser Ile Ser Thr Phe Ile Asp Asn Lys Gly Lys Ser Thr Asp Asn Thr
785                 790                 795                 800

Ser Ala Glu Ala Val Lys Thr Asp Gly Lys Glu Asp Glu Lys Asp Lys
                805                 810                 815

Lys Asn Ile Lys Arg Lys Asp Leu Leu Cys Phe Tyr Leu Phe Leu Arg
            820                 825                 830

Leu Leu Asp Glu Asn Glu Ile Cys Lys Leu Gln His Gln Phe Ile Lys
        835                 840                 845

Tyr Arg Cys Ser Leu Lys Glu Arg Arg Phe Pro Gly Asn Arg Thr Lys
    850                 855                 860

Leu Glu Lys Glu Thr Glu Leu Leu Ala Glu Leu Glu Glu Leu Met Glu
865                 870                 875                 880

Leu Val Arg Phe Thr Met Pro Ser Ile Pro Glu Ile Ser Ala Lys Ala
                885                 890                 895

Glu Ser Gly Tyr Asp Thr Met Ile Lys Lys Tyr Phe Lys Asp Phe Ile
            900                 905                 910

Glu Lys Lys Val Phe Lys Asn Pro Lys Thr Ser Asn Leu Tyr Tyr His
        915                 920                 925

Ser Asp Ser Lys Thr Pro Val Thr Arg Lys Tyr Met Ala Leu Leu Met
    930                 935                 940

Arg Ser Ala Pro Leu His Leu Tyr Lys Asp Ile Phe Lys Gly Tyr Tyr
945                 950                 955                 960

Leu Ile Thr Lys Lys Glu Cys Leu Glu Tyr Ile Lys Leu Ser Asn Ile
                965                 970                 975

Ile Lys Asp Tyr Gln Asn Ser Leu Asn Glu Leu His Glu Gln Leu Glu
            980                 985                 990

Arg Ile Lys Leu Lys Ser Glu Lys  Gln Asn Gly Lys Asp  Ser Leu Tyr
        995                 1000                 1005

Leu Asp  Lys Lys Asp Phe Tyr  Lys Val Lys Glu Tyr  Val Glu Asn
```

```
    1010                1015                1020

Leu Glu  Gln Val Ala Arg Tyr  Lys His Leu Gln His  Lys Ile Asn
    1025                1030                1035

Phe Glu  Ser Leu Tyr Arg Ile  Phe Arg Ile His Val  Asp Ile Ala
    1040                1045                1050

Ala Arg  Met Val Gly Tyr Thr  Gln Asp Trp Glu Arg  Asp Met His
    1055                1060                1065

Phe Leu  Phe Lys Ala Leu Val  Tyr Asn Gly Val Leu  Glu Glu Arg
    1070                1075                1080

Arg Phe  Glu Ala Ile Phe Asn  Asn Asn Asp Asp Asn  Asn Asp Gly
    1085                1090                1095

Arg Ile  Val Lys Lys Ile Gln  Asn Asn Leu Asn Asn  Lys Asn Arg
    1100                1105                1110

Glu Leu  Val Ser Met Leu Cys  Trp Asn Lys Lys Leu  Asn Lys Asn
    1115                1120                1125

Glu Phe  Gly Ala Ile Ile Trp  Lys Arg Asn Pro Ile  Ala His Leu
    1130                1135                1140

Asn His  Phe Thr Gln Thr Glu  Gln Asn Ser Lys Ser  Ser Leu Glu
    1145                1150                1155

Ser Leu  Ile Asn Ser Leu Arg  Ile Leu Leu Ala Tyr  Asp Arg Lys
    1160                1165                1170

Arg Gln  Asn Ala Val Thr Lys  Thr Ile Asn Asp Leu  Leu Leu Asn
    1175                1180                1185

Asp Tyr  His Ile Arg Ile Lys  Trp Glu Gly Arg Val  Asp Glu Gly
    1190                1195                1200

Gln Ile  Tyr Phe Asn Ile Lys  Glu Lys Glu Asp Ile  Glu Asn Glu
    1205                1210                1215

Pro Ile  Ile His Leu Lys His  Leu His Lys Lys Asp  Cys Tyr Ile
    1220                1225                1230

Tyr Lys  Asn Ser Tyr Met Phe  Asp Lys Gln Lys Glu  Trp Ile Cys
    1235                1240                1245

Asn Gly  Ile Lys Glu Glu Val  Tyr Asp Lys Ser Ile  Leu Lys Cys
    1250                1255                1260

Ile Gly  Asn Leu Phe Lys Phe  Asp Tyr Glu Asp Lys  Asn Lys Ser
    1265                1270                1275

Ser Ala  Asn Pro Lys His Thr
    1280                1285


<210> SEQ ID NO 2
<211> LENGTH: 1214
<212> TYPE: PRT
<213> ORGANISM: Unknown
<220> FEATURE:
<223> OTHER INFORMATION: Trichoderma Atroviride Mycovirus

<400> SEQUENCE: 2

Met His Thr Asp Asp Lys Ser Cys Ala Thr Arg Leu Leu Ser Leu Leu
1               5                   10                  15

Gly Val Arg Ser Val Pro Arg Glu Arg Phe Ala Asp Val Asp Lys Val
            20                  25                  30

Gly Val Trp Thr Val Leu Asn Gln Arg Leu Ile Leu Leu Ser Trp His
        35                  40                  45

Val Gly Met Val Ile Asp Ser Thr Phe Glu His Val Asn Ser Asp Gly
    50                  55                  60

His Pro Ser Lys Cys Leu Glu Ile Met Ile Gln Arg Ser Arg Glu Phe
```

```
65                  70                  75                  80

Ala Tyr Ser Ala Glu Arg Ser Gly Leu Cys Gly Tyr Tyr Ile His Ile
                85                  90                  95

Phe Asn Phe Arg Asp His Val Ser Phe Ala Ile Lys Thr Ala His Leu
            100                 105                 110

Lys Lys Tyr Thr Gln Thr Leu Leu Ala Cys Asp Thr Thr Thr Pro Ile
        115                 120                 125

His Glu Thr Val Glu Ala Phe Ser Pro Pro Thr Gly Arg Ala Gly Gly
    130                 135                 140

Lys Val Phe Val Thr Pro Arg Leu Leu Lys Ser Ile Gly Asn Pro Thr
145                 150                 155                 160

Ile Leu Gln Cys Ala Leu Ala Thr Lys Leu Lys Glu Asn Leu His Arg
                165                 170                 175

Leu Asp Trp Glu Gln Ile Met Val Thr Gly Met Ile Leu Leu Gln Tyr
            180                 185                 190

Leu Asn Val Gly Ala Gly Asp Val Leu Trp Tyr Leu Ile Thr Tyr Glu
        195                 200                 205

Lys Leu Trp Asp Ser Lys Phe Leu Asp Ala Val Lys Ile Leu Lys Asp
    210                 215                 220

Ala His Val Glu Thr Arg Ile Lys His Lys Leu Pro Asn Val Ser Ile
225                 230                 235                 240

His Tyr Ala Arg Ser Thr Phe Ala Arg Pro Trp Ala Arg Ser Leu Tyr
                245                 250                 255

Gly Leu Asp Thr Leu Pro Gly Arg Ser Glu Lys Phe Asn Met Asn Phe
            260                 265                 270

Gln Ser Glu Gln Leu Met Arg Met Ile Asp Thr Ser Lys Arg Ala Trp
        275                 280                 285

Pro Ala Ile Val Glu Asp Lys Tyr Gly Asn Asn Tyr Ile Lys Phe Phe
    290                 295                 300

Pro Asp Lys Tyr Thr Glu Gln Val Lys Gln Ile Ala Arg Lys Thr Ala
305                 310                 315                 320

Glu Asp Leu Ile Gln Ser Gln Thr Asn Leu Glu Thr Phe Thr Glu Phe
                325                 330                 335

Phe Ser Asn Arg Met Phe Trp Gly Ala Ser Gly Gly Ala Pro Gly Ala
            340                 345                 350

Ser Val His Trp Asp Asp Thr Lys Glu Lys Leu Arg Val Asn Lys Arg
        355                 360                 365

Gly Ala Leu Leu Ser Leu Lys Glu Gln Lys Ala Arg Asn Ile Leu Glu
    370                 375                 380

Tyr Met Arg Ser His Pro Asp Pro Lys Pro Ile Gln Trp Ser Val Lys
385                 390                 395                 400

Ala Val Lys Tyr Glu Ser Gly Lys Leu Arg Ser Ile Leu Asn Thr Val
                405                 410                 415

Leu Glu Asn Tyr Val Ile Gln Gly Tyr Ile Phe Asn Ala Val Asp Thr
            420                 425                 430

Asn Ser Arg Arg Asp Ser Trp Tyr Ala Asn Thr His Asp Asn Pro Ser
        435                 440                 445

Arg Ile Ala Asn Ala Met Arg Arg Ile Leu Asp Leu Lys Gln Arg Pro
    450                 455                 460

Gly Leu Met Trp Asp Tyr Ala Asp Phe Asn Leu Asn His Thr Phe Phe
465                 470                 475                 480

Leu Met Ser Gln Glu Tyr Leu Ala Arg Val Glu Val Leu Leu Glu Arg
                485                 490                 495
```

```
Cys Asp Ser His Leu Pro Met Asp Val Gln Asn Thr Ile Arg Ala Asp
            500                 505                 510

Met Arg Ala Ala Thr Ala Tyr Ala Ile Leu Ala Arg Tyr Asn Thr Tyr
        515                 520                 525

Leu His Asp Pro Glu Thr Met Ile Thr Thr Gln Ala Val Arg Ser Leu
    530                 535                 540

Gln Ser Gly Glu Arg Gly Thr Ser Ser Ile Asn Ser Asp Ser Asn Glu
545                 550                 555                 560

Thr Asp Thr Thr Ile Val Arg Arg Val Cys Lys Glu Met Leu Gly Ile
                565                 570                 575

Asp Pro Ile Val Pro Val Thr Asp His Ala Gly Asp Asp Ala Phe Glu
            580                 585                 590

Asn Val Ile Ser Met Thr Tyr Ala Pro Leu Val Cys Ser Val Tyr Asn
        595                 600                 605

Leu Thr Gly Ala Ala Gly Gln Ala Tyr Lys Ile Ala Val Ser Tyr Ala
    610                 615                 620

Thr Phe Asn Gly Ala Ser Gly Glu Phe Leu Arg Leu Ser Tyr Asp Ala
625                 630                 635                 640

Ala Ser Asn His Ile Ala Gly Tyr Pro Ile Arg Gly Met Met Gly Phe
                645                 650                 655

Ile His Gly Glu Phe Phe Ala Glu Ala Leu Pro Gln Pro Phe Asp Arg
            660                 665                 670

Leu Ala Ser Phe Leu Asn Gln Arg Asn Lys Leu Gln Arg Arg Gly Trp
        675                 680                 685

Val Ala Pro Asp Ser Leu Phe Asn Ala Val Cys Arg Tyr Asn Thr Arg
    690                 695                 700

Leu Thr Tyr Thr Leu Ser Asp Gly Thr Lys Arg His Phe Tyr Pro Asp
705                 710                 715                 720

Ile Glu Thr Val Leu Thr Pro Ala Ala Phe Gly Gly Val Gly Val Asp
                725                 730                 735

Thr Val Asp Ser Gln Leu Leu Ser Gln Leu Ser Asp Lys Gln Ile Val
            740                 745                 750

Thr Pro Leu His Ala Asn Cys Pro Tyr Asp Ala Ile Val Ile Pro Ser
        755                 760                 765

Gly Glu Gly Lys Thr Thr Leu Ala Arg Lys Tyr Pro Asp Ile Phe Val
    770                 775                 780

Asp His Asp Ser Leu Val Ser Ser Ile Asn Leu Ile Ala Leu Arg Ser
785                 790                 795                 800

Arg Ala Val Ser Ser Gly Asn Trp Glu Pro Leu Asn Ala Tyr Leu Arg
                805                 810                 815

Gly Glu Gly Glu Arg Tyr Met Ser Val Asn Arg Gly Lys Ile Leu Leu
            820                 825                 830

Thr Trp Ser Pro Ser Thr Ala Pro Ser Arg Ser Arg Ile Cys Ala Leu
        835                 840                 845

Leu Leu Gln Gln Pro Val Gly Leu Arg Ala Asn Ile Ala Asn Arg Ser
    850                 855                 860

Ser Ile Met Asn Asp Met Asn Lys Lys Tyr Val His Met Phe Lys Asn
865                 870                 875                 880

Tyr Ser Glu Arg Asp Ala Tyr Leu Met Ser Ile Thr Ala Gly Leu Thr
                885                 890                 895

Gly Leu Thr Tyr Lys Val Tyr Gln Arg Thr Gly Asp Ala Ile Pro Lys
            900                 905                 910
```

```
Phe Asn Trp Pro Arg Val Asp Ser Lys Asp Leu Leu His Arg Ser Lys
        915                 920                 925

Thr Val Ile Lys Asp His Ala Thr Leu His Arg His Asn Leu Pro Met
    930                 935                 940

Asp Val Ser Ile Thr Asp Ala Ile Ala Gln Ser Ala Leu Ser Gly Ala
945                 950                 955                 960

Trp Pro Lys Asp Ala Leu Tyr Lys Ser Ile Ala Glu His Ala Arg Gln
                965                 970                 975

Leu Ala Glu Trp Ala Arg Lys Ser Ser Phe Glu Tyr Lys Ile Ile Ala
            980                 985                 990

Pro Leu Lys Leu Cys Ser Asp Thr  Glu Phe Val Ala Glu  Ala Val Ser
        995                 1000                 1005

Thr Ser  Met Tyr Val Leu Gly  Leu Ser Gly Ser Leu  Asn His Ser
    1010                 1015                 1020

Asn Ala  Gly Gly Gly Leu Thr  Phe Val Leu Asn Asp  Leu Leu Arg
    1025                 1030                 1035

Pro Ala  Thr Lys Arg Leu Lys  His His Tyr Asn Tyr  Ile Pro Thr
    1040                 1045                 1050

Leu Thr  Arg Leu Cys Gly Cys  Ser Val Asn Ala Ser  Thr Gln Tyr
    1055                 1060                 1065

Leu Ile  Lys Cys Ser Asn Gly  Asp Asn Leu Leu Glu  Lys Ile Leu
    1070                 1075                 1080

Ser Leu  Met Ala Ser Glu Arg  Ser Phe Ser His Ser  Lys Gln Arg
    1085                 1090                 1095

Ala Thr  Lys Gln Phe Asp Glu  Val Ile Glu Phe Ile  Asp Arg Leu
    1100                 1105                 1110

Gly Leu  Leu Lys Gln Glu Pro  Leu Leu Ala Phe Gly  Lys Val Val
    1115                 1120                 1125

Ser Pro  Ser Leu Ala Glu Ala  Trp Phe Thr Gly Gly  Leu Gln Leu
    1130                 1135                 1140

Leu Pro  Pro Ala Ile Cys His  Gln Ser Ala Asp Leu  Ser Thr Phe
    1145                 1150                 1155

Val Arg  Asp Ile Thr Leu Asn  Val Ile Glu Thr His  Phe Leu Ala
    1160                 1165                 1170

Arg Leu  Asn Arg Thr Asn Asp  Leu Gln Gln Ile Val  Val Thr Val
    1175                 1180                 1185

His His  Tyr Glu Arg Met Ala  Gln Tyr Ala Ile Asn  Lys Val Leu
    1190                 1195                 1200

Asn Gly  Leu Ile Pro Gly Ile  Ile Met Gln Asp
    1205                 1210
```

```
<210> SEQ ID NO 3
<211> LENGTH: 1302
<212> TYPE: PRT
<213> ORGANISM: Unknown
<220> FEATURE:
<223> OTHER INFORMATION: Bluetongue Virus

<400> SEQUENCE: 3

Met Val Ala Ile Thr Val Gln Gly Ala Gln Leu Ile Lys Arg Val Val
1               5                   10                  15

Glu Arg Phe Tyr Pro Gly Ile Ala Phe Asn Ile Asn Glu Gly Ala Cys
            20                  25                  30

Tyr Ile Tyr Lys Phe Ser Asp His Ile Arg Arg Ile Arg Met Lys His
        35                  40                  45
```

```
Gly Thr Lys Tyr Arg Arg Gln Ala Glu Glu Ile Ile Arg Asn Ile Gly
    50                  55                  60

Leu Arg Lys Glu Arg Leu Tyr Gly Ile Pro Val Leu Asp Glu Val Glu
65                  70                  75                  80

Trp Lys Cys Val Phe Asp Gly Gln Thr Phe Gln Ser Tyr Ala Phe Glu
                85                  90                  95

Val Tyr Val Asn Ser Ile Leu Pro Trp Ser Glu Leu Asp Pro Glu Glu
            100                 105                 110

Glu Phe Leu Arg Asn Tyr Arg Val Ser Arg Glu Met Thr Glu Val Glu
        115                 120                 125

Lys Phe Ile Glu Phe Arg Ala Lys Asn Glu Met Gln Ile Tyr Gly Asp
    130                 135                 140

Ile Pro Ile Lys Val Trp Cys Cys Phe Ile Asn Glu Leu Ser Val Glu
145                 150                 155                 160

Leu Lys His Ile Pro Leu Gly Met Gln Val Met Ala Asp Phe Val Asn
                165                 170                 175

Arg Phe Asp Ser Pro Phe His Gln Gly Asn Arg Asp Leu Ser Asn Leu
            180                 185                 190

Glu Asp Phe Gln Val Ala Tyr Thr Thr Pro Leu Leu Phe Glu Met Cys
        195                 200                 205

Cys Met Glu Ser Ile Leu Glu Phe Asn Ile Lys Met Arg Met Arg Glu
    210                 215                 220

Glu Asp Ile Ser Ala Leu Glu Phe Gly Asp Met Lys Val Asp Pro Val
225                 230                 235                 240

Gly Leu Leu Arg Glu Phe Phe Ile Leu Cys Leu Pro His Pro Lys Lys
                245                 250                 255

Ile Asn Asn Val Leu Arg Ala Pro Tyr Ser Trp Phe Val Lys Met Trp
            260                 265                 270

Gly Val Gly Ala Asp Pro Ile Val Val Leu Gln Ser Thr Ala Gly Asp
        275                 280                 285

Asp Arg Asn Ser Lys Asp Val Phe Tyr Asp Lys Phe Arg Thr Glu Pro
    290                 295                 300

Asn Arg Tyr Lys Ala Leu Phe Arg Ser Ser Phe Tyr Asn Glu Ser Arg
305                 310                 315                 320

Arg Met Asn Glu Glu Lys Ile Leu Glu Ala Val Lys Tyr Ser Gln Lys
                325                 330                 335

Leu Gly Ser His Asp Arg Arg Leu Pro Leu Phe Glu Lys Met Leu Lys
            340                 345                 350

Thr Val Tyr Thr Thr Pro Phe Tyr Pro His Lys Ser Ser Asn Met Ile
        355                 360                 365

Leu Ala Ser Phe Leu Leu Ser Ile Gln Thr Ile Thr Gly Tyr Gly Arg
    370                 375                 380

Ala Trp Val Lys Asn Val Ser Thr Glu Phe Asp Lys Gln Leu Lys Pro
385                 390                 395                 400

Asn Pro Ser Asn Leu Val Gln Asp Val Ser Asp Leu Thr Arg Glu Phe
                405                 410                 415

Phe Lys Gln Ala Tyr Val Glu Ala Lys Glu Arg Arg Glu Glu Ile Val
            420                 425                 430

Lys Pro Glu Asp Leu Tyr Thr Ser Met Leu Arg Leu Ala Arg Asn Thr
        435                 440                 445

Ser Ser Gly Phe Ser Thr Glu Ile Tyr Val Lys Lys Arg Phe Gly Pro
    450                 455                 460

Arg Val Lys Asp Lys Asp Leu Ile Lys Ile Asn Ser Arg Ile Lys Ala
```

```
465                 470                 475                 480

Leu Val Ile Phe Thr Lys Gly His Thr Val Phe Thr Asp Glu Glu Leu
                485                 490                 495

His Lys Lys Tyr Asn Ser Val Glu Leu Tyr Gln Thr Lys Gly Ser Arg
            500                 505                 510

Asp Val Pro Ile Lys Ala Thr Arg Thr Ile Tyr Ser Ile Asn Leu Ser
        515                 520                 525

Val Leu Val Pro Gln Leu Ile Val Thr Leu Pro Leu Asn Glu Tyr Phe
    530                 535                 540

Ser Arg Val Gly Gly Ile Thr Ser Pro Asp Tyr Lys Lys Ile Gly Gly
545                 550                 555                 560

Lys Val Ile Val Gly Asp Leu Glu Ala Thr Gly Ser Arg Val Met Asp
                565                 570                 575

Ala Ala Asp Cys Phe Arg Asn Ser Ala Asp Arg Asp Ile Phe Thr Ile
            580                 585                 590

Ala Ile Asp Tyr Ser Glu Tyr Asp Thr His Leu Thr Arg His Asn Phe
        595                 600                 605

Arg Thr Gly Met Leu Gln Gly Ile Arg Glu Ala Met Ala Pro Tyr Arg
    610                 615                 620

Asp Leu Arg Tyr Glu Gly Tyr Thr Leu Glu Gln Ile Ile Asp Phe Gly
625                 630                 635                 640

Tyr Gly Glu Gly Arg Val Ala Asn Thr Leu Trp Asn Gly Lys Arg Arg
                645                 650                 655

Leu Phe Lys Thr Thr Phe Asp Ala Tyr Ile Arg Leu Asp Glu Ser Glu
            660                 665                 670

Arg Asp Lys Gly Ser Phe Lys Val Pro Lys Gly Val Leu Pro Val Ser
        675                 680                 685

Ser Val Asp Val Ala Asn Arg Ile Ala Val Asp Lys Gly Phe Asp Thr
    690                 695                 700

Leu Val Ala Ala Thr Asp Gly Ser Asp Leu Ala Leu Ile Asp Thr His
705                 710                 715                 720

Leu Ser Gly Glu Asn Ser Thr Leu Ile Ala Asn Ser Met His Asn Met
                725                 730                 735

Ala Ile Gly Thr Leu Ile Gln Arg Glu Val Gly Arg Glu Gln Pro Gly
            740                 745                 750

Ile Leu Thr Phe Leu Ser Glu Gln Tyr Val Gly Asp Asp Thr Leu Phe
        755                 760                 765

Tyr Thr Lys Leu His Thr Thr Asp Thr Lys Val Phe Asp Lys Val Ala
    770                 775                 780

Ala Ser Ile Phe Asp Thr Val Ala Lys Cys Gly His Glu Ala Ser Pro
785                 790                 795                 800

Ser Lys Thr Met Met Thr Pro Tyr Ser Val Glu Lys Thr Gln Thr His
                805                 810                 815

Ala Lys Gln Gly Cys Tyr Val Pro Gln Asp Arg Met Met Ile Ile Ser
            820                 825                 830

Ser Glu Arg Arg Lys Asp Ile Glu Asp Val Gln Gly Tyr Val Arg Ser
        835                 840                 845

Gln Val Gln Thr Met Ile Thr Lys Val Ser Arg Gly Phe Cys His Asp
    850                 855                 860

Leu Ala Gln Leu Ile Leu Met Leu Lys Thr Thr Phe Ile Gly Ala Trp
865                 870                 875                 880

Lys Met Lys Arg Thr Ile Lys Glu Asp Ala Met Tyr Arg Asp Arg Lys
                885                 890                 895
```

```
Phe Asp Ser Asn Asp Glu Asp Gly Phe Thr Leu Ile Gln Ile Arg Asn
            900                 905                 910

Pro Leu Ala Leu Tyr Val Pro Ile Gly Trp Asn Gly Tyr Gly Ala His
        915                 920                 925

Pro Ala Ala Leu Asn Ile Val Met Thr Glu Glu Met Tyr Val Asp Ser
    930                 935                 940

Ile Met Ile Ser Lys Leu Asp Glu Ile Met Ala Pro Ile Arg Arg Ile
945                 950                 955                 960

Val His Asp Ile Pro Pro Cys Trp Asn Glu Thr Gln Gly Asp Lys Arg
                965                 970                 975

Gly Leu Ile Ser Ala Thr Lys Met Ser Phe Phe Ser Lys Met Ala Arg
            980                 985                 990

Pro Ala Val Gln Ala Ala Leu Ser  Asp Pro Gln Ile Met  Asn Leu Val
        995                 1000                 1005

Glu Glu  Leu Pro Leu Gly Glu  Phe Ser Pro Gly Arg  Ile Ser Arg
    1010                 1015                 1020

Thr Met  Met His Ser Ala Leu  Leu Lys Glu Ser Ser  Ala Arg Thr
    1025                 1030                 1035

Leu Leu  Ser Ser Gly Tyr Glu  Leu Glu Tyr Gln Lys  Ala Leu Asn
    1040                 1045                 1050

Ser Trp  Ile Ala Gln Val Ser  Met Arg Leu Gly Glu  Glu Ser Gly
    1055                 1060                 1065

Val Ile  Ser Thr Ser Tyr Ala  Lys Leu Phe Asp Val  Tyr Phe Glu
    1070                 1075                 1080

Gly Glu  Leu Asp Gly Ala Pro  Tyr Met Phe Pro Asp  Gln Asn Leu
    1085                 1090                 1095

Ser Pro  Gln Phe Tyr Ile Gln  Lys Met Met Ile Gly  Pro Arg Val
    1100                 1105                 1110

Ser Ser  Arg Val Arg Asn Ser  Tyr Val Asp Arg Ile  Asp Val Ile
    1115                 1120                 1125

Leu Arg  Lys Asp Val Val Met  Arg Gly Phe Ile Thr  Ala Asn Thr
    1130                 1135                 1140

Ile Leu  Asn Val Ile Glu Lys  Leu Gly Thr Asn His  Ser Val Gly
    1145                 1150                 1155

Asp Leu  Val Thr Val Phe Thr  Leu Met Asn Ile Glu  Thr Arg Val
    1160                 1165                 1170

Ala Glu  Glu Leu Ala Glu Tyr  Met Thr Ser Glu Lys  Ile Arg Phe
    1175                 1180                 1185

Asp Ala  Leu Lys Leu Leu Lys  Lys Gly Ile Ala Gly  Asp Glu Phe
    1190                 1195                 1200

Thr Met  Ser Leu Asn Val Ala  Thr Gln Asp Phe Ile  Asp Thr Tyr
    1205                 1210                 1215

Leu Ala  Tyr Pro Tyr Gln Leu  Thr Lys Thr Glu Val  Asp Ala Ile
    1220                 1225                 1230

Ser Leu  Tyr Cys Thr Gln Met  Val Met Leu Arg Ala  Ala Leu Gly
    1235                 1240                 1245

Leu Pro  Lys Lys Lys Met Lys  Ile Val Val Thr Asp  Asp Ala Lys
    1250                 1255                 1260

Lys Arg  Tyr Lys Ile Arg Leu  Gln Arg Phe Arg Thr  His Val Pro
    1265                 1270                 1275

Lys Ile  Lys Val Leu Lys Lys  Leu Ile Asp Pro Asn  Arg Met Thr
    1280                 1285                 1290
```

```
Val Arg  Asn Leu Glu Asn Gln  Phe Val
    1295                1300


<210> SEQ ID NO 4
<211> LENGTH: 477
<212> TYPE: PRT
<213> ORGANISM: Unknown
<220> FEATURE:
<223> OTHER INFORMATION: Pyrus Pyrifolia

<400> SEQUENCE: 4

Met Glu Gln Asn Ala Phe Asn Gly Phe Glu Phe Val Asp Tyr Ser Glu
1               5                   10                  15

Glu Leu Glu Asn Leu Asn Gln Asn His Ile His Lys Val Arg Arg Glu
            20                  25                  30

Ser Asn Thr Thr Tyr Val Asp Lys Phe Ala Glu Arg Glu Leu Ile Asp
        35                  40                  45

Leu His Pro Glu Tyr His Arg Gln Phe Ile Gln Gly Trp Ser Arg Ser
    50                  55                  60

Tyr Tyr Asn Thr Glu Arg His Met Glu Ala Leu Leu Asn Tyr Gly Thr
65                  70                  75                  80

Arg Asn Ile Pro Val Asp Asn Val Asp Tyr Asn Leu Tyr Gln Gly Cys
                85                  90                  95

Ile Asp Thr Val Lys Asn Gly Leu Arg Ser Leu Pro Arg Val Lys Ala
            100                 105                 110

Phe Asp Val Leu Thr Glu Leu Asn Leu Val Ser Tyr Lys Ser Ser Thr
        115                 120                 125

Ala Ala Gly Tyr Asn Tyr Met Gly Ala Lys Gly Pro Phe Asp Gly Tyr
    130                 135                 140

Asn His Lys Gln Ala Ile Arg Arg Ala Arg Ala Thr Val Gly Asp Val
145                 150                 155                 160

Ser Asp Asn Gly Ile Glu Gly Leu Arg Arg Ala Ile Thr Thr Ala Val
                165                 170                 175

Pro Asp Val Gly Tyr Thr Arg Thr Gln Leu Thr Asp Leu Thr Glu Lys
            180                 185                 190

Thr Lys Ile Arg Asn Val Trp Gly Arg Ala Phe His Tyr Ile Leu Ile
        195                 200                 205

Glu Gly Thr Ser Ala Asp Pro Leu Ile Arg Met Phe Ser Lys Thr Lys
    210                 215                 220

Ser Phe Tyr His Ile Gly Arg Asp Pro Leu Asp Ser Val Pro Asp Val
225                 230                 235                 240

Leu Ser Glu Thr Ala Gly Lys Ala Arg Trp Leu Tyr Ala Ile Asp Trp
                245                 250                 255

Lys Gln Phe Asp Ala Thr Val Ser Arg Phe Glu Ile Asn Ala Ala Phe
            260                 265                 270

Asp Ile Ile Met Asp Leu Ile Glu Phe Pro Asn Tyr Pro Thr Tyr Val
        275                 280                 285

Ala Phe Glu Leu Ser Arg Gln Leu Phe Ile His Lys Lys Ile Ala Ala
    290                 295                 300

Pro Asp Gly Tyr Ile Tyr Trp Ser His Lys Gly Ile Pro Ser Gly Ser
305                 310                 315                 320

Tyr Phe Thr Ser Ile Ile Gly Ser Ile Ile Asn Arg Leu Arg Ile Glu
                325                 330                 335

Tyr Leu Trp Arg Lys Ile Thr Gly His Gly Pro Leu Ala Cys Tyr Thr
            340                 345                 350
```

Gln Gly Asp Asp Ser Leu Ser Cys Asp Asp Glu Phe Thr Pro Pro Glu
355 360 365

Lys Phe Ala Glu Ile Ala Asn Gln Ile Gly Trp Val Leu Asn Pro Glu
370 375 380

Lys Thr Glu Tyr Ser Thr Ile Pro Ser Glu Val His Phe Leu Gly Arg
385 390 395 400

Thr Met Leu Gly Gly Leu Asn Thr Arg Glu Ile Lys Arg Cys Leu Arg
405 410 415

Leu Leu Ile Tyr Pro Glu Tyr Pro Val Asp Ser Gly Arg Ile Ser Ala
420 425 430

Tyr Arg Ala Lys Ser Ile Ser Glu Asp Val Gly Arg Leu Ser Glu Leu
435 440 445

Leu Asn Lys Ile Glu Arg Arg Leu Gln Gly Gln Tyr Gly Ile Ala Ser
450 455 460

Asp Glu Glu Val Pro Asp Tyr Phe Lys Arg Tyr Val Leu
465 470 475

<210> SEQ ID NO 5
<211> LENGTH: 879
<212> TYPE: PRT
<213> ORGANISM: Unknown
<220> FEATURE:
<223> OTHER INFORMATION: Infectious Bursal Disease Virus

<400> SEQUENCE: 5

Met Ser Asp Val Phe Asn Ser Pro Gln Ala Arg Ser Thr Ile Ser Ala
1 5 10 15

Ala Phe Gly Ile Lys Pro Thr Ala Gly Gln Asp Val Glu Glu Leu Leu
20 25 30

Ile Pro Lys Val Trp Val Pro Pro Glu Asp Pro Leu Ala Ser Pro Ser
35 40 45

Arg Leu Ala Lys Phe Leu Arg Glu Asn Gly Tyr Lys Val Leu Gln Pro
50 55 60

Arg Ser Leu Pro Glu Asn Glu Glu Tyr Glu Thr Asp Gln Ile Leu Pro
65 70 75 80

Asp Leu Ala Trp Met Arg Gln Ile Glu Gly Ala Val Leu Lys Pro Thr
85 90 95

Leu Ser Leu Pro Ile Gly Asp Gln Glu Tyr Phe Pro Lys Tyr Tyr Pro
100 105 110

Thr His Arg Pro Ser Lys Glu Lys Pro Asn Ala Tyr Pro Pro Asp Ile
115 120 125

Ala Leu Leu Lys Gln Met Ile Tyr Leu Phe Leu Gln Val Pro Glu Ala
130 135 140

Asn Glu Gly Leu Lys Asp Glu Val Thr Leu Leu Thr Gln Asn Ile Arg
145 150 155 160

Asp Lys Ala Tyr Gly Ser Gly Thr Tyr Met Gly Gln Ala Asn Arg Leu
165 170 175

Val Ala Met Lys Glu Val Ala Thr Gly Arg Asn Pro Asn Lys Asp Pro
180 185 190

Leu Lys Leu Gly Tyr Thr Phe Glu Ser Ile Ala Gln Leu Leu Asp Ile
195 200 205

Thr Leu Pro Val Gly Pro Pro Gly Glu Asp Asp Lys Pro Trp Val Pro
210 215 220

Leu Thr Arg Val Pro Ser Arg Met Leu Val Leu Thr Gly Asp Val Asp
225 230 235 240

```
Gly Asp Phe Glu Val Glu Asp Tyr Leu Pro Lys Ile Asn Leu Lys Ser
                245                 250                 255

Ser Ser Gly Leu Pro Tyr Val Gly Arg Thr Lys Gly Glu Thr Ile Gly
            260                 265                 270

Glu Met Ile Ala Ile Ser Asn Gln Phe Leu Arg Glu Leu Ser Thr Leu
        275                 280                 285

Leu Lys Gln Gly Ala Gly Thr Lys Gly Ser Asn Lys Lys Lys Leu Leu
    290                 295                 300

Ser Met Leu Ser Asp Tyr Trp Tyr Leu Ser Cys Gly Leu Leu Phe Pro
305                 310                 315                 320

Lys Ala Glu Arg Tyr Asp Lys Ser Thr Trp Leu Thr Lys Thr Arg Asn
                325                 330                 335

Ile Trp Ser Ala Pro Ser Pro Thr His Leu Met Ile Ser Met Ile Thr
            340                 345                 350

Trp Pro Val Met Ser Asn Ser Pro Asn Asn Val Leu Asn Ile Glu Gly
        355                 360                 365

Cys Pro Ser Leu Tyr Lys Phe Asn Pro Phe Arg Gly Gly Leu Asn Arg
    370                 375                 380

Ile Val Glu Trp Ile Leu Ala Pro Glu Glu Pro Lys Ala Leu Val Tyr
385                 390                 395                 400

Ala Asp Asn Ile Tyr Ile Val His Ser Asn Thr Trp Tyr Ser Ile Asp
                405                 410                 415

Leu Glu Lys Gly Glu Ala Asn Cys Thr Arg Gln His Met Gln Ala Ala
            420                 425                 430

Met Tyr Tyr Ile Leu Thr Arg Gly Trp Ser Asp Asn Gly Asp Pro Met
        435                 440                 445

Phe Asn Gln Thr Trp Ala Thr Phe Ala Met Asn Ile Ala Pro Ala Leu
    450                 455                 460

Val Val Asp Ser Ser Cys Leu Ile Met Asn Leu Gln Ile Lys Thr Tyr
465                 470                 475                 480

Gly Gln Gly Ser Gly Asn Ala Ala Thr Phe Ile Asn Asn His Leu Leu
                485                 490                 495

Ser Thr Leu Val Leu Asp Gln Trp Asn Leu Met Arg Gln Pro Arg Pro
            500                 505                 510

Asp Ser Glu Glu Phe Lys Ser Ile Glu Asp Lys Leu Gly Ile Asn Phe
        515                 520                 525

Lys Ile Glu Arg Ser Ile Asp Asp Ile Arg Gly Lys Leu Arg Gln Leu
    530                 535                 540

Val Leu Leu Ala Gln Pro Gly Tyr Leu Ser Gly Gly Val Glu Pro Glu
545                 550                 555                 560

Gln Ser Ser Pro Thr Val Glu Leu Asp Leu Leu Gly Trp Ser Ala Thr
                565                 570                 575

Tyr Ser Lys Asp Leu Gly Ile Tyr Val Pro Val Leu Asp Lys Glu Arg
            580                 585                 590

Leu Phe Cys Ser Ala Ala Tyr Pro Lys Gly Val Glu Asn Lys Ser Leu
        595                 600                 605

Lys Ser Lys Val Gly Ile Glu Gln Ala Tyr Lys Val Val Arg Tyr Glu
    610                 615                 620

Ala Leu Arg Leu Val Gly Gly Trp Asn Tyr Pro Leu Leu Asn Lys Ala
625                 630                 635                 640

Cys Lys Asn Asn Ala Gly Ala Ala Arg Arg His Leu Glu Ala Lys Gly
                645                 650                 655

Phe Pro Leu Asp Glu Phe Leu Ala Glu Trp Ser Glu Leu Ser Glu Phe
```

```
            660                 665                 670

Gly Glu Ala Phe Glu Gly Phe Asn Ile Lys Leu Thr Val Thr Ser Glu
        675                 680                 685

Ser Leu Ala Glu Leu Asn Lys Pro Val Pro Pro Lys Pro Pro Asn Val
    690                 695                 700

Asn Arg Pro Val Asn Thr Gly Gly Leu Lys Ala Val Ser Asn Ala Leu
705                 710                 715                 720

Lys Thr Gly Arg Tyr Arg Asn Glu Ala Gly Leu Ser Gly Leu Val Leu
                725                 730                 735

Leu Ala Thr Ala Arg Ser Arg Leu Gln Asp Ala Val Lys Ala Lys Ala
            740                 745                 750

Glu Ala Glu Lys Leu His Lys Ser Lys Pro Asp Asp Pro Asp Ala Asp
        755                 760                 765

Trp Phe Glu Arg Ser Glu Thr Leu Ser Asp Leu Leu Glu Lys Ala Asp
    770                 775                 780

Ile Ala Ser Lys Val Ala His Ser Ala Leu Val Glu Thr Ser Asp Ala
785                 790                 795                 800

Leu Glu Ala Val Gln Ser Thr Ser Val Tyr Thr Pro Lys Tyr Pro Glu
                805                 810                 815

Val Lys Asn Pro Gln Thr Ala Ser Asn Pro Val Val Gly Leu His Leu
            820                 825                 830

Pro Ala Lys Arg Ala Thr Gly Val Gln Ala Ala Leu Leu Gly Ala Gly
        835                 840                 845

Thr Ser Arg Pro Met Gly Met Glu Ala Pro Thr Arg Ser Lys Asn Ala
    850                 855                 860

Val Lys Met Ala Lys Arg Arg Gln Arg Gln Lys Glu Ser Arg Gln
865                 870                 875


<210> SEQ ID NO 6
<211> LENGTH: 461
<212> TYPE: PRT
<213> ORGANISM: Unknown
<220> FEATURE:
<223> OTHER INFORMATION: Polio Virus

<400> SEQUENCE: 6

Gly Glu Ile Gln Trp Met Arg Pro Ser Lys Glu Val Gly Tyr Pro Ile
1               5                   10                  15

Ile Asn Ala Pro Ser Lys Thr Lys Leu Glu Pro Ser Ala Phe His Tyr
            20                  25                  30

Val Phe Glu Gly Val Lys Glu Pro Ala Val Leu Thr Lys Asn Asp Pro
        35                  40                  45

Arg Leu Lys Thr Asp Phe Glu Glu Ala Ile Phe Ser Lys Tyr Val Gly
    50                  55                  60

Asn Lys Ile Thr Glu Val Asp Glu Tyr Met Lys Glu Ala Val Asp His
65                  70                  75                  80

Tyr Ala Gly Gln Leu Met Ser Leu Asp Ile Asn Thr Glu Gln Met Cys
                85                  90                  95

Leu Glu Asp Ala Met Tyr Gly Thr Asp Gly Leu Glu Ala Leu Asp Leu
            100                 105                 110

Ser Thr Ser Ala Gly Tyr Pro Tyr Val Ala Met Gly Lys Lys Lys Arg
        115                 120                 125

Asp Ile Leu Asn Lys Gln Thr Arg Asp Thr Lys Glu Met Gln Lys Leu
    130                 135                 140

Leu Asp Thr Tyr Gly Ile Asn Leu Pro Leu Val Thr Tyr Val Lys Asp
```

```
145                 150                 155                 160

Glu Leu Arg Ser Lys Thr Lys Val Glu Gln Gly Lys Ser Arg Leu Ile
                165                 170                 175

Glu Ala Ser Ser Leu Asn Asp Ser Val Ala Met Arg Met Ala Phe Gly
            180                 185                 190

Asn Leu Tyr Ala Ala Phe His Lys Asn Pro Gly Val Ile Thr Gly Ser
        195                 200                 205

Ala Val Gly Cys Asp Pro Asp Leu Phe Trp Ser Lys Ile Pro Val Leu
    210                 215                 220

Met Glu Glu Lys Leu Phe Ala Phe Asp Tyr Thr Gly Tyr Asp Ala Ser
225                 230                 235                 240

Leu Ser Pro Ala Trp Phe Glu Ala Leu Lys Met Val Leu Glu Lys Ile
                245                 250                 255

Gly Phe Gly Asp Arg Val Asp Tyr Ile Asp Tyr Leu Asn His Ser His
            260                 265                 270

His Leu Tyr Lys Asn Lys Thr Tyr Cys Val Lys Gly Gly Met Pro Ser
        275                 280                 285

Gly Cys Ser Gly Thr Ser Ile Phe Asn Ser Met Ile Asn Asn Leu Ile
    290                 295                 300

Ile Arg Thr Leu Leu Leu Lys Thr Tyr Lys Gly Ile Asp Leu Asp His
305                 310                 315                 320

Leu Lys Met Ile Ala Tyr Gly Asp Asp Val Ile Ala Ser Tyr Pro His
                325                 330                 335

Glu Val Asp Ala Ser Leu Leu Ala Gln Ser Gly Lys Asp Tyr Gly Leu
            340                 345                 350

Thr Met Thr Pro Ala Asp Lys Ser Ala Thr Phe Glu Thr Val Thr Trp
        355                 360                 365

Glu Asn Val Thr Phe Leu Lys Arg Phe Phe Arg Ala Asp Glu Lys Tyr
    370                 375                 380

Pro Phe Leu Ile His Pro Val Met Pro Met Lys Glu Ile His Glu Ser
385                 390                 395                 400

Ile Arg Trp Thr Lys Asp Pro Arg Asn Thr Gln Asp His Val Arg Ser
                405                 410                 415

Leu Cys Leu Leu Ala Trp His Asn Gly Glu Glu Glu Tyr Asn Lys Phe
            420                 425                 430

Leu Ala Lys Ile Arg Ser Val Pro Ile Gly Arg Ala Leu Leu Leu Pro
        435                 440                 445

Glu Tyr Ser Thr Leu Tyr Arg Arg Trp Leu Asp Ser Phe
    450                 455                 460
```

<210> SEQ ID NO 7
<211> LENGTH: 1520
<212> TYPE: PRT
<213> ORGANISM: Caenorhabditis elegans

<400> SEQUENCE: 7

```
Met His Asp Tyr Leu Ser Asp Leu Asn Val Tyr Val Pro Tyr Gln Arg
1               5                   10                  15

Pro Asn Ile Val Leu His Gly Ser Asp Phe Trp Leu Arg Thr Leu Asp
            20                  25                  30

Cys His Thr Glu Ile Pro Leu Ala Ala Ile Tyr Phe Gly Asn Ile Gln
        35                  40                  45

Gly Gly Thr Tyr Phe Asn His Trp Gln Val Ser Phe Ser Arg Glu Asn
    50                  55                  60
```

```
Ile Ser Ser Arg Asp Met Leu His Lys Ile His Ala Glu Phe Glu Phe
65                  70                  75                  80

Asp Lys Thr Asp Met Ile Thr Val Gln Phe Gln Cys Phe Glu Glu Lys
                85                  90                  95

Lys Gln Lys Phe Glu Asp Ser Arg Lys Gln Lys Val Arg Val Asn Tyr
            100                 105                 110

Gln Leu Thr Ile Arg Arg Asp Ser Ile Arg Arg Ile Ile Val Asp Pro
        115                 120                 125

Arg Val Glu Gly Cys Asn Thr Cys Val His Phe Glu Val Asn Cys Pro
    130                 135                 140

Pro Leu Ile Arg Lys Gly Tyr Ile Asp Asn Asp Lys Ser Ser Phe His
145                 150                 155                 160

Lys Pro Phe Tyr Glu Arg Gln Lys Arg Phe Asp Cys Asp Trp Arg Asn
                165                 170                 175

Gly Asn Val Asn His Gly Asn Pro Gln Asp Ala Ala Ile Ala Asp Ser
            180                 185                 190

Pro Phe Phe Thr Ile Glu Phe His Lys Glu Ile Ser Thr Lys Glu Met
        195                 200                 205

Tyr Arg Val Leu Ser Arg Leu Arg Ser Arg Thr Lys Val Leu Ile Glu
    210                 215                 220

Phe Ala Asn Leu Pro Ser Ile Asp Val Pro Met Gly Ser His Tyr Pro
225                 230                 235                 240

Tyr Asn Arg Trp Asn Leu Lys Lys Ser Pro Thr Asp Ser Asn Ala Pro
                245                 250                 255

Ile Phe Arg Glu Phe Leu Lys Glu Ile Phe Pro Pro Lys Tyr Glu Ile
            260                 265                 270

Val Asp Asp Lys Leu Ile Asp Val Asn Glu Glu Arg Lys Phe Ser Ile
        275                 280                 285

Thr Tyr Leu Ile Glu Cys Leu Leu Ser Arg Gly Ala Ile Val Lys Asp
    290                 295                 300

Gln Leu Leu Leu Asn Glu Gln His Trp Lys Asn Phe Leu Glu Ile Ile
305                 310                 315                 320

Ile Trp Tyr Tyr Arg Asn Asp Asn Gln Leu Cys Glu Ala Ala Leu Glu
                325                 330                 335

Asp Leu Val His Leu Ile Asp Gly Arg Lys Arg Ile Gly Ser Ile Leu
            340                 345                 350

Lys Cys Leu Asp Lys Ile Cys Gln Lys Arg Glu Val Met Lys Leu Val
        355                 360                 365

Asn Gly Leu Thr Glu Lys Glu Ser Ile Glu Gly Tyr Gln Arg Val Arg
    370                 375                 380

Lys Val Ile Phe Thr Pro Thr Arg Val Ile Tyr Ile Ala Pro Glu Thr
385                 390                 395                 400

Ile Met Gly Asn Arg Val Leu Arg Lys Phe Asp Lys Asp Gly Thr Arg
                405                 410                 415

Val Leu Arg Val Thr Phe Arg Asp Asp Asn Asn Lys Lys Met Arg Ser
            420                 425                 430

Asn Val Thr Gly Lys Leu Leu Asp Arg Thr Ala Asn Lys Tyr Leu Glu
        435                 440                 445

His Gly Val Arg Ile Ala Asn Arg Glu Tyr Gly Phe Leu Gly Cys Ser
    450                 455                 460

Asn Ser Gln Met Arg Asp Asn Gly Ala Tyr Phe Met Met Arg Phe Thr
465                 470                 475                 480

Asp Lys Gln Leu Asp Arg Phe Tyr Lys Cys Asn Pro Thr Ala Ser Asn
```

```
                485                 490                 495

Ile Asn Phe Lys Pro Lys Ile Asp Glu Val Arg Phe Gln Leu Gly Arg
            500                 505                 510

Phe Ser Glu Ile Glu Asn Val Pro Lys Leu Met Ala Arg Leu Gly Gln
        515                 520                 525

Cys Phe Thr Gln Ser Arg Leu Thr Gly Val Gly Leu Gly Arg Asp Asp
    530                 535                 540

Tyr Cys Ser Thr Tyr Asp Leu Thr Gly Gly Arg Ala Thr Asn Gly Ser
545                 550                 555                 560

Glu Tyr Thr Phe Ser Asp Gly Val Gly Met Met Ser Tyr Gln Phe Ala
                565                 570                 575

Gln Glu Val Ser Gln Ala Met Gln Phe Gly Lys Ala Val Pro Ser Cys
            580                 585                 590

Phe Gln Ile Arg Phe Arg Gly Asn Lys Gly Val Ile Ala Ile Glu Pro
        595                 600                 605

Phe Leu Asp Glu Ile Arg Lys Trp Ala Leu Val Asn Gly Val Thr Ser
    610                 615                 620

Met Lys Met Ala Lys Cys Leu Phe Arg Pro Ser Gln Ile Lys Phe Gln
625                 630                 635                 640

Ala Lys Ala Ile Ser Gly Asp Gln Ile Glu Met Val Lys Phe Ser Ser
                645                 650                 655

Ala Val Leu Val Ala Leu Asn Lys Pro Phe Ile Asn Ile Leu Asp Gln
            660                 665                 670

Val Ser Glu Met Gln Ser Leu Asp Cys His Lys Arg Ile Thr Ser Arg
        675                 680                 685

Ile Glu Glu Leu Met Asp Arg Gln Ile Leu Ser Phe Ala Lys Gln Met
    690                 695                 700

Asn Glu Glu Thr Phe Cys Arg Asn Lys Leu Lys Glu Phe Pro Arg Arg
705                 710                 715                 720

Ile Asp Ile Asp Asn Leu Arg Thr Met Trp Gly Phe Thr Leu Ser Ser
                725                 730                 735

Glu Pro Phe Phe Arg Ser Leu Ile Lys Ala Ser Ile Lys Phe Ser Ile
            740                 745                 750

Thr Lys Gln Leu Cys Lys Glu Gln Ile Gln Ile Pro Ser Glu Leu Gly
        755                 760                 765

Arg Ser Met Leu Gly Val Val Asp Glu Thr Gly Arg Leu Gln Tyr Gly
    770                 775                 780

Gln Ile Phe Val Gln Tyr Thr Lys Asn Tyr Lys Lys Lys Leu Pro Pro
785                 790                 795                 800

Arg Asp Ser Asn Asn Lys Val His Gly Ser Glu Ile Val Thr Gly Thr
                805                 810                 815

Val Leu Leu Thr Lys Asn Pro Cys Ile Val Pro Gly Asp Val Arg Ile
            820                 825                 830

Phe Glu Ala Val Asp Ile Pro Glu Leu His His Met Cys Asp Val Val
        835                 840                 845

Val Phe Pro Gln His Gly Pro Arg Pro His Pro Asp Glu Met Ala Gly
    850                 855                 860

Ser Asp Leu Asp Gly Asp Glu Tyr Ser Val Ile Trp Asp Gln Glu Leu
865                 870                 875                 880

Leu Leu Glu Arg Asn Glu Glu Pro Phe Asp Phe Ala Val Glu Lys Ile
                885                 890                 895

Lys Val Pro Tyr Asp Arg Glu Lys Leu Asp Val Leu Met Arg Glu Phe
            900                 905                 910
```

```
Tyr Val Thr Tyr Leu Lys Leu Asp Ser Val Gly Gln Ile Ser Asn Ser
        915                 920                 925

His Leu His Asn Ser Asp Gln Tyr Gly Leu Asn Ser Arg Val Cys Met
    930                 935                 940

Asp Leu Ala Lys Lys Asn Cys Gln Ala Val Asp Phe Thr Lys Ser Gly
945                 950                 955                 960

Gln Pro Pro Asp Pro Leu Glu Thr Lys Trp Arg Ala Asp Pro Val Thr
                965                 970                 975

Phe Glu Val Ile Pro Pro Glu Asn Pro Glu Arg Ile Pro Asp Phe His
            980                 985                 990

Met Gly Asn Glu Arg Ser Pro Met  Tyr Val Ser Pro Arg  Leu Cys Gly
        995                 1000                1005

Lys Leu  Phe Arg Glu Phe Gln  Ala Ile Asp Asn Val  Ile Lys Ile
    1010                1015                1020

Ser Glu  Glu Arg Asp Glu Gln  Tyr Asn Ile Glu Leu  Asp Glu Thr
    1025                1030                1035

Ile Phe  Val Thr Gly Phe Glu  Arg Tyr Met Glu Ser  Ala Gln Lys
    1040                1045                1050

Gln Leu  Ser Ser Tyr Asn Gly  Gln Leu Arg Ser Ile  Met Glu Asn
    1055                1060                1065

Tyr Gly  Ile Arg Ser Glu Gly  Glu Ile Met Ser Gly  Cys Ile Val
    1070                1075                1080

Glu Met  Arg Asn Arg Ile Ser  Asp Lys Asp Gln Asp  Asp Met Ser
    1085                1090                1095

Phe Tyr  Asn Thr Asn Gln Met  Ile Glu Thr Lys Met  Thr Ser Leu
    1100                1105                1110

Val Cys  Lys Phe Arg Glu Thr  Phe Phe Glu Glu Phe  Gly Gly Phe
    1115                1120                1125

Thr Val  Lys Cys Thr Leu Leu  Pro Asn Ala Tyr Asp  Asn Gly Asn
    1130                1135                1140

Cys Leu  Asn Tyr Arg Cys Glu  Asp Pro Asp Gln Glu  Val Arg Lys
    1145                1150                1155

Lys Ala  Val Ala Trp Tyr Arg  Ala Cys Tyr Glu Cys  Ala Gln Ser
    1160                1165                1170

Thr Arg  Glu Val Arg Lys Leu  Ser Phe Ala Trp Ile  Ala Tyr Asp
    1175                1180                1185

Val Ile  Ala Lys Val Lys Glu  Thr Asn Val Leu Asn  Asn Glu Arg
    1190                1195                1200

Met Gln  Ile Gly Gly Ala Asn  Pro Met Tyr Thr Phe  Leu Glu Glu
    1205                1210                1215

His Arg  Lys Gln Tyr Leu Ile  Asp His Asp Ala Asp  Phe Lys Asn
    1220                1225                1230

Phe Cys  Glu Leu Asp His Leu  Ile Thr Gly Glu Lys  Ser Lys Glu
    1235                1240                1245

Ala Ile  Ser Ile Leu Lys Ile  Tyr Leu Glu Met Ile  Pro Gly Leu
    1250                1255                1260

Asp Ser  Val Phe Phe Met Leu  Met Arg Trp Gly Glu  Ser Leu Arg
    1265                1270                1275

Leu Phe  Asp Gly Lys Pro Ile  Lys Ile Tyr His Phe  Phe Leu Met
    1280                1285                1290

Phe Ile  Leu Phe Ala Thr Arg  Gln Leu Ala Ser Ala  Asp Gly Asn
    1295                1300                1305
```

Ala Glu Pro Phe Phe Lys Ile Ile Glu Lys Glu Glu Tyr Glu Lys
1310 1315 1320

Gln Lys Arg Asp Ser Ser Arg Gly Asn Ile Asp Pro Leu Thr Glu
1325 1330 1335

Lys Lys Arg Ser Asp Met Met Val Lys Phe Phe Gln Phe Met Gly
1340 1345 1350

Cys Arg Lys Phe Arg Lys Met Ser Thr Leu Ser Phe Cys Pro Leu
1355 1360 1365

Asn Phe Ser Ser Ile Phe Met Arg Gly Glu Trp Arg Ile Phe His
1370 1375 1380

Glu Ser Ala Leu Lys Thr Tyr Tyr Asn Ile Leu Phe Asn Leu Arg
1385 1390 1395

Phe Glu Glu Leu Pro Val Ser Ser Asp Pro Thr Ile Thr Ala Glu
1400 1405 1410

Thr Met Asp Arg Glu Cys Glu Pro Phe Val Ile Glu Leu Pro Glu
1415 1420 1425

Asn Ile Asn Val Asn Asp Leu Ile Asn Asn Met Lys Lys His Thr
1430 1435 1440

Asn Val Ser Thr Val Lys Met Arg Arg Gln Glu Lys Asn Pro Ile
1445 1450 1455

Asn Asp Lys Ala Lys Pro Lys Thr Thr Val Arg Tyr Ile Val Ser
1460 1465 1470

Val Ser Gly Thr Leu Glu Ser Ile Gln Met Leu Lys Lys Leu Ser
1475 1480 1485

Ala Val Thr Ile Pro Ile Lys Ser His Trp Glu Gly Glu Glu Val
1490 1495 1500

Ser Gln Gln Met Ala Ser Leu Cys Tyr Gln Lys Val Met Asn Gly
1505 1510 1515

Glu Phe
1520

<210> SEQ ID NO 8
<211> LENGTH: 77
<212> TYPE: PRT
<213> ORGANISM: Artificial Sequence
<220> FEATURE:
<223> OTHER INFORMATION: Synthetic

<400> SEQUENCE: 8

Gly Gly Cys Thr Thr Cys Cys Ala Thr Cys Thr Cys Thr Thr Thr Gly
1 5 10 15

Ala Gly Cys Ala Cys Cys Thr Cys Cys Ala Gly Cys Gly Gly Gly Thr
20 25 30

Thr Gly Thr Gly Gly Ala Ala Gly Gly Thr Cys Cys Ala Gly Thr Thr
35 40 45

Thr Thr Gly Ala Gly Gly Gly Gly Cys Thr Ala Thr Thr Ala Cys Ala
50 55 60

Ala Gly Thr Asn Ala Ala Thr Thr Gly Cys Ala Gly Cys
65 70 75

<210> SEQ ID NO 9
<211> LENGTH: 1032
<212> TYPE: PRT
<213> ORGANISM: Artificial Sequence
<220> FEATURE:
<223> OTHER INFORMATION: Synthetic
<220> FEATURE:
<221> NAME/KEY: NON_CONS

```
<222> LOCATION: (35)..(36)
<223> OTHER INFORMATION: RDRP

<400> SEQUENCE: 9

Met Lys Arg Thr Ala Asp Gly Ser Glu Phe Glu Ser Pro Lys Lys Lys
1               5                   10                  15

Arg Lys Val Ser Gly Ser Glu Thr Pro Gly Thr Ser Glu Ser Ala Thr
            20                  25                  30

Pro Glu Ser Ser Gly Ser Glu Thr Pro Gly Thr Ser Glu Ser Ala Thr
        35                  40                  45

Pro Glu Ser Ile Pro Ala Leu Val Glu Asn Gln Lys Lys Tyr Phe Gly
    50                  55                  60

Thr Tyr Ser Val Met Ala Met Leu Asn Ala Gln Thr Val Leu Asp His
65                  70                  75                  80

Ile Gln Lys Val Ala Asp Ile Glu Gly Glu Gln Asn Glu Asn Asn Glu
                85                  90                  95

Asn Leu Trp Phe His Pro Val Met Ser His Leu Tyr Asn Ala Lys Asn
            100                 105                 110

Gly Tyr Asp Lys Gln Pro Glu Lys Thr Met Phe Ile Ile Glu Arg Leu
        115                 120                 125

Gln Ser Tyr Phe Pro Phe Leu Lys Ile Met Ala Glu Asn Gln Arg Glu
    130                 135                 140

Tyr Ser Asn Gly Lys Tyr Lys Gln Asn Arg Val Glu Val Asn Ser Asn
145                 150                 155                 160

Asp Ile Phe Glu Val Leu Lys Arg Ala Phe Gly Val Leu Lys Met Tyr
                165                 170                 175

Arg Asp Leu Thr Asn Ala Tyr Lys Thr Tyr Glu Glu Lys Leu Asn Asp
            180                 185                 190

Gly Cys Glu Phe Leu Thr Ser Thr Glu Gln Pro Leu Ser Gly Met Ile
        195                 200                 205

Asn Asn Tyr Tyr Thr Val Ala Leu Arg Asn Met Asn Glu Arg Tyr Gly
    210                 215                 220

Tyr Lys Thr Glu Asp Leu Ala Phe Ile Gln Asp Lys Arg Phe Lys Phe
225                 230                 235                 240

Val Lys Asp Ala Tyr Gly Lys Lys Lys Ser Gln Val Asn Thr Gly Phe
                245                 250                 255

Phe Leu Ser Leu Gln Asp Tyr Asn Gly Asp Thr Gln Lys Lys Leu His
            260                 265                 270

Leu Ser Gly Val Gly Ile Ala Leu Leu Ile Cys Leu Phe Leu Asp Lys
        275                 280                 285

Gln Tyr Ile Asn Ile Phe Leu Ser Arg Leu Pro Ile Phe Ser Ser Tyr
    290                 295                 300

Asn Ala Gln Ser Glu Glu Arg Arg Ile Ile Ile Arg Ser Phe Gly Ile
305                 310                 315                 320

Asn Ser Ile Lys Leu Pro Lys Asp Arg Ile His Ser Glu Lys Ser Asn
                325                 330                 335

Lys Ser Val Ala Met Asp Met Leu Asn Glu Val Lys Arg Cys Pro Asp
            340                 345                 350

Glu Leu Phe Thr Thr Leu Ser Ala Glu Lys Gln Ser Arg Phe Arg Ile
        355                 360                 365

Ile Ser Asp Asp His Asn Glu Val Leu Met Lys Arg Ser Ser Asp Arg
    370                 375                 380

Phe Val Pro Leu Leu Leu Gln Tyr Ile Asp Tyr Gly Lys Leu Phe Asp
385                 390                 395                 400
```

```
His Ile Arg Phe His Val Asn Met Gly Lys Leu Arg Tyr Leu Leu Lys
                405                 410                 415

Ala Asp Lys Thr Cys Ile Asp Gly Gln Thr Arg Val Arg Val Ile Glu
            420                 425                 430

Gln Pro Leu Asn Gly Phe Gly Arg Leu Glu Glu Ala Glu Thr Met Arg
        435                 440                 445

Lys Gln Glu Asn Gly Thr Phe Gly Asn Ser Gly Ile Arg Ile Arg Asp
    450                 455                 460

Phe Glu Asn Met Lys Arg Asp Asp Ala Asn Pro Ala Asn Tyr Pro Tyr
465                 470                 475                 480

Ile Val Asp Thr Tyr Thr His Tyr Ile Leu Glu Asn Asn Lys Val Glu
                485                 490                 495

Met Phe Ile Asn Asp Lys Glu Asp Ser Ala Pro Leu Leu Pro Val Ile
            500                 505                 510

Glu Asp Asp Arg Tyr Val Val Lys Thr Ile Pro Ser Cys Arg Met Ser
        515                 520                 525

Thr Leu Glu Ile Pro Ala Met Ala Phe His Met Phe Leu Phe Gly Ser
    530                 535                 540

Lys Lys Thr Glu Lys Leu Ile Val Asp Val His Asn Arg Tyr Lys Arg
545                 550                 555                 560

Leu Phe Gln Ala Met Gln Lys Glu Glu Val Thr Ala Glu Asn Ile Ala
                565                 570                 575

Ser Phe Gly Ile Ala Glu Ser Asp Leu Pro Gln Lys Ile Leu Asp Leu
            580                 585                 590

Ile Ser Gly Asn Ala His Gly Lys Asp Val Asp Ala Phe Ile Arg Leu
        595                 600                 605

Thr Val Asp Asp Met Leu Thr Asp Thr Glu Arg Arg Ile Lys Arg Phe
    610                 615                 620

Lys Asp Asp Arg Lys Ser Ile Arg Ser Ala Asp Asn Lys Met Gly Lys
625                 630                 635                 640

Arg Gly Phe Lys Gln Ile Ser Thr Gly Lys Leu Ala Asp Phe Leu Ala
                645                 650                 655

Lys Asp Ile Val Leu Phe Gln Pro Ser Val Asn Asp Gly Glu Asn Lys
            660                 665                 670

Ile Thr Gly Leu Asn Tyr Arg Ile Met Gln Ser Ala Ile Ala Val Tyr
        675                 680                 685

Asp Ser Gly Asp Asp Tyr Glu Ala Lys Gln Gln Phe Lys Leu Met Phe
    690                 695                 700

Glu Lys Ala Arg Leu Ile Gly Lys Gly Thr Thr Glu Pro His Pro Phe
705                 710                 715                 720

Leu Tyr Lys Val Phe Ala Arg Ser Ile Pro Ala Asn Ala Val Glu Phe
                725                 730                 735

Tyr Glu Arg Tyr Leu Ile Glu Arg Lys Phe Tyr Leu Thr Gly Leu Ser
            740                 745                 750

Asn Glu Ile Lys Lys Gly Asn Arg Val Asp Val Pro Phe Ile Arg Arg
        755                 760                 765

Asp Gln Asn Lys Trp Lys Thr Pro Ala Met Lys Thr Leu Gly Arg Ile
    770                 775                 780

Tyr Ser Glu Asp Leu Pro Val Glu Leu Pro Arg Gln Met Phe Asp Asn
785                 790                 795                 800

Glu Ile Lys Ser His Leu Lys Ser Leu Pro Gln Met Glu Gly Ile Asp
                805                 810                 815
```

```
Phe Asn Asn Ala Asn Val Thr Tyr Leu Ile Ala Glu Tyr Met Lys Arg
            820                 825                 830

Val Leu Asp Asp Asp Phe Gln Thr Phe Tyr Gln Trp Asn Arg Asn Tyr
        835                 840                 845

Arg Tyr Met Asp Met Leu Lys Gly Glu Tyr Asp Arg Lys Gly Ser Leu
    850                 855                 860

Gln His Cys Phe Thr Ser Val Glu Glu Arg Glu Gly Leu Trp Lys Glu
865                 870                 875                 880

Arg Ala Ser Arg Thr Glu Arg Tyr Arg Lys Gln Ala Ser Asn Lys Ile
                885                 890                 895

Arg Ser Asn Arg Gln Met Arg Asn Ala Ser Ser Glu Glu Ile Glu Thr
            900                 905                 910

Ile Leu Asp Lys Arg Leu Ser Asn Ser Arg Asn Glu Tyr Gln Lys Ser
        915                 920                 925

Glu Lys Val Ile Arg Arg Tyr Arg Val Gln Asp Ala Leu Leu Phe Leu
    930                 935                 940

Leu Ala Lys Lys Thr Leu Thr Glu Leu Ala Asp Phe Asp Gly Glu Arg
945                 950                 955                 960

Phe Lys Leu Lys Glu Ile Met Pro Asp Ala Glu Lys Gly Ile Leu Ser
                965                 970                 975

Glu Ile Met Pro Met Ser Phe Thr Phe Glu Lys Gly Gly Lys Lys Tyr
            980                 985                 990

Thr Ile Thr Ser Glu Gly Met Lys  Leu Lys Asn Tyr Gly  Asp Phe Phe
        995                 1000                1005

Val Leu  Ala Ser Asp Lys Arg  Ile Gly Asn Leu Leu  Glu Leu Val
    1010                1015                1020

Gly Ser  Asp Ile Val Ser Lys  Glu Asp
1025                1030


<210> SEQ ID NO 10
<211> LENGTH: 1020
<212> TYPE: PRT
<213> ORGANISM: Artificial Sequence
<220> FEATURE:
<223> OTHER INFORMATION: Synthetic

<400> SEQUENCE: 10

Met Lys Arg Thr Ala Asp Gly Ser Glu Phe Glu Ser Pro Lys Lys Lys
1               5                   10                  15

Arg Lys Val Asn Ile Pro Ala Leu Val Glu Asn Gln Lys Lys Tyr Phe
            20                  25                  30

Gly Thr Tyr Ser Val Met Ala Met Leu Asn Ala Gln Thr Val Leu Asp
        35                  40                  45

His Ile Gln Lys Val Ala Asp Ile Glu Gly Glu Gln Asn Glu Asn Asn
    50                  55                  60

Glu Asn Leu Trp Phe His Pro Val Met Ser His Leu Tyr Asn Ala Lys
65                  70                  75                  80

Asn Gly Tyr Asp Lys Gln Pro Glu Lys Thr Met Phe Ile Ile Glu Arg
                85                  90                  95

Leu Gln Ser Tyr Phe Pro Phe Leu Lys Ile Met Ala Glu Asn Gln Arg
            100                 105                 110

Glu Tyr Ser Asn Gly Lys Tyr Lys Gln Asn Arg Val Glu Val Asn Ser
        115                 120                 125

Asn Asp Ile Phe Glu Val Leu Lys Arg Ala Phe Gly Val Leu Lys Met
    130                 135                 140
```

```
Tyr Arg Asp Leu Thr Asn Ala Tyr Lys Thr Tyr Glu Glu Lys Leu Asn
145                 150                 155                 160

Asp Gly Cys Glu Phe Leu Thr Ser Thr Glu Gln Pro Leu Ser Gly Met
                165                 170                 175

Ile Asn Asn Tyr Tyr Thr Val Ala Leu Arg Asn Met Asn Glu Arg Tyr
            180                 185                 190

Gly Tyr Lys Thr Glu Asp Leu Ala Phe Ile Gln Asp Lys Arg Phe Lys
        195                 200                 205

Phe Val Lys Asp Ala Tyr Gly Lys Lys Lys Ser Gln Val Asn Thr Gly
    210                 215                 220

Phe Phe Leu Ser Leu Gln Asp Tyr Asn Gly Asp Thr Gln Lys Lys Leu
225                 230                 235                 240

His Leu Ser Gly Val Gly Ile Ala Leu Leu Ile Cys Leu Phe Leu Asp
                245                 250                 255

Lys Gln Tyr Ile Asn Ile Phe Leu Ser Arg Leu Pro Ile Phe Ser Ser
            260                 265                 270

Tyr Asn Ala Gln Ser Glu Glu Arg Arg Ile Ile Ile Arg Ser Phe Gly
        275                 280                 285

Ile Asn Ser Ile Lys Leu Pro Lys Asp Arg Ile His Ser Glu Lys Ser
    290                 295                 300

Asn Lys Ser Val Ala Met Asp Met Leu Asn Glu Val Lys Arg Cys Pro
305                 310                 315                 320

Asp Glu Leu Phe Thr Thr Leu Ser Ala Glu Lys Gln Ser Arg Phe Arg
                325                 330                 335

Ile Ile Ser Asp Asp His Asn Glu Val Leu Met Lys Arg Ser Ser Asp
            340                 345                 350

Arg Phe Val Pro Leu Leu Leu Gln Tyr Ile Asp Tyr Gly Lys Leu Phe
        355                 360                 365

Asp His Ile Arg Phe His Val Asn Met Gly Lys Leu Arg Tyr Leu Leu
    370                 375                 380

Lys Ala Asp Lys Thr Cys Ile Asp Gly Gln Thr Arg Val Arg Val Ile
385                 390                 395                 400

Glu Gln Pro Leu Asn Gly Phe Gly Arg Leu Glu Glu Ala Glu Thr Met
                405                 410                 415

Arg Lys Gln Glu Asn Gly Thr Phe Gly Asn Ser Gly Ile Arg Ile Arg
            420                 425                 430

Asp Phe Glu Asn Met Lys Arg Asp Asp Ala Asn Pro Ala Asn Tyr Pro
        435                 440                 445

Tyr Ile Val Asp Thr Tyr Thr His Tyr Ile Leu Glu Asn Asn Lys Val
    450                 455                 460

Glu Met Phe Ile Asn Asp Lys Glu Asp Ser Ala Pro Leu Leu Pro Val
465                 470                 475                 480

Ile Glu Asp Asp Arg Tyr Val Val Lys Thr Ile Pro Ser Cys Arg Met
                485                 490                 495

Ser Thr Leu Glu Ile Pro Ala Met Ala Phe His Met Phe Leu Phe Gly
            500                 505                 510

Ser Lys Lys Thr Glu Lys Leu Ile Val Asp Val His Asn Arg Tyr Lys
        515                 520                 525

Arg Leu Phe Gln Ala Met Gln Lys Glu Glu Val Thr Ala Glu Asn Ile
    530                 535                 540

Ala Ser Phe Gly Ile Ala Glu Ser Asp Leu Pro Gln Lys Ile Leu Asp
545                 550                 555                 560

Leu Ile Ser Gly Asn Ala His Gly Lys Asp Val Asp Ala Phe Ile Arg
```

```
                565                 570                 575

Leu Thr Val Asp Asp Met Leu Thr Asp Thr Glu Arg Arg Ile Lys Arg
            580                 585                 590

Phe Lys Asp Asp Arg Lys Ser Ile Arg Ser Ala Asp Asn Lys Met Gly
        595                 600                 605

Lys Arg Gly Phe Lys Gln Ile Ser Thr Gly Lys Leu Ala Asp Phe Leu
    610                 615                 620

Ala Lys Asp Ile Val Leu Phe Gln Pro Ser Val Asn Asp Gly Glu Asn
625                 630                 635                 640

Lys Ile Thr Gly Leu Asn Tyr Arg Ile Met Gln Ser Ala Ile Ala Val
                645                 650                 655

Tyr Asp Ser Gly Asp Asp Tyr Glu Ala Lys Gln Gln Phe Lys Leu Met
            660                 665                 670

Phe Glu Lys Ala Arg Leu Ile Gly Lys Gly Thr Thr Glu Pro His Pro
        675                 680                 685

Phe Leu Tyr Lys Val Phe Ala Arg Ser Ile Pro Ala Asn Ala Val Glu
    690                 695                 700

Phe Tyr Glu Arg Tyr Leu Ile Glu Arg Lys Phe Tyr Leu Thr Gly Leu
705                 710                 715                 720

Ser Asn Glu Ile Lys Lys Gly Asn Arg Val Asp Val Pro Phe Ile Arg
                725                 730                 735

Arg Asp Gln Asn Lys Trp Lys Thr Pro Ala Met Lys Thr Leu Gly Arg
            740                 745                 750

Ile Tyr Ser Glu Asp Leu Pro Val Glu Leu Pro Arg Gln Met Phe Asp
        755                 760                 765

Asn Glu Ile Lys Ser His Leu Lys Ser Leu Pro Gln Met Glu Gly Ile
    770                 775                 780

Asp Phe Asn Asn Ala Asn Val Thr Tyr Leu Ile Ala Glu Tyr Met Lys
785                 790                 795                 800

Arg Val Leu Asp Asp Asp Phe Gln Thr Phe Tyr Gln Trp Asn Arg Asn
                805                 810                 815

Tyr Arg Tyr Met Asp Met Leu Lys Gly Glu Tyr Asp Arg Lys Gly Ser
            820                 825                 830

Leu Gln His Cys Phe Thr Ser Val Glu Glu Arg Glu Gly Leu Trp Lys
        835                 840                 845

Glu Arg Ala Ser Arg Thr Glu Arg Tyr Arg Lys Gln Ala Ser Asn Lys
    850                 855                 860

Ile Arg Ser Asn Arg Gln Met Arg Asn Ala Ser Ser Glu Glu Ile Glu
865                 870                 875                 880

Thr Ile Leu Asp Lys Arg Leu Ser Asn Ser Arg Asn Glu Tyr Gln Lys
                885                 890                 895

Ser Glu Lys Val Ile Arg Arg Tyr Arg Val Gln Asp Ala Leu Leu Phe
            900                 905                 910

Leu Leu Ala Lys Lys Thr Leu Thr Glu Leu Ala Asp Phe Asp Gly Glu
        915                 920                 925

Arg Phe Lys Leu Lys Glu Ile Met Pro Asp Ala Glu Lys Gly Ile Leu
    930                 935                 940

Ser Glu Ile Met Pro Met Ser Phe Thr Phe Glu Lys Gly Gly Lys Lys
945                 950                 955                 960

Tyr Thr Ile Thr Ser Glu Gly Met Lys Leu Lys Asn Tyr Gly Asp Phe
                965                 970                 975

Phe Val Leu Ala Ser Asp Lys Arg Ile Gly Asn Leu Leu Glu Leu Val
            980                 985                 990
```

Gly Ser Asp Ile Val Ser Lys Glu Asp Gly Ser Lys Arg Thr Ala Asp
995 1000 1005

Gly Ser Glu Phe Glu Pro Lys Lys Lys Arg Lys Val
1010 1015 1020

<210> SEQ ID NO 11
<211> LENGTH: 1014
<212> TYPE: PRT
<213> ORGANISM: Artificial Sequence
<220> FEATURE:
<223> OTHER INFORMATION: Synthetic
<220> FEATURE:
<221> NAME/KEY: NON_CONS
<222> LOCATION: (16)..(17)
<223> OTHER INFORMATION: RDRP

<400> SEQUENCE: 11

Ser Gly Ser Glu Thr Pro Gly Thr Ser Glu Ser Ala Thr Pro Glu Ser
1 5 10 15

Ser Gly Ser Glu Thr Pro Gly Thr Ser Glu Ser Ala Thr Pro Glu Ser
20 25 30

Asn Ile Pro Ala Leu Val Glu Asn Gln Lys Lys Tyr Phe Gly Thr Tyr
35 40 45

Ser Val Met Ala Met Leu Asn Ala Gln Thr Val Leu Asp His Ile Gln
50 55 60

Lys Val Ala Asp Ile Glu Gly Glu Gln Asn Glu Asn Asn Glu Asn Leu
65 70 75 80

Trp Phe His Pro Val Met Ser His Leu Tyr Asn Ala Lys Asn Gly Tyr
85 90 95

Asp Lys Gln Pro Glu Lys Thr Met Phe Ile Ile Glu Arg Leu Gln Ser
100 105 110

Tyr Phe Pro Phe Leu Lys Ile Met Ala Glu Asn Gln Arg Glu Tyr Ser
115 120 125

Asn Gly Lys Tyr Lys Gln Asn Arg Val Glu Val Asn Ser Asn Asp Ile
130 135 140

Phe Glu Val Leu Lys Arg Ala Phe Gly Val Leu Lys Met Tyr Arg Asp
145 150 155 160

Leu Thr Asn Ala Tyr Lys Thr Tyr Glu Glu Lys Leu Asn Asp Gly Cys
165 170 175

Glu Phe Leu Thr Ser Thr Glu Gln Pro Leu Ser Gly Met Ile Asn Asn
180 185 190

Tyr Tyr Thr Val Ala Leu Arg Asn Met Asn Glu Arg Tyr Gly Tyr Lys
195 200 205

Thr Glu Asp Leu Ala Phe Ile Gln Asp Lys Arg Phe Lys Phe Val Lys
210 215 220

Asp Ala Tyr Gly Lys Lys Lys Ser Gln Val Asn Thr Gly Phe Phe Leu
225 230 235 240

Ser Leu Gln Asp Tyr Asn Gly Asp Thr Gln Lys Lys Leu His Leu Ser
245 250 255

Gly Val Gly Ile Ala Leu Leu Ile Cys Leu Phe Leu Asp Lys Gln Tyr
260 265 270

Ile Asn Ile Phe Leu Ser Arg Leu Pro Ile Phe Ser Ser Tyr Asn Ala
275 280 285

Gln Ser Glu Glu Arg Arg Ile Ile Ile Arg Ser Phe Gly Ile Asn Ser
290 295 300

Ile Lys Leu Pro Lys Asp Arg Ile His Ser Glu Lys Ser Asn Lys Ser

```
305                 310                 315                 320

Val Ala Met Asp Met Leu Asn Glu Val Lys Arg Cys Pro Asp Glu Leu
                325                 330                 335

Phe Thr Thr Leu Ser Ala Glu Lys Gln Ser Arg Phe Arg Ile Ile Ser
            340                 345                 350

Asp Asp His Asn Glu Val Leu Met Lys Arg Ser Ser Asp Arg Phe Val
        355                 360                 365

Pro Leu Leu Leu Gln Tyr Ile Asp Tyr Gly Lys Leu Phe Asp His Ile
    370                 375                 380

Arg Phe His Val Asn Met Gly Lys Leu Arg Tyr Leu Leu Lys Ala Asp
385                 390                 395                 400

Lys Thr Cys Ile Asp Gly Gln Thr Arg Val Arg Val Ile Glu Gln Pro
                405                 410                 415

Leu Asn Gly Phe Gly Arg Leu Glu Glu Ala Glu Thr Met Arg Lys Gln
            420                 425                 430

Glu Asn Gly Thr Phe Gly Asn Ser Gly Ile Arg Ile Arg Asp Phe Glu
        435                 440                 445

Asn Met Lys Arg Asp Asp Ala Asn Pro Ala Asn Tyr Pro Tyr Ile Val
    450                 455                 460

Asp Thr Tyr Thr His Tyr Ile Leu Glu Asn Asn Lys Val Glu Met Phe
465                 470                 475                 480

Ile Asn Asp Lys Glu Asp Ser Ala Pro Leu Leu Pro Val Ile Glu Asp
                485                 490                 495

Asp Arg Tyr Val Val Lys Thr Ile Pro Ser Cys Arg Met Ser Thr Leu
            500                 505                 510

Glu Ile Pro Ala Met Ala Phe His Met Phe Leu Phe Gly Ser Lys Lys
        515                 520                 525

Thr Glu Lys Leu Ile Val Asp Val His Asn Arg Tyr Lys Arg Leu Phe
    530                 535                 540

Gln Ala Met Gln Lys Glu Glu Val Thr Ala Glu Asn Ile Ala Ser Phe
545                 550                 555                 560

Gly Ile Ala Glu Ser Asp Leu Pro Gln Lys Ile Leu Asp Leu Ile Ser
                565                 570                 575

Gly Asn Ala His Gly Lys Asp Val Asp Ala Phe Ile Arg Leu Thr Val
            580                 585                 590

Asp Asp Met Leu Thr Asp Thr Glu Arg Arg Ile Lys Arg Phe Lys Asp
        595                 600                 605

Asp Arg Lys Ser Ile Arg Ser Ala Asp Asn Lys Met Gly Lys Arg Gly
    610                 615                 620

Phe Lys Gln Ile Ser Thr Gly Lys Leu Ala Asp Phe Leu Ala Lys Asp
625                 630                 635                 640

Ile Val Leu Phe Gln Pro Ser Val Asn Asp Gly Glu Asn Lys Ile Thr
                645                 650                 655

Gly Leu Asn Tyr Arg Ile Met Gln Ser Ala Ile Ala Val Tyr Asp Ser
            660                 665                 670

Gly Asp Asp Tyr Glu Ala Lys Gln Gln Phe Lys Leu Met Phe Glu Lys
        675                 680                 685

Ala Arg Leu Ile Gly Lys Gly Thr Thr Glu Pro His Pro Phe Leu Tyr
    690                 695                 700

Lys Val Phe Ala Arg Ser Ile Pro Ala Asn Ala Val Glu Phe Tyr Glu
705                 710                 715                 720

Arg Tyr Leu Ile Glu Arg Lys Phe Tyr Leu Thr Gly Leu Ser Asn Glu
                725                 730                 735
```

Ile Lys Lys Gly Asn Arg Val Asp Val Pro Phe Ile Arg Arg Asp Gln
740 745 750

Asn Lys Trp Lys Thr Pro Ala Met Lys Thr Leu Gly Arg Ile Tyr Ser
755 760 765

Glu Asp Leu Pro Val Glu Leu Pro Arg Gln Met Phe Asp Asn Glu Ile
770 775 780

Lys Ser His Leu Lys Ser Leu Pro Gln Met Glu Gly Ile Asp Phe Asn
785 790 795 800

Asn Ala Asn Val Thr Tyr Leu Ile Ala Glu Tyr Met Lys Arg Val Leu
805 810 815

Asp Asp Asp Phe Gln Thr Phe Tyr Gln Trp Asn Arg Asn Tyr Arg Tyr
820 825 830

Met Asp Met Leu Lys Gly Glu Tyr Asp Arg Lys Gly Ser Leu Gln His
835 840 845

Cys Phe Thr Ser Val Glu Glu Arg Glu Gly Leu Trp Lys Glu Arg Ala
850 855 860

Ser Arg Thr Glu Arg Tyr Arg Lys Gln Ala Ser Asn Lys Ile Arg Ser
865 870 875 880

Asn Arg Gln Met Arg Asn Ala Ser Ser Glu Glu Ile Glu Thr Ile Leu
885 890 895

Asp Lys Arg Leu Ser Asn Ser Arg Asn Glu Tyr Gln Lys Ser Glu Lys
900 905 910

Val Ile Arg Arg Tyr Arg Val Gln Asp Ala Leu Leu Phe Leu Leu Ala
915 920 925

Lys Lys Thr Leu Thr Glu Leu Ala Asp Phe Asp Gly Glu Arg Phe Lys
930 935 940

Leu Lys Glu Ile Met Pro Asp Ala Glu Lys Gly Ile Leu Ser Glu Ile
945 950 955 960

Met Pro Met Ser Phe Thr Phe Glu Lys Gly Gly Lys Lys Tyr Thr Ile
965 970 975

Thr Ser Glu Gly Met Lys Leu Lys Asn Tyr Gly Asp Phe Phe Val Leu
980 985 990

Ala Ser Asp Lys Arg Ile Gly Asn Leu Leu Glu Leu Val Gly Ser Asp
995 1000 1005

Ile Val Ser Lys Glu Asp
1010

<210> SEQ ID NO 12
<211> LENGTH: 1012
<212> TYPE: PRT
<213> ORGANISM: Artificial Sequence
<220> FEATURE:
<223> OTHER INFORMATION: Synthetic

<400> SEQUENCE: 12

Met Asn Ile Pro Ala Leu Val Glu Asn Gln Lys Lys Tyr Phe Gly Thr
1 5 10 15

Tyr Ser Val Met Ala Met Leu Asn Ala Gln Thr Val Leu Asp His Ile
20 25 30

Gln Lys Val Ala Asp Ile Glu Gly Glu Gln Asn Glu Asn Asn Glu Asn
35 40 45

Leu Trp Phe His Pro Val Met Ser His Leu Tyr Asn Ala Lys Asn Gly
50 55 60

Tyr Asp Lys Gln Pro Glu Lys Thr Met Phe Ile Ile Glu Arg Leu Gln
65 70 75 80

```
Ser Tyr Phe Pro Phe Leu Lys Ile Met Ala Glu Asn Gln Arg Glu Tyr
                85                  90                  95

Ser Asn Gly Lys Tyr Lys Gln Asn Arg Val Glu Val Asn Ser Asn Asp
            100                 105                 110

Ile Phe Glu Val Leu Lys Arg Ala Phe Gly Val Leu Lys Met Tyr Arg
        115                 120                 125

Asp Leu Thr Asn Ala Tyr Lys Thr Tyr Glu Glu Lys Leu Asn Asp Gly
    130                 135                 140

Cys Glu Phe Leu Thr Ser Thr Glu Gln Pro Leu Ser Gly Met Ile Asn
145                 150                 155                 160

Asn Tyr Tyr Thr Val Ala Leu Arg Asn Met Asn Glu Arg Tyr Gly Tyr
                165                 170                 175

Lys Thr Glu Asp Leu Ala Phe Ile Gln Asp Lys Arg Phe Lys Phe Val
            180                 185                 190

Lys Asp Ala Tyr Gly Lys Lys Lys Ser Gln Val Asn Thr Gly Phe Phe
        195                 200                 205

Leu Ser Leu Gln Asp Tyr Asn Gly Asp Thr Gln Lys Lys Leu His Leu
    210                 215                 220

Ser Gly Val Gly Ile Ala Leu Leu Ile Cys Leu Phe Leu Asp Lys Gln
225                 230                 235                 240

Tyr Ile Asn Ile Phe Leu Ser Arg Leu Pro Ile Phe Ser Ser Tyr Asn
                245                 250                 255

Ala Gln Ser Glu Glu Arg Arg Ile Ile Ile Arg Ser Phe Gly Ile Asn
            260                 265                 270

Ser Ile Lys Leu Pro Lys Asp Arg Ile His Ser Glu Lys Ser Asn Lys
        275                 280                 285

Ser Val Ala Met Asp Met Leu Asn Glu Val Lys Arg Cys Pro Asp Glu
    290                 295                 300

Leu Phe Thr Thr Leu Ser Ala Glu Lys Gln Ser Arg Phe Arg Ile Ile
305                 310                 315                 320

Ser Asp Asp His Asn Glu Val Leu Met Lys Arg Ser Ser Asp Arg Phe
                325                 330                 335

Val Pro Leu Leu Leu Gln Tyr Ile Asp Tyr Gly Lys Leu Phe Asp His
            340                 345                 350

Ile Arg Phe His Val Asn Met Gly Lys Leu Arg Tyr Leu Leu Lys Ala
        355                 360                 365

Asp Lys Thr Cys Ile Asp Gly Gln Thr Arg Val Arg Val Ile Glu Gln
    370                 375                 380

Pro Leu Asn Gly Phe Gly Arg Leu Glu Glu Ala Glu Thr Met Arg Lys
385                 390                 395                 400

Gln Glu Asn Gly Thr Phe Gly Asn Ser Gly Ile Arg Ile Arg Asp Phe
                405                 410                 415

Glu Asn Met Lys Arg Asp Asp Ala Asn Pro Ala Asn Tyr Pro Tyr Ile
            420                 425                 430

Val Asp Thr Tyr Thr His Tyr Ile Leu Glu Asn Asn Lys Val Glu Met
        435                 440                 445

Phe Ile Asn Asp Lys Glu Asp Ser Ala Pro Leu Leu Pro Val Ile Glu
    450                 455                 460

Asp Asp Arg Tyr Val Val Lys Thr Ile Pro Ser Cys Arg Met Ser Thr
465                 470                 475                 480

Leu Glu Ile Pro Ala Met Ala Phe His Met Phe Leu Phe Gly Ser Lys
                485                 490                 495
```

```
Lys Thr Glu Lys Leu Ile Val Asp Val His Asn Arg Tyr Lys Arg Leu
            500                 505                 510

Phe Gln Ala Met Gln Lys Glu Glu Val Thr Ala Glu Asn Ile Ala Ser
        515                 520                 525

Phe Gly Ile Ala Glu Ser Asp Leu Pro Gln Lys Ile Leu Asp Leu Ile
    530                 535                 540

Ser Gly Asn Ala His Gly Lys Asp Val Asp Ala Phe Ile Arg Leu Thr
545                 550                 555                 560

Val Asp Asp Met Leu Thr Asp Thr Glu Arg Arg Ile Lys Arg Phe Lys
                565                 570                 575

Asp Asp Arg Lys Ser Ile Arg Ser Ala Asp Asn Lys Met Gly Lys Arg
            580                 585                 590

Gly Phe Lys Gln Ile Ser Thr Gly Lys Leu Ala Asp Phe Leu Ala Lys
        595                 600                 605

Asp Ile Val Leu Phe Gln Pro Ser Val Asn Asp Gly Glu Asn Lys Ile
    610                 615                 620

Thr Gly Leu Asn Tyr Arg Ile Met Gln Ser Ala Ile Ala Val Tyr Asp
625                 630                 635                 640

Ser Gly Asp Asp Tyr Glu Ala Lys Gln Gln Phe Lys Leu Met Phe Glu
                645                 650                 655

Lys Ala Arg Leu Ile Gly Lys Gly Thr Thr Glu Pro His Pro Phe Leu
            660                 665                 670

Tyr Lys Val Phe Ala Arg Ser Ile Pro Ala Asn Ala Val Glu Phe Tyr
        675                 680                 685

Glu Arg Tyr Leu Ile Glu Arg Lys Phe Tyr Leu Thr Gly Leu Ser Asn
    690                 695                 700

Glu Ile Lys Lys Gly Asn Arg Val Asp Val Pro Phe Ile Arg Arg Asp
705                 710                 715                 720

Gln Asn Lys Trp Lys Thr Pro Ala Met Lys Thr Leu Gly Arg Ile Tyr
                725                 730                 735

Ser Glu Asp Leu Pro Val Glu Leu Pro Arg Gln Met Phe Asp Asn Glu
            740                 745                 750

Ile Lys Ser His Leu Lys Ser Leu Pro Gln Met Glu Gly Ile Asp Phe
        755                 760                 765

Asn Asn Ala Asn Val Thr Tyr Leu Ile Ala Glu Tyr Met Lys Arg Val
    770                 775                 780

Leu Asp Asp Asp Phe Gln Thr Phe Tyr Gln Trp Asn Arg Asn Tyr Arg
785                 790                 795                 800

Tyr Met Asp Met Leu Lys Gly Glu Tyr Asp Arg Lys Gly Ser Leu Gln
                805                 810                 815

His Cys Phe Thr Ser Val Glu Glu Arg Glu Gly Leu Trp Lys Glu Arg
            820                 825                 830

Ala Ser Arg Thr Glu Arg Tyr Arg Lys Gln Ala Ser Asn Lys Ile Arg
        835                 840                 845

Ser Asn Arg Gln Met Arg Asn Ala Ser Ser Glu Glu Ile Glu Thr Ile
    850                 855                 860

Leu Asp Lys Arg Leu Ser Asn Ser Arg Asn Glu Tyr Gln Lys Ser Glu
865                 870                 875                 880

Lys Val Ile Arg Arg Tyr Arg Val Gln Asp Ala Leu Leu Phe Leu Leu
                885                 890                 895

Ala Lys Lys Thr Leu Thr Glu Leu Ala Asp Phe Asp Gly Glu Arg Phe
            900                 905                 910

Lys Leu Lys Glu Ile Met Pro Asp Ala Glu Lys Gly Ile Leu Ser Glu
```

915 920 925

Ile Met Pro Met Ser Phe Thr Phe Glu Lys Gly Gly Lys Lys Tyr Thr
930 935 940

Ile Thr Ser Glu Gly Met Lys Leu Lys Asn Tyr Gly Asp Phe Phe Val
945 950 955 960

Leu Ala Ser Asp Lys Arg Ile Gly Asn Leu Leu Glu Leu Val Gly Ser
965 970 975

Asp Ile Val Ser Lys Glu Asp Gly Ser Leu Gln Leu Pro Pro Leu Glu
980 985 990

Arg Leu Thr Leu Ser Gly Ser Glu Thr Pro Gly Thr Ser Glu Ser Ala
995 1000 1005

Thr Pro Glu Ser
1010

<210> SEQ ID NO 13
<211> LENGTH: 1012
<212> TYPE: PRT
<213> ORGANISM: Artificial Sequence
<220> FEATURE:
<223> OTHER INFORMATION: Synthetic

<400> SEQUENCE: 13

Met Asn Ile Pro Ala Leu Val Glu Asn Gln Lys Lys Tyr Phe Gly Thr
1 5 10 15

Tyr Ser Val Met Ala Met Leu Asn Ala Gln Thr Val Leu Asp His Ile
20 25 30

Gln Lys Val Ala Asp Ile Glu Gly Glu Gln Asn Glu Asn Asn Glu Asn
35 40 45

Leu Trp Phe His Pro Val Met Ser His Leu Tyr Asn Ala Lys Asn Gly
50 55 60

Tyr Asp Lys Gln Pro Glu Lys Thr Met Phe Ile Ile Glu Arg Leu Gln
65 70 75 80

Ser Tyr Phe Pro Phe Leu Lys Ile Met Ala Glu Asn Gln Arg Glu Tyr
85 90 95

Ser Asn Gly Lys Tyr Lys Gln Asn Arg Val Glu Val Asn Ser Asn Asp
100 105 110

Ile Phe Glu Val Leu Lys Arg Ala Phe Gly Val Leu Lys Met Tyr Arg
115 120 125

Asp Leu Thr Asn His Tyr Lys Thr Tyr Glu Glu Lys Leu Asn Asp Gly
130 135 140

Cys Glu Phe Leu Thr Ser Thr Glu Gln Pro Leu Ser Gly Met Ile Asn
145 150 155 160

Asn Tyr Tyr Thr Val Ala Leu Arg Asn Met Asn Glu Arg Tyr Gly Tyr
165 170 175

Lys Thr Glu Asp Leu Ala Phe Ile Gln Asp Lys Arg Phe Lys Phe Val
180 185 190

Lys Asp Ala Tyr Gly Lys Lys Lys Ser Gln Val Asn Thr Gly Phe Phe
195 200 205

Leu Ser Leu Gln Asp Tyr Asn Gly Asp Thr Gln Lys Lys Leu His Leu
210 215 220

Ser Gly Val Gly Ile Ala Leu Leu Ile Cys Leu Phe Leu Asp Lys Gln
225 230 235 240

Tyr Ile Asn Ile Phe Leu Ser Arg Leu Pro Ile Phe Ser Ser Tyr Asn
245 250 255

Ala Gln Ser Glu Glu Arg Arg Ile Ile Ile Arg Ser Phe Gly Ile Asn

-continued

```
            260                 265                 270

Ser Ile Lys Leu Pro Lys Asp Arg Ile His Ser Glu Lys Ser Asn Lys
        275                 280                 285

Ser Val Ala Met Asp Met Leu Asn Glu Val Lys Arg Cys Pro Asp Glu
    290                 295                 300

Leu Phe Thr Thr Leu Ser Ala Glu Lys Gln Ser Arg Phe Arg Ile Ile
305                 310                 315                 320

Ser Asp Asp His Asn Glu Val Leu Met Lys Arg Ser Ser Asp Arg Phe
                325                 330                 335

Val Pro Leu Leu Leu Gln Tyr Ile Asp Tyr Gly Lys Leu Phe Asp His
            340                 345                 350

Ile Arg Phe His Val Asn Met Gly Lys Leu Arg Tyr Leu Leu Lys Ala
        355                 360                 365

Asp Lys Thr Cys Ile Asp Gly Gln Thr Arg Val Arg Val Ile Glu Gln
    370                 375                 380

Pro Leu Asn Gly Phe Gly Arg Leu Glu Glu Ala Glu Thr Met Arg Lys
385                 390                 395                 400

Gln Glu Asn Gly Thr Phe Gly Asn Ser Gly Ile Arg Ile Arg Asp Phe
                405                 410                 415

Glu Asn Met Lys Arg Asp Asp Ala Asn Pro Ala Asn Tyr Pro Tyr Ile
            420                 425                 430

Val Asp Thr Tyr Thr His Tyr Ile Leu Glu Asn Asn Lys Val Glu Met
        435                 440                 445

Phe Ile Asn Asp Lys Glu Asp Ser Ala Pro Leu Leu Pro Val Ile Glu
    450                 455                 460

Asp Asp Arg Tyr Val Val Lys Thr Ile Pro Ser Cys Arg Met Ser Thr
465                 470                 475                 480

Leu Glu Ile Pro Ala Met Ala Phe His Met Phe Leu Phe Gly Ser Lys
                485                 490                 495

Lys Thr Glu Lys Leu Ile Val Asp Val His Asn Arg Tyr Lys Arg Leu
            500                 505                 510

Phe Gln Ala Met Gln Lys Glu Glu Val Thr Ala Glu Asn Ile Ala Ser
        515                 520                 525

Phe Gly Ile Ala Glu Ser Asp Leu Pro Gln Lys Ile Leu Asp Leu Ile
    530                 535                 540

Ser Gly Asn Ala His Gly Lys Asp Val Asp Ala Phe Ile Arg Leu Thr
545                 550                 555                 560

Val Asp Asp Met Leu Thr Asp Thr Glu Arg Arg Ile Lys Arg Phe Lys
                565                 570                 575

Asp Asp Arg Lys Ser Ile Arg Ser Ala Asp Asn Lys Met Gly Lys Arg
            580                 585                 590

Gly Phe Lys Gln Ile Ser Thr Gly Lys Leu Ala Asp Phe Leu Ala Lys
        595                 600                 605

Asp Ile Val Leu Phe Gln Pro Ser Val Asn Asp Gly Glu Asn Lys Ile
    610                 615                 620

Thr Gly Leu Asn Tyr Arg Ile Met Gln Ser Ala Ile Ala Val Tyr Asp
625                 630                 635                 640

Ser Gly Asp Asp Tyr Glu Ala Lys Gln Gln Phe Lys Leu Met Phe Glu
                645                 650                 655

Lys Ala Arg Leu Ile Gly Lys Gly Thr Thr Glu Pro His Pro Phe Leu
            660                 665                 670

Tyr Lys Val Phe Ala Arg Ser Ile Pro Ala Asn Ala Val Glu Phe Tyr
        675                 680                 685
```

Glu Arg Tyr Leu Ile Glu Arg Lys Phe Tyr Leu Thr Gly Leu Ser Asn
    690                 695                 700

Glu Ile Lys Lys Gly Asn Arg Val Asp Val Pro Phe Ile Arg Arg Asp
705                 710                 715                 720

Gln Asn Lys Trp Lys Thr Pro Ala Met Lys Thr Leu Gly Arg Ile Tyr
                725                 730                 735

Ser Glu Asp Leu Pro Val Glu Leu Pro Arg Gln Met Phe Asp Asn Glu
            740                 745                 750

Ile Lys Ser His Leu Lys Ser Leu Pro Gln Met Glu Gly Ile Asp Phe
        755                 760                 765

Asn Asn Ala Asn Val Thr Tyr Leu Ile Ala Glu Tyr Met Lys Arg Val
    770                 775                 780

Leu Asp Asp Asp Phe Gln Thr Phe Tyr Gln Trp Asn Arg Asn Tyr Arg
785                 790                 795                 800

Tyr Met Asp Met Leu Lys Gly Glu Tyr Asp Arg Lys Gly Ser Leu Gln
                805                 810                 815

His Cys Phe Thr Ser Val Glu Glu Arg Glu Gly Leu Trp Lys Glu Arg
            820                 825                 830

Ala Ser Arg Thr Glu Arg Tyr Arg Lys Gln Ala Ser Asn Lys Ile Arg
        835                 840                 845

Ser Asn Arg Gln Met Arg Asn Ala Ser Ser Glu Glu Ile Glu Thr Ile
    850                 855                 860

Leu Asp Lys Arg Leu Ser Asn Ser Arg Asn Glu Tyr Gln Lys Ser Glu
865                 870                 875                 880

Lys Val Ile Arg Arg Tyr Arg Val Gln Asp Ala Leu Leu Phe Leu Leu
                885                 890                 895

Ala Lys Lys Thr Leu Thr Glu Leu Ala Asp Phe Asp Gly Glu Arg Phe
            900                 905                 910

Lys Leu Lys Glu Ile Met Pro Asp Ala Glu Lys Gly Ile Leu Ser Glu
        915                 920                 925

Ile Met Pro Met Ser Phe Thr Phe Glu Lys Gly Gly Lys Lys Tyr Thr
    930                 935                 940

Ile Thr Ser Glu Gly Met Lys Leu Lys Asn Tyr Gly Asp Phe Phe Val
945                 950                 955                 960

Leu Ala Ser Asp Lys Arg Ile Gly Asn Leu Leu Glu Leu Val Gly Ser
                965                 970                 975

Asp Ile Val Ser Lys Glu Asp Gly Ser Leu Gln Leu Pro Pro Leu Glu
            980                 985                 990

Arg Leu Thr Leu Ser Gly Ser Glu  Thr Pro Gly Thr Ser  Glu Ser Ala
        995                 1000                1005

Thr Pro  Glu Ser
    1010

<210> SEQ ID NO 14
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: May repeat up to 30 times

<400> SEQUENCE: 14

Gly Gly Gly Gly Ser 1 5

<210> SEQ ID NO 15
<211> LENGTH: 1
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(1)
<223> OTHER INFORMATION: May repeat up to 30 times

<400> SEQUENCE: 15

Gly
1

<210> SEQ ID NO 16
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: May repeat up to 30 times

<400> SEQUENCE: 16

Glu Ala Ala Ala Lys
1 5

<210> SEQ ID NO 17
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(3)
<223> OTHER INFORMATION: May repeat up to 30 times

<400> SEQUENCE: 17

Gly Gly Ser
1

<210> SEQ ID NO 18
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(4)
<223> OTHER INFORMATION: May repeat up to 30 times

<400> SEQUENCE: 18

Ser Gly Gly Ser
1

<210> SEQ ID NO 19
<211> LENGTH: 60
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: SITE
<222> LOCATION: (3)..(60)
<223> OTHER INFORMATION: May be absent
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:

<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 19

```
Xaa Pro Xaa Pro Xaa Pro Xaa Pro Xaa Pro Xaa Pro Xaa Pro Xaa Pro
1               5                   10                  15

Xaa Pro Xaa Pro Xaa Pro Xaa Pro Xaa Pro Xaa Pro Xaa Pro Xaa Pro
            20                  25                  30

Xaa Pro Xaa Pro Xaa Pro Xaa Pro Xaa Pro Xaa Pro Xaa Pro Xaa Pro
        35                  40                  45

Xaa Pro Xaa Pro Xaa Pro Xaa Pro Xaa Pro Xaa Pro
    50                  55                  60
```

<210> SEQ ID NO 20
<211> LENGTH: 16
<212> TYPE: PRT
<213> ORGANISM: Artificial Sequence
<220> FEATURE:
<223> OTHER INFORMATION: Synthetic

<400> SEQUENCE: 20

```
Ser Gly Ser Glu Thr Pro Gly Thr Ser Glu Ser Ala Thr Pro Glu Ser
1               5                   10                  15
```

<210> SEQ ID NO 21
<211> LENGTH: 32
<212> TYPE: PRT
<213> ORGANISM: Artificial Sequence
<220> FEATURE:
<223> OTHER INFORMATION: Synthetic

<400> SEQUENCE: 21

Ser Gly Gly Ser Ser Gly Gly Ser Ser Gly Ser Glu Thr Pro Gly Thr
1 5 10 15

Ser Glu Ser Ala Thr Pro Glu Ser Ser Gly Gly Ser Ser Gly Gly Ser
20 25 30

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Ser Gly Gly Ser Gly Gly Ser Gly Gly Ser
1 5 10

<210> SEQ ID NO 23
<211> LENGTH: 60
<212> TYPE: PRT
<213> ORGANISM: Artificial Sequence
<220> FEATURE:
<223> OTHER INFORMATION: Synthetic

<400> SEQUENCE: 23

Ser Gly Gly Ser Ser Gly Gly Ser Ser Gly Ser Glu Thr Pro Gly Thr
1 5 10 15

Ser Glu Ser Ala Thr Pro Glu Ser Ala Gly Ser Tyr Pro Tyr Asp Val
20 25 30

Pro Asp Tyr Ala Gly Ser Ala Ala Pro Ala Ala Lys Lys Lys Lys Leu
35 40 45

Asp Gly Ser Gly Ser Gly Gly Ser Ser Gly Gly Ser
50 55 60

<210> SEQ ID NO 24
<211> LENGTH: 19
<212> TYPE: PRT
<213> ORGANISM: Artificial Sequence
<220> FEATURE:
<223> OTHER INFORMATION: Synthetic

<400> SEQUENCE: 24

Met Lys Arg Thr Ala Asp Gly Ser Glu Phe Glu Ser Pro Lys Lys Lys
1 5 10 15

Arg Lys Val

<210> SEQ ID NO 25
<211> LENGTH: 30
<212> TYPE: PRT
<213> ORGANISM: Artificial Sequence
<220> FEATURE:
<223> OTHER INFORMATION: Synthetic

<400> SEQUENCE: 25

Met Asp Ser Leu Leu Met Asn Arg Arg Lys Phe Leu Tyr Gln Phe Lys
1 5 10 15

Asn Val Arg Trp Ala Lys Gly Arg Arg Glu Thr Tyr Leu Cys
20 25 30

<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

Ala Val Lys Arg Pro Ala Ala Thr Lys Lys Ala Gly Gln Ala Lys Lys
1 5 10 15

Lys Lys Leu Asp
20

<210> SEQ ID NO 27
<211> LENGTH: 25
<212> TYPE: PRT
<213> ORGANISM: Artificial Sequence
<220> FEATURE:
<223> OTHER INFORMATION: Synthetic

<400> SEQUENCE: 27

Met Ser Arg Arg Arg Lys Ala Asn Pro Thr Lys Leu Ser Glu Asn Ala
1 5 10 15

Lys Lys Leu Ala Lys Glu Val Glu Asn
20 25

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Pro Ala Ala Lys Arg Val Lys Leu Asp
1 5

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Lys Leu Lys Ile Lys Arg Pro Val Lys
1 5

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Val Ser Arg Lys Arg Pro Arg Pro
1 5

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Glu Gly Ala Pro Pro Ala Lys Arg Ala Arg
1 5 10

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Pro Pro Gln Pro Lys Lys Lys Pro Leu Asp Gly Glu
1               5                   10

<210> SEQ ID NO 33
<211> LENGTH: 21
<212> TYPE: PRT
<213> ORGANISM: Artificial Sequence
<220> FEATURE:
<223> OTHER INFORMATION: Synthetic

<400> SEQUENCE: 33

Ser Gly Gly Ser Lys Arg Thr Ala Asp Gly Ser Glu Phe Glu Pro Lys
1               5                   10                  15

Lys Lys Arg Lys Val
            20

<210> SEQ ID NO 34
<211> LENGTH: 449
<212> TYPE: PRT
<213> ORGANISM: Unknown
<220> FEATURE:
<223> OTHER INFORMATION: Leptotrichia Treviasanii

<400> SEQUENCE: 34

Met Ala Lys Ile Leu Ile Ala Gly Leu Gly Lys Gly Ile Lys Lys Asp
1               5                   10                  15

Gly Lys Tyr Arg Glu Thr Asn Tyr Ser Ile Glu Lys Ile Asp Lys Glu
            20                  25                  30

Asn Ile Ile Tyr Lys Asn Glu Ser Phe Ile Thr Ser Ala Leu Glu Lys
        35                  40                  45

His Phe Glu Ile Asp Lys Thr Ile Tyr Ile Gly Thr Val Gly Ser Met
    50                  55                  60

Trp Asp Asn Leu Tyr Ser Tyr Tyr Cys Asn Lys Tyr Asn Leu Lys Glu
65                  70                  75                  80

Asp Glu Asp Tyr Thr Phe Glu Leu Leu Glu Ala Ser Ser Asn Ala Thr
                85                  90                  95

Gln Asp Ser Glu Phe Ser Glu Ile Asn Ile Lys Lys Phe Asn Asp Ile
            100                 105                 110

Phe Glu Gly Lys Ala Arg Ile Ile Leu Thr Lys Phe Gly Met Asn Thr
        115                 120                 125

Asn Glu Ile Phe Glu Asn Phe Asn Leu Ile Met Glu Ile Gly Asn Met
    130                 135                 140

Leu Asn Asp Gly Asp Glu Ile Tyr Leu Asp Ile Thr His Ser Phe Arg
145                 150                 155                 160

Ser Asn Ala Met Trp Met Phe Leu Val Ile Asn Tyr Ile Thr Asn Val
                165                 170                 175

Leu Asp Lys Asn Val Glu Val Lys Met Ile Ser Tyr Gly Met Phe Glu
            180                 185                 190

Ala Lys Tyr Lys Lys Glu Val Ile Glu Asn Gly Glu Thr Lys Glu Ile
        195                 200                 205

Glu Ile Ser Pro Val Val Asn Leu Lys Ala Phe Phe Asp Leu Met Lys

```
    210                 215                 220

Trp Ile Lys Gly Ala Asn Glu Leu Lys Asn Tyr Gly Asn Ser Tyr Thr
225                 230                 235                 240

Ile Leu Glu Met Ile Asp Asp Lys Asp Val Asn Lys Lys Ile Arg Thr
                245                 250                 255

Phe Ser Asp Ser Leu Asn Leu Asn Tyr Leu Gly Thr Ile Lys Arg Asn
            260                 265                 270

Leu Glu Ser Ile Lys Arg Ile Met Asp Lys Ile Asp Ser Ile Glu Gly
        275                 280                 285

Pro Gly Lys Leu Ile Ile Pro Asn Ile Val Lys Asp Phe Ile Glu Ile
    290                 295                 300

Phe Gly Asn Ile Glu Lys Glu Tyr Glu Phe Leu Phe Lys Ile Ala Glu
305                 310                 315                 320

Trp Asn Phe Asn Gln Lys Arg Tyr Ala Met Val Ala Ile Asn Ile Asn
                325                 330                 335

Glu Gly Leu Arg Glu Phe Val Ala Gly Ile Leu Glu Ile Glu Asp Arg
            340                 345                 350

Val Ser Asp Phe Asn Asp Glu Asn Ser Gly Ile Phe Lys Tyr Phe Lys
        355                 360                 365

Lys Ile Arg Gln Ser Ile Glu Tyr Lys Pro Asn Asn Thr Lys Gly Thr
    370                 375                 380

Phe Asp Lys Lys Glu Glu Lys Ile Tyr Lys Ile Phe Glu His Thr Arg
385                 390                 395                 400

Lys Ile Arg Asn Glu Ile Ala His Ser Lys Gly Glu Lys Asp Thr Ala
                405                 410                 415

Ile Asn Asp Val Glu Ser Leu Lys Asn Tyr Val Lys Asp Ile Asp Thr
            420                 425                 430

Ile Ile Ser Asp Lys Gly Phe Ile Lys Tyr Leu Lys Leu Lys Tyr Asn
        435                 440                 445

Val


<210> SEQ ID NO 35
<211> LENGTH: 1285
<212> TYPE: PRT
<213> ORGANISM: Unknown
<220> FEATURE:
<223> OTHER INFORMATION: Herbinix Hemicellulosilytica

<400> SEQUENCE: 35

Met Lys Leu Thr Arg Arg Arg Ile Ser Gly Asn Ser Val Asp Gln Lys
1               5                   10                  15

Ile Thr Ala Ala Phe Tyr Arg Asp Met Ser Gln Gly Leu Leu Tyr Tyr
            20                  25                  30

Asp Ser Glu Asp Asn Asp Cys Thr Asp Lys Val Ile Glu Ser Met Asp
        35                  40                  45

Phe Glu Arg Ser Trp Arg Gly Arg Ile Leu Lys Asn Gly Glu Asp Asp
    50                  55                  60

Lys Asn Pro Phe Tyr Met Phe Val Lys Gly Leu Val Gly Ser Asn Asp
65                  70                  75                  80

Lys Ile Val Cys Glu Pro Ile Asp Val Asp Ser Asp Pro Asp Asn Leu
                85                  90                  95

Asp Ile Leu Ile Asn Lys Asn Leu Thr Gly Phe Gly Arg Asn Leu Lys
            100                 105                 110

Ala Pro Asp Ser Asn Asp Thr Leu Glu Asn Leu Ile Arg Lys Ile Gln
        115                 120                 125
```

```
Ala Gly Ile Pro Glu Glu Glu Val Leu Pro Glu Leu Lys Lys Ile Lys
    130                 135                 140

Glu Met Ile Gln Lys Asp Ile Val Asn Arg Lys Glu Gln Leu Leu Lys
145                 150                 155                 160

Ser Ile Lys Asn Asn Arg Ile Pro Phe Ser Leu Glu Gly Ser Lys Leu
                165                 170                 175

Val Pro Ser Thr Lys Lys Met Lys Trp Leu Phe Lys Leu Ile Asp Val
            180                 185                 190

Pro Asn Lys Thr Phe Asn Glu Lys Met Leu Glu Lys Tyr Trp Glu Ile
        195                 200                 205

Tyr Asp Tyr Asp Lys Leu Lys Ala Asn Ile Thr Asn Arg Leu Asp Lys
    210                 215                 220

Thr Asp Lys Lys Ala Arg Ser Ile Ser Arg Ala Val Ser Glu Glu Leu
225                 230                 235                 240

Arg Glu Tyr His Lys Asn Leu Arg Thr Asn Tyr Asn Arg Phe Val Ser
                245                 250                 255

Gly Asp Arg Pro Ala Ala Gly Leu Asp Asn Gly Gly Ser Ala Lys Tyr
            260                 265                 270

Asn Pro Asp Lys Glu Glu Phe Leu Leu Phe Leu Lys Glu Val Glu Gln
        275                 280                 285

Tyr Phe Lys Lys Tyr Phe Pro Val Lys Ser Lys His Ser Asn Lys Ser
    290                 295                 300

Lys Asp Lys Ser Leu Val Asp Lys Tyr Lys Asn Tyr Cys Ser Tyr Lys
305                 310                 315                 320

Val Val Lys Lys Glu Val Asn Arg Ser Ile Ile Asn Gln Leu Val Ala
                325                 330                 335

Gly Leu Ile Gln Gln Gly Lys Leu Leu Tyr Tyr Phe Tyr Tyr Asn Asp
            340                 345                 350

Thr Trp Gln Glu Asp Phe Leu Asn Ser Tyr Gly Leu Ser Tyr Ile Gln
        355                 360                 365

Val Glu Glu Ala Phe Lys Lys Ser Val Met Thr Ser Leu Ser Trp Gly
    370                 375                 380

Ile Asn Arg Leu Thr Ser Phe Phe Ile Asp Asp Ser Asn Thr Val Lys
385                 390                 395                 400

Phe Asp Asp Ile Thr Thr Lys Lys Ala Lys Glu Ala Ile Glu Ser Asn
                405                 410                 415

Tyr Phe Asn Lys Leu Arg Thr Cys Ser Arg Met Gln Asp His Phe Lys
            420                 425                 430

Glu Lys Leu Ala Phe Phe Tyr Pro Val Tyr Val Lys Asp Lys Lys Asp
        435                 440                 445

Arg Pro Asp Asp Asp Ile Glu Asn Leu Ile Val Leu Val Lys Asn Ala
    450                 455                 460

Ile Glu Ser Val Ser Tyr Leu Arg Asn Arg Thr Phe His Phe Lys Glu
465                 470                 475                 480

Ser Ser Leu Leu Glu Leu Leu Lys Glu Leu Asp Asp Lys Asn Ser Gly
                485                 490                 495

Gln Asn Lys Ile Asp Tyr Ser Val Ala Ala Glu Phe Ile Lys Arg Asp
            500                 505                 510

Ile Glu Asn Leu Tyr Asp Val Phe Arg Glu Gln Ile Arg Ser Leu Gly
        515                 520                 525

Ile Ala Glu Tyr Tyr Lys Ala Asp Met Ile Ser Asp Cys Phe Lys Thr
    530                 535                 540
```

```
Cys Gly Leu Glu Phe Ala Leu Tyr Ser Pro Lys Asn Ser Leu Met Pro
545                 550                 555                 560

Ala Phe Lys Asn Val Tyr Lys Arg Gly Ala Asn Leu Asn Lys Ala Tyr
                565                 570                 575

Ile Arg Asp Lys Gly Pro Lys Glu Thr Gly Asp Gln Gly Gln Asn Ser
            580                 585                 590

Tyr Lys Ala Leu Glu Glu Tyr Arg Glu Leu Thr Trp Tyr Ile Glu Val
        595                 600                 605

Lys Asn Asn Asp Gln Ser Tyr Asn Ala Tyr Lys Asn Leu Leu Gln Leu
    610                 615                 620

Ile Tyr Tyr His Ala Phe Leu Pro Glu Val Arg Glu Asn Glu Ala Leu
625                 630                 635                 640

Ile Thr Asp Phe Ile Asn Arg Thr Lys Glu Trp Asn Arg Lys Glu Thr
                645                 650                 655

Glu Glu Arg Leu Asn Thr Lys Asn Asn Lys Lys His Lys Asn Phe Asp
            660                 665                 670

Glu Asn Asp Asp Ile Thr Val Asn Thr Tyr Arg Tyr Glu Ser Ile Pro
        675                 680                 685

Asp Tyr Gln Gly Glu Ser Leu Asp Asp Tyr Leu Lys Val Leu Gln Arg
    690                 695                 700

Lys Gln Met Ala Arg Ala Lys Glu Val Asn Glu Lys Glu Glu Gly Asn
705                 710                 715                 720

Asn Asn Tyr Ile Gln Phe Ile Arg Asp Val Val Val Trp Ala Phe Gly
                725                 730                 735

Ala Tyr Leu Glu Asn Lys Leu Lys Asn Tyr Lys Asn Glu Leu Gln Pro
            740                 745                 750

Pro Leu Ser Lys Glu Asn Ile Gly Leu Asn Asp Thr Leu Lys Glu Leu
        755                 760                 765

Phe Pro Glu Glu Lys Val Lys Ser Pro Phe Asn Ile Lys Cys Arg Phe
    770                 775                 780

Ser Ile Ser Thr Phe Ile Asp Asn Lys Gly Lys Ser Thr Asp Asn Thr
785                 790                 795                 800

Ser Ala Glu Ala Val Lys Thr Asp Gly Lys Glu Asp Glu Lys Asp Lys
                805                 810                 815

Lys Asn Ile Lys Arg Lys Asp Leu Leu Cys Phe Tyr Leu Phe Leu Arg
            820                 825                 830

Leu Leu Asp Glu Asn Glu Ile Cys Lys Leu Gln His Gln Phe Ile Lys
        835                 840                 845

Tyr Arg Cys Ser Leu Lys Glu Arg Arg Phe Pro Gly Asn Arg Thr Lys
    850                 855                 860

Leu Glu Lys Glu Thr Glu Leu Leu Ala Glu Leu Glu Glu Leu Met Glu
865                 870                 875                 880

Leu Val Arg Phe Thr Met Pro Ser Ile Pro Glu Ile Ser Ala Lys Ala
                885                 890                 895

Glu Ser Gly Tyr Asp Thr Met Ile Lys Lys Tyr Phe Lys Asp Phe Ile
            900                 905                 910

Glu Lys Lys Val Phe Lys Asn Pro Lys Thr Ser Asn Leu Tyr Tyr His
        915                 920                 925

Ser Asp Ser Lys Thr Pro Val Thr Arg Lys Tyr Met Ala Leu Leu Met
    930                 935                 940

Arg Ser Ala Pro Leu His Leu Tyr Lys Asp Ile Phe Lys Gly Tyr Tyr
945                 950                 955                 960

Leu Ile Thr Lys Lys Glu Cys Leu Glu Tyr Ile Lys Leu Ser Asn Ile
```

```
                965                 970                 975

Ile Lys Asp Tyr Gln Asn Ser Leu Asn Glu Leu His Glu Gln Leu Glu
            980                 985                 990

Arg Ile Lys Leu Lys Ser Glu Lys  Gln Asn Gly Lys Asp  Ser Leu Tyr
        995                 1000                1005

Leu Asp  Lys Lys Asp Phe Tyr  Lys Val Lys Glu Tyr  Val Glu Asn
    1010                1015                1020

Leu Glu  Gln Val Ala Arg Tyr  Lys His Leu Gln His  Lys Ile Asn
    1025                1030                1035

Phe Glu  Ser Leu Tyr Arg Ile  Phe Arg Ile His Val  Asp Ile Ala
    1040                1045                1050

Ala Arg  Met Val Gly Tyr Thr  Gln Asp Trp Glu Arg  Asp Met His
    1055                1060                1065

Phe Leu  Phe Lys Ala Leu Val  Tyr Asn Gly Val Leu  Glu Glu Arg
    1070                1075                1080

Arg Phe  Glu Ala Ile Phe Asn  Asn Asn Asp Asp Asn  Asn Asp Gly
    1085                1090                1095

Arg Ile  Val Lys Lys Ile Gln  Asn Asn Leu Asn Asn  Lys Asn Arg
    1100                1105                1110

Glu Leu  Val Ser Met Leu Cys  Trp Asn Lys Lys Leu  Asn Lys Asn
    1115                1120                1125

Glu Phe  Gly Ala Ile Ile Trp  Lys Arg Asn Pro Ile  Ala His Leu
    1130                1135                1140

Asn His  Phe Thr Gln Thr Glu  Gln Asn Ser Lys Ser  Ser Leu Glu
    1145                1150                1155

Ser Leu  Ile Asn Ser Leu Arg  Ile Leu Leu Ala Tyr  Asp Arg Lys
    1160                1165                1170

Arg Gln  Asn Ala Val Thr Lys  Thr Ile Asn Asp Leu  Leu Leu Asn
    1175                1180                1185

Asp Tyr  His Ile Arg Ile Lys  Trp Glu Gly Arg Val  Asp Glu Gly
    1190                1195                1200

Gln Ile  Tyr Phe Asn Ile Lys  Glu Lys Glu Asp Ile  Glu Asn Glu
    1205                1210                1215

Pro Ile  Ile His Leu Lys His  Leu His Lys Lys Asp  Cys Tyr Ile
    1220                1225                1230

Tyr Lys  Asn Ser Tyr Met Phe  Asp Lys Gln Lys Glu  Trp Ile Cys
    1235                1240                1245

Asn Gly  Ile Lys Glu Glu Val  Tyr Asp Lys Ser Ile  Leu Lys Cys
    1250                1255                1260

Ile Gly  Asn Leu Phe Lys Phe  Asp Tyr Glu Asp Lys  Asn Lys Ser
    1265                1270                1275

Ser Ala  Asn Pro Lys His Thr
    1280                1285


<210> SEQ ID NO 36
<211> LENGTH: 1180
<212> TYPE: PRT
<213> ORGANISM: Unknown
<220> FEATURE:
<223> OTHER INFORMATION: Leptotrichia Wadei

<400> SEQUENCE: 36

Met Lys Ile Thr Lys Ile Asp Gly Val Ser His Tyr Lys Lys Gln Asp
1               5                   10                  15

Lys Gly Ile Leu Lys Lys Lys Trp Lys Asp Leu Asp Glu Arg Lys Gln
```

```
            20                  25                  30

Arg Glu Lys Ile Glu Ala Arg Tyr Asn Lys Gln Ile Glu Ser Lys Ile
        35                  40                  45

Tyr Lys Glu Phe Phe Arg Leu Lys Asn Lys Lys Arg Ile Glu Lys Glu
    50                  55                  60

Glu Asp Gln Asn Ile Lys Ser Leu Tyr Phe Phe Ile Lys Glu Leu Tyr
65                  70                  75                  80

Leu Asn Glu Lys Asn Glu Glu Trp Glu Leu Lys Asn Ile Asn Leu Glu
                85                  90                  95

Ile Leu Asp Asp Lys Glu Arg Val Ile Lys Gly Tyr Lys Phe Lys Glu
            100                 105                 110

Asp Val Tyr Phe Phe Lys Glu Gly Tyr Lys Glu Tyr Tyr Leu Arg Ile
        115                 120                 125

Leu Phe Asn Asn Leu Ile Glu Lys Val Gln Asn Glu Asn Arg Glu Lys
    130                 135                 140

Val Arg Lys Asn Lys Glu Phe Leu Asp Leu Lys Glu Ile Phe Lys Lys
145                 150                 155                 160

Tyr Lys Asn Arg Lys Ile Asp Leu Leu Leu Lys Ser Ile Asn Asn Asn
                165                 170                 175

Lys Ile Asn Leu Glu Tyr Lys Lys Glu Asn Val Asn Glu Glu Ile Tyr
            180                 185                 190

Gly Ile Asn Pro Thr Asn Asp Arg Glu Met Thr Phe Tyr Glu Leu Leu
        195                 200                 205

Lys Glu Ile Ile Glu Lys Lys Asp Glu Gln Lys Ser Ile Leu Glu Glu
    210                 215                 220

Lys Leu Asp Asn Phe Asp Ile Thr Asn Phe Leu Glu Asn Ile Glu Lys
225                 230                 235                 240

Ile Phe Asn Glu Glu Thr Glu Ile Asn Ile Ile Lys Gly Lys Val Leu
                245                 250                 255

Asn Glu Leu Arg Glu Tyr Ile Lys Glu Lys Glu Glu Asn Asn Ser Asp
            260                 265                 270

Asn Lys Leu Lys Gln Ile Tyr Asn Leu Glu Leu Lys Lys Tyr Ile Glu
        275                 280                 285

Asn Asn Phe Ser Tyr Lys Lys Gln Lys Ser Lys Ser Lys Asn Gly Lys
    290                 295                 300

Asn Asp Tyr Leu Tyr Leu Asn Phe Leu Lys Lys Ile Met Phe Ile Glu
305                 310                 315                 320

Glu Val Asp Glu Lys Lys Glu Ile Asn Lys Glu Lys Phe Lys Asn Lys
                325                 330                 335

Ile Asn Ser Asn Phe Lys Asn Leu Phe Val Gln His Ile Leu Asp Tyr
            340                 345                 350

Gly Lys Leu Leu Tyr Tyr Lys Glu Asn Asp Glu Tyr Ile Lys Asn Thr
        355                 360                 365

Gly Gln Leu Glu Thr Lys Asp Leu Glu Tyr Ile Lys Thr Lys Glu Thr
    370                 375                 380

Leu Ile Arg Lys Met Ala Val Leu Val Ser Phe Ala Ala Asn Ser Tyr
385                 390                 395                 400

Tyr Asn Leu Phe Gly Arg Val Ser Gly Asp Ile Leu Gly Thr Glu Val
                405                 410                 415

Val Lys Ser Ser Lys Thr Asn Val Ile Lys Val Gly Ser His Ile Phe
            420                 425                 430

Lys Glu Lys Met Leu Asn Tyr Phe Phe Asp Phe Glu Ile Phe Asp Ala
        435                 440                 445
```

```
Asn Lys Ile Val Glu Ile Leu Glu Ser Ile Ser Tyr Ser Ile Tyr Asn
    450                 455                 460

Val Arg Asn Gly Val Gly His Phe Asn Lys Leu Ile Leu Gly Lys Tyr
465                 470                 475                 480

Lys Lys Lys Asp Ile Asn Thr Asn Lys Arg Ile Glu Glu Asp Leu Asn
                485                 490                 495

Asn Asn Glu Glu Ile Lys Gly Tyr Phe Ile Lys Lys Arg Gly Glu Ile
            500                 505                 510

Glu Arg Lys Val Lys Glu Lys Phe Leu Ser Asn Asn Leu Gln Tyr Tyr
        515                 520                 525

Tyr Ser Lys Glu Lys Ile Glu Asn Tyr Phe Glu Val Tyr Glu Phe Glu
    530                 535                 540

Ile Leu Lys Arg Lys Ile Pro Phe Ala Pro Asn Phe Lys Arg Ile Ile
545                 550                 555                 560

Lys Lys Gly Glu Asp Leu Phe Asn Asn Lys Asn Asn Lys Lys Tyr Glu
                565                 570                 575

Tyr Phe Lys Asn Phe Asp Lys Asn Ser Ala Glu Glu Lys Lys Glu Phe
            580                 585                 590

Leu Lys Thr Arg Asn Phe Leu Leu Lys Glu Leu Tyr Tyr Asn Asn Phe
        595                 600                 605

Tyr Lys Glu Phe Leu Ser Lys Lys Glu Glu Phe Glu Lys Ile Val Leu
    610                 615                 620

Glu Val Lys Glu Glu Lys Lys Ser Arg Gly Asn Ile Asn Asn Lys Lys
625                 630                 635                 640

Ser Gly Val Ser Phe Gln Ser Ile Asp Asp Tyr Asp Thr Lys Ile Asn
                645                 650                 655

Ile Ser Asp Tyr Ile Ala Ser Ile His Lys Lys Glu Met Glu Arg Val
            660                 665                 670

Glu Lys Tyr Asn Glu Glu Lys Gln Lys Asp Thr Ala Lys Tyr Ile Arg
        675                 680                 685

Asp Phe Val Glu Glu Ile Phe Leu Thr Gly Phe Ile Asn Tyr Leu Glu
    690                 695                 700

Lys Asp Lys Arg Leu His Phe Leu Lys Glu Glu Phe Ser Ile Leu Cys
705                 710                 715                 720

Asn Asn Asn Asn Asn Val Val Asp Phe Asn Ile Asn Ile Asn Glu Glu
                725                 730                 735

Lys Ile Lys Glu Phe Leu Lys Glu Asn Asp Ser Lys Thr Leu Asn Leu
            740                 745                 750

Tyr Leu Phe Phe Asn Met Ile Asp Ser Lys Arg Ile Ser Glu Phe Arg
        755                 760                 765

Asn Glu Leu Val Lys Tyr Lys Gln Phe Thr Lys Lys Arg Leu Asp Glu
    770                 775                 780

Glu Lys Glu Phe Leu Gly Ile Lys Ile Glu Leu Tyr Glu Thr Leu Ile
785                 790                 795                 800

Glu Phe Val Ile Leu Thr Arg Glu Lys Leu Asp Thr Lys Lys Ser Glu
                805                 810                 815

Glu Ile Asp Ala Trp Leu Val Asp Lys Leu Tyr Val Lys Asp Ser Asn
            820                 825                 830

Glu Tyr Lys Glu Tyr Glu Glu Ile Leu Lys Leu Phe Val Asp Glu Lys
        835                 840                 845

Ile Leu Ser Ser Lys Glu Ala Pro Tyr Tyr Ala Thr Asp Asn Lys Thr
    850                 855                 860
```

Pro Ile Leu Leu Ser Asn Phe Glu Lys Thr Arg Lys Tyr Gly Thr Gln
865 870 875 880

Ser Phe Leu Ser Glu Ile Gln Ser Asn Tyr Lys Tyr Ser Lys Val Glu
885 890 895

Lys Glu Asn Ile Glu Asp Tyr Asn Lys Lys Glu Glu Ile Glu Gln Lys
900 905 910

Lys Lys Ser Asn Ile Glu Lys Leu Gln Asp Leu Lys Val Glu Leu His
915 920 925

Lys Lys Trp Glu Gln Asn Lys Ile Thr Glu Lys Glu Ile Glu Lys Tyr
930 935 940

Asn Asn Thr Thr Arg Lys Ile Asn Glu Tyr Asn Tyr Leu Lys Asn Lys
945 950 955 960

Glu Glu Leu Gln Asn Val Tyr Leu Leu His Glu Met Leu Ser Asp Leu
965 970 975

Leu Ala Arg Asn Val Ala Phe Phe Asn Lys Trp Glu Arg Asp Phe Lys
980 985 990

Phe Ile Val Ile Ala Ile Lys Gln Phe Leu Arg Glu Asn Asp Lys Glu
995 1000 1005

Lys Val Asn Glu Phe Leu Asn Pro Pro Asp Asn Ser Lys Gly Lys
1010 1015 1020

Lys Val Tyr Phe Ser Val Ser Lys Tyr Lys Asn Thr Val Glu Asn
1025 1030 1035

Ile Asp Gly Ile His Lys Asn Phe Met Asn Leu Ile Phe Leu Asn
1040 1045 1050

Asn Lys Phe Met Asn Arg Lys Ile Asp Lys Met Asn Cys Ala Ile
1055 1060 1065

Trp Val Tyr Phe Arg Asn Tyr Ile Ala His Phe Leu His Leu His
1070 1075 1080

Thr Lys Asn Glu Lys Ile Ser Leu Ile Ser Gln Met Asn Leu Leu
1085 1090 1095

Ile Lys Leu Phe Ser Tyr Asp Lys Lys Val Gln Asn His Ile Leu
1100 1105 1110

Lys Ser Thr Lys Thr Leu Leu Glu Lys Tyr Asn Ile Gln Ile Asn
1115 1120 1125

Phe Glu Ile Ser Asn Asp Lys Asn Glu Val Phe Lys Tyr Lys Ile
1130 1135 1140

Lys Asn Arg Leu Tyr Ser Lys Lys Gly Lys Met Leu Gly Lys Asn
1145 1150 1155

Asn Lys Phe Glu Ile Leu Glu Asn Glu Phe Leu Glu Asn Val Lys
1160 1165 1170

Ala Met Leu Glu Tyr Ser Glu
1175 1180

<210> SEQ ID NO 37
<211> LENGTH: 1154
<212> TYPE: PRT
<213> ORGANISM: Unknown
<220> FEATURE:
<223> OTHER INFORMATION: Paludibacter Propionicigenes

<400> SEQUENCE: 37

Met Arg Val Ser Lys Val Lys Val Lys Asp Gly Gly Lys Asp Lys Met
1 5 10 15

Val Leu Val His Arg Lys Thr Thr Gly Ala Gln Leu Val Tyr Ser Gly
20 25 30

```
Gln Pro Val Ser Asn Glu Thr Ser Asn Ile Leu Pro Glu Lys Lys Arg
        35                  40                  45

Gln Ser Phe Asp Leu Ser Thr Leu Asn Lys Thr Ile Ile Lys Phe Asp
    50                  55                  60

Thr Ala Lys Lys Gln Lys Leu Asn Val Asp Gln Tyr Lys Ile Val Glu
65                  70                  75                  80

Lys Ile Phe Lys Tyr Pro Lys Gln Glu Leu Pro Lys Gln Ile Lys Ala
                85                  90                  95

Glu Glu Ile Leu Pro Phe Leu Asn His Lys Phe Gln Glu Pro Val Lys
            100                 105                 110

Tyr Trp Lys Asn Gly Lys Glu Glu Ser Phe Asn Leu Thr Leu Leu Ile
        115                 120                 125

Val Glu Ala Val Gln Ala Gln Asp Lys Arg Lys Leu Gln Pro Tyr Tyr
    130                 135                 140

Asp Trp Lys Thr Trp Tyr Ile Gln Thr Lys Ser Asp Leu Leu Lys Lys
145                 150                 155                 160

Ser Ile Glu Asn Asn Arg Ile Asp Leu Thr Glu Asn Leu Ser Lys Arg
                165                 170                 175

Lys Lys Ala Leu Leu Ala Trp Glu Thr Glu Phe Thr Ala Ser Gly Ser
            180                 185                 190

Ile Asp Leu Thr His Tyr His Lys Val Tyr Met Thr Asp Val Leu Cys
        195                 200                 205

Lys Met Leu Gln Asp Val Lys Pro Leu Thr Asp Asp Lys Gly Lys Ile
    210                 215                 220

Asn Thr Asn Ala Tyr His Arg Gly Leu Lys Lys Ala Leu Gln Asn His
225                 230                 235                 240

Gln Pro Ala Ile Phe Gly Thr Arg Glu Val Pro Asn Glu Ala Asn Arg
                245                 250                 255

Ala Asp Asn Gln Leu Ser Ile Tyr His Leu Glu Val Val Lys Tyr Leu
            260                 265                 270

Glu His Tyr Phe Pro Ile Lys Thr Ser Lys Arg Arg Asn Thr Ala Asp
        275                 280                 285

Asp Ile Ala His Tyr Leu Lys Ala Gln Thr Leu Lys Thr Thr Ile Glu
    290                 295                 300

Lys Gln Leu Val Asn Ala Ile Arg Ala Asn Ile Ile Gln Gln Gly Lys
305                 310                 315                 320

Thr Asn His His Glu Leu Lys Ala Asp Thr Thr Ser Asn Asp Leu Ile
                325                 330                 335

Arg Ile Lys Thr Asn Glu Ala Phe Val Leu Asn Leu Thr Gly Thr Cys
            340                 345                 350

Ala Phe Ala Ala Asn Asn Ile Arg Asn Met Val Asp Asn Glu Gln Thr
        355                 360                 365

Asn Asp Ile Leu Gly Lys Gly Asp Phe Ile Lys Ser Leu Leu Lys Asp
    370                 375                 380

Asn Thr Asn Ser Gln Leu Tyr Ser Phe Phe Phe Gly Glu Gly Leu Ser
385                 390                 395                 400

Thr Asn Lys Ala Glu Lys Glu Thr Gln Leu Trp Gly Ile Arg Gly Ala
                405                 410                 415

Val Gln Gln Ile Arg Asn Asn Val Asn His Tyr Lys Lys Asp Ala Leu
            420                 425                 430

Lys Thr Val Phe Asn Ile Ser Asn Phe Glu Asn Pro Thr Ile Thr Asp
        435                 440                 445

Pro Lys Gln Gln Thr Asn Tyr Ala Asp Thr Ile Tyr Lys Ala Arg Phe
```

```
    450                 455                 460

Ile Asn Glu Leu Glu Lys Ile Pro Glu Ala Phe Ala Gln Gln Leu Lys
465                 470                 475                 480

Thr Gly Gly Ala Val Ser Tyr Tyr Thr Ile Glu Asn Leu Lys Ser Leu
                485                 490                 495

Leu Thr Thr Phe Gln Phe Ser Leu Cys Arg Ser Thr Ile Pro Phe Ala
            500                 505                 510

Pro Gly Phe Lys Lys Val Phe Asn Gly Gly Ile Asn Tyr Gln Asn Ala
        515                 520                 525

Lys Gln Asp Glu Ser Phe Tyr Glu Leu Met Leu Glu Gln Tyr Leu Arg
    530                 535                 540

Lys Glu Asn Phe Ala Glu Glu Ser Tyr Asn Ala Arg Tyr Phe Met Leu
545                 550                 555                 560

Lys Leu Ile Tyr Asn Asn Leu Phe Leu Pro Gly Phe Thr Thr Asp Arg
                565                 570                 575

Lys Ala Phe Ala Asp Ser Val Gly Phe Val Gln Met Gln Asn Lys Lys
            580                 585                 590

Gln Ala Glu Lys Val Asn Pro Arg Lys Lys Glu Ala Tyr Ala Phe Glu
        595                 600                 605

Ala Val Arg Pro Met Thr Ala Ala Asp Ser Ile Ala Asp Tyr Met Ala
    610                 615                 620

Tyr Val Gln Ser Glu Leu Met Gln Glu Gln Asn Lys Lys Glu Glu Lys
625                 630                 635                 640

Val Ala Glu Glu Thr Arg Ile Asn Phe Glu Lys Phe Val Leu Gln Val
                645                 650                 655

Phe Ile Lys Gly Phe Asp Ser Phe Leu Arg Ala Lys Glu Phe Asp Phe
            660                 665                 670

Val Gln Met Pro Gln Pro Gln Leu Thr Ala Thr Ala Ser Asn Gln Gln
        675                 680                 685

Lys Ala Asp Lys Leu Asn Gln Leu Glu Ala Ser Ile Thr Ala Asp Cys
    690                 695                 700

Lys Leu Thr Pro Gln Tyr Ala Lys Ala Asp Asp Ala Thr His Ile Ala
705                 710                 715                 720

Phe Tyr Val Phe Cys Lys Leu Leu Asp Ala Ala His Leu Ser Asn Leu
                725                 730                 735

Arg Asn Glu Leu Ile Lys Phe Arg Glu Ser Val Asn Glu Phe Lys Phe
            740                 745                 750

His His Leu Leu Glu Ile Ile Glu Ile Cys Leu Leu Ser Ala Asp Val
        755                 760                 765

Val Pro Thr Asp Tyr Arg Asp Leu Tyr Ser Ser Glu Ala Asp Cys Leu
    770                 775                 780

Ala Arg Leu Arg Pro Phe Ile Glu Gln Gly Ala Asp Ile Thr Asn Trp
785                 790                 795                 800

Ser Asp Leu Phe Val Gln Ser Asp Lys His Ser Pro Val Ile His Ala
                805                 810                 815

Asn Ile Glu Leu Ser Val Lys Tyr Gly Thr Thr Lys Leu Leu Glu Gln
            820                 825                 830

Ile Ile Asn Lys Asp Thr Gln Phe Lys Thr Thr Glu Ala Asn Phe Thr
        835                 840                 845

Ala Trp Asn Thr Ala Gln Lys Ser Ile Glu Gln Leu Ile Lys Gln Arg
    850                 855                 860

Glu Asp His His Glu Gln Trp Val Lys Ala Lys Asn Ala Asp Asp Lys
865                 870                 875                 880
```

```
Glu Lys Gln Glu Arg Lys Arg Glu Lys Ser Asn Phe Ala Gln Lys Phe
                885                 890                 895

Ile Glu Lys His Gly Asp Asp Tyr Leu Asp Ile Cys Asp Tyr Ile Asn
            900                 905                 910

Thr Tyr Asn Trp Leu Asp Asn Lys Met His Phe Val His Leu Asn Arg
        915                 920                 925

Leu His Gly Leu Thr Ile Glu Leu Leu Gly Arg Met Ala Gly Phe Val
    930                 935                 940

Ala Leu Phe Asp Arg Asp Phe Gln Phe Phe Asp Glu Gln Gln Ile Ala
945                 950                 955                 960

Asp Glu Phe Lys Leu His Gly Phe Val Asn Leu His Ser Ile Asp Lys
                965                 970                 975

Lys Leu Asn Glu Val Pro Thr Lys Lys Ile Lys Glu Ile Tyr Asp Ile
            980                 985                 990

Arg Asn Lys Ile Ile Gln Ile Asn  Gly Asn Lys Ile Asn  Glu Ser Val
        995                 1000                1005

Arg Ala  Asn Leu Ile Gln Phe  Ile Ser Ser Lys Arg  Asn Tyr Tyr
    1010                1015                1020

Asn Asn  Ala Phe Leu His Val  Ser Asn Asp Glu Ile  Lys Glu Lys
    1025                1030                1035

Gln Met  Tyr Asp Ile Arg Asn  His Ile Ala His Phe  Asn Tyr Leu
    1040                1045                1050

Thr Lys  Asp Ala Ala Asp Phe  Ser Leu Ile Asp Leu  Ile Asn Glu
    1055                1060                1065

Leu Arg  Glu Leu Leu His Tyr  Asp Arg Lys Leu Lys  Asn Ala Val
    1070                1075                1080

Ser Lys  Ala Phe Ile Asp Leu  Phe Asp Lys His Gly  Met Ile Leu
    1085                1090                1095

Lys Leu  Lys Leu Asn Ala Asp  His Lys Leu Lys Val  Glu Ser Leu
    1100                1105                1110

Glu Pro  Lys Lys Ile Tyr His  Leu Gly Ser Ser Ala  Lys Asp Lys
    1115                1120                1125

Pro Glu  Tyr Gln Tyr Cys Thr  Asn Gln Val Met Met  Ala Tyr Cys
    1130                1135                1140

Asn Met  Cys Arg Ser Leu Leu  Glu Met Lys Lys
    1145                1150
```

<210> SEQ ID NO 38
<211> LENGTH: 1120
<212> TYPE: PRT
<213> ORGANISM: Unknown
<220> FEATURE:
<223> OTHER INFORMATION: Listeria Seeligeri

<400> SEQUENCE: 38

```
Met Trp Ile Ser Ile Lys Thr Leu Ile His His Leu Gly Val Leu Phe
1               5                   10                  15

Phe Cys Asp Tyr Met Tyr Asn Arg Arg Glu Lys Lys Ile Ile Glu Val
            20                  25                  30

Lys Thr Met Arg Ile Thr Lys Val Glu Val Asp Arg Lys Lys Val Leu
        35                  40                  45

Ile Ser Arg Asp Lys Asn Gly Gly Lys Leu Val Tyr Glu Asn Glu Met
    50                  55                  60

Gln Asp Asn Thr Glu Gln Ile Met His His Lys Lys Ser Ser Phe Tyr
65                  70                  75                  80
```

```
Lys Ser Val Val Asn Lys Thr Ile Cys Arg Pro Glu Gln Lys Gln Met
                85                  90                  95

Lys Lys Leu Val His Gly Leu Leu Gln Glu Asn Ser Gln Glu Lys Ile
            100                 105                 110

Lys Val Ser Asp Val Thr Lys Leu Asn Ile Ser Asn Phe Leu Asn His
        115                 120                 125

Arg Phe Lys Lys Ser Leu Tyr Tyr Phe Pro Glu Asn Ser Pro Asp Lys
    130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
                165                 170                 175

Lys Asp Met Glu Leu Tyr Ile Asn Trp Ala Glu Asn Tyr Ile Ser Ser
            180                 185                 190

Lys Thr Lys Leu Ile Lys Lys Ser Ile Arg Asn Asn Arg Ile Gln Ser
        195                 200                 205

Thr Glu Ser Arg Ser Gly Gln Leu Met Asp Arg Tyr Met Lys Asp Ile
    210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
                245                 250                 255

Lys Lys Asn Asp Lys Glu Ile Asn Tyr Lys Leu Lys Ser Thr Leu Gln
            260                 265                 270

Asn His Glu Arg Gln Ile Ile Glu Glu Leu Lys Glu Asn Ser Glu Leu
        275                 280                 285

Asn Gln Phe Asn Ile Glu Ile Arg Lys His Leu Glu Thr Tyr Phe Pro
    290                 295                 300

Ile Lys Lys Thr Asn Arg Lys Val Gly Asp Ile Arg Asn Leu Glu Ile
305                 310                 315                 320

Gly Glu Ile Gln Lys Ile Val Asn His Arg Leu Lys Asn Lys Ile Val
                325                 330                 335

Gln Arg Ile Leu Gln Glu Gly Lys Leu Ala Ser Tyr Glu Ile Glu Ser
            340                 345                 350

Thr Val Asn Ser Asn Ser Leu Gln Lys Ile Lys Ile Glu Glu Ala Phe
        355                 360                 365

Ala Leu Lys Phe Ile Asn Ala Cys Leu Phe Ala Ser Asn Asn Leu Arg
    370                 375                 380

Asn Met Val Tyr Pro Val Cys Lys Lys Asp Ile Leu Met Ile Gly Glu
385                 390                 395                 400

Phe Lys Asn Ser Phe Lys Glu Ile Lys His Lys Lys Phe Ile Arg Gln
                405                 410                 415

Trp Ser Gln Phe Phe Ser Gln Glu Ile Thr Val Asp Asp Ile Glu Leu
            420                 425                 430

Ala Ser Trp Gly Leu Arg Gly Ala Ile Ala Pro Ile Arg Asn Glu Ile
        435                 440                 445

Ile His Leu Lys Lys His Ser Trp Lys Lys Phe Phe Asn Asn Pro Thr
    450                 455                 460

Phe Lys Val Lys Lys Ser Lys Ile Ile Asn Gly Lys Thr Lys Asp Val
465                 470                 475                 480

Thr Ser Glu Phe Leu Tyr Lys Glu Thr Leu Phe Lys Asp Tyr Phe Tyr
                485                 490                 495
```

```
Ser Glu Leu Asp Ser Val Pro Glu Leu Ile Ile Asn Lys Met Glu Ser
            500                 505                 510

Ser Lys Ile Leu Asp Tyr Tyr Ser Ser Asp Gln Leu Asn Gln Val Phe
        515                 520                 525

Thr Ile Pro Asn Phe Glu Leu Ser Leu Leu Thr Ser Ala Val Pro Phe
    530                 535                 540

Ala Pro Ser Phe Lys Arg Val Tyr Leu Lys Gly Phe Asp Tyr Gln Asn
545                 550                 555                 560

Gln Asp Glu Ala Gln Pro Asp Tyr Asn Leu Lys Leu Asn Ile Tyr Asn
                565                 570                 575

Glu Lys Ala Phe Asn Ser Glu Ala Phe Gln Ala Gln Tyr Ser Leu Phe
            580                 585                 590

Lys Met Val Tyr Tyr Gln Val Phe Leu Pro Gln Phe Thr Thr Asn Asn
        595                 600                 605

Asp Leu Phe Lys Ser Ser Val Asp Phe Ile Leu Thr Leu Asn Lys Glu
    610                 615                 620

Arg Lys Gly Tyr Ala Lys Ala Phe Gln Asp Ile Arg Lys Met Asn Lys
625                 630                 635                 640

Asp Glu Lys Pro Ser Glu Tyr Met Ser Tyr Ile Gln Ser Gln Leu Met
                645                 650                 655

Leu Tyr Gln Lys Lys Gln Glu Glu Lys Glu Lys Ile Asn His Phe Glu
            660                 665                 670

Lys Phe Ile Asn Gln Val Phe Ile Lys Gly Phe Asn Ser Phe Ile Glu
        675                 680                 685

Lys Asn Arg Leu Thr Tyr Ile Cys His Pro Thr Lys Asn Thr Val Pro
    690                 695                 700

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
                725                 730                 735

Ser Glu Leu Arg Asn Glu Met Ile Lys Phe Ser Cys Ser Leu Gln Ser
            740                 745                 750

Thr Glu Glu Ile Ser Thr Phe Thr Lys Ala Arg Glu Val Ile Gly Leu
        755                 760                 765

Ala Leu Leu Asn Gly Glu Lys Gly Cys Asn Asp Trp Lys Glu Leu Phe
    770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
                805                 810                 815

Val Ile Asn Arg Ser Ile Asp Leu Val Lys Lys Tyr Gly Thr Glu Thr
            820                 825                 830

Ile Leu Glu Lys Leu Phe Ser Ser Ser Asp Asp Tyr Lys Val Ser Ala
        835                 840                 845

Lys Asp Ile Ala Lys Leu His Glu Tyr Asp Val Thr Glu Lys Ile Ala
    850                 855                 860

Gln Gln Glu Ser Leu His Lys Gln Trp Ile Glu Lys Pro Gly Leu Ala
865                 870                 875                 880

Arg Asp Ser Ala Trp Thr Lys Lys Tyr Gln Asn Val Ile Asn Asp Ile
                885                 890                 895

Ser Asn Tyr Gln Trp Ala Lys Thr Lys Val Glu Leu Thr Gln Val Arg
            900                 905                 910

His Leu His Gln Leu Thr Ile Asp Leu Leu Ser Arg Leu Ala Gly Tyr
```

```
        915                 920                 925

Met Ser Ile Ala Asp Arg Asp Phe Gln Phe Ser Ser Asn Tyr Ile Leu
    930                 935                 940

Glu Arg Glu Asn Ser Glu Tyr Arg Val Thr Ser Trp Ile Leu Leu Ser
945                 950                 955                 960

Glu Asn Lys Asn Lys Asn Lys Tyr Asn Asp Tyr Glu Leu Tyr Asn Leu
                965                 970                 975

Lys Asn Ala Ser Ile Lys Val Ser Ser Lys Asn Asp Pro Gln Leu Lys
            980                 985                 990

Val Asp Leu Lys Gln Leu Arg Leu  Thr Leu Glu Tyr Leu  Glu Leu Phe
        995                 1000                 1005

Asp Asn  Arg Leu Lys Glu Lys  Arg Asn Asn Ile Ser  His Phe Asn
    1010                 1015                 1020

Tyr Leu  Asn Gly Gln Leu Gly  Asn Ser Ile Leu Glu  Leu Phe Asp
    1025                 1030                 1035

Asp Ala  Arg Asp Val Leu Ser  Tyr Asp Arg Lys Leu  Lys Asn Ala
    1040                 1045                 1050

Val Ser  Lys Ser Leu Lys Glu  Ile Leu Ser Ser His  Gly Met Glu
    1055                 1060                 1065

Val Thr  Phe Lys Pro Leu Tyr  Gln Thr Asn His His  Leu Lys Ile
    1070                 1075                 1080

Asp Lys  Leu Gln Pro Lys Lys  Ile His His Leu Gly  Glu Lys Ser
    1085                 1090                 1095

Thr Val  Ser Ser Asn Gln Val  Ser Asn Glu Tyr Cys  Gln Leu Val
    1100                 1105                 1110

Arg Thr  Leu Leu Thr Met Lys
    1115                 1120
```

<210> SEQ ID NO 39
<211> LENGTH: 1232
<212> TYPE: PRT
<213> ORGANISM: Unknown
<220> FEATURE:
<223> OTHER INFORMATION: Begeyella Zoohelcum
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (357)..(358)
<223> OTHER INFORMATION: Xaa can be any naturally occurring amino acid
<220> FEATURE:
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (401)..(401)

```
<223> OTHER INFORMATION: Xaa can be any naturally occurring amino acid
<220> FEATURE:
<221> NAME/KEY: misc_feature
<222> LOCATION: (600)..(600)
<223> OTHER INFORMATION: Xaa can be any naturally occurring amino acid
<220> FEATURE:
<221> NAME/KEY: misc_feature
<222> LOCATION: (766)..(766)
<223> OTHER INFORMATION: Xaa can be any naturally occurring amino acid
<220> FEATURE:
<221> NAME/KEY: misc_feature
<222> LOCATION: (893)..(893)
<223> OTHER INFORMATION: Xaa can be any naturally occurring amino acid
<220> FEATURE:
<221> NAME/KEY: misc_feature
<222> LOCATION: (965)..(965)
<223> OTHER INFORMATION: Xaa can be any naturally occurring amino acid

<400> SEQUENCE: 39

Xaa Glu Asn Lys Thr Ser Leu Gly Asn Asn Ile Tyr Tyr Asn Pro Phe
1               5                   10                  15

Lys Pro Gln Asp Lys Ser Tyr Phe Ala Gly Tyr Phe Asn Ala Ala Xaa
            20                  25                  30

Glu Asn Thr Asp Ser Val Phe Arg Glu Leu Gly Lys Arg Leu Lys Gly
        35                  40                  45

Lys Glu Tyr Thr Ser Glu Asn Phe Phe Asp Ala Ile Phe Lys Glu Asn
    50                  55                  60

Ile Ser Leu Val Glu Tyr Glu Arg Tyr Val Lys Leu Leu Ser Asp Tyr
65                  70                  75                  80

Phe Pro Xaa Ala Arg Leu Leu Asp Lys Lys Glu Val Pro Ile Lys Glu
                85                  90                  95

Arg Lys Glu Asn Phe Lys Lys Asn Phe Lys Gly Ile Ile Lys Ala Val
            100                 105                 110

Arg Asp Leu Arg Asn Phe Tyr Thr His Lys Glu His Gly Glu Val Glu
        115                 120                 125

Ile Thr Asp Glu Ile Phe Gly Val Leu Asp Glu Xaa Leu Lys Ser Thr
    130                 135                 140

Val Leu Thr Val Lys Lys Lys Lys Val Lys Thr Asp Lys Thr Lys Glu
145                 150                 155                 160

Ile Leu Lys Lys Ser Ile Glu Lys Gln Leu Asp Ile Leu Cys Gln Lys
                165                 170                 175

Lys Leu Glu Tyr Leu Arg Asp Thr Ala Arg Lys Ile Glu Glu Lys Arg
            180                 185                 190

Arg Asn Gln Arg Glu Arg Gly Glu Lys Glu Leu Val Ala Pro Phe Lys
        195                 200                 205

Tyr Ser Asp Lys Arg Asp Asp Leu Ile Ala Ala Ile Tyr Asn Asp Ala
    210                 215                 220

Phe Asp Val Tyr Ile Asp Lys Lys Lys Asp Ser Leu Lys Glu Ser Ser
225                 230                 235                 240

Lys Ala Lys Tyr Asn Thr Lys Ser Asp Pro Gln Gln Glu Glu Gly Asp
                245                 250                 255

Leu Lys Ile Pro Ile Ser Lys Asn Gly Val Val Phe Leu Leu Ser Leu
            260                 265                 270

Phe Leu Thr Lys Gln Glu Ile His Ala Phe Lys Ser Lys Ile Ala Gly
        275                 280                 285

Phe Lys Ala Thr Val Ile Asp Glu Ala Thr Val Ser Glu Ala Thr Val
    290                 295                 300

Ser His Gly Lys Asn Ser Ile Cys Phe Xaa Ala Thr His Glu Ile Phe
305                 310                 315                 320
```

```
Ser His Leu Ala Tyr Lys Lys Leu Lys Arg Lys Val Arg Thr Ala Glu
                325                 330                 335

Ile Asn Tyr Gly Glu Ala Glu Asn Ala Glu Gln Leu Ser Val Tyr Ala
            340                 345                 350

Lys Glu Thr Leu Xaa Xaa Gln Xaa Leu Asp Glu Leu Ser Lys Val Pro
        355                 360                 365

Asp Val Val Tyr Gln Asn Leu Ser Glu Asp Val Gln Lys Thr Phe Ile
    370                 375                 380

Glu Asp Trp Asn Glu Tyr Leu Lys Glu Asn Asn Gly Asp Val Gly Thr
385                 390                 395                 400

Xaa Glu Glu Glu Gln Val Ile His Pro Val Ile Arg Lys Arg Tyr Glu
                405                 410                 415

Asp Lys Phe Asn Tyr Phe Ala Ile Arg Phe Leu Asp Glu Phe Ala Gln
            420                 425                 430

Phe Pro Thr Leu Arg Phe Gln Val His Leu Gly Asn Tyr Leu His Asp
        435                 440                 445

Ser Arg Pro Lys Glu Asn Leu Ile Ser Asp Arg Arg Ile Lys Glu Lys
    450                 455                 460

Ile Thr Val Phe Gly Arg Leu Ser Glu Leu Glu His Lys Lys Ala Leu
465                 470                 475                 480

Phe Ile Lys Asn Thr Glu Thr Asn Glu Asp Arg Glu His Tyr Trp Glu
                485                 490                 495

Ile Phe Pro Asn Pro Asn Tyr Asp Phe Pro Lys Glu Asn Ile Ser Val
            500                 505                 510

Asn Asp Lys Asp Phe Pro Ile Ala Gly Ser Ile Leu Asp Arg Glu Lys
        515                 520                 525

Gln Pro Val Ala Gly Lys Ile Gly Ile Lys Val Lys Leu Leu Asn Gln
    530                 535                 540

Gln Tyr Val Ser Glu Val Asp Lys Ala Val Lys Ala His Gln Leu Lys
545                 550                 555                 560

Gln Arg Lys Ala Ser Lys Pro Ser Ile Gln Asn Ile Ile Glu Glu Ile
                565                 570                 575

Val Pro Ile Asn Glu Ser Asn Pro Lys Glu Ala Ile Val Phe Gly Gly
            580                 585                 590

Gln Pro Thr Ala Tyr Leu Ser Xaa Asn Asp Ile His Ser Ile Leu Tyr
        595                 600                 605

Glu Phe Phe Asp Lys Trp Glu Lys Lys Lys Glu Lys Leu Glu Lys Lys
    610                 615                 620

Gly Glu Lys Glu Leu Arg Lys Glu Ile Gly Lys Glu Leu Glu Lys Lys
625                 630                 635                 640

Ile Val Gly Lys Ile Gln Ala Gln Ile Gln Gln Ile Ile Asp Lys Asp
                645                 650                 655

Thr Asn Ala Lys Ile Leu Lys Pro Tyr Gln Asp Gly Asn Ser Thr Ala
            660                 665                 670

Ile Asp Lys Glu Lys Leu Ile Lys Asp Leu Lys Gln Glu Gln Asn Ile
        675                 680                 685

Leu Gln Lys Leu Lys Asp Glu Gln Thr Val Arg Glu Lys Glu Tyr Asn
    690                 695                 700

Asp Phe Ile Ala Tyr Gln Asp Lys Asn Arg Glu Ile Asn Lys Val Arg
705                 710                 715                 720

Asp Arg Asn His Lys Gln Tyr Leu Lys Asp Asn Leu Lys Arg Lys Tyr
                725                 730                 735
```

```
Pro Glu Ala Pro Ala Arg Lys Glu Val Leu Tyr Tyr Arg Glu Lys Gly
            740                 745                 750

Lys Val Ala Val Trp Leu Ala Asn Asp Ile Lys Arg Phe Xaa Pro Thr
        755                 760                 765

Asp Phe Lys Asn Glu Trp Lys Gly Glu Gln His Ser Leu Leu Gln Lys
    770                 775                 780

Ser Leu Ala Tyr Tyr Glu Gln Cys Lys Glu Glu Leu Lys Asn Leu Leu
785                 790                 795                 800

Pro Glu Lys Val Phe Gln His Leu Pro Phe Lys Leu Gly Gly Tyr Phe
                805                 810                 815

Gln Gln Lys Tyr Leu Tyr Gln Phe Tyr Thr Cys Tyr Leu Asp Lys Arg
            820                 825                 830

Leu Glu Tyr Ile Ser Gly Leu Val Gln Gln Ala Glu Asn Phe Lys Ser
        835                 840                 845

Glu Asn Lys Val Phe Lys Lys Val Glu Asn Glu Cys Phe Lys Phe Leu
    850                 855                 860

Lys Lys Gln Asn Tyr Thr His Lys Glu Leu Asp Ala Arg Val Gln Ser
865                 870                 875                 880

Ile Leu Gly Tyr Pro Ile Phe Leu Glu Arg Gly Phe Xaa Asp Glu Lys
                885                 890                 895

Pro Thr Ile Ile Lys Gly Lys Thr Phe Lys Gly Asn Glu Ala Leu Phe
            900                 905                 910

Ala Asp Trp Phe Arg Tyr Tyr Lys Glu Tyr Gln Asn Phe Gln Thr Phe
        915                 920                 925

Tyr Asp Thr Glu Asn Tyr Pro Leu Val Glu Leu Glu Lys Lys Gln Ala
    930                 935                 940

Asp Arg Lys Arg Lys Thr Lys Ile Tyr Gln Gln Lys Lys Asn Asp Val
945                 950                 955                 960

Phe Thr Leu Leu Xaa Ala Lys His Ile Phe Lys Ser Val Phe Lys Gln
                965                 970                 975

Asp Ser Ile Asp Gln Phe Ser Leu Glu Asp Leu Tyr Gln Ser Arg Glu
            980                 985                 990

Glu Arg Leu Gly Asn Gln Glu Arg  Ala Arg Gln Thr Gly  Glu Arg Asn
        995                 1000                1005

Thr Asn  Tyr Ile Trp Asn Lys  Thr Val Asp Leu Lys  Leu Cys Asp
    1010                1015                1020

Gly Lys  Ile Thr Val Glu Asn  Val Lys Leu Lys Asn  Val Gly Asp
    1025                1030                1035

Phe Ile  Lys Tyr Glu Tyr Asp  Gln Arg Val Gln Ala  Phe Leu Lys
    1040                1045                1050

Tyr Glu  Glu Asn Ile Glu Trp  Gln Ala Phe Leu Ile  Lys Glu Ser
    1055                1060                1065

Lys Glu  Glu Glu Asn Tyr Pro  Tyr Val Val Glu Arg  Glu Ile Glu
    1070                1075                1080

Gln Tyr  Glu Lys Val Arg Arg  Glu Glu Leu Leu Lys  Glu Val His
    1085                1090                1095

Leu Ile  Glu Glu Tyr Ile Leu  Glu Lys Val Lys Asp  Lys Glu Ile
    1100                1105                1110

Leu Lys  Lys Gly Asp Asn Gln  Asn Phe Lys Tyr Tyr  Ile Leu Asn
    1115                1120                1125

Gly Leu  Leu Lys Gln Leu Lys  Asn Glu Asp Val Glu  Ser Tyr Lys
    1130                1135                1140

Val Phe  Asn Leu Asn Thr Glu  Pro Glu Asp Val Asn  Ile Asn Gln
```

```
    1145                1150                1155

Leu Lys  Gln Glu Ala Thr Asp  Leu Glu Gln Lys Ala  Phe Val Leu
    1160                1165                1170

Thr Tyr  Ile Ala Asn Lys Phe  Ala His Asn Gln Leu  Pro Lys Lys
    1175                1180                1185

Glu Phe  Trp Asp Tyr Cys Gln  Glu Lys Tyr Gly Lys  Ile Glu Lys
    1190                1195                1200

Glu Lys  Thr Tyr Ala Glu Tyr  Phe Ala Glu Val Phe  Lys Lys Glu
    1205                1210                1215

Lys Glu  Ala Leu Ile Lys Leu  Glu His His His His  His His
    1220                1225                1230
```

<210> SEQ ID NO 40
<211> LENGTH: 930
<212> TYPE: PRT
<213> ORGANISM: Unknown
<220> FEATURE:
<223> OTHER INFORMATION: CAS13D, CHAIN A

<400> SEQUENCE: 40

```
Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Val Ala
        35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Gly Asp Val Asn Glu
            100                 105                 110

Val Asn Ile Thr Phe Ser Ser Lys His Gly Phe Gly Ser Gly Val Glu
        115                 120                 125

Ile Asn Thr Ser Asn Pro Thr His Arg Ser Gly Glu Ser Ser Pro Val
    130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Ile Lys Asp Ser Glu Ser Tyr Asp Asp
        195                 200                 205

Phe Met Gly Tyr Leu Ser Ala Arg Asn Thr Tyr Glu Val Phe Thr His
    210                 215                 220

Pro Asp Lys Ser Asn Leu Ser Asp Lys Val Lys Gly Asn Ile Lys Lys
225                 230                 235                 240

Ser Leu Ser Lys Phe Asn Asp Leu Leu Lys Thr Lys Arg Leu Gly Tyr
                245                 250                 255

Phe Gly Leu Glu Glu Pro Lys Thr Lys Asp Thr Arg Ala Ser Glu Ala
            260                 265                 270

Tyr Lys Lys Arg Val Tyr His Met Leu Ala Ile Val Gly Gln Ile Ala
```

```
        275                 280                 285

Gln Cys Val Phe His Asp Lys Ser Gly Ala Lys Arg Phe Asp Leu Tyr
    290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Gly
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Lys Leu Arg Glu Lys Met Leu
    370                 375                 380

Glu Glu Tyr Gly Phe Arg Phe Lys Asp Lys Gln Tyr Asp Ser Val Arg
385                 390                 395                 400

Ser Lys Met Tyr Lys Leu Met Asp Phe Leu Leu Phe Cys Asn Tyr Tyr
                405                 410                 415

Arg Asn Asp Val Ala Ala Gly Glu Ala Leu Val Arg Lys Leu Arg Phe
            420                 425                 430

Ser Met Thr Asp Asp Glu Lys Glu Gly Ile Tyr Ala Asp Glu Ala Ala
        435                 440                 445

Lys Leu Trp Gly Lys Phe Arg Asn Asp Phe Glu Asn Ile Ala Asp His
    450                 455                 460

Met Asn Gly Asp Val Ile Lys Glu Leu Gly Lys Ala Asp Met Asp Phe
465                 470                 475                 480

Asp Glu Lys Ile Leu Asp Ser Glu Lys Lys Asn Ala Ser Asp Leu Leu
                485                 490                 495

Tyr Phe Ser Lys Met Ile Tyr Met Leu Thr Tyr Phe Leu Asp Gly Lys
            500                 505                 510

Glu Ile Asn Asp Leu Leu Thr Thr Leu Ile Ser Lys Phe Asp Asn Ile
        515                 520                 525

Lys Glu Phe Leu Lys Ile Met Lys Ser Ser Ala Val Asp Val Glu Cys
    530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                565                 570                 575

Ala Ser Ala Lys Leu Thr Met Phe Arg Asp Ala Leu Thr Ile Leu Gly
            580                 585                 590

Ile Asp Asp Asn Ile Thr Asp Asp Arg Ile Ser Glu Ile Leu Lys Leu
        595                 600                 605

Lys Glu Lys Gly Lys Gly Ile His Gly Leu Arg Asn Phe Ile Thr Asn
    610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asn Glu Lys Val Val Met Phe
                645                 650                 655

Val Leu Gly Gly Ile Pro Asp Thr Gln Ile Glu Arg Tyr Tyr Lys Ser
            660                 665                 670

Cys Val Glu Phe Pro Asp Met Asn Ser Ser Leu Glu Ala Lys Arg Ser
        675                 680                 685

Glu Leu Ala Arg Met Ile Lys Asn Ile Ser Phe Asp Asp Phe Lys Asn
    690                 695                 700
```

Val Lys Gln Gln Ala Lys Gly Arg Glu Asn Val Ala Lys Glu Arg Ala
705 710 715 720

Lys Ala Val Ile Gly Leu Tyr Leu Thr Val Met Tyr Leu Leu Val Lys
725 730 735

Asn Leu Val Asn Val Asn Ala Arg Tyr Val Ile Ala Ile His Cys Leu
740 745 750

Glu Arg Asp Phe Gly Leu Tyr Lys Glu Ile Ile Pro Glu Leu Ala Ser
755 760 765

Lys Asn Leu Lys Asn Asp Tyr Arg Ile Leu Ser Gln Thr Leu Cys Glu
770 775 780

Leu Cys Asp Asp Arg Asn Glu Ser Ser Asn Leu Phe Leu Lys Lys Asn
785 790 795 800

Lys Arg Leu Arg Lys Cys Val Glu Val Asp Ile Asn Asn Ala Asp Ser
805 810 815

Ser Met Thr Arg Lys Tyr Ala Asn Cys Ile Ala His Leu Thr Val Val
820 825 830

Arg Glu Leu Lys Glu Tyr Ile Gly Asp Ile Arg Thr Val Asp Ser Tyr
835 840 845

Phe Ser Ile Tyr His Tyr Val Met Gln Arg Cys Ile Thr Lys Arg Gly
850 855 860

Asp Asp Thr Lys Gln Glu Glu Lys Ile Lys Tyr Glu Asp Asp Leu Leu
865 870 875 880

Lys Asn His Gly Tyr Thr Lys Asp Phe Val Lys Ala Leu Asn Ser Pro
885 890 895

Phe Gly Tyr Asn Ile Pro Arg Phe Lys Asn Leu Ser Ile Glu Gln Leu
900 905 910

Phe Asp Arg Asn Glu Tyr Leu Thr Glu Lys Leu Glu His His His His
915 920 925

His His
930

<210> SEQ ID NO 41
<211> LENGTH: 954
<212> TYPE: PRT
<213> ORGANISM: Unknown
<220> FEATURE:
<223> OTHER INFORMATION: Eubacterium Siraeum

<400> SEQUENCE: 41

Met Gly Lys Lys Ile His Ala Arg Asp Leu Arg Glu Gln Arg Lys Thr
1 5 10 15

Asp Arg Thr Glu Lys Phe Ala Asp Gln Asn Lys Lys Arg Glu Ala Glu
20 25 30

Arg Ala Val Pro Lys Lys Asp Ala Ala Val Ser Val Lys Ser Val Ser
35 40 45

Ser Val Ser Ser Lys Lys Asp Asn Val Thr Lys Ser Met Ala Lys Ala
50 55 60

Ala Gly Val Lys Ser Val Phe Ala Val Gly Asn Thr Val Tyr Met Thr
65 70 75 80

Ser Phe Gly Arg Gly Asn Asp Ala Val Leu Glu Gln Lys Ile Val Asp
85 90 95

Thr Ser His Glu Pro Leu Asn Ile Asp Asp Pro Ala Tyr Gln Leu Asn
100 105 110

Val Val Thr Met Asn Gly Tyr Ser Val Thr Gly His Arg Gly Glu Thr
115 120 125

```
Val Ser Ala Val Thr Asp Asn Pro Leu Arg Arg Phe Asn Gly Arg Lys
    130                 135                 140

Lys Asp Glu Pro Glu Gln Ser Val Pro Thr Asp Met Leu Cys Leu Lys
145                 150                 155                 160

Pro Thr Leu Glu Lys Lys Phe Phe Gly Lys Glu Phe Asp Asp Asn Ile
                165                 170                 175

His Ile Gln Leu Ile Tyr Asn Ile Leu Asp Ile Glu Lys Ile Leu Ala
            180                 185                 190

Val Tyr Ser Thr Asn Ala Ile Tyr Ala Leu Asn Asn Met Ser Ala Asp
        195                 200                 205

Glu Asn Ile Glu Asn Ser Asp Phe Phe Met Lys Arg Thr Thr Asp Glu
    210                 215                 220

Thr Phe Asp Asp Phe Glu Lys Lys Lys Glu Ser Thr Asn Ser Arg Glu
225                 230                 235                 240

Lys Ala Asp Phe Asp Ala Phe Glu Lys Phe Ile Gly Asn Tyr Arg Leu
                245                 250                 255

Ala Tyr Phe Ala Asp Ala Phe Tyr Val Asn Lys Lys Asn Pro Lys Gly
            260                 265                 270

Lys Ala Lys Asn Val Leu Arg Glu Asp Lys Glu Leu Tyr Ser Val Leu
        275                 280                 285

Thr Leu Ile Gly Lys Leu Ala His Trp Cys Val Ala Ser Glu Glu Gly
    290                 295                 300

Arg Ala Glu Phe Trp Leu Tyr Lys Leu Asp Glu Leu Lys Asp Asp Phe
305                 310                 315                 320

Lys Asn Val Leu Asp Val Val Tyr Asn Arg Pro Val Glu Glu Ile Asn
                325                 330                 335

Asn Arg Phe Ile Glu Asn Asn Lys Val Asn Ile Gln Ile Leu Gly Ser
            340                 345                 350

Val Tyr Lys Asn Thr Asp Ile Ala Glu Leu Val Arg Ser Tyr Tyr Glu
        355                 360                 365

Phe Leu Ile Thr Lys Lys Tyr Lys Asn Met Gly Phe Ser Ile Lys Lys
    370                 375                 380

Leu Arg Glu Ser Met Leu Glu Gly Lys Gly Tyr Ala Asp Lys Glu Tyr
385                 390                 395                 400

Asp Ser Val Arg Asn Lys Leu Tyr Gln Met Thr Asp Phe Ile Leu Tyr
                405                 410                 415

Thr Gly Tyr Ile Asn Glu Asp Ser Asp Arg Ala Asp Asp Leu Val Asn
            420                 425                 430

Thr Leu Arg Ser Ser Leu Lys Glu Asp Asp Lys Thr Thr Val Tyr Cys
        435                 440                 445

Lys Glu Ala Asp Tyr Leu Trp Lys Lys Tyr Arg Glu Ser Ile Arg Glu
    450                 455                 460

Val Ala Asp Ala Leu Asp Gly Asp Asn Ile Lys Lys Leu Ser Lys Ser
465                 470                 475                 480

Asn Ile Glu Ile Gln Glu Asp Lys Leu Arg Lys Cys Phe Ile Ser Tyr
                485                 490                 495

Ala Asp Ser Val Ser Glu Phe Thr Lys Leu Ile Tyr Leu Leu Thr Arg
            500                 505                 510

Phe Leu Ser Gly Lys Glu Ile Asn Asp Leu Val Thr Thr Leu Ile Asn
        515                 520                 525

Lys Phe Asp Asn Ile Arg Ser Phe Leu Glu Ile Met Asp Glu Leu Gly
    530                 535                 540
```

```
Leu Asp Arg Thr Phe Thr Ala Glu Tyr Ser Phe Phe Glu Gly Ser Thr
545                 550                 555                 560

Lys Tyr Leu Ala Glu Leu Val Glu Leu Asn Ser Phe Val Lys Ser Cys
                565                 570                 575

Ser Phe Asp Ile Asn Ala Lys Arg Thr Met Tyr Arg Asp Ala Leu Asp
            580                 585                 590

Ile Leu Gly Ile Glu Ser Asp Lys Thr Glu Glu Asp Ile Glu Lys Met
        595                 600                 605

Ile Asp Asn Ile Leu Gln Ile Asp Ala Asn Gly Asp Lys Lys Leu Lys
    610                 615                 620

Lys Asn Asn Gly Leu Arg Asn Phe Ile Ala Ser Asn Val Ile Asp Ser
625                 630                 635                 640

Asn Arg Phe Lys Tyr Leu Val Arg Tyr Gly Asn Pro Lys Lys Ile Arg
                645                 650                 655

Glu Thr Ala Lys Cys Lys Pro Ala Val Arg Phe Val Leu Asn Glu Ile
            660                 665                 670

Pro Asp Ala Gln Ile Glu Arg Tyr Tyr Glu Ala Cys Cys Pro Lys Asn
        675                 680                 685

Thr Ala Leu Cys Ser Ala Asn Lys Arg Arg Glu Lys Leu Ala Asp Met
    690                 695                 700

Ile Ala Glu Ile Lys Phe Glu Asn Phe Ser Asp Ala Gly Asn Tyr Gln
705                 710                 715                 720

Lys Ala Asn Val Thr Ser Arg Thr Ser Glu Ala Glu Ile Lys Arg Lys
                725                 730                 735

Asn Gln Ala Ile Ile Arg Leu Tyr Leu Thr Val Met Tyr Ile Met Leu
            740                 745                 750

Lys Asn Leu Val Asn Val Asn Ala Arg Tyr Val Ile Ala Phe His Cys
        755                 760                 765

Val Glu Arg Asp Thr Lys Leu Tyr Ala Glu Ser Gly Leu Glu Val Gly
    770                 775                 780

Asn Ile Glu Lys Asn Lys Thr Asn Leu Thr Met Ala Val Met Gly Val
785                 790                 795                 800

Lys Leu Glu Asn Gly Ile Ile Lys Thr Glu Phe Asp Lys Ser Phe Ala
                805                 810                 815

Glu Asn Ala Ala Asn Arg Tyr Leu Arg Asn Ala Arg Trp Tyr Lys Leu
            820                 825                 830

Ile Leu Asp Asn Leu Lys Lys Ser Glu Arg Ala Val Val Asn Glu Phe
        835                 840                 845

Ala Asn Thr Val Cys Ala Leu Asn Ala Ile Arg Asn Ile Asn Ile Asn
    850                 855                 860

Ile Lys Glu Ile Lys Glu Val Glu Asn Tyr Phe Ala Leu Tyr His Tyr
865                 870                 875                 880

Leu Ile Gln Lys His Leu Glu Asn Arg Phe Ala Asp Lys Lys Val Glu
                885                 890                 895

Arg Asp Thr Gly Asp Phe Ile Ser Lys Leu Glu Glu His Lys Thr Tyr
            900                 905                 910

Cys Lys Asp Phe Val Lys Ala Tyr Cys Thr Pro Phe Gly Tyr Asn Leu
        915                 920                 925

Val Arg Tyr Lys Asn Leu Thr Ile Asp Gly Leu Phe Asp Lys Asn Tyr
    930                 935                 940

Pro Gly Lys Asp Asp Ser Asp Glu Gln Lys
945                 950
```

<210> SEQ ID NO 42
<211> LENGTH: 413
<212> TYPE: PRT
<213> ORGANISM: Artificial Sequence
<220> FEATURE:
<223> OTHER INFORMATION: Synthetic

<400> SEQUENCE: 42

```
Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
```

```
                370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410


<210> SEQ ID NO 43
<211> LENGTH: 413
<212> TYPE: PRT
<213> ORGANISM: Artificial Sequence
<220> FEATURE:
<223> OTHER INFORMATION: Synthetic

<400> SEQUENCE: 43

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Thr Asn Val Val Pro Leu Tyr Asp Leu
```

```
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410


<210> SEQ ID NO 44
<211> LENGTH: 413
<212> TYPE: PRT
<213> ORGANISM: Artificial Sequence
<220> FEATURE:
<223> OTHER INFORMATION: Synthetic

<400> SEQUENCE: 44

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Pro Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
```

```
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Gly Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410


<210> SEQ ID NO 45
<211> LENGTH: 413
<212> TYPE: PRT
<213> ORGANISM: Artificial Sequence
<220> FEATURE:
<223> OTHER INFORMATION: Synthetic

<400> SEQUENCE: 45

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
```

```
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410


<210> SEQ ID NO 46
<211> LENGTH: 413
<212> TYPE: PRT
<213> ORGANISM: Artificial Sequence
<220> FEATURE:
<223> OTHER INFORMATION: Synthetic

<400> SEQUENCE: 46

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Pro Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
```

```
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410
```

<210> SEQ ID NO 47
<211> LENGTH: 413
<212> TYPE: PRT
<213> ORGANISM: Artificial Sequence
<220> FEATURE:
<223> OTHER INFORMATION: Synthetic

<400> SEQUENCE: 47

```
Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asn Pro Thr Ser Pro Phe Ser Glu Ala Ser Met Met Gly Leu Leu Thr
```

```
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Arg Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Gly Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410


<210> SEQ ID NO 48
<211> LENGTH: 413
<212> TYPE: PRT
<213> ORGANISM: Artificial Sequence
<220> FEATURE:
<223> OTHER INFORMATION: Synthetic

<400> SEQUENCE: 48

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
```

```
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Arg Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Gly Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410


<210> SEQ ID NO 49
<211> LENGTH: 413
<212> TYPE: PRT
<213> ORGANISM: Artificial Sequence
<220> FEATURE:
<223> OTHER INFORMATION: Synthetic

<400> SEQUENCE: 49

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
```

```
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Arg Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410
```

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50

Pro Lys Lys Lys Arg Lys Val
1 5

<210> SEQ ID NO 51
<211> LENGTH: 33
<212> TYPE: PRT
<213> ORGANISM: Artificial Sequence
<220> FEATURE:
<223> OTHER INFORMATION: Synthetic

<400> SEQUENCE: 51

Gly Cys Cys Ala Ala Cys Ala Thr Gly Ala Gly Gly Ala Thr Cys Ala
1 5 10 15

Cys Cys Cys Ala Thr Gly Thr Cys Thr Gly Cys Ala Gly Gly Gly Cys
20 25 30

Cys

<210> SEQ ID NO 52
<211> LENGTH: 131
<212> TYPE: PRT
<213> ORGANISM: Artificial Sequence
<220> FEATURE:
<223> OTHER INFORMATION: Synthetic

<400> SEQUENCE: 52

Gly Ser Ala Ser Asn Phe Thr Gln Phe Val Leu Val Asp Asn Gly Gly
1 5 10 15

Thr Gly Asp Val Thr Val Ala Pro Ser Asn Phe Ala Asn Gly Val Ala
20 25 30

Glu Trp Ile Ser Ser Asn Ser Arg Ser Gln Ala Tyr Lys Val Thr Cys
35 40 45

Ser Val Arg Gln Ser Ser Ala Gln Asn Arg Lys Tyr Thr Ile Lys Val
50 55 60

Glu Val Pro Lys Val Ala Thr Gln Thr Val Gly Gly Glu Glu Leu Pro
65 70 75 80

Val Ala Gly Trp Arg Ser Tyr Leu Asn Met Glu Leu Thr Ile Pro Ile
85 90 95

Phe Ala Thr Asn Ser Asp Cys Glu Leu Ile Val Lys Ala Met Gln Gly
100 105 110

Leu Leu Lys Asp Gly Asn Pro Ile Pro Ser Ala Ile Ala Ala Asn Ser
115 120 125

Gly Ile Tyr
130

<210> SEQ ID NO 53
<211> LENGTH: 380
<212> TYPE: PRT
<213> ORGANISM: Artificial Sequence
<220> FEATURE:
<223> OTHER INFORMATION: Synthetic

<400> SEQUENCE: 53

Met Gly Ile Gln Gly Leu Ala Lys Leu Ile Ala Asp Val Ala Pro Ser
1 5 10 15

Ala Ile Arg Glu Asn Asp Ile Lys Ser Tyr Phe Gly Arg Lys Val Ala
20 25 30

Ile Asp Ala Ser Met Ser Ile Tyr Gln Phe Leu Ile Ala Val Arg Gln
35 40 45

```
Gly Gly Asp Val Leu Gln Asn Glu Glu Gly Glu Thr Thr Ser His Leu
    50                  55                  60

Met Gly Met Phe Tyr Arg Thr Ile Arg Met Met Glu Asn Gly Ile Lys
65                  70                  75                  80

Pro Val Tyr Val Phe Asp Gly Lys Pro Pro Gln Leu Lys Ser Gly Glu
                85                  90                  95

Leu Ala Lys Arg Ser Glu Arg Arg Ala Glu Ala Glu Lys Gln Leu Gln
            100                 105                 110

Gln Ala Gln Ala Ala Gly Ala Glu Gln Glu Val Glu Lys Phe Thr Lys
        115                 120                 125

Arg Leu Val Lys Val Thr Lys Gln His Asn Asp Glu Cys Lys His Leu
    130                 135                 140

Leu Ser Leu Met Gly Ile Pro Tyr Leu Asp Ala Pro Ser Glu Ala Glu
145                 150                 155                 160

Ala Ser Cys Ala Ala Leu Val Lys Ala Gly Lys Val Tyr Ala Ala Ala
                165                 170                 175

Thr Glu Asp Met Asp Cys Leu Thr Phe Gly Ser Pro Val Leu Met Arg
            180                 185                 190

His Leu Thr Ala Ser Glu Ala Lys Lys Leu Pro Ile Gln Glu Phe His
        195                 200                 205

Leu Ser Arg Ile Leu Gln Glu Leu Gly Leu Asn Gln Glu Gln Phe Val
    210                 215                 220

Asp Leu Cys Ile Leu Leu Gly Ser Asp Tyr Cys Glu Ser Ile Arg Gly
225                 230                 235                 240

Ile Gly Pro Lys Arg Ala Val Asp Leu Ile Gln Lys His Lys Ser Ile
                245                 250                 255

Glu Glu Ile Val Arg Arg Leu Asp Pro Asn Lys Tyr Pro Val Pro Glu
            260                 265                 270

Asn Trp Leu His Lys Glu Ala His Gln Leu Phe Leu Glu Pro Glu Val
        275                 280                 285

Leu Asp Pro Glu Ser Val Glu Leu Lys Trp Ser Glu Pro Asn Glu Glu
    290                 295                 300

Glu Leu Ile Lys Phe Met Cys Gly Glu Lys Gln Phe Ser Glu Glu Arg
305                 310                 315                 320

Ile Arg Ser Gly Val Lys Arg Leu Ser Lys Ser Arg Gln Gly Ser Thr
                325                 330                 335

Gln Gly Arg Leu Asp Asp Phe Phe Lys Val Thr Gly Ser Leu Ser Ser
            340                 345                 350

Ala Lys Arg Lys Glu Pro Glu Pro Lys Gly Ser Thr Lys Lys Lys Ala
        355                 360                 365

Lys Thr Gly Ala Ala Gly Lys Phe Lys Arg Gly Lys
    370                 375                 380
```

<210> SEQ ID NO 54
<211> LENGTH: 2117
<212> TYPE: PRT
<213> ORGANISM: Artificial Sequence
<220> FEATURE:
<223> OTHER INFORMATION: Synthetic

<400> SEQUENCE: 54

```
Met Lys Arg Thr Ala Asp Gly Ser Glu Phe Glu Ser Pro Lys Lys Lys
1               5                   10                  15

Arg Lys Val Asp Lys Lys Tyr Ser Ile Gly Leu Asp Ile Gly Thr Asn
            20                  25                  30
```

```
Ser Val Gly Trp Ala Val Ile Thr Asp Glu Tyr Lys Val Pro Ser Lys
        35                  40                  45

Lys Phe Lys Val Leu Gly Asn Thr Asp Arg His Ser Ile Lys Lys Asn
    50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Arg Tyr Thr Arg Arg Lys Asn Arg
                85                  90                  95

Ile Cys Tyr Leu Gln Glu Ile Phe Ser Asn Glu Met Ala Lys Val Asp
            100                 105                 110

Asp Ser Phe Phe His Arg Leu Glu Glu Ser Phe Leu Val Glu Glu Asp
        115                 120                 125

Lys Lys His Glu Arg His Pro Ile Phe Gly Asn Ile Val Asp Glu Val
    130                 135                 140

Ala Tyr His Glu Lys Tyr Pro Thr Ile Tyr His Leu Arg Lys Lys Leu
145                 150                 155                 160

Val Asp Ser Thr Asp Lys Ala Asp Leu Arg Leu Ile Tyr Leu Ala Leu
                165                 170                 175

Ala His Met Ile Lys Phe Arg Gly His Phe Leu Ile Glu Gly Asp Leu
            180                 185                 190

Asn Pro Asp Asn Ser Asp Val Asp Lys Leu Phe Ile Gln Leu Val Gln
        195                 200                 205

Thr Tyr Asn Gln Leu Phe Glu Glu Asn Pro Ile Asn Ala Ser Gly Val
    210                 215                 220

Asp Ala Lys Ala Ile Leu Ser Ala Arg Leu Ser Lys Ser Arg Arg Leu
225                 230                 235                 240

Glu Asn Leu Ile Ala Gln Leu Pro Gly Glu Lys Lys Asn Gly Leu Phe
                245                 250                 255

Gly Asn Leu Ile Ala Leu Ser Leu Gly Leu Thr Pro Asn Phe Lys Ser
            260                 265                 270

Asn Phe Asp Leu Ala Glu Asp Ala Lys Leu Gln Leu Ser Lys Asp Thr
        275                 280                 285

Tyr Asp Asp Asp Leu Asp Asn Leu Leu Ala Gln Ile Gly Asp Gln Tyr
    290                 295                 300

Ala Asp Leu Phe Leu Ala Ala Lys Asn Leu Ser Asp Ala Ile Leu Leu
305                 310                 315                 320

Ser Asp Ile Leu Arg Val Asn Thr Glu Ile Thr Lys Ala Pro Leu Ser
                325                 330                 335

Ala Ser Met Ile Lys Arg Tyr Asp Glu His His Gln Asp Leu Thr Leu
            340                 345                 350

Leu Lys Ala Leu Val Arg Gln Gln Leu Pro Glu Lys Tyr Lys Glu Ile
        355                 360                 365

Phe Phe Asp Gln Ser Lys Asn Gly Tyr Ala Gly Tyr Ile Asp Gly Gly
    370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
        435                 440                 445

Pro Phe Leu Lys Asp Asn Arg Glu Lys Ile Glu Lys Ile Leu Thr Phe
```

```
    450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
            500                 505                 510

Met Thr Asn Phe Asp Lys Asn Leu Pro Asn Glu Lys Val Leu Pro Lys
        515                 520                 525

His Ser Leu Leu Tyr Glu Tyr Phe Thr Val Tyr Asn Glu Leu Thr Lys
    530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
            580                 585                 590

Phe Asp Ser Val Glu Ile Ser Gly Val Glu Asp Arg Phe Asn Ala Ser
        595                 600                 605

Leu Gly Thr Tyr His Asp Leu Leu Lys Ile Ile Lys Asp Lys Asp Phe
    610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
            660                 665                 670

Arg Tyr Thr Gly Trp Gly Arg Leu Ser Arg Lys Leu Ile Asn Gly Ile
        675                 680                 685

Arg Asp Lys Gln Ser Gly Lys Thr Ile Leu Asp Phe Leu Lys Ser Asp
    690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
            740                 745                 750

Lys Gly Ile Leu Gln Thr Val Lys Val Val Asp Glu Leu Val Lys Val
        755                 760                 765

Met Gly Arg His Lys Pro Glu Asn Ile Val Ile Glu Met Ala Arg Glu
    770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
            820                 825                 830

Tyr Leu Gln Asn Gly Arg Asp Met Tyr Val Asp Gln Glu Leu Asp Ile
        835                 840                 845

Asn Arg Leu Ser Asp Tyr Asp Val Asp Ala Ile Val Pro Gln Ser Phe
    850                 855                 860

Leu Lys Asp Asp Ser Ile Asp Asn Lys Val Leu Thr Arg Ser Asp Lys
865                 870                 875                 880
```

```
Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
            900                 905                 910

Arg Lys Phe Asp Asn Leu Thr Lys Ala Glu Arg Gly Gly Leu Ser Glu
        915                 920                 925

Leu Asp Lys Ala Gly Phe Ile Lys Arg Gln Leu Val Glu Thr Arg Gln
    930                 935                 940

Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
            980                 985                 990

Val Arg Glu Ile Asn Asn Tyr His  His Ala His Asp Ala  Tyr Leu Asn
        995                 1000                1005

Ala Val  Val Gly Thr Ala Leu  Ile Lys Lys Tyr Pro  Lys Leu Glu
    1010                1015                1020

Ser Glu  Phe Val Tyr Gly Asp  Tyr Lys Val Tyr Asp  Val Arg Lys
    1025                1030                1035

Met Ile  Ala Lys Ser Glu Gln  Glu Ile Gly Lys Ala  Thr Ala Lys
    1040                1045                1050

Tyr Phe  Phe Tyr Ser Asn Ile  Met Asn Phe Phe Lys  Thr Glu Ile
    1055                1060                1065

Thr Leu  Ala Asn Gly Glu Ile  Arg Lys Arg Pro Leu  Ile Glu Thr
    1070                1075                1080

Asn Gly  Glu Thr Gly Glu Ile  Val Trp Asp Lys Gly  Arg Asp Phe
    1085                1090                1095

Ala Thr  Val Arg Lys Val Leu  Ser Met Pro Gln Val  Asn Ile Val
    1100                1105                1110

Lys Lys  Thr Glu Val Gln Thr  Gly Gly Phe Ser Lys  Glu Ser Ile
    1115                1120                1125

Leu Pro  Lys Arg Asn Ser Asp  Lys Leu Ile Ala Arg  Lys Lys Asp
    1130                1135                1140

Trp Asp  Pro Lys Lys Tyr Gly  Gly Phe Asp Ser Pro  Thr Val Ala
    1145                1150                1155

Tyr Ser  Val Leu Val Val Ala  Lys Val Glu Lys Gly  Lys Ser Lys
    1160                1165                1170

Lys Leu  Lys Ser Val Lys Glu  Leu Leu Gly Ile Thr  Ile Met Glu
    1175                1180                1185

Arg Ser  Ser Phe Glu Lys Asn  Pro Ile Asp Phe Leu  Glu Ala Lys
    1190                1195                1200

Gly Tyr  Lys Glu Val Lys Lys  Asp Leu Ile Ile Lys  Leu Pro Lys
    1205                1210                1215

Tyr Ser  Leu Phe Glu Leu Glu  Asn Gly Arg Lys Arg  Met Leu Ala
    1220                1225                1230

Ser Ala  Gly Glu Leu Gln Lys  Gly Asn Glu Leu Ala  Leu Pro Ser
    1235                1240                1245

Lys Tyr  Val Asn Phe Leu Tyr  Leu Ala Ser His Tyr  Glu Lys Leu
    1250                1255                1260

Lys Gly  Ser Pro Glu Asp Asn  Glu Gln Lys Gln Leu  Phe Val Glu
    1265                1270                1275
```

```
Gln His  Lys His Tyr Leu Asp  Glu Ile Ile Glu Gln  Ile Ser Glu
    1280                 1285                  1290

Phe Ser  Lys Arg Val Ile Leu  Ala Asp Ala Asn Leu  Asp Lys Val
    1295                 1300                  1305

Leu Ser  Ala Tyr Asn Lys His  Arg Asp Lys Pro Ile  Arg Glu Gln
    1310                 1315                  1320

Ala Glu  Asn Ile Ile His Leu  Phe Thr Leu Thr Asn  Leu Gly Ala
    1325                 1330                  1335

Pro Ala  Ala Phe Lys Tyr Phe  Asp Thr Thr Ile Asp  Arg Lys Arg
    1340                 1345                  1350

Tyr Thr  Ser Thr Lys Glu Val  Leu Asp Ala Thr Leu  Ile His Gln
    1355                 1360                  1365

Ser Ile  Thr Gly Leu Tyr Glu  Thr Arg Ile Asp Leu  Ser Gln Leu
    1370                 1375                  1380

Gly Gly  Asp Ser Gly Gly Ser  Ser Gly Gly Ser Ser  Gly Ser Glu
    1385                 1390                  1395

Thr Pro  Gly Thr Ser Glu Ser  Ala Thr Pro Glu Ser  Ser Gly Gly
    1400                 1405                  1410

Ser Ser  Gly Gly Ser Ser Thr  Leu Asn Ile Glu Asp  Glu Tyr Arg
    1415                 1420                  1425

Leu His  Glu Thr Ser Lys Glu  Pro Asp Val Ser Leu  Gly Ser Thr
    1430                 1435                  1440

Trp Leu  Ser Asp Phe Pro Gln  Ala Trp Ala Glu Thr  Gly Gly Met
    1445                 1450                  1455

Gly Leu  Ala Val Arg Gln Ala  Pro Leu Ile Ile Pro  Leu Lys Ala
    1460                 1465                  1470

Thr Ser  Thr Pro Val Ser Ile  Lys Gln Tyr Pro Met  Ser Gln Glu
    1475                 1480                  1485

Ala Arg  Leu Gly Ile Lys Pro  His Ile Gln Arg Leu  Leu Asp Gln
    1490                 1495                  1500

Gly Ile  Leu Val Pro Cys Gln  Ser Pro Trp Asn Thr  Pro Leu Leu
    1505                 1510                  1515

Pro Val  Lys Lys Pro Gly Thr  Asn Asp Tyr Arg Pro  Val Gln Asp
    1520                 1525                  1530

Leu Arg  Glu Val Asn Lys Arg  Val Glu Asp Ile His  Pro Thr Val
    1535                 1540                  1545

Pro Asn  Pro Tyr Asn Leu Leu  Ser Gly Leu Pro Pro  Ser His Gln
    1550                 1555                  1560

Trp Tyr  Thr Val Leu Asp Leu  Lys Asp Ala Phe Phe  Cys Leu Arg
    1565                 1570                  1575

Leu His  Pro Thr Ser Gln Pro  Leu Phe Ala Phe Glu  Trp Arg Asp
    1580                 1585                  1590

Pro Glu  Met Gly Ile Ser Gly  Gln Leu Thr Trp Thr  Arg Leu Pro
    1595                 1600                  1605

Gln Gly  Phe Lys Asn Ser Pro  Thr Leu Phe Asp Glu  Ala Leu His
    1610                 1615                  1620

Arg Asp  Leu Ala Asp Phe Arg  Ile Gln His Pro Asp  Leu Ile Leu
    1625                 1630                  1635

Leu Gln  Tyr Val Asp Asp Leu  Leu Leu Ala Ala Thr  Ser Glu Leu
    1640                 1645                  1650

Asp Cys  Gln Gln Gly Thr Arg  Ala Leu Leu Gln Thr  Leu Gly Asn
    1655                 1660                  1665

Leu Gly  Tyr Arg Ala Ser Ala  Lys Lys Ala Gln Ile  Cys Gln Lys
```

```
    1670                1675                1680

Gln Val  Lys Tyr Leu Gly Tyr  Leu Leu Lys Glu Gly  Gln Arg Trp
    1685                1690                1695

Leu Thr  Glu Ala Arg Lys Glu  Thr Val Met Gly Gln  Pro Thr Pro
    1700                1705                1710

Lys Thr  Pro Arg Gln Leu Arg  Glu Phe Leu Gly Thr  Ala Gly Phe
    1715                1720                1725

Cys Arg  Leu Trp Ile Pro Gly  Phe Ala Glu Met Ala  Ala Pro Leu
    1730                1735                1740

Tyr Pro  Leu Thr Lys Thr Gly  Thr Leu Phe Asn Trp  Gly Pro Asp
    1745                1750                1755

Gln Gln  Lys Ala Tyr Gln Glu  Ile Lys Gln Ala Leu  Leu Thr Ala
    1760                1765                1770

Pro Ala  Leu Gly Leu Pro Asp  Leu Thr Lys Pro Phe  Glu Leu Phe
    1775                1780                1785

Val Asp  Glu Lys Gln Gly Tyr  Ala Lys Gly Val Leu  Thr Gln Lys
    1790                1795                1800

Leu Gly  Pro Trp Arg Arg Pro  Val Ala Tyr Leu Ser  Lys Lys Leu
    1805                1810                1815

Asp Pro  Val Ala Ala Gly Trp  Pro Pro Cys Leu Arg  Met Val Ala
    1820                1825                1830

Ala Ile  Ala Val Leu Thr Lys  Asp Ala Gly Lys Leu  Thr Met Gly
    1835                1840                1845

Gln Pro  Leu Val Ile Leu Ala  Pro His Ala Val Glu  Ala Leu Val
    1850                1855                1860

Lys Gln  Pro Pro Asp Arg Trp  Leu Ser Asn Ala Arg  Met Thr His
    1865                1870                1875

Tyr Gln  Ala Leu Leu Leu Asp  Thr Asp Arg Val Gln  Phe Gly Pro
    1880                1885                1890

Val Val  Ala Leu Asn Pro Ala  Thr Leu Leu Pro Leu  Pro Glu Glu
    1895                1900                1905

Gly Leu  Gln His Asn Cys Leu  Asp Ile Leu Ala Glu  Ala His Gly
    1910                1915                1920

Thr Arg  Pro Asp Leu Thr Asp  Gln Pro Leu Pro Asp  Ala Asp His
    1925                1930                1935

Thr Trp  Tyr Thr Asp Gly Ser  Ser Leu Leu Gln Glu  Gly Gln Arg
    1940                1945                1950

Lys Ala  Gly Ala Ala Val Thr  Thr Glu Thr Glu Val  Ile Trp Ala
    1955                1960                1965

Lys Ala  Leu Pro Ala Gly Thr  Ser Ala Gln Arg Ala  Glu Leu Ile
    1970                1975                1980

Ala Leu  Thr Gln Ala Leu Lys  Met Ala Glu Gly Lys  Lys Leu Asn
    1985                1990                1995

Val Tyr  Thr Asp Ser Arg Tyr  Ala Phe Ala Thr Ala  His Ile His
    2000                2005                2010

Gly Glu  Ile Tyr Arg Arg Arg  Gly Leu Leu Thr Ser  Glu Gly Lys
    2015                2020                2025

Glu Ile  Lys Asn Lys Asp Glu  Ile Leu Ala Leu Leu  Lys Ala Leu
    2030                2035                2040

Phe Leu  Pro Lys Arg Leu Ser  Ile Ile His Cys Pro  Gly His Gln
    2045                2050                2055

Lys Gly  His Ser Ala Glu Ala  Arg Gly Asn Arg Met  Ala Asp Gln
    2060                2065                2070
```

```
Ala Ala  Arg Lys Ala Ala Ile  Thr Glu Thr Pro Asp  Thr Ser Thr
    2075                 2080                 2085

Leu Leu  Ile Glu Asn Ser Ser  Pro Ser Gly Gly Ser  Lys Arg Thr
    2090                 2095                 2100

Ala Asp  Gly Ser Glu Phe Glu  Pro Lys Lys Lys Arg  Lys Val
    2105                 2110                 2115


<210> SEQ ID NO 55
<211> LENGTH: 1367
<212> TYPE: PRT
<213> ORGANISM: Artificial Sequence
<220> FEATURE:
<223> OTHER INFORMATION: Synthetic

<400> SEQUENCE: 55

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320
```

```
Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735
```

```
Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
```

```
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260

Tyr Leu  Asp Glu Ile Ile Glu  Gln Ile Ser Glu Phe  Ser Lys Arg
    1265                1270                1275

Val Ile  Leu Ala Asp Ala Asn  Leu Asp Lys Val Leu  Ser Ala Tyr
    1280                1285                1290

Asn Lys  His Arg Asp Lys Pro  Ile Arg Glu Gln Ala  Glu Asn Ile
    1295                1300                1305

Ile His  Leu Phe Thr Leu Thr  Asn Leu Gly Ala Pro  Ala Ala Phe
    1310                1315                1320

Lys Tyr  Phe Asp Thr Thr Ile  Asp Arg Lys Arg Tyr  Thr Ser Thr
    1325                1330                1335

Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365
```

<210> SEQ ID NO 56
<211> LENGTH: 33
<212> TYPE: PRT
<213> ORGANISM: Artificial Sequence
<220> FEATURE:
<223> OTHER INFORMATION: Synthetic

<400> SEQUENCE: 56

```
Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
            20                  25                  30

Ser
```

<210> SEQ ID NO 57
<211> LENGTH: 677
<212> TYPE: PRT
<213> ORGANISM: Artificial Sequence
<220> FEATURE:
<223> OTHER INFORMATION: Synthetic

<400> SEQUENCE: 57

```
Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
```

```
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460
```

```
Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro
        675
```

<210> SEQ ID NO 58
<211> LENGTH: 2117
<212> TYPE: PRT
<213> ORGANISM: Artificial Sequence
<220> FEATURE:
<223> OTHER INFORMATION: Synthetic

<400> SEQUENCE: 58

```
Met Lys Arg Thr Ala Asp Gly Ser Glu Phe Glu Ser Pro Lys Lys Lys
1               5                   10                  15

Arg Lys Val Asp Lys Lys Tyr Ser Ile Gly Leu Asp Ile Gly Thr Asn
            20                  25                  30

Ser Val Gly Trp Ala Val Ile Thr Asp Glu Tyr Lys Val Pro Ser Lys
        35                  40                  45

Lys Phe Lys Val Leu Gly Asn Thr Asp Arg His Ser Ile Lys Lys Asn
    50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Arg Tyr Thr Arg Arg Lys Asn Arg
                85                  90                  95

Ile Cys Tyr Leu Gln Glu Ile Phe Ser Asn Glu Met Ala Lys Val Asp
            100                 105                 110

Asp Ser Phe Phe His Arg Leu Glu Glu Ser Phe Leu Val Glu Glu Asp
        115                 120                 125

Lys Lys His Glu Arg His Pro Ile Phe Gly Asn Ile Val Asp Glu Val
    130                 135                 140
```

```
Ala Tyr His Glu Lys Tyr Pro Thr Ile Tyr His Leu Arg Lys Lys Leu
145                 150                 155                 160

Val Asp Ser Thr Asp Lys Ala Asp Leu Arg Leu Ile Tyr Leu Ala Leu
                165                 170                 175

Ala His Met Ile Lys Phe Arg Gly His Phe Leu Ile Glu Gly Asp Leu
            180                 185                 190

Asn Pro Asp Asn Ser Asp Val Asp Lys Leu Phe Ile Gln Leu Val Gln
        195                 200                 205

Thr Tyr Asn Gln Leu Phe Glu Glu Asn Pro Ile Asn Ala Ser Gly Val
    210                 215                 220

Asp Ala Lys Ala Ile Leu Ser Ala Arg Leu Ser Lys Ser Arg Arg Leu
225                 230                 235                 240

Glu Asn Leu Ile Ala Gln Leu Pro Gly Glu Lys Lys Asn Gly Leu Phe
                245                 250                 255

Gly Asn Leu Ile Ala Leu Ser Leu Gly Leu Thr Pro Asn Phe Lys Ser
            260                 265                 270

Asn Phe Asp Leu Ala Glu Asp Ala Lys Leu Gln Leu Ser Lys Asp Thr
        275                 280                 285

Tyr Asp Asp Asp Leu Asp Asn Leu Leu Ala Gln Ile Gly Asp Gln Tyr
    290                 295                 300

Ala Asp Leu Phe Leu Ala Ala Lys Asn Leu Ser Asp Ala Ile Leu Leu
305                 310                 315                 320

Ser Asp Ile Leu Arg Val Asn Thr Glu Ile Thr Lys Ala Pro Leu Ser
                325                 330                 335

Ala Ser Met Ile Lys Arg Tyr Asp Glu His His Gln Asp Leu Thr Leu
            340                 345                 350

Leu Lys Ala Leu Val Arg Gln Gln Leu Pro Glu Lys Tyr Lys Glu Ile
        355                 360                 365

Phe Phe Asp Gln Ser Lys Asn Gly Tyr Ala Gly Tyr Ile Asp Gly Gly
    370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
        435                 440                 445

Pro Phe Leu Lys Asp Asn Arg Glu Lys Ile Glu Lys Ile Leu Thr Phe
    450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
            500                 505                 510

Met Thr Asn Phe Asp Lys Asn Leu Pro Asn Glu Lys Val Leu Pro Lys
        515                 520                 525

His Ser Leu Leu Tyr Glu Tyr Phe Thr Val Tyr Asn Glu Leu Thr Lys
    530                 535                 540

Val Lys Tyr Val Thr Glu Gly Met Arg Lys Pro Ala Phe Leu Ser Gly
545                 550                 555                 560
```

```
Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
            580                 585                 590

Phe Asp Ser Val Glu Ile Ser Gly Val Glu Asp Arg Phe Asn Ala Ser
        595                 600                 605

Leu Gly Thr Tyr His Asp Leu Leu Lys Ile Ile Lys Asp Lys Asp Phe
    610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
            660                 665                 670

Arg Tyr Thr Gly Trp Gly Arg Leu Ser Arg Lys Leu Ile Asn Gly Ile
        675                 680                 685

Arg Asp Lys Gln Ser Gly Lys Thr Ile Leu Asp Phe Leu Lys Ser Asp
    690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
            740                 745                 750

Lys Gly Ile Leu Gln Thr Val Lys Val Val Asp Glu Leu Val Lys Val
        755                 760                 765

Met Gly Arg His Lys Pro Glu Asn Ile Val Ile Glu Met Ala Arg Glu
    770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
            820                 825                 830

Tyr Leu Gln Asn Gly Arg Asp Met Tyr Val Asp Gln Glu Leu Asp Ile
        835                 840                 845

Asn Arg Leu Ser Asp Tyr Asp Val Asp Ala Ile Val Pro Gln Ser Phe
    850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
            900                 905                 910

Arg Lys Phe Asp Asn Leu Thr Lys Ala Glu Arg Gly Gly Leu Ser Glu
        915                 920                 925

Leu Asp Lys Ala Gly Phe Ile Lys Arg Gln Leu Val Glu Thr Arg Gln
    930                 935                 940

Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
```

```
            980                 985                 990

Val Arg Glu Ile Asn Asn Tyr His  His Ala His Asp Ala  Tyr Leu Asn
        995                 1000                1005

Ala Val  Val Gly Thr Ala Leu  Ile Lys Lys Tyr Pro  Lys Leu Glu
    1010                 1015                 1020

Ser Glu  Phe Val Tyr Gly Asp  Tyr Lys Val Tyr Asp  Val Arg Lys
    1025                 1030                 1035

Met Ile  Ala Lys Ser Glu Gln  Glu Ile Gly Lys Ala  Thr Ala Lys
    1040                 1045                 1050

Tyr Phe  Phe Tyr Ser Asn Ile  Met Asn Phe Phe Lys  Thr Glu Ile
    1055                 1060                 1065

Thr Leu  Ala Asn Gly Glu Ile  Arg Lys Arg Pro Leu  Ile Glu Thr
    1070                 1075                 1080

Asn Gly  Glu Thr Gly Glu Ile  Val Trp Asp Lys Gly  Arg Asp Phe
    1085                 1090                 1095

Ala Thr  Val Arg Lys Val Leu  Ser Met Pro Gln Val  Asn Ile Val
    1100                 1105                 1110

Lys Lys  Thr Glu Val Gln Thr  Gly Gly Phe Ser Lys  Glu Ser Ile
    1115                 1120                 1125

Leu Pro  Lys Arg Asn Ser Asp  Lys Leu Ile Ala Arg  Lys Lys Asp
    1130                 1135                 1140

Trp Asp  Pro Lys Lys Tyr Gly  Gly Phe Asp Ser Pro  Thr Val Ala
    1145                 1150                 1155

Tyr Ser  Val Leu Val Val Ala  Lys Val Glu Lys Gly  Lys Ser Lys
    1160                 1165                 1170

Lys Leu  Lys Ser Val Lys Glu  Leu Leu Gly Ile Thr  Ile Met Glu
    1175                 1180                 1185

Arg Ser  Ser Phe Glu Lys Asn  Pro Ile Asp Phe Leu  Glu Ala Lys
    1190                 1195                 1200

Gly Tyr  Lys Glu Val Lys Lys  Asp Leu Ile Ile Lys  Leu Pro Lys
    1205                 1210                 1215

Tyr Ser  Leu Phe Glu Leu Glu  Asn Gly Arg Lys Arg  Met Leu Ala
    1220                 1225                 1230

Ser Ala  Gly Glu Leu Gln Lys  Gly Asn Glu Leu Ala  Leu Pro Ser
    1235                 1240                 1245

Lys Tyr  Val Asn Phe Leu Tyr  Leu Ala Ser His Tyr  Glu Lys Leu
    1250                 1255                 1260

Lys Gly  Ser Pro Glu Asp Asn  Glu Gln Lys Gln Leu  Phe Val Glu
    1265                 1270                 1275

Gln His  Lys His Tyr Leu Asp  Glu Ile Ile Glu Gln  Ile Ser Glu
    1280                 1285                 1290

Phe Ser  Lys Arg Val Ile Leu  Ala Asp Ala Asn Leu  Asp Lys Val
    1295                 1300                 1305

Leu Ser  Ala Tyr Asn Lys His  Arg Asp Lys Pro Ile  Arg Glu Gln
    1310                 1315                 1320

Ala Glu  Asn Ile Ile His Leu  Phe Thr Leu Thr Asn  Leu Gly Ala
    1325                 1330                 1335

Pro Ala  Ala Phe Lys Tyr Phe  Asp Thr Thr Ile Asp  Arg Lys Arg
    1340                 1345                 1350

Tyr Thr  Ser Thr Lys Glu Val  Leu Asp Ala Thr Leu  Ile His Gln
    1355                 1360                 1365

Ser Ile  Thr Gly Leu Tyr Glu  Thr Arg Ile Asp Leu  Ser Gln Leu
    1370                 1375                 1380
```

```
Gly Gly  Asp Ser Gly Gly Ser  Ser Gly Gly Ser Ser  Gly Ser Glu
    1385                 1390                 1395

Thr Pro  Gly Thr Ser Glu Ser  Ala Thr Pro Glu Ser  Ser Gly Gly
    1400                 1405                 1410

Ser Ser  Gly Gly Ser Ser Thr  Leu Asn Ile Glu Asp  Glu Tyr Arg
    1415                 1420                 1425

Leu His  Glu Thr Ser Lys Glu  Pro Asp Val Ser Leu  Gly Ser Thr
    1430                 1435                 1440

Trp Leu  Ser Asp Phe Pro Gln  Ala Trp Ala Glu Thr  Gly Gly Met
    1445                 1450                 1455

Gly Leu  Ala Val Arg Gln Ala  Pro Leu Ile Ile Pro  Leu Lys Ala
    1460                 1465                 1470

Thr Ser  Thr Pro Val Ser Ile  Lys Gln Tyr Pro Met  Ser Gln Glu
    1475                 1480                 1485

Ala Arg  Leu Gly Ile Lys Pro  His Ile Gln Arg Leu  Leu Asp Gln
    1490                 1495                 1500

Gly Ile  Leu Val Pro Cys Gln  Ser Pro Trp Asn Thr  Pro Leu Leu
    1505                 1510                 1515

Pro Val  Lys Lys Pro Gly Thr  Asn Asp Tyr Arg Pro  Val Gln Asp
    1520                 1525                 1530

Leu Arg  Glu Val Asn Lys Arg  Val Glu Asp Ile His  Pro Thr Val
    1535                 1540                 1545

Pro Asn  Pro Tyr Asn Leu Leu  Ser Gly Leu Pro Pro  Ser His Gln
    1550                 1555                 1560

Trp Tyr  Thr Val Leu Asp Leu  Lys Asp Ala Phe Phe  Cys Leu Arg
    1565                 1570                 1575

Leu His  Pro Thr Ser Gln Pro  Leu Phe Ala Phe Glu  Trp Arg Asp
    1580                 1585                 1590

Pro Glu  Met Gly Ile Ser Gly  Gln Leu Thr Trp Thr  Arg Leu Pro
    1595                 1600                 1605

Gln Gly  Phe Lys Asn Ser Pro  Thr Leu Phe Asn Glu  Ala Leu His
    1610                 1615                 1620

Arg Asp  Leu Ala Asp Phe Arg  Ile Gln His Pro Asp  Leu Ile Leu
    1625                 1630                 1635

Leu Gln  Tyr Val Asp Asp Leu  Leu Leu Ala Ala Thr  Ser Glu Leu
    1640                 1645                 1650

Asp Cys  Gln Gln Gly Thr Arg  Ala Leu Leu Gln Thr  Leu Gly Asn
    1655                 1660                 1665

Leu Gly  Tyr Arg Ala Ser Ala  Lys Lys Ala Gln Ile  Cys Gln Lys
    1670                 1675                 1680

Gln Val  Lys Tyr Leu Gly Tyr  Leu Leu Lys Glu Gly  Gln Arg Trp
    1685                 1690                 1695

Leu Thr  Glu Ala Arg Lys Glu  Thr Val Met Gly Gln  Pro Thr Pro
    1700                 1705                 1710

Lys Thr  Pro Arg Gln Leu Arg  Glu Phe Leu Gly Lys  Ala Gly Phe
    1715                 1720                 1725

Cys Arg  Leu Phe Ile Pro Gly  Phe Ala Glu Met Ala  Ala Pro Leu
    1730                 1735                 1740

Tyr Pro  Leu Thr Lys Pro Gly  Thr Leu Phe Asn Trp  Gly Pro Asp
    1745                 1750                 1755

Gln Gln  Lys Ala Tyr Gln Glu  Ile Lys Gln Ala Leu  Leu Thr Ala
    1760                 1765                 1770
```

```
Pro Ala Leu Gly Leu Pro Asp Leu Thr Lys Pro Phe Glu Leu Phe
    1775                1780                1785

Val Asp Glu Lys Gln Gly Tyr Ala Lys Gly Val Leu Thr Gln Lys
    1790                1795                1800

Leu Gly Pro Trp Arg Arg Pro Val Ala Tyr Leu Ser Lys Lys Leu
    1805                1810                1815

Asp Pro Val Ala Ala Gly Trp Pro Pro Cys Leu Arg Met Val Ala
    1820                1825                1830

Ala Ile Ala Val Leu Thr Lys Asp Ala Gly Lys Leu Thr Met Gly
    1835                1840                1845

Gln Pro Leu Val Ile Leu Ala Pro His Ala Val Glu Ala Leu Val
    1850                1855                1860

Lys Gln Pro Pro Asp Arg Trp Leu Ser Asn Ala Arg Met Thr His
    1865                1870                1875

Tyr Gln Ala Leu Leu Leu Asp Thr Asp Arg Val Gln Phe Gly Pro
    1880                1885                1890

Val Val Ala Leu Asn Pro Ala Thr Leu Leu Pro Leu Pro Glu Glu
    1895                1900                1905

Gly Leu Gln His Asn Cys Leu Asp Ile Leu Ala Glu Ala His Gly
    1910                1915                1920

Thr Arg Pro Asp Leu Thr Asp Gln Pro Leu Pro Asp Ala Asp His
    1925                1930                1935

Thr Trp Tyr Thr Asp Gly Ser Ser Leu Leu Gln Glu Gly Gln Arg
    1940                1945                1950

Lys Ala Gly Ala Ala Val Thr Thr Glu Thr Glu Val Ile Trp Ala
    1955                1960                1965

Lys Ala Leu Pro Ala Gly Thr Ser Ala Gln Arg Ala Glu Leu Ile
    1970                1975                1980

Ala Leu Thr Gln Ala Leu Lys Met Ala Glu Gly Lys Lys Leu Asn
    1985                1990                1995

Val Tyr Thr Asp Ser Arg Tyr Ala Phe Ala Thr Ala His Ile His
    2000                2005                2010

Gly Glu Ile Tyr Arg Arg Arg Gly Trp Leu Thr Ser Glu Gly Lys
    2015                2020                2025

Glu Ile Lys Asn Lys Asp Glu Ile Leu Ala Leu Leu Lys Ala Leu
    2030                2035                2040

Phe Leu Pro Lys Arg Leu Ser Ile Ile His Cys Pro Gly His Gln
    2045                2050                2055

Lys Gly His Ser Ala Glu Ala Arg Gly Asn Arg Met Ala Asp Gln
    2060                2065                2070

Ala Ala Arg Lys Ala Ala Ile Thr Glu Thr Pro Asp Thr Ser Thr
    2075                2080                2085

Leu Leu Ile Glu Asn Ser Ser Pro Ser Gly Gly Ser Lys Arg Thr
    2090                2095                2100

Ala Asp Gly Ser Glu Phe Glu Pro Lys Lys Lys Arg Lys Val
    2105                2110                2115
```

<210> SEQ ID NO 59
<211> LENGTH: 677
<212> TYPE: PRT
<213> ORGANISM: Artificial Sequence
<220> FEATURE:
<223> OTHER INFORMATION: Synthetic

<400> SEQUENCE: 59

-continued

```
Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asn Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Lys Ala Gly Phe Cys Arg Leu Phe Ile Pro Gly Phe Ala Glu Met
305                 310                 315                 320

Ala Ala Pro Leu Tyr Pro Leu Thr Lys Pro Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
```

```
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Trp Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro
        675


<210> SEQ ID NO 60
<211> LENGTH: 1943
<212> TYPE: PRT
<213> ORGANISM: Artificial Sequence
<220> FEATURE:
<223> OTHER INFORMATION: Synthetic

<400> SEQUENCE: 60

Met Lys Arg Thr Ala Asp Gly Ser Glu Phe Glu Ser Pro Lys Lys Lys
1               5                   10                  15

Arg Lys Val Asp Lys Lys Tyr Ser Ile Gly Leu Asp Ile Gly Thr Asn
            20                  25                  30

Ser Val Gly Trp Ala Val Ile Thr Asp Glu Tyr Lys Val Pro Ser Lys
        35                  40                  45

Lys Phe Lys Val Leu Gly Asn Thr Asp Arg His Ser Ile Lys Lys Asn
    50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Arg Tyr Thr Arg Arg Lys Asn Arg
                85                  90                  95

Ile Cys Tyr Leu Gln Glu Ile Phe Ser Asn Glu Met Ala Lys Val Asp
```

```
            100                 105                 110

Asp Ser Phe Phe His Arg Leu Glu Glu Ser Phe Leu Val Glu Glu Asp
        115                 120                 125

Lys Lys His Glu Arg His Pro Ile Phe Gly Asn Ile Val Asp Glu Val
    130                 135                 140

Ala Tyr His Glu Lys Tyr Pro Thr Ile Tyr His Leu Arg Lys Lys Leu
145                 150                 155                 160

Val Asp Ser Thr Asp Lys Ala Asp Leu Arg Leu Ile Tyr Leu Ala Leu
                165                 170                 175

Ala His Met Ile Lys Phe Arg Gly His Phe Leu Ile Glu Gly Asp Leu
            180                 185                 190

Asn Pro Asp Asn Ser Asp Val Asp Lys Leu Phe Ile Gln Leu Val Gln
        195                 200                 205

Thr Tyr Asn Gln Leu Phe Glu Glu Asn Pro Ile Asn Ala Ser Gly Val
    210                 215                 220

Asp Ala Lys Ala Ile Leu Ser Ala Arg Leu Ser Lys Ser Arg Arg Leu
225                 230                 235                 240

Glu Asn Leu Ile Ala Gln Leu Pro Gly Glu Lys Lys Asn Gly Leu Phe
                245                 250                 255

Gly Asn Leu Ile Ala Leu Ser Leu Gly Leu Thr Pro Asn Phe Lys Ser
            260                 265                 270

Asn Phe Asp Leu Ala Glu Asp Ala Lys Leu Gln Leu Ser Lys Asp Thr
        275                 280                 285

Tyr Asp Asp Asp Leu Asp Asn Leu Leu Ala Gln Ile Gly Asp Gln Tyr
    290                 295                 300

Ala Asp Leu Phe Leu Ala Ala Lys Asn Leu Ser Asp Ala Ile Leu Leu
305                 310                 315                 320

Ser Asp Ile Leu Arg Val Asn Thr Glu Ile Thr Lys Ala Pro Leu Ser
                325                 330                 335

Ala Ser Met Ile Lys Arg Tyr Asp Glu His His Gln Asp Leu Thr Leu
            340                 345                 350

Leu Lys Ala Leu Val Arg Gln Gln Leu Pro Glu Lys Tyr Lys Glu Ile
        355                 360                 365

Phe Phe Asp Gln Ser Lys Asn Gly Tyr Ala Gly Tyr Ile Asp Gly Gly
    370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
        435                 440                 445

Pro Phe Leu Lys Asp Asn Arg Glu Lys Ile Glu Lys Ile Leu Thr Phe
    450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
            500                 505                 510

Met Thr Asn Phe Asp Lys Asn Leu Pro Asn Glu Lys Val Leu Pro Lys
        515                 520                 525
```

```
His Ser Leu Leu Tyr Glu Tyr Phe Thr Val Tyr Asn Glu Leu Thr Lys
    530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
            580                 585                 590

Phe Asp Ser Val Glu Ile Ser Gly Val Glu Asp Arg Phe Asn Ala Ser
        595                 600                 605

Leu Gly Thr Tyr His Asp Leu Leu Lys Ile Ile Lys Asp Lys Asp Phe
    610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
            660                 665                 670

Arg Tyr Thr Gly Trp Gly Arg Leu Ser Arg Lys Leu Ile Asn Gly Ile
        675                 680                 685

Arg Asp Lys Gln Ser Gly Lys Thr Ile Leu Asp Phe Leu Lys Ser Asp
    690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
            740                 745                 750

Lys Gly Ile Leu Gln Thr Val Lys Val Val Asp Glu Leu Val Lys Val
        755                 760                 765

Met Gly Arg His Lys Pro Glu Asn Ile Val Ile Glu Met Ala Arg Glu
    770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
            820                 825                 830

Tyr Leu Gln Asn Gly Arg Asp Met Tyr Val Asp Gln Glu Leu Asp Ile
        835                 840                 845

Asn Arg Leu Ser Asp Tyr Asp Val Asp Ala Ile Val Pro Gln Ser Phe
    850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
            900                 905                 910

Arg Lys Phe Asp Asn Leu Thr Lys Ala Glu Arg Gly Gly Leu Ser Glu
        915                 920                 925

Leu Asp Lys Ala Gly Phe Ile Lys Arg Gln Leu Val Glu Thr Arg Gln
    930                 935                 940
```

```
Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
            980                 985                 990

Val Arg Glu Ile Asn Asn Tyr His  His Ala His Asp Ala  Tyr Leu Asn
        995                 1000                 1005

Ala Val  Val Gly Thr Ala Leu  Ile Lys Lys Tyr Pro  Lys Leu Glu
    1010                 1015                 1020

Ser Glu  Phe Val Tyr Gly Asp  Tyr Lys Val Tyr Asp  Val Arg Lys
    1025                 1030                 1035

Met Ile  Ala Lys Ser Glu Gln  Glu Ile Gly Lys Ala  Thr Ala Lys
    1040                 1045                 1050

Tyr Phe  Phe Tyr Ser Asn Ile  Met Asn Phe Phe Lys  Thr Glu Ile
    1055                 1060                 1065

Thr Leu  Ala Asn Gly Glu Ile  Arg Lys Arg Pro Leu  Ile Glu Thr
    1070                 1075                 1080

Asn Gly  Glu Thr Gly Glu Ile  Val Trp Asp Lys Gly  Arg Asp Phe
    1085                 1090                 1095

Ala Thr  Val Arg Lys Val Leu  Ser Met Pro Gln Val  Asn Ile Val
    1100                 1105                 1110

Lys Lys  Thr Glu Val Gln Thr  Gly Gly Phe Ser Lys  Glu Ser Ile
    1115                 1120                 1125

Leu Pro  Lys Arg Asn Ser Asp  Lys Leu Ile Ala Arg  Lys Lys Asp
    1130                 1135                 1140

Trp Asp  Pro Lys Lys Tyr Gly  Gly Phe Asp Ser Pro  Thr Val Ala
    1145                 1150                 1155

Tyr Ser  Val Leu Val Val Ala  Lys Val Glu Lys Gly  Lys Ser Lys
    1160                 1165                 1170

Lys Leu  Lys Ser Val Lys Glu  Leu Leu Gly Ile Thr  Ile Met Glu
    1175                 1180                 1185

Arg Ser  Ser Phe Glu Lys Asn  Pro Ile Asp Phe Leu  Glu Ala Lys
    1190                 1195                 1200

Gly Tyr  Lys Glu Val Lys Lys  Asp Leu Ile Ile Lys  Leu Pro Lys
    1205                 1210                 1215

Tyr Ser  Leu Phe Glu Leu Glu  Asn Gly Arg Lys Arg  Met Leu Ala
    1220                 1225                 1230

Ser Ala  Gly Glu Leu Gln Lys  Gly Asn Glu Leu Ala  Leu Pro Ser
    1235                 1240                 1245

Lys Tyr  Val Asn Phe Leu Tyr  Leu Ala Ser His Tyr  Glu Lys Leu
    1250                 1255                 1260

Lys Gly  Ser Pro Glu Asp Asn  Glu Gln Lys Gln Leu  Phe Val Glu
    1265                 1270                 1275

Gln His  Lys His Tyr Leu Asp  Glu Ile Ile Glu Gln  Ile Ser Glu
    1280                 1285                 1290

Phe Ser  Lys Arg Val Ile Leu  Ala Asp Ala Asn Leu  Asp Lys Val
    1295                 1300                 1305

Leu Ser  Ala Tyr Asn Lys His  Arg Asp Lys Pro Ile  Arg Glu Gln
    1310                 1315                 1320

Ala Glu  Asn Ile Ile His Leu  Phe Thr Leu Thr Asn  Leu Gly Ala
    1325                 1330                 1335

Pro Ala  Ala Phe Lys Tyr Phe  Asp Thr Thr Ile Asp  Arg Lys Arg
```

```
    1340                1345                1350

Tyr Thr  Ser Thr Lys Glu Val  Leu Asp Ala Thr Leu  Ile His Gln
    1355                1360                1365

Ser Ile  Thr Gly Leu Tyr Glu  Thr Arg Ile Asp Leu  Ser Gln Leu
    1370                1375                1380

Gly Gly  Asp Ser Gly Gly Ser  Ser Gly Gly Ser Ser  Gly Ser Glu
    1385                1390                1395

Thr Pro  Gly Thr Ser Glu Ser  Ala Thr Pro Glu Ser  Ser Gly Gly
    1400                1405                1410

Ser Ser  Gly Gly Ser Ser Thr  Leu Asn Ile Glu Asp  Glu Tyr Arg
    1415                1420                1425

Leu His  Glu Thr Ser Lys Glu  Pro Asp Val Ser Leu  Gly Ser Thr
    1430                1435                1440

Trp Leu  Ser Asp Phe Pro Gln  Ala Trp Ala Glu Thr  Gly Gly Met
    1445                1450                1455

Gly Leu  Ala Val Arg Gln Ala  Pro Leu Ile Ile Pro  Leu Lys Ala
    1460                1465                1470

Thr Ser  Thr Pro Val Ser Ile  Lys Gln Tyr Pro Met  Ser Gln Glu
    1475                1480                1485

Ala Arg  Leu Gly Ile Lys Pro  His Ile Gln Arg Leu  Leu Asp Gln
    1490                1495                1500

Gly Ile  Leu Val Pro Cys Gln  Ser Pro Trp Asn Thr  Pro Leu Leu
    1505                1510                1515

Pro Val  Lys Lys Pro Gly Thr  Asn Asp Tyr Arg Pro  Val Gln Asp
    1520                1525                1530

Leu Arg  Glu Val Asn Lys Arg  Val Glu Asp Ile His  Pro Thr Val
    1535                1540                1545

Pro Asn  Pro Tyr Asn Leu Leu  Ser Gly Leu Pro Pro  Ser His Gln
    1550                1555                1560

Trp Tyr  Thr Val Leu Asp Leu  Lys Asp Ala Phe Phe  Cys Leu Arg
    1565                1570                1575

Leu His  Pro Thr Ser Gln Pro  Leu Phe Ala Phe Glu  Trp Arg Asp
    1580                1585                1590

Pro Glu  Met Gly Ile Ser Gly  Gln Leu Thr Trp Thr  Arg Leu Pro
    1595                1600                1605

Gln Gly  Phe Lys Asn Ser Pro  Thr Leu Phe Asn Glu  Ala Leu His
    1610                1615                1620

Arg Asp  Leu Ala Asp Phe Arg  Ile Gln His Pro Asp  Leu Ile Leu
    1625                1630                1635

Leu Gln  Tyr Val Asp Asp Leu  Leu Leu Ala Ala Thr  Ser Glu Leu
    1640                1645                1650

Asp Cys  Gln Gln Gly Thr Arg  Ala Leu Leu Gln Thr  Leu Gly Asn
    1655                1660                1665

Leu Gly  Tyr Arg Ala Ser Ala  Lys Lys Ala Gln Ile  Cys Gln Lys
    1670                1675                1680

Gln Val  Lys Tyr Leu Gly Tyr  Leu Leu Lys Glu Gly  Gln Arg Trp
    1685                1690                1695

Leu Thr  Glu Ala Arg Lys Glu  Thr Val Met Gly Gln  Pro Thr Pro
    1700                1705                1710

Lys Thr  Pro Arg Gln Leu Arg  Glu Phe Leu Gly Lys  Ala Gly Phe
    1715                1720                1725

Cys Arg  Leu Phe Ile Pro Gly  Phe Ala Glu Met Ala  Ala Pro Leu
    1730                1735                1740
```

Tyr Pro Leu Thr Lys Pro Gly Thr Leu Phe Asn Trp Gly Pro Asp
1745 1750 1755

Gln Gln Lys Ala Tyr Gln Glu Ile Lys Gln Ala Leu Leu Thr Ala
1760 1765 1770

Pro Ala Leu Gly Leu Pro Asp Leu Thr Lys Pro Phe Glu Leu Phe
1775 1780 1785

Val Asp Glu Lys Gln Gly Tyr Ala Lys Gly Val Leu Thr Gln Lys
1790 1795 1800

Leu Gly Pro Trp Arg Arg Pro Val Ala Tyr Leu Ser Lys Lys Leu
1805 1810 1815

Asp Pro Val Ala Ala Gly Trp Pro Pro Cys Leu Arg Met Val Ala
1820 1825 1830

Ala Ile Ala Val Leu Thr Lys Asp Ala Gly Lys Leu Thr Met Gly
1835 1840 1845

Gln Pro Leu Val Ile Leu Ala Pro His Ala Val Glu Ala Leu Val
1850 1855 1860

Lys Gln Pro Pro Asp Arg Trp Leu Ser Asn Ala Arg Met Thr His
1865 1870 1875

Tyr Gln Ala Leu Leu Leu Asp Thr Asp Arg Val Gln Phe Gly Pro
1880 1885 1890

Val Val Ala Leu Asn Pro Ala Thr Leu Leu Pro Leu Pro Glu Glu
1895 1900 1905

Gly Leu Gln His Asn Cys Leu Asp Asn Ser Arg Leu Ile Asn Ser
1910 1915 1920

Gly Gly Ser Lys Arg Thr Ala Asp Gly Ser Glu Phe Glu Pro Lys
1925 1930 1935

Lys Lys Arg Lys Val
1940

<210> SEQ ID NO 61
<211> LENGTH: 503
<212> TYPE: PRT
<213> ORGANISM: Artificial Sequence
<220> FEATURE:
<223> OTHER INFORMATION: Synthetic

<400> SEQUENCE: 61

Thr Leu Asn Ile Glu Asp Glu Tyr Arg Leu His Glu Thr Ser Lys Glu
1 5 10 15

Pro Asp Val Ser Leu Gly Ser Thr Trp Leu Ser Asp Phe Pro Gln Ala
20 25 30

Trp Ala Glu Thr Gly Gly Met Gly Leu Ala Val Arg Gln Ala Pro Leu
35 40 45

Ile Ile Pro Leu Lys Ala Thr Ser Thr Pro Val Ser Ile Lys Gln Tyr
50 55 60

Pro Met Ser Gln Glu Ala Arg Leu Gly Ile Lys Pro His Ile Gln Arg
65 70 75 80

Leu Leu Asp Gln Gly Ile Leu Val Pro Cys Gln Ser Pro Trp Asn Thr
85 90 95

Pro Leu Leu Pro Val Lys Lys Pro Gly Thr Asn Asp Tyr Arg Pro Val
100 105 110

Gln Asp Leu Arg Glu Val Asn Lys Arg Val Glu Asp Ile His Pro Thr
115 120 125

Val Pro Asn Pro Tyr Asn Leu Leu Ser Gly Leu Pro Pro Ser His Gln
130 135 140

```
Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asn Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Lys Ala Gly Phe Cys Arg Leu Phe Ile Pro Gly Phe Ala Glu Met
305                 310                 315                 320

Ala Ala Pro Leu Tyr Pro Leu Thr Lys Pro Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Asn Ser Arg Leu Ile Asn
            500
```

METHODS AND COMPOSITIONS FOR PRIME EDITING RNA

RELATED APPLICATIONS

This application is a national stage filing under 35 U.S.C. § 371 of International PCT Application PCT/US2020/055156, filed Oct. 9, 2020, which claims priority under 35 U.S.C. § 119(e) to U.S. Provisional Application, U.S. Ser. No. 62/913,480, filed on Oct. 10, 2019, each of which is incorporated herein by reference.

GOVERNMENT SUPPORT

This invention was made with government support under grant numbers AI142756, HG009490, EB022376, and GM118062 awarded by the National Institutes of Health. The government has certain rights in the invention.

REFERENCE TO AN ELECTRONIC SEQUENCE LISTING

The contents of the electronic sequence listing (B119570087US01-SUBSEQ-TNG.txt; Size: 305,640 bytes; and Date of Creation: Jul. 29, 2024) is herein incorporated by reference in its entirety.

BACKGROUND OF THE INVENTION

A variety of nucleic acid-editing technologies have been developed to carry out RNA editing as a means to correct disease-relevant mutations. For example, RNA interference-based therapies (RNAi) uses synthetic, small interfering RNAs (siRNAs) to achieve the targeted knockdown of specific RNA targets.[1,2] However, this approach only enables knockdown of the targeted gene, and cannot install therapeutic mutations, severely limiting its applicability in the treatment of genetic diseases. In another example, trans-splicing ribozymes enable the removal of diseased exons and their replacement with non-diseased versions.[3] However, these enzymes are inefficient and must be targeted to a specific site on the RNA that may or may not be occluded. In addition, trans-splicing ribozymes can result in non-specific editing of a target site. These enzymes are can result in significant off-target effects owing to a small guide sequence. Trans-splicing ribozymes also are not catalytic, meaning that: (i) large amounts of ribozyme are necessary to enable editing; and (ii) highly-transcribed RNA targets are unlikely to be effectively edited by the ribozyme. RNA editing has also been described in the context of base editing which converts one base to another in a target RNA (e.g., see Cox et al., "RNA editing with CRISPR-Cas13," *Science* Nov. 24, 2017, Vol. 258(6366), pp. 1019-1027.

Despite these developments of approaches to edit RNA molecules, technologies which are more flexible and which can introduce a wider range of edits directly in RNA are desired in the art. The present disclosure provides a novel approach for editing RNA.

SUMMARY OF THE INVENTION

The present disclosure provides a novel approach to editing RNA molecules. In certain aspects, the disclosure provides RNA-editing fusion proteins that combine (a) a programmable RNA-binding protein (napRNAbp), such as Cas13, and (b) an RNA-dependent RNA polymerase (RDRP). In still other aspects, the disclosure provides complexes comprising (a) napRNAbp-RDRP fusion proteins, and (b) an RNA prime editing guide RNA ("RpegRNA") that comprise an extension arm containing a desired edit template to be integrated into a target RNA molecule. The RpegRNA associates with the napRNAbp:RDRP fusion protein (through its interaction with the napRNAbp component) and directs the enzyme to bind to an RNA molecule having complementarity with the RpegRNA. The RpegRNA comprises an extension arm on the 3' end of the RpegRNA that comprises a prime sequence that binds to the 3' end of a target RNA to create an RNA/RNA hybrid that provides the substrate for RDRP to polymerize a new RNA sequence at the 3' of the RNA molecule, templated by the extension arm of the RpegRNA.

The present invention relates in part to the discovery that the mechanism of target-primed reverse transcription (TPRT) or "prime editing" can be leveraged or adapted for conducting precision CRISPR/Cas-based nucleic acid editing of RNA with high efficiency and genetic flexibility, as depicted in various embodiments of FIGS. 1-4.

As shown herein, the inventors have used Cas protein: RNA-dependent RNA Polymerase (RDRP) fusion protein to target a specific RNA sequence with a specialized guide RNA, i.e., a RpegRNA.

Accordingly, in aspects, the disclosure relates to a fusion protein comprising a nucleic acid-programmable RNA binding protein (napRNAbp) and an RNA-dependent RNA polymerase (RDRP). In some embodiments, the fusion protein when complexed to a RNA prime editing guide RNA (rpegRNA) is capable of appending a single-strand RNA sequence to a target RNA.

In some embodiments, the single-stand RNA sequence is appended to the 3' terminus of the target RNA or to a 3' terminus which is formed upon cleavage of the target RNA by the fusion protein at a cut site. In some embodiments, the single-strand RNA sequence is polymerized by the RDRP using the rpegRNA as a template.

In some embodiments, the napRNAbp is a Cas13 protein. In some embodiments, the Cas13 protein is a Cas13a, Cas13b, or Cas13d protein. In some embodiments, the Cas13 protein is nuclease inactive. In some embodiments, the Cas13 protein has an amino acid sequence of SEQ ID NO: 1, or an amino acid sequence having at least 70% sequence identity to SEQ ID NO: 1.

In some embodiments, the RDRP is capable of polymerizing a single-strand RNA sequence using rpegRNA as a template.

In some embodiments, the RDRP comprises an amino acid sequence selected from the group consisting of: SEQ ID NO: 2, SEQ ID NO: 3, SEQ ID NO: 4, SEQ ID NO: 5, SEQ ID NO: 6, SEQ ID NO: 7, and SEQ ID NO: 8. In some embodiments, the RDRP comprises an amino acid sequence with at least 70% sequence identity to a sequence selected from the group consisting of: SEQ ID NO: 2, SEQ ID NO: 3, SEQ ID NO: 4, SEQ ID NO: 5, SEQ ID NO: 6, SEQ ID NO: 7, and SEQ ID NO: 8.

In some embodiments, the fusion protein has one of the following structures: N-[RNA-dependent RNA polymerase]-[nucleic acid-programmable RNA binding protein]-C; or N-[nucleic acid-programmable RNA binding protein]-[RNA-dependent RNA polymerase]-C, wherein "]-[" represents a linker sequence.

In some embodiments, the linker sequence has an amino acid sequence selected from the group consisting of SEQ ID NOs: 14-23.

In an aspect, the disclosure relates to an RNA prime editor complex for appending a single-strand RNA sequence to a target RNA comprising any of the fusion proteins disclosed herein and a rpegRNA. In some embodiments, the rpegRNA is capable of programming the fusion protein to bind to the target RNA. In some embodiments, the rpegRNA comprises the following structure: 5'-[spacer sequence]-[scaffold sequence]-[template sequence]-3', wherein the spacer sequence anneals to the target RNA at a complementary protospacer sequence, the scaffold sequence binds the rpegRNA to the nucleic acid-programmable RNA binding protein of the fusion protein, and the template sequence provides an RNA template for synthesis of the single-strand RNA sequence by the RNA-dependent RNA polymerase of the fusion protein. In some embodiments, napRNAbp of the fusion protein comprises a nuclease activity which cleaves the target RNA at a cut site upon binding of the complex thereto. In some embodiments, the napRNAbp of the fusion protein is catalytically inactive.

In an aspect, the disclosure relates to an RNA prime editor complex for appending a single-strand RNA sequence to a target RNA comprising: (i) a first fusion protein comprising a catalytically inactive nucleic acid-programmable RNA binding protein and a RNA-dependent RNA polymerase; (ii) a second fusion protein comprising catalytically active nucleic acid-programmable RNA binding protein that is capable of cleaving the target RNA to generate a free 3' terminus; (iii) an rpegRNA that directs the first fusion protein to a first locus in the target RNA; (iv) a guide RNA that directs the second fusion protein to a second locus in the target RNA. In some embodiments, the second fusion protein cleaves the target RNA at the second locus to produce a 3' terminus, and wherein the first fusion protein appends a single-strand RNA sequence to a target RNA using the rpegRNA as a template.

In an aspect, the disclosure relates to a method for appending a desired single-strand RNA sequence to the 3' end of a target RNA, the method comprising contacting the target RNA with an RNA prime editor complex, said complex comprising a rpegRNA and a fusion protein that comprises an RNA-dependent RNA polymerase and a nucleic acid-programmable RNA binding protein.

In some embodiments, the rpegRNA comprises a spacer sequence, a scaffold sequence, and a template sequence.

In some embodiments, the spacer sequence directs the fusion protein to bind at the complementary protospacer in the target RNA.

In some embodiments, the scaffold sequence binds to the nucleic acid-programmable RNA binding protein of the fusion protein.

In some embodiments, the template sequence is used by the RNA-dependent RNA polymerase in the synthesis of the desired single-strand RNA.

In some embodiments, napRNAbp comprises a nuclease activity which cleaves the target RNA to generate an available 3' terminus.

In some embodiments, the nucleic acid-programmable RNA binding protein comprises an inactive nuclease activity.

In some embodiments, the method is used for appending the desired RNA sequence to an internal 3' terminus of the target RNA. In some embodiments, the method is used for appending the desired RNA sequence to the endogenous 3' terminus of the target RNA.

In some embodiments, the method further comprises contacting the target RNA with a second fusion protein comprising a nucleic acid-programmable RNA binding protein with a nuclease activity and a second guide RNA for introducing a e 3' terminus at a second RNA locus in the target RNA.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DEFINITIONS

Figure 1:
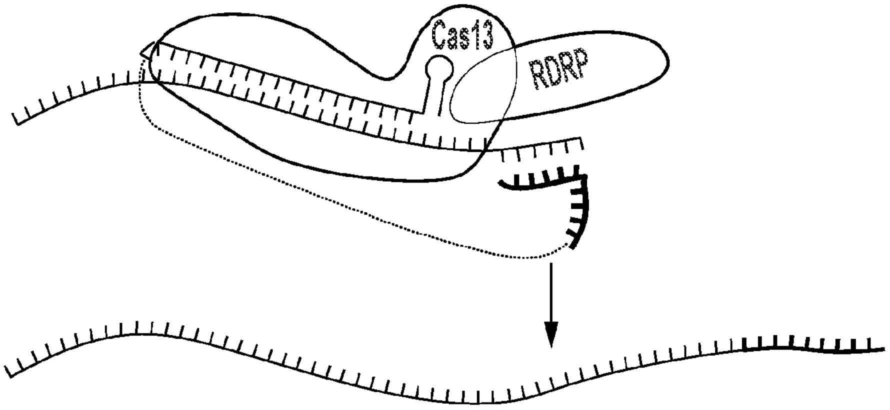
FIG. 1 shows an illustration of Cas13 fused to an RNA-dependent RNA polymerase (RDRP) (Cas13:RDRP) enabling RNA Prime Editing (RPE) at the 3' terminus of an RNA substrate. A rpegRNA enables recruitment of the RDRP to the 3' end of the RNA and subsequent programmed installation of new sequence at the 3' end (red).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

Antisense Strand

In genetics, the “antisense” strand of a segment within double-stranded DNA is the template strand, and which is considered to run in the 3' to 5' orientation. By contrast, the “sense” strand is the segment within double-stranded DNA that runs from 5' to 3', and which is complementary to the antisense strand of DNA, or template strand, which runs from 3' to 5'. In the case of a DNA segment that encodes a protein, the sense strand is the strand of DNA that has the same sequence as the mRNA, which takes the antisense strand as its template during transcription, and eventually undergoes (typically, not always) translation into a protein. The antisense strand is thus responsible for the RNA that is later translated to protein, while the sense strand possesses a nearly identical makeup to that of the mRNA. Note that for each segment of dsDNA, there will possibly be two sets of sense and antisense, depending on which direction one reads (since sense and antisense is relative to perspective). It is ultimately the gene product, or mRNA, that dictates which strand of one segment of dsDNA is referred to as sense or antisense.

Aptamer

An “aptamer” refers to an oligonucleotide or peptide molecule that binds to a specific target molecule. Aptamers include DNA or RNA aptamers that are short single-stranded DNA- or RNA-based oligonucleotides that can selectively bind to small molecular ligands or protein targets with high affinity and specificity, when folded into their unique three-dimensional structures. On the molecular level, aptamers bind to its cognate target through various non-covalent interactions, electrostatic interactions, hydrophobic interactions, and induced fitting.

Further reference can be made to Ku et al., "Nucleic Acid Aptamers: An Emerging Tool for Biotechnology and Biomedical Sensing," *Sensors,* 2015, 15(7): 16281-16313. The present disclosure contemplates the use of any aptamer, including those obtained from commercial sources. For example, numerous aptamers may be obtained from APTAGEN (www.aptagen.com) and include, but are not limited to, thrombin (15mer), HIV-1 TAR RNA hairpin loop (B22-19), human immunoglobulin G (IgG) (Apt 8), reactive green 19 (GR-30), abrin toxin (TA6), malachite green (MG-4), PSMA aptamer (A10-3), tenascin-C (GBI-10), and methylenedianiline (M1). Another example is prequeosine$_1$-1 riboswitch aptamer-one of the smallest natural tertiary RNA structures (also known as evopreQ$_1$-1).

Cas9

The term "Cas9" or "Cas9 nuclease" refers to an RNA-guided nuclease comprising a Cas9 domain, or a fragment thereof (e.g., a protein comprising an active or inactive DNA cleavage domain of Cas9, and/or the gRNA binding domain of Cas9). A "Cas9 domain" as used herein, is a protein fragment comprising an active or inactive cleavage domain of Cas9 and/or the gRNA binding domain of Cas9. A "Cas9 protein" is a full length Cas9 protein. A Cas9 nuclease is also referred to sometimes as a casn1 nuclease or a CRISPR (Clustered Regularly Interspaced Short Palindromic Repeat)-associated nuclease. CRISPR is an adaptive immune system that provides protection against mobile genetic elements (viruses, transposable elements, and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 domain. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821 (2012), the entire contents of which are hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) *RNA Biology* 10:5, 726-737; the entire contents of which are incorporated herein by reference. In some embodiments, a Cas9 nuclease comprises one or more mutations that partially impair or inactivate the DNA cleavage domain.

A nuclease-inactivated Cas9 domain may interchangeably be referred to as a "dCas9" protein (for nuclease-"dead" Cas9). Methods for generating a Cas9 domain (or a fragment thereof) having an inactive DNA cleavage domain are known (see, e.g., Jinek et al., *Science.* 337:816-821(2012); Qi et al., "Repurposing CRISPR as an RNA-Guided Platform for Sequence-Specific Control of Gene Expression" (2013) *Cell.* 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science.* 337:816-821(2012); Qi et al., *Cell.* 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example, a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, at least about 99.8% identical, or at least about 99.9% identical to wild type Cas9. In some embodiments, the Cas9 variant may have 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more amino acid changes compared to wild type Cas9. In some embodiments, the Cas9 variant comprises a fragment of SEQ ID NO: 18 Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9. In some embodiments, the fragment is at least 30%, at least 35%, at least 40%, at least 45%, at least 50%, at least 55%, at least 60%, at least 65%, at least 70%, at least 75%, at least 80%, at least 85%, at least 90%, at least 95% identical, at least 96%, at least 97%, at least 98%, at least 99%, or at least 99.5% of the amino acid length of a corresponding wild type Cas9.

Cas13

The term "Cas13" or "Cas13 domain" embraces any naturally occurring Cas13 from any organism, any naturally-occurring Cas13 equivalent or functional fragment thereof, any Cas13 homolog, ortholog, or paralog from any organism, and any mutant or variant of a Cas13, naturally-occurring or engineered. The term Cas13 is not meant to be particularly limiting and may be referred to as a "Cas13 or equivalent." Exemplary Cas13 proteins are further described herein and/or are described in the art and are incorporated herein by reference. The present disclosure is unlimited with regard to the particular napRNAbp that is employed in the RNA prime editors of the disclosure.

Complementarity

As used herein, the term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

CRISPR

CRISPR is a family of DNA sequences (i.e., CRISPR clusters) in bacteria and archaea that represent snippets of prior infections by a virus that have invaded the prokaryote. The snippets of DNA are used by the prokaryotic cell to detect and destroy DNA from subsequent attacks by similar viruses and effectively compose, along with an array of CRISPR-associated proteins (including Cas9 and homologs thereof) and CRISPR-associated RNA, a prokaryotic immune defense system. In nature, CRISPR clusters are transcribed and processed into CRISPR RNA (crRNA). In certain types of CRISPR systems (e.g., type II CRISPR systems), correct processing of pre-crRNA requires a trans-encoded small RNA (tracrRNA), endogenous ribonuclease 3 (mc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the RNA. Specifically, the target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species—the guide RNA. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. CRISPR biology, as well as Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference.

In certain types of CRISPR systems (e.g., type II CRISPR systems), correct processing of pre-crRNA requires a trans-encoded small RNA (tracrRNA), endogenous ribonuclease 3 (rnc), and a Cas9 protein. The tracrRNA serves as a guide for ribonuclease 3-aided processing of pre-crRNA. Subsequently, Cas9/crRNA/tracrRNA endonucleolytically cleaves linear or circular nucleic acid target complementary to the RNA. Specifically, the target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gRNA") can be engineered so as to incorporate embodiments of both the crRNA and tracrRNA into a single RNA species—the guide RNA.

In general, a "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. The tracrRNA of the system is complementary (fully or partially) to the tracr mate sequence present on the guide RNA.

RNA Synthesis Template

As used herein, the term "RNA synthesis template" refers to the region or portion of the extension arm of a rpegRNA that is utilized as a template strand by a polymerase of a RNA prime editor to encode a 3' single-strand DNA flap that contains the desired edit and which then, through the mechanism of prime editing, replaces the corresponding endogenous strand of DNA at the target site. In various embodiments, the DNA synthesis template is shown in FIG. 3A (in the context of a pegRNA comprising a 5' extension arm), FIG. 3B (in the context of a pegRNA comprising a 3' extension arm), FIG. 3C (in the context of an internal extension arm), FIG. 3D (in the context of a 3' extension arm), and FIG. 3E (in the context of a 5' extension arm). The extension arm, including the DNA synthesis template, may be comprised of DNA or RNA. In the case of RNA, the polymerase of the prime editor can be an RNA-dependent DNA polymerase (e.g., a reverse transcriptase). In the case of DNA, the polymerase of the prime editor can be a DNA-dependent DNA polymerase. In various embodiments (e.g., as depicted in FIGS. 3D-3E), the DNA synthesis template (4) may comprise the "edit template" and the "homology arm", and all or a portion of the optional 5' end modifier region, e2. That is, depending on the nature of the e2 region (e.g., whether it includes a hairpin, toeloop, or stem/loop secondary structure), the polymerase may encode none, some, or all of the e2 region, as well. Said another way, in the case of a 3' extension arm, the DNA synthesis template (3) can include the portion of the extension arm (3) that spans from the 5' end of the primer binding site (PBS) to 3' end of the gRNA core that may operate as a template for the synthesis of a single-strand of DNA by a polymerase (e.g., a reverse transcriptase). In the case of a 5' extension arm, the DNA synthesis template (3) can include the portion of the extension arm (3) that spans from the 5' end of the pegRNA molecule to the 3' end of the edit template. Preferably, the DNA synthesis template excludes the primer binding site (PBS) of pegRNAs either having a 3' extension arm or a 5' extension arm. Certain embodiments described here (e.g, FIG. 71A) refer to an "an RT template," which is inclusive of the edit template and the homology arm, i.e., the sequence of the pegRNA extension arm which is actually used as a template during DNA synthesis. The term "RT template" is equivalent to the term "DNA synthesis template."

In the case of trans prime editing (e.g., FIG. 3G and FIG. 3H), the primer binding site (PBS) and the DNA synthesis template can be engineered into a separate molecule referred to as a trans prime editor RNA template (tPERT).

Downstream

As used herein, the terms "upstream" and "downstream" are terms of relativity that define the linear position of at least two elements located in a nucleic acid molecule (whether single or double-stranded) that is orientated in a 5'-to-3' direction. In particular, a first element is upstream of a second element in a nucleic acid molecule where the first element is positioned somewhere that is 5' to the second element. For example, a SNP is upstream of a Cas9-induced nick site if the SNP is on the 5' side of the nick site. Conversely, a first element is downstream of a second element in a nucleic acid molecule where the first element is positioned somewhere that is 3' to the second element. For example, a SNP is downstream of a Cas9-induced nick site if the SNP is on the 3' side of the nick site. The nucleic acid molecule can be a DNA (double or single stranded). RNA (double or single stranded), or a hybrid of DNA and RNA. The analysis is the same for single strand nucleic acid molecule and a double strand molecule since the terms upstream and downstream are in reference to only a single strand of a nucleic acid molecule, except that one needs to select which strand of the double stranded molecule is being considered. Often, the strand of a double stranded DNA which can be used to determine the positional relativity of at least two elements is the "sense" or "coding" strand. In genetics, a "sense" strand is the segment within double-stranded DNA that runs from 5' to 3', and which is complementary to the antisense strand of DNA, or template strand, which runs from 3' to 5'. Thus, as an example, a SNP nucleobase is "downstream" of a promoter sequence in a genomic DNA (which is double-stranded) if the SNP nucleobase is on the 3' side of the promoter on the sense or coding strand.

Edit Template

The term "edit template" refers to a portion of the extension arm that encodes the desired edit in the single strand 3' DNA flap that is synthesized by the polymerase, e.g., a DNA-dependent DNA polymerase, RNA-dependent DNA polymerase (e.g., a reverse transcriptase). Certain embodiments described here (e.g., FIG. 71A) refer to "an RT template," which refers to both the edit template and the homology arm together, i.e., the sequence of the pegRNA extension arm which is actually used as a template during DNA synthesis. The term "RT edit template" is also equivalent to the term "DNA synthesis template," but wherein the RT edit template reflects the use of a prime editor having a polymerase that is a reverse transcriptase, and wherein the DNA synthesis template reflects more broadly the use of a prime editor having any polymerase.

Effective Amount

The term "effective amount," as used herein, refers to an amount of a biologically active agent that is sufficient to elicit a desired biological response. For example, in some embodiments, an effective amount of a prime editor (PE) may refer to the amount of the editor that is sufficient to edit a target site nucleotide sequence, e.g., a genome. In some embodiments, an effective amount of a prime editor (PE) provided herein, e.g., of a fusion protein comprising a nickase Cas9 domain and a reverse transcriptase may refer to the amount of the fusion protein that is sufficient to induce editing of a target site specifically bound and edited by the fusion protein. As will be appreciated by the skilled artisan, the effective amount of an agent, e.g., a fusion protein, a nuclease, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

Error-Prone Reverse Transcriptase

As used herein, the term "error-prone" reverse transcriptase (or more broadly, any polymerase) refers to a reverse transcriptase (or more broadly, any polymerase) that occurs naturally or which has been derived from another reverse transcriptase (e.g., a wild type M-MLV reverse transcriptase) which has an error rate that is less than the error rate of wild type M-MLV reverse transcriptase. The error rate of wild type M-MLV reverse transcriptase is reported to be in the range of one error in 15,000 (higher) to 27,000 (lower). An error rate of 1 in 15,000 corresponds with an error rate of $6.7\times10^{-5}$. An error rate of 1 in 27,000 corresponds with an error rate of $3.7\times10^{-5}$. See Boutabout et al. (2001) "DNA synthesis fidelity by the reverse transcriptase of the yeast retrotransposon Ty1," *Nucleic Acids Res* 29(11):2217-2222, which is incorporated herein by reference. Thus, for purposes of this application, the term "error prone" refers to those RT that have an error rate that is greater than one error in 15,000 nucleobase incorporation ($6.7\times10^{-5}$ or higher), e.g., 1 error in 14,000 nucleobases ($7.14\times10^{-5}$ or higher), 1 error in 13,000 nucleobases or fewer ($7.7\times10^{-5}$ or higher), 1 error in 12,000 nucleobases or fewer ($7.7\times10^{-5}$ or higher), 1 error in 11,000 nucleobases or fewer ($9.1\times10^{-5}$ or higher), 1 error in 10,000 nucleobases or fewer ($1\times10^{-4}$ or 0.0001 or higher), 1 error in 9,000 nucleobases or fewer (0.00011 or higher), 1 error in 8,000 nucleobases or fewer (0.00013 or higher) 1 error in 7,000 nucleobases or fewer (0.00014 or higher), 1 error in 6,000 nucleobases or fewer (0.00016 or higher), 1 error in 5,000 nucleobases or fewer (0.0002 or higher), 1 error in 4,000 nucleobases or fewer (0.00025 or higher), 1 error in 3,000 nucleobases or fewer (0.00033 or higher), 1 error in 2,000 nucleobase or fewer (0.00050 or higher), or 1 error in 1,000 nucleobases or fewer (0.001 or higher), or 1 error in 500 nucleobases or fewer (0.002 or higher), or 1 error in 250 nucleobases or fewer (0.004 or higher).

Extein

The term “extein,” as used herein, refers to an polypeptide sequence that is flanked by an intein and is ligated to another extein during the process of protein splicing to form a mature, spliced protein. Typically, an intein is flanked by two extein sequences that are ligated together when the intein catalyzes its own excision. Exteins, accordingly, are the protein analog to exons found in mRNA. For example, a polypeptide comprising an intein may be of the structure extein(N)-intein-extein(C). After excision of the intein and splicing of the two exteins, the resulting structures are extein(N)-extein(C) and a free intein. In various configurations, the exteins may be separate proteins (e.g., half of a Cas9 or Prime editor), each fused to a split-intein, wherein the excision of the split inteins causes the splicing together of the extein sequences.

Extension Arm

The term “extension arm” refers to a nucleotide sequence component of a pegRNA which provides several functions, including a primer binding site and an edit template for reverse transcriptase. In some embodiments, e.g., FIG. 3D, the extension arm is located at the 3' end of the guide RNA. In other embodiments, e.g., FIG. 3E, the extension arm is located at the 5' end of the guide RNA. In some embodiments, the extension arm also includes a homology arm. In various embodiments, the extension arm comprises the following components in a 5' to 3' direction: the homology arm, the edit template, and the primer binding site. Since polymerization activity of the reverse transcriptase is in the 5' to 3' direction, the preferred arrangement of the homology arm, edit template, and primer binding site is in the 5' to 3' direction such that the reverse transcriptase, once primed by an annealed primer sequence, polymerases a single strand of DNA using the edit template as a complementary template strand. Further details, such as the length of the extension arm, are described elsewhere herein.

The extension arm may also be described as comprising generally two regions: a primer binding site (PBS) and a DNA synthesis template, as shown in FIG. 3G (top), for instance. The primer binding site binds to the primer sequence that is formed from the endogenous DNA strand of the target site when it becomes nicked by the prime editor complex, thereby exposing a 3' end on the endogenous nicked strand. As explained herein, the binding of the primer sequence to the primer binding site on the extension arm of the pegRNA creates a duplex region with an exposed 3' end (i.e., the 3' of the primer sequence), which then provides a substrate for a polymerase to begin polymerizing a single strand of DNA from the exposed 3' end along the length of the DNA synthesis template. The sequence of the single strand DNA product is the complement of the DNA synthesis template. Polymerization continues towards the 5' of the DNA synthesis template (or extension arm) until polymerization terminates. Thus, the DNA synthesis template represents the portion of the extension arm that is encoded into a single strand DNA product (i.e., the 3' single strand DNA flap containing the desired genetic edit information) by the polymerase of the prime editor complex and which ultimately replaces the corresponding endogenous DNA strand of the target site that sits immediate downstream of the PE-induced nick site. Without being bound by theory, polymerization of the DNA synthesis template continues towards the 5' end of the extension arm until a termination event. Polymerization may terminate in a variety of ways, including, but not limited to (a) reaching a 5' terminus of the pegRNA (e.g., in the case of the 5' extension arm wherein the DNA polymerase simply runs out of template), (b) reaching an impassable RNA secondary structure (e.g., hairpin or stem/loop), or (c) reaching a replication termination signal, e.g., a specific nucleotide sequence that blocks or inhibits the polymerase, or a nucleic acid topological signal, such as, supercoiled DNA or RNA.

Flap Endonuclease (e.g., FEN1)

As used herein, the term “flap endonuclease” refers to an enzyme that catalyzes the removal of 5' single strand DNA flaps. These are naturally occurring enzymes that process the removal of 5' flaps formed during cellular processes, including DNA replication. The prime editing methods herein described may utilize endogenously supplied flap endonucleases or those provided in trans to remove the 5' flap of endogenous DNA formed at the target site during prime editing. Flap endonucleases are known in the art and can be found described in Patel et al., “Flap endonucleases pass 5'-flaps through a flexible arch using a disorder-thread-order mechanism to confer specificity for free 5'-ends,” *Nucleic Acids Research,* 2012, 40(10): 4507-4519, Tsutakawa et al., “Human flap endonuclease structures, DNA double-base flipping, and a unified understanding of the FEN1 superfamily,” *Cell,* 2011, 145(2): 198-211, and Balakrishnan et al., “Flap Endonuclease 1,” *Annu Rev Biochem,* 2013, Vol 82: 119-138 (each of which are incorporated herein by reference). An exemplary flap endonuclease is FEN1, which can be represented by the following amino acid sequence:

| DESCRIPTION | SEQUENCE | SEQ ID NO: |
|---|---|---|
| FEN1 WILD TYPE | MGIQGLAKLIADVAPSAIRENDIKSYFGRKVAIDASMSI YQFLIAVRQGGDVLQNEEGETTSHLMGMFYRTIRMME NGIKPVYVFDGKPPQLKSGELAKRSERRAEAEKQLQQ AQAAGAEQEVEKFTKRLVKVTKQHNDECKHLLSLMGI PYLDAPSEAEASCAALVKAGKVYAAATEDMDCLTFGS PVLMRHLTASEAKKLPIQEFHLSRILQELGLNQEQFVDL CILLGSDYCESIRGIGPKRAVDLIQKHKSIEEIVRRLDPN KYPVPENWLHKEAHQLFLEPEVLDPESVELKWSEPNE EELIKFMCGEKQFSEERIRSGVKRLSKSRQGSTQGRLD DFFKVTGSLSSAKRKEPEPKGSTKKKAKTGAAGKFKR GK | SEQ ID NO: 53 |

Functional Equivalent

The term "functional equivalent" refers to a second biomolecule that is equivalent in function, but not necessarily equivalent in structure to a first biomolecule. For example, a "Cas9 equivalent" refers to a protein that has the same or substantially the same functions as Cas9, but not necessarily the same amino acid sequence. In the context of the disclosure, the specification refers throughout to "a protein X, or a functional equivalent thereof." In this context, a "functional equivalent" of protein X embraces any homolog, paralog, fragment, naturally occurring, engineered, mutated, or synthetic version of protein X which bears an equivalent function.

Fusion Protein

The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. Another example includes a Cas9 or equivalent thereof to a reverse transcriptase. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference.

Gene of Interest (GOI)

The term "gene of interest" or "GOI" refers to a gene that encodes a biomolecule of interest (e.g., a protein or an RNA molecule). A protein of interest can include any intracellular protein, membrane protein, or extracellular protein, e.g., a nuclear protein, transcription factor, nuclear membrane transporter, intracellular organelle associated protein, a membrane receptor, a catalytic protein, and enzyme, a therapeutic protein, a membrane protein, a membrane transport protein, a signal transduction protein, or an immunological protein (e.g., an IgG or other antibody protein), etc. The gene of interest may also encode an RNA molecule, including, but not limited to, messenger RNA (mRNA), transfer RNA (tRNA), ribosomal RNA (rRNA), small nuclear RNA (snRNA), antisense RNA, guide RNA, microRNA (miRNA), small interfering RNA (siRNA), and cell-free RNA (cfRNA).

Guide RNA ("2RNA")

As used herein, the term "guide RNA" is a particular type of guide nucleic acid which is mostly commonly associated with a Cas protein of a CRISPR-Cas9 and which associates with Cas9, directing the Cas9 protein to a specific sequence in a DNA molecule that includes complementarity to protospacer sequence of the guide RNA. However, this term also embraces the equivalent guide nucleic acid molecules that associate with Cas9 equivalents, homologs, orthologs, or paralogs, whether naturally occurring or non-naturally occurring (e.g., engineered or recombinant), and which otherwise program the Cas9 equivalent to localize to a specific target nucleotide sequence. The Cas9 equivalents may include other napDNAbp from any type of CRISPR system (e.g., type II, V, VI), including Cpf1 (a type-V CRISPR-Cas systems), C2c1 (a type V CRISPR-Cas system), C2c2 (a type VI CRISPR-Cas system) and C2c3 (a type V CRISPR-Cas system). Further Cas-equivalents are described in Makarova et al., "C2c2 is a single-component programmable RNA-guided RNA-targeting CRISPR effector," Science 2016; 353(6299), the contents of which are incorporated herein by reference. Exemplary sequences are and structures of guide RNAs are provided herein. In addition, methods for designing appropriate guide RNA sequences are provided herein. As used herein, the "guide RNA" may also be referred to as a "traditional guide RNA" to contrast it with the modified forms of guide RNA termed "prime editing guide RNAs" (or "pegRNAs") which have been invented for the prime editing methods and composition disclosed herein.

Guide RNAs or pegRNAs may comprise various structural elements that include, but are not limited to:

Spacer sequence—the sequence in the guide RNA or pegRNA (having about 20 nts in length) which binds to the protospacer in the target DNA.

gRNA core (or gRNA scaffold or backbone sequence)—refers to the sequence within the gRNA that is responsible for Cas9 binding, it does not include the 20 bp spacer/targeting sequence that is used to guide Cas9 to target DNA.

Extension arm—a single strand extension at the 3' end or the 5' end of the pegRNA which comprises a primer binding site and a DNA synthesis template sequence that encodes via a polymerase (e.g., a reverse transcriptase) a single stranded DNA flap containing the genetic change of interest, which then integrates into the endogenous DNA by replacing the corresponding endogenous strand, thereby installing the desired genetic change.

Transcription terminator—the guide RNA or pegRNA may comprise a transcriptional termination sequence at the 3' of the molecule.

G-Quadruplex

The term "G-quadruplex" refers to its ordinary and customary meaning. A G-quadruplex is a complex three-dimensional nucleic acid moiety formed in nucleic acid sequences that are rich in guanine (G). They are helical in shape and formed from interconnected stacks of guanine tetrads (or "G-tetrads"), which individually are flat, ring-shaped structures formed from four guanines, and which can be stabilized by the presence of a cation (e.g., potassium) which sits in a central channel between pairs of G-tetrads. G-quadruplexes are a diverse collection of structures and not a single structure. Further reference to G-quadruplexes can be found in (1) Kwok et al., "G-Quadruplexes: Prediction, Characterization, and Biological Application," *Trends in Biotechnology,* 2017, Vol. 35(10; pp. 997-1013; (2) Hansel-Hertsch R. et al., "DNA G-quadruplexes in the human genome: detection, functions and therapeutic potential," *Nat. Rev. Mol. Cell Biol.,* 2017; 18: 279-284; and (3) Millevoi S. et al., "G-quadruplexes in RNA biology," *Wiley Interdiscip. Rev. RNA.,* 2012; 3: 495-507, each of which are incorporated herein by reference.

Homology Arm

The term "homology arm" refers to a portion of the extension arm that encodes a portion of the resulting reverse transcriptase-encoded single strand DNA flap that is to be integrated into the target DNA site by replacing the endogenous strand. The portion of the single strand DNA flap encoded by the homology arm is complementary to the non-edited strand of the target DNA sequence, which facilitates the displacement of the endogenous strand and annealing of the single strand DNA flap in its place, thereby installing the edit. This component is further defined elsewhere. The homology arm is part of the DNA synthesis template since it is by definition encoded by the polymerase of the prime editors described herein.

Host Cell

The term "host cell," as used herein, refers to a cell that can host, replicate, and express a vector described herein, e.g., a vector comprising a nucleic acid molecule encoding a fusion protein comprising a Cas9 or Cas9 equivalent and a reverse transcriptase.

Inteins

As used herein, the term "intein" refers to auto-processing polypeptide domains found in organisms from all domains of life. An intein (intervening protein) carries out a unique auto-processing event known as protein splicing in which it excises itself out from a larger precursor polypeptide through the cleavage of two peptide bonds and, in the process, ligates the flanking extein (external protein) sequences through the formation of a new peptide bond. This rearrangement occurs post-translationally (or possibly co-translationally), as intein genes are found embedded in frame within other protein-coding genes. Furthermore, intein-mediated protein splicing is spontaneous; it requires no external factor or energy source, only the folding of the intein domain. This process is also known as cis-protein splicing, as opposed to the natural process of trans-protein splicing with "split inteins." Inteins are the protein equivalent of the self-splicing RNA introns (see Perler et al., Nucleic Acids Res. 22:1125-1127 (1994)), which catalyze their own excision from a precursor protein with the concomitant fusion of the flanking protein sequences, known as exteins (reviewed in Perler et al., Curr. Opin. Chem. Biol. 1:292-299 (1997); Perler, F. B. Cell 92(1):1-4 (1998); Xu et al., EMBO J. 15(19):5146-5153 (1996)).

As used herein, the term "protein splicing" refers to a process in which an interior region of a precursor protein (an intein) is excised and the flanking regions of the protein (exteins) are ligated to form the mature protein. This natural process has been observed in numerous proteins from both prokaryotes and eukaryotes (Perler, F. B., Xu, M. Q., Paulus, H. Current Opinion in Chemical Biology 1997, 1, 292-299; Perler, F. B. Nucleic Acids Research 1999, 27, 346-347). The intein unit contains the necessary components needed to catalyze protein splicing and often contains an endonuclease domain that participates in intein mobility (Perler, F. B., Davis, E. O., Dean, G. E., Gimble, F. S., Jack, W. E., Neff, N., Noren, C. J., Thomer, J., Belfort, M. Nucleic Acids Research 1994, 22, 1127-1127). The resulting proteins are linked, however, not expressed as separate proteins. Protein splicing may also be conducted in trans with split inteins expressed on separate polypeptides spontaneously combine to form a single intein which then undergoes the protein splicing process to join to separate proteins.

The elucidation of the mechanism of protein splicing has led to a number of intein-based applications (Comb, et al., U.S. Pat. No. 5,496,714; Comb, et al., U.S. Pat. No. 5,834,247; Camarero and Muir, J. Amer. Chem. Soc., 121:5597-5598 (1999); Chong, et al., Gene, 192:271-281 (1997), Chong, et al., Nucleic Acids Res., 26:5109-5115 (1998); Chong, et al., J. Biol. Chem., 273:10567-10577 (1998); Cotton, et al. J. Am. Chem. Soc., 121:1100-1101 (1999); Evans, et al., J. Biol. Chem., 274:18359-18363 (1999); Evans, et al., J. Biol. Chem., 274:3923-3926 (1999); Evans, et al., Protein Sci., 7:2256-2264 (1998); Evans, et al., J. Biol. Chem., 275:9091-9094 (2000); Iwai and Pluckthun, FEBS Lett. 459:166-172 (1999); Mathys, et al., Gene, 231:1-13 (1999); Mills, et al., Proc. Natl. Acad. Sci. USA 95:3543-3548 (1998); Muir, et al., Proc. Natl. Acad. Sci. USA 95:6705-6710 (1998); Otomo, et al., Biochemistry 38:16040-16044 (1999); Otomo, et al., J. Biolmol. NMR 14:105-114 (1999); Scott, et al., Proc. Natl. Acad. Sci. USA 96:13638-13643 (1999); Severinov and Muir, J. Biol. Chem., 273:16205-16209 (1998); Shingledecker, et al., Gene, 207:187-195 (1998); Southworth, et al., EMBO J. 17:918-926 (1998); Southworth, et al., Biotechniques, 27:110-120 (1999); Wood, et al., Nat. Biotechnol., 17:889-892 (1999); Wu, et al., Proc. Natl. Acad. Sci. USA 95:9226-9231 (1998a); Wu, et al., Biochim Biophys Acta 1387:422-432 (1998b); Xu, et al., Proc. Natl. Acad. Sci. USA 96:388-393 (1999); Yamazaki, et al., J. Am. Chem. Soc., 120:5591-5592 (1998)). Each reference is incorporated herein by reference.

Ligand-Dependent Intein

The term "ligand-dependent intein," as used herein refers to an intein that comprises a ligand-binding domain. Typically, the ligand-binding domain is inserted into the amino acid sequence of the intein, resulting in a structure intein (N)-ligand-binding domain-intein (C). Typically, ligand-dependent inteins exhibit no or only minimal protein splicing activity in the absence of an appropriate ligand, and a marked increase of protein splicing activity in the presence of the ligand. In some embodiments, the ligand-dependent intein does not exhibit observable splicing activity in the absence of ligand but does exhibit splicing activity in the presence of the ligand. In some embodiments, the ligand-dependent intein exhibits an observable protein splicing activity in the absence of the ligand, and a protein splicing activity in the presence of an appropriate ligand that is at least 5 times, at least 10 times, at least 50 times, at least 100 times, at least 150 times, at least 200 times, at least 250 times, at least 500 times, at least 1000 times, at least 1500 times, at least 2000 times, at least 2500 times, at least 5000 times, at least 10000 times, at least 20000 times, at least 25000 times, at least 50000 times, at least 100000 times, at least 500000 times, or at least 1000000 times greater than the activity observed in the absence of the ligand. In some embodiments, the increase in activity is dose dependent over at least 1 order of magnitude, at least 2 orders of magnitude, at least 3 orders of magnitude, at least 4 orders of magnitude, or at least 5 orders of magnitude, allowing for fine-tuning of intein activity by adjusting the concentration of the ligand. Suitable ligand-dependent inteins are known in the art, and in include those provided below and those described in published U.S. Patent Application U.S. 2014/0065711 A1; Mootz et al., "Protein splicing triggered by a small molecule." *J. Am. Chem. Soc.* 2002; 124, 9044-9045; Mootz et al., "Conditional protein splicing: a new tool to control protein structure and function in vitro and in vivo." *J. Am. Chem. Soc.* 2003; 125, 10561-10569; Buskirk et al., *Proc. Natl. Acad. Sci. USA.* 2004; 101, 10505-10510); Skretas & Wood, "Regulation of protein activity with small-molecule-controlled inteins." *Protein Sci.* 2005; 14, 523-532; Schwartz, et al., "Post-translational enzyme activation in an animal via optimized conditional protein splicing." *Nat. Chem. Biol.* 2007; 3, 50-54; Peck et al., *Chem. Biol.* 2011; 18 (5), 619-630; the entire contents of each are hereby incorporated by reference. Exemplary sequences are as follows:

| NAME | SEQUENCE OF LIGAND-DEPENDENT INTEIN |
| --- | --- |
| 2-4 INTEIN: | CLAEGTRIFDPVTGTTHRIEDVVDGRKPIHVVAAAKDGTLLARPVV<br>SWFDQGTRDVIGLRIAGGAIVWATPDHKVLTEYGWRAAGELRKGD<br>RVAGPGGSGNSLALSLTADQMVSALLDAEPPILYSEYDPTSPFSEAS<br>MMGLLTNLADRELVHMINWAKRVPGFVDLTLHDQAHLLECAWLEI<br>LMIGLVWRSMEHPGKLLFAPNLLLDRNQGKCVEGMVEIFDMLLAT<br>SSRFRMMNLQGEEFVCLKSIILLNSGVYTFLSSTLKSLEEKDHIHRA<br>LDKITDTLIHLMAKAGLTLQQQHQRLAQLLLILSHIRHMSNKGMEH<br>LYSMKYKNVVPLYDLLLEMLDAHRLHAGGSGASRVQAFADALDD<br>KFLHDMLAEELRYSVIREVLPTRRARTFDLEVEELHTLVAEGVVVH<br>NC (SEQ ID NO: 42) |
| 3-2 INTEIN | CLAEGTRIFDPVTGTTHRIEDVVDGRKPIHVVAVAKDGTLLARPVVS<br>WFDQGTRDVIGLRIAGGAIVWATPDHKVLTEYGWRAAGELRKGDR<br>VAGPGGSGNSLALSLTADQMVSALLDAEPPILYSEYDPTSPFSEASM<br>MGLLTNLADRELVHMINWAKRVPGFVDLTLHDQAHLLECAWLEIL<br>MIGLVWRSMEHPGKLLFAPNLLLDRNQGKCVEGMVEIFDMLLATS<br>SRFRMMNLQGEEFVCLKSIILLNSGVYTFLSSTLKSLEEKDHIHRAL<br>DKITDTLIHLMAKAGLTLQQQHQRLAQLLLILSHIRHMSNKGMEHL<br>YSMKYTNVVPLYDLLLEMLDAHRLHAGGSGASRVQAFADALDDK<br>FLHDMLAEELRYSVIREVLPTRRARTFDLEVEELHTLVAEGVVVHN<br>C (SEQ ID NO: 43) |
| 30R3-1 INTEIN | CLAEGTRIFDPVTGTTHRIEDVVDGRKPIHVVAAAKDGTLLARPVV<br>SWFDQGTRDVIGLRIAGGATVWATPDHKVLTEYGWRAAGELRKG<br>DRVAGPGGSGNSLALSLTADQMVSALLDAEPPIPYSEYDPTSPFSEA<br>SMMGLLTNLADRELVHMINWAKRVPGFVDLTLHDQAHLLECAWL<br>EILMIGLVWRSMEHPGKLLFAPNLLLDRNQGKCVEGMVEIFDMLL<br>ATSSRFRMMNLQGEEFVCLKSIILLNSGVYTFLSSTLKSLEEKDHIH<br>RALDKITDTLIHLMAKAGLTLQQQHQRLAQLLLILSHIRHMSNKGM<br>EHLYSMKYKNVVPLYDLLLEMLDAHRLHAGGSGASRVQAFADAL<br>DDKFLHDMLAEGLRYSVIREVLPTRRARTFDLEVEELHTLVAEGVV<br>VHNC (SEQ ID NO: 44) |
| 30R3-2 INTEIN | CLAEGTRIFDPVTGTTHRIEDVVDGRKPIHVVAAAKDGTLLARPVV<br>SWFDQGTRDVIGLRIAGGATVWATPDHKVLTEYGWRAAGELRKG<br>DRVAGPGGSGNSLALSLTADQMVSALLDAEPPILYSEYDPTSPFSEA<br>SMMGLLTNLADRELVHMINWAKRVPGFVDLTLHDQAHLLECAWL<br>EILMIGLVWRSMEHPGKLLFAPNLLLDRNQGKCVEGMVEIFDMLL<br>ATSSRFRMMNLQGEEFVCLKSIILLNSGVYTFLSSTLKSLEEKDHIH<br>RALDKITDTLIHLMAKAGLTLQQQHQRLAQLLLILSHIRHMSNKGM<br>EHLYSMKYKNVVPLYDLLLEMLDAHRLHAGGSGASRVQAFADAL<br>DDKFLHDMLAEELRYSVIREVLPTRRARTFDLEVEELHTLVAEGVV<br>VHNC (SEQ ID NO: 45) |
| 30R3-3 INTEIN | CLAEGTRIFDPVTGTTHRIEDVVDGRKPIHVVAAAKDGTLLARPVV<br>SWFDQGTRDVIGLRIAGGATVWATPDHKVLTEYGWRAAGELRKG<br>DRVAGPGGSGNSLALSLTADQMVSALLDAEPPIPYSEYDPTSPFSEA<br>SMMGLLTNLADRELVHMINWAKRVPGFVDLTLHDQAHLLECAWL<br>EILMIGLVWRSMEHPGKLLFAPNLLLDRNQGKCVEGMVEIFDMLL<br>ATSSRFRMMNLQGEEFVCLKSIILLNSGVYTFLSSTLKSLEEKDHIH<br>RALDKITDTLIHLMAKAGLTLQQQHQRLAQLLLILSHIRHMSNKGM<br>EHLYSMKYKNVVPLYDLLLEMLDAHRLHAGGSGASRVQAFADAL<br>DDKFLHDMLAEELRYSVIREVLPTRRARTFDLEVEELHTLVAEGVV<br>VHNC (SEQ ID NO: 46) |
| 37R3-1 INTEIN | CLAEGTRIFDPVTGTTHRIEDVVDGRKPIHVVAAAKDGTLLARPVV<br>SWFDQGTRDVIGLRIAGGATVWATPDHKVLTEYGWRAAGELRKG<br>DRVAGPGGSGNSLALSLTADQMVSALLDAEPPILYSEYNPTSPFSEA<br>SMMGLLTNLADRELVHMINWAKRVPGFVDLTLHDQAHLLERAWL<br>EILMIGLVWRSMEHPGKLLFAPNLLLDRNQGKCVEGMVEIFDMLL<br>ATSSRFRMMNLQGEEFVCLKSIILLNSGVYTFLSSTLKSLEEKDHIH<br>RALDKITDTLIHLMAKAGLTLQQQHQRLAQLLLILSHIRHMSNKGM<br>EHLYSMKYKNVVPLYDLLLEMLDAHRLHAGGSGASRVQAFADAL<br>DDKFLHDMLAEGLRYSVIREVLPTRRARTFDLEVEELHTLVAEGVV<br>VHNC (SEQ ID NO: 47) |
| 37R3-2 INTEIN | CLAEGTRIFDPVTGTTHRIEDVVDGRKPIHVVAAAKDGTLLARPVV<br>SWFDQGTRDVIGLRIAGGAIVWATPDHKVLTEYGWRAAGELRKGD<br>RVAGPGGSGNSLALSLTADQMVSALLDAEPPILYSEYDPTSPFSEAS<br>MMGLLTNLADRELVHMINWAKRVPGFVDLTLHDQAHLLERAWLEI<br>LMIGLVWRSMEHPGKLLFAPNLLLDRNQGKCVEGMVEIFDMLLAT<br>SSRFRMMNLQGEEFVCLKSIILLNSGVYTFLSSTLKSLEEKDHIHRA<br>LDKITDTLIHLMAKAGLTLQQQHQRLAQLLLILSHIRHMSNKGMEH<br>LYSMKYKNVVPLYDLLLEMLDAHRLHAGGSGASRVQAFADALDD<br>KFLHDMLAEGLRYSVIREVLPTRRARTFDLEVEELHTLVAEGVVVH<br>NC (SEQ ID NO: 48) |
| 37R3-3 INTEIN | CLAEGTRIFDPVTGTTHRIEDVVDGRKPIHVVAVAKDGTLLARPVVS<br>WFDQGTRDVIGLRIAGGATVWATPDHKVLTEYGWRAAGELRKGD |

-continued

| NAME | SEQUENCE OF LIGAND-DEPENDENT INTEIN |
|---|---|
| | RVAGPGGSGNSLALSLTADQMVSALLDAEPPILYSEYDPTSPFSEAS MMGLLTNLADRELVHMINWAKRVPGFVDLTLHDQAHLLERAWLEI LMIGLVWRSMEHPGKLLFAPNLLLDRNQGKCVEGMVEIFDMLLAT SSRFRMMNLQGEEFVCLKSIILLNSGVYTFLSSTLKSLEEKDHIHRA LDKITDTLIHLMAKAGLTLQQQHQRLAQLLLILSHIRHMSNKGMEH LYSMKYKNVVPLYDLLLEMLDAHRLHAGGSGASRVQAFADALDD KFLHDMLAEELRYSVIREVLPTRRARTFDLEVEELHTLVAEGVVVH NC (SEQ ID NO: 49) |

Linker

The term "linker," as used herein, refers to a molecule linking two other molecules or moieties. The linker can be an amino acid sequence in the case of a linker joining two fusion proteins. For example, a Cas9 can be fused to a reverse transcriptase by an amino acid linker sequence. The linker can also be a nucleotide sequence in the case of joining two nucleotide sequences together. For example, in the instant case, the traditional guide RNA is linked via a spacer or linker nucleotide sequence to the RNA extension of a prime editing guide RNA which may comprise a RT template sequence and an RT primer binding site. In other embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

Isolated

"Isolated" means altered or removed from the natural state. For example, a nucleic 20 acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In some embodiments, a gene of interest is encoded by an isolated nucleic acid. As used herein, the term "isolated," refers to the characteristic of a material as provided herein being removed from its original or native environment (e.g., the natural environment if it is naturally occurring). Therefore, a naturally-occurring polynucleotide or protein or polypeptide present in a living animal is not isolated, but the same polynucleotide or polypeptide, separated by human intervention from some or all of the coexisting materials in the natural system, is isolated. An artificial or engineered material, for example, a non-naturally occurring nucleic acid construct, such as the expression constructs and vectors described herein, are, accordingly, also referred to as isolated. A material does not have to be purified in order to be isolated. Accordingly, a material may be part of a vector and/or part of a composition, and still be isolated in that such vector or composition is not part of the environment in which the material is found in nature.

MS2 Tagging Technique

In various embodiments (e.g., as depicted in the embodiments of FIGS. 72-73 and in Example 19), the term "MS2 tagging technique" refers to the combination of an "RNA-protein interaction domain" (aka "RNA-protein recruitment domain or protein") paired up with an RNA-binding protein that specifically recognizes and binds to the RNA-protein interaction domain, e.g., a specific hairpin structure. These types of systems can be leveraged to recruit a variety of functionalities to a prime editor complex that is bound to a target site. The MS2 tagging technique is based on the natural interaction of the MS2 bacteriophage coat protein ("MCP" or "MS2cp") with a stem-loop or hairpin structure present in the genome of the phage, i.e., the "MS2 hairpin." In the case of prime editing, the MS2 tagging technique comprises introducing the MS2 hairpin into a desired RNA molecule involved in prime editing (e.g., a pegRNA or a tPERT), which then constitutes a specific interactable binding target for an RNA-binding protein that recognizes and binds to that structure. In the case of the MS2 hairpin, it is recognized and bound by the MS2 bacteriophage coat protein (MCP). And, if MCP is fused to another protein (e.g., a reverse transcriptase or other DNA polymerase), then the MS2 hairpin may be used to "recruit" that other protein in trans to the target site occupied by the prime editing complex.

The prime editors described herein may incorporate as an aspect any known RNA-protein interaction domain to recruit or "co-localize" specific functions of interest to a prime editor complex. A review of other modular RNA-protein interaction domains are described in the art, for example, in Johansson et al., "RNA recognition by the MS2 phage coat protein," *Sem Virol.,* 1997, Vol. 8(3): 176-185; Delebecque et al., "Organization of intracellular reactions with rationally designed RNA assemblies," *Science,* 2011, Vol. 333: 470-474; Mali et al., "Cas9 transcriptional activators for target specificity screening and paired nickases for cooperative genome engineering," *Nat. Biotechnol.,* 2013, Vol. 31: 833-838; and Zalatan et al., "Engineering complex synthetic transcriptional programs with CRISPR RNA scaffolds," *Cell,* 2015, Vol. 160: 339-350, each of which are incorporated herein by reference in their entireties. Other systems include the PP7 hairpin, which specifically recruits the PCP protein, and the "com" hairpin, which specifically recruits the Com protein. See Zalatan et al.

The nucleotide sequence of the MS2 hairpin (or equivalently referred to as the "MS2 aptamer") is:

(SEQ ID NO: 51)
GCCAACATGAGGATCACCCATGTCTGCAGGGCC.

The amino acid sequence of the MCP or MS2cp is:

(SEQ ID NO: 52)
GSASNFTQFVLVDNGGTGDVTVAPSNFANGVAEWISSNSRSQAYKVTCS

VRQSSAQNRKYTIKVEVPKVATQTVGGEELPVAGWRSYLNMELTIPIFA

TNSDCELIVKAMQGLLKDGNPIPSAIAANSGIY.

The MS2 hairpin (or "MS2 aptamer") may also be referred to as a type of "RNA effector recruitment domain"

(or equivalently as "RNA-binding protein recruitment domain" or simply as "recruitment domain") since it is a physical structure (e.g., a hairpin) that is installed into a pegRNA or tPERT that effectively recruits other effector functions (e.g., RNA-binding proteins having various functions, such as DNA polymerases or other DNA-modifying enzymes) to the pegRNA or rPERT that is so modified, and thus, co-localizing effector functions in trans to the prime editing machinery. This application is not intended to be limited in any way to any particular RNA effector recruitment domains and may include any available such domain, including the MS2 hairpin. Example 19 and FIG. 72(*b*) depicts the use of the MS2 aptamer joined to a DNA synthesis domain (i.e., the tPERT molecule) and a prime editor that comprises an MS2cp protein fused to a PE2 to cause the co-localization of the prime editor complex (MS2cp-PE2:sgRNA complex) bound to the target DNA site and the DNA synthesis domain of the tPERT molecule to effectuate the napDNAbp As used herein, the term "nucleic acid programmable DNA binding protein" or "napDNAbp," of which Cas9 is an example, refer to a proteins which use RNA:DNA hybridization to target and bind to specific sequences in a DNA molecule. Each napDNAbp is associated with at least one guide nucleic acid (e.g., guide RNA), which localizes the napDNAbp to a DNA sequence that comprises a DNA strand (i.e., a target strand) that is complementary to the guide nucleic acid, or a portion thereof (e.g., the protospacer of a guide RNA). In other words, the guide nucleic-acid "programs" the napDNAbp (e.g., Cas9 or equivalent) to localize and bind to a complementary sequence.

Without being bound by theory, the binding mechanism of a napDNAbp-guide RNA complex, in general, includes the step of forming an R-loop whereby the napDNAbp induces the unwinding of a double-strand DNA target, thereby separating the strands in the region bound by the napDNAbp. The guide RNA protospacer then hybridizes to the "target strand." This displaces a "non-target strand" that is complementary to the target strand, which forms the single strand region of the R-loop. In some embodiments, the napDNAbp includes one or more nuclease activities, which then cut the DNA leaving various types of lesions. For example, the napDNAbp may comprises a nuclease activity that cuts the non-target strand at a first location, and/or cuts the target strand at a second location. Depending on the nuclease activity, the target DNA can be cut to form a "double-stranded break" whereby both strands are cut. In other embodiments, the target DNA can be cut at only a single site, i.e., the DNA is "nicked" on one strand. Exemplary napDNAbp with different nuclease activities include "Cas9 nickase" ("nCas9") and a deactivated Cas9 having no nuclease activities ("dead Cas9" or "dCas9"). Exemplary sequences for these and other napDNAbp are provided herein.

Nickase

The term "nickase" refers to a Cas9 with one of the two nuclease domains inactivated. This enzyme is capable of cleaving only one strand of a target DNA.

Nuclear Localization Sequence (NLS)

The term "nuclear localization sequence" or "NLS" refers to an amino acid sequence that promotes import of a protein into the cell nucleus, for example, by nuclear transport. Nuclear localization sequences are known in the art and would be apparent to the skilled artisan. For example, NLS sequences are described in Plank et al., international PCT application, PCT/EP2000/011690, filed Nov. 23, 2000, published as WO/2001/038547 on May 31, 2001, the contents of which are incorporated herein by reference for its disclosure of exemplary nuclear localization sequences. In some embodiments, a NLS comprises the amino acid sequence PKKKRKV (SEQ ID NO: 50) or MDSLLMNRRKFLYQFKNVRWAKGRRETYLC (SEQ ID NO: 25).

Nucleic Acid Molecule

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5 bromouridine, C5 fluorouridine, C5 iodouridine, C5 propynyl uridine, C5 propynyl cytidine, C5 methylcytidine, 7 deazaadenosine, 7 deazaguanosine, 8 oxoadenosine, 8 oxoguanosine, 0(6) methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5' N phosphoramidite linkages).

Nucleotide Structural Motifs (or Nucleic Acid Moiety)

As used herein, the term "nucleotide structural motif" or equivalently, "nucleic acid moiety," refers to nucleic acid molecule or a portion thereof, which forms a secondary or tertiary structure due to basepairing interactions within a single nucleic acid polymer or between two or more nucleic acid polymers. Such nucleotide structural motifs can be formed from DNA, RNA, or a hybrid of DNA and RNA. The term is not meant to refer to standard DNA double-helices. Examples of nucleic acid moieties include, but are not limited to, a toe-loop, hairpin, stem-loop, pseudoknot, aptamer, G quadraplex, tRNA, ribozyme, riboswitch, A-form DNA, B-form DNA, or Z-form DNA.

pegRNA

As used herein, the terms "prime editing guide RNA" or "pegRNA" or "pegRNA" refers to a specialized form of a guide RNA that has been modified to include one or more additional sequences for implementing the prime editing methods and compositions described herein. As described herein, the prime editing guide RNA comprise one or more "extended regions" of nucleic acid sequence. The extended regions may comprise, but are not limited to, single-stranded RNA or DNA. Further, the extended regions may occur at the 3' end of a traditional guide RNA. In other arrangements, the extended regions may occur at the 5' end of a traditional guide RNA. In still other arrangements, the extended region may occur at an intramolecular region of the traditional guide RNA, for example, in the gRNA core region which associates and/or binds to the napDNAbp. The extended region comprises a "DNA synthesis template" which encodes (by the polymerase of the prime editor) a single-stranded DNA which, in turn, has been designed to be (a) homologous with the endogenous target DNA to be edited, and (b) which comprises at least one desired nucleotide change (e.g., a transition, a transversion, a deletion, or an insertion) to be introduced or integrated into the endogenous target DNA. The extended region may also comprise other functional sequence elements, such as, but not limited to, a "primer binding site" and a "spacer or linker" sequence, or other structural elements, such as, but not limited to aptamers, stem loops, hairpins, toe loops (e.g., a 3' toeloop), or an RNA-protein recruitment domain (e.g., MS2 hairpin). As used herein the "primer binding site" comprises a sequence that hybridizes to a single-strand DNA sequence having a 3' end generated from the nicked DNA of the R-loop.

In certain embodiments, the pegRNAs are represented by FIG. 3A, which shows a pegRNA having a 5' extension arm, a spacer, and a gRNA core. The 5' extension further comprises in the 5' to 3' direction a reverse transcriptase template, a primer binding site, and a linker. As shown, the reverse transcriptase template may also be referred to more broadly as the "DNA synthesis template" where the polymerase of a prime editor described herein is not an RT, but another type of polymerase.

In certain other embodiments, the pegRNAs are represented by FIG. 3B, which shows a pegRNA having a 5' extension arm, a spacer, and a gRNA core. The 5' extension further comprises in the 5' to 3' direction a reverse transcriptase template, a primer binding site, and a linker. As shown, the reverse transcriptase template may also be referred to more broadly as the "DNA synthesis template" where the polymerase of a prime editor described herein is not an RT, but another type of polymerase.

In still other embodiments, the pegRNAs are represented by FIG. 3D, which shows a pegRNA having in the 5' to 3' direction a spacer (1), a gRNA core (2), and an extension arm (3). The extension arm (3) is at the 3' end of the pegRNA. The extension arm (3) further comprises in the 5' to 3' direction a "primer binding site" (A), an "edit template" (B), and a "homology arm" (C). The extension arm (3) may also comprise an optional modifier region at the 3' and 5' ends, which may be the same sequences or different sequences. In addition, the 3' end of the pegRNA may comprise a transcriptional terminator sequence. These sequence elements of the pegRNAs are further described and defined herein.

In still other embodiments, the pegRNAs are represented by FIG. 3E, which shows a pegRNA having in the 5' to 3' direction an extension arm (3), a spacer (1), and a gRNA core (2). The extension arm (3) is at the 5' end of the pegRNA. The extension arm (3) further comprises in the 3' to 5' direction a "primer binding site" (A), an "edit template" (B), and a "homology arm" (C). The extension arm (3) may also comprise an optional modifier region at the 3' and 5' ends, which may be the same sequences or different sequences. The pegRNAs may also comprise a transcriptional terminator sequence at the 3' end. These sequence elements of the pegRNAs are further described and defined herein.

PE1

As used herein, "PE1" refers to a PE complex comprising a fusion protein comprising Cas9(H840A) and a wild type MMLV RT having the following structure: [NLS]-[Cas9(H840A)]-[linker]-[MMLV_RT(wt)]+a desired pegRNA, wherein the PE fusion has the amino acid sequence of SEQ ID NO: 54, which is shown as follows;

(SEQ ID NO: 54)

MKRTADGSEFESPKKKRKVDKKYSIGLDIGTNSVGWAVITDEYKVPSKKFKVLGNTD

RHSIKKNLIGALLFDSGETAEATRLKRTARRRYTRRKNRICYLQEIFSNEMAKVDDS

FFHRLEESFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASGVDAKAI

LSARLSKSRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLSASMIKRYD

EHHQDLTLLKALVRQQLPEKYKEIFFDQSKNGYAGYIDGGASQEEFYKFIKPILEK

MDGTEELLVKLNREDLLRKQRTFDNGSIPHQIHLGELHAILRRQEDFYPFLKDNRE

KIEKILTFRIPYYVGPLARGNSRFAWMTRKSEETITPWNFEEVVDKGASAQSFIERM

TNFDKNLPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKIIKDKDFLD

NEENEDILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSGQGDSLH

EHIANLAGSPAIKKGILQTVKVVDELVKVMGRHKPENIVIEMARENQTTQKGQKNS

RERMKRIEEGIKELGSQILKEHPVENTQLQNEKLYLYYLQNGRDMYVDQELDINRL

SDYDVDAIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSRMNTKYD

ENDKLIREVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEITLANGEIR

KRPLIETNGETGEIVWDKGRDFATVRKVLSMPQVNIVKKTEVQTGGFSKESILPKR

NSDKLIARKKDWDPKKYGGFDSPTVAYSVLVVAKVEKGKSKKLKSVKELLGITIME

RSSFEKNPIDFLEAKGYKEVKKDLIIKLPKYSLFELENGRKRMLASAGELQKGNEL

-continued

ALPSKYVNFLYLASHYEKLKGSPEDNEQKQLFVEQHKHYLDEIIEQISEFSKRVILA

DANLDKVLSAYNKHRDKPIREQAENIIHLFTLTNLGAPAAFKYFDTTIDRKRYTSTK

EVLDATLIHQSITGLYETRIDLSQLGGDSGGSSGGSSGSETPGTSESATPESSGGSSGG

SS*TLNIEDEYRLHETSKEPDVSLGSTWLSDFPQAWAETGGMGLAVRQAPLIIPLKATSTPVSIKQ*

*YPMSQEARLGIKPHIQRLLDQGILVPCQSPWNTPLLPVKKPGTNDYRPVQDLREVNKRVEDIH*

*PTVPNPYNLLSGLPPSHQWYTVLDLKDAFFCLRLHPTSQPLFAFEWRDPEMGISGQLTWTRL*

*PQGFKNSPTLFDEALHRDLADFRIQHPDLILLQYVDDLLLAATSELDCQQGTRALLQTLGNLG*

*YRASAKKAQICQKQVKYLGYLLKEGQRWLTEARKETVMGQPTPKTPRQLREFLGTAGFCRLW*

*IPGFAEMAAPLYPLTKTGTLFNWGPDQQKAYQEIKQALLTAPALGLPDLTKPFELFVDEKQGY*

*AKGVLTQKLGPWRRPVAYLSKKLDPVAAGWPPCLRMVAAIAVLTKDAGKLTMGQPLVILAPH*

*AVEALVKQPPDRWLSNARMTHYQALLLDTDRVQFGPVVALNPATLLPLPEEGLQHNCLDILAE*

*AHGTRPDLTDQPLPDADHTWYTDGSSLLQEGQRKAGAAVTTETEVIWAKALPAGTSAQRAELI*

*ALTQALKMAEGKKLNVYTDSRYAFATAHIHGEIYRRRGLLTSEGKEIKNKDEILALLKALFLPKR*

*LSIIHCPGHQKGHSAEARGNRMADQAARKAAITETPDTSTLLIENSSP*SGGSKRTADGSEFEP

KKKRKV

KEY:
NUCLEAR LOCALIZATION SEQUENCE (NLS) TOP:(SEQ ID NO: 24), BOTTOM: (SEQ ID NO: 33)
CAS9(H840A) (SEQ ID NO: 55)
33-AMINO ACID LINKER (SEQ ID NO: 56)
*M-MLV reverse transcriptase* (SEQ ID NO: 57).

PE2

As used herein, "PE2" refers to a PE complex comprising a fusion protein comprising Cas9(H840A) and a variant MMLV RT having the following structure: [NLS]-[Cas9 (H840A)]-[linker]-[MMLV_RT(D200N)(T330P)(L603W) (T306K)(W313F)]+a desired pegRNA, wherein the PE fusion has the amino acid sequence of SEQ ID NO: 58, which is shown as follows:

(SEQ ID NO: 58)
MKRTADGSEFESPKKKRKVDKKYSIGLDIGTNSVGWAVITDEYKVPSKKFKVLGNTD

RHSIKKNLIGALLFDSGETAEATRLKRTARRRYTRRKNRICYLQEIFSNEMAKVDDS

FFHRLEESFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASGVDAKAI

LSARLSKSRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLSASMIKRYD

EHHQDLTLLKALVRQQLPEKYKEIFFDQSKNGYAGYIDGGASQEEFYKFIKPILEK

MDGTEELLVKLNREDLLRKQRTFDNGSIPHQIHLGELHAILRRQEDFYPFLKDNRE

KIEKILTFRIPYYVGPLARGNSRFAWMTRKSEETITPWNFEEVVDKGASAQSFIERM

TNFDKNLPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKIIKDKDFLD

NEENEDILEDIVLTLTLFEDREMIEERLKTYAHLFDDKVMKQLKRRRYTGWGRLSR

KLINGIRDKQSGKTILDFLKSDGFANRNFMQLIHDDSLTFKEDIQKAQVSGQGDSLH

EHIANLAGSPAIKKGILQTVKVVDELVKVMGRHKPENIVIEMARENQTTQKGQKNS

RERMKRIEEGIKELGSQILKEHPVENTQLQNEKLYLYYLQNGRDMYVDQELDINRL

SDYDVDAIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSRMNTKYD

ENDKLIREVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEITLANGEIR

-continued

KRPLIETNGETGEIVWDKGRDFATVRKVLSMPQVNIVKKTEVQTGGFSKESILPKR

NSDKLIARKKDWDPKKYGGFDSPTVAYSVLVVAKVEKGKSKKLKSVKELLGITIME

RSSFEKNPIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISEFSKRVILA

DANLDKVLSAYNKHRDKPIREQAENIIHLFTLTNLGAPAAFKYFDTTIDRKRYTSTK

EVLDATLIHQSITGLYETRIDLSQLGGDSGGSSGGSSGSETPGTSESATPESSGGSSGG

SS*TLNIEDEYRLHETSKEPDVSLGSTWLSDFPQAWAETGGMGLAVRQAPLIIPLKATSTPVSIKQ*

*YPMSQEARLGIKPHIQRLLDQGILVPCQSPWNTPLLPVKKPGTNDYRPVQDLREVNKRVEDIH*

*PTVPNPYNLLSGLPPSHQWYTVLDLKDAFFCLRLHPTSQPLFAFEWRDPEMGISGQLTWTRL*

*PQGFKNSPTLFNEALHRDLADFRIQHPDLILLQYVDDLLLAATSELDCQQGTRALLQTLGNLG*

*YRASAKKAQICQKQVKYLGYLLKEGQRWLTEARKETVMGQPTPKTPRQLREFLGKAGFCRLF*

*IPGFAEMAAPLYPLTKPGTLFNWGPDQQKAYQEIKQALLTAPALGLPDLTKPFELFVDEKQGY*

*AKGVLTQKLGPWRRPVAYLSKKLDPVAAGWPPCLRMVAAIAVLTKDAGKLTMGQPLVILAPH*

*AVEALVKOPPDRWLSNARMTHYQALLLDTDRVQFGPVVALNPATLLPLPEEGLOHNCLDILAE*

*AHGTRPDLTDQPLPDADHTWYTDGSSLLQEGQRKAGAAVTTETEVIWAKALPAGTSAQRAELI*

*ALTQALKMAEGKKLNVYTDSRYAFATAHIHGEIYRRRGWLTSEGKEIKNKDEILALLKALFLPK*

*RLSIIHCPGHQKGHSAEARGNRMADQAARKAAITETPDTSTLLIENSSP*SGGSKRTADGSEFEP

KKKRKV

KEY:

NUCLEAR LOCALIZATION SEQUENCE (NLS) TOP:(SEQ ID NO: 24), BOTTOM: (SEQ ID NO: 33)

CAS9(H840A) (SEQ ID NO: 55)

33-AMINO ACID LINKER (SEQ ID NO: 56)

*M-MLV reverse transcriptase* (SEQ ID NO: 59).

PE3

As used herein, "PE3" refers to PE2 plus a second-strand nicking guide RNA that complexes with the PE2 and introduces a nick in the non-edited DNA strand in order to induce preferential replacement of the edited strand.

PE3b

As used herein, "PE3b" refers to PE3 but wherein the second-strand nicking guide RNA is designed for temporal control such that the second strand nick is not introduced until after the installation of the desired edit. This is achieved by designing a gRNA with a spacer sequence that matches only the edited strand, but not the original allele. Using this strategy, referred to hereafter as PE3b, mismatches between the protospacer and the unedited allele should disfavor nicking by the sgRNA until after the editing event on the PAM strand takes place.

PE-Short

As used herein, "PE-short" refers to a PE construct that is fused to a C-terminally truncated reverse transcriptase, and has the following amino acid sequence:

(SEQ ID NO: 60)

MKRTADGSEFESPKKKRKVDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMIK

RYDEHHQDLTLLKALVRQQLPEKYKEIFFDQSKNGYAGYIDGGASQEEFYKFIKPI

LEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

-continued

DFLDNEENEDILEDIVLTLTLFEDREMIEERLKTYAHLFDDKVMKQLKRRRYTGW

GRLSRKLINGIRDKQSGKTILDFLKSDGFANRNFMQLIHDDSLTFKEDIQKAQVSGQ

GDSLHEHIANLAGSPAIKKGILQTVKVVDELVKVMGRHKPENIVIEMARENQTTQK

GQKNSRERMKRIEEGIKELGSQILKEHPVENTQLQNEKLYLYYLQNGRDMYVDQE

LDINRLSDYDVDAIVPQSFLKDDSIDNKVLTRSDKNRGKSDNVPSEEVVKKMKNYW

RQLLNAKLITQRKFDNLTKAERGGLSELDKAGFIKRQLVETRQITKHVAQILDSRM

NTKYDENDKLIREVKVITLKSKLVSDFRKDFQFYKVREINNYHHAHDAYLNAVVGT

ALIKKYPKLESEFVYGDYKVYDVRKMIAKSEQEIGKATAKYFFYSNIMNFFKTEITL

ANGEIRKRPLIETNGETGEIVWDKGRDFATVRKVLSMPQVNIVKKTEVQTGGFSKE

SILPKRNSDKLIARKKDWDPKKYGGFDSPTVAYSVLVVAKVEKGKSKKLKSVKEL

LGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFS

KRVILADANLDKVLSAYNKHRDKPIREQAENIIHLFTLTNLGAPAAFKYFDTTIDRK

RYTSTKEVLDATLIHQSITGLYETRIDLSQLGGDSGGSSGGSSGSETPGTSESATPESS

GGSSGGSS*TLNIEDEYRLHETSKEPDVSLGSTWLSDFPQAWAETGGMGLAVRQAPLIIPLKAT*

*STPVSIKQYPMSQEARLGIKPHIQRLLDQGILVPCQSPWNTPLLPVKKPGTNDYRPVQDLREV*

*NKRVEDIHPTVPNPYNLLSGLPPSHQWYTVLDLKDAFFCLRLHPTSQPLFAFEWRDPEMGIS*

*GQLTWTRLPQGFKNSPTLFNEALHRDLADFRIQHPDLILLQYVDDLLLAATSELDCQQGTRA*

*LLQTLGNLGYRASAKKAQICQKQVKYLGYLLKEGQRWLTEARKETVMGQPTPKTPRQLREFL*

*GKAGFCRLFIPGFAEMAAPLYPLTKPGTLFNWGPDQQKAYQEIKQALLTAPALGLPDLTKPF*

*ELFVDEKQGYAKGVLTQKLGPWRRPVAYLSKKLDPVAAGWPPCLRMVAAIAVLTKDAGKLT*

*MGQPLVILAPHAVEALVKOPPDRWLSNARMTHYQALLLDTDRVQFGPVVALNPATLLPLPEE*

*GLQHNCLDNSRLIN*SGGSKRTADGSEFEPKKKRKV

KEY:

NUCLEAR LOCALIZATION SEQUENCE (NLS) TOP:(SEQ ID NO: 24), BOTTOM: (SEQ ID NO: 33)

CAS9(H840A) (SEQ ID NO: 55)

33-AMINO ACID LINKER 1 (SEQ ID NO: 56)

*M-MLV TRUNCATED REVERSE TRANSCRIPTASE* (SEQ ID NO: 61)

Peptide Tag

The term "peptide tag" refers to a peptide amino acid sequence that is genetically fused to a protein sequence to impart one or more functions onto the proteins that facilitate the manipulation of the protein for various purposes, such as, visualization, purification, solubilization, and separation, etc. Peptide tags can include various types of tags categorized by purpose or function, which may include "affinity tags" (to facilitate protein purification), "solubilization tags" (to assist in proper folding of proteins), "chromatography tags" (to alter chromatographic properties of proteins), "epitope tags" (to bind to high affinity antibodies), "fluorescence tags" (to facilitate visualization of proteins in a cell or in vitro).

Polymerase

As used herein, the term "polymerase" refers to an enzyme that synthesizes a nucleotide strand and which may be used in connection with the prime editor systems described herein. The polymerase can be a "template-dependent" polymerase (i.e., a polymerase which synthesizes a nucleotide strand based on the order of nucleotide bases of a template strand). The polymerase can also be a "template-independent" polymerase (i.e., a polymerase which synthesizes a nucleotide strand without the requirement of a template strand). A polymerase may also be further categorized as a "DNA polymerase" or an "RNA polymerase." In various embodiments, the prime editor system comprises a DNA polymerase. In various embodiments, the DNA polymerase can be a "DNA-dependent DNA polymerase" (i.e., whereby the template molecule is a strand of DNA). In such cases, the DNA template molecule can be a pegRNA, wherein the extension arm comprises a strand of DNA. In such cases, the pegRNA may be referred to as a chimeric or hybrid pegRNA which comprises an RNA portion (i.e., the guide RNA components, including the spacer and the gRNA core) and a DNA portion (i.e., the extension arm). In various other embodiments, the DNA polymerase can be an "RNA-dependent DNA polymerase" (i.e., whereby the template molecule is a strand of RNA). In such cases, the pegRNA is RNA, i.e., including an RNA extension. The term "polymerase" may also refer to an enzyme that catalyzes the polymerization of nucleotide (i.e., the polymerase activity). Generally, the enzyme will initiate synthesis at the 3'-end of a primer annealed to a polynucleotide template sequence (e.g., such as a primer sequence annealed to the primer binding site of a pegRNA), and will proceed toward the 5' end of the template strand. A "DNA polymerase" catalyzes the polymerization of deoxynucleotides. As used herein in reference to a DNA polymerase, the term DNA polymerase includes a "functional fragment thereof". A "functional fragment thereof" refers to any portion of a wild-type or mutant DNA polymerase that encompasses less than the entire amino acid sequence of the polymerase and which retains the ability, under at least one set of conditions, to catalyze the polymerization of a polynucleotide. Such a functional fragment may exist as a separate entity, or it may be a constituent of a larger polypeptide, such as a fusion protein.

Prime Editing

As used herein, the term "prime editing" refers to a novel approach for gene editing using napDNAbps, a polymerase (e.g., a reverse transcriptase), and specialized guide RNAs that include a DNA synthesis template for encoding desired new genetic information (or deleting genetic information) that is then incorporated into a target DNA sequence. Certain embodiments of prime editing are described in the embodiments of FIGS. 1A-1H and FIG. 72(*a*)-72(*c*), among other figures.

Prime editing represents an entirely new platform for genome editing that is a versatile and precise genome editing method that directly writes new genetic information into a specified DNA site using a nucleic acid programmable DNA binding protein ("napDNAbp") working in association with a polymerase (i.e., in the form of a fusion protein or otherwise provided in trans with the napDNAbp), wherein the prime editing system is programmed with a prime editing (PE) guide RNA ("pegRNA") that both specifies the target site and templates the synthesis of the desired edit in the form of a replacement DNA strand by way of an extension (either DNA or RNA) engineered onto a guide RNA (e.g., at the 5' or 3' end, or at an internal portion of a guide RNA). The replacement strand containing the desired edit (e.g., a single nucleobase substitution) shares the same (or is homologous to) sequence as the endogenous strand (immediately downstream of the nick site) of the target site to be edited (with the exception that it includes the desired edit). Through DNA repair and/or replication machinery, the endogenous strand downstream of the nick site is replaced by the newly synthesized replacement strand containing the desired edit. In some cases, prime editing may be thought of as a "search-and-replace" genome editing technology since the prime editors, as described herein, not only search and locate the desired target site to be edited, but at the same time, encode a replacement strand containing a desired edit which is installed in place of the corresponding target site endogenous DNA strand. The prime editors of the present disclosure relate, in part, to the discovery that the mechanism of target-primed reverse transcription (TPRT) or "prime editing" can be leveraged or adapted for conducting precision CRISPR/Cas-based genome editing with high efficiency and genetic flexibility (e.g., as depicted in various embodiments of FIGS. 1A-1F). TPRT is naturally used by mobile DNA elements, such as mammalian non-LTR retrotransposons and bacterial Group II introns[28, 29]. The inventors have herein used Cas protein-reverse transcriptase fusions or related systems to target a specific DNA sequence with a guide RNA, generate a single strand nick at the target site, and use the nicked DNA as a primer for reverse transcription of an engineered reverse transcriptase template that is integrated with the guide RNA. However, while the concept begins with prime editors that use reverse transcriptase as the DNA polymerase component, the prime editors described herein are not limited to reverse transcriptases but may include the use of virtually any DNA polymerase. Indeed, while the application throughout may refer to prime editors with "reverse transcriptases," it is set forth here that reverse transcriptases are only one type of DNA polymerase that may work with prime editing. Thus, where ever the specification mentions a "reverse transcriptase," the person having ordinary skill in the art should appreciate that any suitable DNA polymerase may be used in place of the reverse transcriptase. Thus, in one aspect, the prime editors may comprise Cas9 (or an equivalent napDNAbp) which is programmed to target a DNA sequence by associating it with a specialized guide RNA (i.e., pegRNA) containing a spacer sequence that anneals to a complementary protospacer in the target DNA. The specialized guide RNA also contains new genetic information in the form of an extension that encodes a replacement strand of DNA containing a desired genetic alteration which is used to replace a corresponding endogenous DNA strand at the target site. To transfer information from the pegRNA to the target DNA, the mechanism of prime editing involves nicking the target site in one strand of the DNA to expose a 3'-hydroxyl group. The exposed 3'-hydroxyl group can then be used to prime the DNA polymerization of the edit-encoding extension on pegRNA directly into the target site. In various embodiments, the extension which provides the template for polymerization of the replacement strand containing the edit can be formed from RNA or DNA. In the case of an RNA extension, the polymerase of the prime editor can be an RNA-dependent DNA polymerase (such as, a reverse transcriptase). In the case of a DNA extension, the polymerase of the prime editor may be a DNA-dependent DNA polymerase. The newly synthesized strand (i.e., the replacement DNA strand containing the desired edit) that is formed by the herein disclosed prime editors would be homologous to the genomic target sequence (i.e., have the same sequence as) except for the inclusion of a desired nucleotide change (e.g., a single nucleotide change, a deletion, or an insertion, or a combination thereof). The newly synthesized (or replacement) strand of DNA may also be referred to as a single strand DNA flap, which would compete for hybridization with the complementary homologous endogenous DNA strand, thereby displacing the corresponding endogenous strand. In certain embodiments, the system can be combined with the use of an error-prone reverse transcriptase enzyme (e.g., provided as a fusion protein with the Cas9 domain, or provided in trans to the Cas9 domain). The error-prone reverse transcriptase enzyme can introduce alterations during synthesis of the single strand DNA flap. Thus, in certain embodiments, error-prone reverse transcriptase can be utilized to introduce nucleotide changes to the target DNA. Depending on the error-prone reverse transcriptase that is used with the system, the changes can be random or non-random. Resolution of the hybridized intermediate (comprising the single strand DNA flap synthesized by the reverse transcriptase hybridized to the endogenous DNA strand) can include removal of the resulting displaced flap of endogenous DNA (e.g., with a 5' end DNA flap endonuclease, FEN1), ligation of the synthesized single strand DNA flap to the target DNA, and assimilation of the desired nucleotide change as a result of cellular DNA repair and/or replication processes. Because templated DNA synthesis offers single nucleotide precision for the modification of any nucleotide, including insertions and deletions, the scope of this approach is very broad and could foreseeably be used for myriad applications in basic science and therapeutics.

In various embodiments, prime editing operates by contacting a target DNA molecule (for which a change in the nucleotide sequence is desired to be introduced) with a nucleic acid programmable DNA binding protein (napDNAbp) complexed with a prime editing guide RNA (pegRNA). In reference to FIG. 1G, the prime editing guide RNA (pegRNA) comprises an extension at the 3' or 5' end of the guide RNA, or at an intramolecular location in the guide RNA and encodes the desired nucleotide change (e.g., single nucleotide change, insertion, or deletion). In step (a), the napDNAbp/pegRNA complex contacts the DNA molecule and the extended pegRNA guides the napDNAbp to bind to a target locus. In step (b), a nick in one of the strands of DNA of the target locus is introduced (e.g., by a nuclease or chemical agent), thereby creating an available 3' end in one of the strands of the target locus. In certain embodiments, the nick is created in the strand of DNA that corresponds to the R-loop strand, i.e., the strand that is not hybridized to the guide RNA sequence, i.e., the "non-target strand." The nick, however, could be introduced in either of the strands. That is, the nick could be introduced into the R-loop "target strand" (i.e., the strand hybridized to the protospacer of the extended pegRNA) or the "non-target strand" (i.e., the strand forming the single-stranded portion of the R-loop and which is complementary to the target strand). In step (c), the 3' end of the DNA strand (formed by the nick) interacts with the extended portion of the guide RNA in order to prime reverse transcription (i.e., "target-primed RT"). In certain embodiments, the 3' end DNA strand hybridizes to a specific RT priming sequence on the extended portion of the guide RNA, i.e., the "reverse transcriptase priming sequence" or "primer binding site" on the pegRNA. In step (d), a reverse transcriptase (or other suitable DNA polymerase) is introduced which synthesizes a single strand of DNA from the 3' end of the primed site towards the 5' end of the prime editing guide RNA. The DNA polymerase (e.g., reverse transcriptase) can be fused to the napDNAbp or alternatively can be provided in trans to the napDNAbp. This forms a single-strand DNA flap comprising the desired nucleotide change (e.g., the single base change, insertion, or deletion, or a combination thereof) and which is otherwise homologous to the endogenous DNA at or adjacent to the nick site. In step (e), the napDNAbp and guide RNA are released. Steps (f) and (g) relate to the resolution of the single strand DNA flap such that the desired nucleotide change becomes incorporated into the target locus. This process can be driven towards the desired product formation by removing the corresponding 5' endogenous DNA flap that forms once the 3' single strand DNA flap invades and hybridizes to the endogenous DNA sequence. Without being bound by theory, the cells endogenous DNA repair and replication processes resolves the mismatched DNA to incorporate the nucleotide change(s) to form the desired altered product. The process can also be driven towards product formation with "second strand nicking," as exemplified in FIG. 1F. This process may introduce at least one or more of the following genetic changes: transversions, transitions, deletions, and insertions.

The term "prime editor (PE) system" or "prime editor (PE)" or "PE system" or "PE editing system" refers the compositions involved in the method of genome editing using prime editing described herein, including, but not limited to the napDNAbps, reverse transcriptases, fusion proteins (e.g., comprising napDNAbps and reverse transcriptases), prime editing guide RNAs, and complexes comprising fusion proteins and prime editing guide RNAs, as well as accessory elements, such as second strand nicking components (e.g., second strand sgRNAs) and 5' endogenous DNA flap removal endonucleases (e.g., FEN1) for helping to drive the prime editing process towards the edited product formation.

Although in the embodiments described thus far the pegRNA constitutes a single molecule comprising a guide RNA (which itself comprises a spacer sequence and a gRNA core or scaffold) and a 5' or 3' extension arm comprising the primer binding site and a DNA synthesis template (e.g., see FIG. 3D, the pegRNA may also take the form of two individual molecules comprised of a guide RNA and a trans prime editor RNA template (tPERT), which essentially houses the extension arm (including, in particular, the primer binding site and the DNA synthesis domain) and an RNA-protein recruitment domain (e.g., MS2 aptamer or hairpin) in the same molecule which becomes co-localized or recruited to a modified prime editor complex that comprises a tPERT recruiting protein (e.g., MS2cp protein, which binds to the MS2 aptamer). See FIG. 3G and FIG. 3H as an example of a tPERT that may be used with prime editing.

Prime Editor

The term "prime editor" refers to the herein described fusion constructs comprising a napDNAbp (e.g., Cas9 nickase) and a reverse transcriptase and is capable of carrying out prime editing on a target nucleotide sequence in the presence of a pegRNA. The term "prime editor" may refer to the fusion protein or to the fusion protein complexed with a pegRNA, and/or further complexed with a second-strand nicking sgRNA. In some embodiments, the prime editor may also refer to the complex comprising a fusion protein (reverse transcriptase fused to a napDNAbp), a pegRNA, and a regular guide RNA capable of directing the second-site nicking step of the non-edited strand as described herein. In other embodiments, the reverse transcriptase component of the "primer editor" may be provided in trans.

Primer Binding Site

The term "primer binding site" or "the PBS" refers to the nucleotide sequence located on a pegRNA as component of the extension arm (typically at the 3' end of the extension arm) and serves to bind to the primer sequence that is formed after Cas9 nicking of the target sequence by the prime editor. As detailed elsewhere, when the Cas9 nickase component of a prime editor nicks one strand of the target DNA sequence, a 3'-ended ssDNA flap is formed, which serves a primer sequence that anneals to the primer binding site on the pegRNA to prime reverse transcription. FIGS. 27 and 28 show embodiments of the primer binding site located on a 3' and 5' extension arm, respectively.

Promoter

The term "promoter" is art-recognized and refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active in the presence of a specific condition. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

Protospacer

As used herein, the term "protospacer" refers to the sequence (~20 bp) in DNA adjacent to the PAM (protospacer adjacent motif) sequence. The protospacer shares the same sequence as the spacer sequence of the guide RNA. The guide RNA anneals to the complement of the protospacer sequence on the target DNA (specifically, one strand thereof, i.e., the "target strand" versus the "non-target strand" of the target DNA sequence). In order for Cas9 to function it also requires a specific protospacer adjacent motif (PAM) that varies depending on the bacterial species of the Cas9 gene. The most commonly used Cas9 nuclease, derived from *S. pyogenes*, recognizes a PAM sequence of NGG that is found directly downstream of the target sequence in the genomic DNA, on the non-target strand. The skilled person will appreciate that the literature in the state of the art sometimes refers to the "protospacer" as the ~20-nt target-specific guide sequence on the guide RNA itself, rather than referring to it as a "spacer." Thus, in some cases, the term "protospacer" as used herein may be used interchangeably with the term "spacer." The context of the description surrounding the appearance of either "protospacer" or "spacer" will help inform the reader as to whether the term is in reference to the gRNA or the DNA target.

Protospacer Adjacent Motif (PAM)

As used herein, the term "protospacer adjacent sequence" or "PAM" refers to an approximately 2-6 base pair DNA sequence that is an important targeting component of a Cas9 nuclease. Typically, the PAM sequence is on either strand, and is downstream in the 5' to 3' direction of Cas9 cut site. The canonical PAM sequence (i.e., the PAM sequence that is associated with the Cas9 nuclease of *Streptococcus pyogenes* or SpCas9) is 5'-NGG-3' wherein "N" is any nucleobase followed by two guanine ("G") nucleobases. Different PAM sequences can be associated with different Cas9 nucleases or equivalent proteins from different organisms. In addition, any given Cas9 nuclease, e.g., SpCas9, may be modified to alter the PAM specificity of the nuclease such that the nuclease recognizes alternative PAM sequence.

For example, with reference to the canonical SpCas9 amino acid sequence is SEQ ID NO: 18, the PAM sequence can be modified by introducing one or more mutations, including (a) D1135V, R1335Q, and T1337R "the VQR variant", which alters the PAM specificity to NGAN or NGNG, (b) D1135E, R1335Q, and T1337R "the EQR variant", which alters the PAM specificity to NGAG, and (c) D1135V, G1218R, R1335E, and T1337R "the VRER variant", which alters the PAM specificity to NGCG. In addition, the D1135E variant of canonical SpCas9 still recognizes NGG, but it is more selective compared to the wild type SpCas9 protein.

It will also be appreciated that Cas9 enzymes from different bacterial species (i.e., Cas9 orthologs) can have varying PAM specificities. For example, Cas9 from *Staphylococcus aureus* (SaCas9) recognizes NGRRT or NGRRN. In addition, Cas9 from *Neisseria meningitis* (NmCas) recognizes NNNNGATT. In another example, Cas9 from *Streptococcus thermophilis* (StCas9) recognizes NNAGAAW. In still another example, Cas9 from *Treponema denticola* (TdCas) recognizes NAAAAC. These are example are not meant to be limiting. It will be further appreciated that non-SpCas9s bind a variety of PAM sequences, which makes them useful when no suitable SpCas9 PAM sequence is present at the desired target cut site. Furthermore, non-SpCas9s may have other characteristics that make them more useful than SpCas9. For example, Cas9 from *Staphylococcus aureus* (SaCas9) is about 1 kilobase smaller than SpCas9, so it can be packaged into adeno-associated virus (AAV). Further reference may be made to Shah et al., "Protospacer recognition motifs: mixed identities and functional diversity," *RNA Biology,* 10(5): 891-899 (which is incorporated herein by reference).

Reverse Transcriptase

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation. Avian myoblastosis virus (AMV) reverse transcriptase was the first widely used RNA-dependent DNA polymerase (Verma, Biochim. Biophys. Acta 473:1 (1977)). The enzyme has 5'-3' RNA-directed DNA polymerase activity, 5'-3' DNA-directed DNA polymerase activity, and RNase H activity. RNase H is a processive 5' and 3' ribonuclease specific for the RNA strand for RNA-DNA hybrids (Perbal, A Practical Guide to Molecular Cloning, New York: Wiley & Sons (1984)). Errors in transcription cannot be corrected by reverse transcriptase because known viral reverse transcriptases lack the 3'-5' exonuclease activity necessary for proofreading (Saunders and Saunders, Microbial Genetics Applied to Biotechnology, London: Croom Helm (1987)). A detailed study of the activity of AMV reverse transcriptase and its associated RNase H activity has been presented by Berger et al., Biochemistry 22:2365-2372 (1983). Another reverse transcriptase which is used extensively in molecular biology is reverse transcriptase originating from Moloney murine leukemia virus (M-MLV). See, e.g., Gerard, G. R., DNA 5:271-279 (1986) and Kotewicz, M. L., et al., Gene 35:249-258 (1985). M-MLV reverse transcriptase substantially lacking in RNase H activity has also been described. See, e.g., U.S. Pat. No. 5,244,797. The invention contemplates the use of any such reverse transcriptases, or variants or mutants thereof.

In addition, the invention contemplates the use of reverse transcriptases which are error-prone, i.e., which may be referred to as error-prone reverse transcriptases or reverse transcriptases which do not support high fidelity incorporation of nucleotides during polymerization. During synthesis of the single-strand DNA flap based on the RT template integrated with the guide RNA, the error-prone reverse transcriptase can introduce one or more nucleotides which are mismatched with the RT template sequence, thereby introducing changes to the nucleotide sequence through erroneous polymerization of the single-strand DNA flap. These errors introduced during synthesis of the single strand DNA flap then become integrated into the double strand molecule through hybridization to the corresponding endogenous target strand, removal of the endogenous displaced strand, ligation, and then through one more round of endogenous DNA repair and/or sequencing processes.

Reverse Transcription

As used herein, the term "reverse transcription" indicates the capability of enzyme to synthesize DNA strand (that is, complementary DNA or cDNA) using RNA as a template. In some embodiments, the reverse transcription can be "error-prone reverse transcription," which refers to the properties of certain reverse transcriptase enzymes which are error-prone in their DNA polymerization activity.

Protein, Peptide, and Polypeptide

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, Molecular Cloning: A Laboratory Manual (4th ed., Cold Spring Harbor Laboratory Press, Cold Spring Harbor, N.Y. (2012)), the entire contents of which are incorporated herein by reference.

Protein Splicing

The term "protein splicing," as used herein, refers to a process in which a sequence, an intein (or split inteins, as the case may be), is excised from within an amino acid sequence, and the remaining fragments of the amino acid sequence, the exteins, are ligated via an amide bond to form a continuous amino acid sequence. The term "trans" protein splicing refers to the specific case where the inteins are split inteins and they are located on different proteins.

Second-Strand Nicking

The resolution of heteroduplex DNA (i.e., containing one edited and one non-edited strand) formed as a result of prime editing determines long-term editing outcomes. In words, a goal of prime editing is to resolve the heteroduplex DNA (the edited strand paired with the endogenous non-edited strand) formed as an intermediate of PE by permanently integrating the edited strand into the complement, endogenous strand. The approach of "second-strand nicking" can be used herein to help drive the resolution of heteroduplex DNA in favor of permanent integration of the edited strand into the DNA molecule. As used herein, the concept of "second-strand nicking" refers to the introduction of a second nick at a location downstream of the first nick (i.e., the initial nick site that provides the free 3' end for use in priming of the reverse transcriptase on the extended portion of the guide RNA), preferably on the unedited strand. In certain embodiments, the first nick and the second nick are on opposite strands. In other embodiments, the first nick and the second nick are on opposite strands. In yet another embodiment, the first nick is on the non-target strand (i.e., the strand that forms the single strand portion of the R-loop), and the second nick is on the target strand. In still other embodiments, the first nick is on the edited strand, and the second nick is on the unedited strand. The second nick can be positioned at least 5 nucleotides downstream of the first nick, or at least 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, or 150 or more nucleotides downstream of the first nick. The second nick, in certain embodiments, can be introduced between about 5-150 nucleotides on the unedited strand away from the site of the pegRNA-induced nick, or between about 5-140, or between about 5-130, or between about 5-120, or between about 5-110, or between about 5-100, or between about 5-90, or between about 5-80, or between about 5-70, or between about 5-60, or between about 5-50, or between about 5-40, or between about 5-30, or between about 5-20, or between about 5-10. In one embodiment, the second nick is introduced between 14-116 nucleotides away from the pegRNA-induced nick. Without being bound by theory, the second nick induces the cell's endogenous DNA repair and replication processes towards replacement or editing of the unedited strand, thereby permanently installing the edited sequence on both strands and resolving the heteroduplex that is formed as a result of PE. In some embodiments, the edited strand is the non-target strand and the unedited strand is the target strand. In other embodiments, the edited strand is the target strand, and the unedited strand is the non-target strand.

Sense Strand

In genetics, a "sense" strand is the segment within double-stranded DNA that runs from 5' to 3', and which is complementary to the antisense strand of DNA, or template strand, which runs from 3' to 5'. In the case of a DNA segment that encodes a protein, the sense strand is the strand of DNA that has the same sequence as the mRNA, which takes the antisense strand as its template during transcription, and eventually undergoes (typically, not always) translation into a protein. The antisense strand is thus responsible for the RNA that is later translated to protein, while the sense strand possesses a nearly identical makeup to that of the mRNA. Note that for each segment of dsDNA, there will possibly be two sets of sense and antisense, depending on which direction one reads (since sense and antisense is relative to perspective). It is ultimately the gene product, or mRNA, that dictates which strand of one segment of dsDNA is referred to as sense or antisense.

In the context of a pegRNA, the first step is the synthesis of a single-strand complementary DNA (i.e., the 3' ssDNA flap, which becomes incorporated) oriented in the 5' to 3' direction which is templated off of the pegRNA extension arm. Whether the 3' ssDNA flap should be regarded as a sense or antisense strand depends on the direction of transcription since it well accepted that both strands of DNA may serve as a template for transcription (but not at the same time). Thus, in some embodiments, the 3' ssDNA flap (which overall runs in the 5' to 3' direction) will serve as the sense strand because it is the coding strand. In other embodiments, the 3' ssDNA flap (which overall runs in the 5' to 3' direction) will serve as the antisense strand and thus, the template for transcription.

Spacer Sequence

As used herein, the term "spacer sequence" in connection with a guide RNA or a pegRNA refers to the portion of the guide RNA or pegRNA of about 20 nucleotides which contains a nucleotide sequence that is complementary to the protospacer sequence in the target DNA sequence. The spacer sequence anneals to the protospacer sequence to form a ssRNA/ssDNA hybrid structure at the target site and a corresponding R loop ssDNA structure of the endogenous DNA strand that is complementary to the protospacer sequence.

Subject

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

Split Intein

Although inteins are most frequently found as a contiguous domain, some exist in a naturally split form. In this case, the two fragments are expressed as separate polypeptides and must associate before splicing takes place, so-called protein trans-splicing.

An exemplary split intein is the Ssp DnaE intein, which comprises two subunits, namely, DnaE-N and DnaE-C. The two different subunits are encoded by separate genes, namely dnaE-n and dnaE-c, which encode the DnaE-N and DnaE-C subunits, respectively. DnaE is a naturally occurring split intein in *Synechocytis* sp. PCC6803 and is capable of directing trans-splicing of two separate proteins, each comprising a fusion with either DnaE-N or DnaE-C.

Additional naturally occurring or engineered split-intein sequences are known in the or can be made from whole-intein sequences described herein or those available in the art. Examples of split-intein sequences can be found in Stevens et al., "A promiscuous split intein with expanded protein engineering applications," PNAS, 2017, Vol. 114: 8538-8543; Iwai et al., "Highly efficient protein trans-splicing by a naturally split DnaE intein from Nostc punctiforme, FEBS Lett, 580: 1853-1858, each of which are incorporated herein by reference. Additional split intein sequences can be found, for example, in WO 2013/045632, WO 2014/055782, WO 2016/069774, and EP2877490, the contents each of which are incorporated herein by reference.

In addition, protein splicing in trans has been described in vivo and in vitro (Shingledecker, et al., *Gene* 207:187 (1998), Southworth, et al., *EMBO J.* 17:918 (1998); Mills, et al., *Proc. Natl. Acad. Sci. USA,* 95:3543-3548 (1998); Lew, et al., *J. Biol. Chem.,* 273:15887-15890 (1998); Wu, et al., *Biochim. Biophys. Acta* 35732:1 (1998b), Yamazaki, et al., *J. Am. Chem. Soc.* 120:5591 (1998), Evans, et al., *J. Biol. Chem.* 275:9091 (2000); Otomo, et al., *Biochemistry* 38:16040-16044 (1999); Otomo, et al., *J. Biolmol. NMR* 14:105-114 (1999); Scott, et al., *Proc. Natl. Acad. Sci. USA* 96:13638-13643 (1999)) and provides the opportunity to express a protein as to two inactive fragments that subsequently undergo ligation to form a functional product, e.g., as shown in FIGS. 66 and 67 with regard to the formation of a complete Prime editor from two separately-expressed halves.

Target Site

The term "target site" refers to a sequence within a nucleic acid molecule that is edited by a prime editor (PE) disclosed herein. The target site further refers to the sequence within a nucleic acid molecule to which a complex of the prime editor (PE) and gRNA binds.

tPERT

See definition for "trans prime editor RNA template (tPERT)."

Temporal Second-Strand Nicking

As used herein, the term "temporal second-strand nicking" refers to a variant of second strand nicking whereby the installation of the second nick in the unedited strand occurs only after the desired edit is installed in the edited strand. This avoids concurrent nicks on both strands that could lead to double-stranded DNA breaks. The second-strand nicking guide RNA is designed for temporal control such that the second strand nick is not introduced until after the installation of the desired edit. This is achieved by designing a gRNA with a spacer sequence that matches only the edited strand, but not the original allele. Using this strategy, mismatches between the protospacer and the unedited allele should disfavor nicking by the sgRNA until after the editing event on the PAM strand takes place.

Trans Prime Editing

As used herein, the term "trans prime editing" refers to a modified form of prime editing that utilizes a split pegRNA, i.e., wherein the pegRNA is separated into two separate molecules: an sgRNA and a trans prime editing RNA template (tPERT). The sgRNA serves to target the prime editor (or more generally, to target the napDNAbp component of the prime editor) to the desired genomic target site, while the tPERT is used by the polymerase (e.g., a reverse transcriptase) to write new DNA sequence into the target locus once the tPERT is recruited in trans to the prime editor by the interaction of binding domains located on the prime editor and on the tPERT. In one embodiment, the binding domains can include RNA-protein recruitment moieties, such as a MS2 aptamer located on the tPERT and an MS2cp protein fused to the prime editor. An advantage of trans prime editing is that by separating the DNA synthesis template from the guide RNA, one can potentially use longer length templates.

An embodiment of trans prime editing is shown in FIGS. 3G and 3H. FIG. 3G shows the composition of the trans prime editor complex on the left ("RP-PE:gRNA complex), which comprises an napDNAbp fused to each of a polymerase (e.g., a reverse transcriptase) and a rPERT recruiting protein (e.g., MS2sc), and which is complexed with a guide RNA. FIG. 3G further shows a separate tPERT molecule, which comprises the extension arm features of a pegRNA, including the DNA synthesis template and the primer binding sequence. The tPERT molecule also includes an RNA-protein recruitment domain (which, in this case, is a stem loop structure and can be, for example, MS2 aptamer). As depicted in the process described in FIG. 3H, the RP-PE:gRNA complex binds to and nicks the target DNA sequence. Then, the recruiting protein (RP) recruits a tPERT to co-localize to the prime editor complex bound to the DNA target site, thereby allowing the primer binding site to bind to the primer sequence on the nicked strand, and subsequently, allowing the polymerase (e.g., RT) to synthesize a single strand of DNA against the DNA synthesis template up through the 5' of the tPERT.

While the tPERT is shown in FIG. 3G and FIG. 3H as comprising the PBS and DNA synthesis template on the 5' end of the RNA-protein recruitment domain, the tPERT in other configurations may be designed with the PBS and DNA synthesis template located on the 3' end of the RNA-protein recruitment domain. However, the tPERT with the 5' extension has the advantage that synthesis of the single strand of DNA will naturally terminate at the 5' end of the tPERT and thus, does not risk using any portion of the RNA-protein recruitment domain as a template during the DNA synthesis stage of prime editing.

Transitions

As used herein, "transitions" refer to the interchange of purine nucleobases (A↔G) or the interchange of pyrimidine nucleobases (C↔T). This class of interchanges involves nucleobases of similar shape. The compositions and methods disclosed herein are capable of inducing one or more transitions in a target DNA molecule. The compositions and methods disclosed herein are also capable of inducing both transitions and transversion in the same target DNA molecule. These changes involve A↔G, G↔A, C↔T, or T↔C. In the context of a double-strand DNA with Watson-Crick paired nucleobases, transversions refer to the following base pair exchanges: A:T↔G:C, G:G↔A:T, C:G↔T:A, or T:A↔C:G. The compositions and methods disclosed herein are capable of inducing one or more transitions in a target DNA molecule. The compositions and methods disclosed herein are also capable of inducing both transitions and transversion in the same target DNA molecule, as well as other nucleotide changes, including deletions and insertions.

Transversions

As used herein, "transversions" refer to the interchange of purine nucleobases for pyrimidine nucleobases, or in the reverse and thus, involve the interchange of nucleobases with dissimilar shape. These changes involve T↔A, T↔G, C↔G, C↔A, A↔T, A↔C, G↔C, and G↔T. In the context of a double-strand DNA with Watson-Crick paired nucleobases, transversions refer to the following base pair exchanges: T:A↔A:T, T:A↔G:C, C:G↔G:C, C:G↔A:T, A:T↔T:A, A:T↔C:G, G:C↔C:G, and G:C↔T:A. The compositions and methods disclosed herein are capable of inducing one or more transversions in a target DNA molecule. The compositions and methods disclosed herein are also capable of inducing both transitions and transversion in the same target DNA molecule, as well as other nucleotide changes, including deletions and insertions.

Treatment

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

Upstream

As used herein, the terms "upstream" and "downstream" are terms of relativity that define the linear position of at least two elements located in a nucleic acid molecule (whether single or double-stranded) that is orientated in a 5'-to-3' direction. In particular, a first element is upstream of a second element in a nucleic acid molecule where the first element is positioned somewhere that is 5' to the second element. For example, a SNP is upstream of a Cas9-induced nick site if the SNP is on the 5' side of the nick site. Conversely, a first element is downstream of a second element in a nucleic acid molecule where the first element is positioned somewhere that is 3' to the second element. For example, a SNP is downstream of a Cas9-induced nick site if the SNP is on the 3' side of the nick site. The nucleic acid molecule can be a DNA (double or single stranded). RNA (double or single stranded), or a hybrid of DNA and RNA. The analysis is the same for single strand nucleic acid molecule and a double strand molecule since the terms upstream and downstream are in reference to only a single strand of a nucleic acid molecule, except that one needs to select which strand of the double stranded molecule is being considered. Often, the strand of a double stranded DNA which can be used to determine the positional relativity of at least two elements is the "sense" or "coding" strand. In genetics, a "sense" strand is the segment within double-stranded DNA that runs from 5' to 3', and which is complementary to the antisense strand of DNA, or template strand, which runs from 3' to 5'. Thus, as an example, a SNP nucleobase is "downstream" of a promoter sequence in a genomic DNA (which is double-stranded) if the SNP nucleobase is on the 3' side of the promoter on the sense or coding strand.

Variant

As used herein the term "variant" should be taken to mean the exhibition of qualities that have a pattern that deviates from what occurs in nature, e.g., a variant Cas9 is a Cas9 comprising one or more changes in amino acid residues as compared to a wild type Cas9 amino acid sequence. The term "variant" encompasses homologous proteins having at least 75%, or at least 80%, or at least 85%, or at least 90%, or at least 95%, or at least 99% percent identity with a reference sequence and having the same or substantially the same functional activity or activities as the reference sequence. The term also encompasses mutants, truncations, or domains of a reference sequence, and which display the same or substantially the same functional activity or activities as the reference sequence.

Vector

The term "vector," as used herein, refers to a nucleic acid that can be modified to encode a gene of interest and that is able to enter into a host cell, mutate and replicate within the host cell, and then transfer a replicated form of the vector into another host cell. Exemplary suitable vectors include viral vectors, such as retroviral vectors or bacteriophages and filamentous phage, and conjugative plasmids. Additional suitable vectors will be apparent to those of skill in the art based on the instant disclosure.

Wild Type

As used herein the term "wild type" is a term of the art understood by skilled persons and means the typical form of an organism, strain, gene or characteristic as it occurs in nature as distinguished from mutant or variant forms.

5' Endogenous DNA Flap

As used herein, the term "5' endogenous DNA flap" refers to the strand of DNA situated immediately downstream of the PE-induced nick site in the target DNA. The nicking of the target DNA strand by PE exposes a 3' hydroxyl group on the upstream side of the nick site and a 5' hydroxyl group on the downstream side of the nick site. The endogenous strand ending in the 3' hydroxyl group is used to prime the DNA polymerase of the prime editor (e.g., wherein the DNA polymerase is a reverse transcriptase). The endogenous strand on the downstream side of the nick site and which begins with the exposed 5' hydroxyl group is referred to as the "5' endogenous DNA flap" and is ultimately removed and replaced by the newly synthesized replacement strand (i.e., "3' replacement DNA flap") the encoded by the extension of the pegRNA.

5' Endogenous DNA Flap Removal

As used herein, the term "5' endogenous DNA flap removal" or "5' flap removal" refers to the removal of the 5' endogenous DNA flap that forms when the RT-synthesized single-strand DNA flap competitively invades and hybridizes to the endogenous DNA, displacing the endogenous strand in the process. Removing this endogenous displaced strand can drive the reaction towards the formation of the desired product comprising the desired nucleotide change. The cell's own DNA repair enzymes may catalyze the removal or excision of the 5' endogenous flap (e.g., a flap endonuclease, such as EXO1 or FEN1). Also, host cells may be transformed to express one or more enzymes that catalyze the removal of said 5' endogenous flaps, thereby driving the process toward product formation (e.g., a flap endonuclease). Flap endonucleases are known in the art and can be found described in Patel et al., "Flap endonucleases pass 5'-flaps through a flexible arch using a disorder-thread-order mechanism to confer specificity for free 5'-ends," *Nucleic Acids Research,* 2012, 40(10): 4507-4519 and Tsutakawa et al., "Human flap endonuclease structures, DNA double-base flipping, and a unified understanding of the FEN1 superfamily," *Cell,* 2011, 145(2): 198-211 (each of which are incorporated herein by reference).

3' Replacement DNA Flap

As used herein, the term "3' replacement DNA flap" or simply, "replacement DNA flap," refers to the strand of DNA that is synthesized by the prime editor and which is encoded by the extension arm of the prime editor pegRNA. More in particular, the 3' replacement DNA flap is encoded by the polymerase template of the pegRNA. The 3' replacement DNA flap comprises the same sequence as the 5' endogenous DNA flap except that it also contains the edited sequence (e.g., single nucleotide change). The 3' replacement DNA flap anneals to the target DNA, displacing or replacing the 5' endogenous DNA flap (which can be excised, for example, by a 5' flap endonuclease, such as FEN1 or EXO1) and then is ligated to join the 3' end of the 3' replacement DNA flap to the exposed 5' hydroxyl end of endogenous DNA (exposed after excision of the 5' endogenous DNA flap, thereby reforming a phosphodiester bond and installing the 3' replacement DNA flap to form a heteroduplex DNA containing one edited strand and one unedited strand. DNA repair processes resolve the heteroduplex by copying the information in the edited strand to the complementary strand permanently installs the edit in to the DNA. This resolution process can be driven further to completion by nicking the unedited strand, i.e., by way of "second-strand nicking," as described herein.

DETAILED DESCRIPTION OF CERTAIN EMBODIMENTS

The disclosure relates to a fusion protein comprising a nucleic acid-programmable RNA binding protein (napRNAbp) and an RNA-dependent RNA polymerase (RDRP). In some embodiments, the fusion protein when complexed to an RNA prime editing guide RNA (RpegRNA) is capable of appending a single-strand RNA sequence to a target RNA (e.g., to the 3' end of the target RNA, or to the 3' end of the RNA generated after cutting the RNA at a cut site). In some embodiments, the single-stand RNA sequence is appended to the 3' terminus of the target RNA or to a 3' terminus which is formed upon cleavage of the target RNA by the fusion protein at a cut site. In some embodiments, the single-strand RNA sequence is polymerized by the RDRP using the RpegRNA as a template.

The present disclosure provides a novel approach to editing RNA molecules. In certain aspects, the disclosure provides RNA-editing fusion proteins that combine (a) a programmable RNA-binding protein (napRNAbp), such as Cas13, and (b) an RNA-dependent RNA polymerase (RDRP). In still other aspects, the disclosure provides complexes comprising (a) napRNAbp-RDRP fusion proteins, and (b) an RNA prime editing guide RNA ("RpegRNA") that comprise an extension arm containing a desired edit template to be integrated into a target RNA molecule. The RpegRNA associates with the napRNAbp:RDRP fusion protein (through its interaction with the napRNAbp component) and directs the enzyme to bind to an RNA molecule having complementarity with the RpegRNA. The RpegRNA comprises an extension arm on the 3' end of the RpegRNA that comprises a prime sequence that binds to the 3' end of a target RNA to create an RNA/RNA hybrid that provides the substrate for RDRP to polymerize a new RNA sequence at the 3' of the RNA molecule, templated by the extension arm of the RpegRNA.

The present invention relates in part to the discovery that the mechanism of target-primed reverse transcription (TPRT) or "prime editing" can be leveraged or adapted for conducting precision CRISPR/Cas-based nucleic acid editing of RNA with high efficiency and genetic flexibility, as depicted in various embodiments of FIGS. 1-4.

As shown herein, the inventors have used Cas protein: RNA-dependent RNA Polymerase (RDRP) fusion proteins to target a specific RNA sequence with a specialized guide RNA, i.e., a RpegRNA.

RNA Prime Editor Embodiments

The present disclosure provides compositions and methods for the targeted modification of RNA molecules by RNA prime editing. The compositions and methods may be conducted in vitro or in vivo within cells (e.g., human cells) for the therapeutic correction of disease-causing mutations and/or installation of motifs or mutations in RNA molecules of interest as a tool for scientific research. The disclosure provides compositions and methods for conducting RNA prime editing of a target RNA molecule (e.g., an RNA transcript) that enables the incorporation of one or more nucleotide changes and/or targeted mutagenesis of a target RNA molecule. The nucleotide changes can include a single-nucleotide change, an insertion of one or more nucleotides, or a deletion of one or more nucleotides. More in particular, the disclosure provides a variety of configurations of the RNA prime editors each comprising a nucleic acid programmable RNA binding proteins (napRNAbp), such as Cas13, and an RNA-dependent RNA polymerase (RDRP), which are provided as fusion proteins or which can be separately provided in trans. The RNA prime editors are guided to a target RNA site by a guide RNA, which can be a rpegRNA that includes a template region for the synthesis of an RNA sequence to be installed on the RNA molecule attached to an available 3' terminus. In others embodiments, the RNA template can be provided in trans. This application throughout describes a variety of amino acid and nucleotide sequences relating to various aspects of the present disclosure, including exemplary Cas13 sequences, RDRP sequences, fusion protein sequences, RpegRNAs, and other sequences.

napRNAbp (e.g., Cas13)

The RPE RNA editing system described herein comprises a nucleic acid programmable RNA binding protein (napRNAbp) domain. The napRNAbp is associated with at least one nucleic acid (e.g., an RPE guide RNA), which localizes the napRNAbp to an RNA sequence that comprises an RNA strand (i.e., a target strand) that is complementary to the guide nucleic acid, or a portion thereof (e.g. the protospacer of a guide RNA). In other words, the guide nucleic acid "programs" the napRNAbp domain to localize and bind to a complementary sequence of the target strand. Binding of the napRNAbp domain to a complementary sequence enables the RNA-dependent RNA polymerase domain of the RPE to access and enzymatically edit the target strand.

The below description of napRNAbps which can be used in connection with the disclosed nucleobase modification domains is not meant to be limiting in any way. The napRNAbp can be a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). Type VI CRISPR systems utilize a Cas13 protein. In some embodiments, the RPE RNA editing system described herein comprises Cas13, or any variant or equivalent that may be used in place of Cas13 in the RPE editing system. This includes any naturally occurring variant, mutant, or otherwise engineered version of Cas13 that is known or that can be made or evolved through a directed evolution or otherwise mutagenic process. In some embodiments, the napRNAbp has an inactive nuclease, e.g., are "dead" proteins.

As used herein, the term "Cas protein" refers to a full-length Cas protein obtained from nature, a recombinant Cas protein having a sequences that differs from a naturally occurring Cas protein, or any fragment of a Cas protein that nevertheless retains all or a significant amount of the requisite basic functions needed for the disclosed methods, i.e., possession of nucleic-acid programmable binding of the Cas protein to a target RNA. The Cas proteins contemplated herein embrace CRISPR Cas13 proteins, as well as Cas13 equivalents, variants (e.g., nuclease inactive Cas13 (dCas13)) homologs, orthologs, or paralogs, whether naturally occurring or non-naturally occurring (e.g., engineered or recombinant).

The term "Cas13" or "Cas13 domain" embraces any naturally occurring Cas13 from any organism, any naturally-occurring Cas13 equivalent or functional fragment thereof, any Cas13 homolog, ortholog, or paralog from any organism, and any mutant or variant of a Cas13, naturally-occurring or engineered. The term Cas13 is not meant to be particularly limiting and may be referred to as a "Cas13 or equivalent." Exemplary Cas13 proteins are further described herein and/or are described in the art and are incorporated herein by reference. The present disclosure is unlimited with regard to the particular napRNAbp that is employed in the RNA prime editors of the disclosure.

An exemplary Cas13 sequence is provided as follows; however, these specific examples are not meant to be limiting. The RNA prime editors of the present disclosure may use any suitable napRNAbp, including any suitable Cas13 or Cas13 equivalent:

| SEQ ID NO: | SEQUENCE | DESCRIPTION |
|---|---|---|
| 1 | MKLTRRRISGNSVDQKITAAFYRDMSQGLLYYDSEDNDCTDKVIESMDFER<br>SWRGRILKNGEDDKNPFYMFVKGLVGSNDKIVCEPIDVDSDPDNLDILINK<br>NLTGFGRNLKAPDSNDTLENLIRKIQAGIPEEEVLPELKKIKEMIQKDIVN<br>RKEQLLKSIKNNRIPFSLEGSKLVPSTKKMKWLFKLIDVPNKTENEKMLEK<br>YWEIYDYDKLKANITNRLDKTDKKARSISRAVSEELREYHKNLRTNYNRFV<br>SGDRPAAGLDNGGSAKYNPDKEEFLLFLKEVEQYFKKYFPVKSKHSNKSKD<br>KSLVDKYKNYCSYKVVKKEVNRSIINQLVAGLIQQGKLLYYFYYNDTWQED<br>FLNSYGLSYIQVEEAFKKSVMTSLSWGINRLISFFIDDSNTVKEDDITTKK<br>AKEAIESNYFNKLRTCSRMQDHFKEKLAFFYPVYVKDKKDRPDDDIENLIV<br>LVKNAIESVSYLRNRTFHFKESSLLELLKELDDKNSGQNKIDYSVAAEFIK<br>RDIENLYDVFREQIRSLGIAEYYKADMISDCFKTCGLEFALYSPKNSLMPA<br>FKNVYKRGANLNKAYIRDKGPKETGDQGQNSYKALEEYRELIWYIEVKNND<br>QSYNAYKNLLQLIYYHAFLPEVRENEALITDFINRTKEWNRKETEERLNTK<br>NNKKHKNFDENDDITVNTYRYESIPDYQGESLDDYLKVLQRKQMARAKEVN<br>EKEEGNNNYIQFIRDVVVWAFGAYLENKLKNYKNELQPPLSKENIGLNDTL<br>KELFPEEKVKSPFNIKCRFSISTFIDNKGKSTDNTSAEAVKTDGKEDEKDK<br>KNIKRKDLLCFYLFLRLLDENEICKLQHQFIKYRCSLKERRFPGNRTKLEK<br>ETELLAELEELMELVRFTMPSIPEISAKAESGYDTMIKKYFKDFIEKKVFK<br>NPKISNLYYHSDSKTPVTRKYMALLMRSAPLHLYKDIFKGYYLITKKECLE<br>YIKLSNIIKDYQNSLNELHEQLERIKLKSEKQNGKDSLYLDKKDFYKVKEY<br>VENLEQVARYKHLQHKINFESLYRIFRIHVDIAARMVGYTQDWERDMHFLE<br>KALVYNGVLEERRFEAIFNNNDDNNDGRIVKKIQNNLNNKNRELVSMLCWN<br>KKLNKNEFGAIIWKRNPIAHLNHFTQTEQNSKSSLESLINSLRILLAYDRK<br>RQNAVTKTINDLLLNDYHIRIKWEGRVDEGQIYFNIKEKEDIENEPIIHLK<br>HLHKKDCYIYKNSYMEDKQKEWICNGIKEEVYDKSILKCIGNLFKFDYEDK<br>NKSSANPKHT | CAS13A<br>CRISPR-<br>ASSOCIATED<br>ENDORIBONUCLEASE<br>CAS13A<br>[HERBINIX<br>HEMICELLULOS-<br>ILYTICA].<br>WP_103203632 |
| 34 | MAKILIAGLG KGIKKDGKYR ETNYSIEKID KENIIYKNES<br>FITSALEKHF EIDKTIYIGT VGSMWDNLYS YYCNKYNLKE<br>DEDYTFELLE ASSNATQDSE FSEINIKKFN DIFEGKARII<br>LTKFGMNTNE IFENENLIME IGNMLNDGDE IYLDITHSFR<br>SNAMWMFLVI NYITNVLDKN VEVKMISYGM FEAKYKKEVI<br>ENGETKEIEI SPVVNLKAFF DLMKWIKGAN ELKNYGNSYT<br>ILEMIDDKDV NKKIRTFSDS LNLNYLGTIK RNLESIKRIM<br>DKIDSIEGPG KLIIPNIVKD FIEIFGNIEK EYEFLFKIAE<br>WNFNQKRYAM VAININEGLR EFVAGILEIE DRVSDFNDEN<br>SGIFKYFKKI RQSIEYKPNN TKGTFDKKEE KIYKIFEHTR | CAS13 FROM<br>*LEPTOTRICHIA*<br>*TREVIASANII*<br>ACCESSION NO.<br>BBM57444 |

-continued

| SEQ ID NO: | SEQUENCE | DESCRIPTION |
|---|---|---|
| | KIRNEIAHSK GEKDTAINDV ESLKNYVKDI DTIISDKGFI KYLKLKYNV | |
| 35 | 1 MKLTRRRISG NSVDQKITAA FYRDMSQGLL YYDSEDNDCT DKVIESMDFE RSWRGRILKN | CAS13A OF *HERBINIX HEMICELLULO-SILYTICA* ACCESSION NO. WP_103203632 |
| | 61 GEDDKNPFYM FVKGLVGSND KIVCEPIDVD SDPDNLDILI NKNLTGFGRN LKAPDSNDTL | |
| | 121 ENLIRKIQAG IPEEEVLPEL KKIKEMIQKD IVNRKEQLLK SIKNNRIPFS LEGSKLVPST | |
| | 181 KKMKWLFKLI DVPNKTFNEK MLEKYWEIYD YDKLKANITN RLDKTDKKAR SISRAVSEEL | |
| | 241 REYHKNLRTN YNRFVSGDRP AAGLDNGGSA KYNPDKEEFL LFLKEVEQYF KKYFPVKSKH | |
| | 301 SNKSKDKSLV DKYKNYCSYK VVKKEVNRSI INQLVAGLIQ QGKLLYYFYY NDTWQEDFLN | |
| | 361 SYGLSYIQVE EAFKKSVMTS LSWGINRLTS FFIDDSNTVK FDDITTKKAK EAIESNYFNK | |
| | 421 LRTCSRMQDH FKEKLAFFYP VYVKDKKDRP DDDIENLIVL VKNAIESVSY LRNRTFHFKE | |
| | 481 SSLLELLKEL DDKNSGQNKI DYSVAAEFIK RDIENLYDVF REQIRSLGIA EYYKADMISD | |
| | 541 CFKTCGLEFA LYSPKNSLMP AFKNVYKRGA NLNKAYIRDK GPKETGDQGQ NSYKALEEYR | |
| | 601 ELTWYIEVKN NDQSYNAYKN LLQLIYYHAF LPEVRENEAL ITDFINRTKE WNRKETEERL | |
| | 661 NTKNNKKHKN FDENDDITVN TYRYESIPDY QGESLDDYLK VLQRKQMARA KEVNEKEEGN | |
| | 721 NNYIQFIRDV VVWAFGAYLE NKLKNYKNEL QPPLSKENIG LNDTLKELFP EEKVKSPFNI | |
| | 781 KCRFSISTFI DNKGKSTDNT SAEAVKTDGK EDEKDKKNIK RKDLLCFYLF LRLLDENEIC | |
| | 841 KLQHQFIKYR CSLKERRFPG NRTKLEKETE LLAELEELME LVRFTMPSIP EISAKAESGY | |
| | 901 DTMIKKYFKD FIEKKVFKNP KTSNLYYHSD SKTPVTRKYM ALLMRSAPLH LYKDIFKGYY | |
| | 961 LITKKECLEY IKLSNIIKDY QNSLNELHEQ LERIKLKSEK QNGKDSLYLD KKDFYKVKEY | |
| | 1021 VENLEQVARY KHLQHKINFE SLYRIFRIHV DIAARMVGYT QDWERDMHFL FKALVYNGVL | |
| | 1081 EERRFEAIFN NNDDNNDGRI VKKIQNNLNN KNRELVSMLC WNKKLNKNEF GAIIWKRNPI | |
| | 1141 AHLNHFTQTE QNSKSSLESL INSLRILLAY DRKRQNAVTK TINDLLLNDY HIRIKWEGRV | |
| | 1201 DEGQIYFNIK EKEDIENEPI IHLKHLHKKD CYIYKNSYMF DKQKEWICNG IKEEVYDKSI | |
| | 1261 LKCIGNLFKF DYEDKNKSSA NPKHT | |
| 36 | 1 MKITKIDGVS HYKKQDKGIL KKKWKDLDER KQREKIEARY NKQIESKIYK EFFRLKNKKR | CAS13A OF *LEPTOTRICHIA WADEI* ACCESSION NO. WP_036059678 |
| | 61 IEKEEDQNIK SLYFFIKELY LNEKNEEWEL KNINLEILDD KERVIKGYKF KEDVYFFKEG | |
| | 121 YKEYYLRILF NNLIEKVQNE NREKVRKNKE FLDLKEIFKK YKNRKIDLLL KSINNNKINL | |
| | 181 EYKKENVNEE IYGINPTNDR EMTFYELLKE IIEKKDEQKS ILEEKLDNED ITNFLENIEK | |
| | 241 IFNEETEINI IKGKVLNELR EYIKEKEENN SDNKLKQIYN LELKKYIENN FSYKKQKSKS | |
| | 301 KNGKNDYLYL NFLKKIMFIE EVDEKKEINK EKFKNKINSN FKNLFVQHIL DYGKLLYYKE | |
| | 361 NDEYIKNTGQ LETKDLEYIK TKETLIRKMA VLVSFAANSY YNLFGRVSGD ILGTEVVKSS | |
| | 421 KTNVIKVGSH IFKEKMLNYF FDFEIFDANK IVEILESISY SIYNVRNGVG HENKLILGKY | |
| | 481 KKKDININKR IEEDLNNNEE IKGYFIKKRG EIERKVKEKF LSNNLQYYYS KEKIENYFEV | |
| | 541 YEFEILKRKI PFAPNFKRII KKGEDLENNK NNKKYEYFKN FDKNSAEEKK EFLKTRNELL | |
| | 601 KELYYNNFYK EFLSKKEEFE KIVLEVKEEK KSRGNINNKK SGVSFQSIDD YDTKINISDY | |
| | 661 IASIHKKEME RVEKYNEEKQ KDTAKYIRDE VEEIFLTGFI NYLEKDKRLH FLKEEFSILC | |
| | 721 NNNNNVVDEN ININEEKIKE FLKENDSKTL NLYLFENMID SKRISEFRNE LVKYKQFTKK | |
| | 781 RLDEEKEFLG IKIELYETLI EFVILTREKL DTKKSEEIDA WLVDKLYVKD SNEYKEYEEI | |

-continued

| SEQ ID NO: | SEQUENCE | | DESCRIPTION |
|---|---|---|---|
| | 841 | LKLFVDEKIL SSKEAPYYAT DNKTPILLSN FEKTRKYGTQ SFLSEIQSNY KYSKVEKENI | |
| | 901 | EDYNKKEEIE QKKKSNIEKL QDLKVELHKK WEQNKITEKE IEKYNNTTRK INEYNYLKNK | |
| | 961 | EELQNVYLLH EMLSDLLARN VAFFNKWERD FKFIVIAIKQ FLRENDKEKV NEFLNPPDNS | |
| | 1021 | KGKKVYFSVS KYKNIVENID GIHKNEMNLI FLNNKFMNRK IDKMNCAIWV YFRNYIAHFL | |
| | 1081 | HLHTKNEKIS LISQMNLLIK LFSYDKKVQN HILKSTKILL EKYNIQINFE ISNDKNEVEK | |
| | 1141 | YKIKNRLYSK KGKMLGKNNK FEILENEFLE NVKAMLEYSE | |
| 37 | 1 | MRVSKVKVKD GGKDKMVLVH RKTTGAQLVY SGQPVSNETS NILPEKKRQS FDLSTINKTI | CAS13A OF *PALUDIBACTER PROPIONICIGENES* ACCESSION NO. WP_013443710 |
| | 61 | IKFDTAKKQK LNVDQYKIVE KIFKYPKQEL PKQIKAEEIL PFLNHKFQEP VKYWKNGKEE | |
| | 121 | SENLTLLIVE AVQAQDKRKL QPYYDWKTWY IQTKSDLLKK SIENNRIDLT ENLSKRKKAL | |
| | 181 | LAWETEFTAS GSIDLTHYHK VYMTDVLCKM LQDVKPLTDD KGKINTNAYH RGLKKALQNH | |
| | 241 | QPAIFGTREV PNEANRADNQ LSIYHLEVVK YLEHYFPIKT SKRRNTADDI AHYLKAQTLK | |
| | 301 | TTIEKQLVNA IRANIIQQGK TNHHELKADT TSNDLIRIKT NEAFVLNLTG TCAFAANNIR | |
| | 361 | NMVDNEQTND ILGKGDFIKS LLKDNTNSQL YSFFFGEGLS TNKAEKETQL WGIRGAVQQI | |
| | 421 | RNNVNHYKKD ALKTVFNISN FENPTITDPK QQTNYADTIY KARFINELEK IPEAFAQQLK | |
| | 481 | TGGAVSYYTI ENLKSLLTTF QFSLCRSTIP FAPGFKKVEN GGINYQNAKQ DESFYELMLE | |
| | 541 | QYLRKENFAE ESYNARYFML KLIYNNLFLP GFTTDRKAFA DSVGFVQMQN KKQAEKVNPR | |
| | 601 | KKEAYAFEAV RPMTAADSIA DYMAYVQSEL MQEQNKKEEK VAEETRINFE KFVLQVFIKG | |
| | 661 | FDSFLRAKEF DFVQMPQPQL TATASNQQKA DKLNQLEASI TADCKLTPQY AKADDATHIA | |
| | 721 | FYVFCKLLDA AHLSNLRNEL IKFRESVNEF KFHHLLEIIE ICLLSADVVP TDYRDLYSSE | |
| | 781 | ADCLARLRPF IEQGADITNW SDLFVQSDKH SPVIHANIEL SVKYGTTKLL EQIINKDTQF | |
| | 841 | KITEANFTAW NTAQKSIEQL IKQREDHHEQ WVKAKNADDK EKQERKREKS NFAQKFIEKH | |
| | 901 | GDDYLDICDY INTYNWLDNK MHFVHLNRLH GLTIELLGRM AGFVALFDRD FQFFDEQQIA | |
| | 961 | DEFKLHGFVN LHSIDKKLNE VPTKKIKEIY DIRNKIIQIN GNKINESVRA NLIQFISSKR | |
| | 1021 | NYYNNAFLHV SNDEIKEKQM YDIRNHIAHF NYLTKDAADF SLIDLINELR ELLHYDRKLK | |
| | 1081 | NAVSKAFIDL FDKHGMILKL KLNADHKLKV ESLEPKKIYH LGSSAKDKPE YQYCTNQVMM | |
| | 1141 | AYCNMCRSLL EMKK | |
| 38 | 1 | MWISIKTLIH HLGVLFFCDY MYNRREKKII EVKTMRITKV EVDRKKVLIS RDKNGGKLVY | CAS13A OF *LISTERIA SEELIGERI* ACCESSION NO: WP_01298577 |
| | 61 | ENEMQDNTEQ IMHHKKSSFY KSVVNKTICR PEQKQMKKLV HGLLQENSQE KIKVSDVTKL | |
| | 121 | NISNFLNHRF KKSLYYFPEN SPDKSEEYRI EINLSQLLED SLKKQQGTFI CWESFSKDME | |
| | 181 | LYINWAENYI SSKTKLIKKS IRNNRIQSTE SRSGQLMDRY MKDILNKNKP FDIQSVSEKY | |
| | 241 | QLEKLTSALK ATFKEAKKND KEINYKLKST LQNHERQIIE ELKENSELNQ FNIEIRKHLE | |
| | 301 | TYFPIKKINR KVGDIRNLEI GEIQKIVNHR LKNKIVQRIL QEGKLASYEI ESTVNSNSLQ | |
| | 361 | KIKIEEAFAL KFINACLFAS NNLRNMVYPV CKKDILMIGE FKNSFKEIKH KKFIRQWSQF | |
| | 421 | FSQEITVDDI ELASWGLRGA IAPIRNEIIH LKKHSWKKFF NNPTFKVKKS KIINGKTKDV | |
| | 481 | TSEFLYKETL FKDYFYSELD SVPELIINKM ESSKILDYYS SDQLNQVFTI PNFELSLLTS | |
| | 541 | AVPFAPSFKR VYLKGEDYQN QDEAQPDYNL KLNIYNEKAF NSEAFQAQYS LFKMVYYQVE | |
| | 601 | LPQFTINNDL FKSSVDFILT LNKERKGYAK AFQDIRKMNK DEKPSEYMSY IQSQLMLYQK | |

-continued

| SEQ ID NO: | | SEQUENCE | DESCRIPTION |
|---|---|---|---|
| | 661 | KQEEKEKINH FEKFINQVFI KGENSFIEKN RLTYICHPTK NTVPENDNIE IPFHTDMDDS | |
| | 721 | NIAFWLMCKL LDAKQLSELR NEMIKFSCSL QSTEEISTFT KAREVIGLAL LNGEKGCNDW | |
| | 781 | KELFDDKEAW KKNMSLYVSE ELLQSLPYTQ EDGQTPVINR SIDLVKKYGT ETILEKLESS | |
| | 841 | SDDYKVSAKD IAKLHEYDVT EKIAQQESLH KQWIEKPGLA RDSAWTKKYQ NVINDISNYQ | |
| | 901 | WAKTKVELTQ VRHLHQLTID LLSRLAGYMS IADRDFQFSS NYILERENSE YRVTSWILLS | |
| | 961 | ENKNKNKYND YELYNLKNAS IKVSSKNDPQ LKVDLKQLRL TLEYLELFDN RLKEKRNNIS | |
| | 1021 | HFNYLNGQLG NSILELEDDA RDVLSYDRKL KNAVSKSLKE ILSSHGMEVT FKPLYQTNHH | |
| | 1081 | LKIDKLQPKK IHHLGEKSTV SSNQVSNEYC QLVRTLLTMK | |
| 39 | 1 | XENKISLGNN IYYNPFKPQD KSYFAGYFNA AXENTDSVFR ELGKRLKGKE YTSENFFDAI | CAS13B (R1177A) MUTANT OF *BEGEYELLA ZOOHELCUM* ACCESSION NO. 6AAY_A |
| | 61 | FKENISLVEY ERYVKLLSDY FPXARLLDKK EVPIKERKEN FKKNFKGIIK AVRDLRNFYT | |
| | 121 | HKEHGEVEIT DEIFGVLDEX LKSTVLTVKK KKVKTDKTKE ILKKSIEKQL DILCQKKLEY | |
| | 181 | LRDTARKIEE KRRNQRERGE KELVAPFKYS DKRDDLIAAI YNDAFDVYID KKKDSLKESS | |
| | 241 | KAKYNTKSDP QQEEGDLKIP ISKNGVVFLL SLFLTKQEIH AFKSKIAGFK ATVIDEATVS | |
| | 301 | EATVSHGKNS ICFXATHEIF SHLAYKKLKR KVRTAEINYG EAENAEQLSV YAKETLXXQX | |
| | 361 | LDELSKVPDV VYQNLSEDVQ KTFIEDWNEY LKENNGDVGT XEEEQVIHPV IRKRYEDKFN | |
| | 421 | YFAIRFLDEF AQFPTLRFQV HLGNYLHDSR PKENLISDRR IKEKITVFGR LSELEHKKAL | |
| | 481 | FIKNTETNED REHYWEIFPN PNYDFPKENI SVNDKDFPIA GSILDREKQP VAGKIGIKVK | |
| | 541 | LLNQQYVSEV DKAVKAHQLK QRKASKPSIQ NIIEEIVPIN ESNPKEAIVF GGQPTAYLSX | |
| | 601 | NDIHSILYEF FDKWEKKKEK LEKKGEKELR KEIGKELEKK IVGKIQAQIQ QIIDKDTNAK | |
| | 661 | ILKPYQDGNS TAIDKEKLIK DLKQEQNILQ KLKDEQTVRE KEYNDFIAYQ DKNREINKVR | |
| | 721 | DRNHKQYLKD NLKRKYPEAP ARKEVLYYRE KGKVAVWLAN DIKRFXPTDF KNEWKGEQHS | |
| | 781 | LLQKSLAYYE QCKEELKNLL PEKVFQHLPF KLGGYFQQKY LYQFYTCYLD KRLEYISGLV | |
| | 841 | QQAENFKSEN KVFKKVENEC FKFLKKQNYT HKELDARVQS ILGYPIFLER GFXDEKPTII | |
| | 901 | KGKTFKGNEA LFADWFRYYK EYQNFQTFYD TENYPLVELE KKQADRKRKT KIYQQKKNDV | |
| | 961 | FTLLXAKHIF KSVFKQDSID QFSLEDLYQS REERLGNQER ARQTGERNTN YIWNKTVDLK | |
| | 1021 | LCDGKITVEN VKLKNVGDFI KYEYDQRVQA FLKYEENIEW QAFLIKESKE EENYPYVVER | |
| | 1081 | EIEQYEKVRR EELLKEVHLI EEYILEKVKD KEILKKGDNQ NFKYYILNGL LKQLKNEDVE | |
| | 1141 | SYKVENLNTE PEDVNINQLK QEATDLEQKA FVLTYIANKF AHNQLPKKEF WDYCQEKYGK | |
| | 1201 | IEKEKTYAEY FAEVFKKEKE ALIKLEHHHH HH | |
| 40 | 1 | MAKKNKMKPR ELREAQKKAR QLKAAEINNN AAPAIAAMPA AEVIAPVAEK KKSSVKAAGM | CAS13D, CHAIN A ACCESSION NO. CIV9_A |
| | 61 | KSILVSENKM YITSFGKGNS AVLEYEVDNN DYNKTQLSSK DNSNIELGDV NEVNITFSSK | |
| | 121 | HGFGSGVEIN TSNPTHRSGE SSPVRGDMLG LKSELEKRFF GKTFDDNIHI QLIYNILDIE | |
| | 181 | KILAVYVINI VYALNNMLGI KDSESYDDEM GYLSARNTYE VFTHPDKSNL SDKVKGNIKK | |
| | 241 | SLSKFNDLLK TKRLGYFGLE EPKTKDTRAS EAYKKRVYHM LAIVGQIAQC VFHDKSGAKR | |
| | 301 | FDLYSFINNI DPEYRDTLDY LVEERLKSIN KDFIEGNKVN ISLLIDMMKG YEADDIIRLY | |
| | 361 | YDFIVLKSQK NLGFSIKKLR EKMLEEYGER FKDKQYDSVR SKMYKLMDFL LFCNYYRNDV | |
| | 421 | AAGEALVRKL RFSMIDDEKE GIYADEAAKL WGKERNDFEN IADHMNGDVI KELGKADMDF | |

-continued

| SEQ ID NO: | | SEQUENCE | DESCRIPTION |
|---|---|---|---|
| | 481 | DEKILDSEKK NASDLLYFSK MIYMLTYFLD GKEINDLLTT LISKFDNIKE FLKIMKSSAV | |
| | 541 | DVECELTAGY KLFNDSQRIT NELFIVKNIA SMRKPAASAK LIMFRDALTI LGIDDNITDD | |
| | 601 | RISEILKLKE KGKGIHGLRN FITNNVIESS RFVYLIKYAN AQKIREVAKN EKVVMFVLGG | |
| | 661 | IPDTQIERYY KSCVEFPDMN SSLEAKRSEL ARMIKNISFD DFKNVKQQAK GRENVAKERA | |
| | 721 | KAVIGLYLTV MYLLVKNLVN VNARYVIAIH CLERDFGLYK EIIPELASKN LKNDYRILSQ | |
| | 781 | TLCELCDDRN ESSNLFLKKN KRLRKCVEVD INNADSSMTR KYANCIAHLT VVRELKEYIG | |
| | 841 | DIRTVDSYFS IYHYVMQRCI TKRGDDTKQE EKIKYEDDLL KNHGYTKDFV KALNSPFGYN | |
| | 901 | IPRFKNLSIE QLFDRNEYLT EKLEHHHHHH | |
| 41 | 1 | MGKKIHARDL REQRKTDRTE KFADQNKKRE AERAVPKKDA AVSVKSVSSV SSKKDNVTKS | ES CAS13D, CHAIN A, FROM |
| | 61 | MAKAAGVKSV FAVGNTVYMT SFGRGNDAVL EQKIVDTSHE PLNIDDPAYQ LNVVTMNGYS | *EUBACTERIUM SIRAEUM* DSM |
| | 121 | VTGHRGETVS AVTDNPLRRF NGRKKDEPEQ SVPTDMLCLK PTLEKKFFGK EFDDNIHIQL | 15702 ACCESSION NO. |
| | 181 | IYNILDIEKI LAVYSTNAIY ALNNMSADEN IENSDFFMKR TTDETFDDFE KKKESTNSRE | 6E9F_A |
| | 241 | KADFDAFEKF IGNYRLAYFA DAFYVNKKNP KGKAKNVLRE DKELYSVLTL IGKLAHWCVA | |
| | 301 | SEEGRAEFWL YKLDELKDDF KNVLDVVYNR PVEEINNRFI ENNKVNIQIL GSVYKNTDIA | |
| | 361 | ELVRSYYEFL ITKKYKNMGF SIKKLRESML EGKGYADKEY DSVRNKLYQM TDFILYTGYI | |
| | 421 | NEDSDRADDL VNTLRSSLKE DDKTTVYCKE ADYLWKKYRE SIREVADALD GDNIKKLSKS | |
| | 481 | NIEIQEDKLR KCFISYADSV SEFTKLIYLL TRFLSGKEIN DLVTTLINKF DNIRSFLEIM | |
| | 541 | DELGLDRIFT AEYSFFEGST KYLAELVELN SFVKSCSFDI NAKRTMYRDA LDILGIESDK | |
| | 601 | TEEDIEKMID NILQIDANGD KKLKKNNGLR NFIASNVIDS NRFKYLVRYG NPKKIRETAK | |
| | 661 | CKPAVRFVLN EIPDAQIERY YEACCPKNTA LCSANKRREK LADMIAEIKF ENFSDAGNYQ | |
| | 721 | KANVTSRISE AEIKRKNQAI IRLYLTVMYI MLKNLVNVNA RYVIAFHCVE RDTKLYAESG | |
| | 781 | LEVGNIEKNK TNLTMAVMGV KLENGIIKTE FDKSFAENAA NRYLRNARWY KLILDNLKKS | |
| | 841 | ERAVVNEFAN TVCALNAIRN ININIKEIKE VENYFALYHY LIQKHLENRF ADKKVERDTG | |
| | 901 | DFISKLEEHK TYCKDFVKAY CTPFGYNLVR YKNLTIDGLF DKNYPGKDDS DEQK | |

The present application contemplates any Cas13 homolog (e.g., Cas13a, Cas13b, Cas13c, or Cas13d), variant, or equivalent there of having an amino acid sequence that is at least 80%, or 85%, or 90%, or 95%, or 99% identical with SEQ ID NO: 1, or with any of the sequences of SEQ ID NOs: 34-41.

Other Cas13 sequences that may be used can include, but are not limited to: (a) Cas13a of *Leptotrichia wadei* (Ref Seq No. WP_03059678.1); (b) Cas13a of *Leptotrichia buccalis* (Ref Seq No. WP_015770004.1); (c) any Cas13b sequence known in the art, (d) any Cas13d sequence known in the art, and (e) any Pumby sequence known in the art, or any homology, variant, or equivalent there of having an amino acid sequence that is at least 80%, or 85%, or 90%, or 95%, or 99% identical with any of these alternate Cas13 sequences.

In some embodiments, the disclosed RNA prime editors may comprise a catalytically inactive, or "dead," napRNAbp domain. In certain embodiments, the base editors described herein may include a dead Cas13 that has no nuclease activity due to one or more mutations. The nuclease inactivation may be due to one or mutations that result in one or more substitutions and/or deletions in the amino acid sequence of the encoded protein, or any variants thereof having at least 80%, at least 85%, at least 90%, at least 95%, or at least 99% sequence identity thereto. As used herein, the term "dCas13" refers to a nuclease-inactive Cas13 or nuclease-dead Cas13, or a functional fragment thereof, and embraces any naturally occurring dCas13 from any organism, any naturally-occurring dCas13 equivalent or functional fragment thereof, any dCas13 homolog, ortholog, or paralog from any organism, and any mutant or variant of a dCas13, naturally-occurring or engineered. The term dCas13 is not meant to be particularly limiting and may be referred to as a "dCas13 or equivalent."

RNA-Dependent RNA Polymerase (RDRP)

As used herein, the term "polymerase" refers to an enzyme that synthesizes a nucleotide strand and which may be used in connection with the RNA prime editing system described herein. The polymerase may be a wild type polymerase, a functional fragment, a mutant, a variant, or a truncated variant, and the like. The polymerase may include wild type polymerases from eukaryotic, prokaryotic, archael, or viral organisms, and/or the polymerase may be modified by genetic engineering, mutagenesis, directed evolution-based processes. The polymerase can be a "template-dependent" polymerase (i.e., a polymerase which synthesizes a nucleotide strand based on the order of nucleotide bases of a template strand). The polymerase can also be a "template-independent" polymerase (i.e., a polymerase which synthesizes a nucleotide strand without the requirement of a template strand). A polymerase may also be further categorized as a "DNA polymerase" or an "RNA polymerase." In various embodiments, the RPE RNA editing system described herein comprises an RNA polymerase. In various embodiments, the RPE RNA editing system described herein comprises an RNA-dependent DNA polymerase (RDRP), or any variant or equivalent that may be used in place of the RDRP component in the RPE editing system. A list of exemplary RDRP sequences is provided as follows:

| SEQ ID NO: | SEQUENCE | DESCRIPTION |
|---|---|---|
| 2 | MHTDDKSCATRLLSLLGVRSVPRERFADVDKVGVWTVLNQRLILLSWHVGM<br>VIDSTFEHVNSDGHPSKCLEIMIQRSREFAYSAERSGLCGYYIHIFNFRDH<br>VSFAIKTAHLKKYTQTLLACDTTTPIHETVEAFSPPTGRAGGKVFVTPRLL<br>KSIGNPTILQCALATKLKENLHRLDWEQIMVTGMILLQYLNVGAGDVLWYL<br>ITYEKLWDSKFLDAVKILKDAHVETRIKHKLPNVSIHYARSTFARPWARSL<br>YGLDTLPGRSEKFNMNFQSEQLMRMIDTSKRAWPAIVEDKYGNNYIKFFPD<br>KYTEQVKQIARKTAEDLIQSQTNLETFTEFFSNRMFWGASGGAPGASVHWD<br>DTKEKLRVNKRGALLSLKEQKARNILEYMRSHPDPKPIQWSVKAVKYESGK<br>LRSILNTVLENYVIQGYIFNAVDTNSRRDSWYANTHDNPSRIANAMRRILD<br>LKQRPGLMWDYADFNLNHTFFLMSQEYLARVEVLLERCDSHLPMDVQNTIR<br>ADMRAATAYAILARYNTYLHDPETMITTQAVRSLQSGERGTSSINSDSNET<br>DTTIVRRVCKEMLGIDPIVPVTDHAGDDAFENVISMTYAPLVCSVYNLTGA<br>AGQAYKIAVSYATENGASGEFLRLSYDAASNHIAGYPIRGMMGFIHGEFFA<br>EALPQPFDRLASFLNQRNKLQRRGWVAPDSLFNAVCRYNTRLTYTLSDGTK<br>RHFYPDIETVLTPAAFGGVGVDTVDSQLLSQLSDKQIVTPLHANCPYDAIV<br>IPSGEGKTTLARKYPDIFVDHDSLVSSINLIALRSRAVSSGNWEPLNAYLR<br>GEGERYMSVNRGKILLTWSPSTAPSRSRICALLLQQPVGLRANIANRSSIM<br>NDMNKKYVHMFKNYSERDAYLMSITAGLTGLTYKVYQRTGDAIPKFNWPRV<br>DSKDLLHRSKTVIKDHATLHRHNLPMDVSITDAIAQSALSGAWPKDALYKS<br>IAEHARQLAEWARKSSFEYKIIAPLKLCSDTEFVAEAVSTSMYVLGLSGSL<br>NHSNAGGGLTFVLNDLLRPATKRLKHHYNYIPTLTRLCGCSVNASTQYLIK<br>CSNGDNLLEKILSLMASERSFSHSKQRATKQFDEVIEFIDRLGLLKQEPLL<br>AFGKVVSPSLAEAWFTGGLQLLPPAICHQSADLSTFVRDITLNVIETHFLA<br>RLNRTNDLQQIVVTVHHYERMAQYAINKVLNGLIPGIIMQD | RNA-DEPENDENT<br>RNA POLYMERASE<br>[*TRICHODERMA*<br>*ATROVIRIDE*<br>MYCOVIRUS]<br>REFSEQ<br>YP_009342055- |
| 3 | MVAITVQGAQLIKRVVERFYPGIAFNINEGACYIYKFSDHIRRIRMKHGTK<br>YRRQAEEIIRNIGLRKERLYGIPVLDEVEWKCVEDGQTFQSYAFEVYVNSI<br>LPWSELDPEEEFLRNYRVSREMTEVEKFIEFRAKNEMQIYGDIPIKVWCCF<br>INELSVELKHIPLGMQVMADFVNREDSPFHQGNRDLSNLEDFQVAYTTPLL<br>FEMCCMESILEFNIKMRMREEDISALEFGDMKVDPVGLLREFFILCLPHPK<br>KINNVLRAPYSWFVKMWGVGADPIVVLQSTAGDDRNSKDVFYDKERTEPNR<br>YKALFRSSFYNESRRMNEEKILEAVKYSQKLGSHDRRLPLFEKMLKTVYTT<br>PFYPHKSSNMILASFLLSIQTITGYGRAWVKNVSTEFDKQLKPNPSNLVQD<br>VSDLTREFFKQAYVEAKERREEIVKPEDLYTSMLRLARNTSSGESTEIYVK<br>KRFGPRVKDKDLIKINSRIKALVIFTKGHTVFTDEELHKKYNSVELYQTKG<br>SRDVPIKATRTIYSINLSVLVPQLIVTLPLNEYFSRVGGITSPDYKKIGGK<br>VIVGDLEATGSRVMDAADCFRNSADRDIFTIAIDYSEYDTHLTRHNFRTGM<br>LQGIREAMAPYRDLRYEGYTLEQIIDFGYGEGRVANTLWNGKRRLFKTTED<br>AYIRLDESERDKGSFKVPKGVLPVSSVDVANRIAVDKGFDTLVAATDGSDL<br>ALIDTHLSGENSTLIANSMHNMAIGTLIQREVGREQPGILTFLSEQYVGDD<br>TLFYTKLHTTDTKVEDKVAASIFDTVAKCGHEASPSKTMMTPYSVEKTQTH<br>AKQGCYVPQDRMMIISSERRKDIEDVQGYVRSQVQTMITKVSRGFCHDLAQ<br>LILMLKTTFIGAWKMKRTIKEDAMYRDRKFDSNDEDGETLIQIRNPLALYV<br>PIGWNGYGAHPAALNIVMTEEMYVDSIMISKLDEIMAPIRRIVHDIPPCWN<br>ETQGDKRGLISATKMSFFSKMARPAVQAALSDPQIMNLVEELPLGEFSPGR<br>ISRTMMHSALLKESSARTLLSSGYELEYQKALNSWIAQVSMRLGEESGVIS<br>TSYAKLFDVYFEGELDGAPYMEPDQNLSPQFYIQKMMIGPRVSSRVRNSYV<br>DRIDVILRKDVVMRGFITANTILNVIEKLGTNHSVGDLVTVFILMNIETRV<br>AEELAEYMTSEKIRFDALKLLKKGIAGDEFTMSLNVATQDFIDTYLAYPYQ<br>LTKTEVDAISLYCTQMVMLRAALGLPKKKMKIVVTDDAKKRYKIRLQRFRT<br>HVPKIKVLKKLIDPNRMTVRNLENQFV | RNA-DEPENDENT<br>RNA POLYMERASE<br>[BLUETONGUE<br>VIRUS].<br>ADI49523 |
| 4 | MEQNAFNGFEFVDYSEELENLNQNHIHKVRRESNTTYVDKFAERELIDLHP<br>EYHRQFIQGWSRSYYNTERHMEALLNYGTRNIPVDNVDYNLYQGCIDTVKN<br>GLRSLPRVKAFDVLTELNLVSYKSSTAAGYNYMGAKGPFDGYNHKQAIRRA<br>RATVGDVSDNGIEGLRRAITTAVPDVGYTRTQLTDLTEKTKIRNVWGRAFH<br>YILIEGTSADPLIRMFSKTKSFYHIGRDPLDSVPDVLSETAGKARWLYAID<br>WKQFDATVSRFEINAAFDIIMDLIEFPNYPTYVAFELSRQLFIHKKIAAPD<br>GYIYWSHKGIPSGSYFTSIIGSIINRLRIEYLWRKITGHGPLACYTQGDDS<br>LSCDDEFTPPEKFAEIANQIGWVLNPEKTEYSTIPSEVHFLGRTMLGGLNT<br>REIKRCLRLLIYPEYPVDSGRISAYRAKSISEDVGRLSELLNKIERRLQGQ<br>YGIASDEEVPDYFKRYVL | RNA-DEPENDENT<br>RNA POLYMERASE<br>[*PYRUS*<br>*PYRIFOLIA*].<br>BAA34783 |
| 5 | MSDVFNSPQARSTISAAFGIKPTAGQDVEELLIPKVWVPPEDPLASPSRLA<br>KFLRENGYKVLQPRSLPENEEYETDQILPDLAWMRQIEGAVLKPTLSLPIG<br>DQEYFPKYYPTHRPSKEKPNAYPPDIALLKQMIYLFLQVPEANEGLKDEVT | RNA-DEPENDENT<br>RNA POLYMERASE<br>[INFECTIOUS |

-continued

| SEQ ID NO: | SEQUENCE | DESCRIPTION |
|---|---|---|
| | LLTQNIRDKAYGSGTYMGQANRLVAMKEVATGRNPNKDPLKLGYTFESIAQ<br>LLDITLPVGPPGEDDKPWVPLTRVPSRMLVLTGDVDGDFEVEDYLPKINLK<br>SSSGLPYVGRTKGETIGEMIAISNQFLRELSTLLKQGAGTKGSNKKKLLSM<br>LSDYWYLSCGLLFPKAERYDKSTWLTKTRNIWSAPSPTHLMISMITWPVMS<br>NSPNNVLNIEGCPSLYKFNPERGGLNRIVEWILAPEEPKALVYADNIYIVH<br>SNTWYSIDLEKGEANCTRQHMQAAMYYILTRGWSDNGDPMENQTWATFAMN<br>IAPALVVDSSCLIMNLQIKTYGQGSGNAATFINNHLLSTLVLDQWNLMRQP<br>RPDSEEFKSIEDKLGINFKIERSIDDIRGKLRQLVLLAQPGYLSGGVEPEQ<br>SSPTVELDLLGWSATYSKDLGIYVPVLDKERLFCSAAYPKGVENKSLKSKV<br>GIEQAYKVVRYEALRLVGGWNYPLLNKACKNNAGAARRHLEAKGFPLDEFL<br>AEWSELSEFGEAFEGFNIKLTVTSESLAELNKPVPPKPPNVNRPVNTGGLK<br>AVSNALKTGRYRNEAGLSGLVLLATARSRLQDAVKAKAEAEKLHKSKPDDP<br>DADWFERSETLSDLLEKADIASKVAHSALVETSDALEAVQSTSVYTPKYPE<br>VKNPQTASNPVVGLHLPAKRATGVQAALLGAGTSRPMGMEAPTRSKNAVKM<br>AKRRQRQKESRQ | BURSAL DISEASE<br>VIRUS].<br>ABS18957 |
| 6 | GEIQWMRPSKEVGYPIINAPSKTKLEPSAFHYVFEGVKEPAVLTKNDPRLK<br>TDFEEAIFSKYVGNKITEVDEYMKEAVDHYAGQLMSLDINTEQMCLEDAMY<br>GTDGLEALDLSTSAGYPYVAMGKKKRDILNKQTRDTKEMQKLLDTYGINLP<br>LVTYVKDELRSKTKVEQGKSRLIEASSLNDSVAMRMAFGNLYAAFHKNPGV<br>ITGSAVGCDPDLFWSKIPVLMEEKLFAFDYTGYDASLSPAWFEALKMVLEK<br>IGFGDRVDYIDYLNHSHHLYKNKTYCVKGGMPSGCSGTSIFNSMINNLIIR<br>TLLLKTYKGIDLDHLKMIAYGDDVIASYPHEVDASLLAQSGKDYGLIMTPA<br>DKSATFETVTWENVTFLKRFFRADEKYPFLIHPVMPMKEIHESIRWTKDPR<br>NTQDHVRSLCLLAWHNGEEEYNKFLAKIRSVPIGRALLLPEYSTLYRRWLD<br>SE | POLIO VIRUS<br>RDRP |
| 7 | MHDYLSDLNVYVPYQRPNIVLHGSDFWLRTLDCHTEIPLAAIYFGNIQGGT<br>YFNHWQVSFSRENISSRDMLHKIHAEFEFDKTDMITVQFQCFEEKKQKFED<br>SRKQKVRVNYQLTIRRDSIRRIIVDPRVEGCNTCVHFEVNCPPLIRKGYID<br>NDKSSFHKPFYERQKRFDCDWRNGNVNHGNPQDAAIADSPFFTIEFHKEIS<br>TKEMYRVLSRLRSRTKVLIEFANLPSIDVPMGSHYPYNRWNLKKSPTDSNA<br>PIFREFLKEIFPPKYEIVDDKLIDVNEERKFSITYLIECLLSRGAIVKDQL<br>LLNEQHWKNFLEIIIWYYRNDNQLCEAALEDLVHLIDGRKRIGSILKCLDK<br>ICQKREVMKLVNGLTEKESIEGYQRVRKVIFTPTRVIYIAPETIMGNRVLR<br>KFDKDGTRVLRVTFRDDNNKKMRSNVTGKLLDRTANKYLEHGVRIANREYG<br>FLGCSNSQMRDNGAYFMMRFTDKQLDRFYKCNPTASNINFKPKIDEVRFQL<br>GRFSEIENVPKLMARLGQCFTQSRLTGVGLGRDDYCSTYDLIGGRATNGSE<br>YTFSDGVGMMSYQFAQEVSQAMQFGKAVPSCFQIRERGNKGVIAIEPFLDE<br>IRKWALVNGVTSMKMAKCLFRPSQIKFQAKAISGDQIEMVKESSAVLVALN<br>KPFINILDQVSEMQSLDCHKRITSRIEELMDRQILSFAKQMNEETFCRNKL<br>KEFPRRIDIDNLRTMWGFTLSSEPFERSLIKASIKESITKQLCKEQIQIPS<br>ELGRSMLGVVDETGRLQYGQIFVQYTKNYKKKLPPRDSNNKVHGSEIVTGT<br>VLLTKNPCIVPGDVRIFEAVDIPELHHMCDVVVFPQHGPRPHPDEMAGSDL<br>DGDEYSVIWDQELLLERNEEPFDFAVEKIKVPYDREKLDVLMREFYVTYLK<br>LDSVGQISNSHLHNSDQYGLNSRVCMDLAKKNCQAVDFTKSGQPPDPLETK<br>WRADPVTFEVIPPENPERIPDFHMGNERSPMYVSPRLCGKLFREFQAIDNV<br>IKISEERDEQYNIELDETIFVTGFERYMESAQKQLSSYNGQLRSIMENYGI<br>RSEGEIMSGCIVEMRNRISDKDQDDMSFYNTNQMIETKMTSLVCKFRETFF<br>EEFGGFTVKCTLLPNAYDNGNCLNYRCEDPDQEVRKKAVAWYRACYECAQS<br>TREVRKLSFAWIAYDVIAKVKETNVLNNERMQIGGANPMYTFLEEHRKQYL<br>IDHDADFKNFCELDHLITGEKSKEAISILKIYLEMIPGLDSVFFMLMRWGE<br>SLRLFDGKPIKIYHFFLMFILFATRQLASADGNAEPFFKIIEKEEYEKQKR<br>DSSRGNIDPLTEKKRSDMMVKFFQFMGCRKFRKMSTLSFCPLNFSSIFMRG<br>EWRIFHESALKTYYNILFNLRFEELPVSSDPTITAETMDRECEPFVIELPE<br>NINVNDLINNMKKHTNVSTVKMRRQEKNPINDKAKPKTTVRYIVSVSGTLE<br>SIQMLKKLSAVTIPIKSHWEGEEVSQQMASLCYQKVMNGEF | *C. ELEGANS* RDRP |

The present application contemplates any RDRP homology, variant, or equivalent there of having an amino acid sequence that is at least 80%, or 85%, or 90%, or 95%, or 99% identical with any of SEQ ID NOs: 2-7.

RpegRNA

As used herein, the terms "RNA prime editing guide RNA" or "RpegRNA" refer to a specialized form of a guide RNA that has been modified to include one or more additional sequences for implementing the RNA prime editing methods and compositions described herein. The RPE RNA editing system described herein comprises an RpegRNA to direct the Cas13 component to the target RNA molecule of interest. In general RpegRNA have structures that are similar to PEgRNA editing systems and comprise (a) a spacer sequence, which comprises a sequence complementary to the target RNA sequence, (b) a core sequence which allows the RpegRNA to bind to the napRNAbp component, and (c) an extension arm, which comprises a (i) primer sequence that anneals to the 3' end of the RNA (or an internal 3' end created after cleavage of the target RNA) to create a double stranded RNA substrate for polymerization by the RDRP, and (ii) a template region that provides the coding template for the RDRP to synthesize new RNA at the natural 3' end (or at an internal 3' end created after RNA cleavage) (see FIGS. 1-4). A exemplary RpegRNA sequence is provided as follows:

| | | |
|---|---|---|
| 8 | GGCTTCCATCTCTTTGAGCACCTCCAGCGG*GTTGTGGAAGGTCCAGTTTTG*<br>*AGGGGCTATTACAA*GTNAATTGCAGC | RPEGRNA, BOUND BY PSPCAS13B. UNDERLINED IS SPACER, ITALICIZED IS PSPCAS13B DIRECT REPEAT, FOLLOWING IS TEMPLATE, BOLD IS BINDING SITE. |

Cas13-RDRP Fusion Proteins

The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas13 that directs the binding of the protein to a target site) and an RNA polymerase. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, Molecular Cloning: A Laboratory Manual (4th ed., Cold Spring Harbor Laboratory Press, Cold Spring Harbor, N.Y. (2012)), the entire contents of which are incorporated herein by reference.

The RPE RNA editing system described herein comprises a fusion protein comprising an napRNAbp (e.g., Cas13) and an RNA-dependent DNA polymerase (RDRP), optionally fused by a linker. A non-limiting list of exemplary Cas13-RDRP fusion protein sequences is provided as follows:

| | | |
|---|---|---|
| 9 | MKRTADGSEFESPKKKRKVSGSETPGTSESATPES[X]SGSETPGTSESAT<br>PESIPALVENQKKYFGTYSVMAMLNAQTVLDHIQKVADIEGEQNENNENLW<br>FHPVMSHLYNAKNGYDKQPEKTMFIIERLQSYFPFLKIMAENQREYSNGKY<br>KQNRVEVNSNDIFEVLKRAFGVLKMYRDLTNAYKTYEEKLNDGCEFLISTE<br>QPLSGMINNYYTVALRNMNERYGYKTEDLAFIQDKRFKFVKDAYGKKKSQV<br>NTGFFLSLQDYNGDTQKKLHLSGVGIALLICLFLDKQYINIFLSRLPIFSS<br>YNAQSEERRIIIRSFGINSIKLPKDRIHSEKSNKSVAMDMLNEVKRCPDEL<br>FTTLSAEKQSRFRIISDDHNEVLMKRSSDRFVPLLLQYIDYGKLFDHIRFH<br>VNMGKLRYLLKADKTCIDGQTRVRVIEQPLNGFGRLEEAETMRKQENGTFG<br>NSGIRIRDFENMKRDDANPANYPYIVDTYTHYILENNKVEMFINDKEDSAP<br>LLPVIEDDRYVVKTIPSCRMSTLEIPAMAFHMFLFGSKKTEKLIVDVHNRY<br>KRLFQAMQKEEVTAENIASFGIAESDLPQKILDLISGNAHGKDVDAFIRLT<br>VDDMLTDTERRIKRFKDDRKSIRSADNKMGKRGFKQISTGKLADFLAKDIV<br>LFQPSVNDGENKITGLNYRIMQSAIAVYDSGDDYEAKQQFKLMFEKARLIG<br>KGTTEPHPFLYKVFARSIPANAVEFYERYLIERKFYLTGLSNEIKKGNRVD<br>VPFIRRDQNKWKTPAMKTLGRIYSEDLPVELPRQMEDNEIKSHLKSLPQME<br>GIDENNANVTYLIAEYMKRVLDDDFQTFYQWNRNYRYMDMLKGEYDRKGSL<br>QHCFTSVEEREGLWKERASRTERYRKQASNKIRSNRQMRNASSEEIETILD<br>KRLSNSRNEYQKSEKVIRRYRVQDALLFLLAKKTLTELADFDGERFKLKEI<br>MPDAEKGILSEIMPMSFTFEKGGKKYTITSEGMKLKNYGDFFVLASDKRIG<br>NLLELVGSDIVSKED | DCAS13B FUSED N-TERMINALLY TO AN RDRP AND TARGETED TO THE NUCLEUS |
| 10 | MKRTADGSEFESPKKKRKVNIPALVENQKKYFGTYSVMAMLNAQTVLDHIQ<br>KVADIEGEQNENNENLWFHPVMSHLYNAKNGYDKQPEKTMFIIERLQSYFP<br>FLKIMAENQREYSNGKYKQNRVEVNSNDIFEVLKRAFGVLKMYRDLTNAYK<br>TYEEKLNDGCEFLISTEQPLSGMINNYYTVALRNMNERYGYKTEDLAFIQD<br>KRFKFVKDAYGKKKSQVNTGFFLSLQDYNGDTQKKLHLSGVGIALLICLEL<br>DKQYINIFLSRLPIFSSYNAQSEERRIIIRSFGINSIKLPKDRIHSEKSNK<br>SVAMDMLNEVKRCPDELFTTLSAEKQSRFRIISDDHNEVLMKRSSDRFVPL<br>LLQYIDYGKLFDHIRFHVNMGKLRYLLKADKTCIDGQTRVRVIEQPLNGFG<br>RLEEAETMRKQENGTFGNSGIRIRDFENMKRDDANPANYPYIVDTYTHYIL<br>ENNKVEMFINDKEDSAPLLPVIEDDRYVVKTIPSCRMSTLEIPAMAFHMEL<br>FGSKKTEKLIVDVHNRYKRLFQAMQKEEVTAENIASFGIAESDLPQKILDL<br>ISGNAHGKDVDAFIRLTVDDMLTDTERRIKRFKDDRKSIRSADNKMGKRGF<br>KQISTGKLADFLAKDIVLFQPSVNDGENKITGLNYRIMQSAIAVYDSGDDY<br>EAKQQFKLMFEKARLIGKGTTEPHPFLYKVFARSIPANAVEFYERYLIERK<br>FYLTGLSNEIKKGNRVDVPFIRRDQNKWKTPAMKTLGRIYSEDLPVELPRQ<br>MFDNEIKSHLKSLPQMEGIDENNANVTYLIAEYMKRVLDDDFQTFYQWNRN<br>YRYMDMLKGEYDRKGSLQHCFTSVEEREGLWKERASRTERYRKQASNKIRS<br>NRQMRNASSEEIETILDKRLSNSRNEYQKSEKVIRRYRVQDALLELLAKKT<br>LTELADFDGEREKLKEIMPDAEKGILSEIMPMSFTFEKGGKKYTITSEGMK<br>LKNYGDFFVLASDKRIGNLLELVGSDIVSKEDGSKRTADGSEFEPKKKRKV<br>[X] | DCAS13B FUSED C-TERMINALLY TO AN RDRP AND TARGETED TO THE NUCLEUS |
| 11 | SGSETPGTSESATPES[X]SGSETPGTSESATPESNIPALVENQKKYFGTY<br>SVMAMLNAQTVLDHIQKVADIEGEQNENNENLWFHPVMSHLYNAKNGYDKQ | DCAS13B FUSED N-TERMINALLY TO |

-continued

| | | |
|---|---|---|
| | PEKTMFIIERLQSYFPFLKIMAENQREYSNGKYKQNRVEVNSNDIFEVLKR<br>AFGVLKMYRDLTNAYKTYEEKLNDGCEFLISTEQPLSGMINNYYTVALRNM<br>NERYGYKTEDLAFIQDKRFKFVKDAYGKKKSQVNTGFFLSLQDYNGDTQKK<br>LHLSGVGIALLICLFLDKQYINIFLSRLPIFSSYNAQSEERRIIIRSFGIN<br>SIKLPKDRIHSEKSNKSVAMDMLNEVKRCPDELFTTLSAEKQSRFRIISDD<br>HNEVLMKRSSDRFVPLLLQYIDYGKLFDHIRFHVNMGKLRYLLKADKTCID<br>GQTRVRVIEQPLNGFGRLEEAETMRKQENGTFGNSGIRIRDFENMKRDDAN<br>PANYPYIVDTYTHYILENNKVEMFINDKEDSAPLLPVIEDDRYVVKTIPSC<br>RMSTLEIPAMAFHMFLFGSKKTEKLIVDVHNRYKRLFQAMQKEEVTAENIA<br>SFGIAESDLPQKILDLISGNAHGKDVDAFIRLTVDDMLTDTERRIKRFKDD<br>RKSIRSADNKMGKRGFKQISTGKLADFLAKDIVLFQPSVNDGENKITGLNY<br>RIMQSAIAVYDSGDDYEAKQQFKLMFEKARLIGKGTTEPHPFLYKVFARSI<br>PANAVEFYERYLIERKFYLTGLSNEIKKGNRVDVPFIRRDQNKWKTPAMKT<br>LGRIYSEDLPVELPRQMEDNEIKSHLKSLPQMEGIDENNANVTYLIAEYMK<br>RVLDDDFQTFYQWNRNYRYMDMLKGEYDRKGSLQHCFTSVEEREGLWKERA<br>SRTERYRKQASNKIRSNRQMRNASSEEIETILDKRLSNSRNEYQKSEKVIR<br>RYRVQDALLFLLAKKTLTELADFDGEREKLKEIMPDAEKGILSEIMPMSFT<br>FEKGGKKYTITSEGMKLKNYGDFFVLASDKRIGNLLELVGSDIVSKED | AN RDRP AND<br>TARGETED TO THE<br>CYTOPLASM |
| 12 | MNIPALVENQKKYFGTYSVMAMLNAQTVLDHIQKVADIEGEQNENNENLWE<br>HPVMSHLYNAKNGYDKQPEKTMFIIERLQSYFPFLKIMAENQREYSNGKYK<br>QNRVEVNSNDIFEVLKRAFGVLKMYRDLTNAYKTYEEKLNDGCEFLISTEQ<br>PLSGMINNYYTVALRNMNERYGYKTEDLAFIQDKRFKFVKDAYGKKKSQVN<br>TGFFLSLQDYNGDTQKKLHLSGVGIALLICLFLDKQYINIFLSRLPIFSSY<br>NAQSEERRIIIRSFGINSIKLPKDRIHSEKSNKSVAMDMLNEVKRCPDELF<br>TTLSAEKQSRFRIISDDHNEVLMKRSSDRFVPLLLQYIDYGKLFDHIRFHV<br>NMGKLRYLLKADKTCIDGQTRVRVIEQPLNGFGRLEEAETMRKQENGTEGN<br>SGIRIRDFENMKRDDANPANYPYIVDTYTHYILENNKVEMFINDKEDSAPL<br>LPVIEDDRYVVKTIPSCRMSTLEIPAMAFHMFLFGSKKTEKLIVDVHNRYK<br>RLFQAMQKEEVTAENIASFGIAESDLPQKILDLISGNAHGKDVDAFIRLTV<br>DDMLTDTERRIKRFKDDRKSIRSADNKMGKRGFKQISTGKLADFLAKDIVL<br>FQPSVNDGENKITGLNYRIMQSAIAVYDSGDDYEAKQQFKLMFEKARLIGK<br>GTTEPHPFLYKVFARSIPANAVEFYERYLIERKFYLTGLSNEIKKGNRVDV<br>PFIRRDQNKWKTPAMKTLGRIYSEDLPVELPRQMEDNEIKSHLKSLPQMEG<br>IDENNANVTYLIAEYMKRVLDDDFQTFYQWNRNYRYMDMLKGEYDRKGSLQ<br>HCFTSVEEREGLWKERASRTERYRKQASNKIRSNRQMRNASSEEIETILDK<br>RLSNSRNEYQKSEKVIRRYRVQDALLFLLAKKTLTELADFDGEREKLKEIM<br>PDAEKGILSEIMPMSFTFEKGGKKYTITSEGMKLKNYGDFFVLASDKRIGN<br>LLELVGSDIVSKEDGSLQLPPLERLTLSGSETPGTSESATPES[X] | DCAS13B FUSED<br>C-TERMINALLY TO<br>AN RDRP AND<br>TARGETED TO THE<br>CYTOPLASM |
| 13 | MNIPALVENQKKYFGTYSVMAMLNAQTVLDHIQKVADIEGEQNENNENLWE<br>HPVMSHLYNAKNGYDKQPEKTMFIIERLQSYFPFLKIMAENQREYSNGKYK<br>QNRVEVNSNDIFEVLKRAFGVLKMYRDLTNHYKTYEEKLNDGCEFLISTEQ<br>PLSGMINNYYTVALRNMNERYGYKTEDLAFIQDKRFKFVKDAYGKKKSQVN<br>TGFFLSLQDYNGDTQKKLHLSGVGIALLICLFLDKQYINIFLSRLPIFSSY<br>NAQSEERRIIIRSFGINSIKLPKDRIHSEKSNKSVAMDMLNEVKRCPDELF<br>TTLSAEKQSRFRIISDDHNEVLMKRSSDRFVPLLLQYIDYGKLFDHIRFHV<br>NMGKLRYLLKADKTCIDGQTRVRVIEQPLNGFGRLEEAETMRKQENGTEGN<br>SGIRIRDFENMKRDDANPANYPYIVDTYTHYILENNKVEMFINDKEDSAPL<br>LPVIEDDRYVVKTIPSCRMSTLEIPAMAFHMFLFGSKKTEKLIVDVHNRYK<br>RLFQAMQKEEVTAENIASFGIAESDLPQKILDLISGNAHGKDVDAFIRLTV<br>DDMLTDTERRIKRFKDDRKSIRSADNKMGKRGFKQISTGKLADFLAKDIVL<br>FQPSVNDGENKITGLNYRIMQSAIAVYDSGDDYEAKQQFKLMFEKARLIGK<br>GTTEPHPFLYKVFARSIPANAVEFYERYLIERKFYLTGLSNEIKKGNRVDV<br>PFIRRDQNKWKTPAMKTLGRIYSEDLPVELPRQMEDNEIKSHLKSLPQMEG<br>IDENNANVTYLIAEYMKRVLDDDFQTFYQWNRNYRYMDMLKGEYDRKGSLQ<br>HCFTSVEEREGLWKERASRTERYRKQASNKIRSNRQMRNASSEEIETILDK<br>RLSNSRNEYQKSEKVIRRYRVQDALLFLLAKKTLTELADFDGEREKLKEIM<br>PDAEKGILSEIMPMSFTFEKGGKKYTITSEGMKLKNYGDFFVLASDKRIGN<br>LLELVGSDIVSKEDGSLQLPPLERLTLSGSETPGTSESATPES[X] | WTCAS13B FUSED<br>C-TERMINALLY TO<br>AN RDRP AND<br>TARGETED TO THE<br>CYTOPLASM |

The following sequence belong to the following family of proteins:

- Nucleic acid-programmable RNA binding protein: SEQ ID NO: 1 and 34-41;
- RNA-dependent RNA polymerase: SEQ ID NO: 2-7;
- rpegRNA sequences: SEQ ID NO: 8;
- Fusion proteins (napRNAbp:RDRP): SEQ ID NO: 9-13, wherein [X] represents an RDRP, examples of which are listed below. Only examples of truncated Cas13b are listed for the fusions. Other Cas13 proteins that are potentially usable include Cas13a, -13c, and 13d, either truncated or full-length. Examples include either an NLS or NES to direct the RNA prime editor to the nucleus or cytoplasm, respectively. Other NLSs or NESs are also envisioned.

Mutants

It should be appreciated that any of the amino acid sequences described herein may also include mutations that result in acceptable substitutions of amino acids. For example, mutation of an amino acid with a hydrophobic side chain (e.g., alanine, valine, isoleucine, leucine, methionine, phenylalanine, tyrosine, or tryptophan) may be a mutation to a second amino acid with a different hydrophobic side chain (e.g., alanine, valine, isoleucine, leucine, methionine, phenylalanine, tyrosine, or tryptophan). For example, a mutation of an alanine to a threonine (e.g., a A262T mutation) may also be a mutation from an alanine to an amino acid that is similar in size and chemical properties to a threonine, for example, serine. As another example, mutation of an amino acid with a positively charged side chain (e.g., arginine, histidine, or lysine) may be a mutation to a second amino acid with a different positively charged side chain (e.g., arginine, histidine, or lysine). As another example, mutation of an amino acid with a polar side chain (e.g., serine, threonine, asparagine, or glutamine) may be a mutation to a second amino acid with a different polar side chain (e.g., serine, threonine, asparagine, or glutamine). Additional similar amino acid pairs include, but are not limited to, the following: phenylalanine and tyrosine; asparagine and glutamine; methionine and cysteine; aspartic acid and glutamic acid; and arginine and lysine. The skilled artisan would recognize that such conservative amino acid substitutions will likely have minor effects on protein structure and are likely to be well tolerated without compromising function. In some embodiments, any amino of the amino acid mutations provided herein from one amino acid to a threonine may be an amino acid mutation to a serine. In some embodiments, any amino of the amino acid mutations provided herein from one amino acid to an arginine may be an amino acid mutation to a lysine. In some embodiments, any amino of the amino acid mutations provided herein from one amino acid to an isoleucine, may be an amino acid mutation to an alanine, valine, methionine, or leucine. In some embodiments, any amino of the amino acid mutations provided herein from one amino acid to a lysine may be an amino acid mutation to an arginine. In some embodiments, any amino of the amino acid mutations provided herein from one amino acid to an aspartic acid may be an amino acid mutation to a glutamic acid or asparagine. In some embodiments, any amino of the amino acid mutations provided herein from one amino acid to a valine may be an amino acid mutation to an alanine, isoleucine, methionine, or leucine. In some embodiments, any amino of the amino acid mutations provided herein from one amino acid to a glycine may be an amino acid mutation to an alanine. It should be appreciated, however, that additional conserved amino acid residues would be recognized by the skilled artisan and any of the amino acid mutations to other conserved amino acid residues are also within the scope of this disclosure.

In some embodiments, the present disclosure may utilize any variant, mutant, or equivalent of the exemplary Cas13 or RDRP proteins disclosed herein. Any available methods may be utilized to obtain or construct a variant or mutant Cas13 or RDRP protein. The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, Molecular Cloning: A Laboratory Manual (4th ed., Cold Spring Harbor Laboratory Press, Cold Spring Harbor, N.Y. (2012)). Mutations can include a variety of categories, such as single base polymorphisms, microduplication regions, indel, and inversions, and is not meant to be limiting in any way. Mutations can include "loss-of-function" mutations which is the normal result of a mutation that reduces or abolishes a protein activity. Most loss-of-function mutations are recessive, because in a heterozygote the second chromosome copy carries an unmutated version of the gene coding for a fully functional protein whose presence compensates for the effect of the mutation. Mutations also embrace "gain-of-function" mutations, which is one which confers an abnormal activity on a protein or cell that is otherwise not present in a normal condition. Many gain-of-function mutations are in regulatory sequences rather than in coding regions, and can therefore have a number of consequences. For example, a mutation might lead to one or more genes being expressed in the wrong tissues, these tissues gaining functions that they normally lack. Because of their nature, gain-of-function mutations are usually dominant.

Mutations can be introduced into a reference Cas13 or RDRP protein using site-directed mutagenesis. Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation. More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

Mutations may also be introduced by directed evolution processes, such as phage-assisted continuous evolution (PACE) or phage-assisted noncontinuous evolution (PANCE). The term "phage-assisted continuous evolution (PACE)," as used herein, refers to continuous evolution that employs phage as viral vectors. The general concept of PACE technology has been described, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; U.S. Application, U.S. Pat. No. 9,023,594, issued May 5, 2015; U.S. Pat. No. 9,771,574, issued Sep. 26, 2017; U.S. Pat. No. 9,394,537, issued Jul. 19, 2016; International PCT Application, PCT/US2015/012022, filed Jan. 20, 2015, published as WO 2015/134121 on Sep. 11, 2015; U.S. Pat. No. 10,179,911, issued Jan. 15, 2019; International PCT Application, PCT/US2016/027795, filed Apr. 15, 2016, published as WO 2016/168631 on Oct. 20, 2016, and International Patent Publication WO 2019/023680, published Jan. 31, 2019, the entire contents of each of which are incorporated herein by reference. Variant Cas9s may also be obtain by phage-assisted non-continuous evolution (PANCE)," which as used herein, refers to non-continuous evolution that employs phage as viral vectors. PANCE is a simplified technique for rapid in vivo directed evolution using serial flask transfers of evolving 'selection phage' (SP), which contain a gene of interest to be evolved, across fresh *E. coli* host cells, thereby allowing genes inside the host *E. coli* to be held constant while genes contained in the SP continuously evolve. Serial flask transfers have long served as a widely-accessible approach for laboratory evolution of microbes, and, more recently, analogous approaches have been developed for bacteriophage evolution. The PANCE system features lower stringency than the PACE system.

Any of the references noted above are hereby incorporated by reference in their entireties, if not already stated so.

In various embodiments, the RNA prime editor fusion proteins contemplated herein may also include any variants of the above-disclosed sequences having an amino acid sequence that is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to any of the above indicated RNA prime editor fusion sequences.

The RPE fusion proteins may comprise various other domains besides the Cas13 domain and the RDRP domains. For example, the RPE fusion proteins may comprise one or more linkers that join the Cas13 domain with the RDRP domain. The linkers may also join other functional domains, such as nuclear localization sequences (NLS) to the RPE fusion proteins or a domain thereof.

Linkers

As defined above, the term "linker," as used herein, refers to a chemical group or a molecule linking two molecules or moieties, e.g., a binding domain and a cleavage domain of a nuclease. In some embodiments, a linker joins a gRNA binding domain of an RNA-programmable nuclease and the catalytic domain of a recombinase. In some embodiments, a linker joins a Cas13 and RDRP. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker may comprise a peptide or a non-peptide moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The linker may be as simple as a covalent bond, or it may be a polymeric linker many atoms in length. In certain embodiments, the linker is a polypeptide or based on amino acids. In other embodiments, the linker is not peptide-like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker is based on a phenyl ring. The linker may included functionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In some other embodiments, the linker comprises the amino acid sequence $(GGGGS)_N$(SEQ ID NO: 14), $(G)_N$ (SEQ ID NO: 15), $(EAAAK)_N$ (SEQ ID NO: 16), $(GGS)_N$ (SEQ ID NO: 17), $(SGGS)_N$ (SEQ ID NO: 18), $(XP)_N$ (SEQ ID NO: 19), or any combination thereof, wherein n is independently an integer between 1 and 30, and wherein X is any amino acid. In some embodiments, the linker comprises the amino acid sequence $(GGS)_N$ (SEQ ID NO: 17), wherein n is 1, 3, or 7. In some embodiments, the linker comprises the amino acid sequence SGSETPGTSESATPES (SEQ ID NO: 20). In some embodiments, the linker comprises the amino acid sequence SGGSSGGSSGSETPGTSESATPESSGGSSGGS (SEQ ID NO: 21). In some embodiments, the linker comprises the amino acid sequence SGGSGGSGGS (SEQ ID NO: 22). In some embodiments, the linker comprises the amino acid sequence SGGS (SEQ ID NO: 18). In other embodiments, the linker comprises the amino acid sequence SGGSSGGSSGSETPGTSESATPESAGSYPYDVPDYAGSAAPAAKKKKLDGSGSGGSSGGS (SEQ ID NO: 23, 60AA).

In certain embodiments, linkers may be used to link any of the peptides or peptide domains or moieties of the invention (e.g., a napRNAbp linked or fused to a RDRP).

NLS

In various embodiments, the RPE fusion proteins may comprise one or more nuclear localization sequences (NLS), which help promote translocation of a protein into the cell nucleus. In certain embodiments, the RPE fusion proteins comprise at least two NLSs. In embodiments with at least two NLSs, the NLSs can be the same NLSs, or they can be different NLSs. In addition, the NLSs may be expressed as part of a fusion protein with the other portions of the RPEs. The location of the NLS fusion can be at the N-terminus, the C-terminus, or within a sequence of an RPE (e.g., inserted between the napRNAbp domain (e.g., Cas13) and the RNA-dependent RNA polymerase.

The NLSs may be any known NLS in the art. The NLSs may also be any NLSs for nuclear localization discovered in the future. The NLSs also may be any naturally occurring NLS, or any non-naturally occurring NLS (e.g., an NLS with one or more desired mutations).

The term "nuclear localization sequence" or "NLS" refers to an amino acid sequence that promotes import of a protein into the cell nucleus, for example, by nuclear transport. Nuclear localization sequences are known in the art and would be apparent to the skilled artisan. For example, NLS sequences are described in Plank et al., International PCT application PCT/EP2000/011690, filed Nov. 23, 2000, published as WO/2001/038547 on May 31, 2001, the contents of which are incorporated herein by reference.

A representative nuclear localization signal is a peptide sequence that directs the protein to the nucleus of the cell in which the sequence is expressed. A nuclear localization signal is predominantly basic, can be positioned almost anywhere in a protein's amino acid sequence, generally comprises a short sequence of four amino acids (Autieri & Agrawal, (1998) *J. Biol. Chem.* 273: 14731-37, incorporated herein by reference) to eight amino acids, and is typically rich in lysine and arginine residues (Magin et al., (2000) *Virology* 274: 11-16, incorporated herein by reference). Nuclear localization signals often comprise proline residues. A variety of nuclear localization signals have been identified and have been used to effect transport of biological molecules from the cytoplasm to the nucleus of a cell. See, e.g., Tinland et al., (1992) *Proc. Natl. Acad. Sci. U.S.A.* 89:7442-46; Moede et al., (1999) *FEBS Lett.* 461:229-34, which is incorporated herein by reference. Translocation is currently thought to involve nuclear pore proteins. Such sequences are well-known in the art and can include the following examples:

| DESCRIPTION | SEQUENCE | SEQ ID NO: |
|---|---|---|
| NLS OF SV40 LARGE T-AG | PKKKRKV | SEQ ID NO: 50 |
| NLS | MKRTADGSEFESPKKKRKV | SEQ ID NO: 24 |
| NLS | MDSLLMNRRKFLYQFKNVRWAKGRRETYLC | SEQ ID NO: 25 |
| NLS OF NUCLEOPLASMIN | AVKRPAATKKAGQAKKKKLD | SEQ ID NO: 26 |
| NLS OF EGL-13 | MSRRRKANPTKLSENAKKLAKEVEN | SEQ ID NO: 27 |
| NLS OF C-MYC | PAAKRVKLD | SEQ ID NO: 28 |
| NLS OF TUS-PROTEIN | KLKIKRPVK | SEQ ID NO: 29 |
| NLS OF POLYOMA LARGE T-AG | VSRKRPRP | SEQ ID NO: 30 |
| NLS OF HEPATITIS D VIRUS ANTIGEN | EGAPPAKRAR | SEQ ID NO: 31 |
| NLS OF MURINE P53 | PPQPKKKPLDGE | SEQ ID NO: 32 |
| NLS OF PE1 AND PE2 | SGGSKRTADGSEFEPKKKRKV | SEQ ID NO: 33 |

regions encoded between the RPE and the N-terminally, C-terminally, or internally-attached NLS amino acid sequence, e.g, and in the central region of proteins. Thus, the present disclosure also provides for nucleotide constructs, vectors, and host cells for expressing fusion proteins that comprise an RPE and one or more NLSs.

The RPEs described herein may also comprise nuclear localization signals which are linked to an RPE through one or more linkers, e.g., and polymeric, amino acid, nucleic acid, polysaccharide, chemical, or nucleic acid linker element. The linkers within the contemplated scope of the disclosure are not intended to have any limitations and can be any suitable type of molecule (e.g., polymer, amino acid, polysaccharide, nucleic acid, lipid, or any synthetic chemical linker domain) and be joined to the RPE by any suitable strategy that effectuates forming a bond (e.g., covalent linkage, hydrogen bonding) between the prime editor and the one or more NLSs.

The NLS examples above are non-limiting. The RPE fusion proteins may comprise any known NLS sequence, including any of those described in Cokol et al., "Finding nuclear localization signals," *EMBO Rep.,* 2000, 1(5): 411-415 and Freitas et al., "Mechanisms and Signals for the Nuclear Import of Proteins," *Current Genomics,* 2009, 10(8): 550-7, each of which are incorporated herein by reference.

The present disclosure contemplates any suitable means by which to modify an RPE to include one or more NLSs. In one aspect, the RPE may be engineered to express an RPE protein that is translationally fused at its N-terminus or its C-terminus (or both) to one or more NLSs, i.e., to form an RPE-NLS fusion construct. In other embodiments, the RPE-encoding nucleotide sequence may be genetically modified to incorporate a reading frame that encodes one or more NLSs in an internal region of the encoded RPE. In addition, the NLSs may include various amino acid linkers or spacer

Methods of Treatment

The instant disclosure provides methods for the treatment of a subject diagnosed with a disease associated with or caused by a point mutation that can be corrected by RNA prime editing of RNA molecules (e.g., mRNA transcripts comprising said mutations). For example, in some embodiments, a method is provided that comprises administering to a subject having such a disease, e.g., a cancer associated with a point mutation as described above, an effective amount of the RNA prime editing system described herein that corrects the point mutation or introduces a deactivating mutation into a disease-associated RNA. In some embodiments, a method is provided that comprises administering to a subject having such a disease, e.g., a cancer associated with a point mutation as described above, an effective amount of the RNA prime editing system described herein that corrects the defective RNA molecule. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting a point mutation or introducing a deactivating mutation into a disease-associated RNA will be known to those of skill in the art, and the disclosure is not limited in this respect.

The instant disclosure provides methods for the treatment of additional diseases or disorders, e.g., diseases or disorders that are associated or caused by a point mutation that can be corrected by RNA prime editing. Some such diseases are described herein, and additional suitable diseases that can be treated with the strategies and fusion proteins provided herein will be apparent to those of skill in the art based on the instant disclosure. Exemplary suitable diseases and disorders are listed below. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment and determination of homologous residues. Exemplary suitable diseases and disorders include, without limitation: 2-methyl-3-hydroxybutyric aciduria; 3 beta-Hydroxysteroid dehydrogenase deficiency; 3-Methylglutaconic aciduria; 3-Oxo-5 alpha-steroid delta 4-dehydrogenase deficiency; 46,XY sex reversal, type 1, 3, and 5; 5-Oxoprolinase deficiency; 6-pyruvoyl-tetrahydropterin synthase deficiency; Aarskog syndrome; Aase syndrome; Achondrogenesis type 2; Achromatopsia 2 and 7; Acquired long QT syndrome; Acrocallosal syndrome, Schinzel type; Acrocapitofemoral dysplasia; Acrodysostosis 2, with or without hormone resistance; Acroerythrokeratoderma; Acromicric dysplasia; Acth-independent macronodular adrenal hyperplasia 2; Activated PI3K-delta syndrome; Acute intermittent porphyria; deficiency of Acyl-CoA dehydrogenase family, member 9; Adams-Oliver syndrome 5 and 6; Adenine phosphoribosyltransferase deficiency; Adenylate kinase deficiency; hemolytic anemia due to Adenylosuccinate lyase deficiency; Adolescent nephronophthisis; Renal-hepatic-pancreatic dysplasia; Meckel syndrome type 7; Adrenoleukodystrophy; Adult junctional epidermolysis bullosa; Epidermolysis bullosa, junctional, localisata variant; Adult neuronal ceroid lipofuscinosis; Adult neuronal ceroid lipofuscinosis; Adult onset ataxia with oculomotor apraxia; ADULT syndrome; Afibrinogenemia and congenital Afibrinogenemia; autosomal recessive Agammaglobulinemia 2; Age-related macular degeneration 3, 6, 11, and 12; Aicardi Goutieres syndromes 1, 4, and 5; Chilbain lupus 1; Alagille syndromes 1 and 2; Alexander disease; Alkaptonuria; Allan-Herndon-Dudley syndrome; Alopecia universalis congenital; Alpers encephalopathy; Alpha-1-antitrypsin deficiency; autosomal dominant, autosomal recessive, and X-linked recessive Alport syndromes; Alzheimer disease, familial, 3, with spastic paraparesis and apraxia; Alzheimer disease, types, 1, 3, and 4; hypocalcification type and hypomaturation type, IIA1 Amelogenesis imperfecta; Aminoacylase 1 deficiency; Amish infantile epilepsy syndrome; Amyloidogenic transthyretin amyloidosis; Amyloid Cardiomyopathy, Transthyretin-related; Cardiomyopathy; Amyotrophic lateral sclerosis types 1, 6, 15 (with or without frontotemporal dementia), 22 (with or without frontotemporal dementia), and 10; Frontotemporal dementia with TDP43 inclusions, TARDBP-related; Andermann syndrome; Andersen Tawil syndrome; Congenital long QT syndrome; Anemia, nonspherocytic hemolytic, due to G6PD deficiency; Angelman syndrome; Severe neonatal-onset encephalopathy with microcephaly; susceptibility to Autism, X-linked 3; Angiopathy, hereditary, with nephropathy, aneurysms, and muscle cramps; Angiotensin i-converting enzyme, benign serum increase; Aniridia, cerebellar ataxia, and mental retardation; Anonychia; Antithrombin III deficiency; Antley-Bixler syndrome with genital anomalies and disordered steroidogenesis; Aortic aneurysm, familial thoracic 4, 6, and 9; Thoracic aortic aneurysms and aortic dissections; Multisystemic smooth muscle dysfunction syndrome; Moyamoya disease 5; Aplastic anemia; Apparent mineralocorticoid excess; Arginase deficiency; Argininosuccinate lyase deficiency; Aromatase deficiency; Arrhythmogenic right ventricular cardiomyopathy types 5, 8, and 10; Primary familial hypertrophic cardiomyopathy; Arthrogryposis multiplex congenita, distal, X-linked; Arthrogryposis renal dysfunction cholestasis syndrome; Arthrogryposis, renal dysfunction, and cholestasis 2; Asparagine synthetase deficiency; Abnormality of neuronal migration; Ataxia with vitamin E deficiency; Ataxia, sensory, autosomal dominant; Ataxia-telangiectasia syndrome; Hereditary cancer-predisposing syndrome; Atransferrinemia; Atrial fibrillation, familial, 11, 12, 13, and 16; Atrial septal defects 2, 4, and 7 (with or without atrioventricular conduction defects); Atrial standstill 2; Atrioventricular septal defect 4; *Atrophia bulborum* hereditaria; ATR-X syndrome; Auriculocondylar syndrome 2; Autoimmune disease, multisystem, infantile-onset; Autoimmune lymphoproliferative syndrome, type 1a; Autosomal dominant hypohidrotic ectodermal dysplasia; Autosomal dominant progressive external ophthalmoplegia with mitochondrial DNA deletions 1 and 3; Autosomal dominant torsion dystonia 4; Autosomal recessive centronuclear myopathy; Autosomal recessive congenital ichthyosis 1, 2, 3, 4A, and 4B; Autosomal recessive cutis laxa type IA and 1B; Autosomal recessive hypohidrotic ectodermal dysplasia syndrome; Ectodermal dysplasia 11b; hypohidrotic/hair/tooth type, autosomal recessive; Autosomal recessive hypophosphatemic bone disease; Axenfeld-Rieger syndrome type 3; Bainbridge-Ropers syndrome; Bannayan-Riley-Ruvalcaba syndrome; PTEN hamartoma tumor syndrome; Baraitser-Winter syndromes 1 and 2; Barakat syndrome; Bardet-Biedl syndromes 1, 11, 16, and 19; Bare lymphocyte syndrome type 2, complementation group E; Bartter syndrome antenatal type 2; Bartter syndrome types 3, 3 with hypocalciuria, and 4; Basal ganglia calcification, idiopathic, 4; Beaded hair; Benign familial hematuria; Benign familial neonatal seizures 1 and 2; Seizures, benign familial neonatal, 1, and/or myokymia; Seizures, Early infantile epileptic encephalopathy 7; Benign familial neonatal-infantile seizures; Benign hereditary chorea; Benign scapuloperoneal muscular dystrophy with cardiomyopathy; Bernard-Soulier syndrome, types A1 and A2 (autosomal dominant); Bestrophinopathy, autosomal recessive; beta Thalassemia; Bethlem myopathy and Bethlem myopathy 2; Bietti crystalline corneoretinal dystrophy; Bile acid synthesis defect, congenital, 2; Biotinidase deficiency; Birk Barel mental retardation dysmorphism syndrome; Blepharophimosis, ptosis, and epicanthus inversus; Bloom syndrome;

Borjeson-Forssman-Lehmann syndrome; Boucher Neuhauser syndrome; Brachydactyly types A1 and A2; Brachydactyly with hypertension; Brain small vessel disease with hemorrhage; Branched-chain ketoacid dehydrogenase kinase deficiency; Branchiootic syndromes 2 and 3; Breast cancer, early-onset; Breast-ovarian cancer, familial 1, 2, and 4; Brittle cornea syndrome 2; Brody myopathy; Bronchiectasis with or without elevated sweat chloride 3; Brown-Vialetto-Van laere syndrome and Brown-Vialetto-Van Laere syndrome 2; Brugada syndrome; Brugada syndrome 1; Ventricular fibrillation; Paroxysmal familial ventricular fibrillation; Brugada syndrome and Brugada syndrome 4; Long QT syndrome; Sudden cardiac death; Bull eye macular dystrophy; Stargardt disease 4; Cone-rod dystrophy 12; Bullous ichthyosiform erythroderma; Burn-Mckeown syndrome; Candidiasis, familial, 2, 5, 6, and 8; Carbohydrate-deficient glycoprotein syndrome type I and II; Carbonic anhydrase VA deficiency, hyperammonemia due to; Carcinoma of colon; Cardiac arrhythmia; Long QT syndrome, LQT1 subtype; Cardioencephalomyopathy, fatal infantile, due to cytochrome c oxidase deficiency; Cardiofaciocutaneous syndrome; Cardiomyopathy; Danon disease; Hypertrophic cardiomyopathy; Left ventricular noncompaction cardiomyopathy; Carnevale syndrome; Carney complex, type 1; Carnitine acylcarnitine translocase deficiency; Carnitine palmitoyltransferase I, II, II (late onset), and II (infantile) deficiency; Cataract 1, 4, autosomal dominant, autosomal dominant, multiple types, with microcornea, coppock-like, juvenile, with microcornea and glucosuria, and nuclear diffuse nonprogressive; Catecholaminergic polymorphic ventricular tachycardia; Caudal regression syndrome; Cd8 deficiency, familial; Central core disease; Centromeric instability of chromosomes 1, 9 and 16 and immunodeficiency; Cerebellar ataxia infantile with progressive external ophthalmoplegi and Cerebellar ataxia, mental retardation, and dysequilibrium syndrome 2; Cerebral amyloid angiopathy, APP-related; Cerebral autosomal dominant and recessive arteriopathy with subcortical infarcts and leukoencephalopathy; Cerebral cavernous malformations 2; Cerebrooculofacioskeletal syndrome 2; Cerebro-oculo-facio-skeletal syndrome; Cerebroretinal microangiopathy with calcifications and cysts; Ceroid lipofuscinosis neuronal 2, 6, 7, and 10; Ch\xc3\xa9diak-Higashi syndrome, Chediak-Higashi syndrome, adult type; Charcot-Marie-Tooth disease types 1B, 2B2, 2C, 2F, 2I, 2U (axonal), 1C (demyelinating), dominant intermediate C, recessive intermediate A, 2A2, 4C, 4D, 4H, IF, IVF, and X; Scapuloperoneal spinal muscular atrophy; Distal spinal muscular atrophy, congenital nonprogressive; Spinal muscular atrophy, distal, autosomal recessive, 5; CHARGE association; Childhood hypophosphatasia; Adult hypophosphatasia; Cholecystitis; Progressive familial intrahepatic cholestasis 3; Cholestasis, intrahepatic, of pregnancy 3; Cholestanol storage disease; Cholesterol monooxygenase (side-chain cleaving) deficiency; Chondrodysplasia Blomstrand type; Chondrodysplasia punctata 1, X-linked recessive and 2 X-linked dominant; CHOPS syndrome; Chronic granulomatous disease, autosomal recessive cytochrome b-positive, types 1 and 2; Chudley-McCullough syndrome; Ciliary dyskinesia, primary, 7, 11, 15, 20 and 22; Citrullinemia type I; Citrullinemia type I and II; Cleidocranial dysostosis; C-like syndrome; Cockayne syndrome type A; Coenzyme Q10 deficiency, primary 1, 4, and 7; Coffin Siris/Intellectual Disability; Coffin-Lowry syndrome; Cohen syndrome; Cold-induced sweating syndrome 1; COLE-CARPENTER SYNDROME 2; Combined cellular and humoral immune defects with granulomas; Combined d-2- and l-2-hydroxyglutaric aciduria; Combined malonic and methylmalonic aciduria; Combined oxidative phosphorylation deficiencies 1, 3, 4, 12, 15, and 25; Combined partial and complete 17-alpha-hydroxylase/17,20-lyase deficiency; Common variable immunodeficiency 9; Complement component 4, partial deficiency of, due to dysfunctional c1 inhibitor; Complement factor B deficiency; Cone monochromatism; Cone-rod dystrophy 2 and 6; Cone-rod dystrophy amelogenesis imperfecta; Congenital adrenal hyperplasia and Congenital adrenal hypoplasia, X-linked; Congenital amegakaryocytic thrombocytopenia; Congenital aniridia; Congenital central hypoventilation; Hirschsprung disease 3; Congenital contractural arachnodactyly; Congenital contractures of the limbs and face, hypotonia, and developmental delay; Congenital disorder of glycosylation types 1B, 1D, 1G, 1H, 1J, 1K, 1N, 1P, 2C, 2J, 2K, IIm; Congenital dyserythropoietic anemia, type I and II; Congenital ectodermal dysplasia of face; Congenital erythropoietic porphyria; Congenital generalized lipodystrophy type 2; Congenital heart disease, multiple types, 2; Congenital heart disease; Interrupted aortic arch; Congenital lipomatous overgrowth, vascular malformations, and epidermal nevi; Non-small cell lung cancer; Neoplasm of ovary; Cardiac conduction defect, nonspecific; Congenital microvillous atrophy; Congenital muscular dystrophy; Congenital muscular dystrophy due to partial LAMA2 deficiency; Congenital muscular dystrophy-dystroglycanopathy with brain and eye anomalies, types A2, A7, A8, A11, and A14; Congenital muscular dystrophy-dystroglycanopathy with mental retardation, types B2, B3, B5, and B15; Congenital muscular dystrophy-dystroglycanopathy without mental retardation, type B5; Congenital muscular hypertrophy-cerebral syndrome; Congenital myasthenic syndrome, acetazolamide-responsive; Congenital myopathy with fiber type disproportion; Congenital ocular coloboma; Congenital stationary night blindness, type 1A, 1B, 1C, 1E, 1F, and 2A; Coproporphyria; Cornea plana 2; Corneal dystrophy, Fuchs endothelial, 4; Corneal endothelial dystrophy type 2; Corneal fragility keratoglobus, blue sclerae and joint hypermobility; Cornelia de Lange syndromes 1 and 5; Coronary artery disease, autosomal dominant 2; Coronary heart disease; Hyperalphalipoproteinemia 2; Cortical dysplasia, complex, with other brain malformations 5 and 6; Cortical malformations, occipital; Corticosteroid-binding globulin deficiency; Corticosterone methyloxidase type 2 deficiency; Costello syndrome; Cowden syndrome 1; Coxa plana; Craniodiaphyseal dysplasia, autosomal dominant; Craniosynostosis 1 and 4; Craniosynostosis and dental anomalies; Creatine deficiency, X-linked; Crouzon syndrome; Cryptophthalmos syndrome; Cryptorchidism, unilateral or bilateral; Cushing symphalangism; Cutaneous malignant melanoma 1; Cutis laxa with osteodystrophy and with severe pulmonary, gastrointestinal, and urinary abnormalities; Cyanosis, transient neonatal and atypical nephropathic; Cystic fibrosis; Cystinuria; Cytochrome c oxidase i deficiency; Cytochrome-c oxidase deficiency; D-2-hydroxyglutaric aciduria 2; Darier disease, segmental; Deafness with labyrinthine aplasia microtia and microdontia (LAMM); Deafness, autosomal dominant 3a, 4, 12, 13, 15, autosomal dominant nonsyndromic sensorineural 17, 20, and 65; Deafness, autosomal recessive 1A, 2, 3, 6, 8, 9, 12, 15, 16, 18b, 22, 28, 31, 44, 49, 63, 77, 86, and 89; Deafness, cochlear, with myopia and intellectual impairment, without vestibular involvement, autosomal dominant, X-linked 2; Deficiency of 2-methylbutyryl-CoA dehydrogenase; Deficiency of 3-hydroxyacyl-CoA dehydrogenase; Deficiency of alpha-mannosidase; Deficiency of aromatic-L-amino-acid decarboxylase; Deficiency of bisphosphoglycerate mutase; Deficiency of butyryl-CoA dehydrogenase; Deficiency of ferroxidase; Deficiency of galactokinase; Deficiency of guanidinoacetate methyltransferase; Deficiency of hyaluronoglucosaminidase; Deficiency of ribose-5-phosphate isomerase; Deficiency of steroid 11-beta-monooxygenase; Deficiency of UDPglucose-hexose-1-phosphate uridylyltransferase; Deficiency of xanthine oxidase; Dejerine-Sottas disease; Charcot-Marie-Tooth disease, types ID and IVF; Dejerine-Sottas syndrome, autosomal dominant; Dendritic cell, monocyte, B lymphocyte, and natural killer lymphocyte deficiency; Desbuquois dysplasia 2; Desbuquois syndrome; DFNA 2 Nonsyndromic Hearing Loss; Diabetes mellitus and insipidus with optic atrophy and deafness; Diabetes mellitus, type 2, and insulin-dependent, 20; Diamond-Blackfan anemia 1, 5, 8, and 10; Diarrhea 3 (secretory sodium, congenital, syndromic) and 5 (with tufting enteropathy, congenital); Dicarboxylic aminoaciduria; Diffuse palmoplantar keratoderma, Bothnian type; Digitorenocerebral syndrome; Dihydropteridine reductase deficiency; Dilated cardiomyopathy 1A, 1AA, 1C, 1G, 1BB, 1DD, 1FF, 1HH, 1I, 1KK, 1N, 1S, 1Y, and 3B; Left ventricular noncompaction 3; Disordered steroidogenesis due to cytochrome p450 oxidoreductase deficiency; Distal arthrogryposis type 2B; Distal hereditary motor neuronopathy type 2B; Distal myopathy Markesbery-Griggs type; Distal spinal muscular atrophy, X-linked 3; Distichiasis-lymphedema syndrome; Dominant dystrophic epidermolysis bullosa with absence of skin; Dominant hereditary optic atrophy; Donnai Barrow syndrome; Dopamine beta hydroxylase deficiency; Dopamine receptor d2, reduced brain density of; Dowling-degos disease 4; Doyne honeycomb retinal dystrophy; Malattia leventinese; Duane syndrome type 2; Dubin-Johnson syndrome; Duchenne muscular dystrophy; Becker muscular dystrophy; Dysfibrinogenemia; Dyskeratosis congenita autosomal dominant and autosomal dominant, 3; Dyskeratosis congenita, autosomal recessive, 1, 3, 4, and 5; Dyskeratosis congenita X-linked; Dyskinesia, familial, with facial myokymia; Dysplasminogenemia; Dystonia 2 (torsion, autosomal recessive), 3 (torsion, X-linked), 5 (Dopa-responsive type), 10, 12, 16, 25, 26 (Myoclonic); Seizures, benign familial infantile, 2; Early infantile epileptic encephalopathy 2, 4, 7, 9, 10, 11, 13, and 14; Atypical Rett syndrome; Early T cell progenitor acute lymphoblastic leukemia; Ectodermal dysplasia skin fragility syndrome; Ectodermal dysplasia-syndactyly syndrome 1; Ectopia lentis, isolated autosomal recessive and dominant; Ectrodactyly, ectodermal dysplasia, and cleft lip/palate syndrome 3; Ehlers-Danlos syndrome type 7 (autosomal recessive), classic type, type 2 (progeroid), hydroxylysine-deficient, type 4, type 4 variant, and due to tenascin-X deficiency; Eichsfeld type congenital muscular dystrophy; Endocrine-cerebroosteodysplasia; Enhanced s-cone syndrome; Enlarged vestibular aqueduct syndrome; Enterokinase deficiency; Epidermodysplasia verruciformis; Epidermolysa bullosa simplex and limb girdle muscular dystrophy, simplex with mottled pigmentation, simplex with pyloric atresia, simplex, autosomal recessive, and with pyloric atresia; Epidermolytic palmoplantar keratoderma; Familial febrile seizures 8; Epilepsy, childhood absence 2, 12 (idiopathic generalized, susceptibility to) 5 (nocturnal frontal lobe), nocturnal frontal lobe type 1, partial, with variable foci, progressive myoclonic 3, and X-linked, with variable learning disabilities and behavior disorders; Epileptic encephalopathy, childhood-onset, early infantile, 1, 19, 23, 25, 30, and 32; Epiphyseal dysplasia, multiple, with myopia and conductive deafness; Episodic ataxia type 2; Episodic pain syndrome, familial, 3; Epstein syndrome; Fechtner syndrome; Erythropoietic protoporphyria; Estrogen resistance; Exudative vitreoretinopathy 6; Fabry disease and Fabry disease, cardiac variant; Factor H, VII, X, v and factor viii, combined deficiency of 2, xiii, a subunit, deficiency; Familial adenomatous polyposis 1 and 3; Familial amyloid nephropathy with urticaria and deafness; Familial cold urticarial; Familial aplasia of the vermis; Familial benign pemphigus; Familial cancer of breast; Breast cancer, susceptibility to; Osteosarcoma; Pancreatic cancer 3; Familial cardiomyopathy; Familial cold autoinflammatory syndrome 2; Familial colorectal cancer; Familial exudative vitreoretinopathy, X-linked; Familial hemiplegic migraine types 1 and 2; Familial hypercholesterolemia; Familial hypertrophic cardiomyopathy 1, 2, 3, 4, 7, 10, 23 and 24; Familial hypokalemia-hypomagnesemia; Familial hypoplastic, glomerulocystic kidney; Familial infantile myasthenia; Familial juvenile gout; Familial Mediterranean fever and Familial mediterranean fever, autosomal dominant; Familial porencephaly; Familial porphyria cutanea tarda; Familial pulmonary capillary hemangiomatosis; Familial renal glucosuria; Familial renal hypouricemia; Familial restrictive cardiomyopathy 1; Familial type 1 and 3 hyperlipoproteinemia; Fanconi anemia, complementation group E, I, N, and O; Fanconi-Bickel syndrome; Favism, susceptibility to; Febrile seizures, familial, 11; Feingold syndrome 1; Fetal hemoglobin quantitative trait locus 1; FG syndrome and FG syndrome 4; Fibrosis of extraocular muscles, congenital, 1, 2, 3a (with or without extraocular involvement), 3b; Fish-eye disease; Fleck corneal dystrophy; Floating-Harbor syndrome; Focal epilepsy with speech disorder with or without mental retardation; Focal segmental glomerulosclerosis 5; Forebrain defects; Frank Ter Haar syndrome; Borrone Di Rocco Crovato syndrome; Frasier syndrome; Wilms tumor 1; Freeman-Sheldon syndrome; Frontometaphyseal dysplasia land 3; Frontotemporal dementia; Frontotemporal dementia and/or amyotrophic lateral sclerosis 3 and 4; Frontotemporal Dementia Chromosome 3-Linked and Frontotemporal dementia ubiquitin-positive; Fructose-biphosphatase deficiency; Fuhrmann syndrome; Gamma-aminobutyric acid transaminase deficiency; Gamstorp-Wohlfart syndrome; Gaucher disease type 1 and Subacute neuronopathic; Gaze palsy, familial horizontal, with progressive scoliosis; Generalized dominant dystrophic epidermolysis bullosa; Generalized epilepsy with febrile seizures plus 3, type 1, type 2; Epileptic encephalopathy Lennox-Gastaut type; Giant axonal neuropathy; Glanzmann thrombasthenia; Glaucoma 1, open angle, e, F, and G; Glaucoma 3, primary congenital, d; Glaucoma, congenital and Glaucoma, congenital, Coloboma; Glaucoma, primary open angle, juvenile-onset; Glioma susceptibility 1; Glucose transporter type 1 deficiency syndrome; Glucose-6-phosphate transport defect; GLUT1 deficiency syndrome 2; Epilepsy, idiopathic generalized, susceptibility to, 12; Glutamate formiminotransferase deficiency; Glutaric acidemia IIA and IIB; Glutaric aciduria, type 1; Gluthathione synthetase deficiency; Glycogen storage disease 0 (muscle), II (adult form), IXa2, IXc, type 1A; type II, type IV, IV (combined hepatic and myopathic), type V, and type VI; Goldmann-Favre syndrome; Gordon syndrome; Gorlin syndrome; Holoprosencephaly sequence; Holoprosencephaly 7; Granulomatous disease, chronic, X-linked, variant; Granulosa cell tumor of the ovary; Gray platelet syndrome; Griscelli syndrome type 3; Groenouw corneal dystrophy type I; Growth and mental retardation, mandibulofacial dysostosis, microcephaly, and cleft palate; Growth hormone deficiency with pituitary anomalies; Growth hormone insensitivity with immunodeficiency; GTP cyclohydrolase I deficiency; Hajdu-Cheney syndrome; Hand foot uterus syndrome; Hearing impairment; Hemangioma, capillary infantile; Hematologic neoplasm; Hemochromatosis type 1, 2B, and 3; Microvascular complications of diabetes 7; Transferrin serum level quantitative trait locus 2; Hemoglobin H disease, nondeletional; Hemolytic anemia, nonspherocytic, due to glucose phosphate isomerase deficiency; Hemophagocytic lymphohistiocytosis, familial, 2; Hemophagocytic lymphohistiocytosis, familial, 3; Heparin cofactor II deficiency; Hereditary acrodermatitis enteropathica; Hereditary breast and ovarian cancer syndrome; Ataxia-telangiectasia-like disorder; Hereditary diffuse gastric cancer; Hereditary diffuse leukoencephalopathy with spheroids; Hereditary factors II, IX, VIII deficiency disease; Hereditary hemorrhagic telangiectasia type 2; Hereditary insensitivity to pain with anhidrosis; Hereditary lymphedema type I; Hereditary motor and sensory neuropathy with optic atrophy; Hereditary myopathy with early respiratory failure; Hereditary neuralgic amyotrophy; Hereditary Nonpolyposis Colorectal Neoplasms; Lynch syndrome I and II; Hereditary pancreatitis; Pancreatitis, chronic, susceptibility to; Hereditary sensory and autonomic neuropathy type IIB and IIA; Hereditary sideroblastic anemia; Hermansky-Pudlak syndrome 1, 3, 4, and 6; Heterotaxy, visceral, 2, 4, and 6, autosomal; Heterotaxy, visceral, X-linked; Heterotopia; Histiocytic medullary reticulosis; Histiocytosis-lymphadenopathy plus syndrome; Holocarboxylase synthetase deficiency; Holoprosencephaly 2, 3, 7, and 9; Holt-Oram syndrome; Homocysteinemia due to MTHFR deficiency, CBS deficiency, and Homocystinuria, pyridoxine-responsive; Homocystinuria-Megaloblastic anemia due to defect in cobalamin metabolism, cblE complementation type; Howel-Evans syndrome; Hurler syndrome; Hutchinson-Gilford syndrome; Hydrocephalus; Hyperammonemia, type III; Hypercholesterolaemia and Hypercholesterolemia, autosomal recessive; Hyperekplexia 2 and Hyperekplexia hereditary; Hyperferritinemia cataract syndrome; Hyperglycinuria; Hyperimmunoglobulin D with periodic fever; Mevalonic aciduria; Hyperimmunoglobulin E syndrome; Hyperinsulinemic hypoglycemia familial 3, 4, and 5; Hyperinsulinism-hyperammonemia syndrome; Hyperlysinemia; Hypermanganesemia with dystonia, polycythemia and cirrhosis; Hyperornithinemia-hyperammonemia-homocitrullinuria syndrome; Hyperparathyroidism 1 and 2; Hyperparathyroidism, neonatal severe; Hyperphenylalaninemia, bh4-deficient, a, due to partial pts deficiency, BH4-deficient, D, and non-pku; Hyperphosphatasia with mental retardation syndrome 2, 3, and 4; Hypertrichotic osteochondrodysplasia; Hypobetalipoproteinemia, familial, associated with apob32; Hypocalcemia, autosomal dominant 1; Hypocalciuric hypercalcemia, familial, types 1 and 3; Hypochondrogenesis; Hypochromic microcytic anemia with iron overload; Hypoglycemia with deficiency of glycogen synthetase in the liver; Hypogonadotropic hypogonadism 11 with or without anosmia; Hypohidrotic ectodermal dysplasia with immune deficiency; Hypohidrotic X-linked ectodermal dysplasia; Hypokalemic periodic paralysis 1 and 2; Hypomagnesemia 1, intestinal; Hypomagnesemia, seizures, and mental retardation; Hypomyelinating leukodystrophy 7; Hypoplastic left heart syndrome; Atrioventricular septal defect and common atrioventricular junction; Hypospadias 1 and 2, X-linked; Hypothyroidism, congenital, nongoitrous, 1; Hypotrichosis 8 and 12; Hypotrichosis-lymphedema-telangiectasia syndrome; I blood group system; Ichthyosis bullosa of Siemens; Ichthyosis exfoliativa; Ichthyosis prematurity syndrome; Idiopathic basal ganglia calcification 5; Idiopathic fibrosing alveolitis, chronic form; Dyskeratosis congenita, autosomal dominant, 2 and 5; Idiopathic hypercalcemia of infancy; Immune dysfunction with T-cell inactivation due to calcium entry defect 2; Immunodeficiency 15, 16, 19, 30, 31C, 38, 40, 8, due to defect in cd3-zeta, with hyper IgM type 1 and 2, and X-Linked, with magnesium defect, Epstein-Barr virus infection, and neoplasia; Immunodeficiency-centromeric instability-facial anomalies syndrome 2; Inclusion body myopathy 2 and 3; Nonaka myopathy; Infantile convulsions and paroxysmal choreoathetosis, familial; Infantile cortical hyperostosis; Infantile GM1 gangliosidosis; Infantile hypophosphatasia; Infantile nephronophthisis; Infantile nystagmus, X-linked; Infantile Parkinsonism-dystonia; Infertility associated with multi-tailed spermatozoa and excessive DNA; Insulin resistance; Insulin-resistant diabetes mellitus and acanthosis nigricans; Insulin-dependent diabetes mellitus secretory diarrhea syndrome; Interstitial nephritis, karyomegalic; Intrauterine growth retardation, metaphyseal dysplasia, adrenal hypoplasia congenita, and genital anomalies; Iodotyrosyl coupling defect; IRAK4 deficiency; Iridogoniodysgenesis dominant type and type 1; Iron accumulation in brain; Ischiopatellar dysplasia; Islet cell hyperplasia; Isolated 17,20-lyase deficiency; Isolated lutropin deficiency; Isovaleryl-CoA dehydrogenase deficiency; Jankovic Rivera syndrome; Jervell and Lange-Nielsen syndrome 2; Joubert syndrome 1, 6, 7, 9/15 (digenic), 14, 16, and 17, and Orofaciodigital syndrome xiv; Junctional epidermolysis bullosa gravis of Herlitz; Juvenile GM>1< gangliosidosis; Juvenile polyposis syndrome; Juvenile polyposis/hereditary hemorrhagic telangiectasia syndrome; Juvenile retinoschisis; Kabuki make-up syndrome; Kallmann syndrome 1, 2, and 6; Delayed puberty; Kanzaki disease; Karak syndrome; Kartagener syndrome; Kenny-Caffey syndrome type 2; Keppen-Lubinsky syndrome; Keratoconus 1; Keratosis follicularis; Keratosis palmoplantaris striata 1; Kindler syndrome; L-2-hydroxyglutaric aciduria; Larsen syndrome, dominant type; Lattice corneal dystrophy Type III; Leber amaurosis; Zellweger syndrome; Peroxisome biogenesis disorders; Zellweger syndrome spectrum; Leber congenital amaurosis 11, 12, 13, 16, 4, 7, and 9; Leber optic atrophy; Aminoglycoside-induced deafness; Deafness, nonsyndromic sensorineural, mitochondrial; Left ventricular noncompaction 5; Left-right axis malformations; Leigh disease; Mitochondrial short-chain Enoyl-CoA Hydratase 1 deficiency; Leigh syndrome due to mitochondrial complex I deficiency; Leiner disease; Leri Weill dyschondrosteosis; Lethal congenital contracture syndrome 6; Leukocyte adhesion deficiency type I and III; Leukodystrophy, Hypomyelinating, 11 and 6; Leukoencephalopathy with ataxia, with Brainstem and Spinal Cord Involvement and Lactate Elevation, with vanishing white matter, and progressive, with ovarian failure; Leukonychia totalis; Lewy body dementia; Lichtenstein-Knorr Syndrome; Li-Fraumeni syndrome 1; Lig4 syndrome; Limb-girdle muscular dystrophy, type 1B, 2A, 2B, 2D, C1, C5, C9, C14; Congenital muscular dystrophy-dystroglycanopathy with brain and eye anomalies, type A14 and B14; Lipase deficiency combined; Lipid proteinosis; Lipodystrophy, familial partial, type 2 and 3; Lissencephaly 1, 2 (X-linked), 3, 6 (with microcephaly), X-linked; Subcortical laminar heterotopia, X-linked; Liver failure acute infantile; Loeys-Dietz syndrome 1, 2, 3; Long QT syndrome 1, 2, 2/9, 2/5, (digenic), 3, 5 and 5, acquired, susceptibility to; Lung cancer; Lymphedema, hereditary, id; Lymphedema, primary, with myelodysplasia; Lymphoproliferative syndrome 1, 1 (X-linked), and 2; Lysosomal acid lipase deficiency; Macrocephaly, macrosomia, facial dysmorphism syndrome; Macular dystrophy, vitelliform, adult-onset; Malignant hyperthermia susceptibility type 1; Malignant lymphoma, non-Hodgkin; Malignant melanoma; Malignant tumor of prostate; Mandibuloacral dysostosis; Mandibuloacral dysplasia with type A or B lipodystrophy, atypical; Mandibulofacial dysostosis, Treacher Collins type, autosomal recessive; Mannose-binding protein deficiency; Maple syrup urine disease type 1A and type 3; Marden Walker like syndrome; Marfan syndrome; Marinesco-Sj\xc3\xb6gren syndrome; Martsolf syndrome; Maturity-onset diabetes of the young, type 1, type 2, type 11, type 3, and type 9; May-Hegglin anomaly; MYH9 related disorders; Sebastian syndrome; McCune-Albright syndrome; Somatotroph adenoma; Sex cord-stromal tumor; Cushing syndrome; McKusick Kaufman syndrome; McLeod neuroacanthocytosis syndrome; Meckel-Gruber syndrome; Medium-chain acyl-coenzyme A dehydrogenase deficiency; Medulloblastoma; Megalencephalic leukoencephalopathy with subcortical cysts land 2a; Megalencephaly cutis marmorata telangiectatica congenital; PIK3CA Related Overgrowth Spectrum; Megalencephaly-polymicrogyria-polydactyly-hydrocephalus syndrome 2; Megaloblastic anemia, thiamine-responsive, with diabetes mellitus and sensorineural deafness; Meier-Gorlin syndromes land 4; Melnick-Needles syndrome; Meningioma; Mental retardation, X-linked, 3, 21, 30, and 72; Mental retardation and microcephaly with pontine and cerebellar hypoplasia; Mental retardation X-linked syndromic 5; Mental retardation, anterior maxillary protrusion, and strabismus; Mental retardation, autosomal dominant 12, 13, 15, 24, 3, 30, 4, 5, 6, and 9; Mental retardation, autosomal recessive 15, 44, 46, and 5; Mental retardation, stereotypic movements, epilepsy, and/or cerebral malformations; Mental retardation, syndromic, Claes-Jensen type, X-linked; Mental retardation, X-linked, nonspecific, syndromic, Hedera type, and syndromic, wu type; Merosin deficient congenital muscular dystrophy; Metachromatic leukodystrophy juvenile, late infantile, and adult types; Metachromatic leukodystrophy; Metatrophic dysplasia; Methemoglobinemia types I and 2; Methionine adenosyltransferase deficiency, autosomal dominant; Methylmalonic acidemia with homocystinuria; Methylmalonic aciduria cblB type; Methylmalonic aciduria due to methylmalonyl-CoA mutase deficiency; METHYLMALONIC ACIDURIA, mut(0) TYPE; Microcephalic osteodysplastic primordial dwarfism type 2; Microcephaly with or without chorioretinopathy, lymphedema, or mental retardation; Microcephaly, hiatal hernia and nephrotic syndrome; Microcephaly; Hypoplasia of the corpus callosum; Spastic paraplegia 50, autosomal recessive; Global developmental delay; CNS hypomyelination; Brain atrophy; Microcephaly, normal intelligence and immunodeficiency; Microcephaly-capillary malformation syndrome; Microcytic anemia; Microphthalmia syndromic 5, 7, and 9; Microphthalmia, isolated 3, 5, 6, 8, and with coloboma 6; Microspherophakia; Migraine, familial basilar; Miller syndrome; Minicore myopathy with external ophthalmoplegia; Myopathy, congenital with cores; Mitchell-Riley syndrome; mitochondrial 3-hydroxy-3-methylglutaryl-CoA synthase deficiency; Mitochondrial complex I, II, III, III (nuclear type 2, 4, or 8) deficiency; Mitochondrial DNA depletion syndrome 11, 12 (cardiomyopathic type), 2, 4B (MNGIE type), 8B (MNGIE type); Mitochondrial DNA-depletion syndrome 3 and 7, hepatocerebral types, and 13 (encephalomyopathic type); Mitochondrial phosphate carrier and pyruvate carrier deficiency; Mitochondrial trifunctional protein deficiency; Long-chain 3-hydroxyacyl-CoA dehydrogenase deficiency; Miyoshi muscular dystrophy 1; Myopathy, distal, with anterior tibial onset; Mohr-Tranebjaerg syndrome; Molybdenum cofactor deficiency, complementation group A; Mowat-Wilson syndrome; Mucolipidosis III Gamma; Mucopolysaccharidosis type VI, type VI (severe), and type VII; Mucopolysaccharidosis, MPS-I-H/S, MPS-II, MPS-III-A, MPS-III-B, MPS-III-C, MPS-IV-A, MPS-IV-B; Retinitis Pigmentosa 73; Gangliosidosis GM1 type1 (with cardiac involvement) 3; Multicentric osteolysis nephropathy; Multicentric osteolysis, nodulosis and arthropathy; Multiple congenital anomalies; Atrial septal defect 2; Multiple congenital anomalies-hypotonia-seizures syndrome 3; Multiple Cutaneous and Mucosal Venous Malformations; Multiple endocrine neoplasia, types land 4; Multiple epiphyseal dysplasia 5 or Dominant; Multiple gastrointestinal atresias; Multiple pterygium syndrome Escobar type; Multiple sulfatase deficiency; Multiple synostoses syndrome 3; Muscle AMP guanine oxidase deficiency; Muscle eye brain disease; Muscular dystrophy, congenital, megaconial type; Myasthenia, familial infantile, 1; Myasthenic Syndrome, Congenital, 11, associated with acetylcholine receptor deficiency; Myasthenic Syndrome, Congenital, 17, 2A (slow-channel), 4B (fast-channel), and without tubular aggregates; Myeloperoxidase deficiency; MYH-associated polyposis; Endometrial carcinoma; Myocardial infarction 1; Myoclonic dystonia; Myoclonic-Atonic Epilepsy; Myoclonus with epilepsy with ragged red fibers; Myofibrillar myopathy 1 and ZASP-related; Myoglobinuria, acute recurrent, autosomal recessive; Myoneural gastrointestinal encephalopathy syndrome; Cerebellar ataxia infantile with progressive external ophthalmoplegia; Mitochondrial DNA depletion syndrome 4B, MNGIE type; Myopathy, centronuclear, 1, congenital, with excess of muscle spindles, distal, 1, lactic acidosis, and sideroblastic anemia 1, mitochondrial progressive with congenital cataract, hearing loss, and developmental delay, and tubular aggregate, 2; Myopia 6; Myosclerosis, autosomal recessive; Myotonia congenital; Congenital myotonia, autosomal dominant and recessive forms; Nail-patella syndrome; Nance-Horan syndrome; Nanophthalmos 2; Navajo neurohepatopathy; Nemaline myopathy 3 and 9; Neonatal hypotonia; Intellectual disability; Seizures; Delayed speech and language development; Mental retardation, autosomal dominant 31; Neonatal intrahepatic cholestasis caused by citrin deficiency; Nephrogenic diabetes insipidus, Nephrogenic diabetes insipidus, X-linked; Nephrolithiasis/osteoporosis, hypophosphatemic, 2; Nephronophthisis 13, 15 and 4; Infertility; Cerebello-oculo-renal syndrome (nephronophthisis, oculomotor apraxia and cerebellar abnormalities); Nephrotic syndrome, type 3, type 5, with or without ocular abnormalities, type 7, and type 9; Nestor-Guillermo progeria syndrome; Neu-Laxova syndrome 1; Neurodegeneration with brain iron accumulation 4 and 6; Neuroferritinopathy; Neurofibromatosis, type land type 2; Neurofibrosarcoma; Neurohypophyseal diabetes insipidus; Neuropathy, Hereditary Sensory, Type IC; Neutral 1 amino acid transport defect; Neutral lipid storage disease with myopathy; Neutrophil immunodeficiency syndrome; Nicolaides-Baraitser syndrome; Niemann-Pick disease type C1, C2, type A, and type C1, adult form; Non-ketotic hyperglycinemia; Noonan syndrome 1 and 4, LEOPARD syndrome 1; Noonan syndrome-like disorder with or without juvenile myelomonocytic leukemia; Normokalemic periodic paralysis, potassium-sensitive; Norum disease; Epilepsy, Hearing Loss, And Mental Retardation Syndrome; Mental Retardation, X-Linked 102 and syndromic 13; Obesity; Ocular albinism, type I; Oculocutaneous albinism type 1B, type 3, and type 4; Oculodentodigital dysplasia; Odontohypophosphatasia; Odontotrichomelic syndrome; Oguchi disease; Oligodontia-colorectal cancer syndrome; Opitz G/BBB syndrome; Optic atrophy 9; Oral-facial-digital syndrome; Ornithine aminotransferase deficiency; Orofacial cleft 11 and 7, Cleft lip/palate-ectodermal dysplasia syndrome; Orstavik Lindemann Solberg syndrome; Osteoarthritis with mild chondrodysplasia; Osteochondritis dissecans; Osteogenesis imperfecta type 12, type 5, type 7, type 8, type I, type III, with normal sclerae, dominant form, recessive perinatal lethal; Osteopathia striata with cranial sclerosis; Osteopetrosis autosomal dominant type 1 and 2, recessive 4, recessive 1, recessive 6; Osteoporosis with pseudoglioma; Oto-palato-digital syndrome, types I and II; Ovarian dysgenesis 1; Ovarioleukodystrophy; Pachyonychia congenita 4 and type 2; Paget disease of bone, familial; Pallister-Hall syndrome; Palmoplantar keratoderma, nonepidermolytic, focal or diffuse; Pancreatic agenesis and congenital heart disease; Papillon-Lef\xc3\xa8vre syndrome; Paragangliomas 3; Paramyotonia congenita of von Eulenburg; Parathyroid carcinoma; Parkinson disease 14, 15, 19 (juvenile-onset), 2, 20 (early-onset), 6, (autosomal recessive early-onset, and 9; Partial albinism; Partial hypoxanthine-guanine phosphoribosyltransferase deficiency; Patterned dystrophy of retinal pigment epithelium; PC-K6a; Pelizaeus-Merzbacher disease; Pendred syndrome; Peripheral demyelinating neuropathy, central dysmyelination; Hirschsprung disease; Permanent neonatal diabetes mellitus; Diabetes mellitus, permanent neonatal, with neurologic features; Neonatal insulin-dependent diabetes mellitus; Maturity-onset diabetes of the young, type 2; Peroxisome biogenesis disorder 14B, 2A, 4A, 5B, 6A, 7A, and 7B; Perrault syndrome 4; Perry syndrome; Persistent hyperinsulinemic hypoglycemia of infancy; familial hyperinsulinism; Phenotypes; Phenylketonuria; Pheochromocytoma; Hereditary Paraganglioma-Pheochromocytoma Syndromes; Paragangliomas 1; Carcinoid tumor of intestine; Cowden syndrome 3; Phosphoglycerate dehydrogenase deficiency; Phosphoglycerate kinase 1 deficiency; Photosensitive trichothiodystrophy; Phytanic acid storage disease; Pick disease; Pierson syndrome; Pigmentary retinal dystrophy; Pigmented nodular adrenocortical disease, primary, 1; Pilomatrixoma; Pitt-Hopkins syndrome; Pituitary dependent hypercortisolism; Pituitary hormone deficiency, combined 1, 2, 3, and 4; Plasminogen activator inhibitor type 1 deficiency; Plasminogen deficiency, type I; Platelet-type bleeding disorder 15 and 8; Poikiloderma, hereditary fibrosing, with tendon contractures, myopathy, and pulmonary fibrosis; Polycystic kidney disease 2, adult type, and infantile type; Polycystic lipomembranous osteodysplasia with sclerosing leukoencephalopathy; Polyglucosan body myopathy 1 with or without immunodeficiency; Polymicrogyria, asymmetric, bilateral frontoparietal; Polyneuropathy, hearing loss, ataxia, retinitis pigmentosa, and cataract; Pontocerebellar hypoplasia type 4; Popliteal pterygium syndrome; Porencephaly 2; Porokeratosis 8, disseminated superficial actinic type; Porphobilinogen synthase deficiency; Porphyria cutanea tarda; Posterior column ataxia with retinitis pigmentosa; Posterior polar cataract type 2; Prader-Willi-like syndrome; Premature ovarian failure 4, 5, 7, and 9; Primary autosomal recessive microcephaly 10, 2, 3, and 5; Primary ciliary dyskinesia 24; Primary dilated cardiomyopathy; Left ventricular noncompaction 6; 4, Left ventricular noncompaction 10; Paroxysmal atrial fibrillation; Primary hyperoxaluria, type I, type, and type III; Primary hypertrophic osteoarthropathy, autosomal recessive 2; Primary hypomagnesemia; Primary open angle glaucoma juvenile onset 1; Primary pulmonary hypertension; Primrose syndrome; Progressive familial heart block type 1B; Progressive familial intrahepatic cholestasis 2 and 3; Progressive intrahepatic cholestasis; Progressive myoclonus epilepsy with ataxia; Progressive pseudorheumatoid dysplasia; Progressive sclerosing poliodystrophy; Prolidase deficiency; Proline dehydrogenase deficiency; Schizophrenia 4; Properdin deficiency, X-linked; Propionic academia; Proprotein convertase 1/3 deficiency; Prostate cancer, hereditary, 2; Protan defect; Proteinuria; Finnish congenital nephrotic syndrome; Proteus syndrome; Breast adenocarcinoma; Pseudoachondroplastic spondyloepiphyseal dysplasia syndrome; Pseudohypoaldosteronism type 1 autosomal dominant and recessive and type 2; Pseudohypoparathyroidism type 1A, Pseudopseudohypoparathyroidism; Pseudoneonatal adrenoleukodystrophy; Pseudoprimary hyperaldosteronism; Pseudoxanthoma elasticum; Generalized arterial calcification of infancy 2; Pseudoxanthoma elasticum-like disorder with multiple coagulation factor deficiency; Psoriasis susceptibility 2; PTEN hamartoma tumor syndrome; Pulmonary arterial hypertension related to hereditary hemorrhagic telangiectasia; Pulmonary Fibrosis And/Or Bone Marrow Failure, Telomere-Related, 1 and 3; Pulmonary hypertension, primary, 1, with hereditary hemorrhagic telangiectasia; Purine-nucleoside phosphorylase deficiency; Pyruvate carboxylase deficiency; Pyruvate dehydrogenase E1-alpha deficiency; Pyruvate kinase deficiency of red cells; Raine syndrome; Rasopathy; Recessive dystrophic epidermolysis bullosa; Nail disorder, nonsyndromic congenital, 8; Reifenstein syndrome; Renal adysplasia; Renal carnitine transport defect; Renal coloboma syndrome; Renal dysplasia; Renal dysplasia, retinal pigmentary dystrophy, cerebellar ataxia and skeletal dysplasia; Renal tubular acidosis, distal, autosomal recessive, with late-onset sensorineural hearing loss, or with hemolytic anemia; Renal tubular acidosis, proximal, with ocular abnormalities and mental retardation; Retinal cone dystrophy 3B; Retinitis pigmentosa; Retinitis pigmentosa 10, 11, 12, 14, 15, 17, and 19; Retinitis pigmentosa 2, 20, 25, 35, 36, 38, 39, 4, 40, 43, 45, 48, 66, 7, 70, 72; Retinoblastoma; Rett disorder; Rhabdoid tumor predisposition syndrome 2; Rhegmatogenous retinal detachment, autosomal dominant; Rhizomelic chondrodysplasia punctata type 2 and type 3; Roberts-SC phocomelia syndrome; Robinow Sorauf syndrome; Robinow syndrome, autosomal recessive, autosomal recessive, with brachy-syn-polydactyly; Rothmund-Thomson syndrome; Rapadilino syndrome; RRM2B-related mitochondrial disease; Rubinstein-Taybi syndrome; Salla disease; Sandhoff disease, adult and infantil types; Sarcoidosis, early-onset; Blau syndrome; Schindler disease, type 1; Schizencephaly; Schizophrenia 15; Schneckenbecken dysplasia; Schwannomatosis 2; Schwartz Jampel syndrome type 1; Sclerocornea, autosomal recessive; Sclerosteosis; Secondary hypothyroidism; Segawa syndrome, autosomal recessive; Senior-Loken syndrome 4 and 5; Sensory ataxic neuropathy, dysarthria, and ophthalmoparesis; Sepiapterin reductase deficiency; SeSAME syndrome; Severe combined immunodeficiency due to ADA deficiency, with microcephaly, growth retardation, and sensitivity to ionizing radiation, atypical, autosomal recessive, T cell-negative, B cell-positive, NK cell-negative of NK-positive; Severe congenital neutropenia; Severe congenital neutropenia 3, autosomal recessive or dominant; Severe congenital neutropenia and 6, autosomal recessive; Severe myoclonic epilepsy in infancy; Generalized epilepsy with febrile seizures plus, types 1 and 2; Severe X-linked myotubular myopathy; Short QT syndrome 3; Short stature with nonspecific skeletal abnormalities; Short stature, auditory canal atresia, mandibular hypoplasia, skeletal abnormalities; Short stature, onychodysplasia, facial dysmorphism, and hypotrichosis; Primordial dwarfism; Short-rib thoracic dysplasia 11 or 3 with or without polydactyly; Sialidosis type I and II; Silver spastic paraplegia syndrome; Slowed nerve conduction velocity, autosomal dominant; Smith-Lemli-Opitz syndrome; Snyder Robinson syndrome; Somatotroph adenoma; Prolactinoma; familial, Pituitary adenoma predisposition; Sotos syndrome 1 or 2; Spastic ataxia 5, autosomal recessive, Charlevoix-Saguenay type, 1, 10, or 11, autosomal recessive; Amyotrophic lateral sclerosis type 5; Spastic paraplegia 15, 2, 3, 35, 39, 4, autosomal dominant, 55, autosomal recessive, and 5A; Bile acid synthesis defect, congenital, 3; Spermatogenic failure 11, 3, and 8; Spherocytosis types 4 and 5; Spheroid body myopathy; Spinal muscular atrophy, lower extremity predominant 2, autosomal dominant; Spinal muscular atrophy, type II; Spinocerebellar ataxia 14, 21, 35, 40, and 6; Spinocerebellar ataxia autosomal recessive 1 and 16; Splenic hypoplasia; Spondylocarpotarsal synostosis syndrome; Spondylocheirodysplasia, Ehlers-Danlos syndrome-like, with immune dysregulation, Aggrecan type, with congenital joint dislocations, short limb-hand type, Sedaghatian type, with cone-rod dystrophy, and Kozlowski type; Parastremmatic dwarfism; Stargardt disease 1; Cone-rod dystrophy 3; Stickler syndrome type 1; Kniest dysplasia; Stickler syndrome, types 1 (nonsyndromic ocular) and 4; Sting-associated vasculopathy, infantile-onset; Stormorken syndrome; Sturge-Weber syndrome, Capillary malformations, congenital, 1; Succinyl-CoA acetoacetate transferase deficiency; Sucrase-isomaltase deficiency; Sudden infant death syndrome; Sulfite oxidase deficiency, isolated; Supravalvar aortic stenosis; Surfactant metabolism dysfunction, pulmonary, 2 and 3; Symphalangism, proximal, 1b; Syndactyly Cenani Lenz type; Syndactyly type 3; Syndromic X-linked mental retardation 16; Talipes equinovarus; Tangier disease; TARP syndrome; Tay-Sachs disease, B1 variant, Gm2-gangliosidosis (adult), Gm2-gangliosidosis (adult-onset); Temtamy syndrome; Tenorio Syndrome; Terminal osseous dysplasia; Testosterone 17-beta-dehydrogenase deficiency; Tetraamelia, autosomal recessive; Tetralogy of Fallot; Hypoplastic left heart syndrome 2; Truncus arteriosus; Malformation of the heart and great vessels; Ventricular septal defect 1; Thiel-Behnke corneal dystrophy; Thoracic aortic aneurysms and aortic dissections; Marfanoid habitus; Three M syndrome 2; Thrombocytopenia, platelet dysfunction, hemolysis, and imbalanced globin synthesis; Thrombocytopenia, X-linked; Thrombophilia, hereditary, due to protein C deficiency, autosomal dominant and recessive; Thyroid agenesis; Thyroid cancer, follicular; Thyroid hormone metabolism, abnormal; Thyroid hormone resistance, generalized, autosomal dominant; Thyrotoxic periodic paralysis and Thyrotoxic periodic paralysis 2; Thyrotropin-releasing hormone resistance, generalized; Timothy syndrome; TNF receptor-associated periodic fever syndrome (TRAPS); Tooth agenesis, selective, 3 and 4; Torsades de pointes; Townes-Brocks-branchiootorenal-like syndrome; Transient bullous dermolysis of the newborn; Treacher collins syndrome 1; Trichomegaly with mental retardation, dwarfism and pigmentary degeneration of retina; Trichorhinophalangeal dysplasia type I; Trichorhinophalangeal syndrome type 3; Trimethylaminuria; Tuberous sclerosis syndrome; Lymphangiomyomatosis; Tuberous sclerosis 1 and 2; Tyrosinase-negative oculocutaneous albinism; Tyrosinase-positive oculocutaneous albinism; Tyrosinemia type I; UDPglucose-4-epimerase deficiency; Ullrich congenital muscular dystrophy; Ulna and fibula absence of with severe limb deficiency; Upshaw-Schulman syndrome; Urocanate hydratase deficiency; Usher syndrome, types 1, 1B, 1D, 1G, 2A, 2C, and 2D; Retinitis pigmentosa 39; UV-sensitive syndrome; Van der Woude syndrome; Van Maldergem syndrome 2; Hennekam lymphangiectasia-lymphedema syndrome 2; Variegate porphyria; Ventriculomegaly with cystic kidney disease; Verheij syndrome; Very long chain acyl-CoA dehydrogenase deficiency; Vesicoureteral reflux 8; Visceral heterotaxy 5, autosomal; Visceral myopathy; Vitamin D-dependent rickets, types land 2; Vitelliform dystrophy; von Willebrand disease type 2M and type 3; Waardenburg syndrome type 1, 4C, and 2E (with neurologic involvement); Klein-Waardenberg syndrome; Walker-Warburg congenital muscular dystrophy; Warburg micro syndrome 2 and 4; Warts, hypogammaglobulinemia, infections, and myelokathexis; Weaver syndrome; Weill-Marchesani syndrome 1 and 3; Weill-Marchesani-like syndrome; Weissenbacher-Zweymuller syndrome; Werdnig-Hoffmann disease; Charcot-Marie-Tooth disease; Werner syndrome; WFS1-Related Disorders; Wiedemann-Steiner syndrome; Wilson disease; Wolfram-like syndrome, autosomal dominant; Worth disease; Van Buchem disease type 2; Xeroderma pigmentosum, complementation group b, group D, group E, and group G; X-linked agammaglobulinemia; X-linked hereditary motor and sensory neuropathy; X-linked ichthyosis with steryl-sulfatase deficiency; X-linked periventricular heterotopia; Oto-palato-digital syndrome, type I; X-linked severe combined immunodeficiency; Zimmermann-Laband syndrome and Zimmermann-Laband syndrome 2; and Zonular pulverulent cataract 3.

In a particular aspect, the instant disclosure provides TPRT-based methods for the treatment of a subject diagnosed with an expansion repeat disorder (also known as a repeat expansion disorder or a trinucleotide repeat disorder). Expansion repeat disorders occur when microsatellite repeats expand beyond a threshold length. Currently, at least 30 genetic diseases are believed to be caused by repeat expansions. Scientific understanding of this diverse group of disorders came to lights in the early 1990's with the discovery that trinucleotide repeats underlie several major inherited conditions, including Fragile X, Spinal and Bulbar Muscular Atrophy, Myotonic Dystrophy, and Huntington's disease (Nelson et al, "The unstable repeats—three evolving faces of neurological disease," *Neuron*, Mar. 6, 2013, Vol. 77; 825-843, which is incorporated herein by reference), as well as Haw River Syndrome, Jacobsen Syndrome, Dentatorubral-pallidoluysian atrophy (DRPLA), Machado-Joseph disease, Synpolydactyly (SPD II), Hand-foot genital syndrome (HFGS), Cleidocranial dysplasia (CCD), Holoprosencephaly disorder (HPE), Congenital central hypventilation syndrome (CCHS), ARX-nonsyndromic X-linked mental retardation (XLMR), and Oculopharyngeal muscular dystrophy (OPMD) (see. Microsatellite repeat instability was found to be a hallmark of these conditions, as was anticipation—the phenomenon in which repeat expansion can occur with each successive generation, which leads to a more severe phenotype and earlier age of onset in the offspring. Repeat expansions are believed to cause diseases via several different mechanisms. Namely, expansions may interfere with cellular functioning at the level of the gene, the mRNA transcript, and/or the encoded protein. In some conditions, mutations act via a loss-of-function mechanism by silencing repeat-containing genes. In others, disease results from gain-of-function mechanisms, whereby either the mRNA transcript or protein takes on new, aberrant functions.

Pharmaceutical Compositions

Other aspects of the present disclosure relate to pharmaceutical compositions comprising any of the various components of the prime editing system described herein (e.g., including, but not limited to, the napRNAbps, RDRPs, fusion proteins (e.g., comprising napRNAbp:RDRP fusions), rpegRNAs, and complexes comprising fusion proteins and rpegRNAs, as well as accessory elements.

The term "pharmaceutical composition", as used herein, refers to a composition formulated for pharmaceutical use. In some embodiments, the pharmaceutical composition further comprises a pharmaceutically acceptable carrier. In some embodiments, the pharmaceutical composition comprises additional agents (e.g. for specific delivery, increasing half-life, or other therapeutic compounds).

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, the pharmaceutical composition is formulated for delivery to a subject, e.g., for gene editing. Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration.

In some embodiments, the pharmaceutical composition described herein is administered locally to a diseased site (e.g., tumor site). In some embodiments, the pharmaceutical composition described herein is administered to a subject by injection, by means of a catheter, by means of a suppository, or by means of an implant, the implant being of a porous, non-porous, or gelatinous material, including a membrane, such as a sialastic membrane, or a fiber.

In other embodiments, the pharmaceutical composition described herein is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105). Other controlled release systems are discussed, for example, in Langer, supra.

In some embodiments, the pharmaceutical composition is formulated in accordance with routine procedures as a composition adapted for intravenous or subcutaneous administration to a subject, e.g., a human. In some embodiments, pharmaceutical composition for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. Compounds can be entrapped in "stabilized plasmid-lipid particles" (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., *Gene Ther.* 1999, 6:1438-47). Positively charged lipids such as N-[1-(2,3-dioleoyloxi)propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757; each of which is incorporated herein by reference.

The pharmaceutical composition described herein may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

Further, the pharmaceutical composition can be provided as a pharmaceutical kit comprising (a) a container containing a compound of the invention in lyophilized form and (b) a second container containing a pharmaceutically acceptable diluent (e.g., sterile water) for injection. The pharmaceutically acceptable diluent can be used for reconstitution or dilution of the lyophilized compound of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierce-able by a hypodermic injection needle. The active agent in the composition is a compound of the invention. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

Viral Delivery Methods

Figure 2:
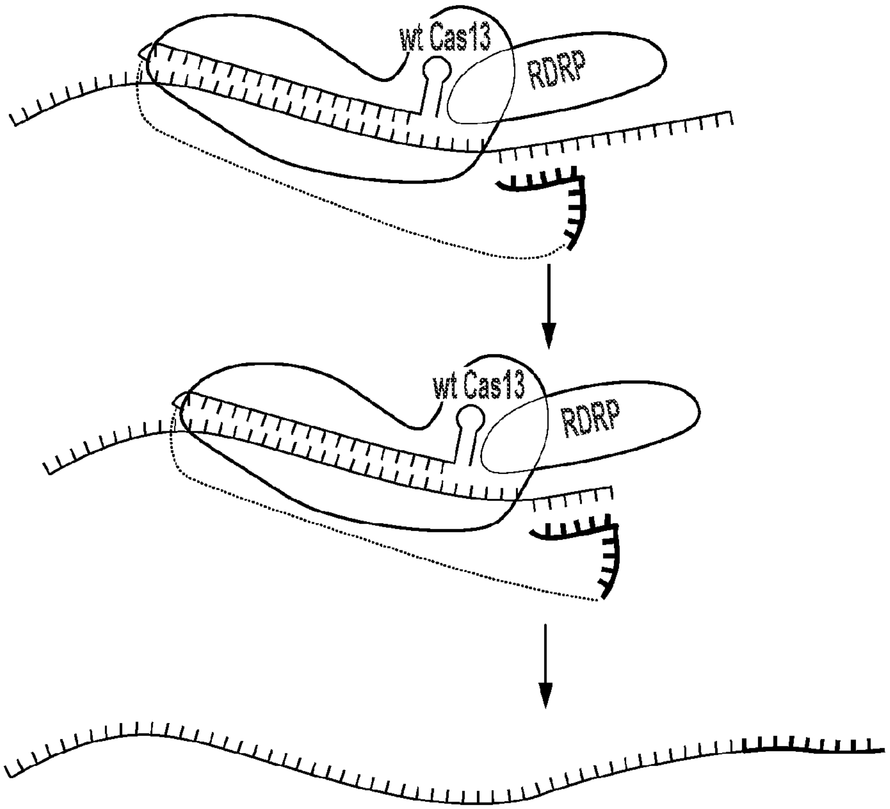
FIG. 2 shows an illustration of wild-type Cas13:RDRP fusion targeting an internal site within an RNA substrate to enable RPE.
Figure 3:
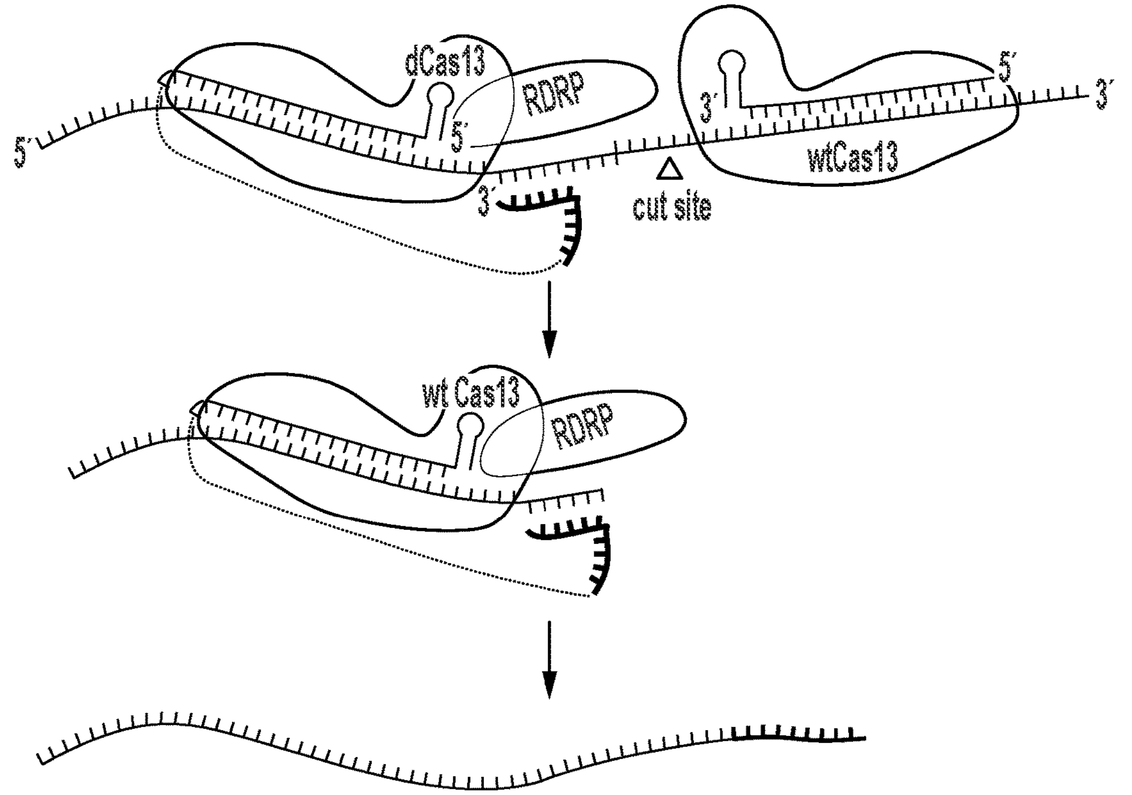
FIG. 3 shows an illustration of a tandem dCas13:RDRP wtCas13 strategy for affecting RPE at an internal site within an RNA substrate.
Figure 4:
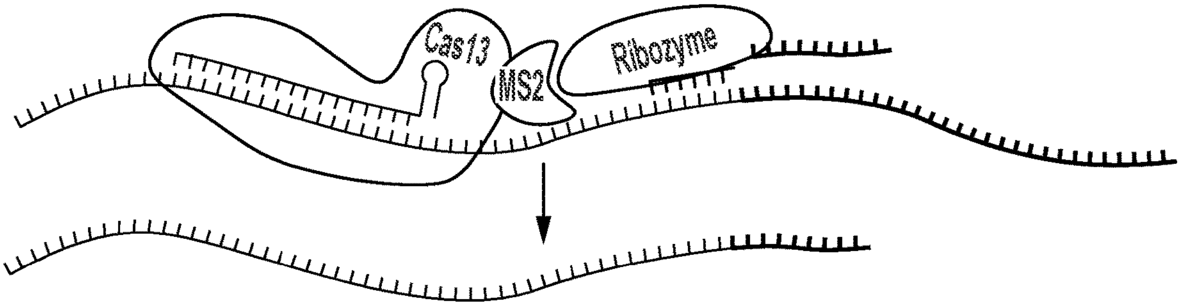
FIG. 4 shows an illustration of Cas13:MS2 fusion protein recruiting a trans-splicing ribozyme to an messenger RNA (mRNA) transcript to affect RNA editing.

In some aspects, the invention provides methods comprising delivering one or more polynucleotides, such as or one or more vectors as described herein encoding one or more components of the RNA prime editor (RPE) system described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a RNA prime editor as described herein in combination with (and optionally complexed with) a guide sequence is delivered to a cell. The nucleic acid constructs may be designed in accordance with the particular embodiment of RNA prime editing that is implements. For example, FIGS. 1-4 depict various exemplary embodiments of RNA prime editors. In some embodiments, the prime editor comprises a fusion protein of a Cas13 (e.g., or other napRNAbp) and an RDRP complexed with a rpegRNA, e.g., as shown in FIGS. 1 and 2. In the embodiment of FIG. 3, the RNA prime editing approach involves delivering a second napRNAbp (e.g., a second Cas13) and traditional guide RNA that binds nearby and installs an internal cut site in the target RNA molecule from which RNA extension may proceed. In the embodiment of FIG. 4, the RNA prime editor does not require a rpegRNA comprising the RNA template sequence. Rather, the RNA template sequence is provided in trans, e.g., by a ribozyme that is co-localized to the target RNA by an MS2 targeting system. Any suitable number and/or arrangements of expression vectors may be prepared that are capable of expressing the protein and guide RNA components of the various embodiments of RNA prime editors envisioned here. Separate nucleic acid constructs may also be provided for separate expression of a napRNAbp (e.g., a Cas13 domain) and an RDRP. In addition, the nucleic acid constructs may also include a nucleotide sequence encoding one or more guide RNAs for conducting RNA prime editing, include an rpegRNA which comprises an extended regions having a template sequence. The template sequence may also be provided in trans in other embodiments. Each of these components may be configured to be expressed from one or more nucleic acid vectors in any suitable manner utilizing one or more promoters.

Conventional viral and non-viral based gene transfer methods can be used to introduce nucleic acids in mammalian cells or target tissues. Such methods can be used to administer nucleic acids encoding components of a RNA prime editor to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bihm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a viruses can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. Reference is made to US 2003/0087817, published May 8, 2003, International Patent Application No. WO 2016/205764, published Dec. 22, 2016, International Patent Application No. WO 2018/071868, published Apr. 19, 2018, U.S. Patent Publication No. 2018/0127780, published May 10, 2018, and International Patent Application No. PCT/US2020/033873, the disclosures of each of which are incorporated herein by reference.

In various embodiments, the disclosed expression constructs may be engineered for delivery in one or more rAAV vectors. An rAAV as related to any of the methods and compositions provided herein may be of any serotype including any derivative or pseudotype (e.g., 1, 2, 3, 4, 5, 6, 7, 8, 9, 10, 11, 12, 13, 2/1, 2/5, 2/8, 2/9, 3/1, 3/5, 3/8, or 3/9). An rAAV may comprise a genetic load (i.e., a recombinant nucleic acid vector that expresses a gene of interest, such as a whole or split fusion protein that is carried by the rAAV into a cell) that is to be delivered to a cell. An rAAV may be chimeric.

As used herein, the serotype of an rAAV refers to the serotype of the capsid proteins of the recombinant virus. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. A non-limiting example of derivatives and pseudotypes that have chimeric VP1 proteins is rAAV2/5-1VP1u, which has the genome of AAV2, capsid backbone of AAV5 and VP1u of AAV1. Other non-limiting example of derivatives and pseudotypes that have chimeric VP1 proteins are rAAV2/5-8VP1u, rAAV2/9-1VP1u, and rAAV2/9-8VP1u.

AAV derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of making or packaging rAAV particles are known in the art and reagents are commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP2 region as described herein), and transfected into a recombinant cells such that the rAAV particle can be packaged and subsequently purified.

Additional methods for the delivery of nucleic acids to cells are known to those skilled in the art. See, for example, US 2003/0087817, incorporated herein by reference.

It should be appreciated that any fusion protein, e.g., any of the fusion proteins provided herein, may be introduced into the cell in any suitable way, either stably or transiently. In some embodiments, a fusion protein may be transfected into the cell. In some embodiments, the cell may be transduced or transfected with a nucleic acid construct that encodes a fusion protein. For example, a cell may be transduced (e.g., with a virus encoding a fusion protein), or transfected (e.g., with a plasmid encoding a fusion protein) with a nucleic acid that encodes a fusion protein, or the translated fusion protein. Such transduction may be a stable or transient transduction. In some embodiments, cells expressing a fusion protein or containing a fusion protein may be transduced or transfected with one or more gRNA molecules, for example when the fusion protein comprises a Cas9 (e.g., nCas9) domain. In some embodiments, a plasmid expressing a fusion protein may be introduced into cells through electroporation, transient (e.g., lipofection) and stable genome integration (e.g., piggybac) and viral transduction or other methods known to those of skill in the art.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a base editor as described herein in combination with (and optionally complexed with) a guide sequence is delivered to a cell.

Exemplary delivery strategies are described herein elsewhere, which include vector-based strategies, RPE ribonucleoprotein complex delivery, and delivery of RPE by mRNA methods.

In some embodiments, the method of delivery provided comprises nucleofection, microinjection, biolistics, virosomes, liposomes, immunoliposomes, polycation or lipid: nucleic acid conjugates, naked DNA, artificial virions, and agent-enhanced uptake of DNA.

Exemplary methods of delivery of nucleic acids include lipofection, nucleofection, electroporation, stable genome integration (e.g., piggybac), microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™, Lipofectin™ and SF Cell Line 4D-Nucleofector X Kit™ (Lonza)). Cationic and neutral lipids that are suitable for efficient receptor-recognition lipofection of polynucleotides include those of Feigner, WO 91/17424; WO 91/16024. Delivery may be to cells (e.g. in vitro or ex vivo administration) or target tissues (e.g. in vivo administration). Delivery may be achieved through the use of RNP complexes.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

In other embodiments, the method of delivery and vector provided herein is an RNP complex. RNP delivery of fusion proteins markedly increases the DNA specificity of base editing. RNP delivery of fusion proteins leads to decoupling of on- and off-target DNA editing. RNP delivery ablates off-target editing at non-repetitive sites while maintaining on-target editing comparable to plasmid delivery, and greatly reduces off-target DNA editing even at the highly repetitive VEGFA site 2. See Rees, H. A. et al., Improving the DNA specificity and applicability of base editing through protein engineering and protein delivery, *Nat. Commun.* 8, 15790 (2017), U.S. Pat. No. 9,526,784, issued Dec. 27, 2016, and U.S. Pat. No. 9,737,604, issued Aug. 22, 2017, each of which is incorporated by reference herein.

Additional methods for the delivery of nucleic acids to cells are known to those skilled in the art. See, for example, US 2003/0087817, incorporated herein by reference.

Other aspects of the present disclosure provide methods of delivering the prime editor constructs into a cell to form a complete and functional prime editor within a cell. For example, in some embodiments, a cell is contacted with a composition described herein (e.g., compositions comprising nucleotide sequences encoding the split Cas9 or the split prime editor or AAV particles containing nucleic acid vectors comprising such nucleotide sequences). In some embodiments, the contacting results in the delivery of such nucleotide sequences into a cell, wherein the N-terminal portion of the Cas9 protein or the prime editor and the C-terminal portion of the Cas9 protein or the prime editor are expressed in the cell and are joined to form a complete Cas9 protein or a complete prime editor.

It should be appreciated that any rAAV particle, nucleic acid molecule or composition provided herein may be introduced into the cell in any suitable way, either stably or transiently. In some embodiments, the disclosed proteins may be transfected into the cell. In some embodiments, the cell may be transduced or transfected with a nucleic acid molecule. For example, a cell may be transduced (e.g., with a virus encoding a split protein), or transfected (e.g., with a plasmid encoding a split protein) with a nucleic acid molecule that encodes a split protein, or an rAAV particle containing a viral genome encoding one or more nucleic acid molecules. Such transduction may be a stable or transient transduction. In some embodiments, cells expressing a split protein or containing a split protein may be transduced or transfected with one or more guide RNA sequences, for example in delivery of a split Cas9 (e.g., nCas9) protein. In some embodiments, a plasmid expressing a split protein may be introduced into cells through electroporation, transient (e.g., lipofection) and stable genome integration (e.g., piggybac) and viral transduction or other methods known to those of skill in the art.

In certain embodiments, the compositions provided herein comprise a lipid and/or polymer. In certain embodiments, the lipid and/or polymer is cationic. The preparation of such lipid particles is well known. See, e.g. U.S. Pat. Nos. 4,880,635; 4,906,477; 4,911,928; 4,917,951; 4,920,016; 4,921,757; and 9,737,604, each of which is incorporated herein by reference.

The guide RNAs and/or rpegRNAs used in the present disclosure may be 15-1000 nucleotides in length and comprise a sequence of at least 10, at least 15, or at least 20 contiguous nucleotides that is complementary to a target nucleotide sequence. The guide RNA may comprise a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to a target nucleotide sequence. The guide RNA may be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, the target nucleotide sequence is a DNA sequence in a genome, e.g. a eukaryotic genome. In certain embodiments, the target nucleotide sequence is in a mammalian (e.g. a human) genome.

The compositions of this disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent, i.e., a carrier or vehicle.

Treatment of a disease or disorder includes delaying the development or progression of the disease, or reducing disease severity. Treating the disease does not necessarily require curative results.

As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

As used herein "onset" or "occurrence" of a disease includes initial onset and/or recurrence. Conventional methods, known to those of ordinary skill in the art of medicine, can be used to administer the isolated polypeptide or pharmaceutical composition to the subject, depending upon the type of disease to be treated or the site of the disease.

Kits, Vectors, Cells

Some aspects of this disclosure provide kits comprising a nucleic acid construct comprising a nucleotide sequence encoding the various components of the RNA prime editing system described herein (e.g., including, but not limited to, the napRNAbps, RDRPs, fusion proteins (e.g., comprising napRNAbps and RDRPs), RpegRNAs, and complexes comprising fusion proteins and the RpegRNAs, as well as accessory elements. In some embodiments, the nucleotide sequence comprises a heterologous promoter that drives expression of the prime editing system components.

Some aspects of this disclosure provide kits comprising one or more nucleic acid constructs encoding the various components of the prime editing system described herein, e.g., the comprising a nucleotide sequence encoding the components of the prime editing system capable of modifying a target DNA sequence. In some embodiments, the nucleotide sequence comprises a heterologous promoter that drives expression of the RNA prime editing system components.

Some aspects of this disclosure provides kits comprising a nucleic acid construct, comprising (a) a nucleotide sequence encoding a napRNAbp (e.g., a Cas13 domain) and an RDRP (expressed as separate protein products or as a fusion protein) and (b) a heterologous promoter that drives expression of the sequence of (a). Separate nucleic acid constructs may also be provide for separate expression of a napRNAbp (e.g., a Cas13 domain) and an RDRP. In addition, the nucleic acid constructs may also include a nucleotide sequence encoding one or more guide RNAs for conducting RNA prime editing, include an rpegRNA which comprises an extended regions having a template sequence. The template sequence may also be provided in trans in other embodiments. Each of these components may be configured to be expressed from one or more nucleic acid vectors in any suitable manner utilizing one or more promoters.

Some aspects of this disclosure provide cells comprising any of the constructs disclosed herein. In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A 172, A20, A253, A431, A-549, ALC, B16, B35, BCP-1 cells, BEAS-2B, bEnd.3, BHK-21, BR 293. BxPC3. C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK 11, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In addition, the present disclosure involves targeting an RNA molecule with a cell. Such cells may be manipulated using RNA prime editing under in vitro conditions, i.e., where the cells are provided in culture. In other embodiments, the RNA prime editing may be conducted under ex vivo conditions, i.e., whereby cells are removed from a subject and manipulated outside of the body. In still other embodiments, the RNA prime editing may be conducted in vivo, whereby the components of the RNA prime editor are provided to a subject (e.g., by delivery of expression vectors, or by delivery of particles comprising RNA prime editor) in an effective amount and delivered to one or more cells in which RNA editing is desired. Thus, in such methods the target locus of interest may be comprised in a nucleic acid molecule within a cell, in particular a eukaryotic cell, such as a mammalian cell or a plant cell. The mammalian cell many be a non-human primate, bovine, porcine, rodent or mouse cell. The cell may be a non-mammalian eukaryotic cell such as poultry, fish or shrimp. The plant cell may be of a crop plant such as cassava, com, sorghum, wheat, or rice. The plant cell may also be of an algae, tree or vegetable. The modification introduced to the cell by the present invention may be such that the cell and progeny of the cell are altered for improved production of biologic products such as an antibody, starch, alcohol or other desired cellular output. The modification introduced to the cell by the present invention may be such that the cell and progeny of the cell include an alteration that changes the biologic product produced.

The mammalian cell many be a non-human mammal, e.g., primate, bovine, ovine, porcine, canine, rodent, Leporidae such as monkey, cow, sheep, pig, dog, rabbit, rat or mouse cell. The cell may be a non-mammalian eukaryotic cell such as poultry bird (e.g., chicken), vertebrate fish (e.g., salmon) or shellfish (e.g., oyster, claim, lobster, shrimp) cell. The cell may also be a plant cell. The plant cell may be of a monocot or dicot or of a crop or grain plant such as cassava, corn, sorghum, soybean, wheat, oat or rice. The plant cell may also be of an algae, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinaeia*; plants of the genus *Capsicum*; cotton, tobacco, asparagus, carrot, cabbage, broccoli, cauliflower, tomato, eggplant, pepper, lettuce, spinach, strawberry, blueberry, raspberry, blackberry, grape, coffee, cocoa, etc).

Vectors

Some aspects of the present disclosure relate to using recombinant virus vectors (e.g., adeno-associated virus vectors, adenovirus vectors, or herpes simplex virus vectors) for the delivery of the prime editors or components thereof described herein, e.g., the split Cas9 protein or a split nucleobase prime editors, into a cell. In the case of a split-PE approach, the N-terminal portion of a PE fusion protein and the C-terminal portion of a PE fusion are delivered by separate recombinant virus vectors (e.g., adeno-associated virus vectors, adenovirus vectors, or herpes simplex virus vectors) into the same cell, since the full-length Cas9 protein or prime editors exceeds the packaging limit of various virus vectors, e.g., rAAV (~4.9 kb).

Thus, in one embodiment, the disclosure contemplates vectors capable of delivering split prime editor fusion proteins, or split components thereof. In some embodiments, a composition for delivering the split Cas9 protein or split prime editor into a cell (e.g., a mammalian cell, a human cell) is provided. In some embodiments, the composition of the present disclosure comprises: (i) a first recombinant adeno-associated virus (rAAV) particle comprising a first nucleotide sequence encoding a N-terminal portion of a Cas9 protein or prime editor fused at its C-terminus to an intein-N; and (ii) a second recombinant adeno-associated virus (rAAV) particle comprising a second nucleotide sequence encoding an intein-C fused to the N-terminus of a C-terminal portion of the Cas9 protein or prime editor. The rAAV particles of the present disclosure comprise a rAAV vector (i.e., a recombinant genome of the rAAV) encapsidated in the viral capsid proteins.

In some embodiments, the rAAV vector comprises: (1) a heterologous nucleic acid region comprising the first or second nucleotide sequence encoding the N-terminal portion or C-terminal portion of a split Cas9 protein or a split prime editor in any form as described herein, (2) one or more nucleotide sequences comprising a sequence that facilitates expression of the heterologous nucleic acid region (e.g., a promoter), and (3) one or more nucleic acid regions comprising a sequence that facilitate integration of the heterologous nucleic acid region (optionally with the one or more nucleic acid regions comprising a sequence that facilitates expression) into the genome of a cell. In some embodiments, viral sequences that facilitate integration comprise Inverted Terminal Repeat (ITR) sequences. In some embodiments, the first or second nucleotide sequence encoding the N-terminal portion or C-terminal portion of a split Cas9 protein or a split prime editor is flanked on each side by an ITR sequence. In some embodiments, the nucleic acid vector further comprises a region encoding an AAV Rep protein as described herein, either contained within the region flanked by ITRs or outside the region. The ITR sequences can be derived from any AAV serotype (e.g., 1, 2, 3, 4, 5, 6, 7, 8, 9, or 10) or can be derived from more than one serotype. In some embodiments, the ITR sequences are derived from AAV2 or AAV6.

Thus, in some embodiments, the rAAV particles disclosed herein comprise at least one rAAV2 particle, rAAV6 particle, rAAV8 particle, rPHP.B particle, rPHP.eB particle, or rAAV9 particle, or a variant thereof. In particular embodiments, the disclosed rAAV particles are rPHP.B particles, rPHP.eB particles, rAAV9 particles.

ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

In some embodiments, the rAAV vector of the present disclosure comprises one or more regulatory elements to control the expression of the heterologous nucleic acid region (e.g., promoters, transcriptional terminators, and/or other regulatory elements). In some embodiments, the first and/or second nucleotide sequence is operably linked to one or more (e.g., 1, 2, 3, 4, 5, or more) transcriptional terminators. Non-limiting examples of transcriptional terminators that may be used in accordance with the present disclosure include transcription terminators of the bovine growth hormone gene (bGH), human growth hormone gene (hGH), SV40, CW3, ϕ, or combinations thereof. The efficiencies of several transcriptional terminators have been tested to determine their respective effects in the expression level of the split Cas9 protein or the split prime editor. In some embodiments, the transcriptional terminator used in the present disclosure is a bGH transcriptional terminator. In some embodiments, the rAAV vector further comprises a Woodchuck Hepatitis Virus Posttranscriptional Regulatory Element (WPRE). In certain embodiments, the WPRE is a truncated WPRE sequence, such as “W3.” In some embodiments, the WPRE is inserted 5' of the transcriptional terminator. Such sequences, when transcribed, create a tertiary structure which enhances expression, in particular, from viral vectors.

In some embodiments, the vectors used herein may encode the PE fusion proteins, or any of the components thereof (e.g., napDNAbp, linkers, or polymerases). In addition, the vectors used herein may encode the PEgRNAs, and/or the accessory gRNA for second strand nicking. The vectors may be capable of driving expression of one or more coding sequences in a cell. In some embodiments, the cell may be a prokaryotic cell, such as, e.g., a bacterial cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild-type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the promoters that may be used in the prime editor vectors may be constitutive, inducible, or tissue-specific. In some embodiments, the promoters may be a constitutive promoters. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EFla) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EFla promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech). In some embodiments, the promoter may be a tissue-specific promoter. In some embodiments, the tissue-specific promoter is exclusively or predominantly expressed in liver tissue. Non-limiting exemplary tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphs1 promoter, OG-2 promoter, SP-B promoter, SYN1 promoter, and WASP promoter.

In some embodiments, the prime editor vectors (e.g., including any vectors encoding the prime editor fusion protein and/or the PEgRNAs, and/or the accessory second strand nicking gRNAs) may comprise inducible promoters to start expression only after it is delivered to a target cell. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In additional embodiments, the prime editor vectors (e.g., including any vectors encoding the prime editor fusion protein and/or the PEgRNAs, and/or the accessory second strand nicking gRNAs) may comprise tissue-specific promoters to start expression only after it is delivered into a specific tissue. Non-limiting exemplary tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphs1 promoter, OG-2 promoter, SP-B promoter, SYN1 promoter, and WASP promoter.

In some embodiments, the nucleotide sequence encoding the PEgRNA (or any guide RNAs used in connection with prime editing) may be operably linked to at least one transcriptional or translational control sequence. In some embodiments, the nucleotide sequence encoding the guide RNA may be operably linked to at least one promoter. In some embodiments, the promoter may be recognized by RNA polymerase III (Pol III). Non-limiting examples of Pol III promoters include U6, HI and tRNA promoters. In some embodiments, the nucleotide sequence encoding the guide RNA may be operably linked to a mouse or human U6 promoter. In other embodiments, the nucleotide sequence encoding the guide RNA may be operably linked to a mouse or human HI promoter. In some embodiments, the nucleotide sequence encoding the guide RNA may be operably linked to a mouse or human tRNA promoter. In embodiments with more than one guide RNA, the promoters used to drive expression may be the same or different. In some embodiments, the nucleotide encoding the crRNA of the guide RNA and the nucleotide encoding the tracr RNA of the guide RNA may be provided on the same vector. In some embodiments, the nucleotide encoding the crRNA and the nucleotide encoding the tracr RNA may be driven by the same promoter. In some embodiments, the crRNA and tracr RNA may be transcribed into a single transcript. For example, the crRNA and tracr RNA may be processed from the single transcript to form a double-molecule guide RNA.

Alternatively, the crRNA and tracr RNA may be transcribed into a single-molecule guide RNA.

In some embodiments, the nucleotide sequence encoding the guide RNA may be located on the same vector comprising the nucleotide sequence encoding the PE fusion protein. In some embodiments, expression of the guide RNA and of the PE fusion protein may be driven by their corresponding promoters. In some embodiments, expression of the guide RNA may be driven by the same promoter that drives expression of the PE fusion protein. In some embodiments, the guide RNA and the PE fusion protein transcript may be contained within a single transcript. For example, the guide RNA may be within an untranslated region (UTR) of the Cas9 protein transcript. In some embodiments, the guide RNA may be within the 5' UTR of the PE fusion protein transcript. In other embodiments, the guide RNA may be within the 3' UTR of the PE fusion protein transcript. In some embodiments, the intracellular half-life of the PE fusion protein transcript may be reduced by containing the guide RNA within its 3' UTR and thereby shortening the length of its 3' UTR. In additional embodiments, the guide RNA may be within an intron of the PE fusion protein transcript. In some embodiments, suitable splice sites may be added at the intron within which the guide RNA is located such that the guide RNA is properly spliced out of the transcript. In some embodiments, expression of the Cas9 protein and the guide RNA in close proximity on the same vector may facilitate more efficient formation of the CRISPR complex.

The prime editor vector system may comprise one vector, or two vectors, or three vectors, or four vectors, or five vector, or more. In some embodiments, the vector system may comprise one single vector, which encodes both the PE fusion protein and PEgRNA. In other embodiments, the vector system may comprise two vectors, wherein one vector encodes the PE fusion protein and the other encodes the PEgRNA. In additional embodiments, the vector system may comprise three vectors, wherein the third vector encodes the second strand nicking gRNA used in the herein methods.

In some embodiments, the composition comprising the rAAV particle (in any form contemplated herein) further comprises a pharmaceutically acceptable carrier. In some embodiments, the composition is formulated in appropriate pharmaceutical vehicles for administration to human or animal subjects.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1. Prime Editing to Modify the Sequence of an RNA Target Molecule

This example relates to the use of a programmable RNA binding protein to direct programmable RNA modifying enzymes to install mutations in a target RNA molecule as a means to correct disease-causing mutations or otherwise to install sequence changes in a target RNA molecule. A variety of strategies for the targeting of these complexes are contemplated here, such as Cas13 proteins (as is true for REPAIR and RESCUE[4, 5]), or Pumby proteins,[7] or homologs, orthologs, or variants of these proteins. It was surprisingly discovered that RNA could be directly edited using a fusion protein comprising a nucleic acid-programmable RNA binding protein (napRNAbp) and an RNA-dependent RNA polymerase (RDRP) when complexed with a specialized guide RNA called an RNA prime editing guide RNA. This approach is referred to as "RNA prime editing" in reference to the recently described method of prime editing which edits DNA sequences.

Prime editing (PE) was recently developed to edit target DNA sequences (see Azalone et al., "Search-and-replace genome editing without double-strand breaks of donor DNA," *Nature,* 2019, Vol. 576, pp. 149-157, incorporated herein by reference; also see International PCT Publications which are directed to prime editing: WO2020/191239, WO2020/191153, WO2020/191171, WO2020/191248, WO2020/191234, WO2020/191233, WO2020/191245, WO2020/191242, WO2020/191243, WO2020/191246, WO2020/191249, and WO2020/191241, each of which are incorporated herein by reference). Prime editing involves contacting a target DNA with a prime editor and a prime editing guide RNA (pegRNA). The prime editor is a fusion protein comprising a nucleic acid programmable DNA binding protein (napDNAbp) fused to a reverse transcriptase (RT). Prime editing comprises contacting a DNA molecule comprising a target nucleotide sequence with a prime editor and a pegRNA, nicking of one of the strands by the prime editor, followed by the synthesis of a new strand of DNA from the exposed 3' end of the cut target DNA by the RT-dependent synthesis from the exposed 3' end of the cut target DNA of a replacement strand of DNA containing the desired edit (e.g., insertion, deletion, or substitution) which results in the synthesis of a replacement strand of DNA nucleotide editing at the target nucleotide sequence.

The present specification describes a novel nucleic acid-editing system-namely, RNA prime editing—that is capable of directly editing the sequence of a target RNA molecule. RNA prime editing of a target RNA molecule comprises contacting a target RNA molecule with a RNA prime editor and an RNA prime editing guide RNA (rpegRNA). The RNA prime editor comprises a nucleic acid programmable RNA binding protein (e.g., Cas13) fused with an RNA-dependent RNA polymerase (RDRP). In other embodiments, the RNA prime editor may be provided as a complex with separately expressed napRNAbp, pegRNA, and RDRP components. When complexed with the rpegRNA, the RNA prime editor (and specifically, the napRNAbp component) is guided to and binds the target RNA molecule due to a region (i.e., the spacer) in the rpegRNA that is complementary to a region of the target RNA molecule having a free 3' terminus (e.g., the natural 3' terminus of the RNA molecule, or a 3' terminus formed as a result of nuclease action on the target RNA by the RNA prime editor. The RNA prime editor, and specifically, the RNA-dependent RNA polymerase (e.g., provided separately or fused to the napRNAbp), then synthesizes a strand of RNA from the 3' terminus which is templated by the rpegRNA (specifically, the extension arm of the rpegRNA that encodes the desired edited sequence), thereby installing a modified sequence in the target RNA molecule at the natural 3' terminus or at a nuclease-generated 3' terminus within the target RNA molecule. These aspects are depicted in FIG. 1.

In contrast to Cas9, Cas13 enzymes cleave their cognate RNA target outside of the protospacer binding site,[8] and can do so at a variable position relative to the protospacer. As such, it is possible that the Cas13:rpegRNA complex remains bound to the RNA target following cleavage for sufficient time to enable the fused or separately-provided RDRP to bind to the newly cleaved RNA. As such, targeting a wild-type Cas13:RDRP fusion or a separately provided Cas13 and RDRP components to a specific site using a rpegRNA could effectively enable programmable replacement of the 3'-portion of the RNA with an edited one, encoded by the rpegRNA.

RNA prime editing requires a 3' terminus, which is required by the RDRP to begin RNA synthesis. A 3' terminus naturally exists in any RNA molecule and thus RNA prime editing may operate to extend the naturally present 3' terminus of an RNA molecule. Alternatively, a 3' terminus may be formed at an internal site in a target RNA molecule by nuclease-induced cleavage of a phosphodiester bond between any two adjacent ribonucleotides in the target RNA molecule, as depicted in FIG. 2.

In another embodiment, as depicted in FIG. 3, the internal 3' terminus may be formed by a second napRNAbp (e.g., Cas13) complexed with a second guide RNA that targets the napRNAbp to a nearby RNA locus or binding site to install a cut site thereby forming a 3' terminus. The RNA prime editor may be programmed to bind to a site upstream of the 3' terminus, wherein the extension arm of the rpegRNA may then bind upstream of the cut site to provide a template sequence (that includes the desired edit) for the synthesis of new RNA beginning at the 3' terminus.

Various design considerations for RNA prime editing are contemplated as follows. First, whether the RPE is directed to the nucleus or cytoplasm will likely vary based on what RNA transcript is targeted. Typically, targeting of RNA prime editors to the nucleus results in improved editing efficacy in other editing strategies. Second, location of where the RPE is targeted on the RNA transcript relative to the location of the installed edit should be considered. Cas13 is reported to cleave its RNA substrate non-specifically near the targeted site, and can only be targeted to accessible regions of the RNA substrate. Designing an RPE such that Cas13-cleavaged leads to both RDRP-mediated nucleotide addition and subsequent mutation installation is contemplated. Third, in various embodiments where the new RNA sequence is installed at an internal 3' terminus, the rpegRNA can be longer than pegRNAs used in prime editing of DNA, because the rpregRNA can encode the remainder of the RNA sequence that is lost due to generation of the internal 3' terminus. Thus, expression platforms capable of expressing rpegRNAs are contemplated. Fourth, if multiple napRNAbp (e.g., Cas13) versions are targeted to the same RNA, the spacing of their binding sites will be contemplated.

Alternative RNA prime editors that do require a rpegRNA are also contemplated wherein the template portion of the rpegRNA is separately delivered by another protein (e.g., a ribozyme complexed with a template sequence. Such an embodiment is depicted in FIG. 4, which depicts an RNA prime editor that comprises a Cas13 complexed with a traditional guide RNA that targets the Cas13/guide RNA complex to bind to a target site on an RNA molecule. A ribozyme complexed with a template strand could become co-localized with the Cas13 protein through a recruitment system, such as an MS2-tagging system. In the case of the MS2-tagging system, the Cas13 could be complexed with an RNA-protein recruitment domain or protein (such as the MS2 hairpin structure), which would recruit a ribozyme fused to a MS2 bacteriophage coat protein (MCP). In this way, the MS2 hairpin on the Cas13 "recruits" in trans the ribozyme to the target site occupied by the RNA prime editing complex. In the case of trans-splicing ribozymes, this approach could be used to cleave a target RNA to remove its 3' "exon" (which forms an available 3' terminus) with subsequent installation of a replacement exon by the action of a RDRP (which can be provide in trans or in cis as a fusion protein with either the Cas13 domain or the recruited ribozyme component).[3] In embodiments where the RDRP is provided separately in trans, the napDNAbp or ribozyme components could be modified to include another recruitment system, such as an MS2-tagging system, to enhance the co-localization of the RDRP to the target site in the RNA. The MS2-tagging system is further described in Schechner D M, et al. Nat. Methods., 2015, which is incorporated herein by reference.

REFERENCES

The following references are incorporated herein by reference in their entireties.

1. Fire A, et al. Nature 1998.
2. Setten, R L, et al. Nat. Rev. Drug Discovery 2019.
3. Lee, C H, et al. Prog. Mol Biol. Trans. Sci., 2018.
4. Cox, D B T, et al. Science 2017.
5. Abudayyeh, O O, et al. Science 2019.
6. Kim, D, et al. Annu. Rev. Biochem., 2019.
7. Adamala, K P, et al. Proc. Natl. Acad. Sci. USA, 2016.
8. Abudayyeh, O O, et al. Science 2016.
9. Schechner, D M, et al. Nat. Methods., 2015.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A fusion protein comprising a nucleic acid-programmable RNA binding protein and an RNA-dependent RNA polymerase.

2. The fusion protein of claim 1, wherein the fusion protein when complexed to an RNA prime editing guide RNA (rpegRNA) is capable of appending a single-stranded RNA sequence to a target RNA.

3. The fusion protein of claim 2, wherein the single-stranded RNA sequence is appended to the 3' terminus of the target RNA or to a 3' terminus which is formed upon cleavage of the target RNA by the fusion protein at a cut site.

4. The fusion protein of claim 2, wherein the single-stranded RNA sequence is polymerized by the RNA-dependent RNA polymerase using the rpegRNA as a template.

5. The fusion protein of claim 2, wherein the rpegRNA comprises the following structure: 5'-[spacer sequence]-[scaffold sequence]-[template sequence]-3', wherein the spacer sequence anneals to the target RNA at a complementary protospacer sequence, the scaffold sequence binds the rpegRNA to the nucleic acid-programmable RNA binding protein of the fusion protein, and the template sequence provides an RNA template for synthesis of the single-stranded RNA sequence by the RNA-dependent RNA polymerase of the fusion protein.

6. The fusion protein of claim 1, wherein the nucleic acid-programmable RNA binding protein is a Cas13 protein.

7. The fusion protein of claim 6, wherein the Cas13 protein is a Cas13a, Cas13b, or Cas13d protein.

8. The fusion protein of claim 6, wherein the Cas13 protein is nuclease inactive.

9. The fusion protein of claim 6, wherein the Cas13 protein has an amino acid sequence at least 80% identical to the amino acid sequence of SEQ ID NO: 1.

10. The fusion protein of claim 1, wherein the RNA-dependent RNA polymerase is capable of polymerizing a single-stranded RNA sequence using an rpegRNA as a template.

11. The fusion protein of claim 1, wherein the RNA-dependent RNA polymerase comprises an amino acid sequence at least 80% identical to an amino acid sequence selected from the group consisting of SEQ ID NOs: 2-7.

12. The fusion protein of claim 1, wherein the fusion protein has the structure: $NH_2$-[RNA-dependent RNA polymerase]-[nucleic acid-programmable RNA binding protein]-COOH or $NH_2$-[nucleic acid-programmable RNA binding protein]-[RNA-dependent RNA polymerase]-COOH, wherein "]-[" represents a linker sequence.

13. The fusion protein of claim 12, wherein the linker sequence has an amino acid sequence selected from the group consisting of SEQ ID NOs: 14-23.

14. An RNA prime editor complex for appending a single-stranded RNA sequence to a target RNA comprising a fusion protein of claim 1 and an rpegRNA.

15. The RNA prime editor complex of claim 14, wherein the rpegRNA is capable of programming the fusion protein to bind to the target RNA.

16. The RNA prime editor complex of claim 14, wherein the nucleic acid-programmable RNA binding protein of the fusion protein comprises a nuclease activity which cleaves the target RNA at a cut site upon binding of the complex thereto.

17. The RNA prime editor complex of claim 14, wherein the nucleic acid-programmable RNA binding protein of the fusion protein is catalytically inactive.

18. A method for appending a desired single-stranded RNA sequence to the 3' end of a target RNA, the method comprising contacting the target RNA with an RNA prime editor complex of claim 14.

19. The fusion protein of claim 1, wherein the fusion protein comprises an amino acid sequence at least 80% identical to any one of SEQ ID NOs: 9-13.

20. An RNA prime editor complex for appending a single-stranded RNA sequence to a target RNA comprising: (i) a first fusion protein comprising a catalytically inactive nucleic acid-programmable RNA binding protein and an RNA-dependent RNA polymerase; (ii) a second fusion protein comprising a catalytically active nucleic acid-programmable RNA binding protein that is capable of cleaving the target RNA to generate a free 3' terminus; (iii) an rpegRNA that directs the first fusion protein to a first locus in the target RNA; and (iv) a guide RNA that directs the second fusion protein to a second locus in the target RNA.

* * * * *